(12) United States Patent
Hatakeyama et al.

(10) Patent No.: US 10,374,166 B2
(45) Date of Patent: Aug. 6, 2019

(54) POLYCYCLIC AROMATIC COMPOUND

(71) Applicants: Kwansei Gakuin Educational Foundation, Nishinomiya, Hyogo (JP); JNC Corporation, Chiyoda-ku, Tokyo (JP)

(72) Inventors: Takuji Hatakeyama, Hyogo (JP); Soichiro Nakatsuka, Hyogo (JP); Kiichi Nakajima, Hyogo (JP); Hiroki Hirai, Hyogo (JP); Yohei Ono, Chiba (JP); Kazushi Shiren, Chiba (JP); Jingping Ni, Chiba (JP); Takeshi Matsushita, Chiba (JP); Toshiaki Ikuta, Chiba (JP)

(73) Assignees: KWANSEI GAKUIN EDUCATIONAL FOUNDATION, Nishinomiya (JP); JNC CORPORATION, Tokyo (JP)

( * ) Notice: Subject to any disclaimer, the term of this patent is extended or adjusted under 35 U.S.C. 154(b) by 247 days.

(21) Appl. No.: 14/508,554

(22) Filed: Oct. 7, 2014

(65) Prior Publication Data
US 2015/0236274 A1 Aug. 20, 2015

(30) Foreign Application Priority Data
Feb. 18, 2014 (JP) .................... 2014-028750

(51) Int. Cl.
C07F 5/02 (2006.01)
H01L 51/00 (2006.01)
H01L 51/50 (2006.01)
C07F 9/6568 (2006.01)

(52) U.S. Cl.
CPC ............ H01L 51/0072 (2013.01); C07F 5/02 (2013.01); C07F 9/65685 (2013.01); H01L 51/008 (2013.01); H01L 51/0052 (2013.01); H01L 51/0054 (2013.01); H01L 51/0059 (2013.01); H01L 51/0071 (2013.01); H01L 51/5012 (2013.01); H01L 51/5016 (2013.01); H01L 51/5056 (2013.01); H01L 51/5072 (2013.01); H01L 51/5088 (2013.01); Y02E 10/549 (2013.01)

(58) Field of Classification Search
None
See application file for complete search history.

(56) References Cited

U.S. PATENT DOCUMENTS

| | | |
|---|---|---|
| 2007/0106103 A1 | 5/2007 | Ikeda et al. |
| 2009/0295275 A1 | 12/2009 | Parham et al. |
| 2012/0319052 A1 | 12/2012 | Brocke et al. |
| 2014/0058099 A1 | 2/2014 | Wakamiya et al. |
| 2015/0295186 A1 | 10/2015 | Parham et al. |

FOREIGN PATENT DOCUMENTS

| | | |
|---|---|---|
| CN | 102782894 A | 11/2012 |
| JP | 2001-017223 A | 1/2001 |
| JP | 2005-170911 A | 6/2005 |
| JP | 2012-234873 A | 11/2012 |
| KR | 10-2012-0087935 A | 8/2012 |
| WO | WO 2004/061047 A2 | 7/2004 |
| WO | WO 2012/118164 A1 | 9/2012 |
| WO | WO 2014/008967 A2 | 1/2014 |

OTHER PUBLICATIONS

Journal of the American Chemical Society, (2014), vol. 136(40), pp. 14299-14306.*
Chen et al., "How to design more efficient organic dyes for dye-sensitized solar cells? Adding more $sp^2$-hybridized nitrogen in the triphenylamine donor," Journal of Power Sources, 2013, 223:86-93.
Faldt et al., "Synthesis, structure and properties of various molecules based on the 4,8,12-trioxa-4,8-12,12c-tetrahydrodibenzo[cd,mn]pyrene system with an evaluation of the effect differing molecular substitution patterns has on the space group symmetry," J. Chem. Soc., Perkin Trans., 1997, 2:2219-2227.
Krebs et al., "Synthesis, Structure and Properties of 4,8,12-Trioxa-12c-Phospha-4,8,12,12c-tetrahydrodibenzo[cd,mn]pyrene, a Molecular Pyroelectric," J. Am. Chem. Soc., 1997, 119:1208-1216.
Kuratsu et al., "Synthesis, Structure, and Electron-Donating Ability of 2,2':6',2''-Dioxatriphyenylamine and Its Sulfur Analogue," Chemistry Letters, 2004, 33(9):1174-1175.
Kuratsu et al., "2,2':6',2'':6'',6-Trioxytriphenylamine: Synthesis and Properties of the Radical Cation and Neutral Species," Angew. Chem. Int. Ed., 2005, 44:4056-4058.
Kuratsu et al., "(Nitronyl Nitroxide)-Substitute Trioxytriphenylamine Radical Cation Tetrachlorogallate Salt: A 2p-Electron-Based Weak Ferromagnet Composed of a Triplet Diradical Cation," Chem. Asian J., 2012, 7:1604-1609.
Madsen et al., "Evaluation of the Solid State Dipole Moment and Pyroelectric Coefficient of Phosphangulene by Multipolar Modeling of X-ray Structure Factors," Chem. Eur. J., 2000, 6(10):1797-1804.
Tai et al., "Theoretical Design of Π-Conjugated Heteropolycyclic Compounds Containing a Tricoordinated Boron Center," J. Phys. Chem. C, 2013, 117:14999-15008.
Hatakeyama et al., "Tandem Phospha-Friedel-Crafts Reaction toward Curved 7-Conjugated Frameworks with a Phosphorus Ring Junction," Organic Letters, 2011, 13(8):2130-2133.

(Continued)

Primary Examiner — Dawn L Garrett
(74) Attorney, Agent, or Firm — Foley & Lardner LLP

(57) ABSTRACT

A novel polycyclic aromatic compound in which plural aromatic rings are linked via boron atoms, oxygen atoms and the like is provided, and therefore, the range of selection of the material for organic electroluminescent elements can be widened. Also, an excellent organic electroluminescent element is provided by using the novel polycyclic aromatic compound as a material for an organic electroluminescent element.

42 Claims, 1 Drawing Sheet

(56) References Cited

OTHER PUBLICATIONS

Kobayashi et al., "Synthesis of Dibenzochalcogenaborins and Systematic Comparisons of Their Optical Properties by Changing a Bridging Chalcogen Atom," Chem. Asian J., 2009 (Online Nov. 19, 2008), 4:42-49.

Hashimoto, Sigma, "Syntheses of Polycyclic Aromatic Compounds with Heteroatom Junctions via Tandem Hetero-Friedel Crafts Reactions," Dissertation, Kyoto University, 2013, 173 pages.

* cited by examiner

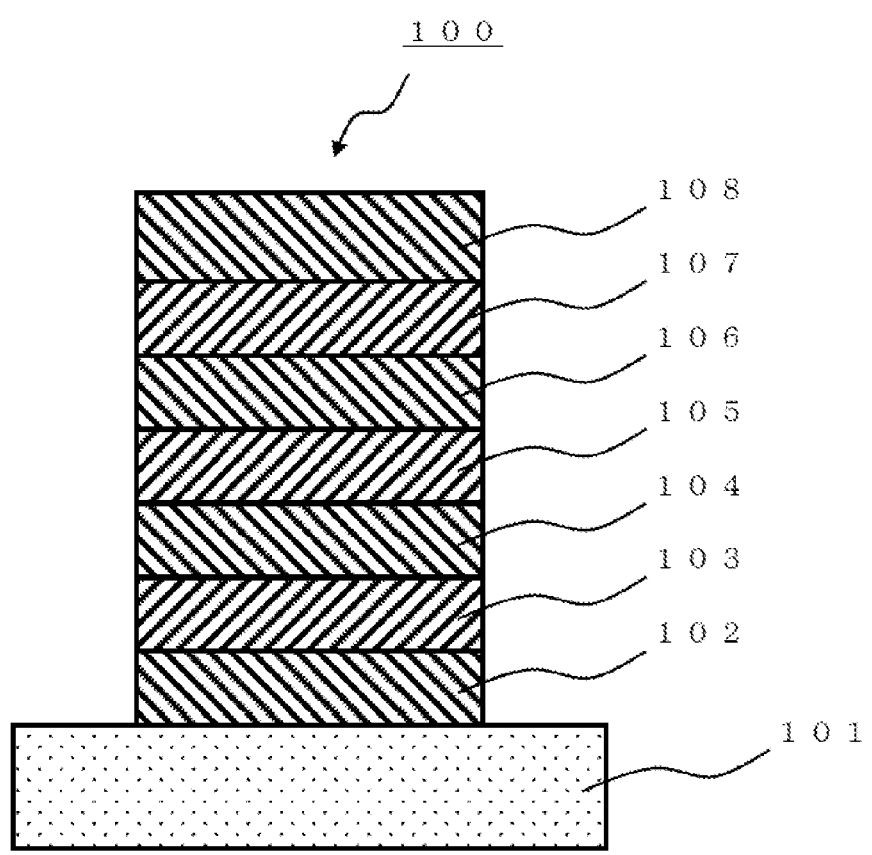

POLYCYCLIC AROMATIC COMPOUND

CROSS-REFERENCE TO RELATED APPLICATIONS

This application claims priority from Japanese application JP 2014-028750, filed Feb. 18, 2014.

TECHNICAL FIELD

The present invention relates to a polycyclic aromatic compound, and an organic electroluminescent (EL) element, an organic field effect transistor and an organic thin film solar cell using the polycyclic aromatic compound, as well as a display apparatus and a lighting apparatus.

RELATED ART

Conventionally, since display apparatuses employing light emitting elements that are electroluminescent can be subjected to reduction of power consumption and thickness reduction, various studies have been conducted thereon. Furthermore, organic electroluminescent elements formed from organic materials have been a subject of active investigation, from the viewpoint that weight reduction or size expansion can be easily achieved. Particularly, active research has been hitherto conducted on the development of organic materials having luminescence characteristics for blue light, which is one of the primary colors of light, and the development of organic materials having charge transport capability for holes, electrons and the like (having a potential for serving as a semiconductor or a superconductor), irrespective of whether the organic materials are high molecular weight compounds or low molecular weight compounds.

An organic EL element has a structure having a pair of electrodes composed of a positive electrode and a negative electrode, and a single layer or plural layers that are disposed between the pair of electrodes and contain organic compounds. Those layers include a layer containing an organic compound, a light emitting layer, a charge transport/injection layer for transporting or injecting charges such as holes or electrons, and the like, and various organic materials suitable for these layers have been developed.

Regarding the materials for light emitting layers, for example, benzofluorene-based compounds and the like have been developed (WO 2004/061047). Furthermore, regarding hole transporting materials, for example, triphenylamine-based compounds and the like have been developed (JP 2001-172232 A). Also, regarding electron transporting materials, for example, anthracene-based compounds and the like have been developed (JP 2005-170911 A).

Furthermore, in recent years, materials obtained by improving triphenylamine derivatives have also been reported as materials that are used in organic EL elements and organic thin film solar cells (WO 2012/118164). These materials are materials characterized in that N,N'-diphenyl-N,N'-bis(3-methylphenyl)-1,1'-biphenyl-4,4'-diamine (TPD), which has been already put to practical use, is used as a base material, and flatness thereof is increased by connecting the aromatic rings that constitute triphenylamine. In this document, for example, evaluation of the charge transporting characteristics of a NO-linked system compound (compound 1 of page 63) has been made; however, there is no description on the method for producing materials other than the NO-linked system compound. Also, when the element that connects is different, the overall electron state of the compound is different; however, in this regard, the characteristics obtainable from materials other than the NO-linked system compound are still not known. For example, since a compound having a conjugated structure involving high energy of triplet exciton (T1) can emit phosphorescent light having a shorter wavelength, the compound is useful as a material for blue light emitting layer. There is also a demand for a novel compound having a conjugated structure with high T1 as an electron transporting material or a hole transporting material that interposes a light emitting layer.

A host material for organic EL elements is generally a molecule in which plural existing aromatic rings of benzene, carbazole or the like are linked via single bonds, phosphorus atoms or silicon atoms. This is because when a number of aromatic rings having a relatively small conjugated system are connected, the large HOMO-LUMO gap required from a host material (band gap Eg in a thin film) is secured. Furthermore, in a host material for organic EL elements that use phosphorescent materials or thermally activated delayed fluorescence materials, high triplet excitation energy ($E_T$) is needed; however, the triplet excitation energy ($E_T$) can be increased by localizing SOMO1 and SOMO2 in the triplet excitation state (T1) by connecting a donor-like or acceptor-like aromatic ring or substituent to the molecule, and thereby reducing the exchange interaction between the two orbitals. However, aromatic rings having small conjugated systems do not have sufficient redox stability, and an element which uses a molecule obtained by connecting existing aromatic rings as the host material, does not have a sufficient service life. On the other hand, polycyclic aromatic compounds having extended π-conjugated systems generally have excellent redox stability; however, since the HOMO-LUMO gap (band gap Eg in a thin film) or the triplet excitation energy ($E_T$) is low, polycyclic aromatic compounds have been considered to be unsuitable as host materials.

CITATION LIST

Patent Literatures

Patent Document 1: WO 2004/061047
Patent Document 2: JP 2001-172232 A
Patent Document 3: JP 2005-170911 A
Patent Document 4: WO 2012/118164

SUMMARY

Problems to be Resolved by the Invention

As described above, various materials that are used in organic EL elements have been developed; however, in order to increase the selection range of the material for organic EL elements, it is desired to develop materials formed from compounds different from the conventional compounds. Particularly, the organic EL characteristics obtainable from materials other than the NO-linked system compounds reported in Patent Documents 1-4, and the methods for producing such materials are not yet known.

Means of Solving the Problems

The inventors of the present invention conducted a thorough investigation in order to solve the problems described above, and as a result, the inventors found a novel polycyclic aromatic compound in which plural aromatic rings are linked via boron atoms, oxygen atoms and the like, and succeeded in production thereof. Also, the inventors found that when an organic EL element was configured by disposing a layer containing this polycyclic aromatic compound between a pair of electrodes, an excellent organic EL element was obtained, thus completing the present invention. That is, the present invention provides a polycyclic aromatic compound such as follows or an oligomer thereof, and a material for organic EL element containing a polycyclic aromatic compound such as follows or an oligomer thereof.

[1] A polycyclic aromatic compound represented by the following general formula (1), or an oligomer of a polycyclic aromatic compound having plural structures that are each represented by the following general formula (1):

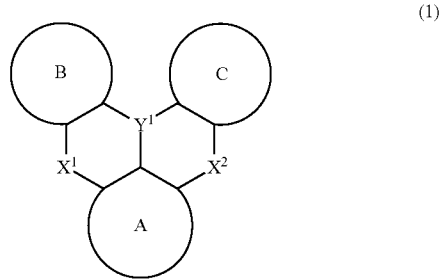

(1)

wherein in formula (1), ring A, ring B and ring C each independently represent an aryl ring or a heteroaryl ring, while at least one hydrogen atom in these rings may be substituted;

$Y^1$ represents B, P, P=O, P=S, Al, Ga, As, Si—R or Ge—R, wherein R of the moieties Si—R and Ge—R represents an aryl or an alkyl;

$X^1$ and $X^2$ each independently represent O, N—R, S or Se, wherein R of the moiety N—R represents an aryl or alkyl which may be substituted, and R of the moiety N—R may be bonded to the ring B and/or ring C by a linking group or a single bond; and at least one hydrogen atom in the compound or structure represented by formula (1) may be substituted by a deuterium atom.

[2] The polycyclic aromatic compound or the oligomer thereof described in the above item [1], wherein ring A, ring B and ring C each independently represent an aryl ring or a heteroaryl ring, while at least one hydrogen atom in these rings may be substituted by a substituted or unsubstituted aryl, a substituted or unsubstituted heteroaryl, a substituted or unsubstituted diarylamino, a substituted or unsubstituted alkyl, a substituted or unsubstituted alkoxy, or a substituted or unsubstituted aryloxy, and these rings have a 5-membered or 6-membered ring that shares a bond(s) with the fused bicyclic structure at the center of the above formula constructed by $Y^1$, $X^1$ and $X^2$;

$Y^1$ represents B, P, P=O, P=S, Al, Ga, As, Si—R or Ge—R, wherein R of the moieties Si—R and Ge—R represents an aryl or an alkyl;

$X^1$ and $X^2$ each independently represent O, N—R, S or Se, wherein R of the moiety N—R represents an aryl or alkyl which may be substituted by an alkyl, R of the moiety N—R may be bonded to the ring B and/or ring C by —O—, —S—, —C(—R)$_2$— or a single bond, and R of the moiety —C(—R)$_2$— represents a hydrogen atom or an alkyl;

at least one hydrogen atom in the compound or structure represented by formula (1) may be substituted by a deuterium atom; and the oligomer is a dimer or a trimer, which has two or three of the structure represented by general formula (1).

[3] The polycyclic aromatic compound described in the above item [1], which is represented by the following general formula (2):

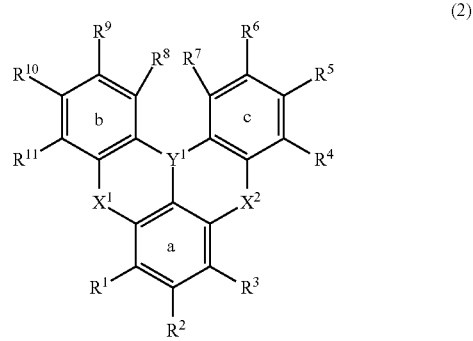

(2)

wherein in formula (2), $R^1$, $R^2$, $R^3$, $R^4$, $R^5$, $R^6$, $R^7$, $R^8$, $R^9$, $R^{10}$ and $R^{11}$ each independently represent a hydrogen atom, an aryl, a heteroaryl, a diarylamino, an alkyl, an alkoxy or an aryloxy, while at least one hydrogen atom in these may be substituted by an aryl, a heteroaryl or an alkyl, adjacent groups among $R^1$ to $R^{11}$ may be bonded to each other and form an aryl ring or a heteroaryl ring together with the ring a, ring b or ring c, at least one hydrogen atom in the ring thus formed may be substituted by an aryl, a heteroaryl, a diarylamino, an alkyl, an alkoxy or an aryloxy, and at least one hydrogen atom in these substituents may be substituted by an aryl, a heteroaryl or an alkyl;

$Y^1$ represents B, P, P=O, P=S, Al, Ga, As, Si—R or Ge—R, wherein R of the moieties Si—R and Ge—R represents an aryl having 6 to 12 carbon atoms or an alkyl having 1 to 6 carbon atoms; and $X^1$ and $X^2$ each independently represent O, N—R, S or Se, wherein R of the moiety N—R represents an aryl having 6 to 12 carbon atoms or an alkyl having 1 to 6 carbon atoms, R of the moiety N—R may be bonded to the ring b and/or ring c by —O—, —S—, —C(—R)$_2$— or a single bond, and R of the moiety —C(—R)$_2$— represents an alkyl having 1 to 6 carbon atoms.

[4] The polycyclic aromatic compound described in the above item [3], wherein $R^1$, $R^2$, $R^3$, $R^4$, $R^5$, $R^6$, $R^7$, $R^8$, $R^9$, $R^{10}$ and $R^{11}$ each independently represent a hydrogen atom, an aryl having 6 to 30 carbon atoms, a heteroaryl having 2 to 30 carbon atoms, or a diarylamino (provided that the aryl is an aryl having 6 to 12 carbon atoms), while adjacent groups among $R^1$ to $R^{11}$ are bonded to each other and form an aryl ring having 9 to 16 carbon atoms or a heteroaryl ring having 6 to 15 carbon atoms together with the ring a, ring b or ring c, and at least one hydrogen atom in the ring thus formed may be substituted by an aryl having 6 to 10 carbon atoms;

$Y^1$ represents B, P, P=O, P=S or Si—R, wherein R in the moiety Si—R represents an aryl having 6 to 10 carbon atoms or an alkyl having 1 to 4 carbon atoms; and $X^1$ and $X^2$ each independently represent O, N—R or S, wherein R in the moiety N—R represents an aryl having 6 to 10 carbon atoms or an alkyl having 1 to 4 carbon atoms.

[5] The polycyclic aromatic compound or the oligomer thereof described in the above item [1], wherein at least one hydrogen atom in the compound or structure represented by the formula (1) may be substituted by fluorine atoms.

[6] The polycyclic aromatic compound described in the above item [1], which is represented by the following formula (1-1), the following formula (1-2), the following formula (1-4), the following formula (1-10), the following formula (1-49), the following formula (1-81), the following formula (1-91), the following formula (1-100), the following formula (1-141), the following formula (1-151), the following formula (1-176), the following formula (1-411), the following formula (1-447), the following formula (1-501), the following formula (1-601), or the following formula (1-701):

(1-1)

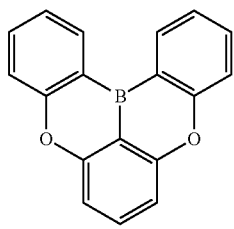

(1-2)

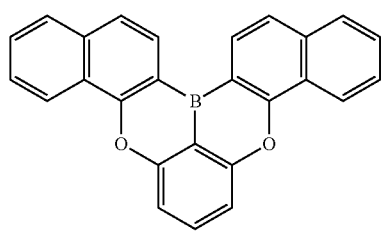

(1-4)

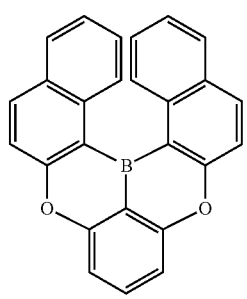

(1-10)

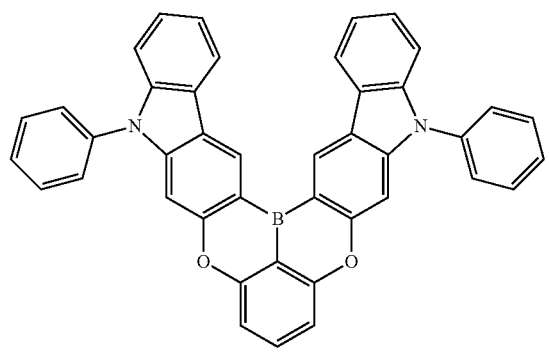

(1-49)

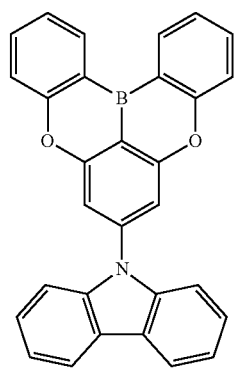

(1-81)

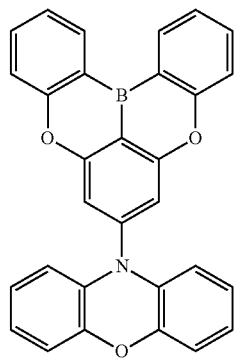

(1-91)

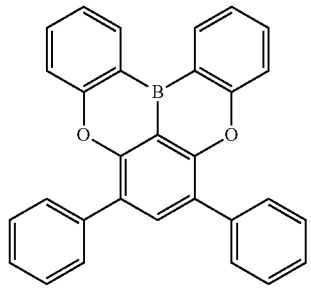

(1-100)

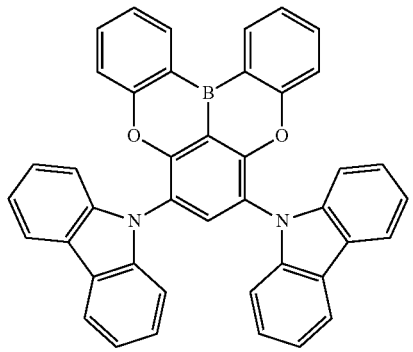

(1-141)
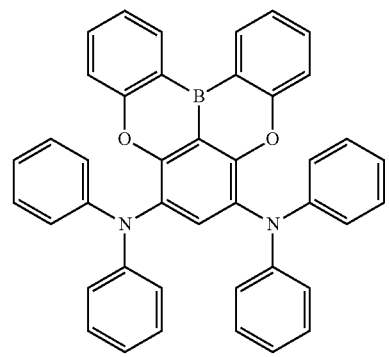

(1-151)
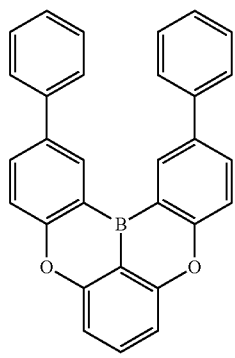

(1-176)
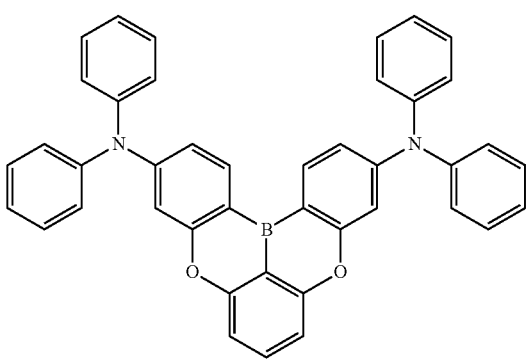

(1-411)
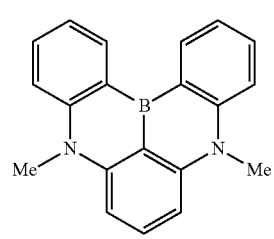

(1-447)
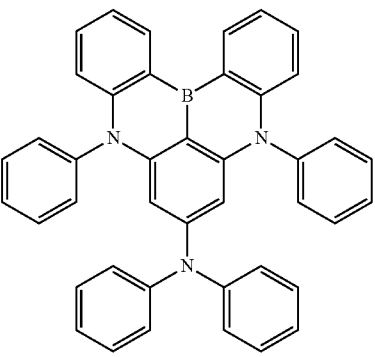

(1-501)
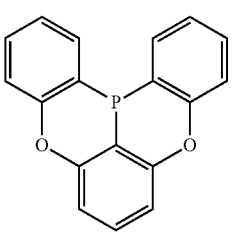

(1-601)
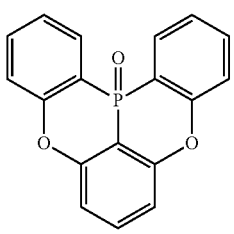

(1-701)
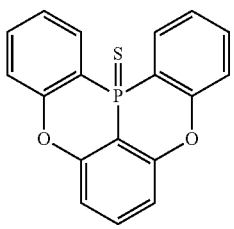

[7] The polycyclic aromatic compound described in the above item [1], which is represented by the following formula (1-21), the following formula (1-23), the following formula (1-24), the following formula (1-50), the following formula (1-152), the following formula (1-201), the following formula (1-401), the following formula (1-422), the following formula (1-1048), the following formula (1-1049), the following formula (1-1050), the following formula (1-1069), the following formula (1-1084), the following formula (1-1090), the following formula (1-1092), the following formula (1-1101), the following formula (1-1102), the following formula (1-1103), the following formula (1-1145), the following formula (1-1152), the following formula (1-1159), the following formula (1-1187), the following formula (1-1190), the following formula (1-1191), the following formula (1-1192), the following formula (1-1201), the following formula (1-1210), the following formula (1-1247), the following formula (1-1250), the following formula (1-1251), the following formula (1-1252), or the following formula (1-1271):

(1-21)
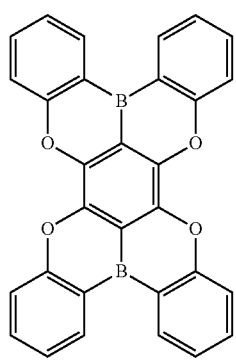
(1-23)
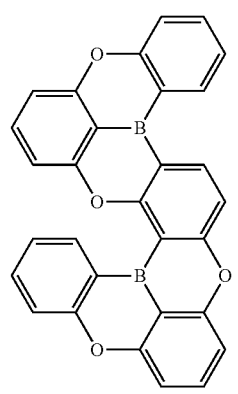
(1-24)
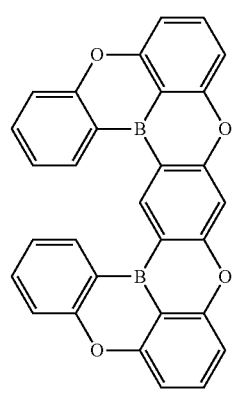
(1-50)
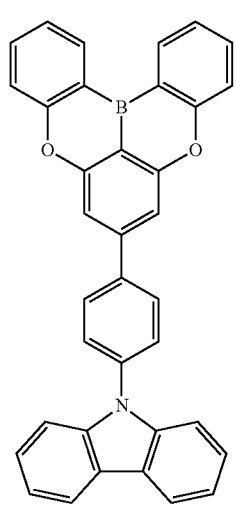
(1-152)
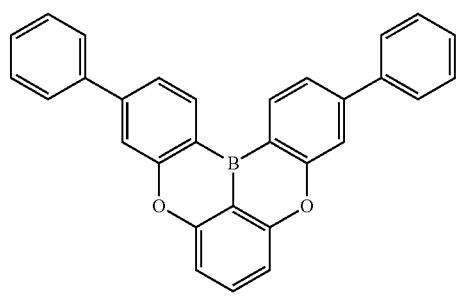
(1-201)
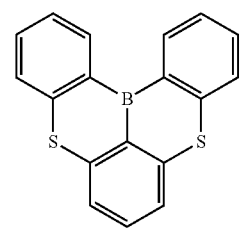
(1-401)
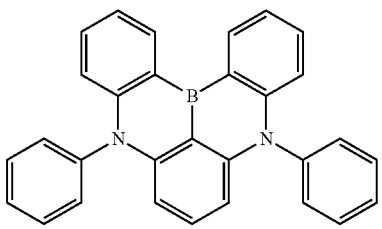
(1-422)
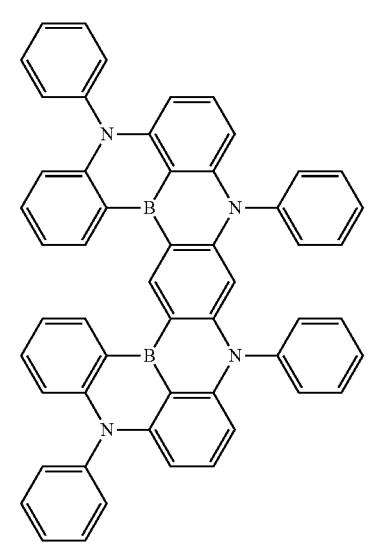

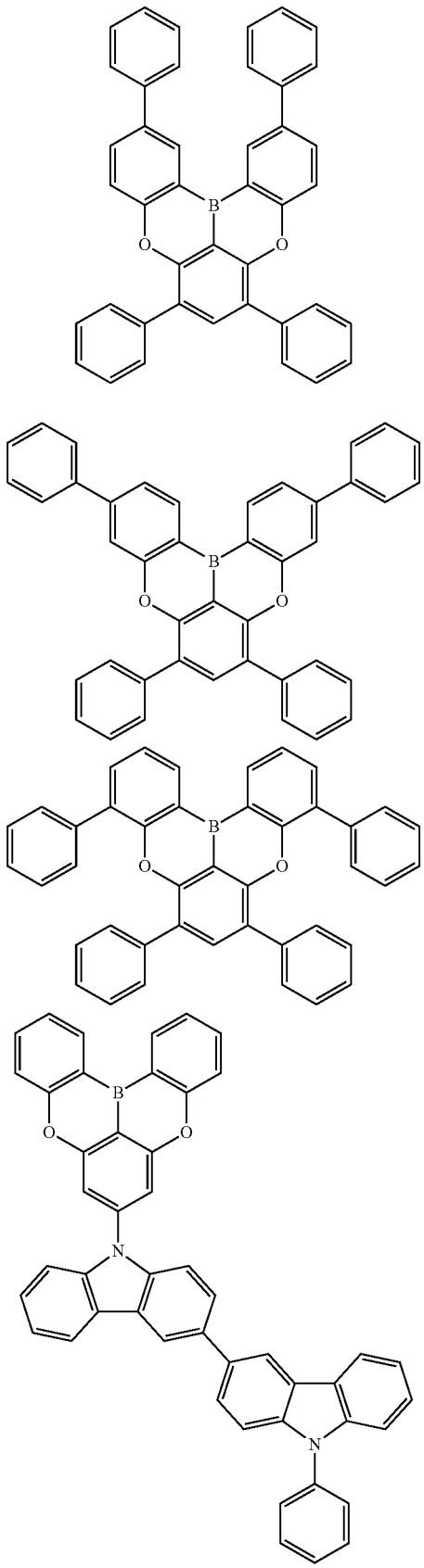
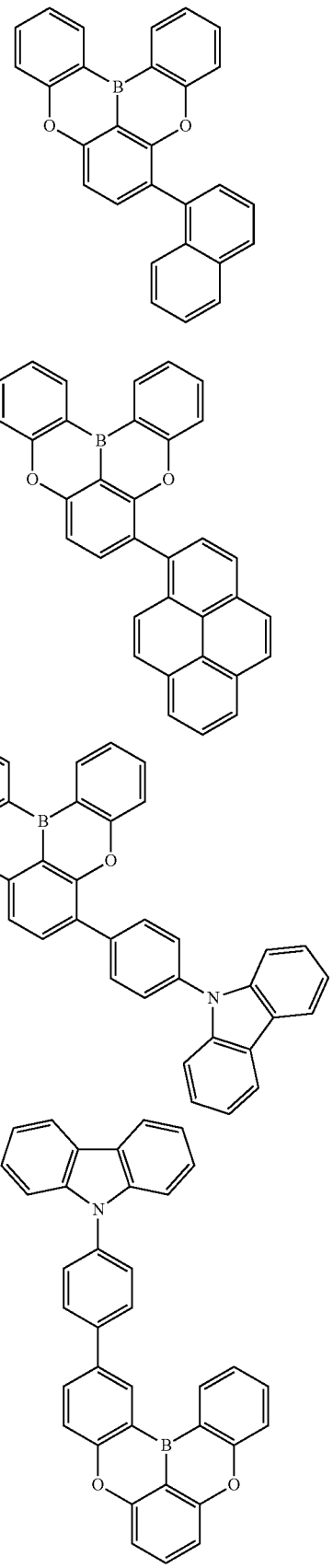

(1-1102)
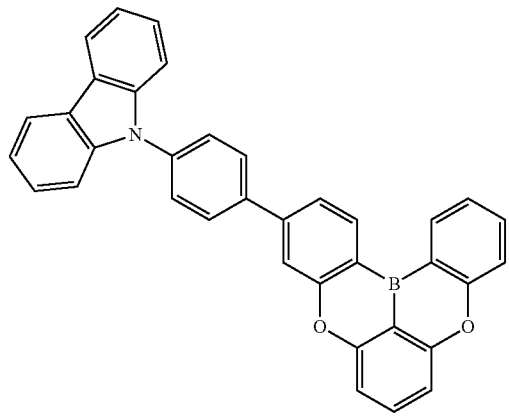
(1-1103)
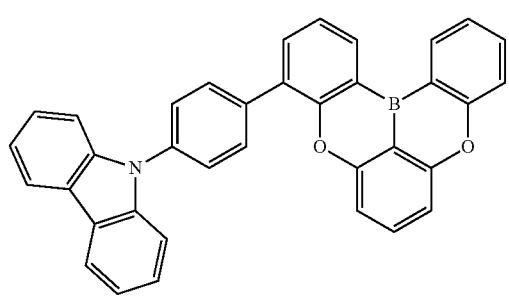
(1-1145)
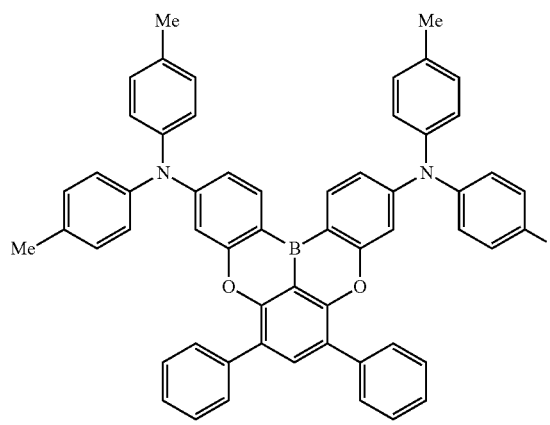
(1-1152)
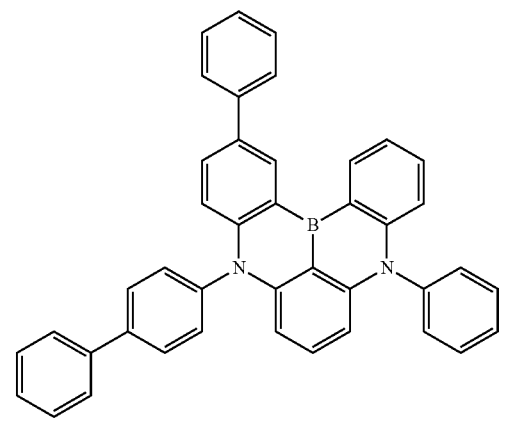
(1-1159)
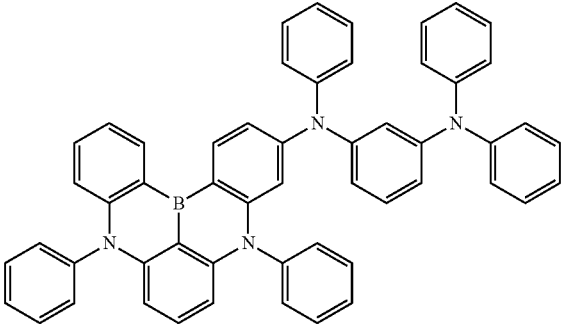
(1-1187)
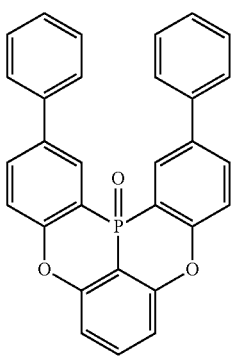
(1-1190)
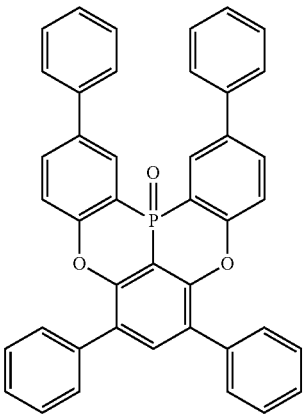
(1-1191)
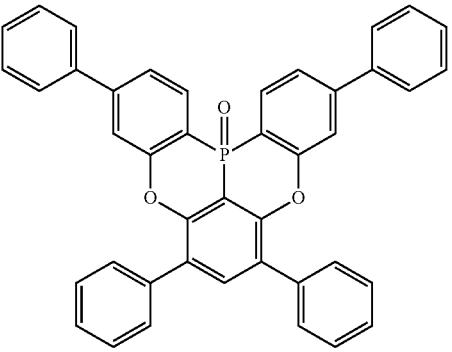

(1-1192) 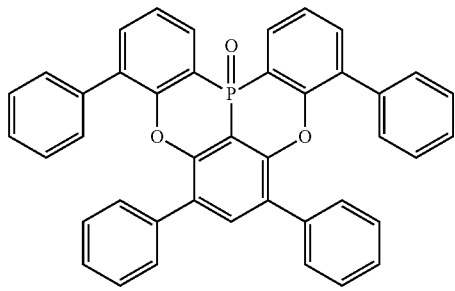

(1-1201) 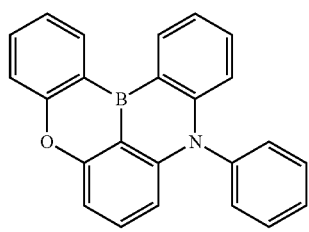

(1-1210) 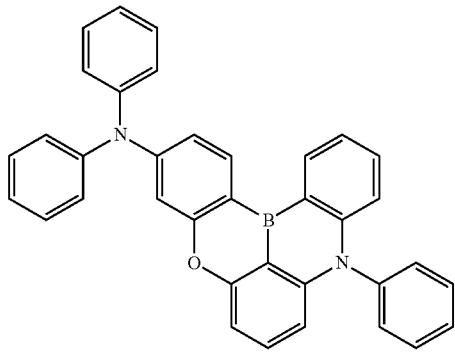

(1-1247) 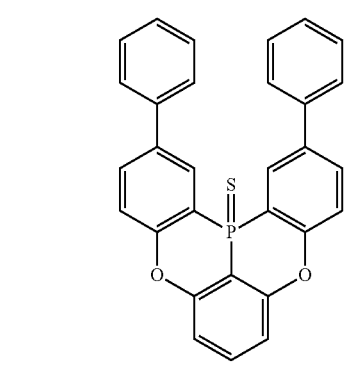

(1-1250) 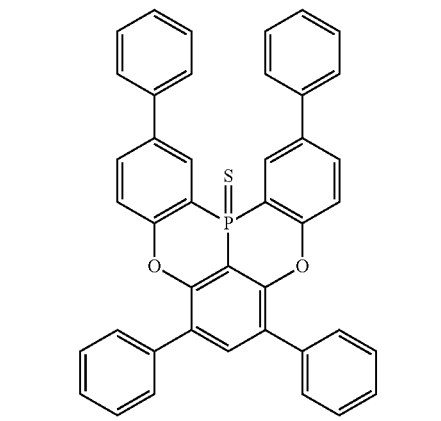

(1-1251) 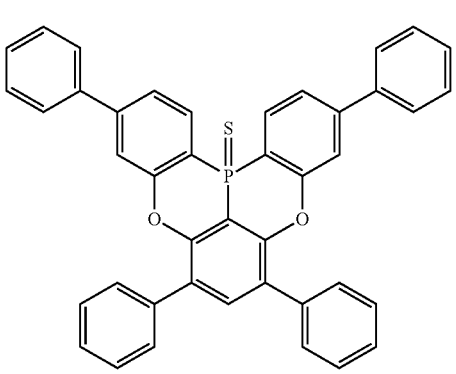

(1-1252) 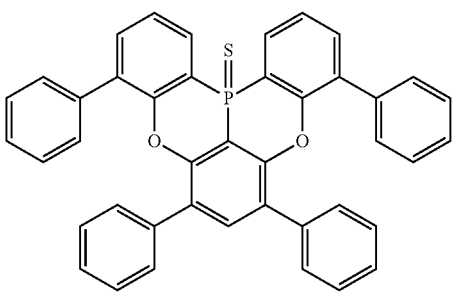

(1-1271) 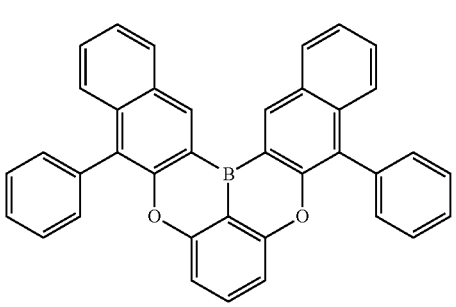

[8] A material for an organic device, containing the polycyclic aromatic compound or the oligomer thereof described in any one of the above items [1] to [7].

[9] The material for an organic device described in the above item [8], wherein the material for an organic device is a material for an organic electroluminescent element, a material for an organic field effect transistor, or a material for an organic thin film solar cell.

[10] The material for an organic electroluminescent element described in the above item [9], which is a material for a light emitting layer.

[11] The material for an organic electroluminescent element described in the above item [9], which is a material for a hole injection layer or a material for a hole transport layer.

[12] An organic electroluminescent element, including a pair of electrodes composed of a positive electrode and a negative electrode; and a light emitting layer that is disposed between the pair of electrodes and contains the material for a light emitting layer described in the above item [10].

[13] An organic electroluminescent element, including a pair of electrodes composed of a positive electrode and a negative electrode; a light emitting layer that is disposed between the pair of electrodes; and a hole injection layer and/or a hole transport layer that is disposed between the positive electrode and the light emitting layer and contains the material for a hole layer described in the above item [11].

[14] The organic electroluminescent element described in the above item [12] or [13], further including an electron transport layer and/or an electron injection layer that is disposed between the negative electrode and the light emitting layer, wherein at least one of the electron transport layer and the electron injection layer contains at least one selected from the group consisting of a quinolinol-based metal complex, a pyridine derivative, a phenanthroline derivative, a borane derivative, and a benzimidazole derivative.

[15] The organic electroluminescent element described in the above [14], wherein the electron transport layer and/or electron injection layer further contains at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

[16] A display apparatus including the organic electroluminescent element described in any one of the above items [12] to [15].

[17] A lighting apparatus including the organic electroluminescent element described in any one of the above items [12] to [15].

Advantageous Effect of the Invention

According to preferred embodiments of the present invention, a novel polycyclic aromatic compound that can be used as, for example, a material for an organic EL element can be provided, and an excellent organic EL element can be provided by using this polycyclic aromatic compound.

Specifically, the inventors of the present invention found that a polycyclic aromatic compound in which aromatic rings are linked via a heteroelement such as boron, phosphorus, oxygen, nitrogen or sulfur, has a large HOMO-LUMO gap (band gap Eg in a thin film) and high triplet excitation energy ($E_T$). This is speculated to be because, since a 6-membered ring containing a heteroelement has low aromaticity, a decrease in the HOMO-LUMO gap that comes along with extension of the conjugated system is suppressed, and SOMO1 and SOMO2 of the triplet excitation state (T1) are localized by electronic perturbation of the heteroelement. Furthermore, the polycyclic aromatic compound containing a heteroelement related to the present invention is such that due to the localization of SOMO1 and SOMO2 in the triplet excitation state (T1), the exchange interaction between the two orbitals is reduced, and therefore, the energy difference between the triplet excitation state (T1) and the single excitation state (S1) is small. Also, since the polycyclic aromatic compound exhibits thermally activated delayed fluorescence, the compound is also useful as a fluorescent material for an organic EL element. Furthermore, a material having high triplet excitation energy ($E_T$) is also useful as an electron transport layer or a hole transport layer of a phosphorescence organic EL element or an organic EL element using a thermally activated delayed fluorescence. Also, since these polycyclic aromatic compounds can have the energy of HOMO and LUMO arbitrarily shifted by introducing a substituent, the ionization potential or the electron affinity can be optimized in accordance with the peripheral materials.

BRIEF DESCRIPTION OF DRAWINGS

The FIGURE is a schematic cross-sectional diagram illustrating an organic EL element related to the present exemplary embodiment.

DETAILED DESCRIPTION

1. Polycyclic Aromatic Compound and Oligomer Thereof

The invention of the present application relates to a polycyclic aromatic compound represented by the following general formula (1), or an oligomer of a polycyclic aromatic compound having plural structures each represented by the following general formula (1). The invention of the present application preferably relates to a polycyclic aromatic compound represented by the following general formula (2), or an oligomer of a polycyclic aromatic compound having plural structures each represented by the following general formula (2).

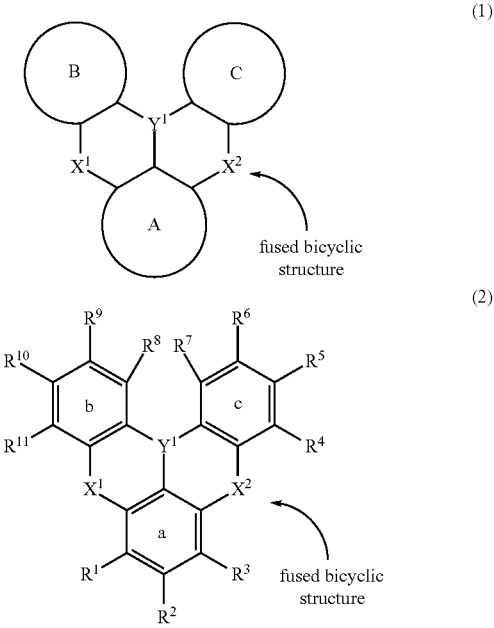

Ring A, ring B and ring C in the general formula (1) each independently represent an aryl ring or a heteroaryl ring, and at least one hydrogen atom in these rings may be substituted by a substituent. This substituent is preferably a substituted or unsubstituted aryl, a substituted or unsubstituted heteroaryl, a substituted or unsubstituted diarylamino, a substituted or unsubstituted alkyl, a substituted or unsubstituted alkoxy, or a substituted or unsubstituted aryloxy. Examples of the substituent in the case in which these groups have a substituent, include an aryl, a heteroaryl, and an alkyl. Furthermore, the aryl ring or heteroaryl ring preferably has a 5-membered ring or 6-membered ring that shares a bond with the fused bicyclic structure at the center of the general formula (1) constructed by $Y^1$, $X^1$ and $X^2$ (hereinafter, this structure is also referred to as "structure D").

Here, the "fused bicyclic structure (structure D)" means a structure in which two saturated hydrocarbon rings that are configured to include $Y^1$, $X^1$ and $X^2$ and indicated at the center of the general formula (1), are fused. Furthermore, a "6-membered ring sharing a bond with the fused bicyclic structure" means, for example, ring a (benzene ring (6-membered ring)) fused to the structure D as represented by the above general formula (2). Furthermore, the phrase "aryl ring or heteroaryl ring (which is ring A) has this 6-membered ring" means that the ring A is formed from this 6-membered ring only, or the ring A is formed such that other rings are further fused to this 6-membered ring so as to include this 6-membered ring. In other words, the "aryl ring or heteroaryl ring (which is ring A) having a 6-membered ring" as used herein means that the 6-membered ring that constitutes the entirety or a portion of the ring A is fused to the structure D. The same explanation applies to the "ring B (ring b)", "ring C (ring c)", and the "5-membered ring".

The ring A (or ring B or ring C) in the general formula (1) corresponds to the ring a and its substituents $R^1$ to $R^3$ in the general formula (2) (or ring b and its substituents $R^4$ to $R^7$, or ring c and its substituents $R^8$ to $R^{11}$). That is, general formula (2) corresponds to a structure in which "rings A to C having 6-membered rings" have been selected as the rings A to C of the general formula (1). For this meaning, the respective rings of general formula (2) are represented by small letters a to c.

In general formula (2), adjacent groups among the substituents $R^1$ to $R^{11}$ of the ring a, ring b and ring c may be bonded to each other and form an aryl ring or a heteroaryl ring together with the ring a, ring b or ring c, and at least one hydrogen atom in the ring thus formed may be substituted by an aryl, a heteroaryl, a diarylamino, an alkyl, an alkoxy or an aryloxy, while at least one hydrogen atom in these substituents may be substituted by an aryl, a heteroaryl or an alkyl. Therefore, the polycyclic aromatic compound represented by general formula (2) is such that the ring structure that constitutes the compound changes as indicated by the following formula (2-1) and formula (2-2), as a result of the mutual bonding form of the substituents in the ring a, ring b or ring c. Ring A', ring B' and ring C' in the respective formulas correspond to ring A, ring B and ring C, respectively, in the general formula (1).

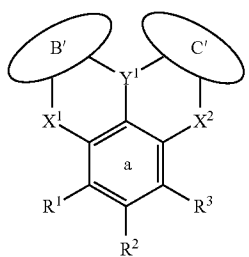

(2-1)

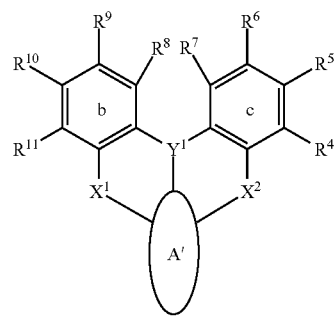

(2-2)

Ring A', ring B' and ring C' in the above formula (2-1) and formula (2-2) each represent, to be explained in connection with the general formula (2), an aryl ring or a heteroaryl ring formed by bonding between adjacent groups among the substituents $R^1$ to $R^{11}$, together with the ring a, ring b and ring c, respectively (may also be referred to as a fused ring obtained as another ring structure is fused to the ring a, ring b or ring c). In addition, although it is not suggested in the formula, there is also a compound in which all of the ring a, ring b and ring c have been changed to ring A', ring B' and ring C'. Furthermore, it can be seen from the above formula (2-1) and formula (2-2), for example, $R^8$ of ring b and $R^7$ of ring c, $R^{11}$ of ring b and $R^1$ of ring a, $R^4$ of ring c and $R^3$ of ring a, and the like do not correspond to "adjacent groups", and these are not to be bonded. That is, the expression "adjacent groups" means adjacent groups on the same ring.

A compound represented by the above formula (2-1) or formula (2-2) corresponds to, for example, a compound represented by any one of formulas (1-2) to (1-17) listed as specific compounds that are described below. That is, for example, the compound represented by formula (2-1) or formula (2-2) is a compound having ring A' (or ring B' or ring C') that is formed when a benzene ring, an indole ring, a pyrrole ring, a benzofuran ring or a benzothiophene ring is fused to the benzene ring which is ring a (or ring b or ring c), and the fused ring A' (or fused ring B' or fused ring C') that could be formed is a naphthalene ring, a carbazole ring, an indole ring, a dibenzofuran ring, or a dibenzothiophene ring.

$Y^1$ in the general formula (1) represents B, P, P=O, P=S, Al, Ga, As, Si—R or Ge—R, and R of the moieties Si—R and Ge—R represents an aryl or an alkyl. In the case of P=O, P=S, Si—R or Ge—R, the atom that is bonded to ring A, ring B or ring C is P, Si or Ge. $Y^1$ is preferably B, P, P=O, P=S or Si—R, and particularly preferably B. This explanation also applies to $Y^1$ in the general formula (2).

$X^1$ and $X^2$ in the general formula (1) each independently represent O, N—R, S or Se, while R of the moiety N—R represents an aryl or alkyl which may be substituted, and R of the moiety N—R may be bonded to the ring B and/or ring C by a linking group or a single bond. The linking group is preferably —O—, —S— or —C(—R)$_2$—. Meanwhile, R of the moiety "—C(—R)$_2$—" represents a hydrogen atom or an alkyl. This explanation also applies to $X^1$ and $X^2$ in the general formula (2).

Here, the provision that "R of the moiety N—R is bonded to ring B and/or ring C by a linking group or a single bond" for the general formula (1) corresponds to the provision that "R of the moiety N—R is bonded to ring b and/or ring c by —O—, —S—, —C(—R)$_2$— or a single bond" for the general formula (2).

This provision can be expressed by a compound having a ring structure represented by the following formula (2-3), in which $X^1$ or $X^2$ is incorporated into the fused ring B' and the fused ring C'. That is, for example, the compound is a compound having ring B' (or ring C') that is formed as another ring is fused to a benzene ring which is ring b (or ring c) in the general formula (2) so as to incorporate $X^1$ (or $X^2$). This compound corresponds to, for example, a compound represented by any one of formulas (1-451) to (1-462) listed as specific examples that are described below, and the fused ring B' (or fused ring C') that could be formed is, for example, a phenoxazine ring, a phenothiazine ring, or an acridine ring.

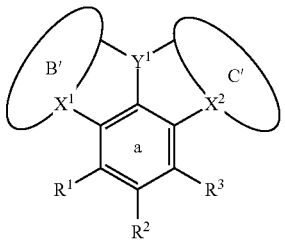

(2-3)

The "aryl ring" as the ring A, ring B or ring C of the general formula (1) is, for example, an aryl ring having 6 to 30 carbon atoms, and the aryl ring is preferably an aryl ring having 6 to 16 carbon atoms, more preferably an aryl ring having 6 to 12 carbon atoms, and particularly preferably an aryl ring having 6 to 10 carbon atoms. Meanwhile, this "aryl ring" corresponds to the "aryl ring formed by bonding between adjacent groups among $R^1$ to $R^{11}$, together with ring a, ring b or ring c" defined by general formula (2). Also, since ring a (or ring b or ring c) is already configured by a benzene ring having 6 carbon atoms, a carbon number of 9 in total of a fused ring obtained when a 5-membered ring is fused to this benzene ring, becomes the lower limit of the carbon number.

Specific examples of the "aryl ring" include a benzene ring which is a monocyclic system; a biphenyl ring which is a bicyclic system; a naphthalene ring which is a fused bicyclic system; a terphenyl ring (m-terphenyl, o-terphenyl, or p-terphenyl) which is a tricyclic system; an acenaphthylene ring, a fluorene ring, a phenalene ring and a phenanthrene ring, which are fused tricyclic systems; a triphenylene ring, a pyrene ring and a naphthacene ring, which are fused tetracyclic systems; and a perylene ring and a pentacene ring, which are fused pentacyclic systems.

The "heteroaryl ring" as the ring A, ring B or ring C of the general formula (1) is, for example, a heteroaryl ring having 2 to 30 carbon atoms, and the heteroaryl ring is preferably a heteroaryl ring having 2 to 25 carbon atoms, more preferably a heteroaryl ring having 2 to 20 carbon atoms, even more preferably a heteroaryl ring having 2 to 15 carbon atoms, and particularly preferably a heteroaryl ring having 2 to 10 carbon atoms. Furthermore, the "heteroaryl ring" may be, for example, a heterocyclic ring containing 1 to 5 heteroatoms selected from oxygen, sulfur and nitrogen in addition to carbon as the ring-constituting atoms. Meanwhile, this "heteroaryl ring" corresponds to the "heteroaryl ring formed by bonding between adjacent groups among $R^1$ to $R^{11}$, together with the ring a, ring b or ring c" defined by general formula (2), and since the ring a (or ring b or ring c) is already composed of a benzene ring having 6 carbon atoms, a carbon number of 6 in total of a fused ring obtained when a 5-membered ring is fused to this benzene ring, becomes the lower limit of the carbon number.

Specific examples of the "heteroaryl ring" include a pyrrole ring, an oxazole ring, an isoxazole ring, a triazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzoxazole ring, a benzothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazane ring, an oxadiazole ring, and a thianthrene ring.

At least one hydrogen atom in the aforementioned "aryl ring" or "heteroaryl ring" may be substituted by a substituted or unsubstituted "aryl", a substituted or unsubstituted "heteroaryl", a substituted or unsubstituted "diarylamino", a substituted or unsubstituted "alkyl", a substituted or unsubstituted "alkoxy", or a substituted or unsubstituted "aryloxy", which is a primary substituent. Examples of the aryl of the "aryl", "heteroaryl" and "diarylamino" as these primary substituents, and the aryl of "aryloxy" include a monovalent group of the "aryl ring" or "heteroaryl ring" described above.

Furthermore, the "alkyl" as the primary substituent may be any of a straight chain or a branched chain, and examples thereof include a linear alkyl having 1 to 24 carbon atoms and a branched alkyl having 3 to 24 carbon atoms. The alkyl is preferably an alkyl having 1 to 18 carbon atoms (branched alkyl having 3 to 18 carbon atoms), more preferably an alkyl having 1 to 12 carbon atoms (branched alkyl having 3 to 12 carbon atoms), even more preferably an alkyl having 1 to 6 carbon atoms (branched alkyl having 3 to 6 carbon atoms), and particularly preferably an alkyl having 1 to 4 carbon atoms (branched alkyl having 3 to 4 carbon atoms).

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

Furthermore, the "alkoxy" as a primary substituent may be, for example, a linear alkoxy having 1 to 24 carbon atoms or a branched alkoxy having 3 to 24 carbon atoms. The alkoxy is preferably an alkoxy having 1 to 18 carbon atoms (branched alkoxy having 3 to 18 carbon atoms), more preferably an alkoxy having 1 to 12 carbon atoms (branched alkoxy having 3 to 12 carbon atoms), even more preferably an alkoxy having 1 to 6 carbon atoms (branched alkoxy having 3 to 6 carbon atoms), and particularly preferably an alkoxy having 1 to 4 carbon atoms (branched alkoxy having 3 to 4 carbon atoms).

Specific examples of the alkoxy include methoxy, ethoxy, propoxy, isopropoxy, butoxy, isobutoxy, s-butoxy, t-butoxy, pentyloxy, hexyloxy, heptyloxy, and octyloxy.

The substituted or unsubstituted "aryl", substituted or unsubstituted "heteroaryl", substituted or unsubstituted "diarylamino", substituted or unsubstituted "alkyl", substituted or unsubstituted "alkoxy", or substituted or unsubstituted "aryloxy", which is the primary substituent, is such that at least one hydrogen atom thereof may be substituted by a secondary substituent, as it is explained to be substituted or unsubstituted. Examples of this secondary substituent include an aryl, a heteroaryl, and an alkyl, and for the details thereof, reference can be made to the explanations on the monovalent group of the "aryl ring" or "heteroaryl ring" described above and the "alkyl" as the primary substituent. Furthermore, regarding the aryl or heteroaryl as the secondary substituent, an aryl or heteroaryl in which at least one hydrogen atom thereof has been substituted by an aryl such as phenyl (specific examples are described above), or an alkyl such as methyl (specific examples are described above), is also included in the aryl or heteroaryl as the secondary substituent. For instance, when the secondary substituent is a carbazolyl group, a carbazolyl group in which at least one hydrogen atom at the 9-position has been substituted by an aryl such as phenyl, or an alkyl such as methyl, is also included in the heteroaryl as the secondary substituent.

Examples of the aryl, heteroaryl, the aryl of the diarylamino, or the aryl of the aryloxy for $R^1$ to $R^{11}$ of general formula (2) include the monovalent groups of the "aryl ring" or "heteroaryl ring" explained in the general formula (1). Furthermore, regarding the alkyl or alkoxy for $R^1$ to $R^{11}$, reference can be made to the explanation on the "alkyl" or "alkoxy" as the primary substituent in the explanation of the general formula (1). In addition, the same also applies to the aryl, heteroaryl or alkyl as the substituent for these groups. Furthermore, the same also applies to the heteroaryl, diarylamino, alkyl, alkoxy or aryloxy in the case of forming an aryl ring or a heteroaryl ring by bonding between adjacent groups among $R^1$ to $R^{11}$ together with the ring a, ring b or ring c, and the aryl, heteroaryl or alkyl as the further substituent.

R of the moieties Si—R and Ge—R for $Y^1$ in the general formula (1) represents an aryl or an alkyl, and examples of this aryl or alkyl include those described above. Particularly, an aryl having 6 to 10 carbon atoms (for example, phenyl or naphthyl), and an alkyl having 1 to 4 carbon atoms (for example, methyl or ethyl) are preferred. This explanation also applies to $Y^1$ for the general formula (2).

R of the moiety N—R for $X^1$ and $X^2$ of the general formula (1) represents an aryl or an alkyl, both of which may be substituted by the secondary substituents described above, and at least one hydrogen in the aryl may be substituted by, for example, an alkyl. Examples of this aryl or alkyl include those described above. Particularly, an aryl having 6 to 10 carbon atoms (for example, phenyl or naphthyl) and an alkyl having 1 to 4 carbon atoms (for example, methyl or ethyl) are preferred. This explanation also applies to $X^1$ and $X^2$ in the general formula (2).

R of the moiety "—C(—R)$_2$—" as a linking group for the general formula (1) represents a hydrogen atom or an alkyl, and examples of this alkyl include those described above. Particularly, an alkyl having 1 to 4 carbon atoms (for example, methyl or ethyl) is preferred. This explanation also applies to "—C(—R)$_2$—" as a linking group for general formula (2).

Furthermore, the invention of the present application is an oligomer of a polycyclic aromatic compound having plural unit structures each represented by general formula (1), and preferably an oligomer of a polycyclic aromatic compound having plural unit structures each represented by general formula (2). The oligomer is preferably a dimer to a hexamer, more preferably a dimer to a trimer, and a particularly preferably a dimer. The oligomer may be in a form having a plural number of the unit structures described above in one compound, and for example, the oligomer may be in a form in which a plural number of the unit structures are linked via a linking group such as a single bond, an alkylene group having 1 to 3 carbon atoms, a phenylene group, or a naphthylene group, as well as a form in which a plural number of the unit structures are linked such that any ring contained in the unit structure (ring A, ring B or ring C, or ring a, ring b or ring c) is shared by the plural unit structures, or may be in a form in which the unit structures are linked such that any rings contained in the unit structures (ring A, ring B or ring C, or ring a, ring b or ring c) are fused.

Examples of such an oligomer include oligomer compounds represented by the following formula (2-4), formula (2-5-1) to formula (2-5-4), and formula (2-6). An oligomer compound represented by the following formula (2-4) corresponds to, for example, a compound represented by formula (1-21) described below. That is, to explain this in view of general formula (2), the oligomer is an oligomer compound in which plural unit structures each represented by general formula (2) are carried in one compound such that a benzene ring as ring a is shared. Furthermore, oligomer compounds represented by the following formula (2-5-1) to formula (2-5-4) correspond to, for example, compounds represented by the following formulas (1-22) to (1-25). That is, to explain this in view of general formula (2), such an oligomer is an oligomer compound in which plural unit structures each represented by general formula (2) are carried in one compound such that a benzene ring as ring b (or ring c) is shared. Furthermore, an oligomer compound represented by the following formula (2-6) corresponds to, for example, a compound represented by any one of the following formulas (1-31) to (1-37). That is, to explain this in view of general formula (2), for example, the oligomer is an oligomer compound in which plural unit structures each represented by general formula (2) are carried out in one compound such that a benzene ring as ring b (or ring a or ring c) of a certain unit structure and a benzene ring as ring b (or ring a or ring c) are fused.

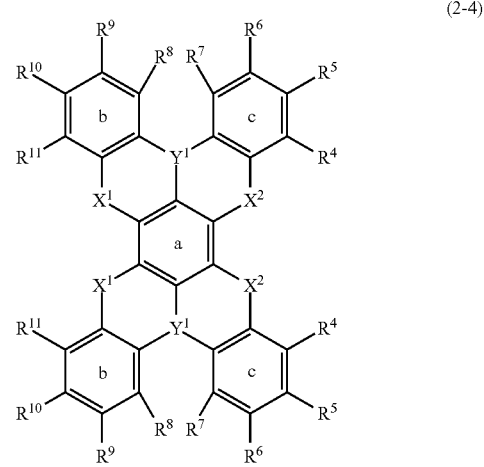

(2-4)

(2-5-1) 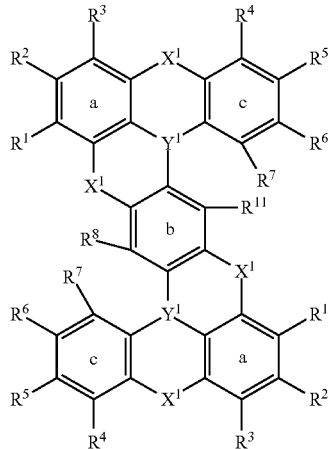

(2-5-2) 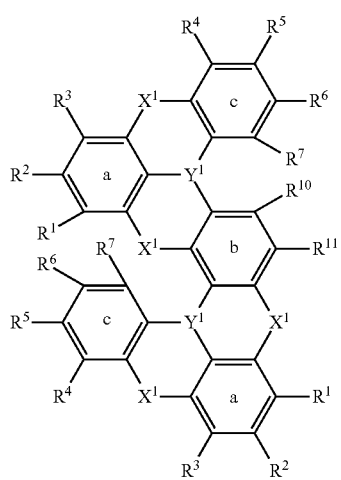

(2-5-3) 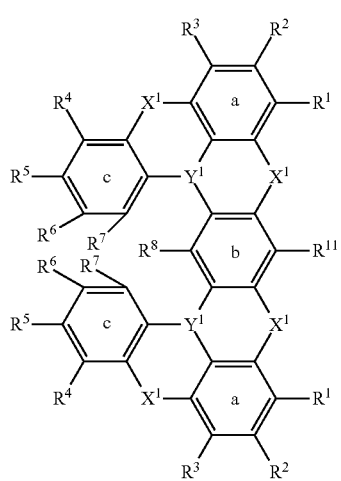

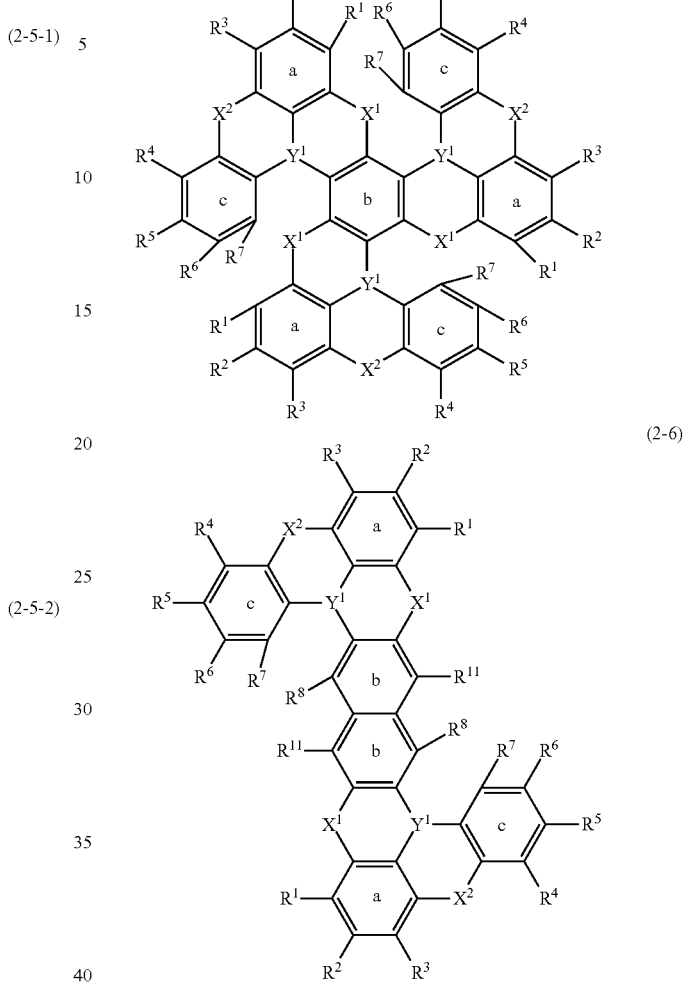

(2-5-4)

(2-6)

The oligomer compound may be an oligomer in which an oligomer form represented by formula (2-4) and an oligomer form represented by any one of formula (2-5-1) to formula (2-5-4) or formula (2-6) are combined; may be an oligomer in which an oligomer form represented by any one of formula (2-5-1) to formula (2-5-4) and an oligomer form represented by formula (2-6) are combined; or may be an oligomer in which an oligomer form represented by formula (2-4), an oligomer form represented by any one of formula (2-5-1) to formula (2-5-4), and an oligomer form represented by formula (2-6) are combined.

Furthermore, all or a portion of the hydrogen atoms in the chemical structures of the polycyclic aromatic compound represented by general formula (1) or (2) and an oligomer thereof may be deuterium atoms.

Also, all or a portion of the hydrogen atoms in the chemical structures of the polycyclic aromatic compound represented by general formula (1) or (2) and an oligomer thereof may be fluorine atoms. For example, in regard to formula (1), the hydrogen atoms in the ring A, ring B, ring C (ring A to ring C are aryl rings or heteroaryl rings), substituents of the ring A to ring C, R (=alkyl or aryl) when $Y^1$ represents Si—R or Ge—R, and R (=alkyl or aryl) when $X^1$ and $X^2$ each represent N—R, may be substituted by fluorine atoms, and among these, a form in which all or a portion of the hydrogen atoms in the aryl or heteroaryl have been substituted by fluorine atoms may be mentioned.

More specific examples of the polycyclic aromatic compound of the present invention and oligomers thereof include, for example, compounds represented by the following formulas (1-1) to (1-825) and compounds represented by the following formulas (1-1001) to (1-1281).

(1-1)
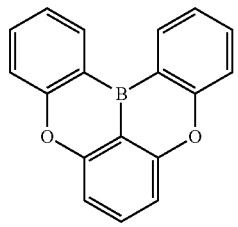

(1-2)
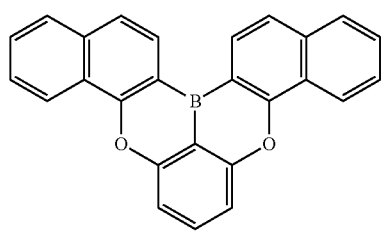

(1-3)
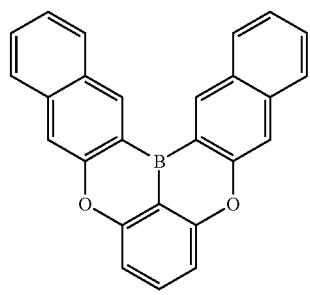

(1-4)
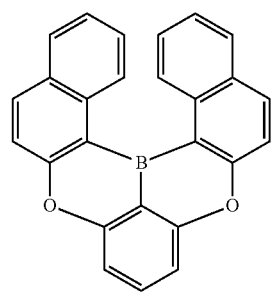

(1-5)
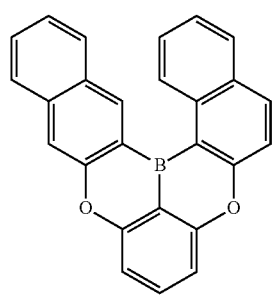

-continued (1-6)
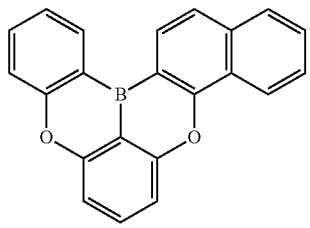

(1-7)
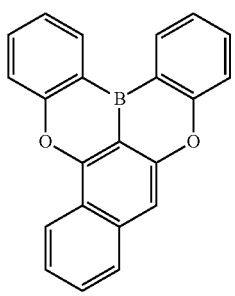

(1-8)
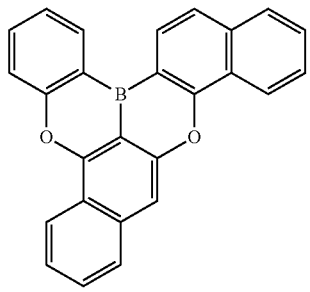

(1-9)
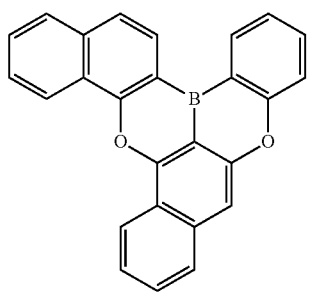

(1-10)
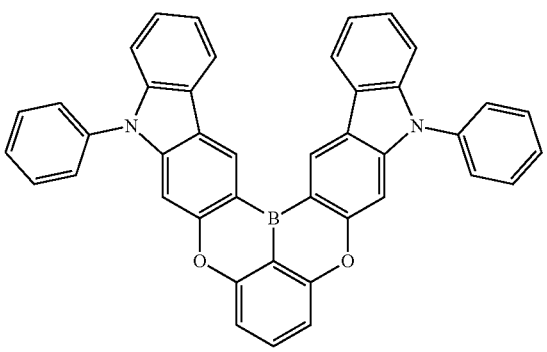

(1-11)
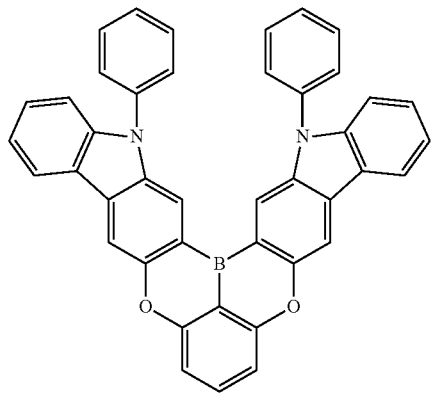
(1-12)
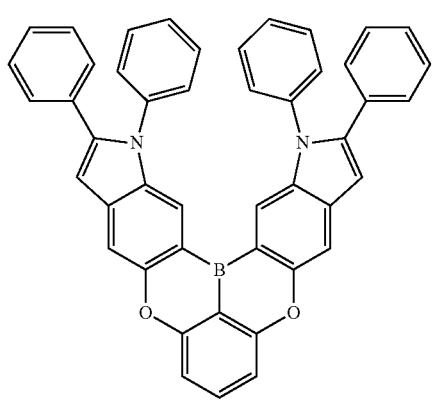
(1-13)
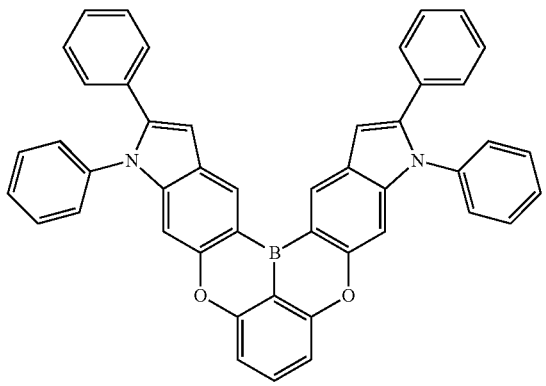
(1-14)
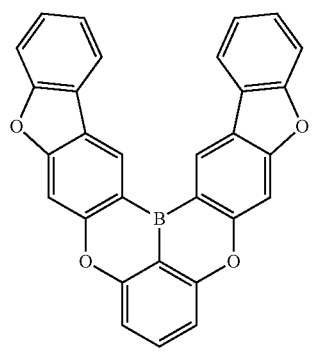
(1-15)
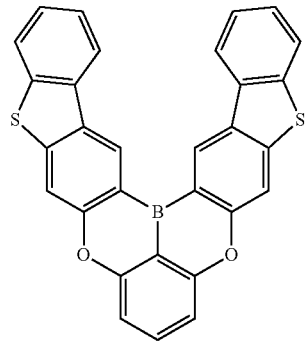
(1-16)
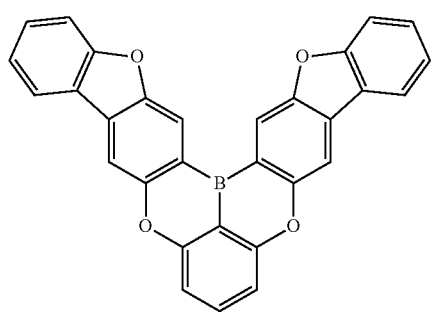
(1-17)
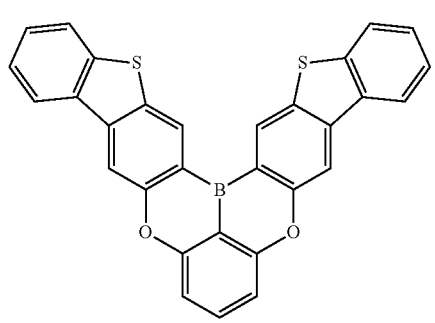
(1-21)
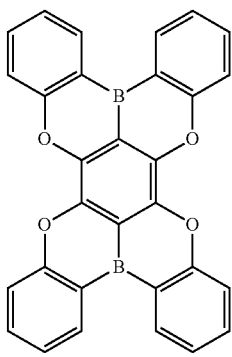

(1-22)
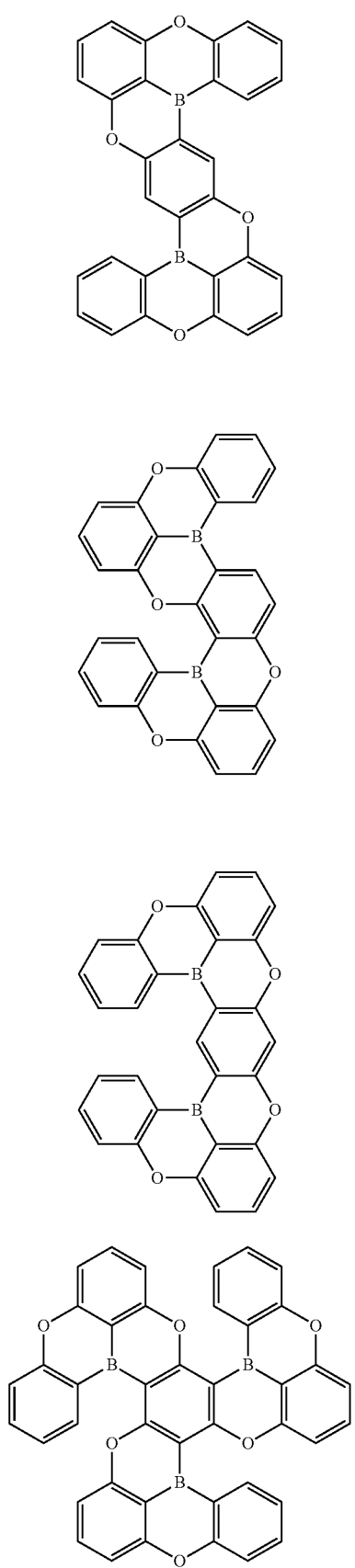
(1-23)
(1-24)
(1-25)
(1-31)
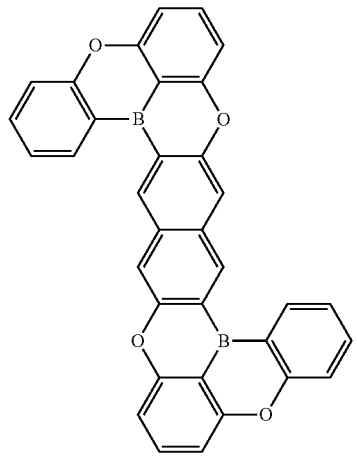
(1-32)
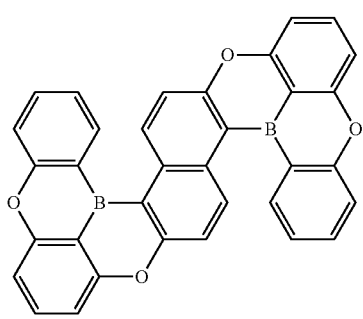
(1-33)
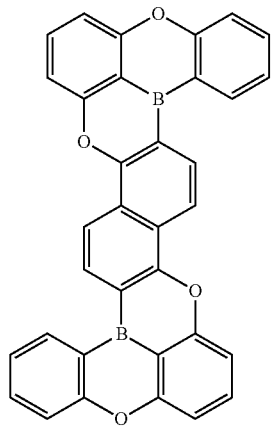
(1-34)
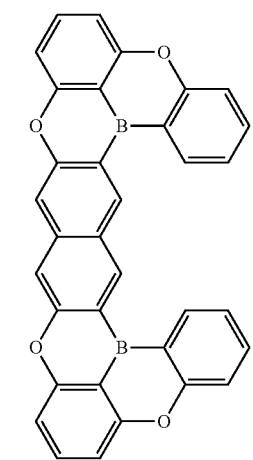

(1-35)
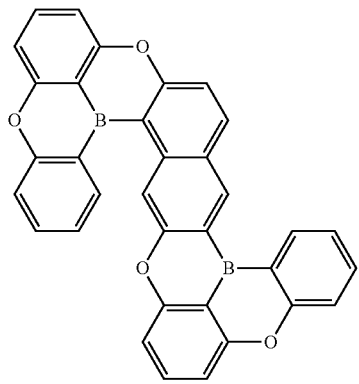
(1-36)
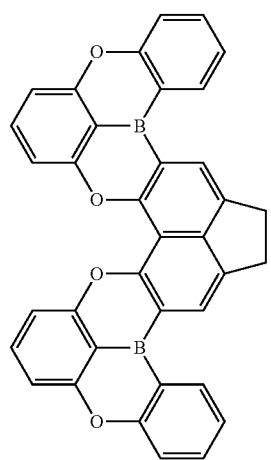
(1-37)
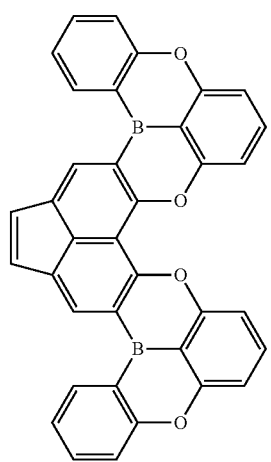
(1-41)
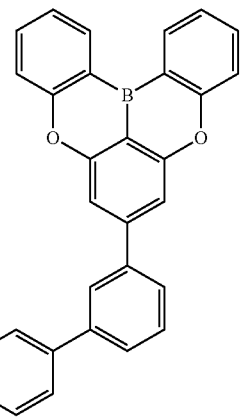
(1-42)
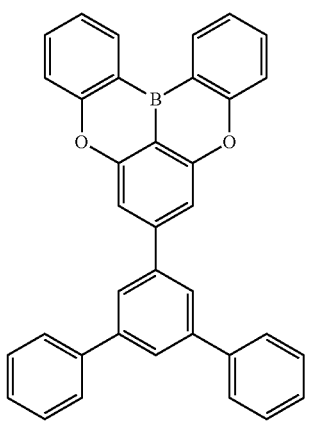
(1-43)
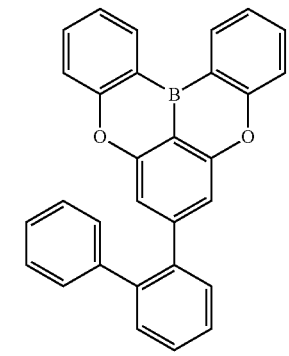
(1-44)
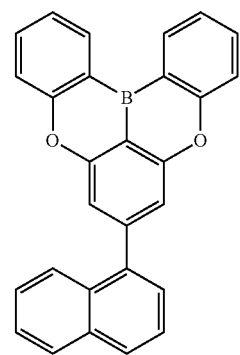

(1-45)
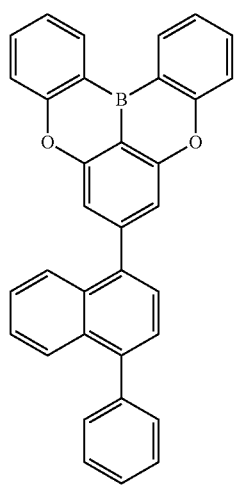
(1-46)
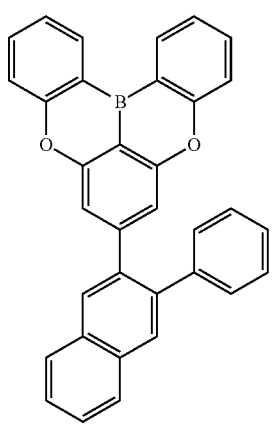
(1-47)
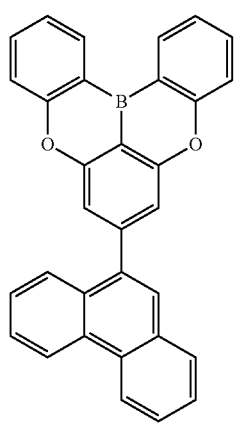
(1-48)
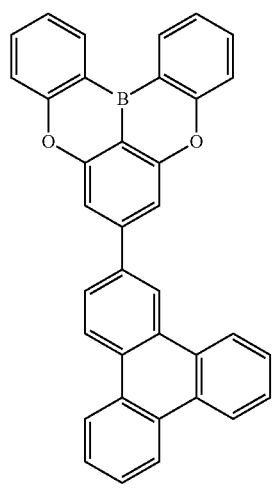
(1-49)
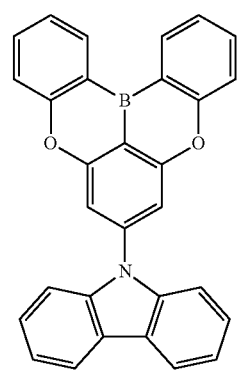
(1-50)
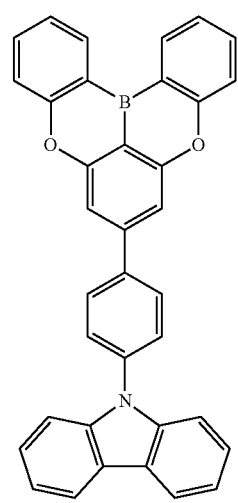

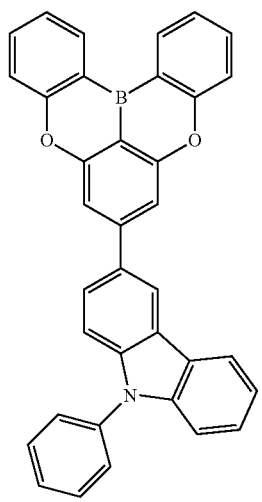
(1-51)
(1-52)
(1-61)
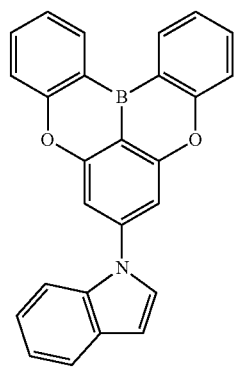
(1-62)
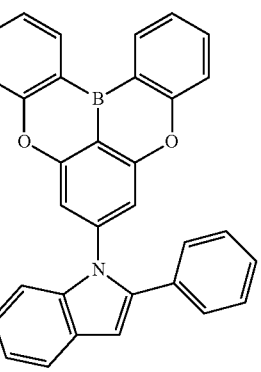
(1-63)
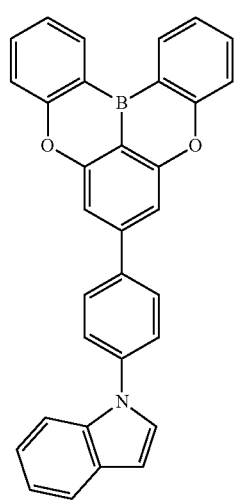
(1-64)

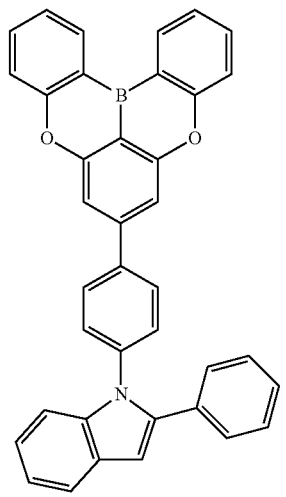
(1-65)
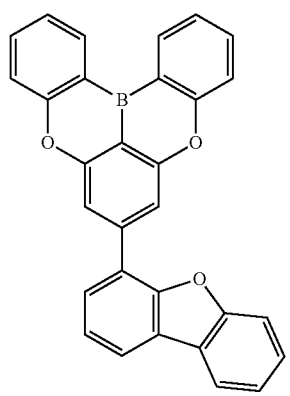
(1-68)
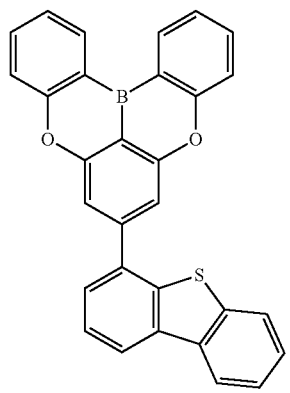
(1-69)
(1-66)
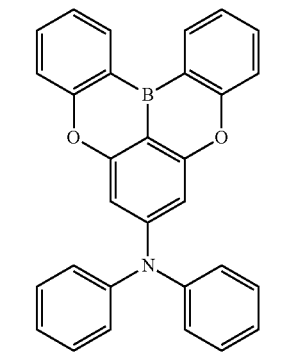
(1-70)
(1-67)
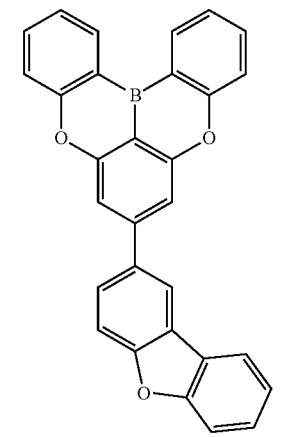
(1-71)

(1-72)
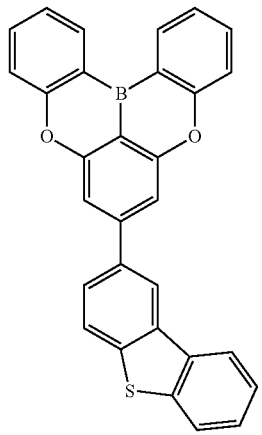
(1-73)
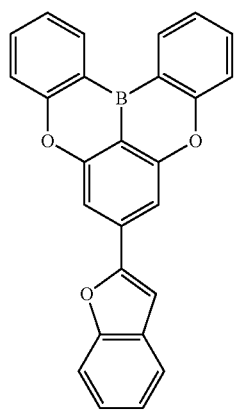
(1-74)
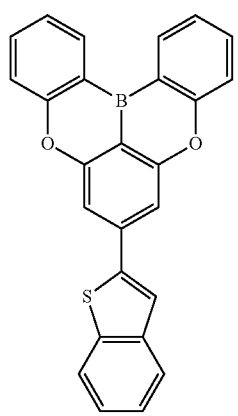
(1-75)
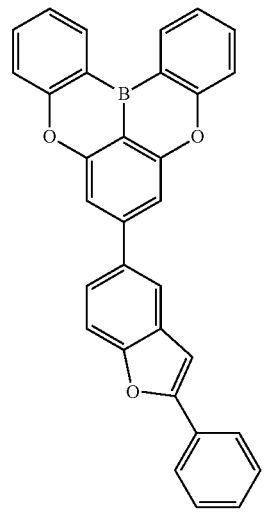
(1-76)
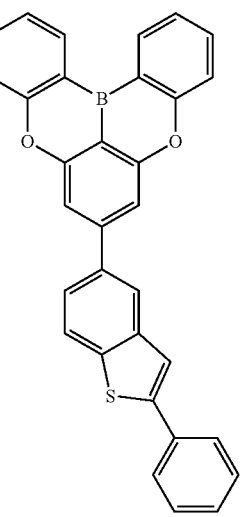
(1-77)
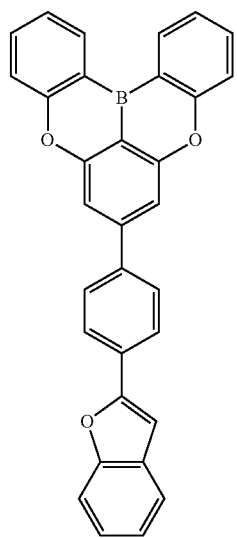

-continued
(1-78)
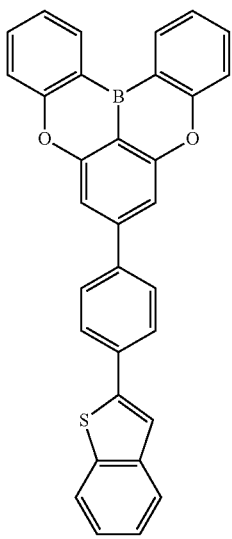
(1-79)
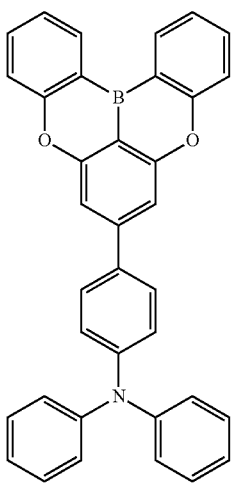
(1-80)
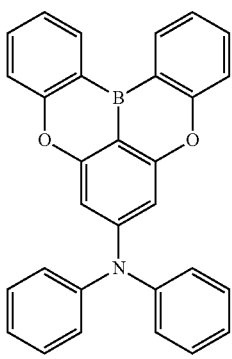
(1-81)
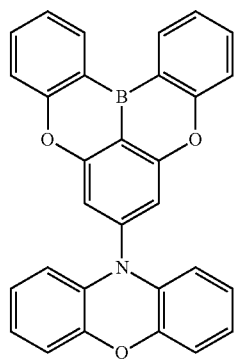
(1-82)
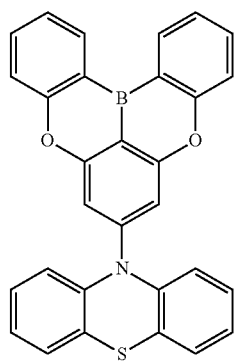
(1-83)
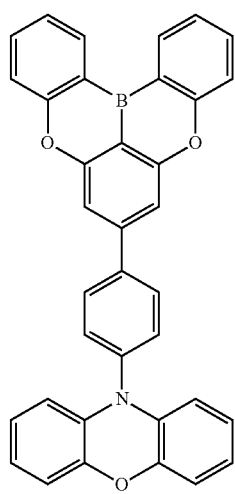

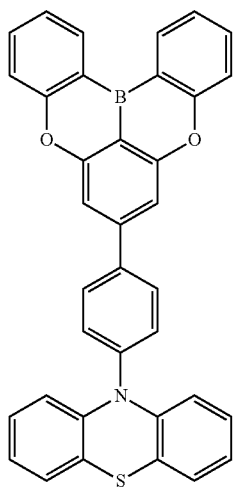
(1-84)
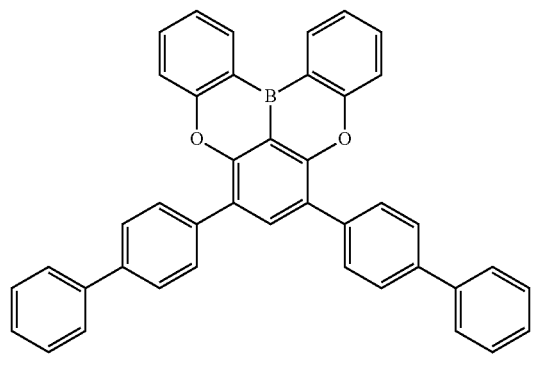
(1-94)
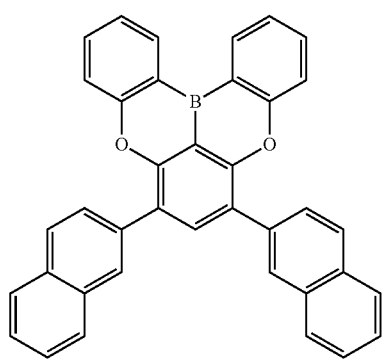
(1-91)
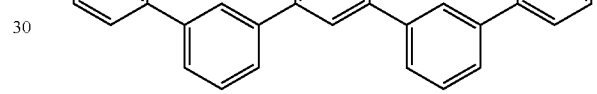
(1-95)
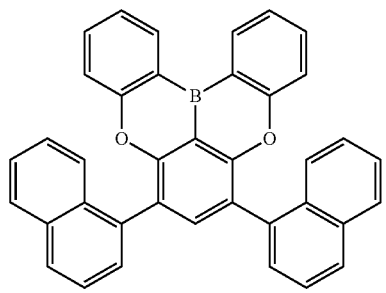
(1-92)
(1-96)
(1-93)
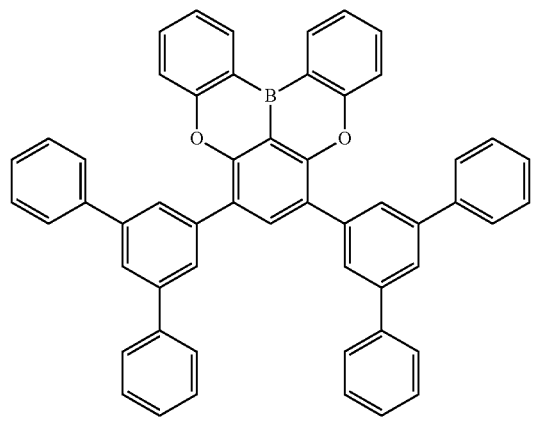
(1-97)

(1-98)
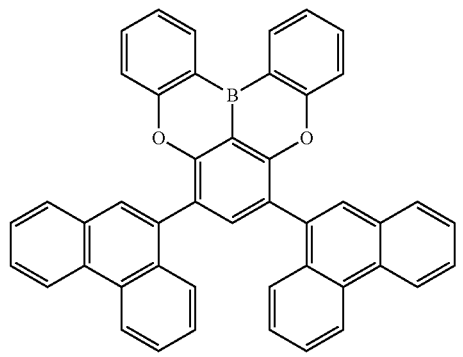
(1-99)
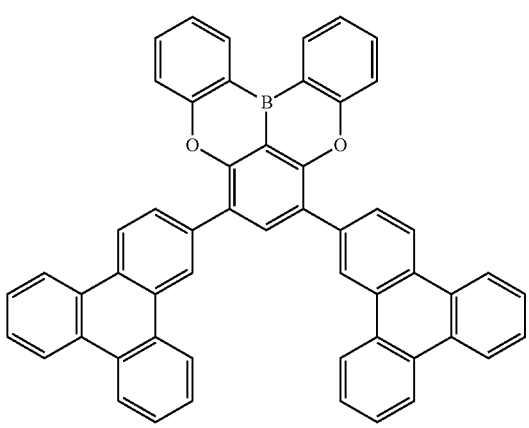
(1-100)
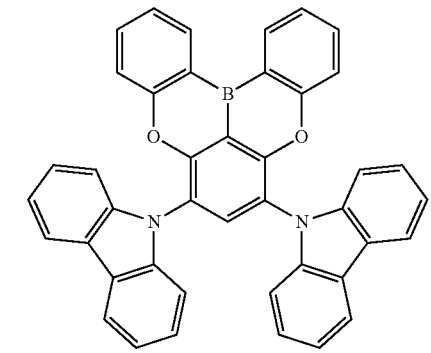
(1-101)
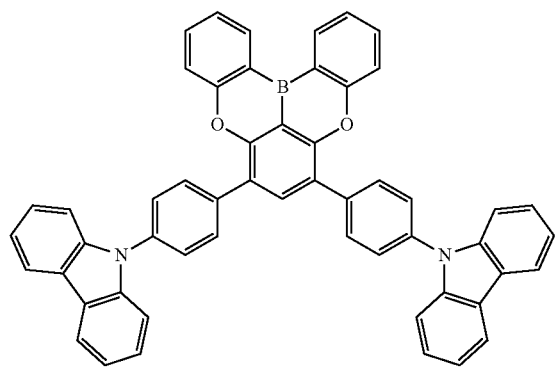
(1-111)
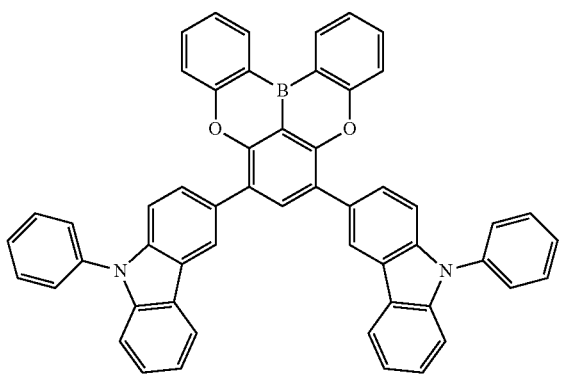
(1-112)
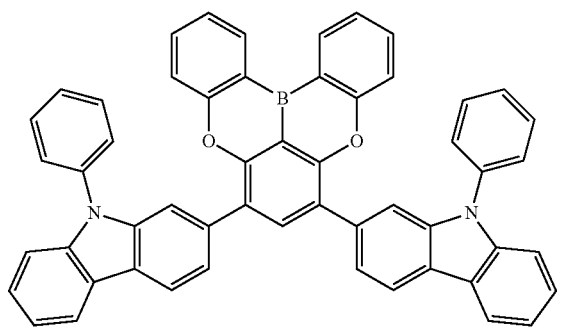
(1-113)
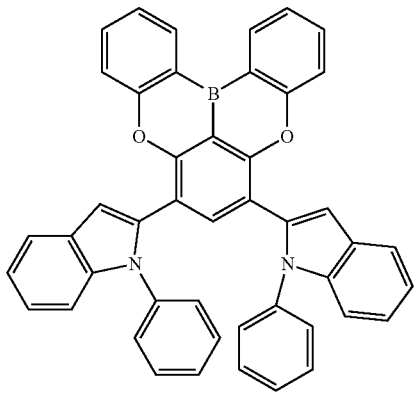
(1-114)
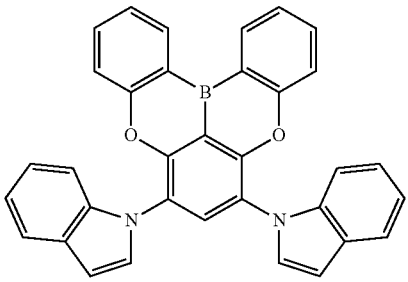

(1-115)
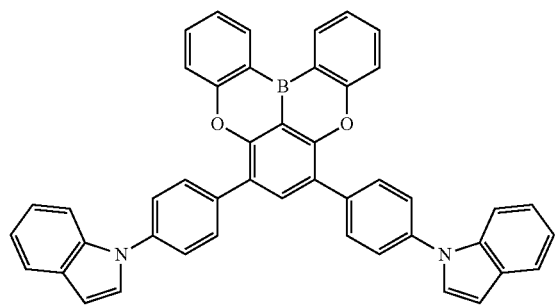
(1-116)
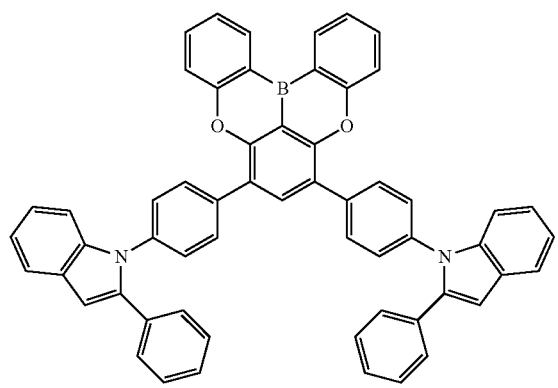
(1-117)
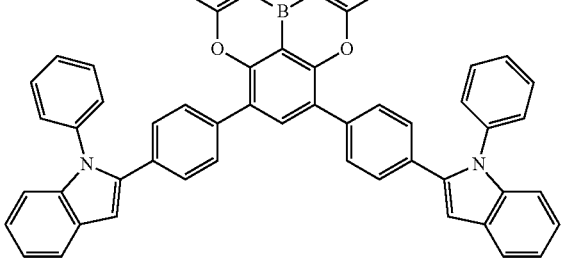
(1-118)
(1-121)
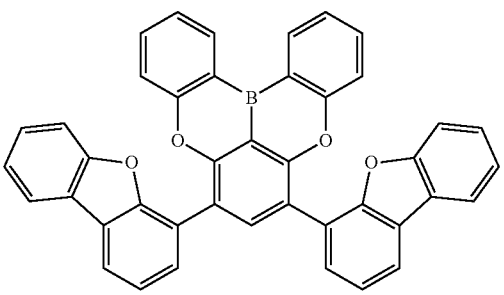
(1-122)
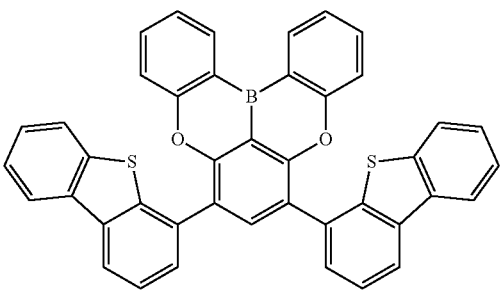
(1-123)
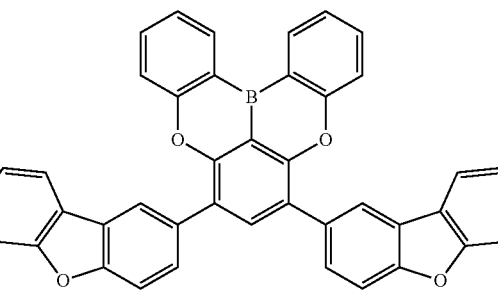
(1-124)
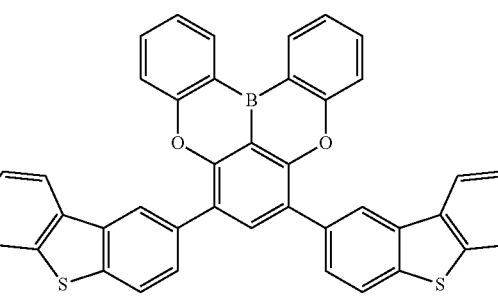
(1-125)
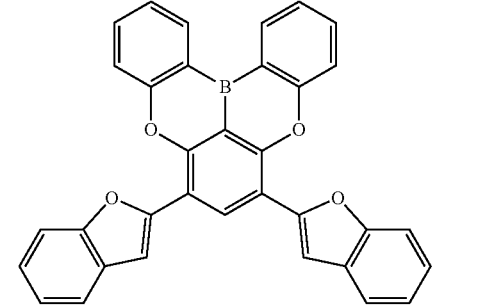

(1-126)
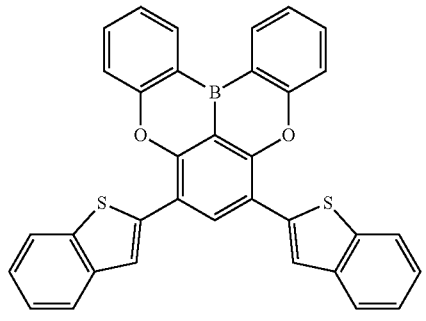
(1-127)
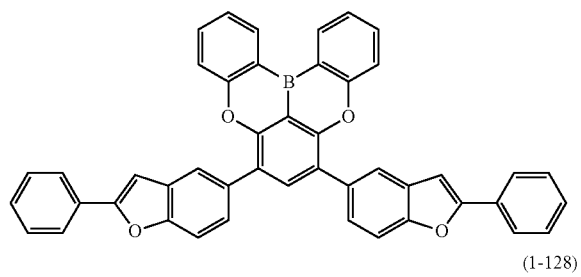
(1-128)
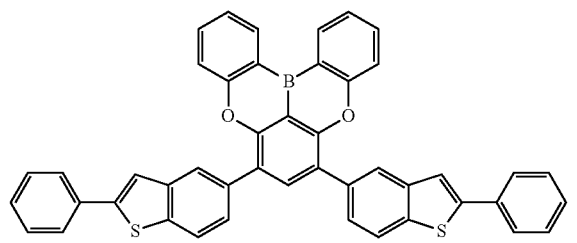
(1-129)
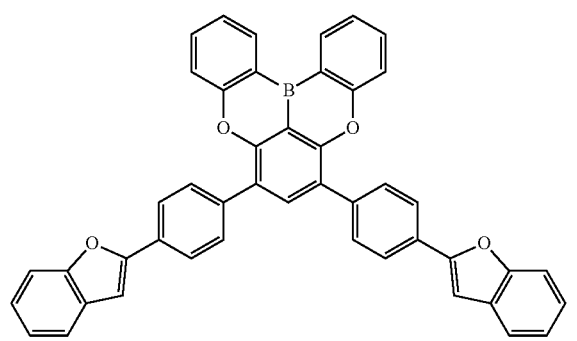
(1-130)
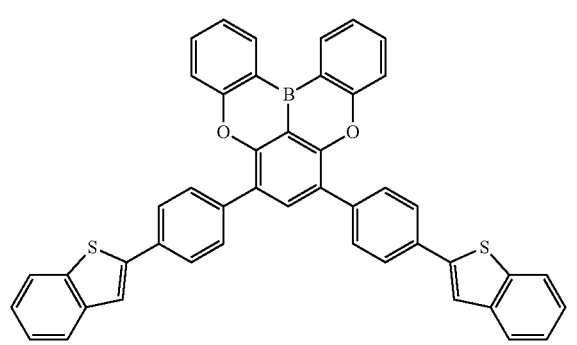
(1-141)
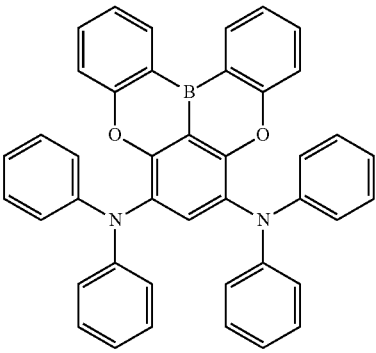
(1-142)
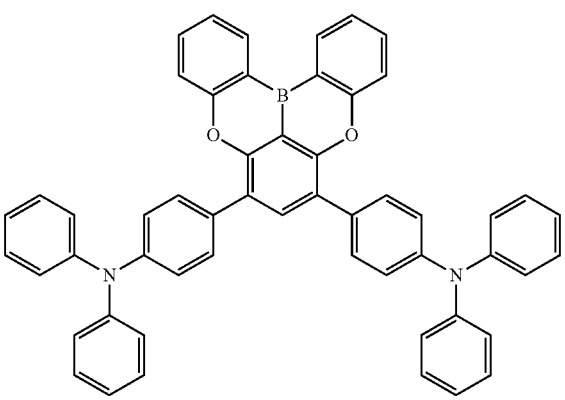
(1-143)
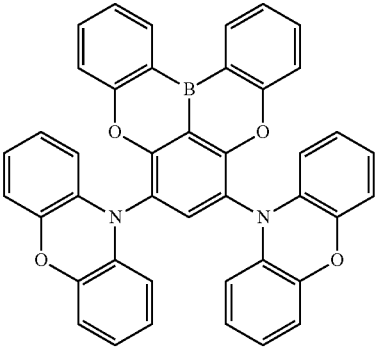
(1-144)
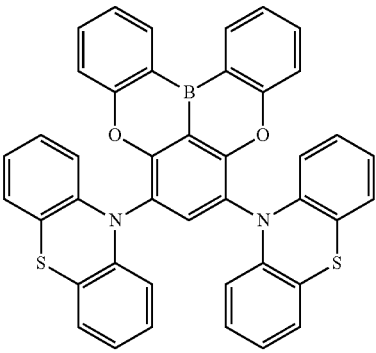

(1-145)
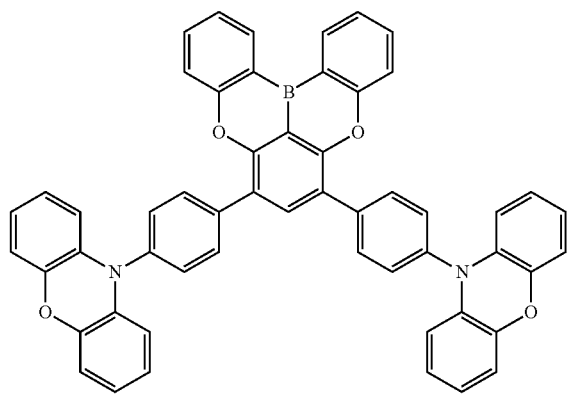
(1-146)
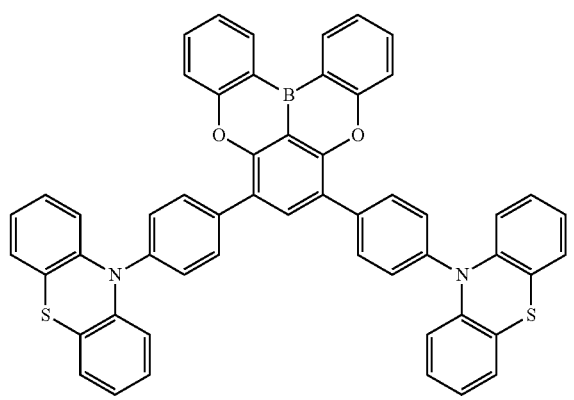
(1-151)
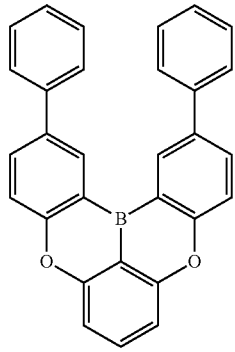
(1-152)
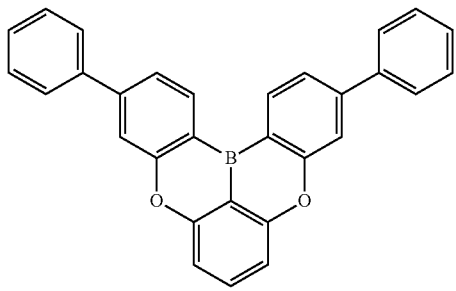
(1-153)
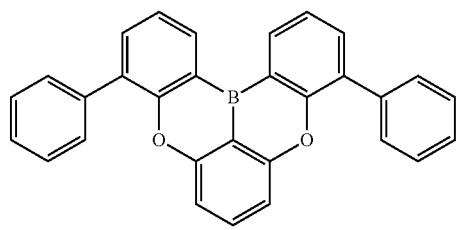
(1-154)
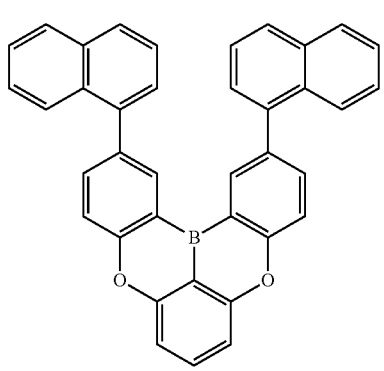
(1-155)
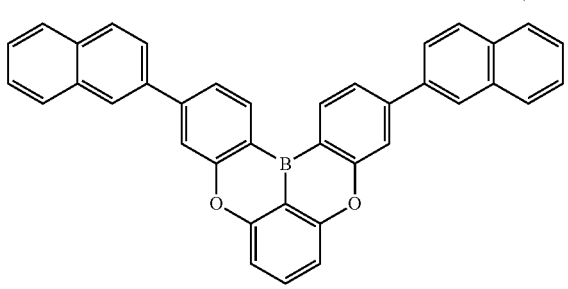
(1-156)
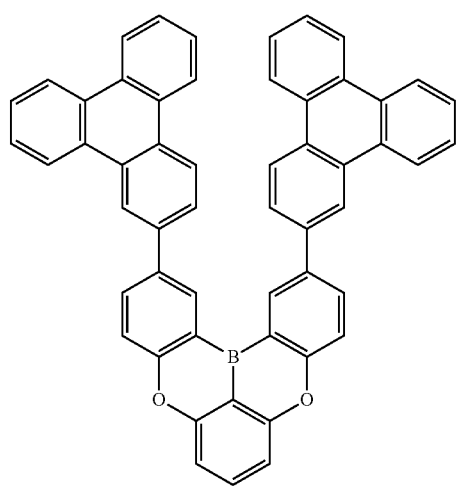

(1-157)
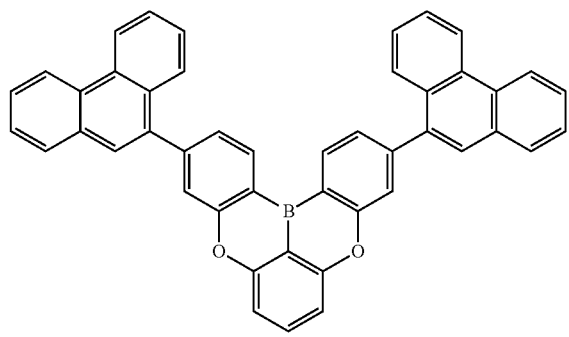
(1-158)
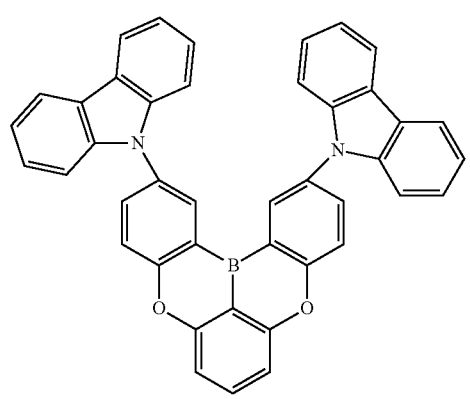
(1-159)
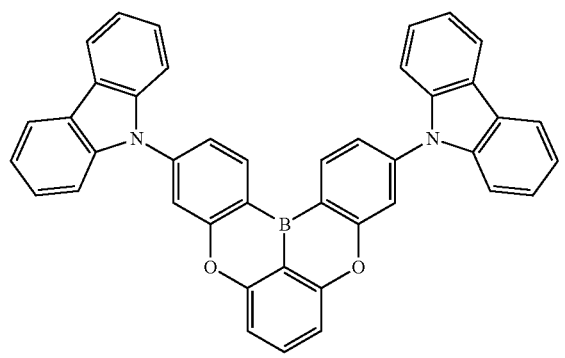
(1-160)
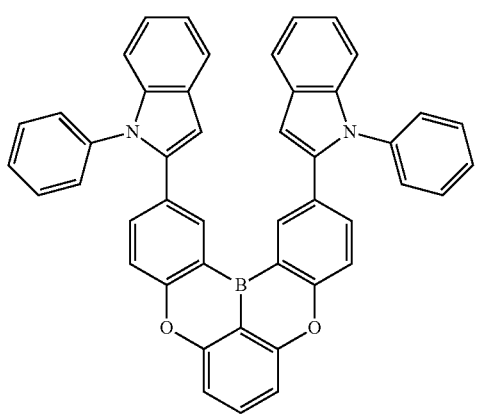
(1-161)
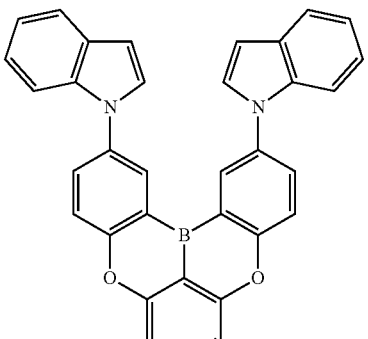
(1-171)
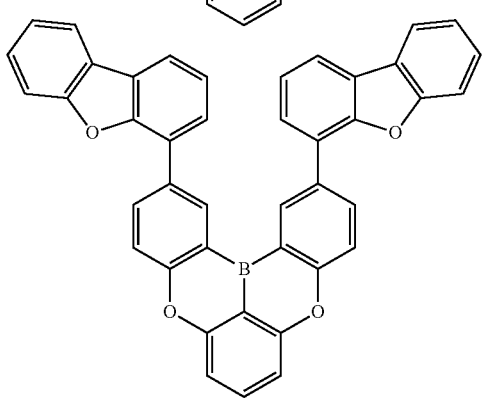
(1-172)
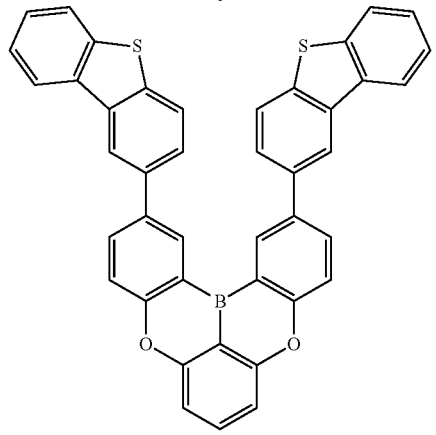
(1-173)
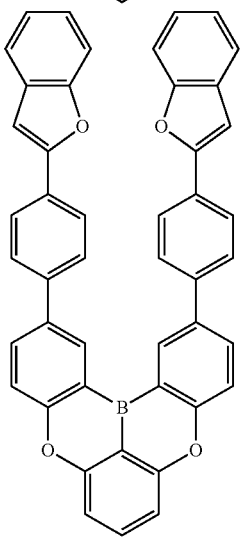

(1-174)
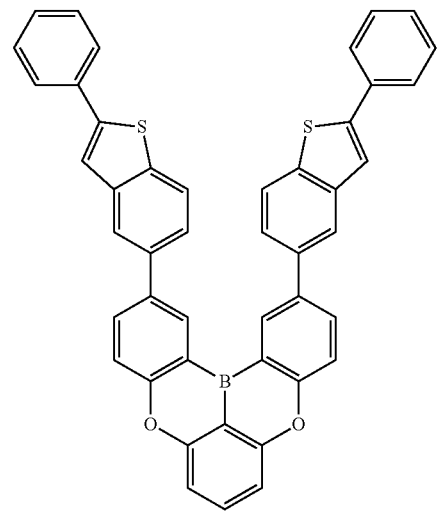
(1-175)
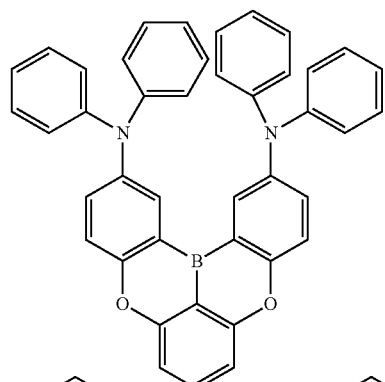
(1-176)
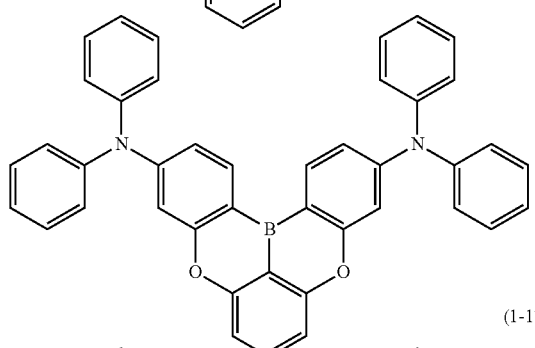
(1-177)
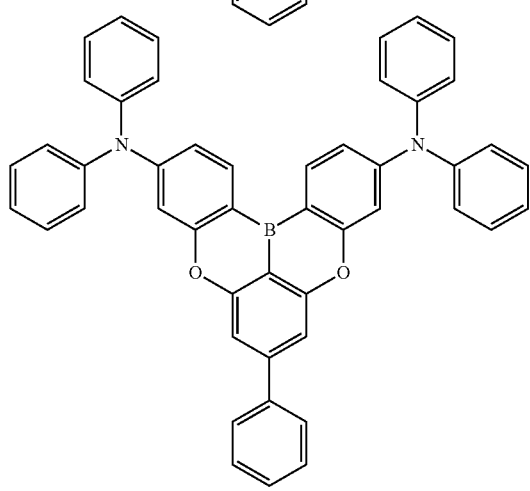
(1-178)
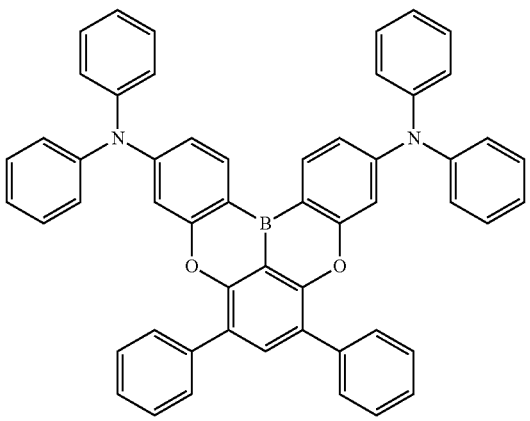
(1-179)
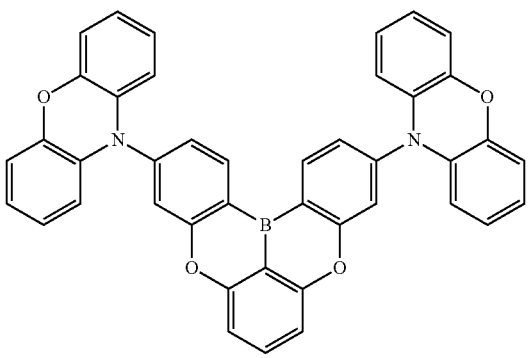
(1-201)
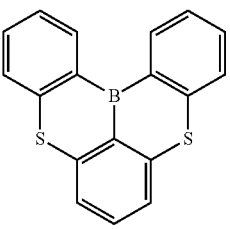
(1-202)
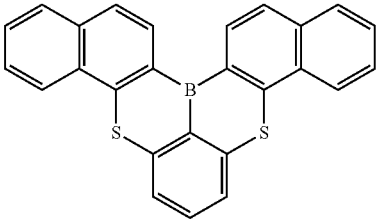
(1-203)
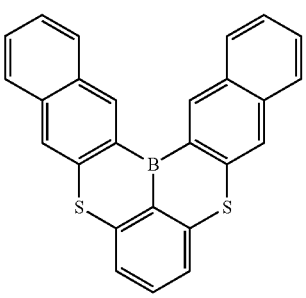

(1-204)
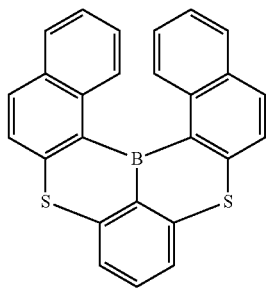
(1-205)
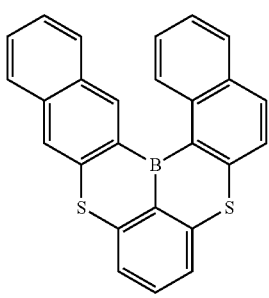
(1-206)
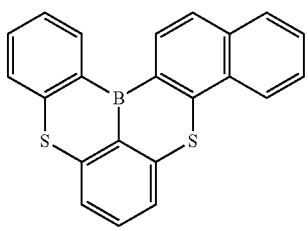
(1-207)
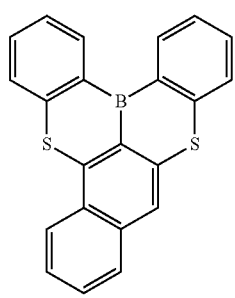
(1-208)
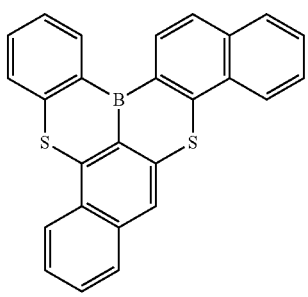
(1-209)
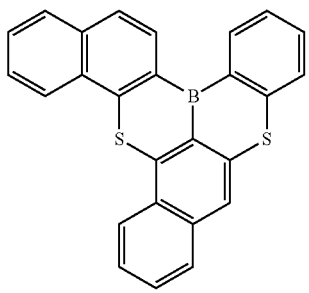
(1-221)
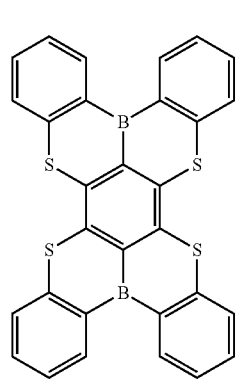
(1-222)
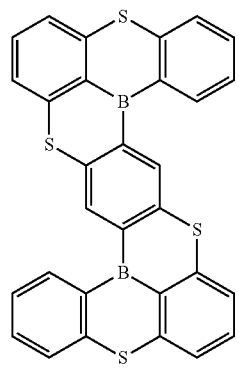
(1-223)
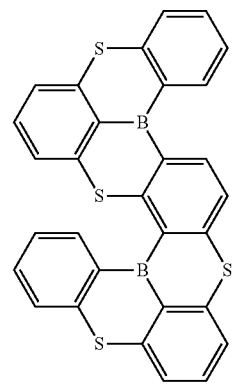

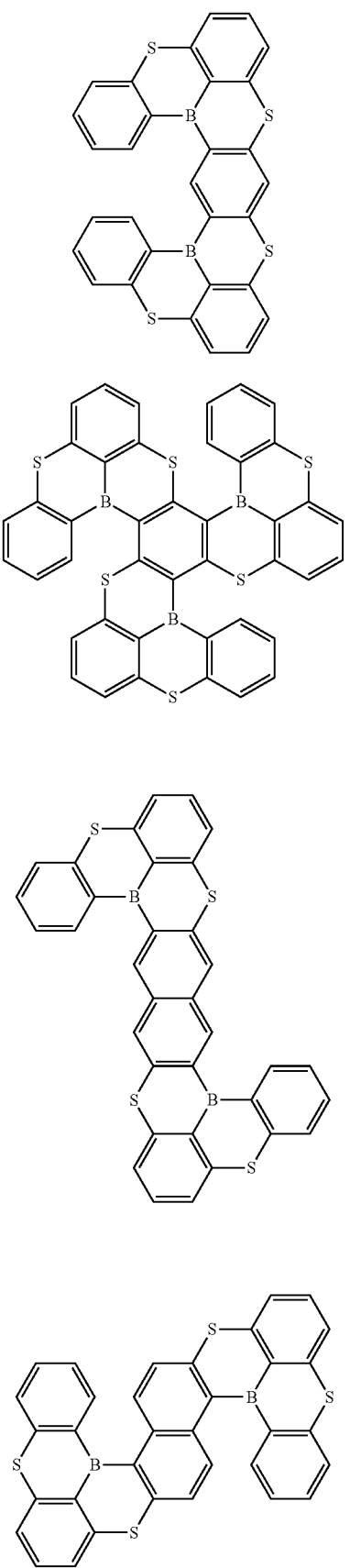
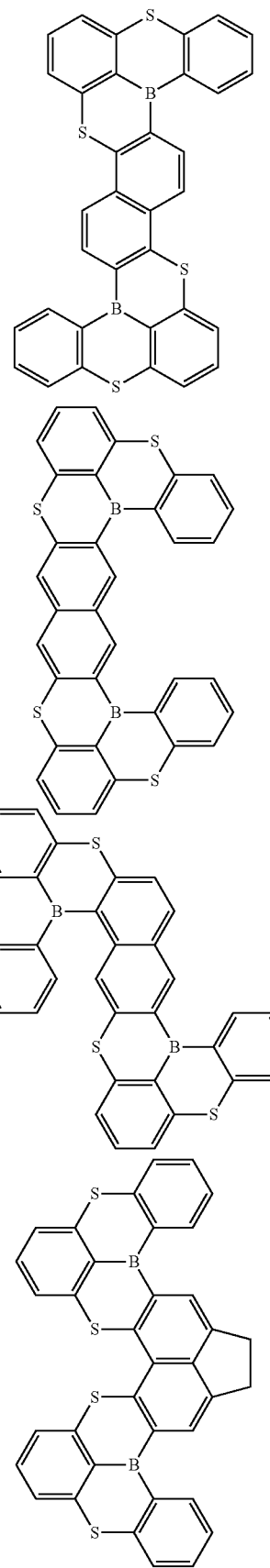

-continued
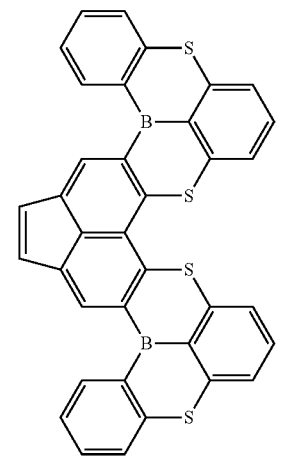
(1-237)
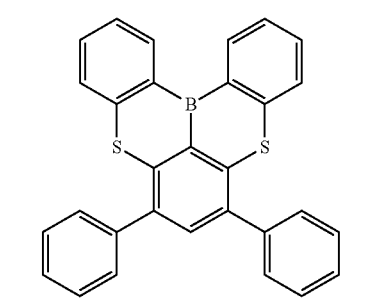
(1-241)
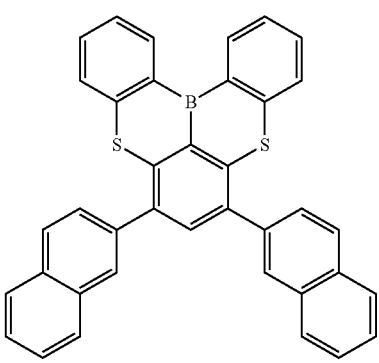
(1-242)
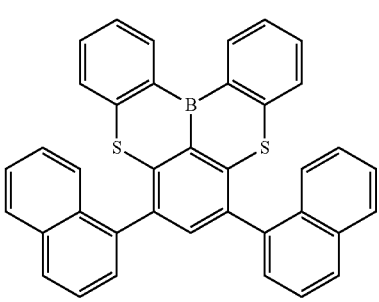
(1-243)
-continued
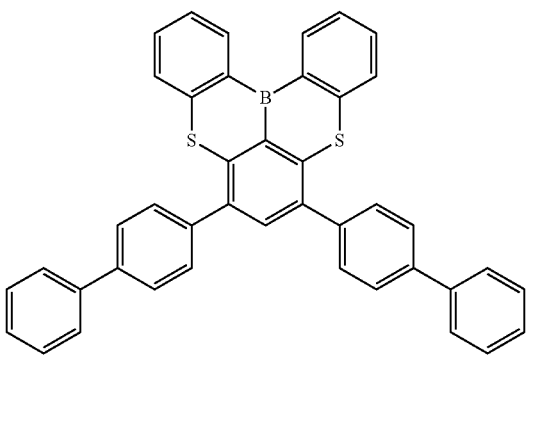
(1-244)
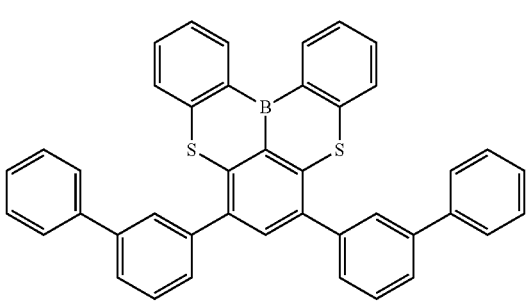
(1-245)
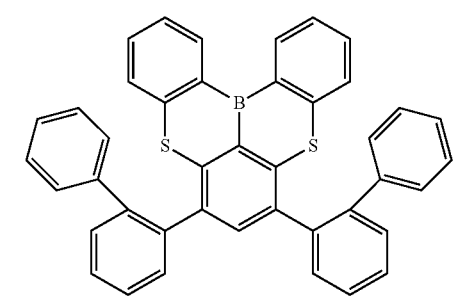
(1-246)
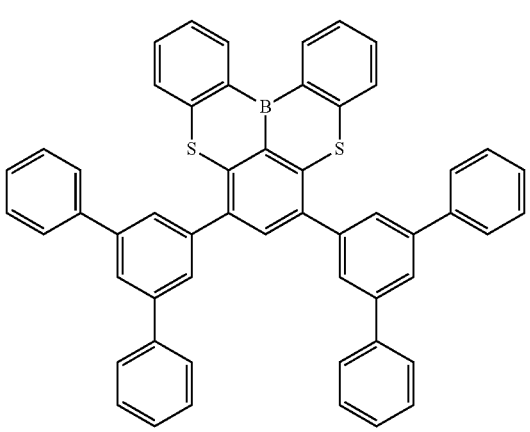
(1-247)

(1-248)
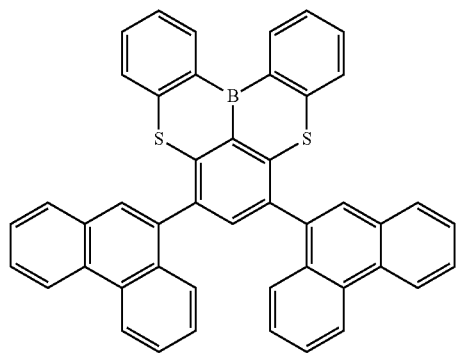
(1-261)
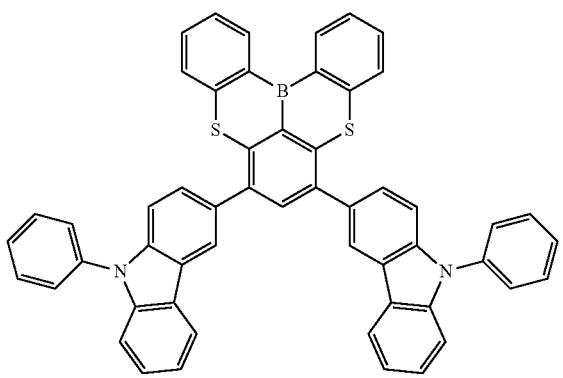
(1-249)
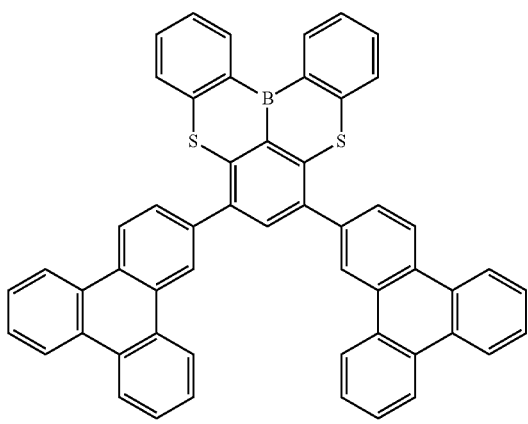
(1-262)
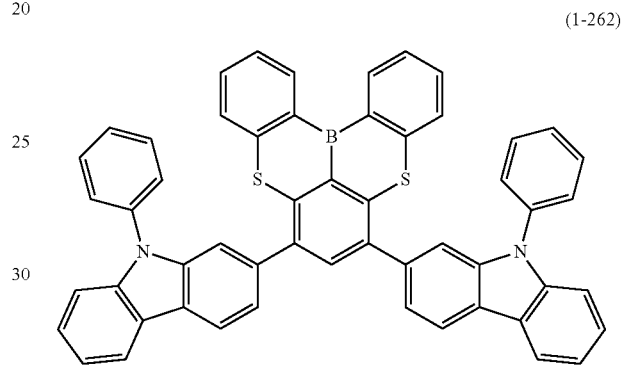
(1-250)
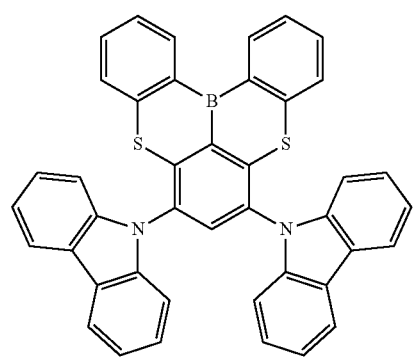
(1-263)
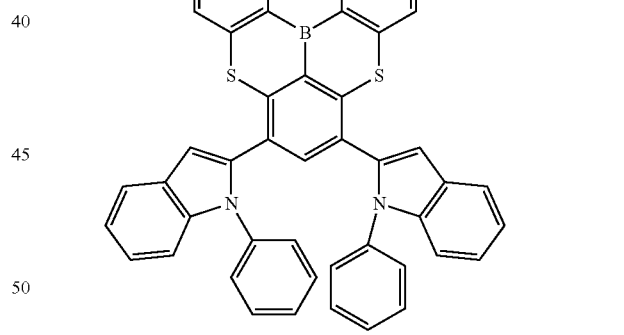
(1-251)
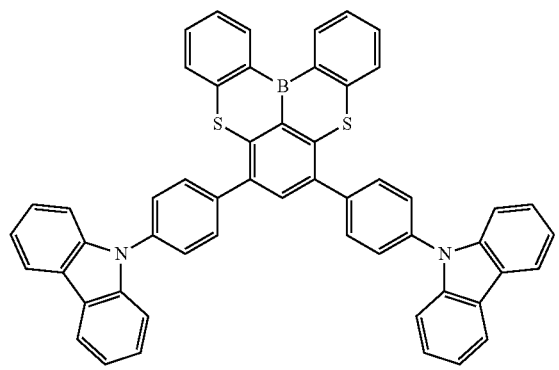
(1-264)
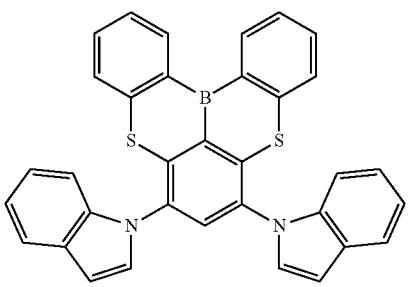

(1-265)
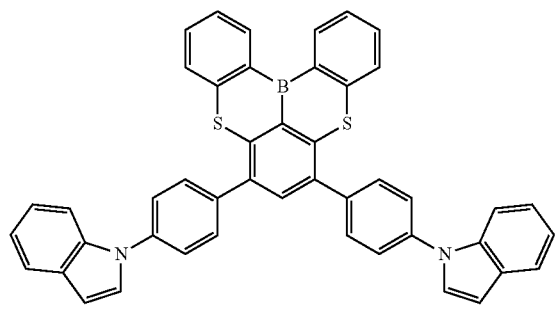
(1-266)
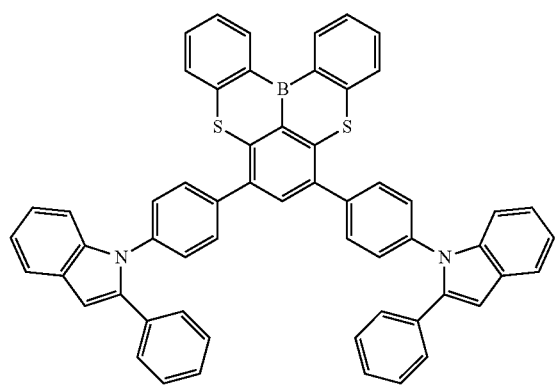
(1-267)
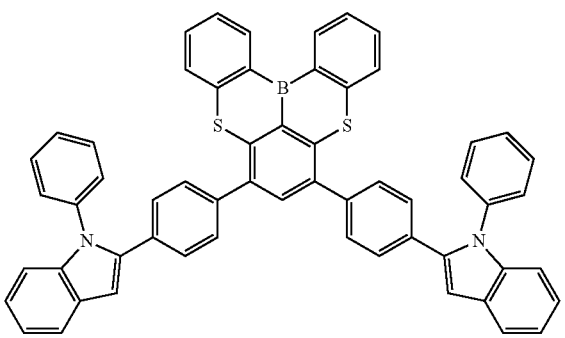
(1-268)
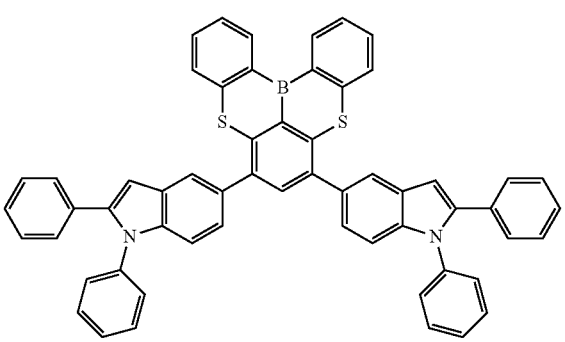
(1-271)
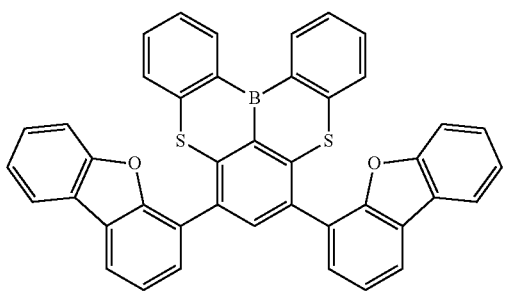
(1-272)
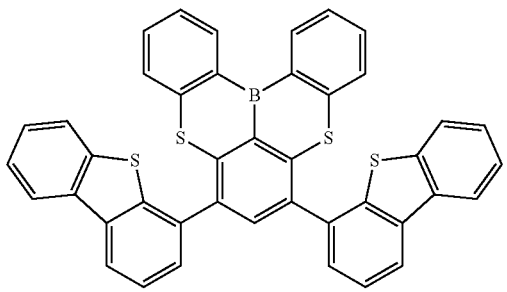
(1-273)
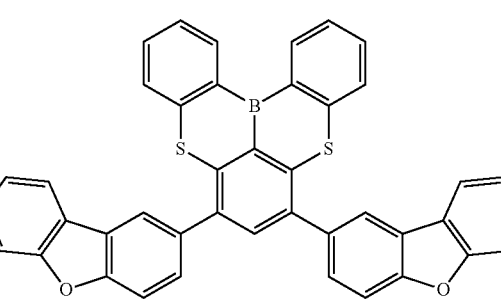
(1-274)
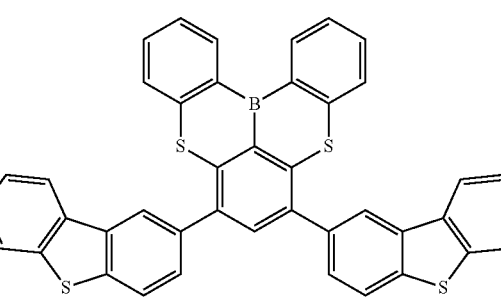
(1-275)
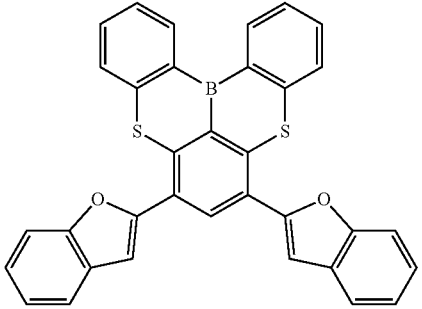

(1-276)
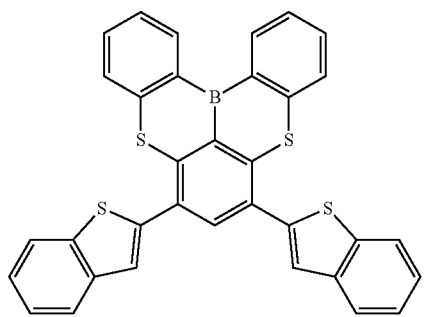
(1-277)
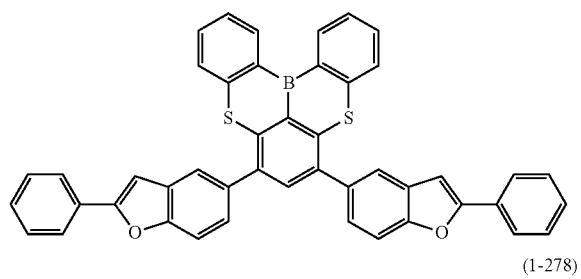
(1-278)
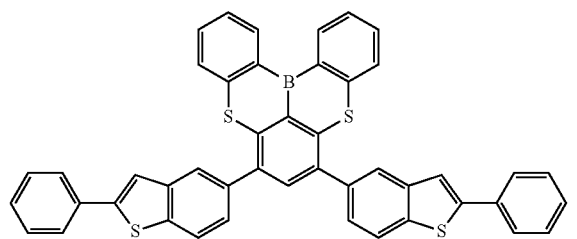
(1-279)
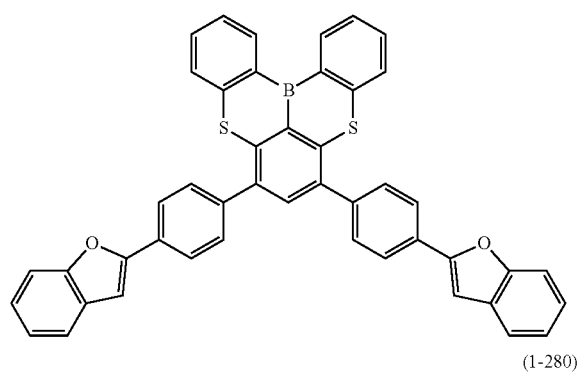
(1-280)
(1-291)
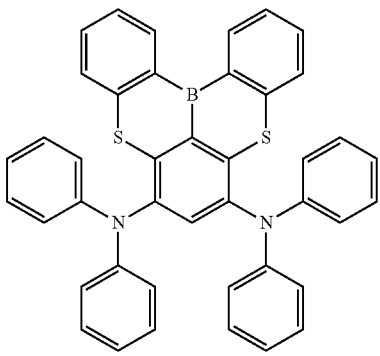
(1-292)
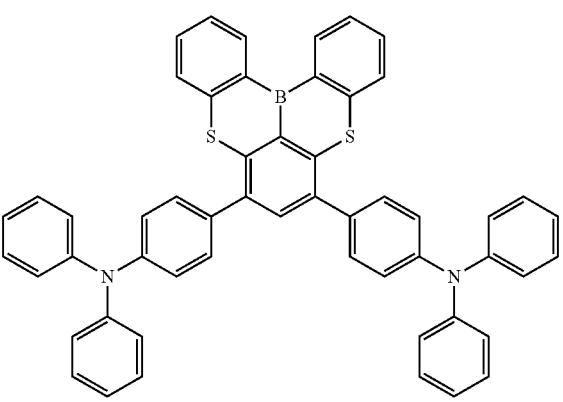
(1-293)
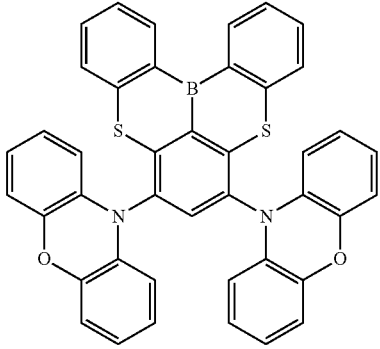
(1-294)
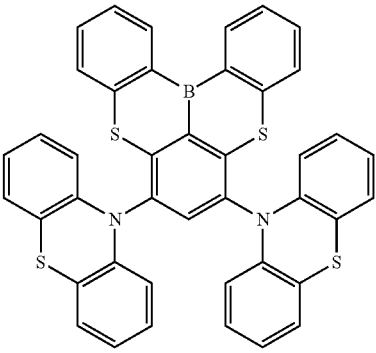

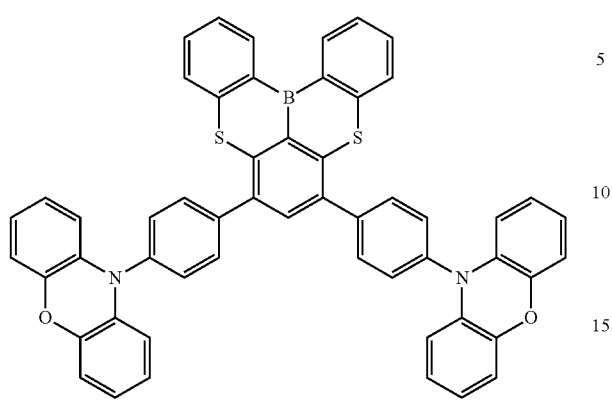
(1-295)
(1-296)
(1-301)
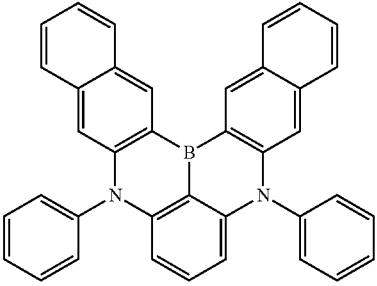
(1-403)
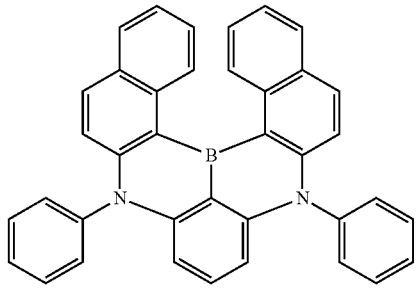
(1-404)
(1-405)
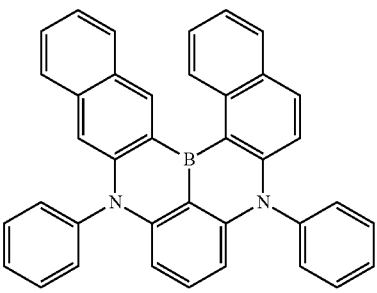
(1-401)
(1-402)
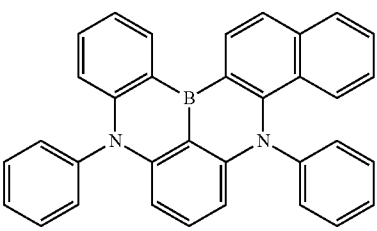
(1-406)
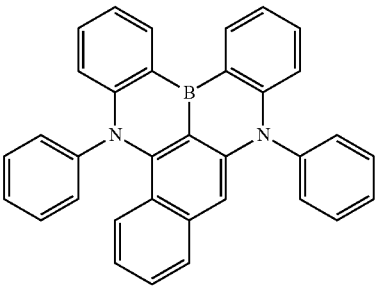
(1-407)

(1-408)
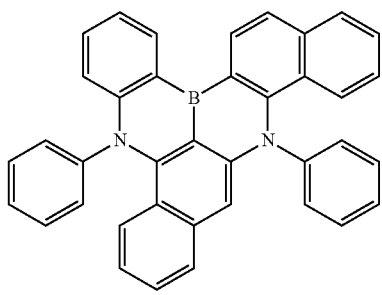
(1-409)
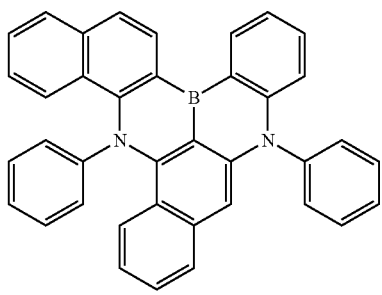
(1-411)
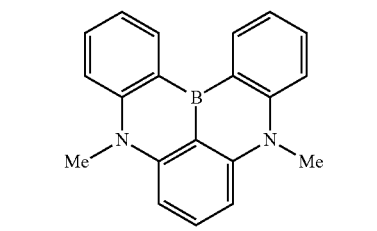
(1-412)
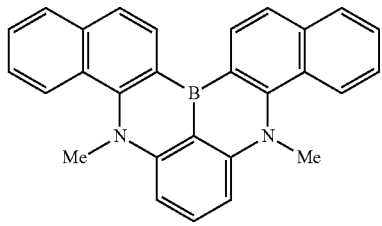
(1-413)
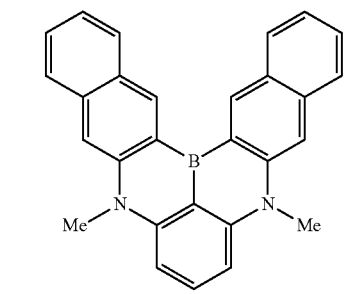
(1-414)
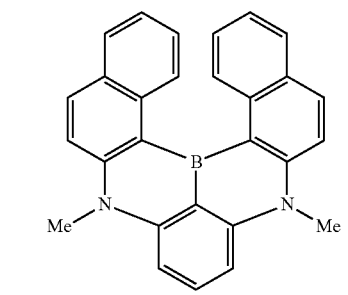
(1-415)
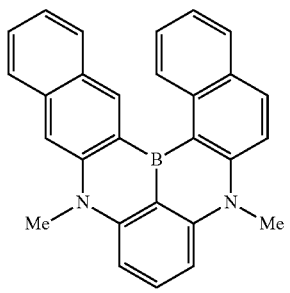
(1-416)
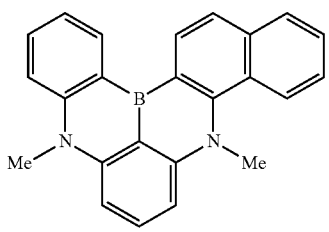
(1-417)
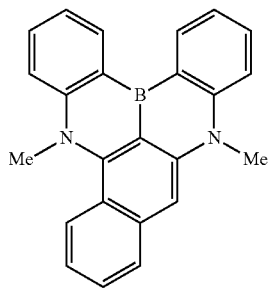
(1-418)
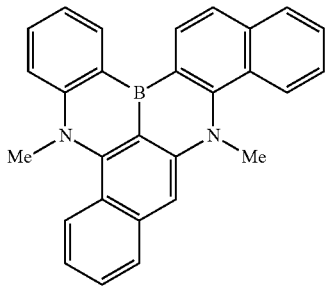
(1-419)
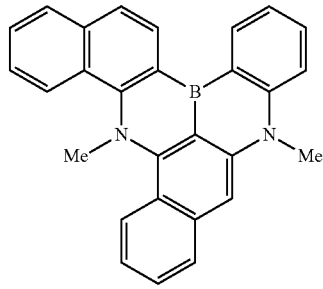

(1-421)
(1-422)
(1-431)
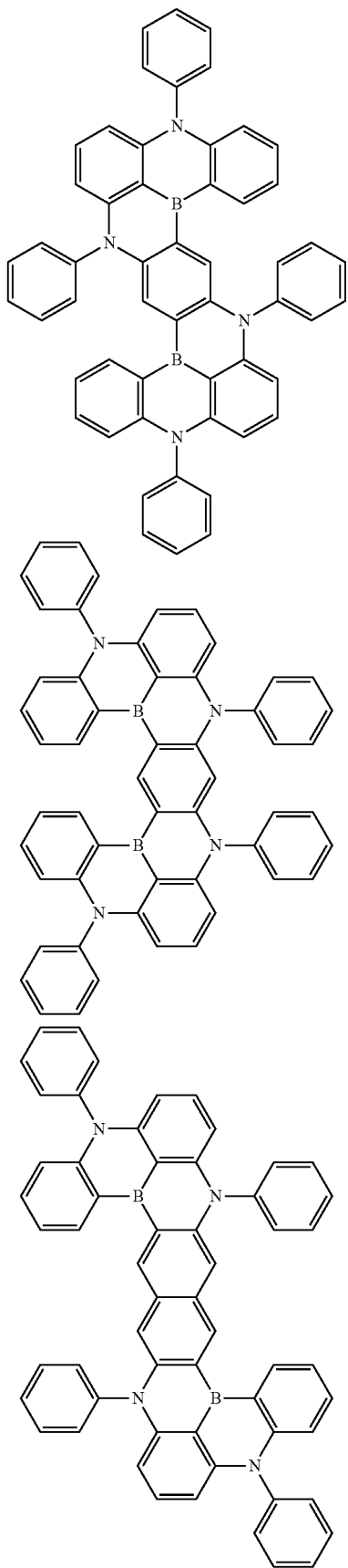
(1-432)
(1-433)
(1-434)
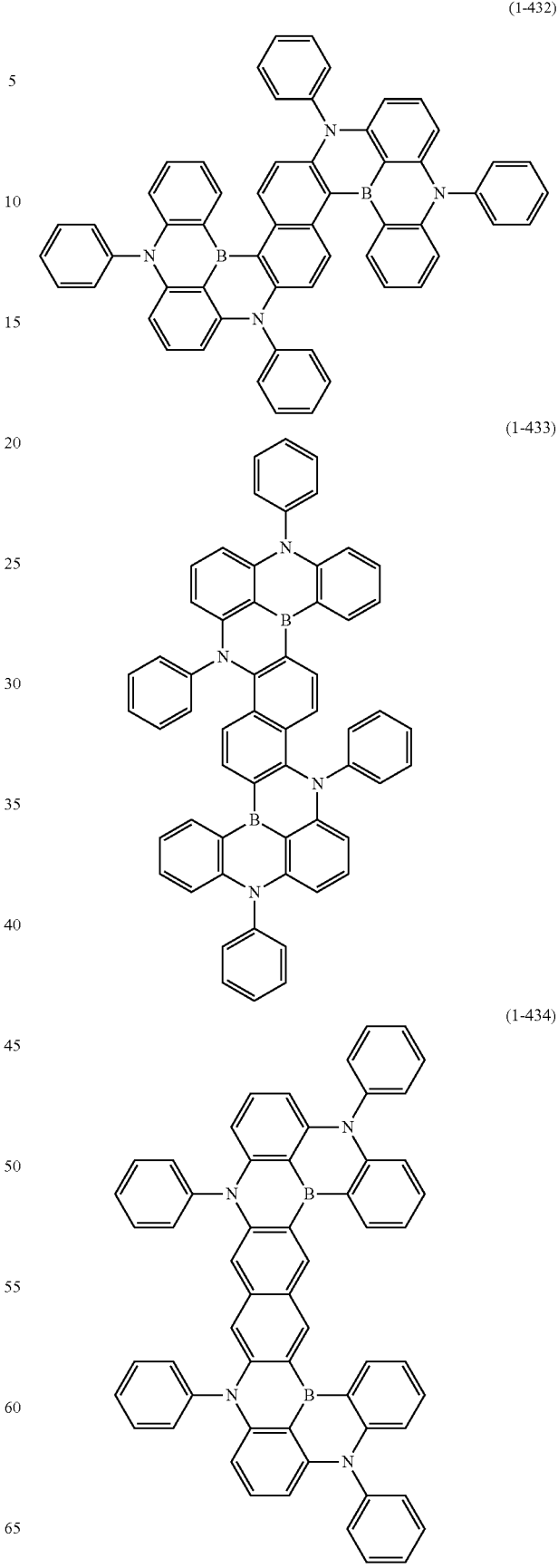

(1-435)
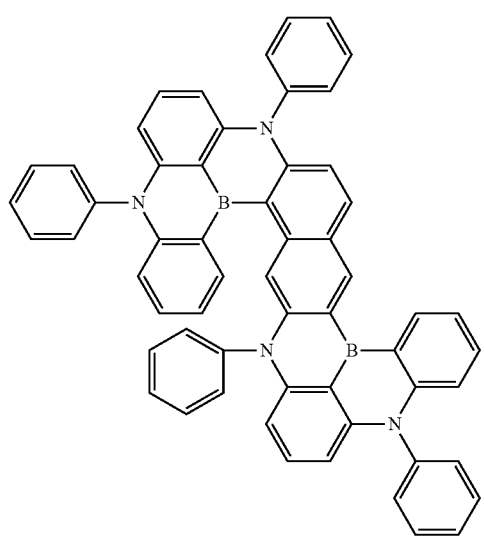
(1-441)
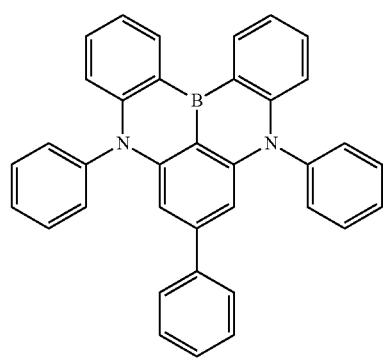
(1-442)
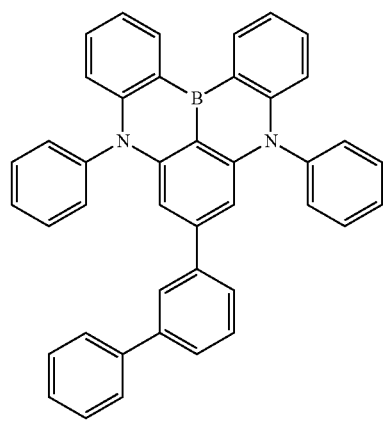
(1-443)
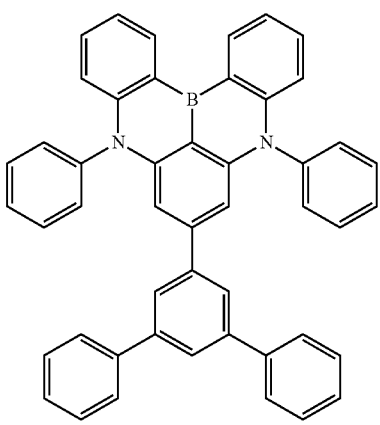
(1-444)
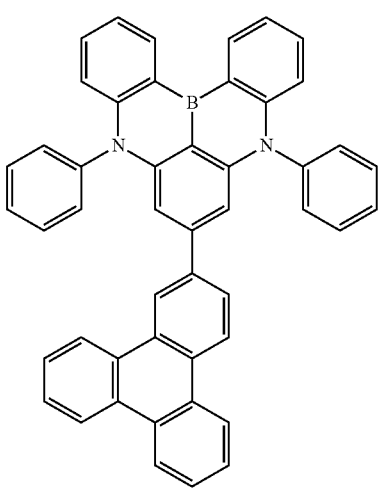
(1-445)
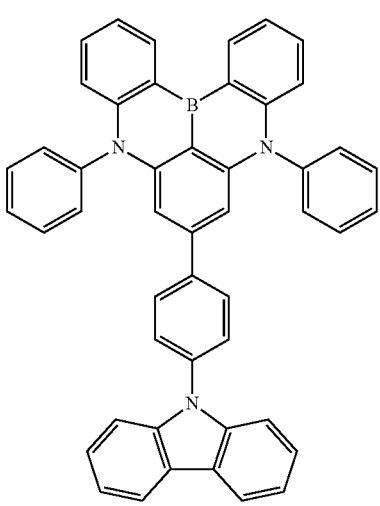

(1-446)
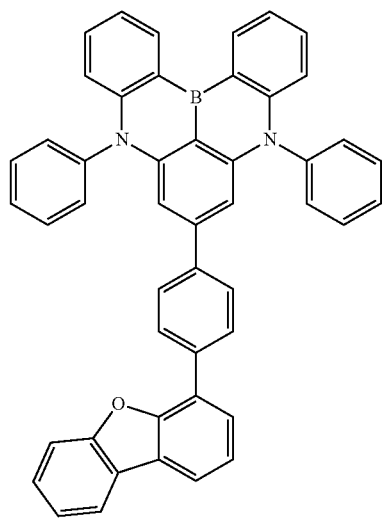
(1-447)
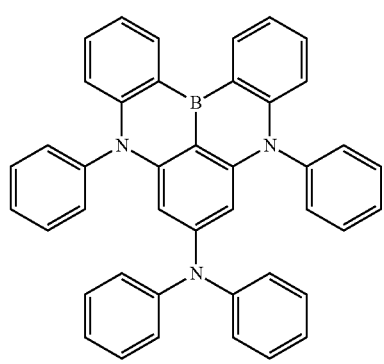
(1-451)
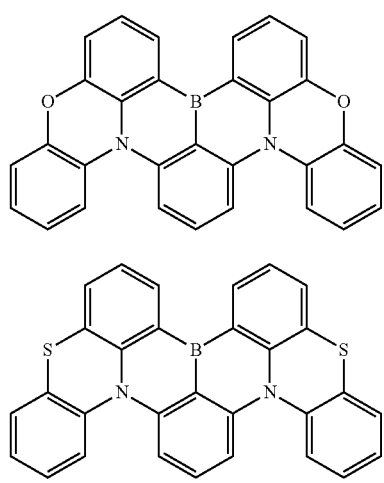
(1-452)
(1-453)
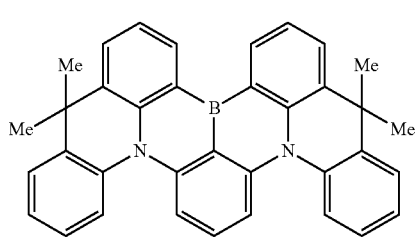
(1-454)
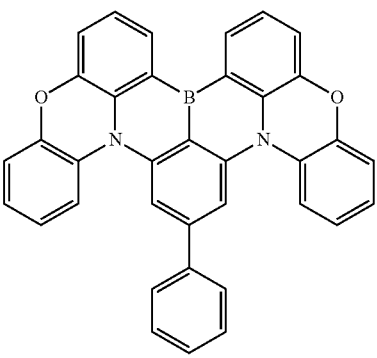
(1-456)
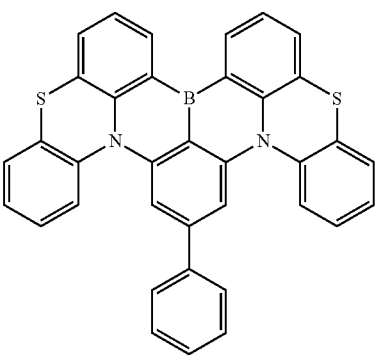
(1-456)
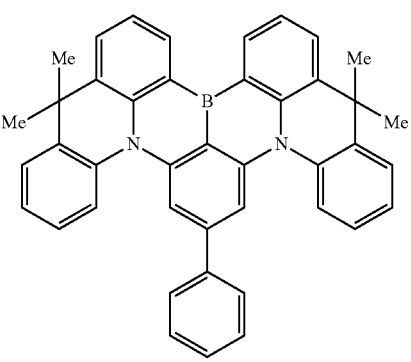
(1-457)
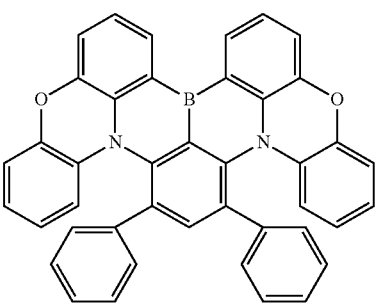

(1-458)
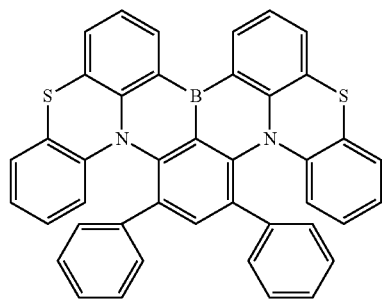
(1-459)
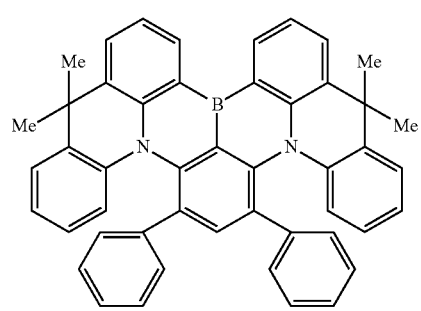
(1-460)
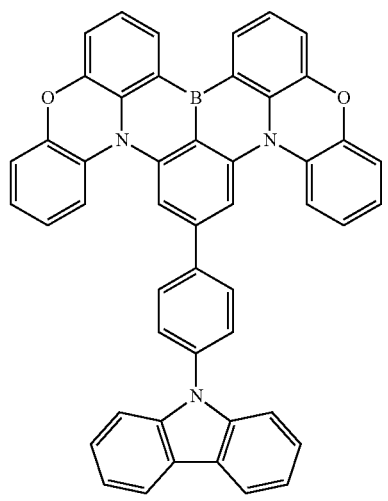
(1-461)
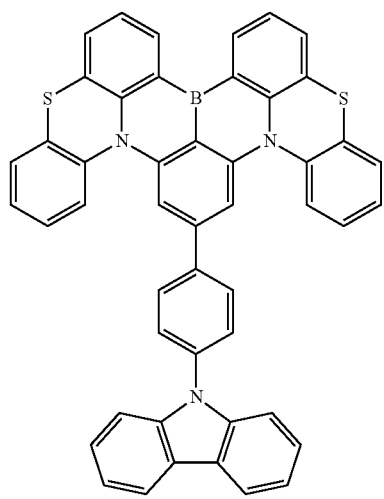
(1-462)
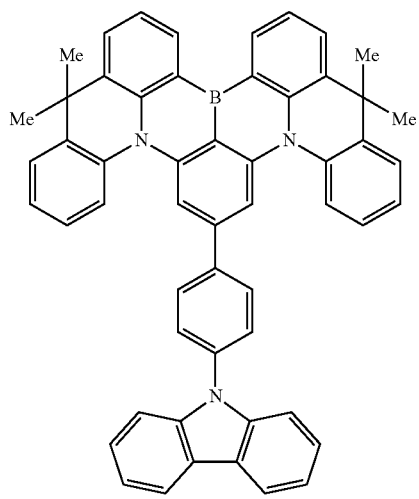
(1-501)
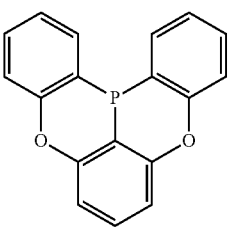
(1-502)
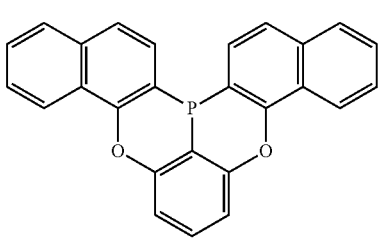
(1-503)
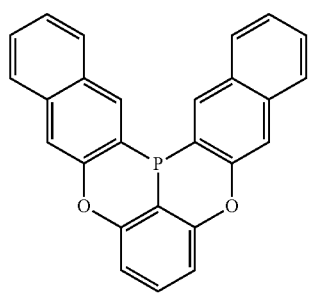
(1-504)
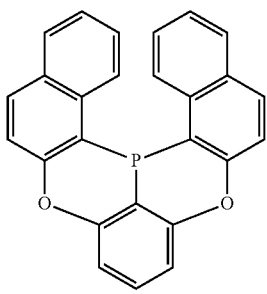

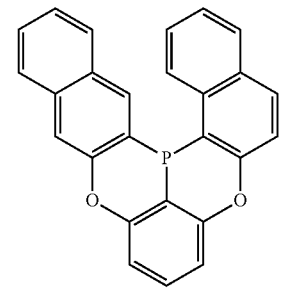 (1-505)
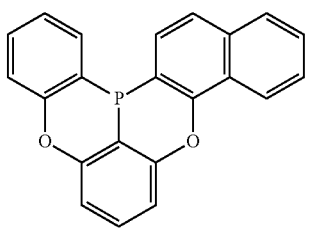 (1-506)
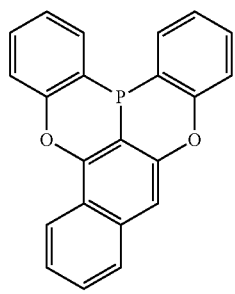 (1-507)
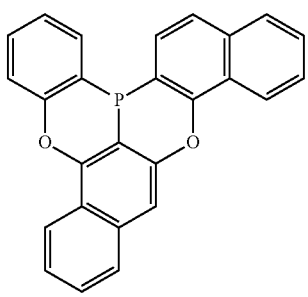 (1-508)
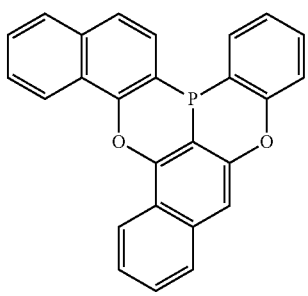 (1-509)
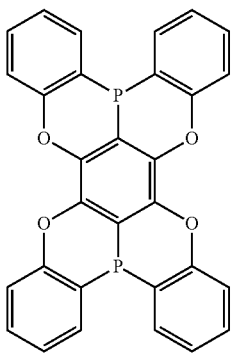 (1-521)
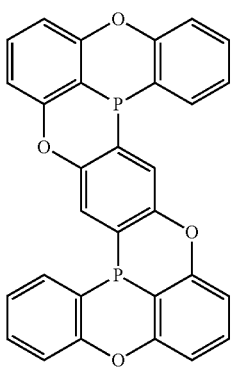 (1-522)
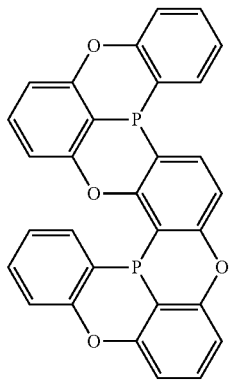 (1-523)
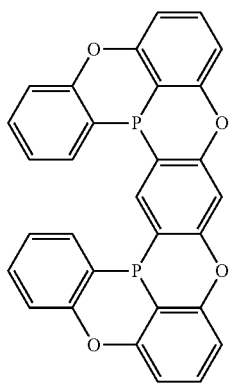 (1-524)

(1-525)
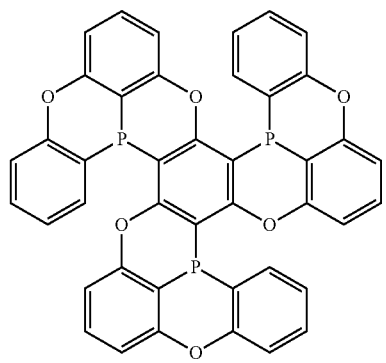
(1-531)
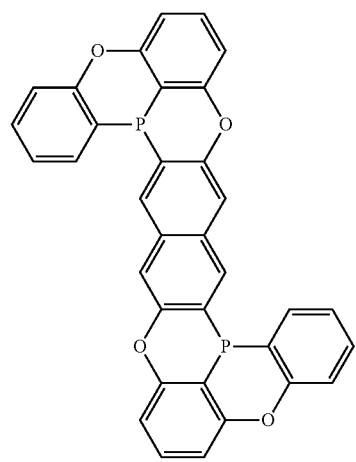
(1-532)
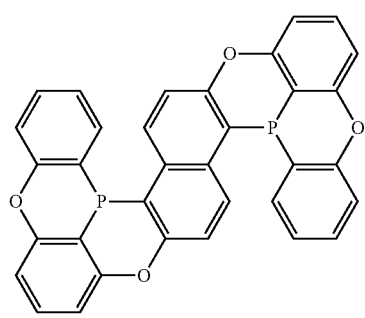
(1-533)
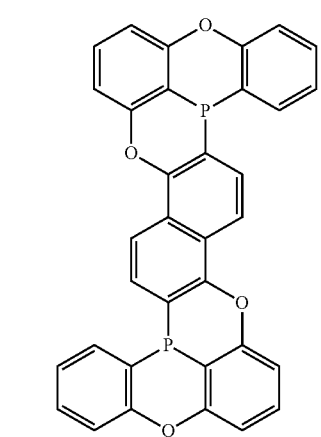
(1-534)
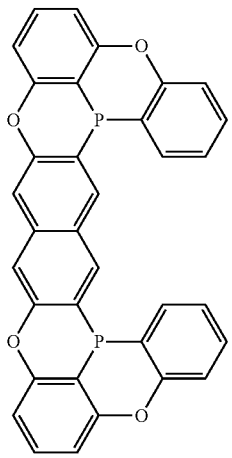
(1-535)
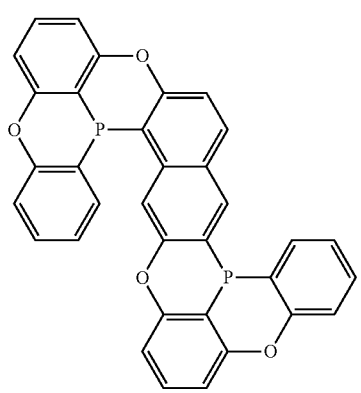
(1-536)
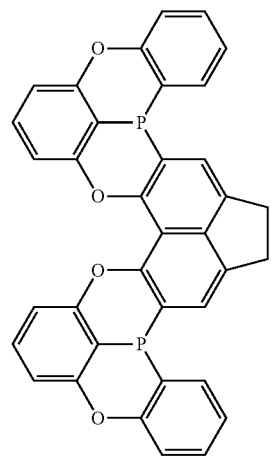

-continued
(1-537)
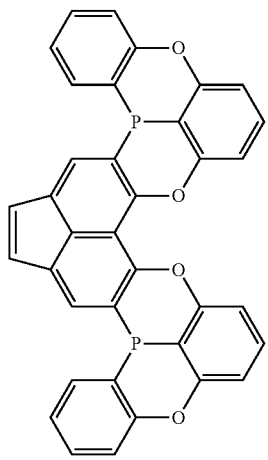
(1-601)
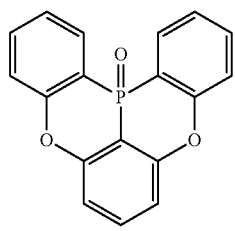
(1-602)
-continued
(1-605)
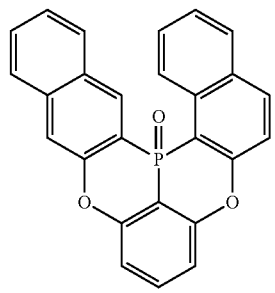
(1-606)
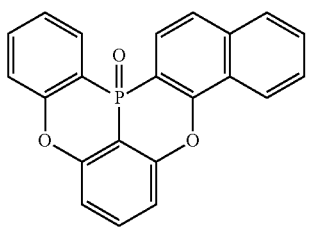
(1-607)
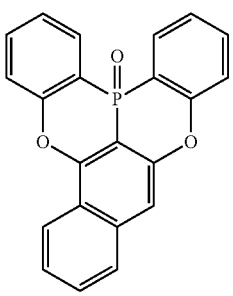
(1-603)
(1-608)
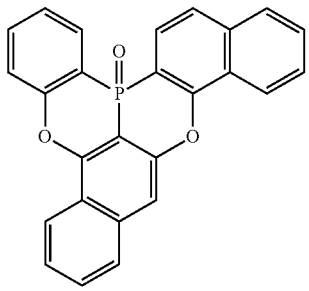
(1-604)
(1-609)
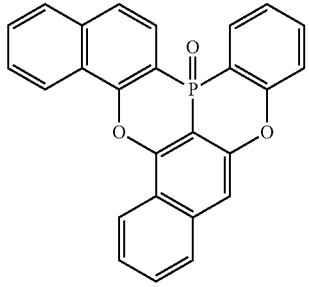

(1-621)
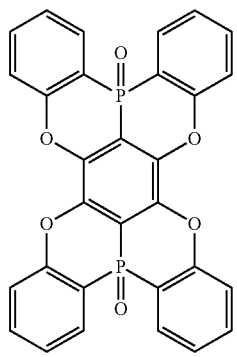
(1-625)
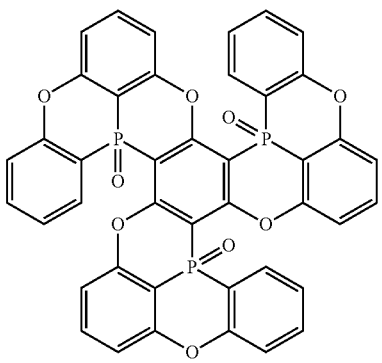
(1-622)
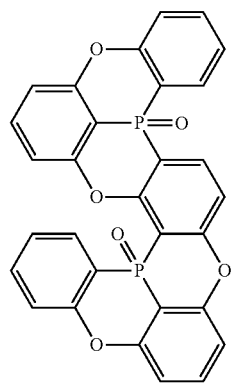
(1-631)
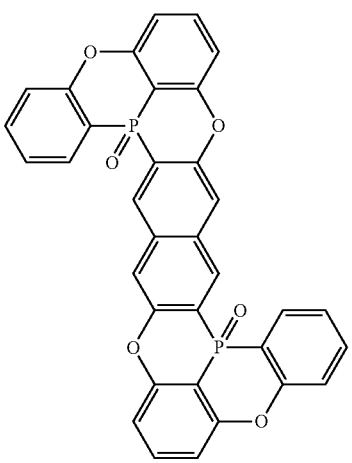
(1-623)
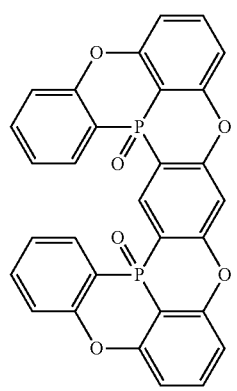
(1-632)
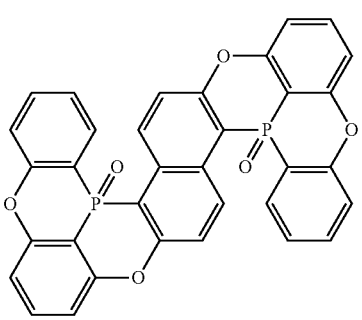
(1-624)
(1-633)
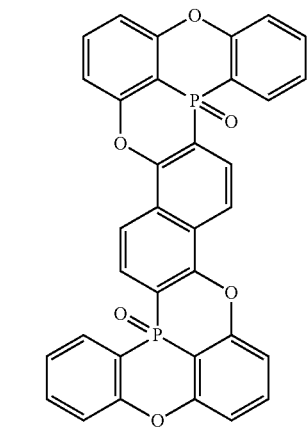

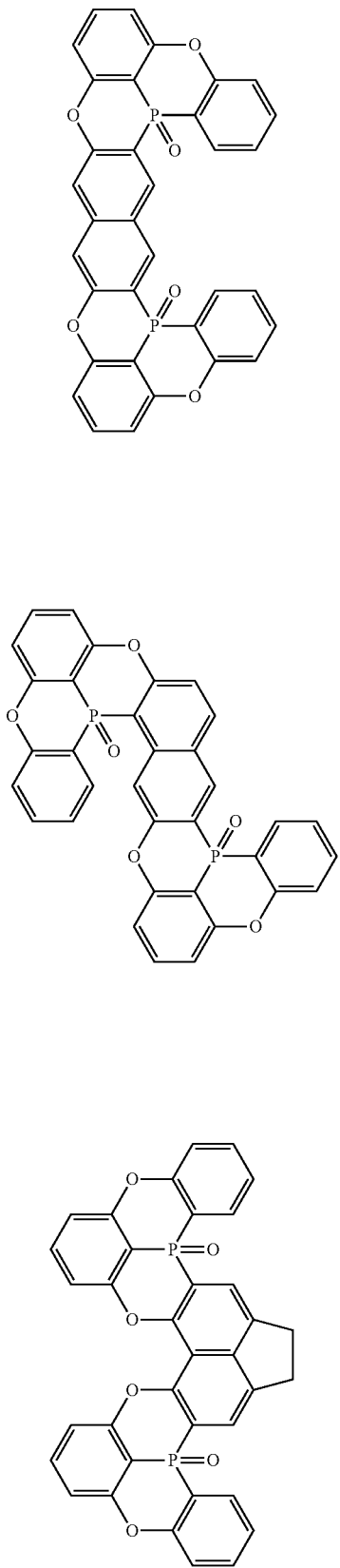
(1-634)
(1-635)
(1-636)
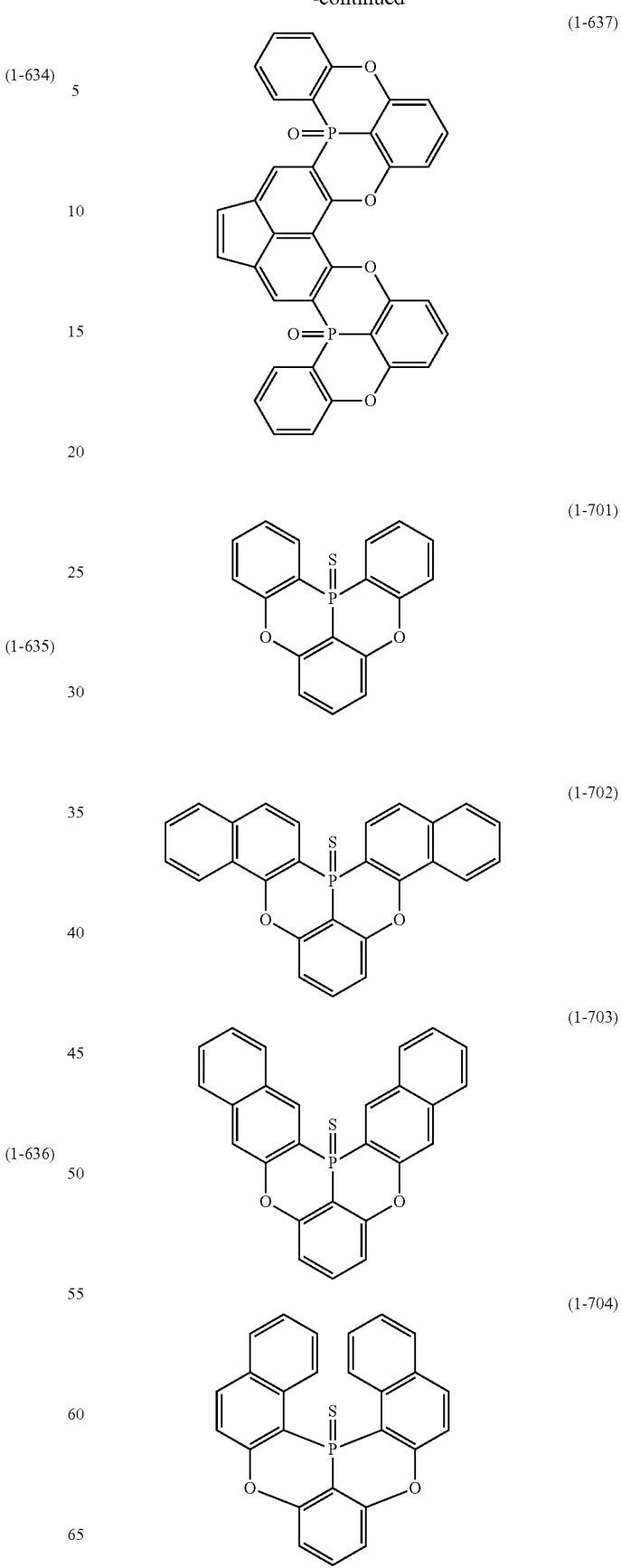
(1-637)
(1-701)
(1-702)
(1-703)
(1-704)

(1-705)
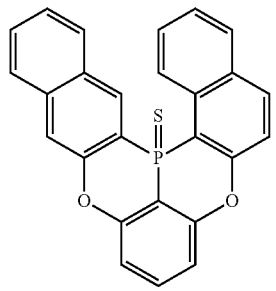
(1-706)
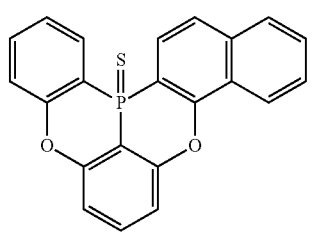
(1-707)
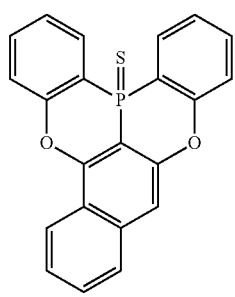
(1-708)
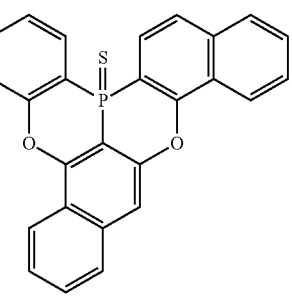
(1-709)
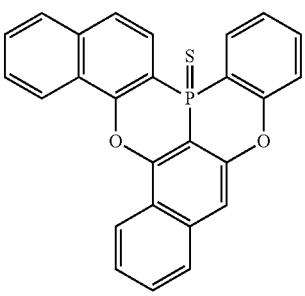
(1-721)
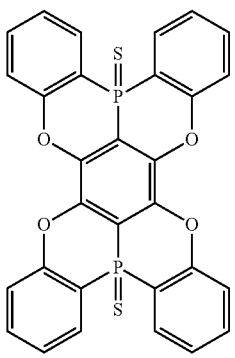
(1-722)
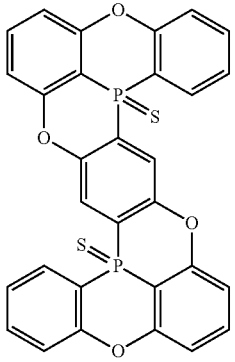
(1-723)
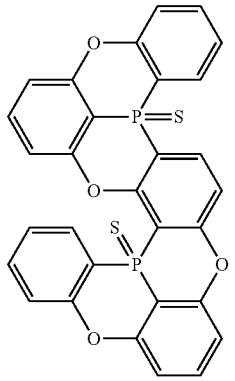
(1-724)
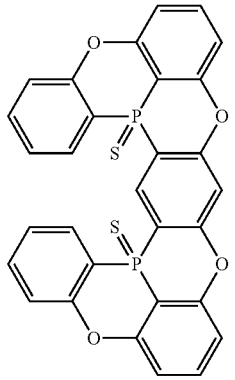

-continued
(1-725)
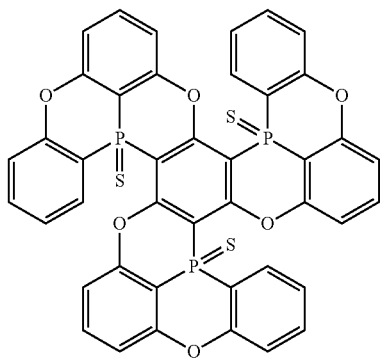
(1-731)
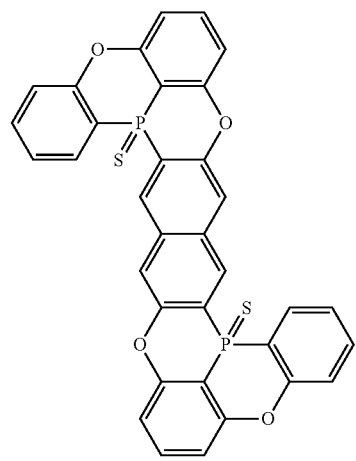
(1-732)
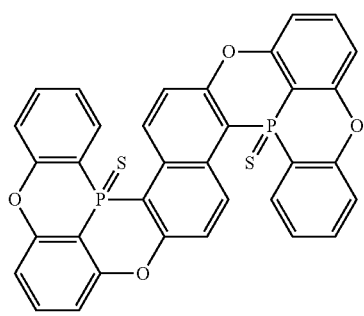
(1-733)
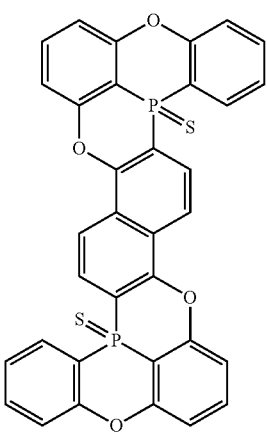
-continued
(1-734)
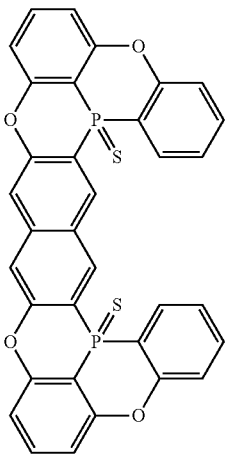
(1-735)
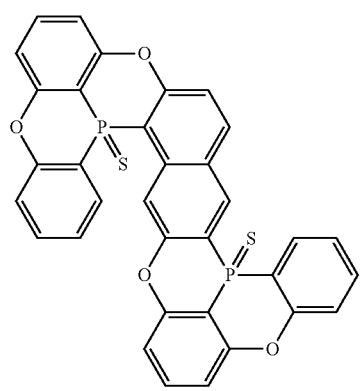
(1-736)
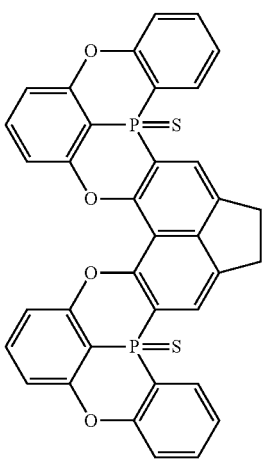

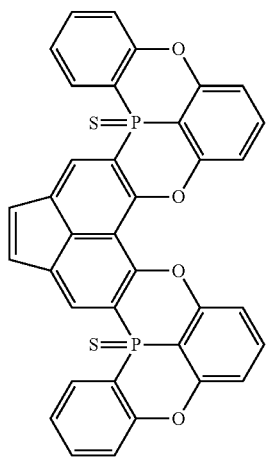
(1-737)
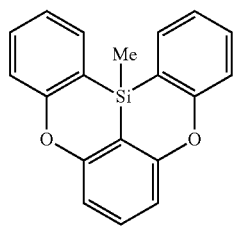
(1-801)
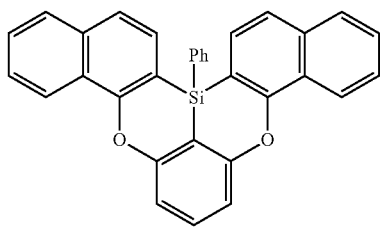
(1-802)
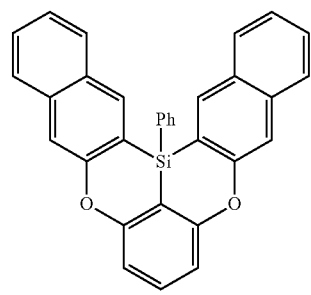
(1-803)
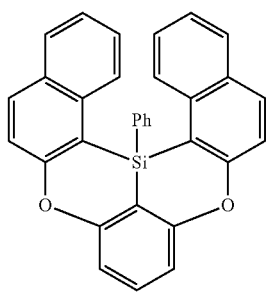
(1-804)
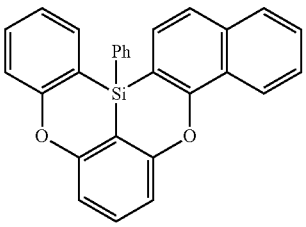
(1-805)
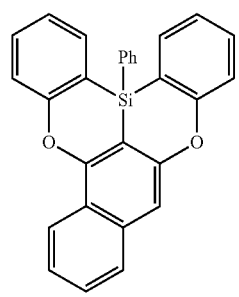
(1-806)
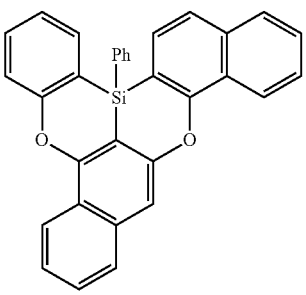
(1-807)
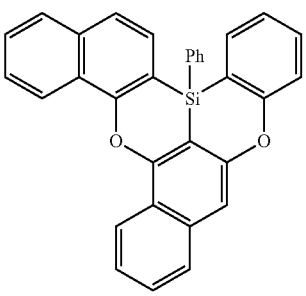
(1-808)
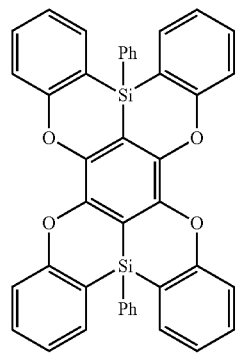
(1-821)

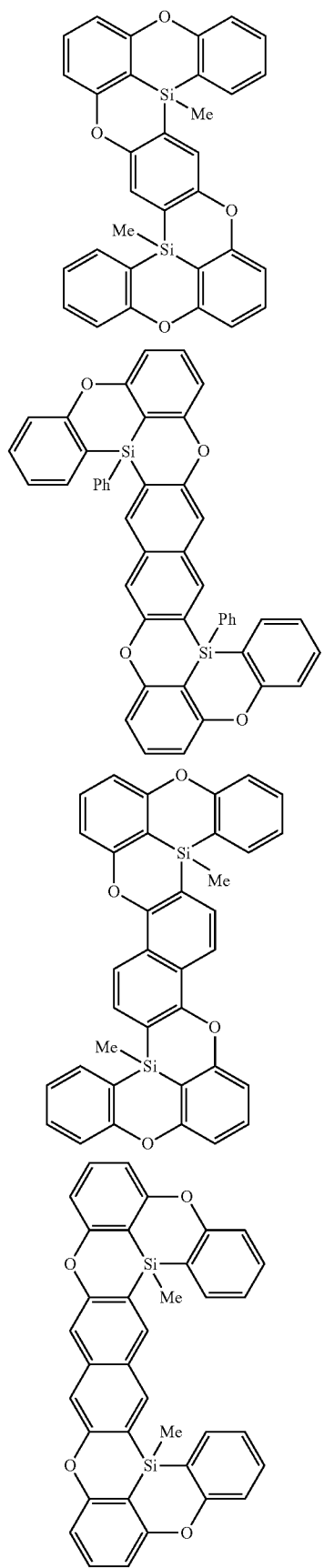

-continued
(1-1006)
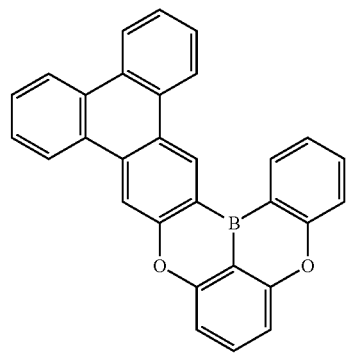
(1-1007)
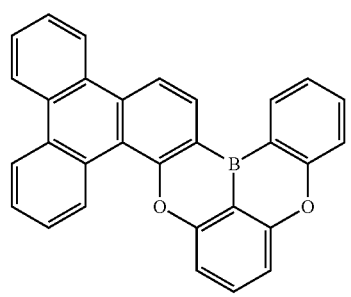
(1-1008)
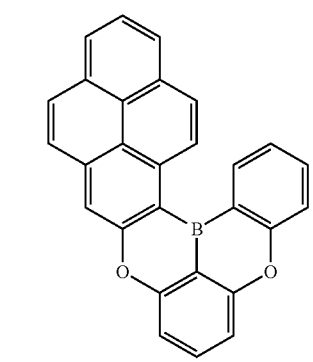
(1-1009)
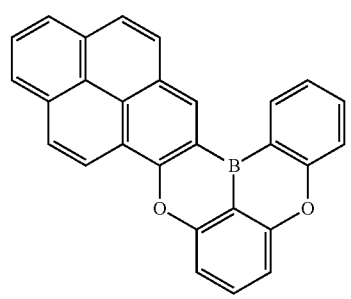
(1-1010)
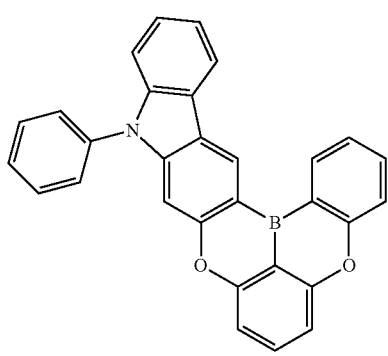
(1-1011)
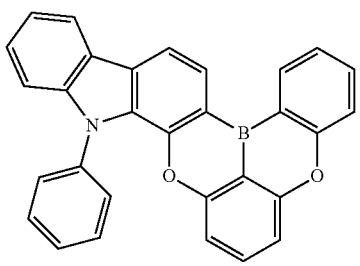
(1-1012)
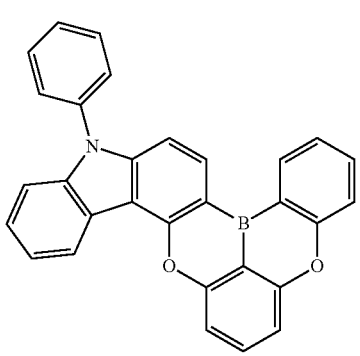
(1-1013)
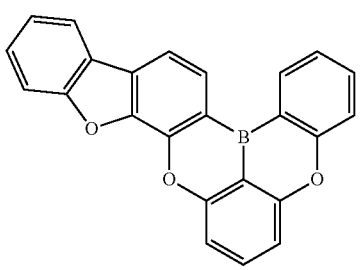
(1-1014)
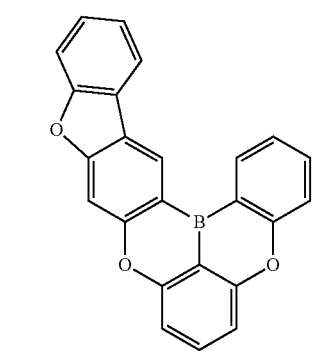
(1-1015)
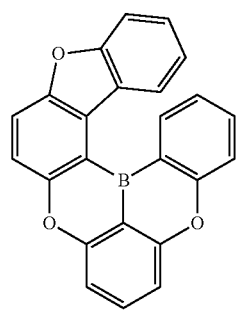

(1-1016)
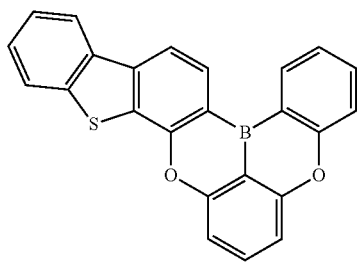
(1-1017)
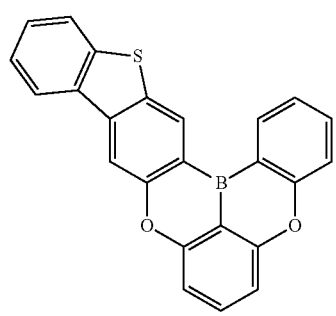
(1-1018)
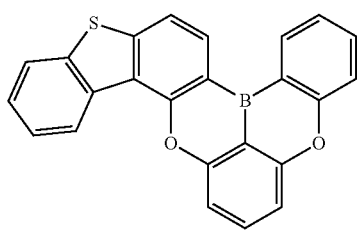
(1-1021)
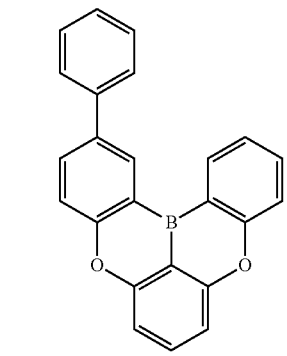
(1-1022)
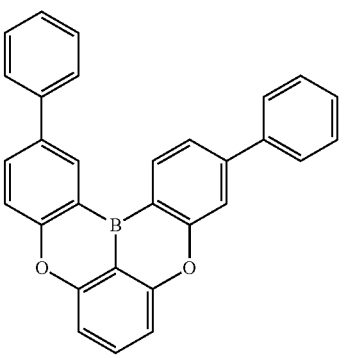
(1-1023)
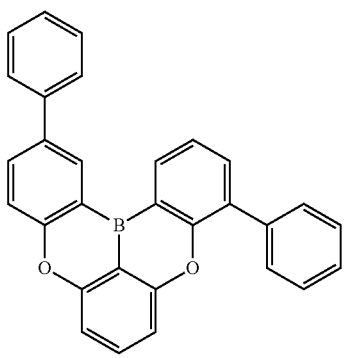
(1-1024)
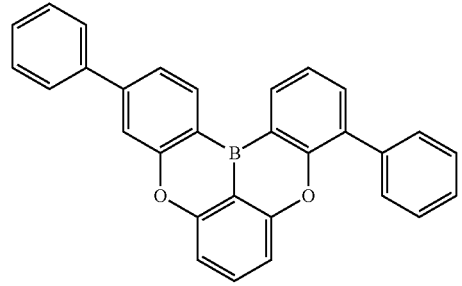
(1-1025)
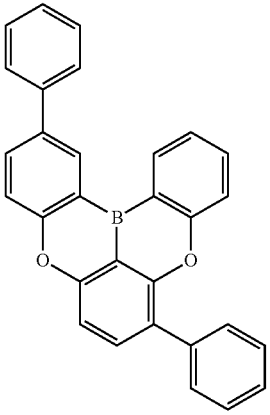
(1-1026)
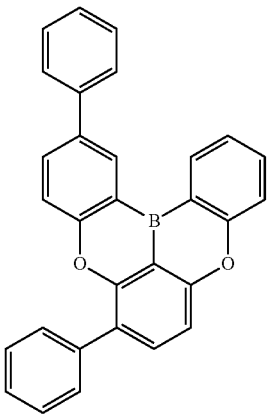

(1-1027)
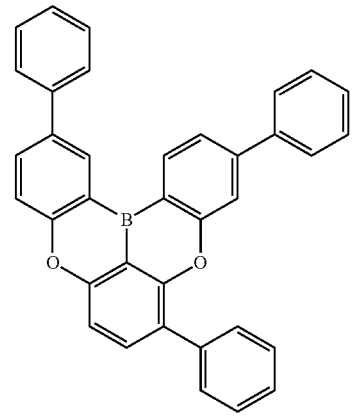
(1-1028)
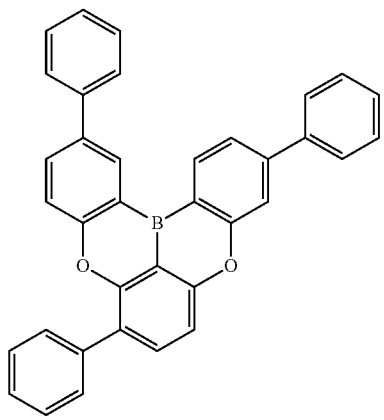
(1-1029)
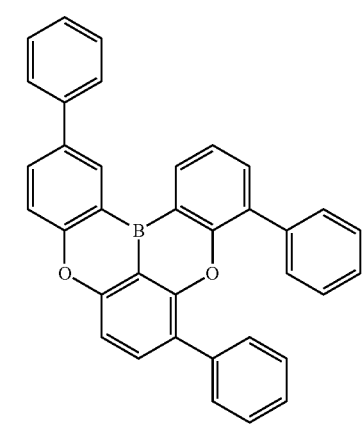
(1-1030)
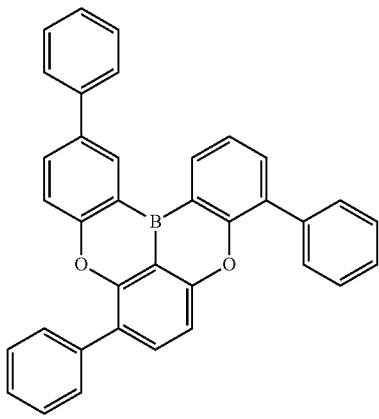
(1-1031)
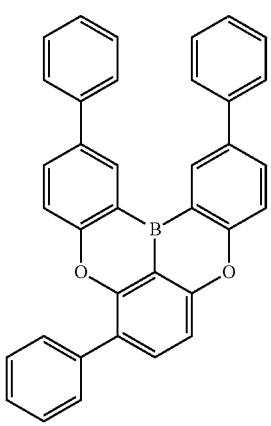
(1-1032)
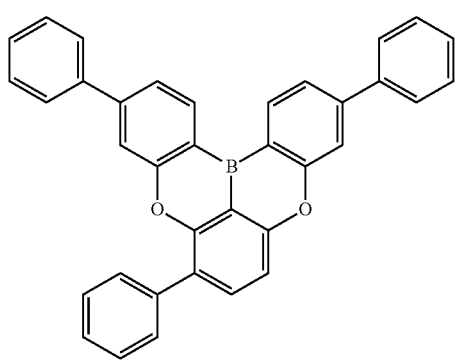
(1-1033)
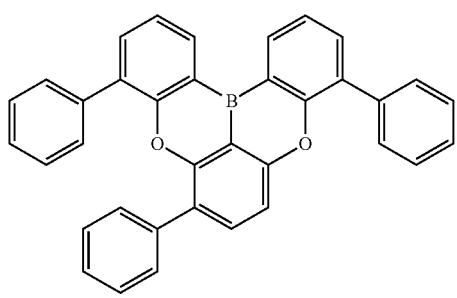

(1-1034)
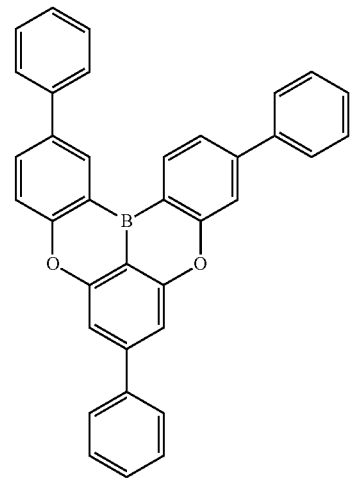
(1-1035)
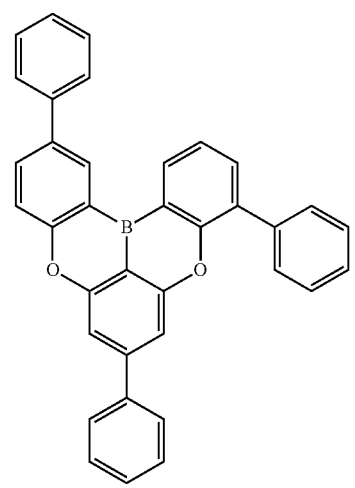
(1-1036)
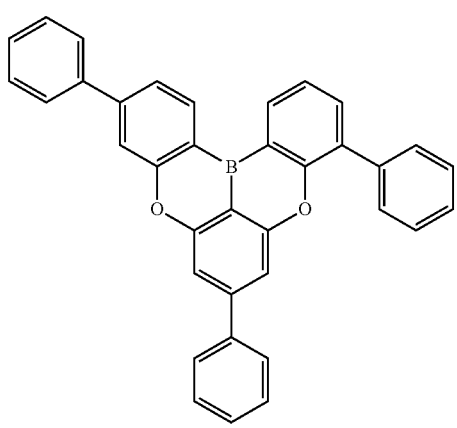
(1-1037)
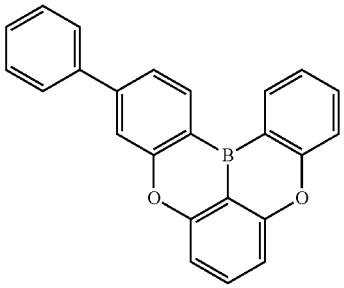
(1-1038)
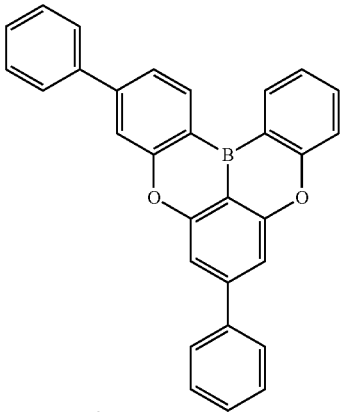
(1-1039)
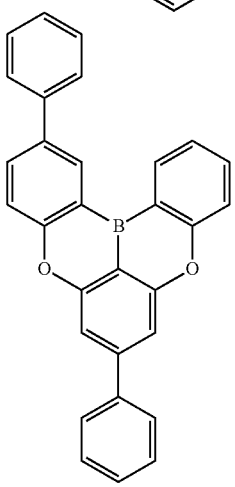
(1-1041)
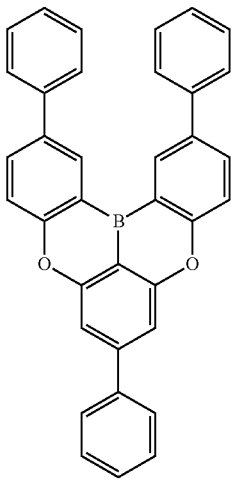

(1-1042)
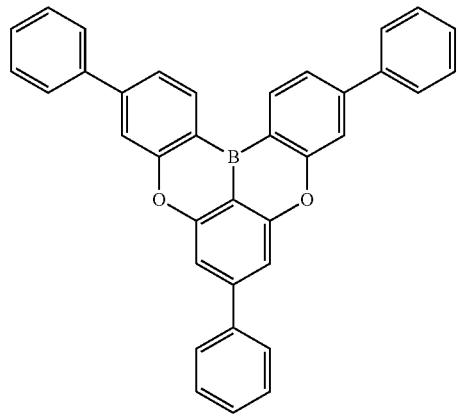
(1-1043)
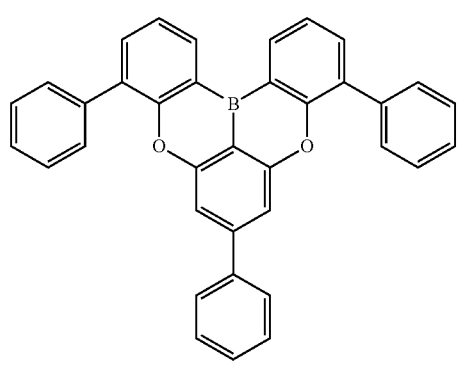
(1-1044)
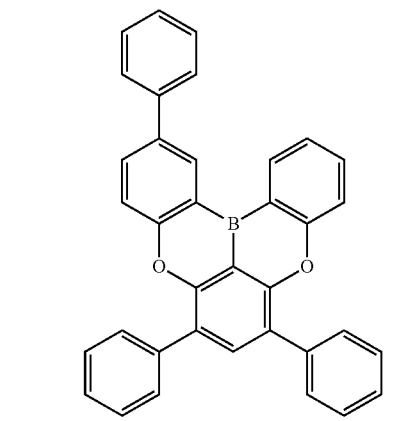
(1-1045)
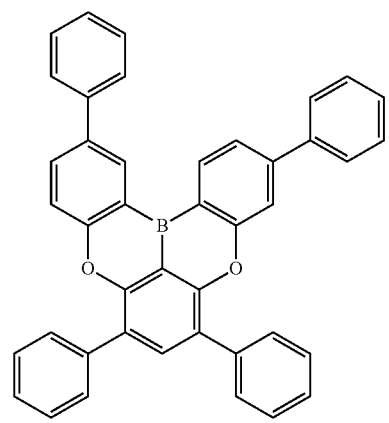
(1-1046)
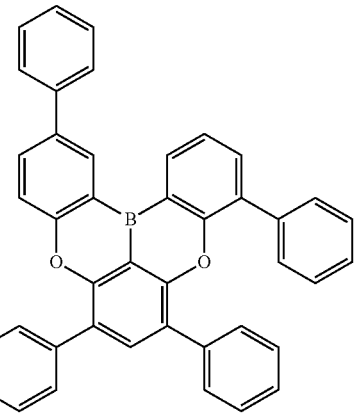
(1-1047)
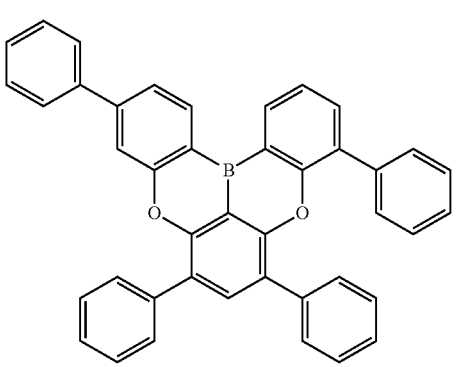
(1-1048)
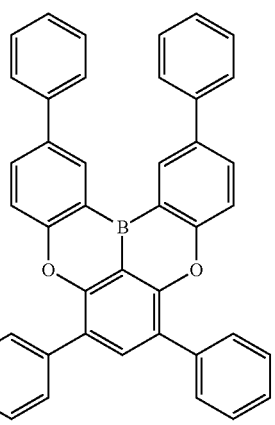
(1-1049)
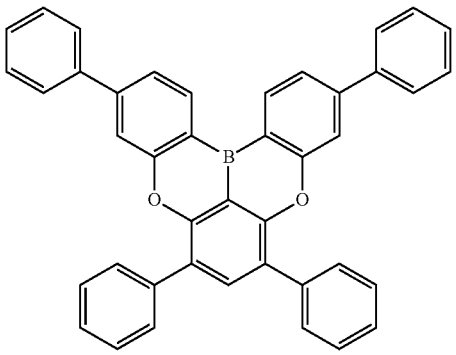

(1-1050)
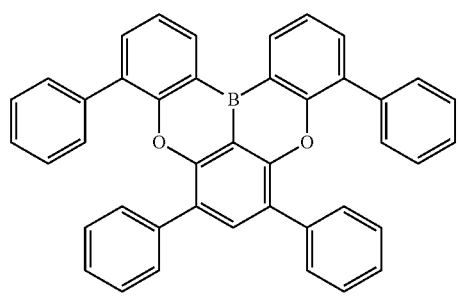
(1-1061)
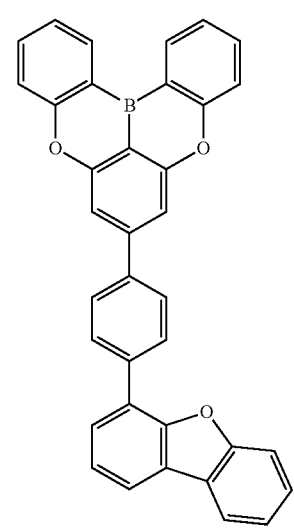
(1-1062)
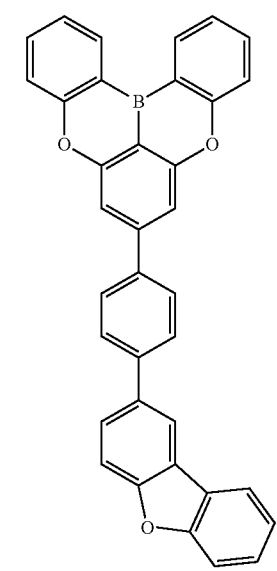
(1-1063)
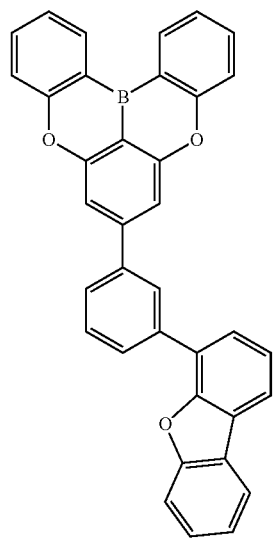
(1-1064)
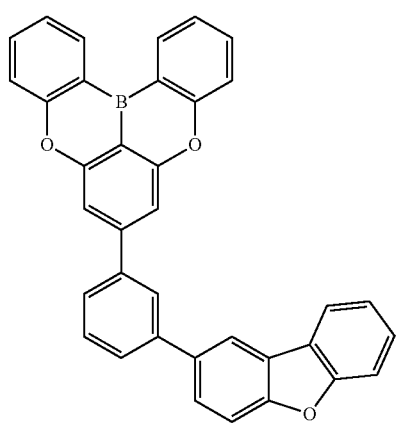
(1-1065)
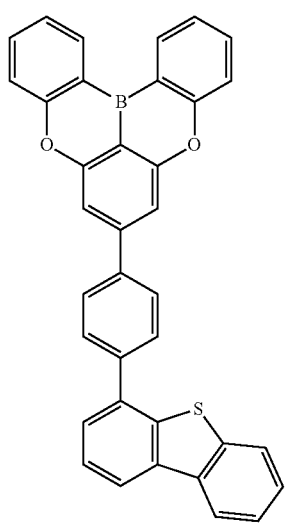

(1-1066)
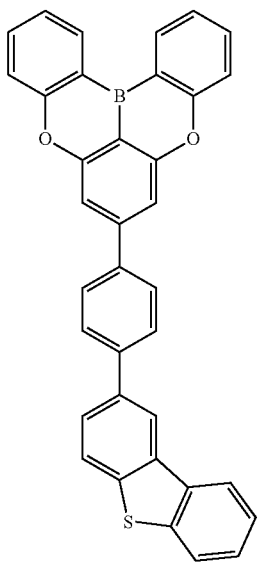
(1-1067)
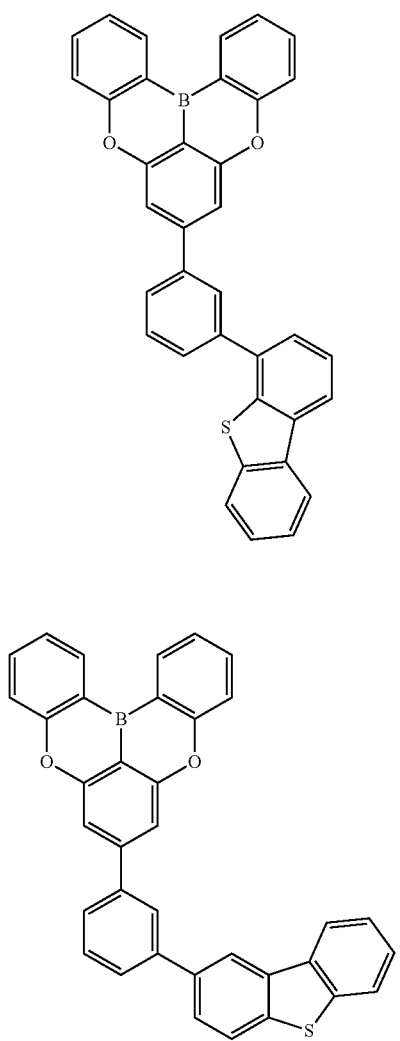
(1-1068)
(1-1069)
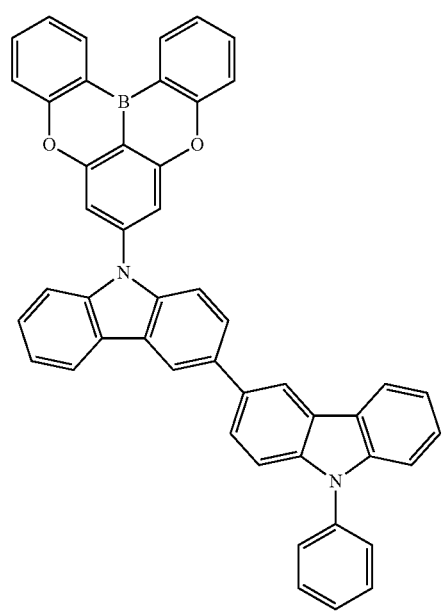
(1-1070)
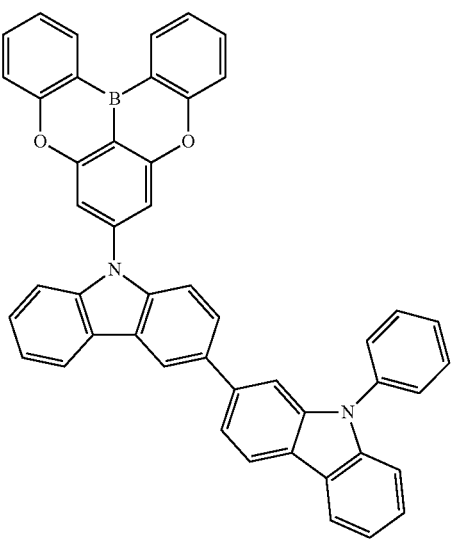
(1-1071)
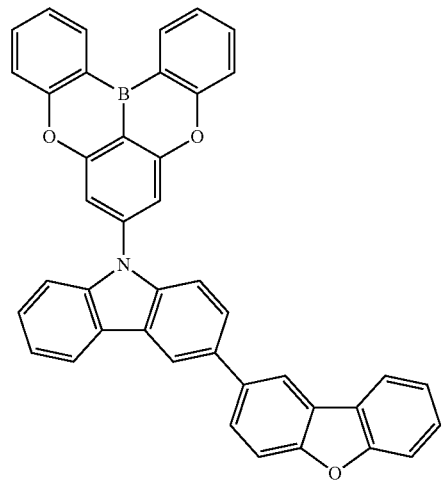

(1-1072)
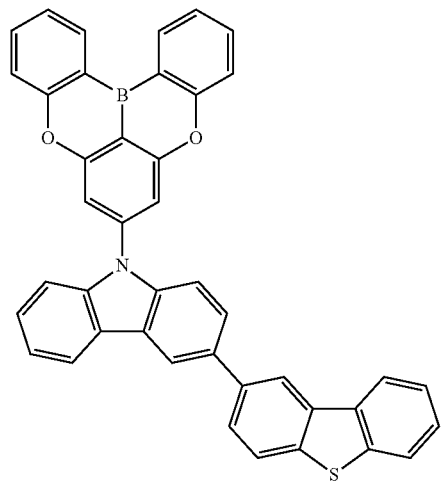
(1-1081)
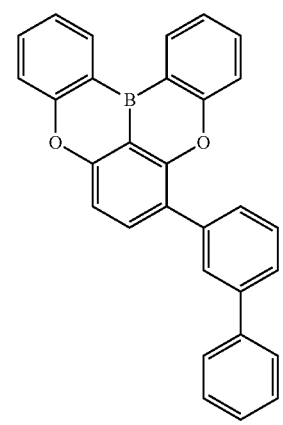
(1-1082)
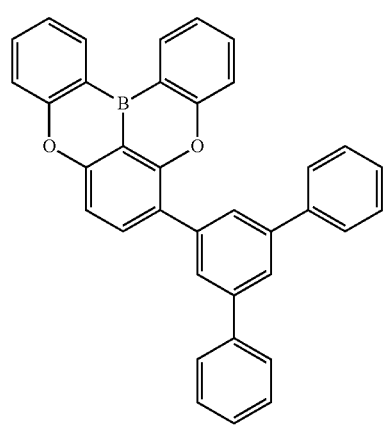
(1-1083)
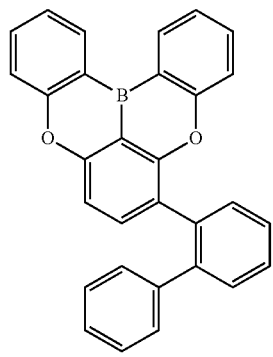
(1-1084)
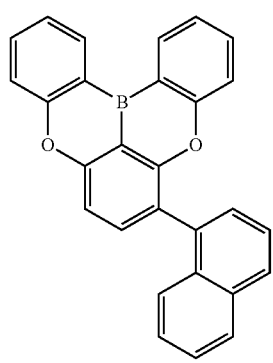
(1-1085)
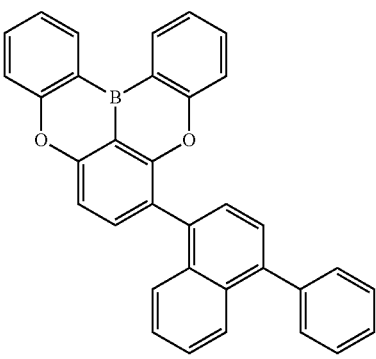
(1-1086)
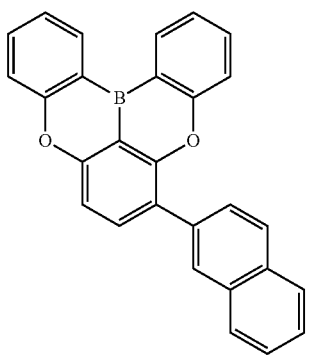

(1-1087)
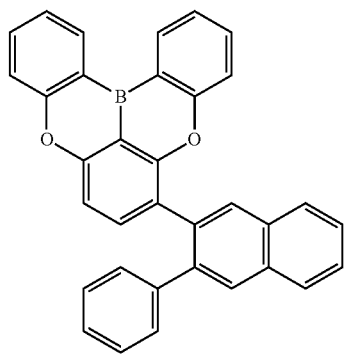
(1-1088)
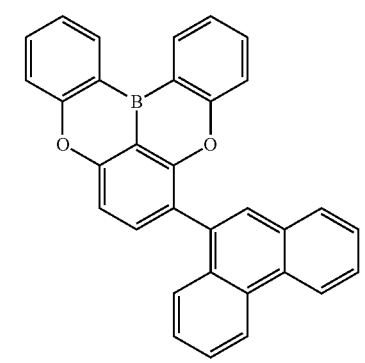
(1-1089)
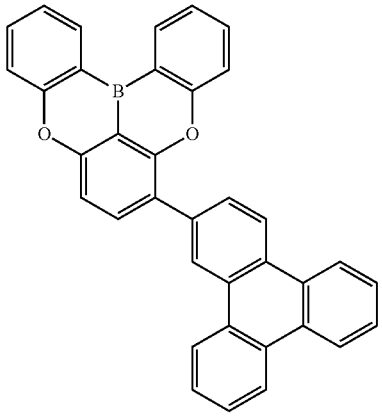
(1-1090)
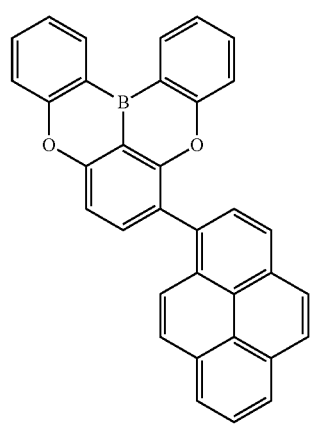
(1-1091)
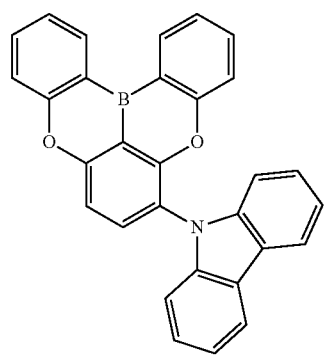
(1-1092)
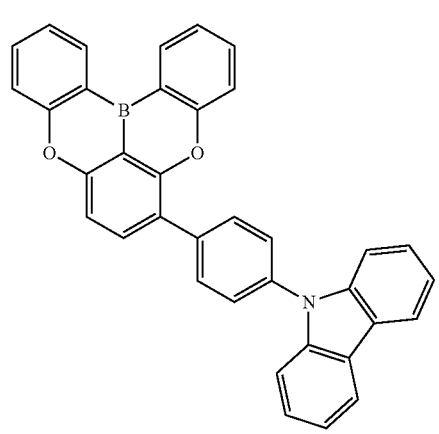
(1-1093)
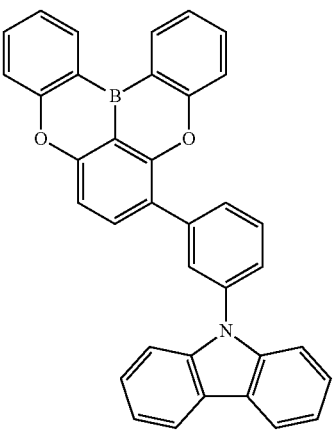
(1-1094)
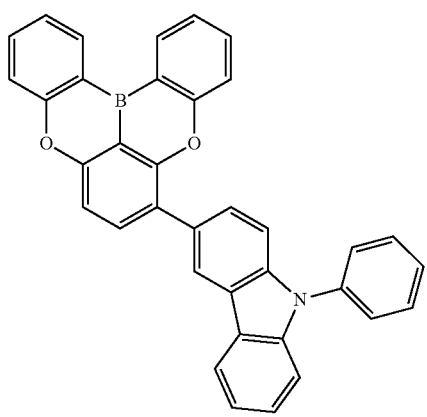

(1-1095)
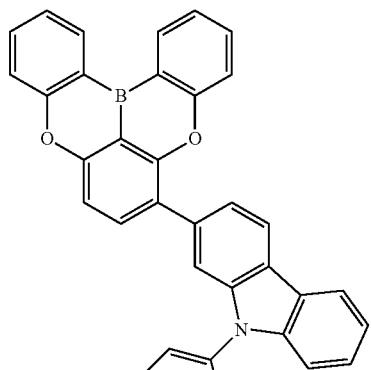
(1-1096)
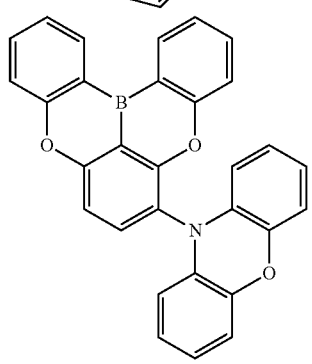
(1-1101)
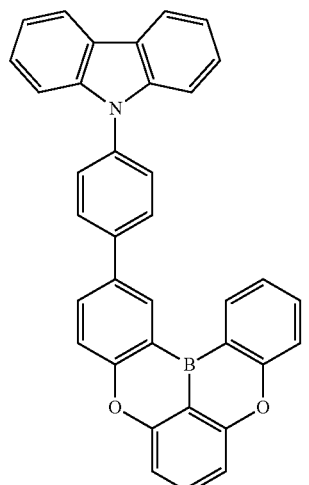
(1-1102)
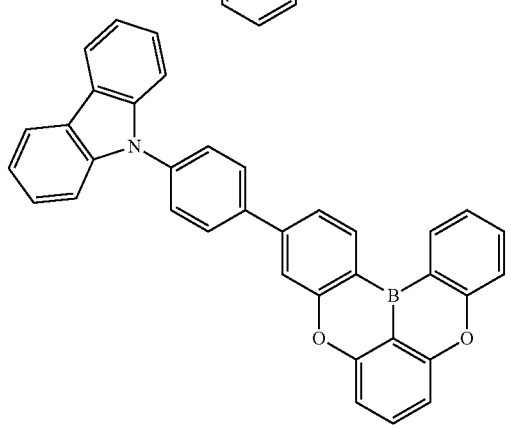
(1-1103)
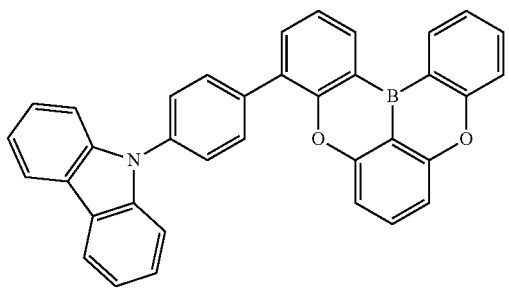
(1-1104)
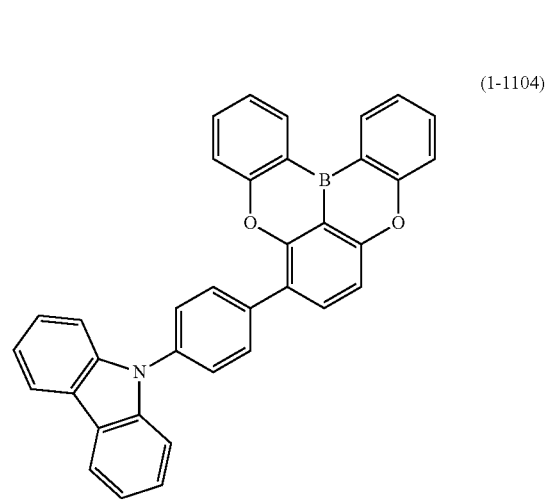
(1-1105)
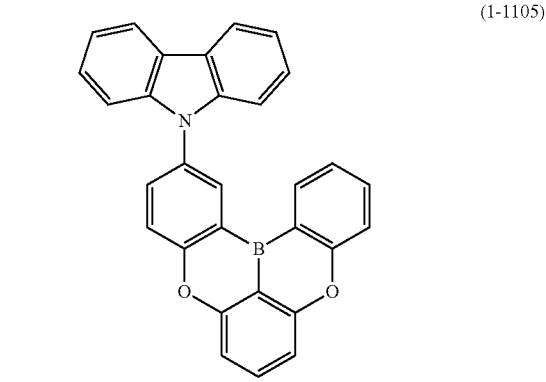
(1-1106)
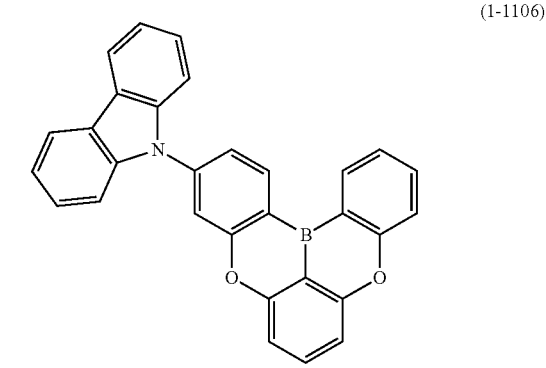

(1-1107)
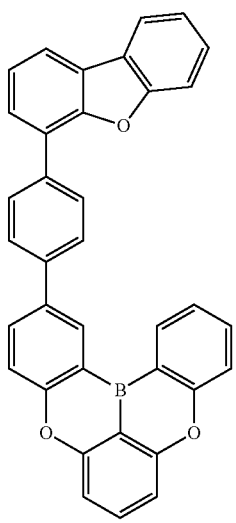
(1-1108)
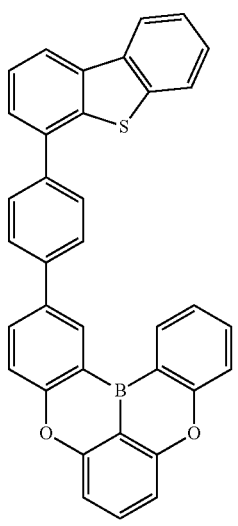
(1-1109)
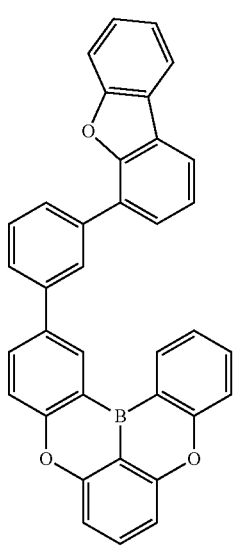
(1-1110)
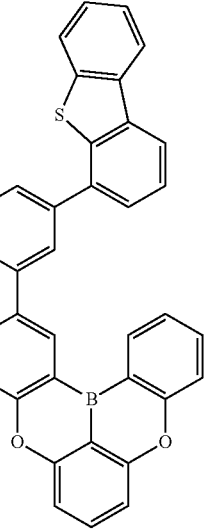
(1-1111)
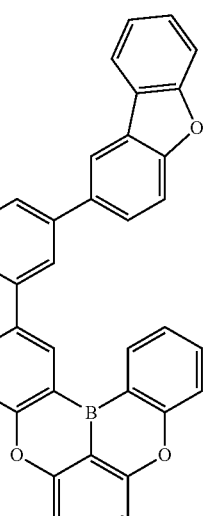
(1-1112)
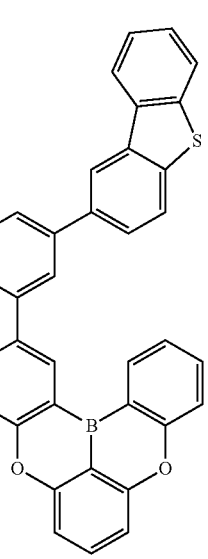

(1-1113)
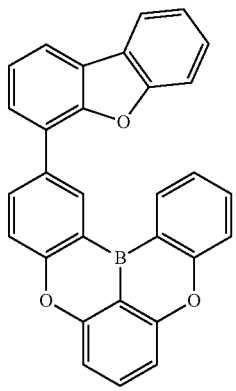
(1-1114)
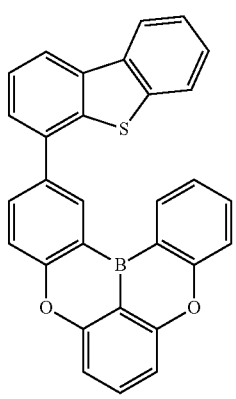
(1-1121)
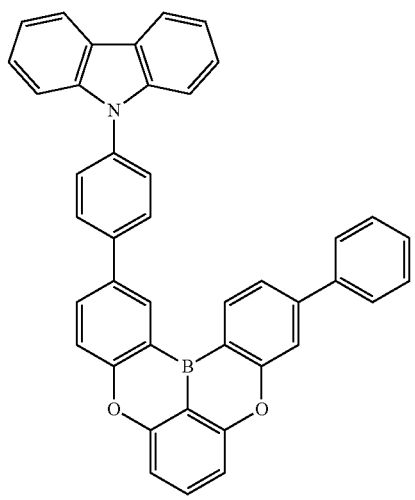
(1-1122)
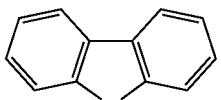
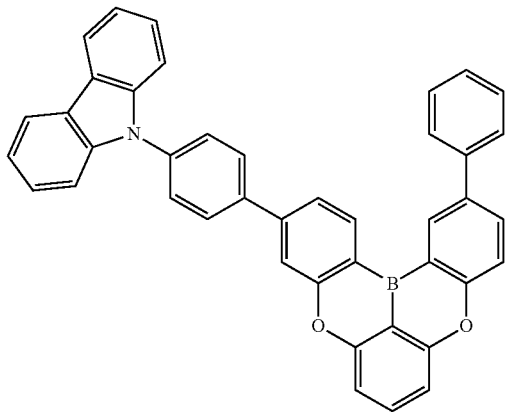
(1-1123)
(1-1124)
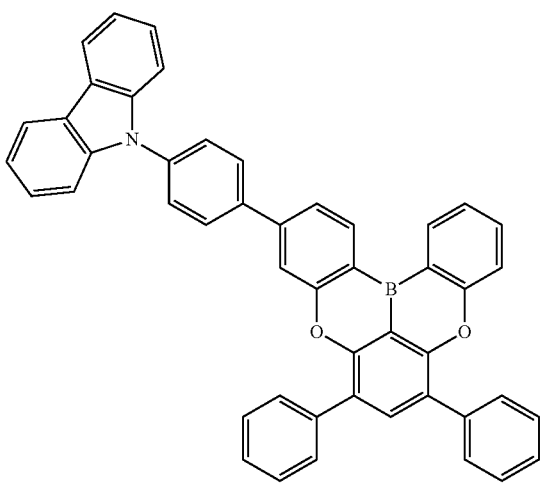

-continued
(1-1125)
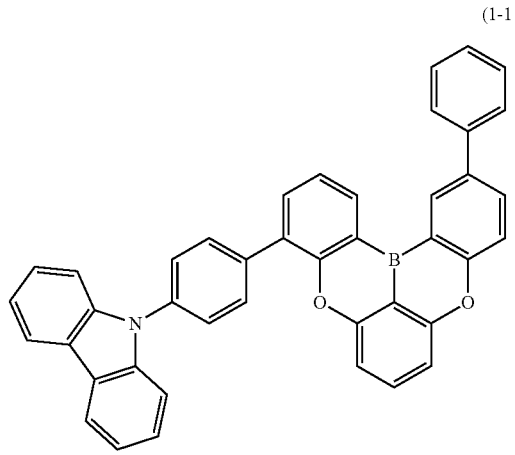
(1-1126)
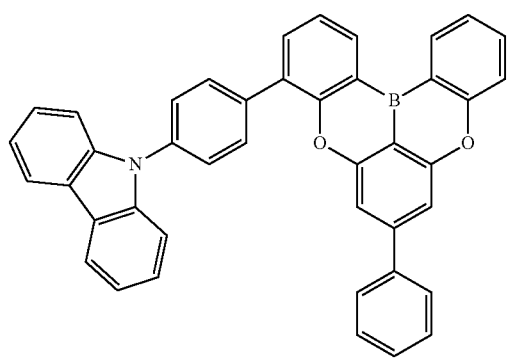
(1-1127)
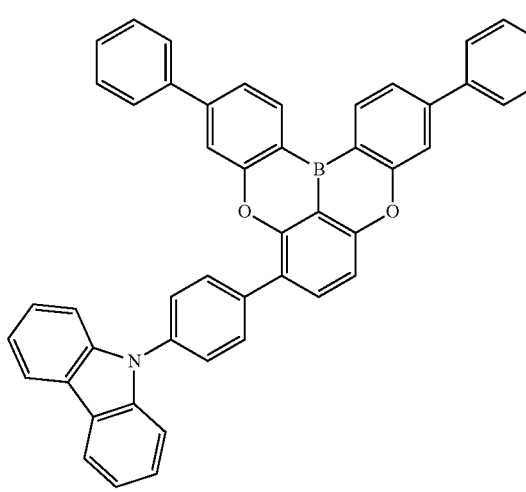
(1-1128)
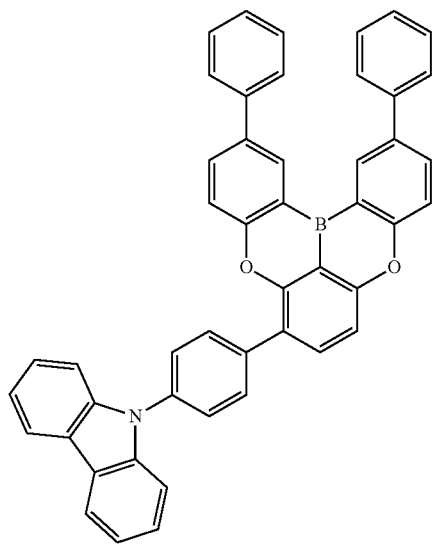
(1-1129)
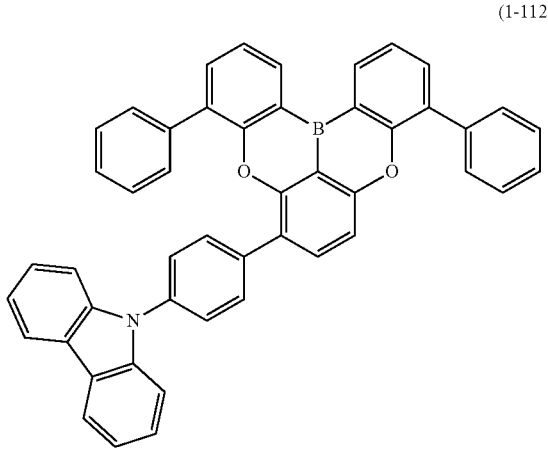
(1-1130)
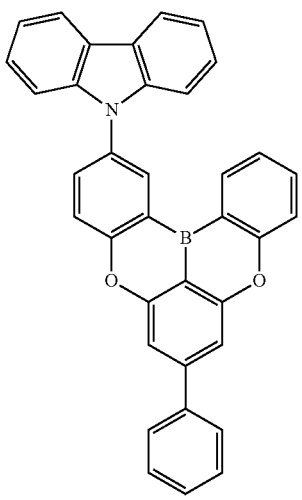

(1-1131)
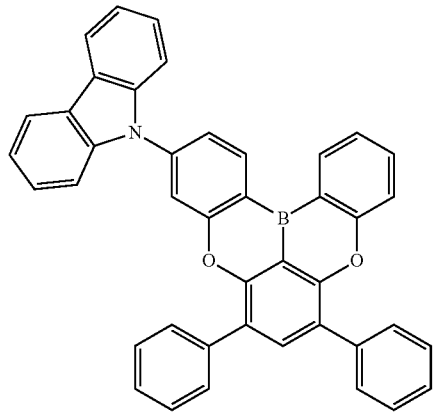
(1-1132)
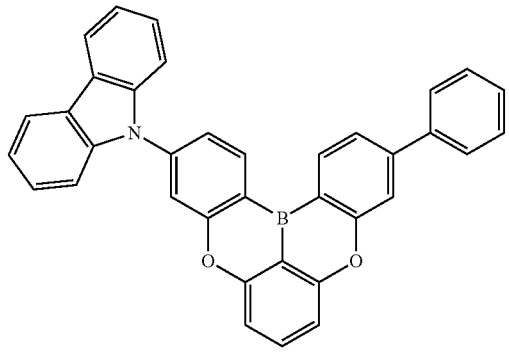
(1-1141)
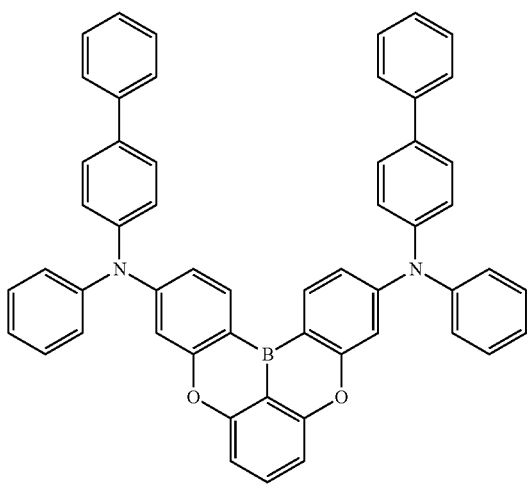
(1-1142)
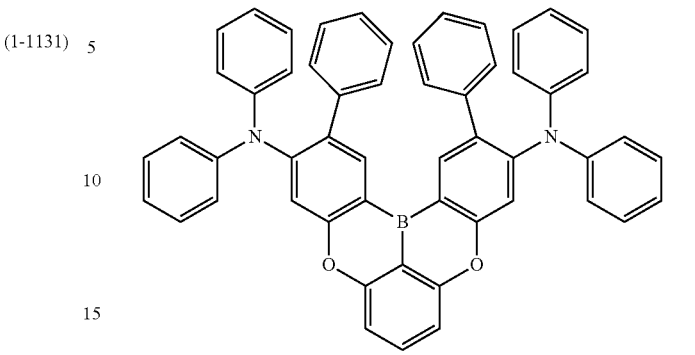
(1-1143)
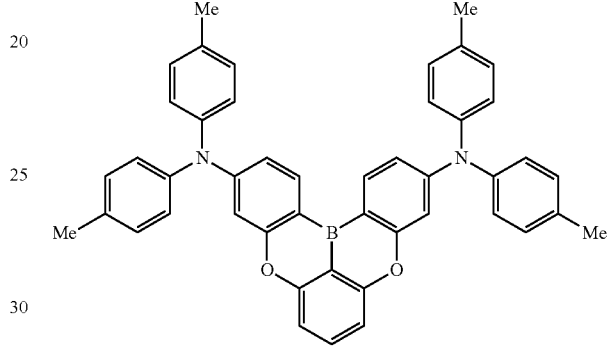
(1-1144)
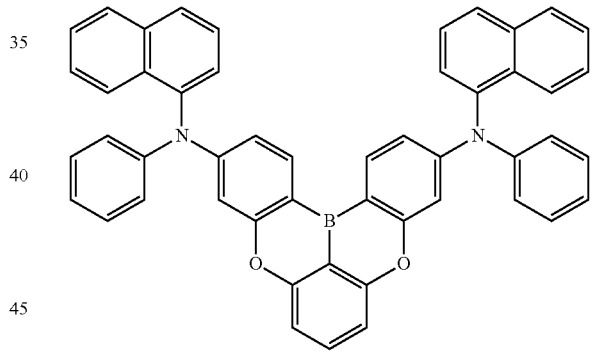
(1-1145)
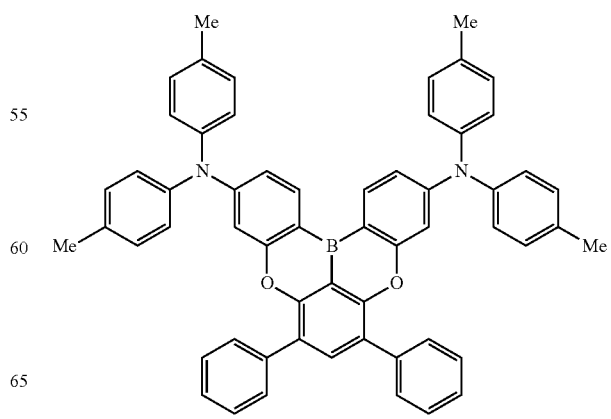

-continued
(1-1146)
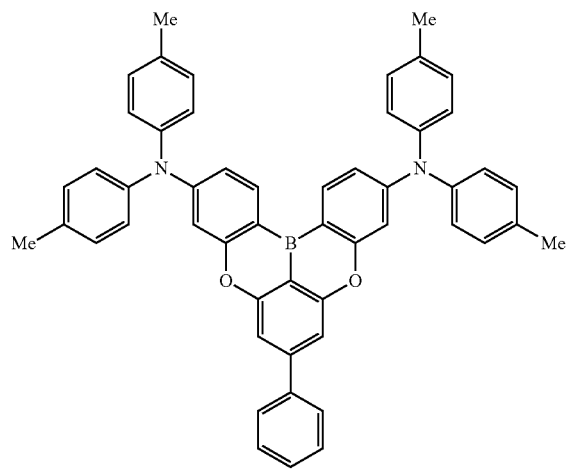
(1-1147)
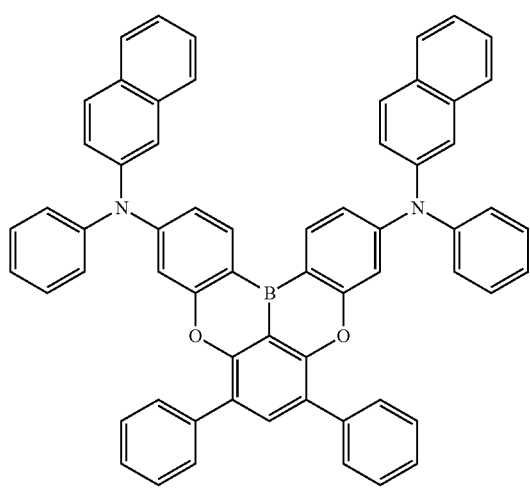
(1-1148)
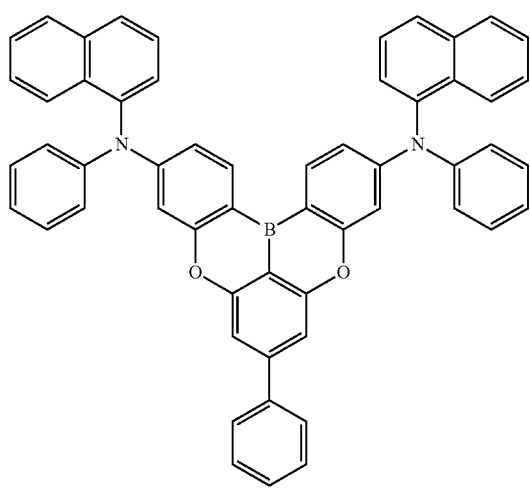
-continued
(1-1151)
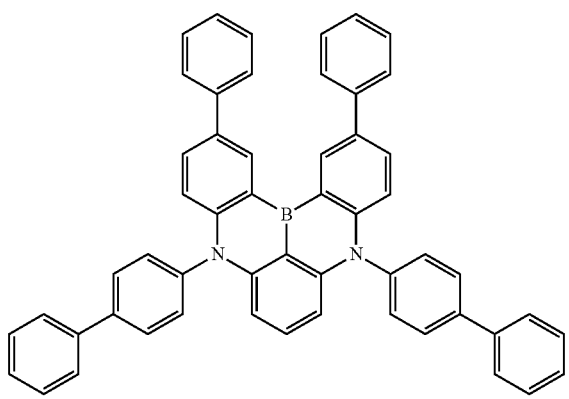
(1-1152)
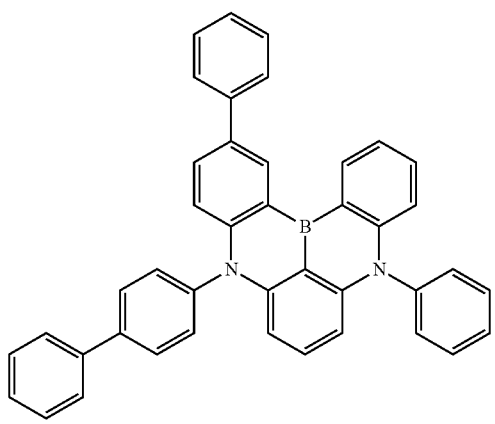
(1-1153)
(1-1154)
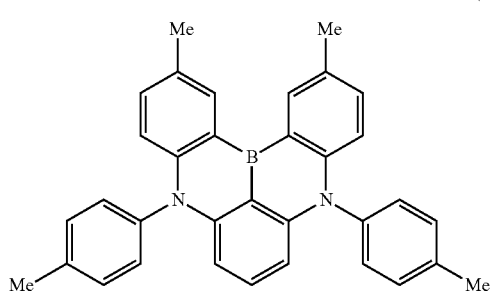

-continued
(1-1155)
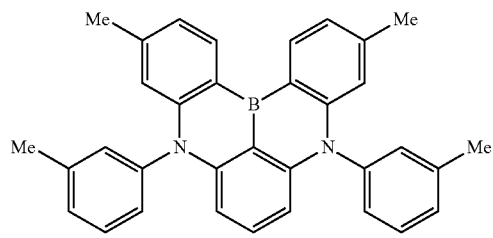
(1-1156)
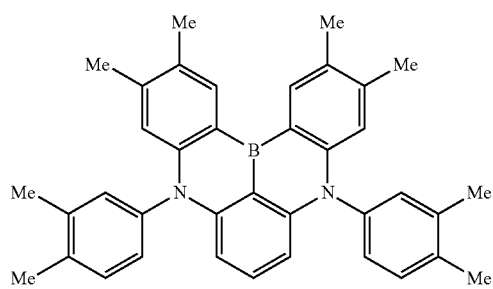
(1-1157)
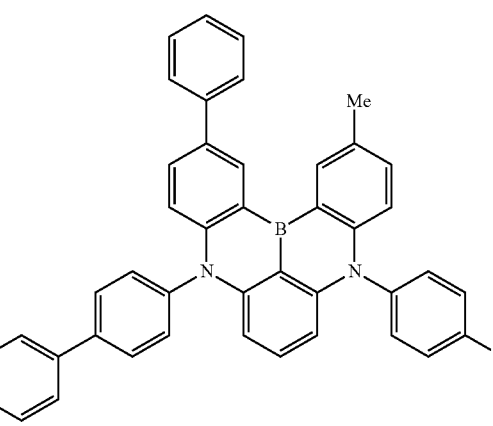
(1-1158)
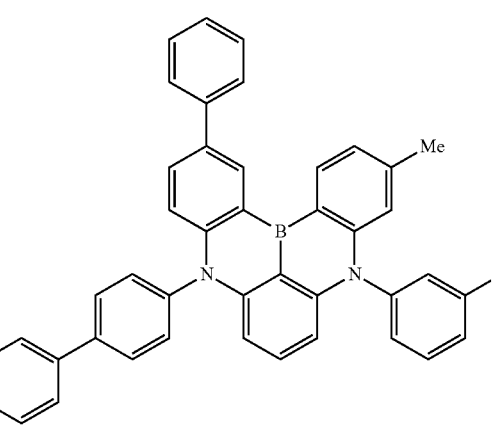
(1-1159)
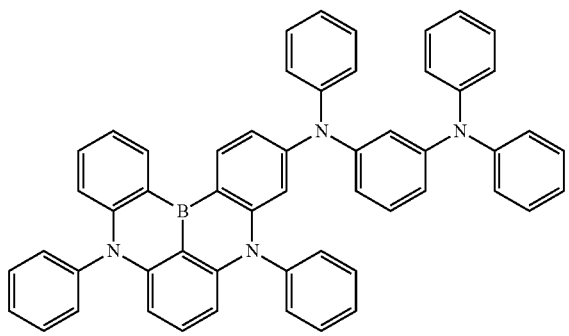
(1-1161)
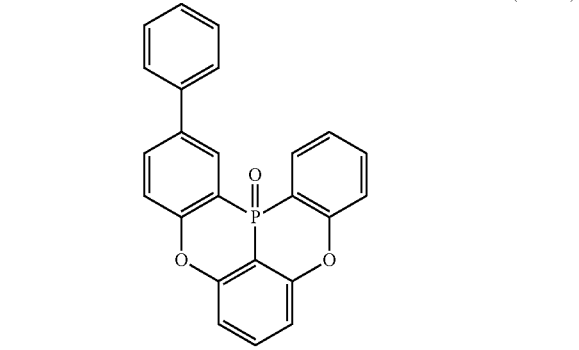
(1-1162)
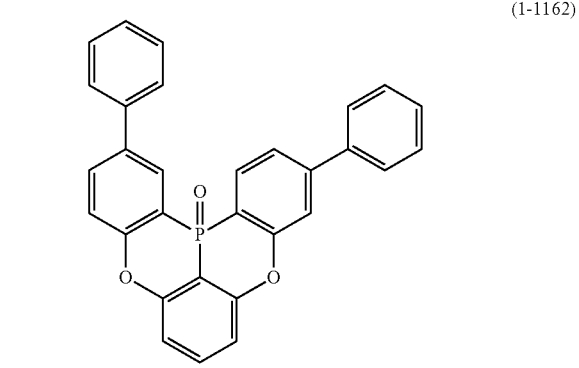
(1-1163)
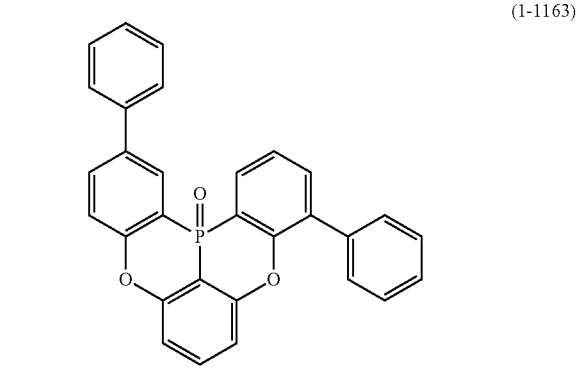

(1-1164)
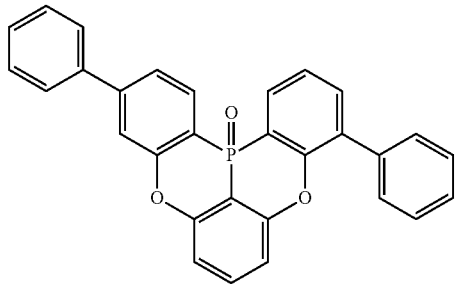
(1-1165)
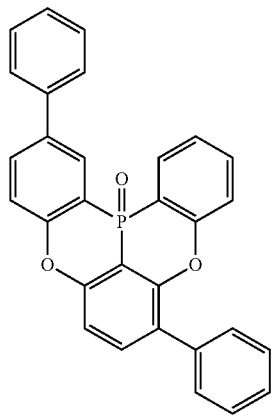
(1-1166)
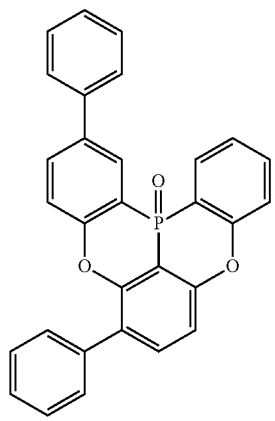
(1-1167)
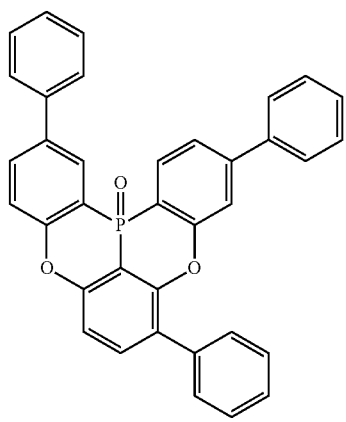
(1-1168)
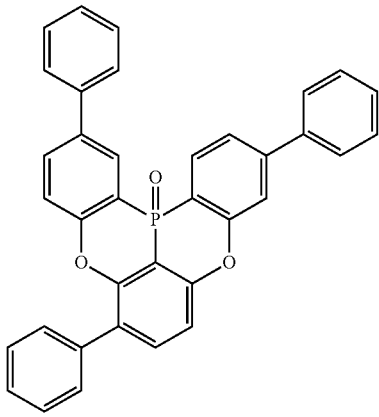
(1-1169)
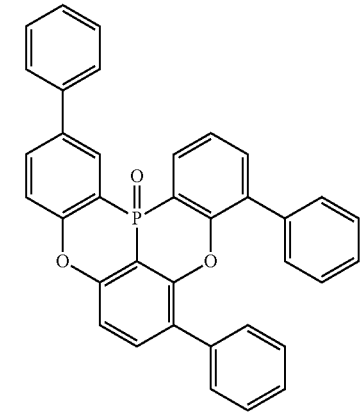
(1-1170)
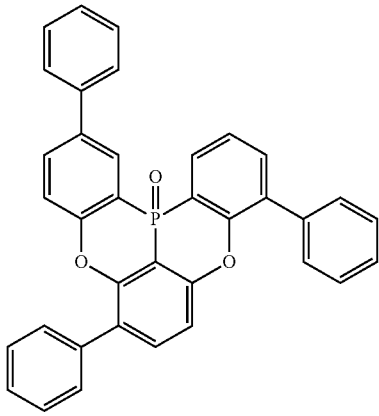
(1-1171)
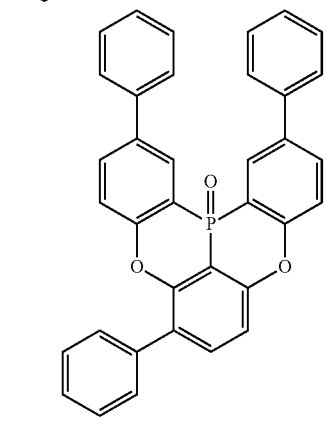

(1-1172)
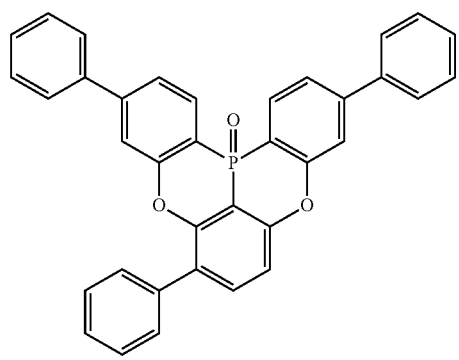
(1-1173)
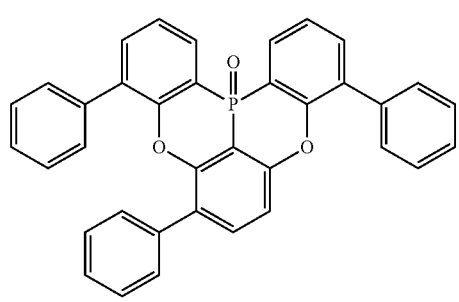
(1-1174)
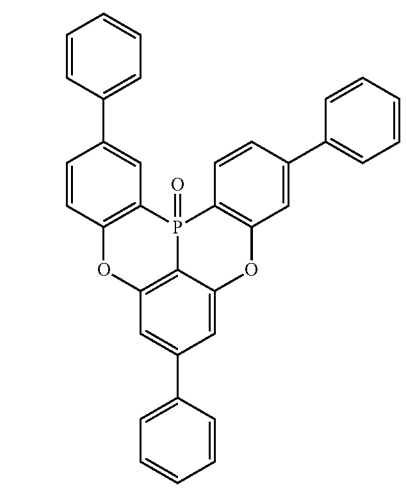
(1-1175)
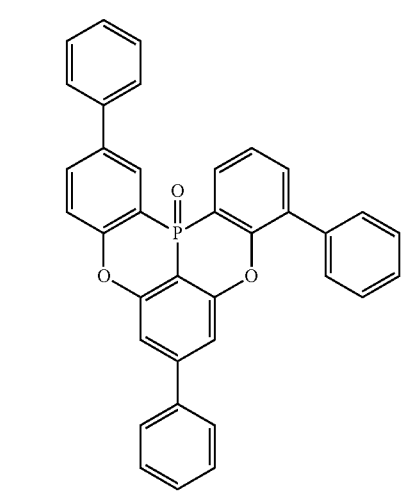
(1-1176)
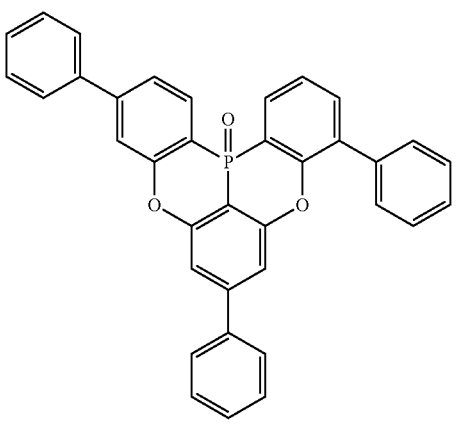
(1-1177)
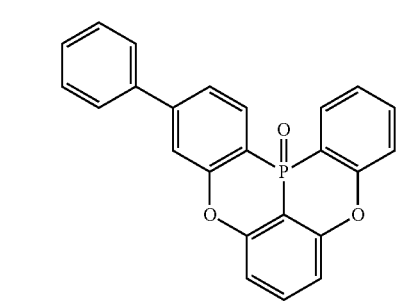
(1-1178)
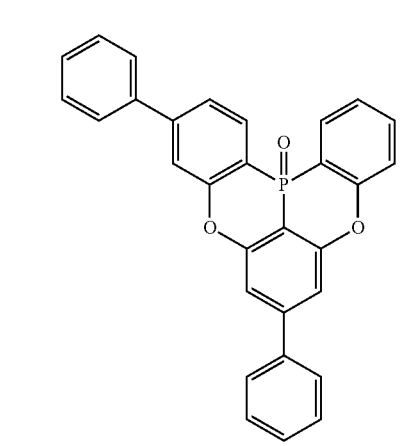
(1-1179)
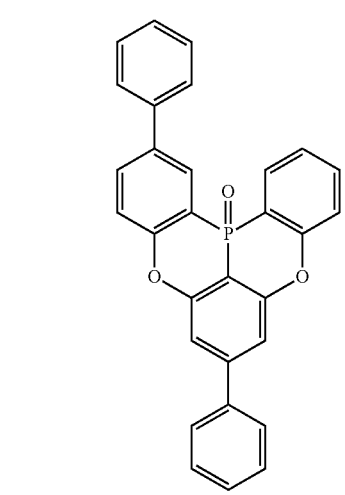

(1-1181)
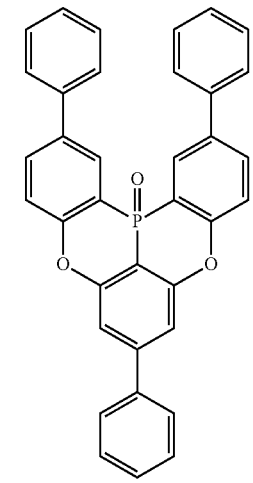
(1-1182)
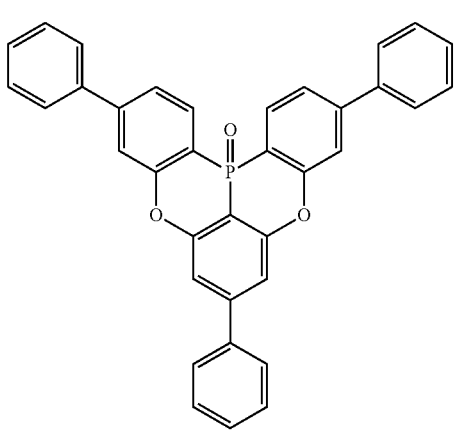
(1-1183)
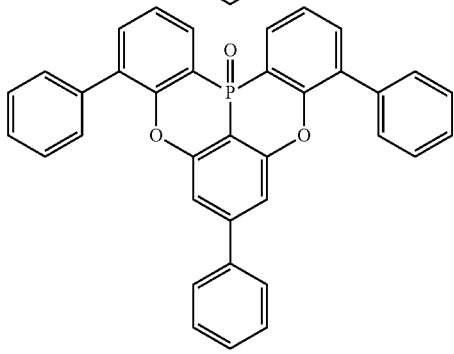
(1-1184)
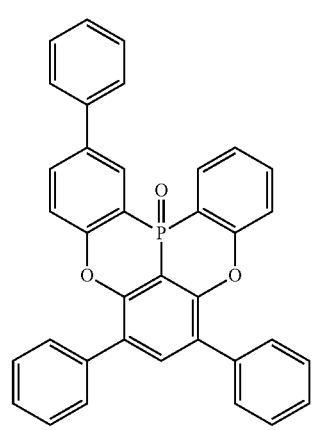
(1-1185)
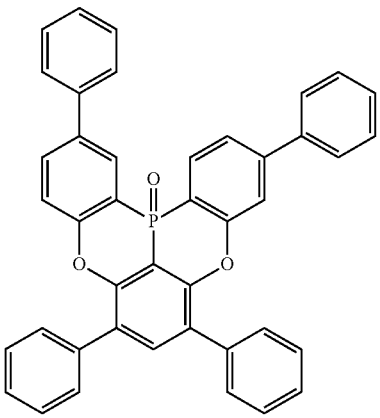
(1-1186)
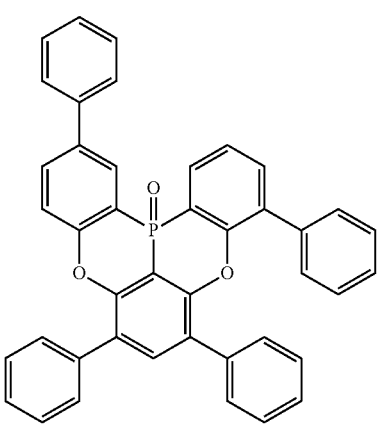
(1-1187)
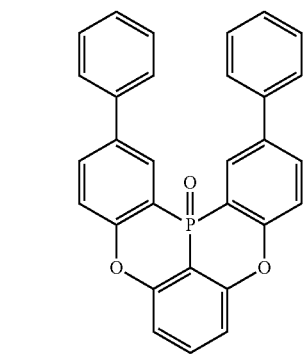
(1-1188)

(1-1189)
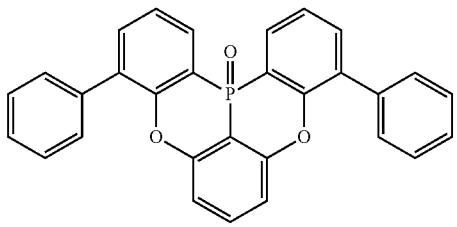
(1-1190)
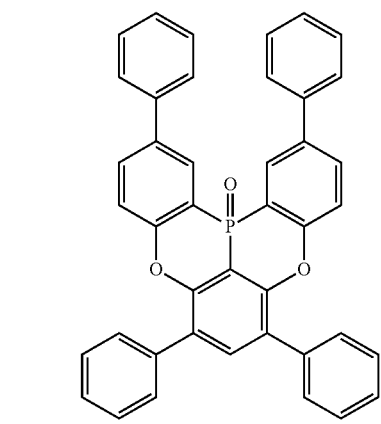
(1-1191)
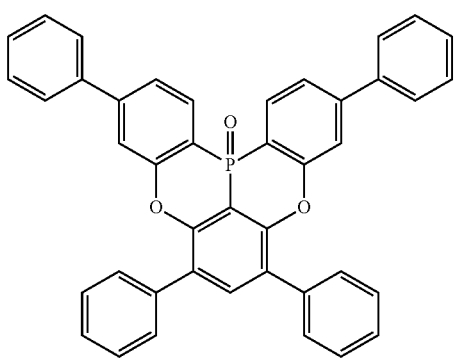
(1-1192)
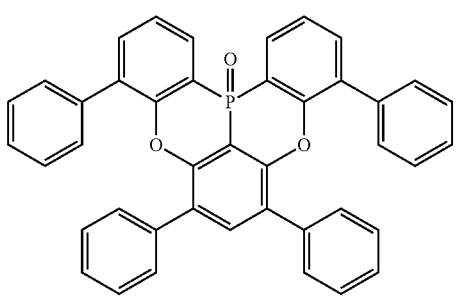
(1-1201)
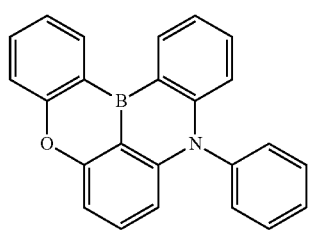
(1-1202)
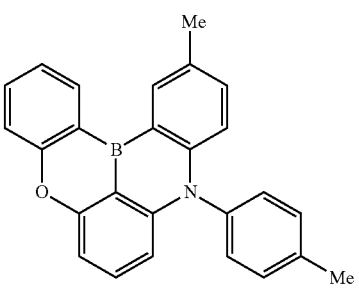
(1-1203)
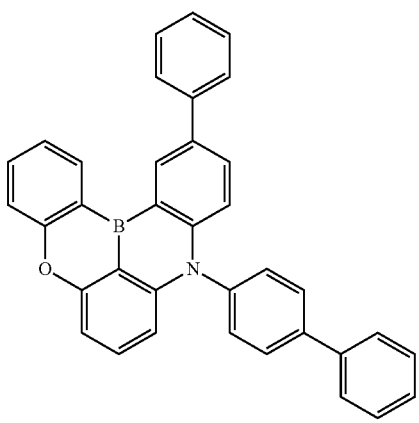
(1-1204)
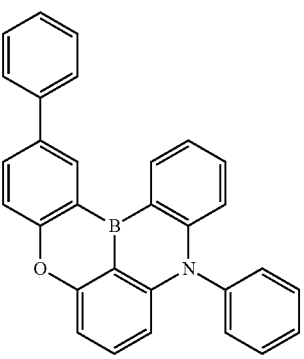
(1-1205)
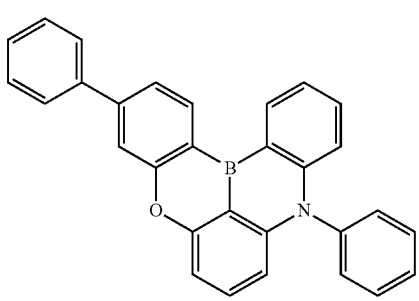

(1-1206)
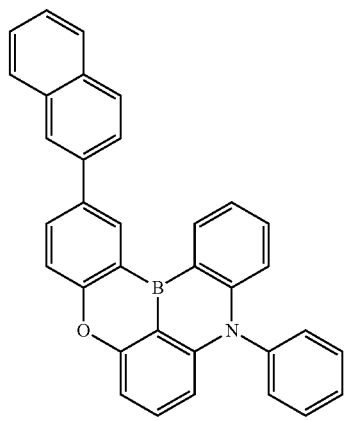
(1-1207)
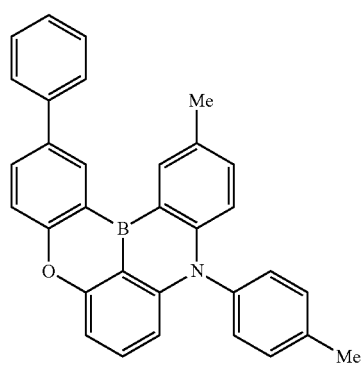
(1-1208)
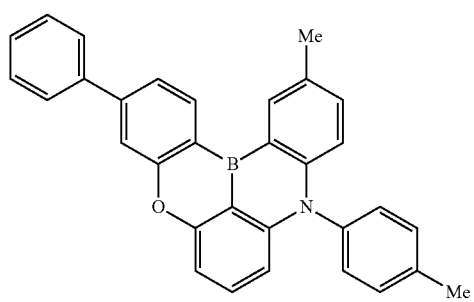
(1-1209)
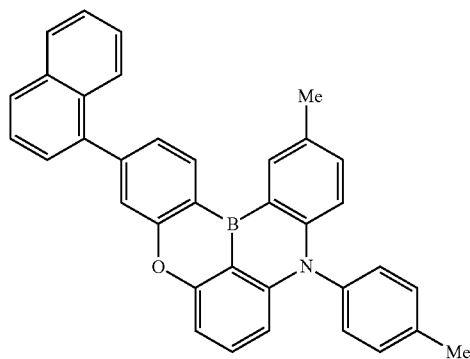
(1-1210)
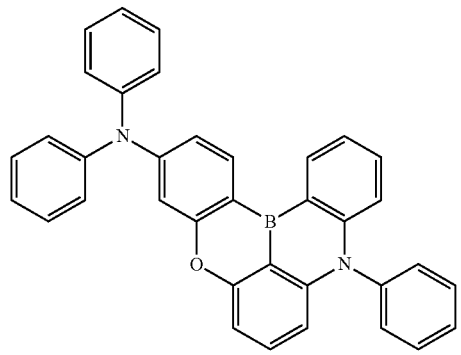
(1-1211)
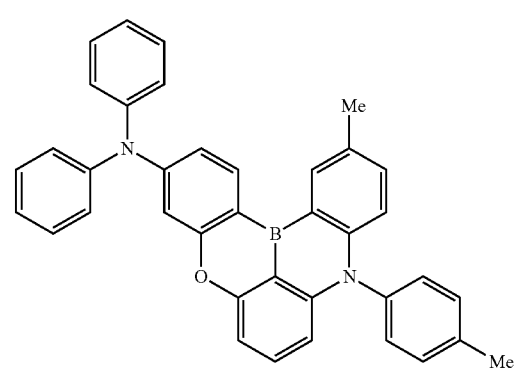
(1-1221)
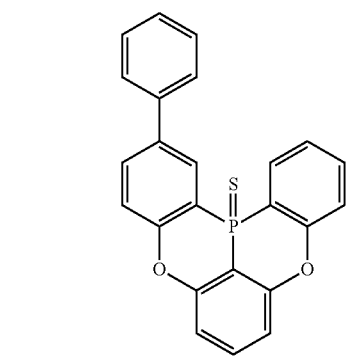
(1-1222)
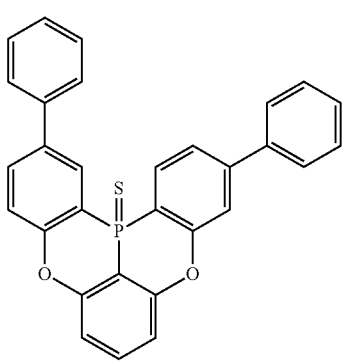

(1-1223)
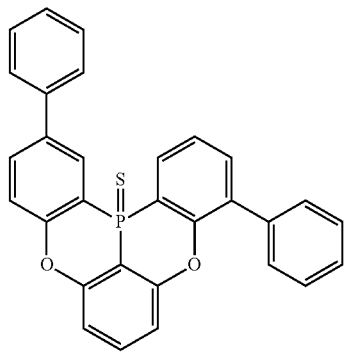
(1-1224)
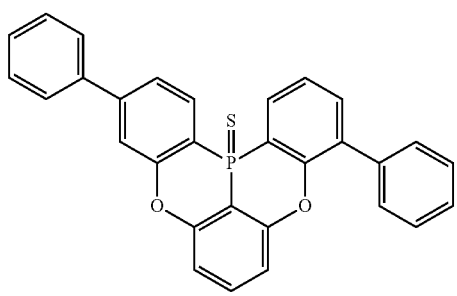
(1-1225)
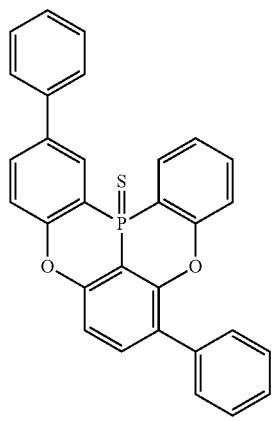
(1-1226)
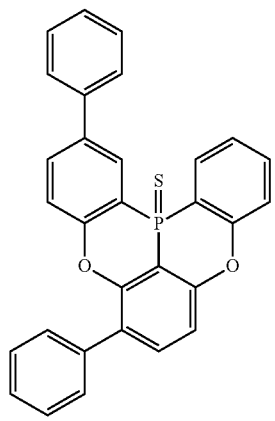
(1-1227)
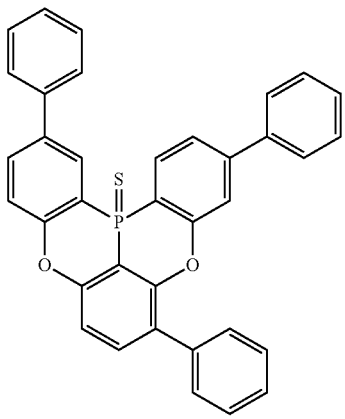
(1-1228)
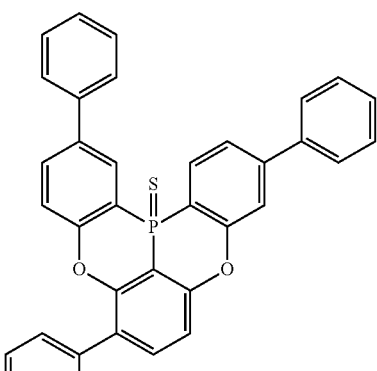
(1-1229)
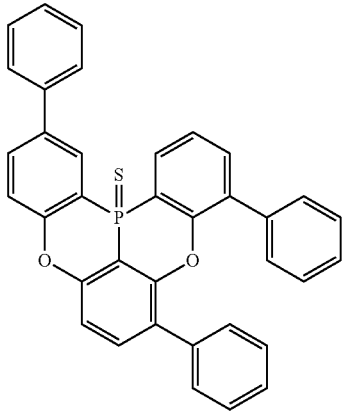
(1-1230)
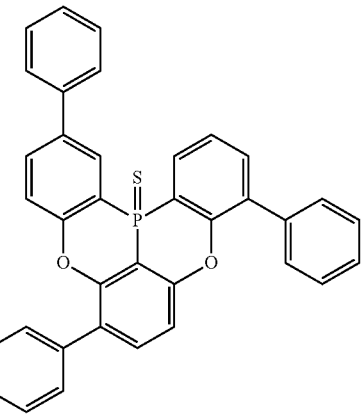

(1-1231)
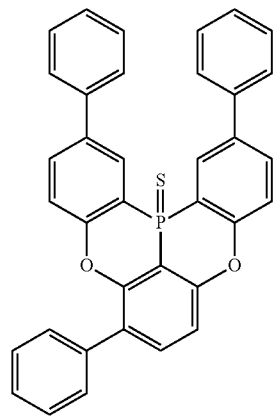
(1-1232)
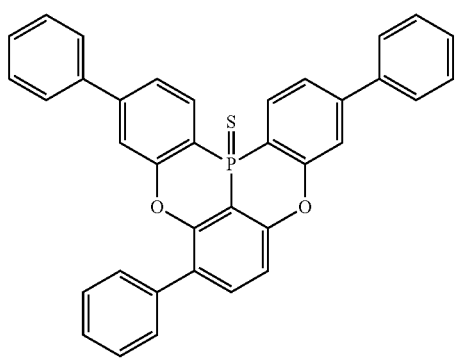
(1-1233)
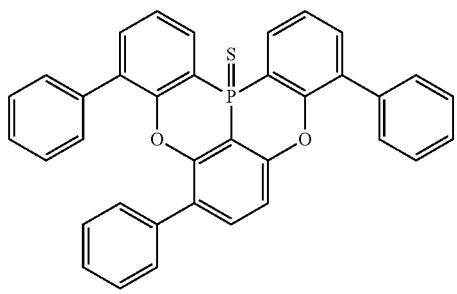
(1-1234)
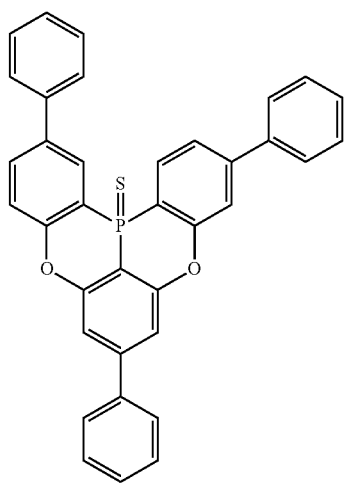
(1-1235)
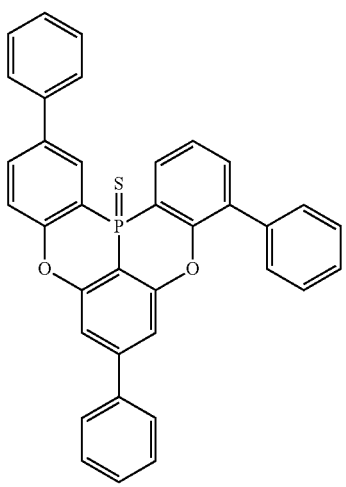
(1-1236)
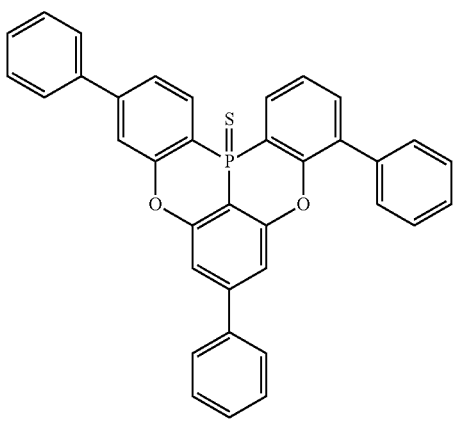
(1-1241)
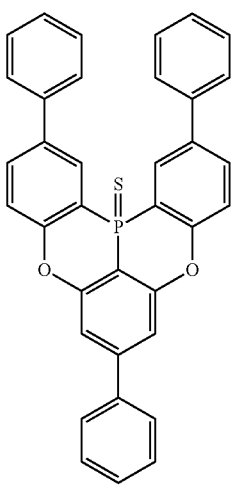

(1-1242)
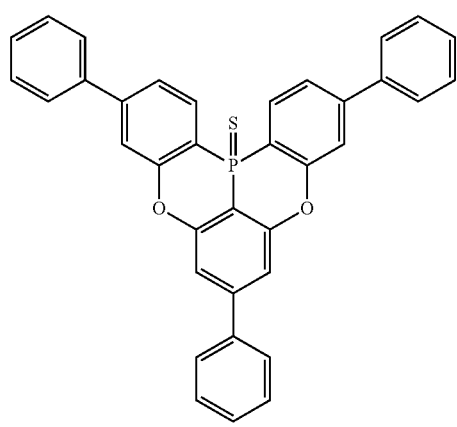
(1-1243)
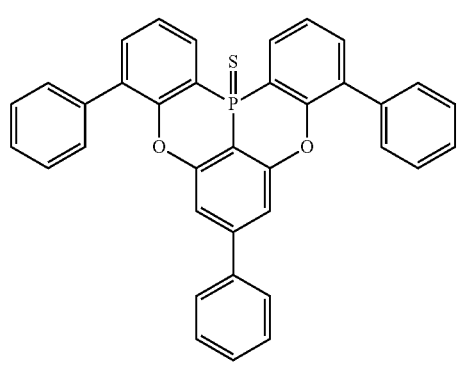
(1-1244)
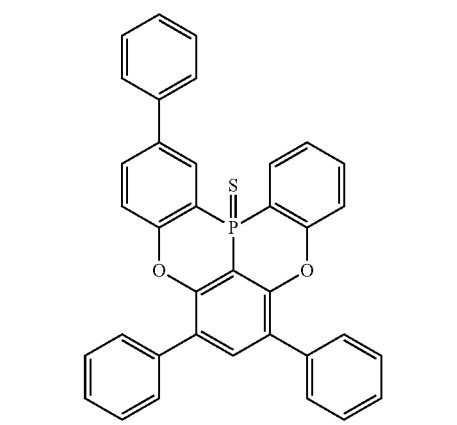
(1-1245)
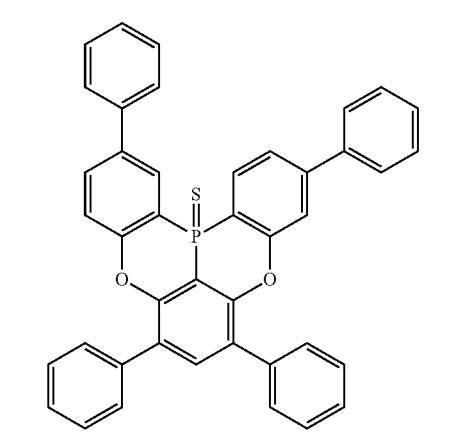
(1-1246)
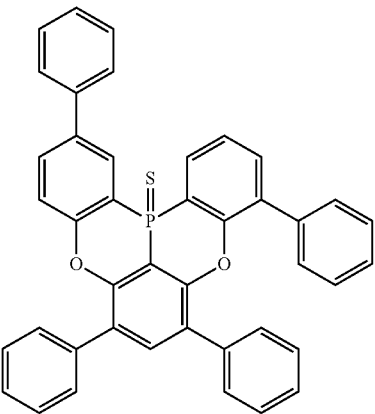
(1-1247)
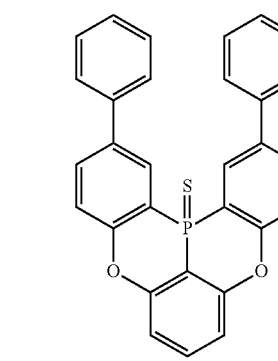
(1-1248)
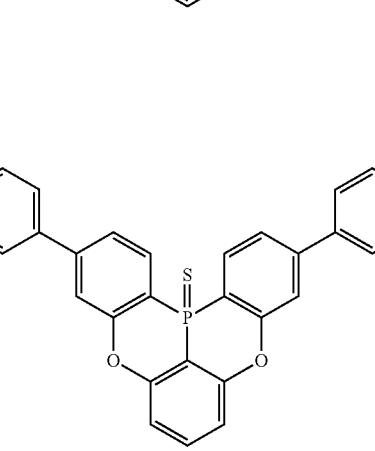
(1-1249)
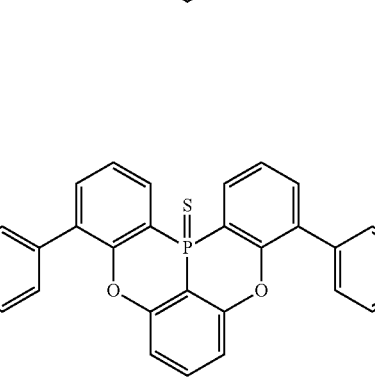

149
-continued
(1-1250)
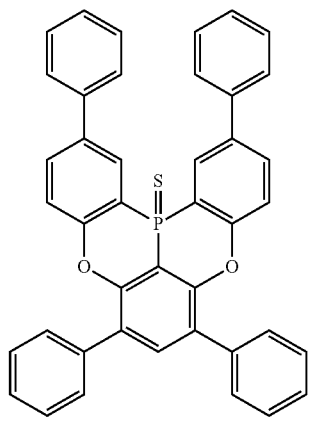
(1-1251)
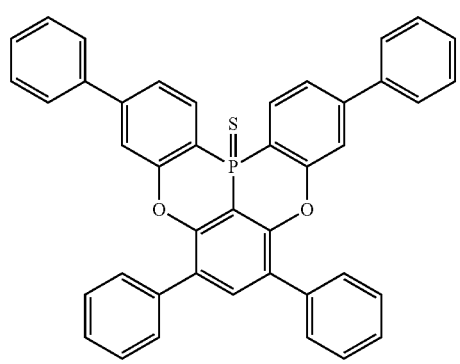
(1-1252)
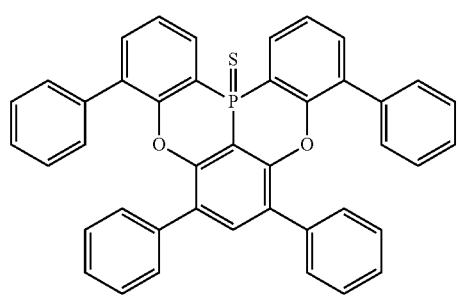
(1-1271)
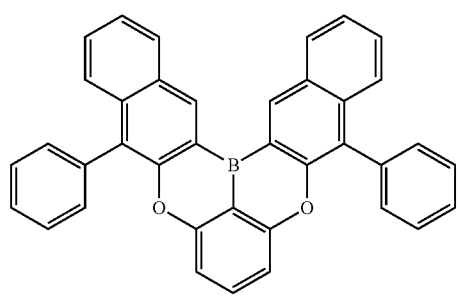
150
-continued
(1-1272)
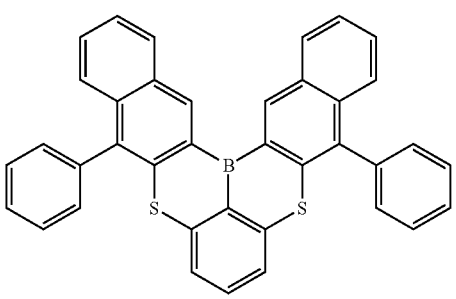
(1-1273)
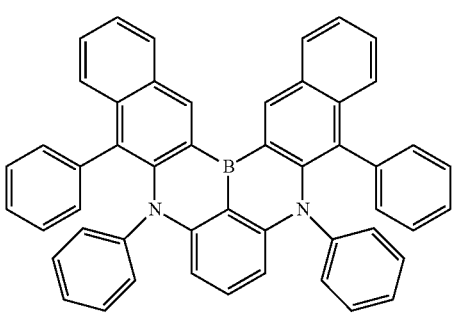
(1-1274)
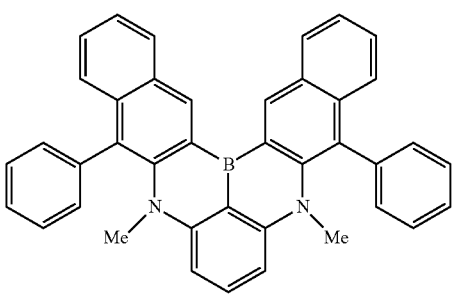
(1-1275)
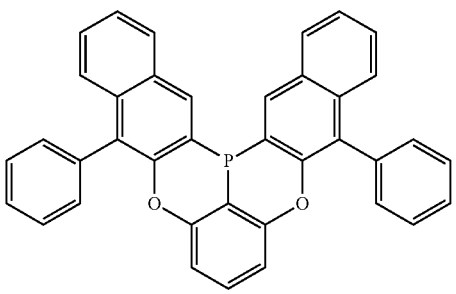
(1-1276)
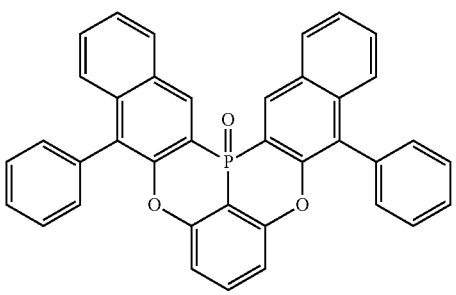

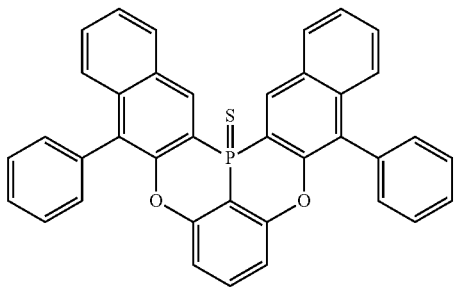
(1-1277)

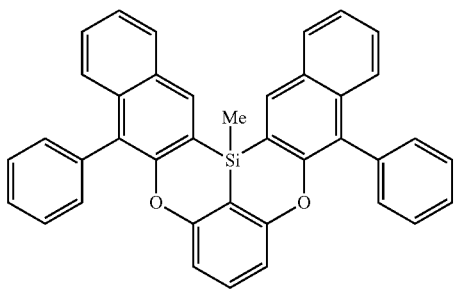
(1-1278)

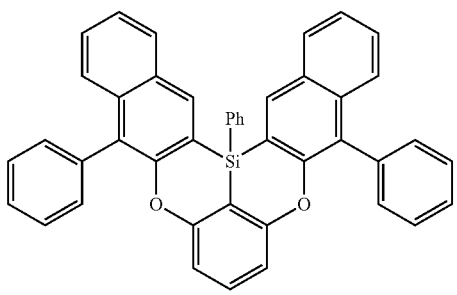
(1-1279)

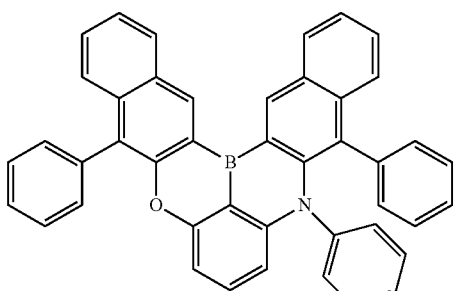
(1-1280)

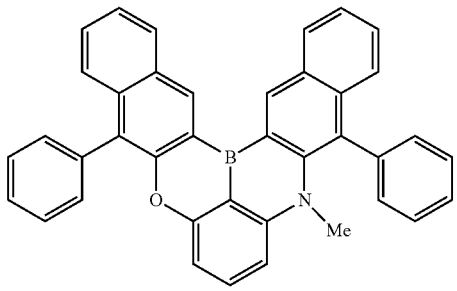
(1-1281)

Furthermore, a specific example of the polycyclic aromatic compound of the present invention and oligomers thereof may be a compound in which at least one hydrogen atom in one or plural phenyl groups or one phenylene group in the compound has been substituted by one or plural alkyls each having 1 to 3 carbon atoms (preferably one or plural methyl groups). A more preferred example may be a compound in which the hydrogen atoms at the ortho-positions of one phenyl group (both of the two sites, preferably any one site) or the hydrogen atoms at the ortho-positions of one phenylene group (all of the four sites at maximum, preferably any one site) have been substituted by methyl groups.

Examples of such a compound, even among the compounds represented by the above formulas (1-1) to (1-825) and the compounds represented by the above formulas (1-1001) to (1-1281), include compounds containing phenyl groups or phenylene groups, in which at least one hydrogen atom in one or plural phenyl groups or one phenylene group has been substituted by one or plural alkyls each having 1 to 3 carbon atoms (preferably one or plural methyl groups). More preferred examples of such a compound include compounds in which the hydrogen atoms at the ortho-positions of one phenyl group (both of two sites, preferably any one site) or the hydrogen atoms at the ortho-positions of one phenylene group (all of four sites at maximum, preferably any one site) have been substituted by methyl groups.

Particularly, further examples include compounds in which at least one hydrogen atom in one or plural phenyl groups or one phenylene group in the compounds represented by formula (1-41), formula (1-42), formula (1-45), formula (1-50), formula (1-79), formula (1-83), formula (1-84), formula (1-91), formula (1-94), formula (1-95), formula (1-97), formula (1-151), formula (1-152), formula (1-1021) to formula (1-1036), formula (1-1037), formula (1-1038), formula (1-1039), formula (1-1048), formula (1-1049), formula (1-1050), formula (1-1077), formula (1-1078), formula (1-1079), formula (1-1187), formula (1-1190), formula (1-1191) and formula (1-1192), has been substituted by one or plural alkyls each having 1 to 3 carbon atoms (preferably one or plural methyl groups). More preferred examples include compounds in which the hydrogen atoms at the ortho-positions of one phenyl group (both of two sites, preferably any one site) or the hydrogen atoms at the ortho-positions of one phenylene group (all of four sites at maximum, preferably any one site) have been substituted by methyl groups.

When at least one hydrogen atom at the ortho-positions of terminal phenyl groups or a p-phenylene group in a compound is substituted by a methyl group or the like, adjoining aromatic rings are likely to intersect each other perpendicularly, and conjugation is weakened. As a result, the triplet excitation energy ($E_T$) can be increased.

Specific examples thereof include compounds represented by the following formula (1-41-1) to formula (1-1192-9).

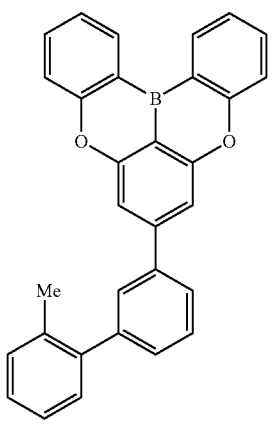
(1-41-1)

(1-42-1)
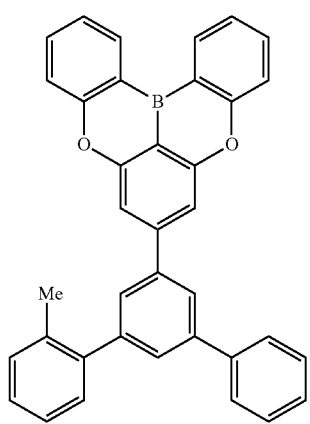
(1-50-1)
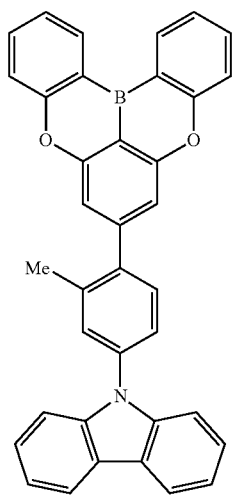
(1-42-2)
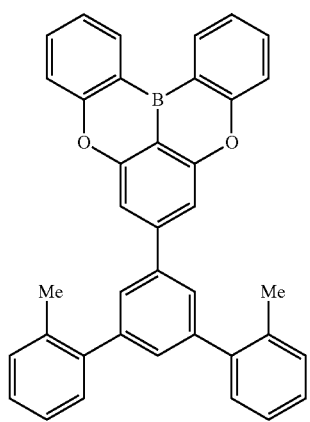
(1-50-2)
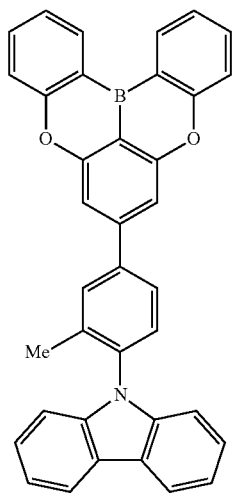
(1-45-1)
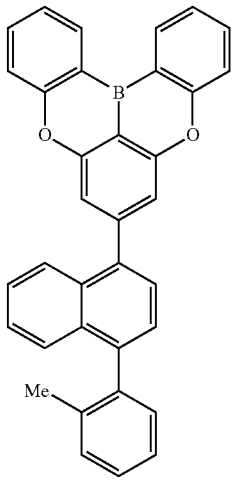
(1-79-1)

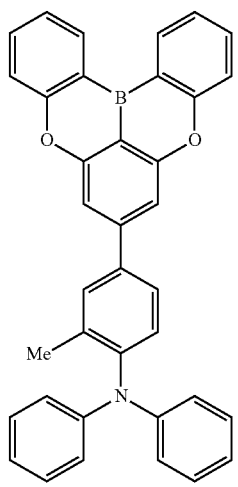 (1-79-2)
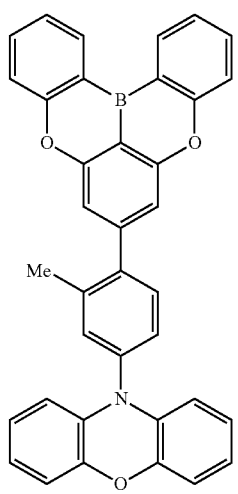 (1-83-1)
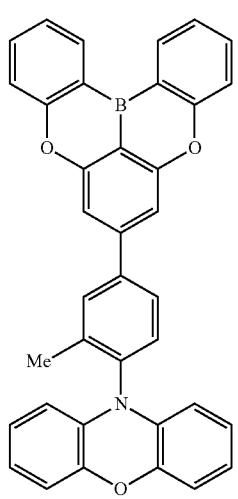 (1-83-2)
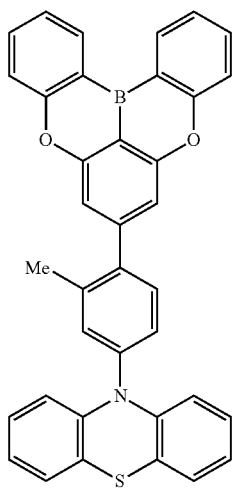 (1-84-1)
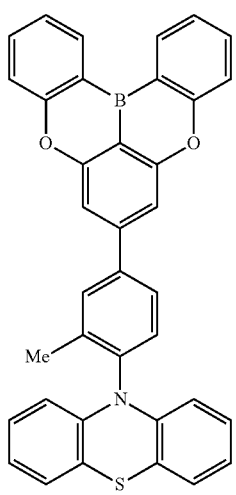 (1-84-2)
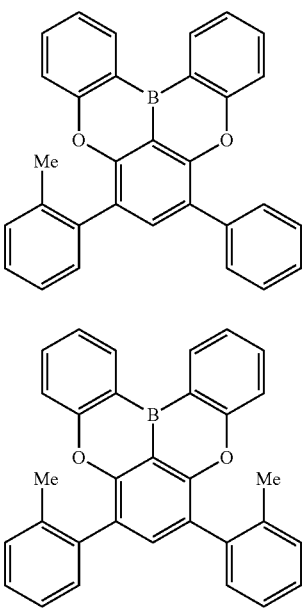
(1-91-1)
(1-91-2)

(1-94-1)
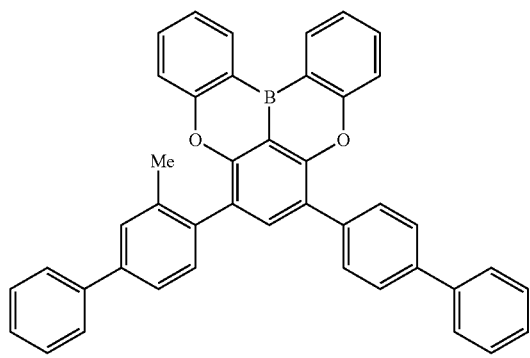
(1-94-4)
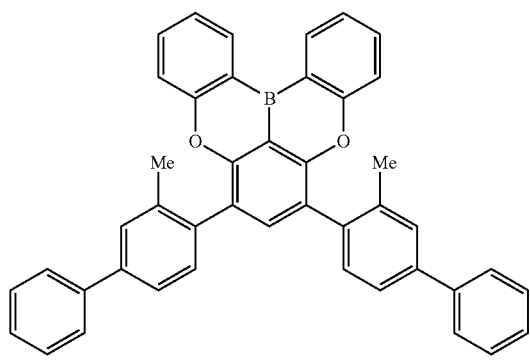
(1-94-2)
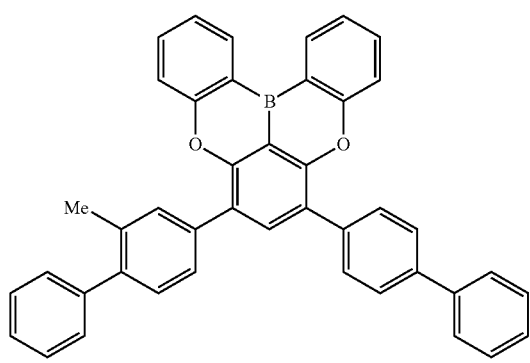
(1-94-5)
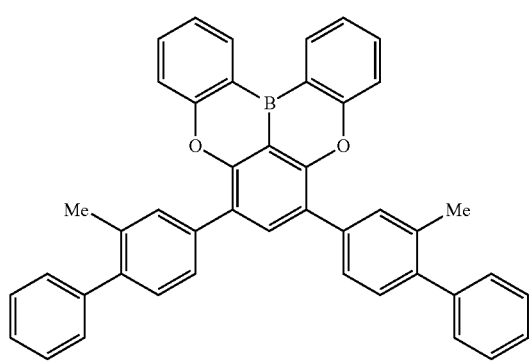
(1-94-3)
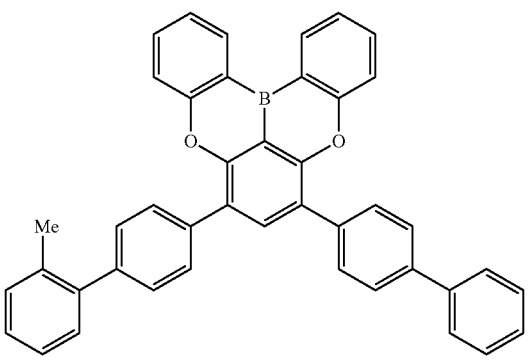
(1-94-6)
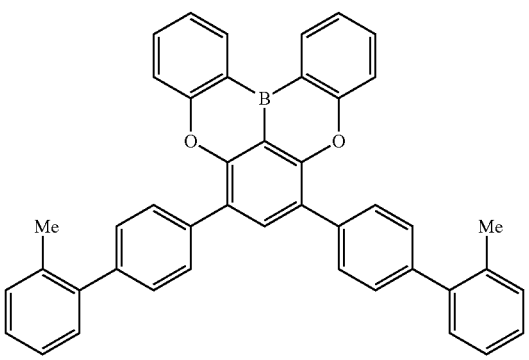
(1-95-1)
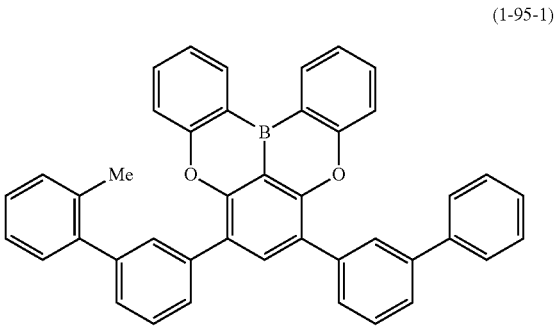
(1-95-2)
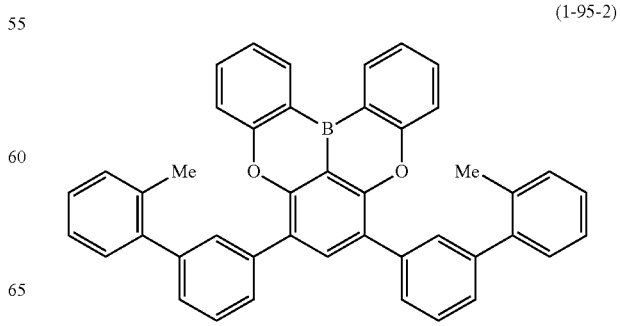

(1-97-1)
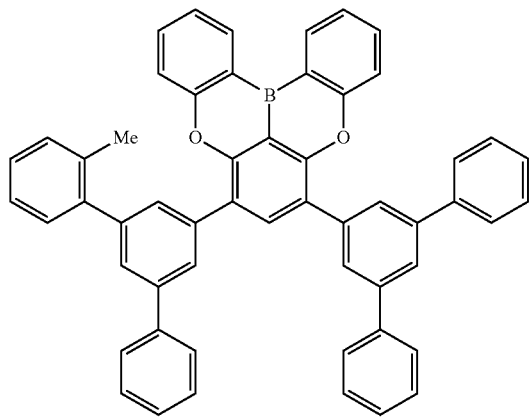
(1-97-2)
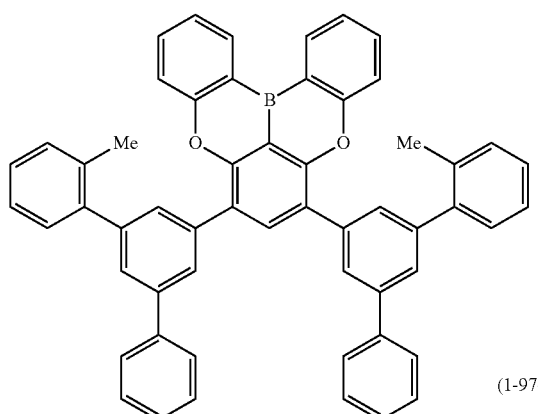
(1-97-3)
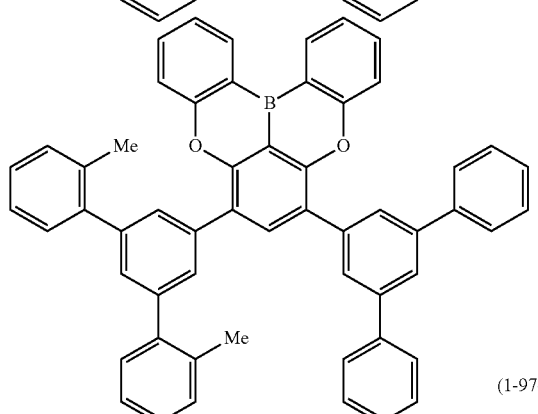
(1-97-4)
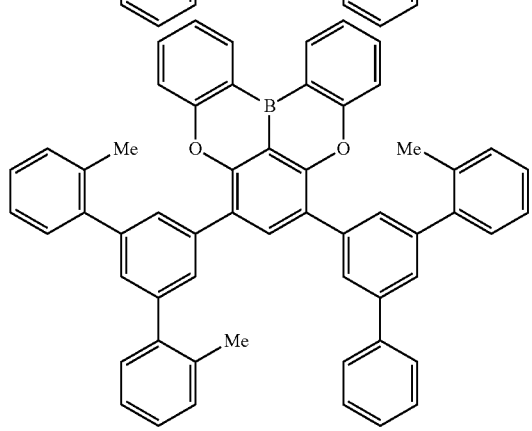
(1-97-5)
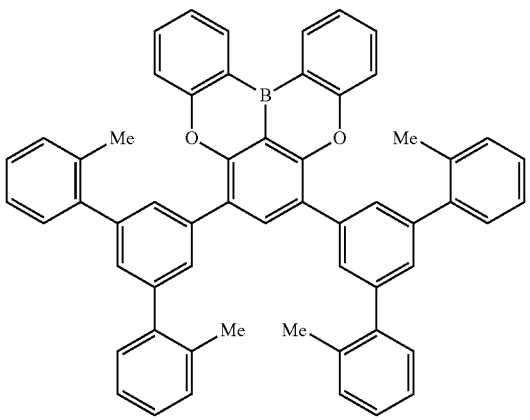
(1-151-1)
(1-151-2)
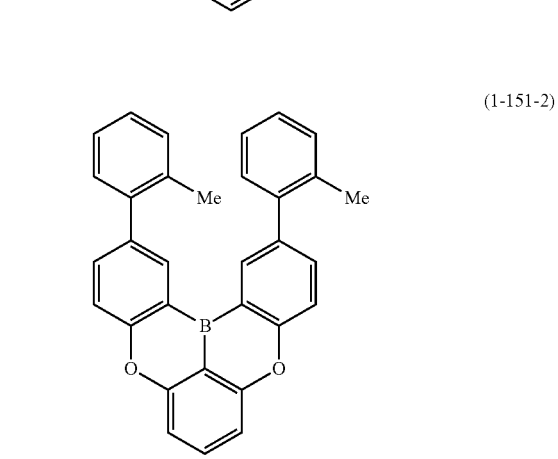
(1-152-1)
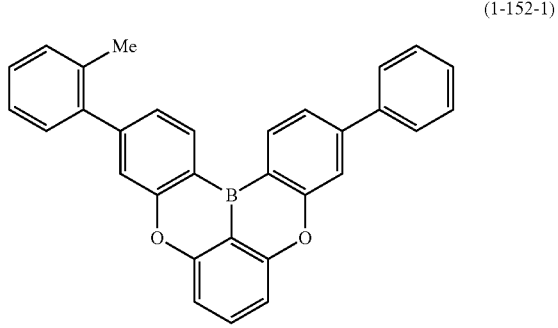

(1-152-2)
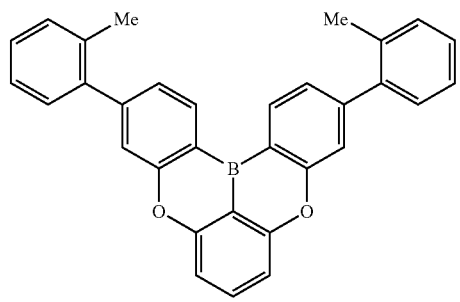
(1-1022-3)
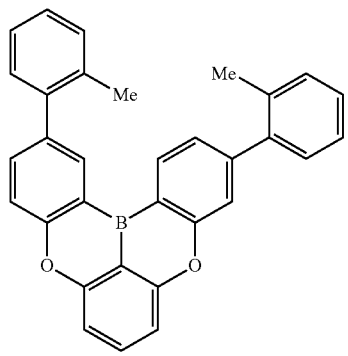
(1-1021-1)
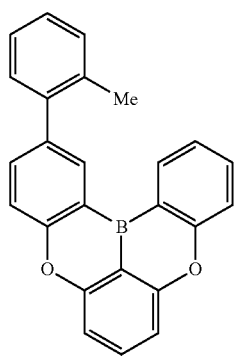
(1-1023-1)
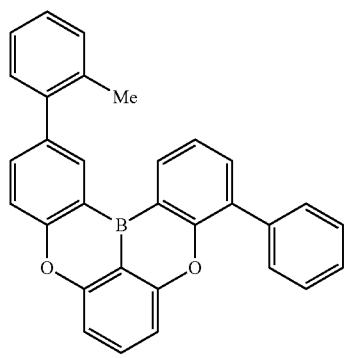
(1-1022-1)
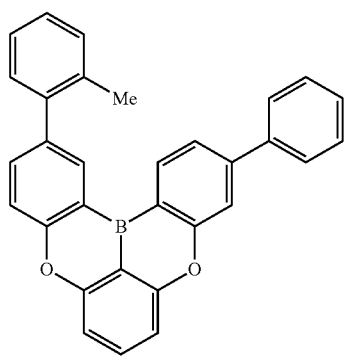
(1-1023-2)
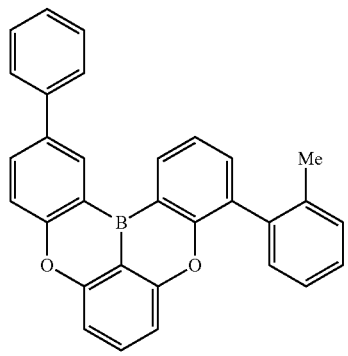
(1-1022-2)
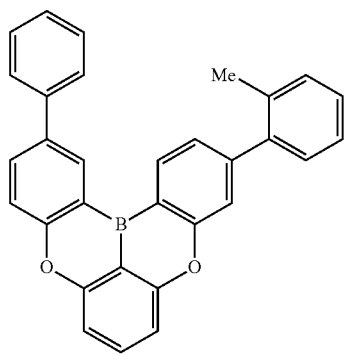
(1-1023-3)
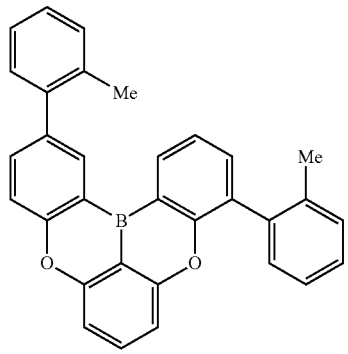

-continued
(1-1024-1)
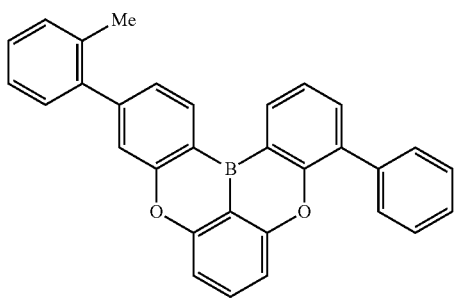
(1-1024-2)
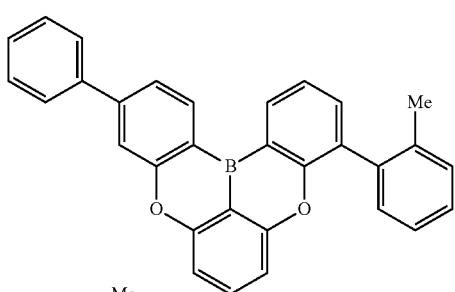
(1-1024-3)
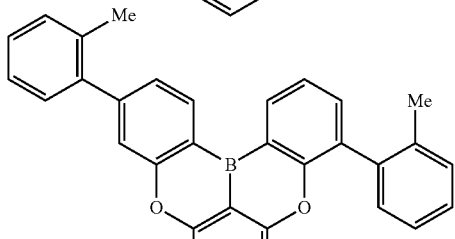
(1-1025-1)
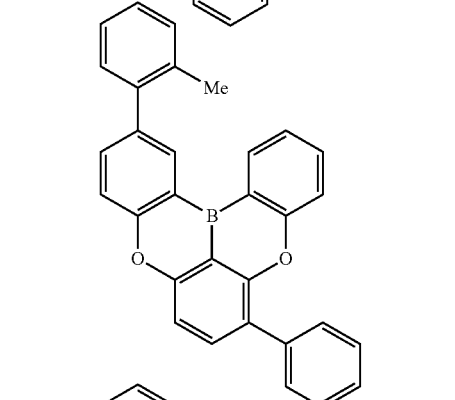
(1-1025-2)
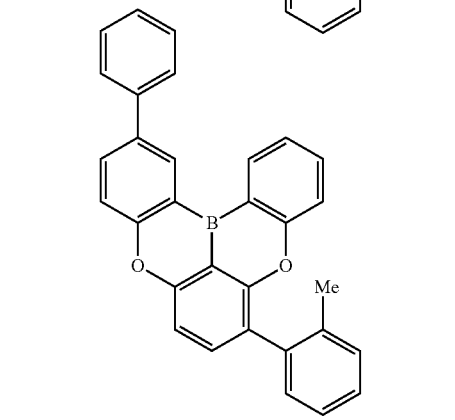
-continued
(1-1025-3)
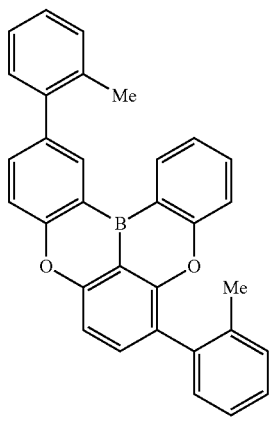
(1-1026-1)
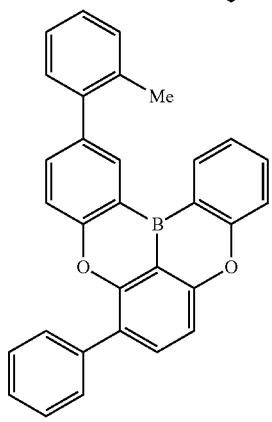
(1-1026-2)
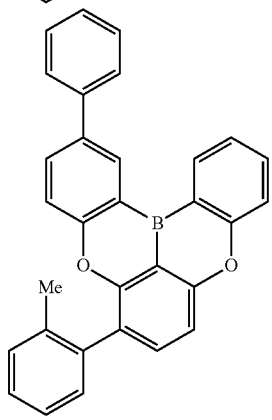
(1-1026-3)

(1-1027-1)
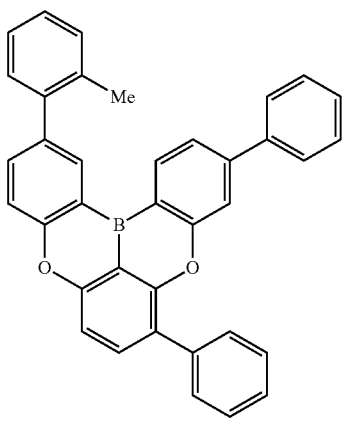
(1-1027-2)
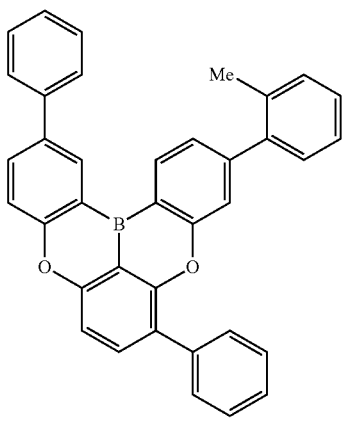
(1-1027-3)
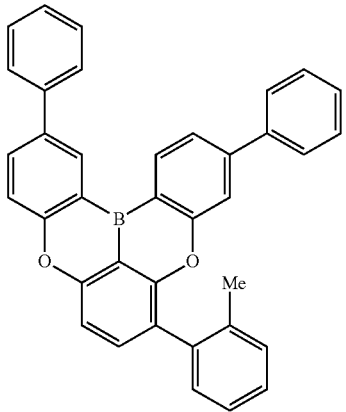
(1-1027-4)
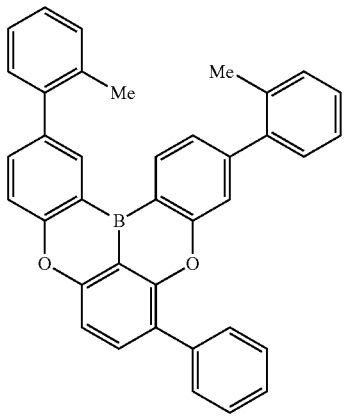
(1-1027-5)
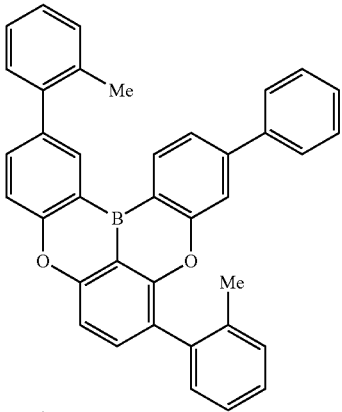
(1-1027-6)
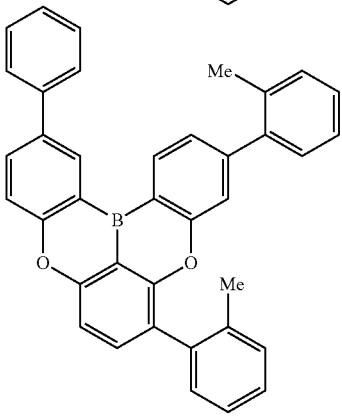
(1-1027-7)
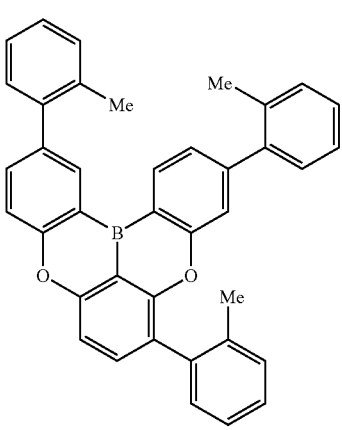
(1-1028-1)
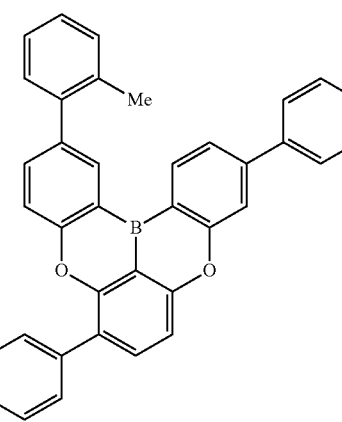

(1-1028-2)
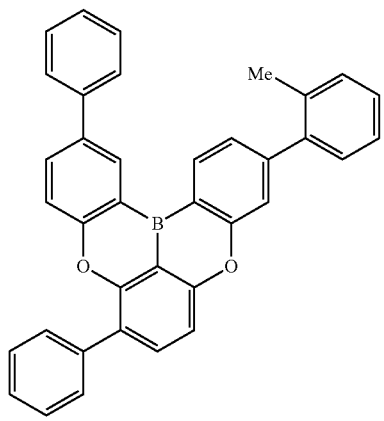
(1-1028-3)
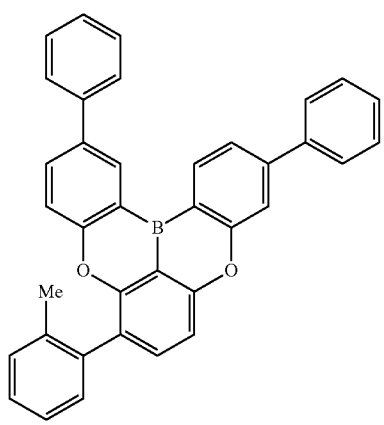
(1-1028-4)
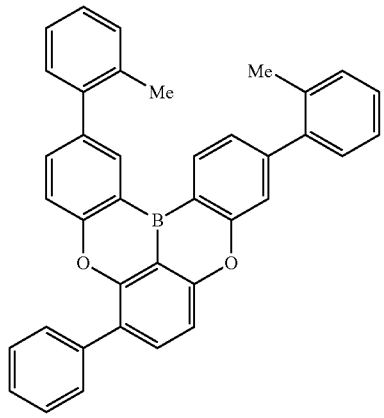
(1-1028-5)
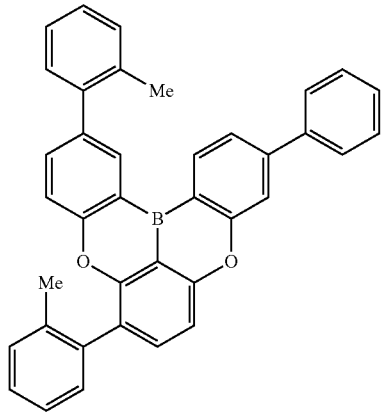
(1-1028-6)
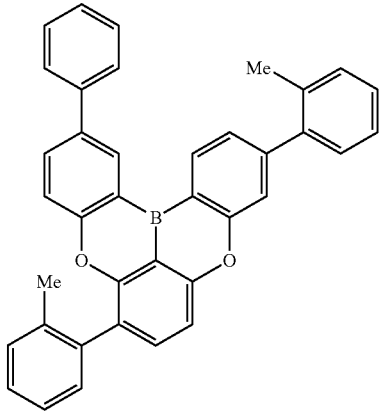
(1-1028-7)
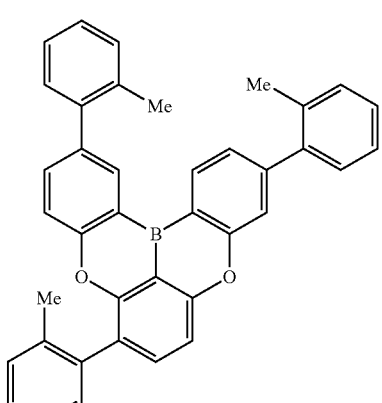
(1-1029-1)
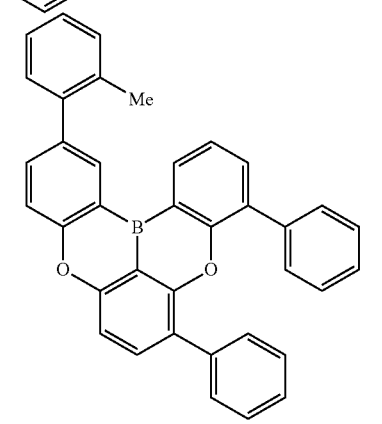
(1-1029-2)
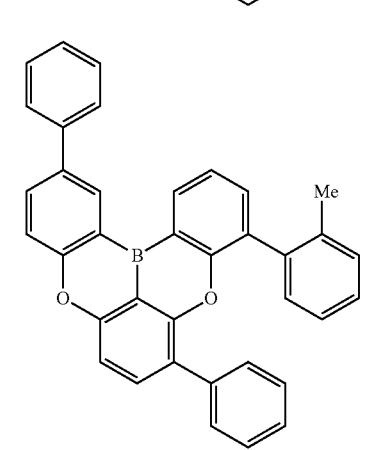

(1-1029-3)
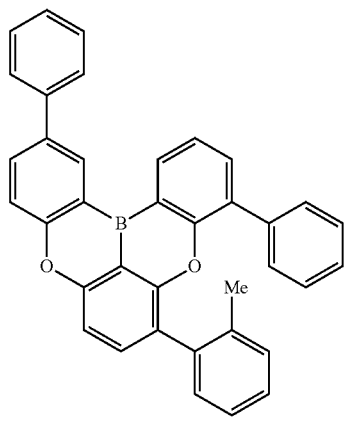
(1-1029-4)
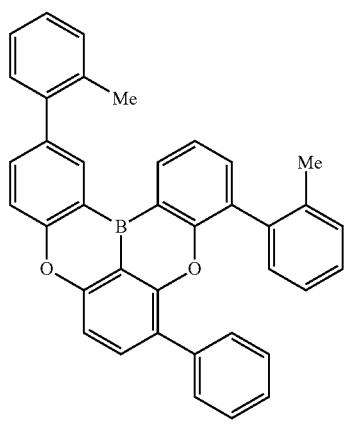
(1-1029-5)
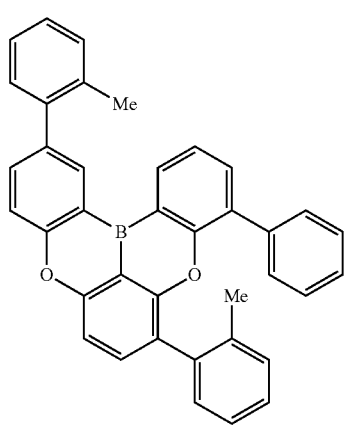
(1-1029-6)
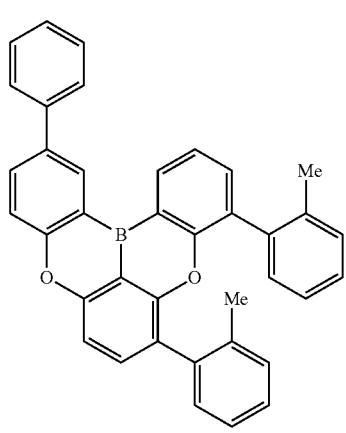
(1-1029-7)
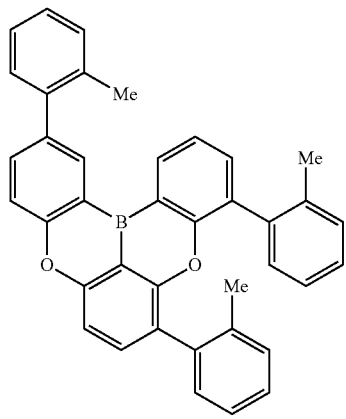
(1-1030-1)
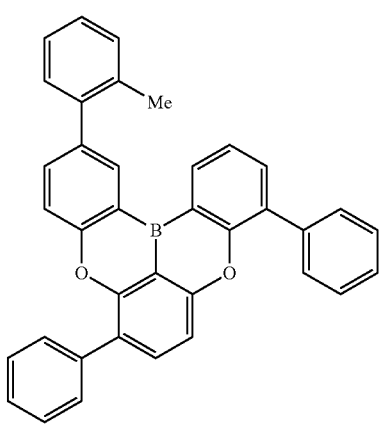
(1-1030-2)
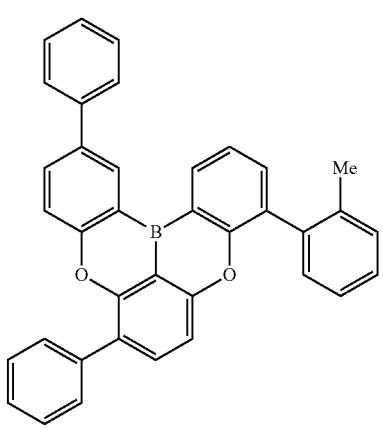
(1-1030-3)
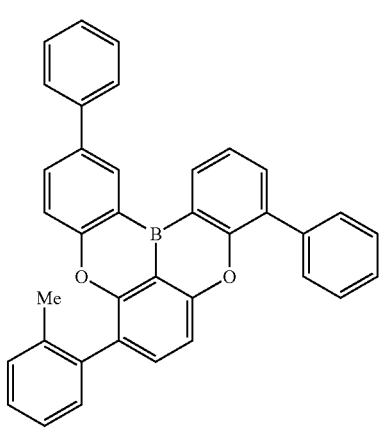

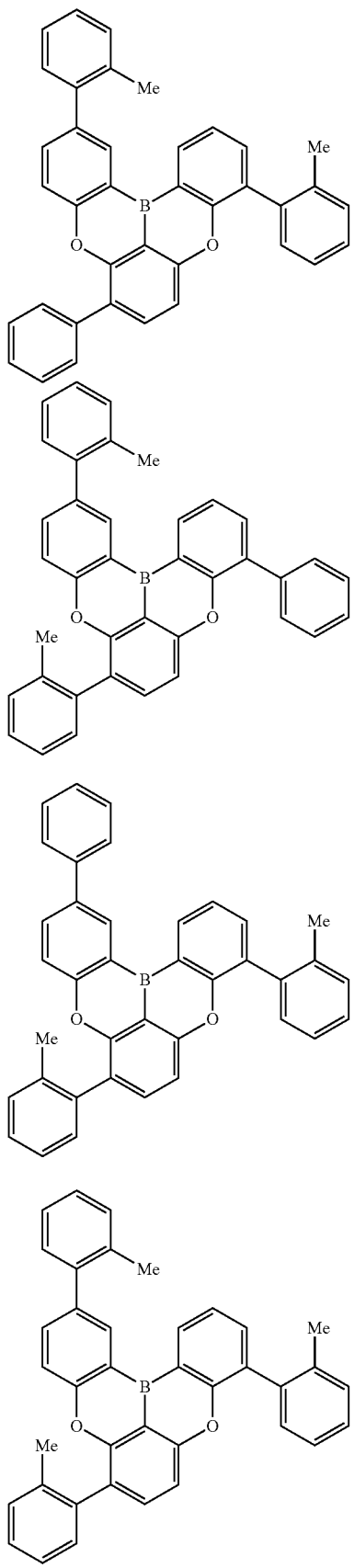
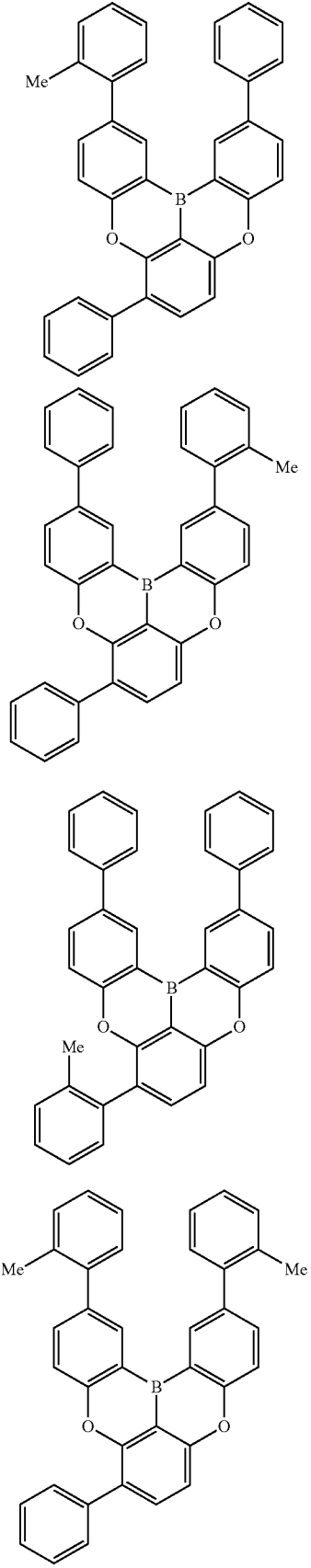

(1-1031-5)
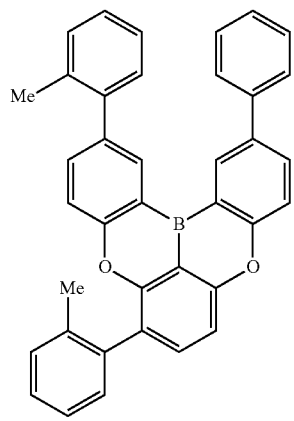
(1-1031-6)
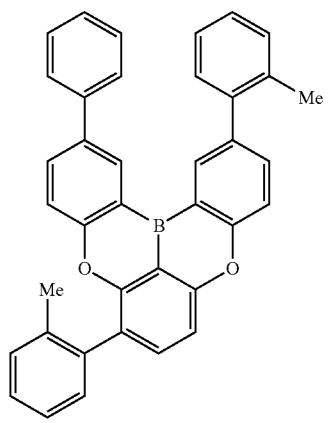
(1-1031-7)
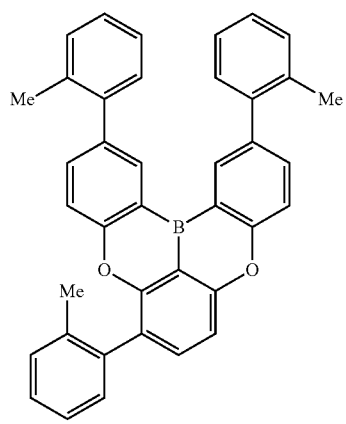
(1-1032-1)
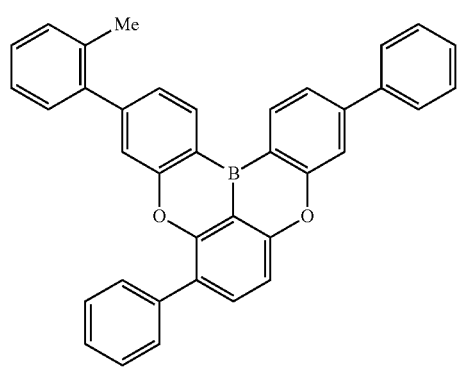
(1-1032-2)
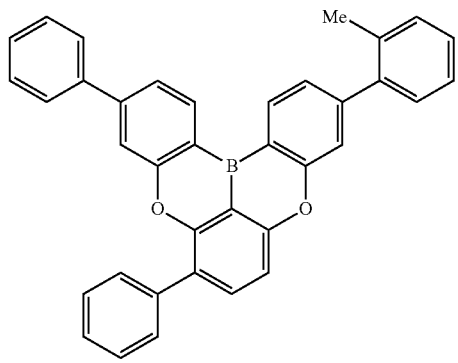
(1-1032-3)
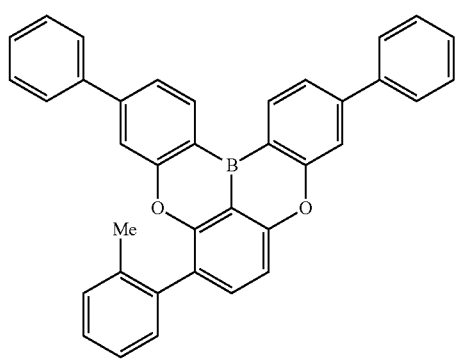
(1-1032-4)
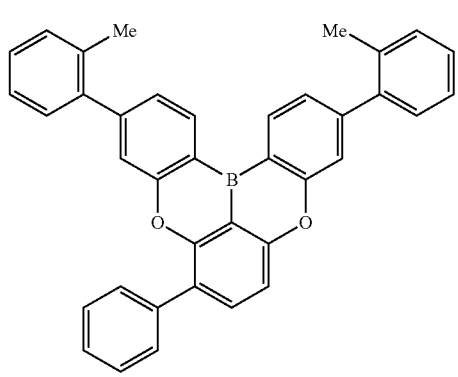
(1-1032-5)
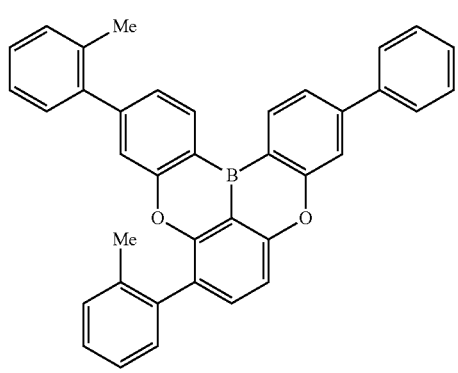

-continued
(1-1032-6)
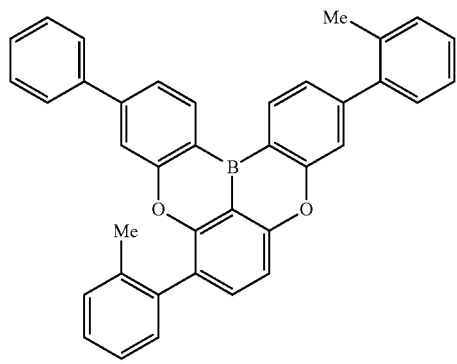
(1-1032-7)
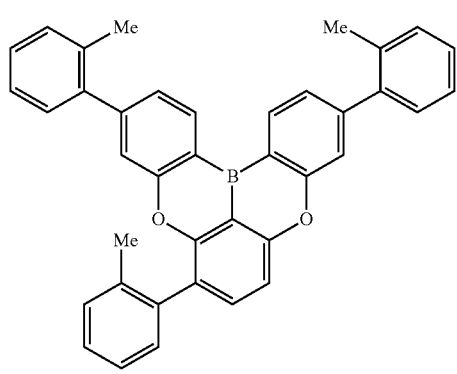
(1-1033-1)
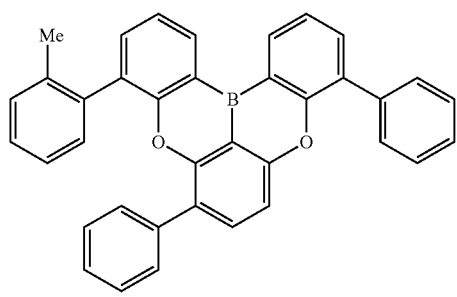
(1-1033-2)
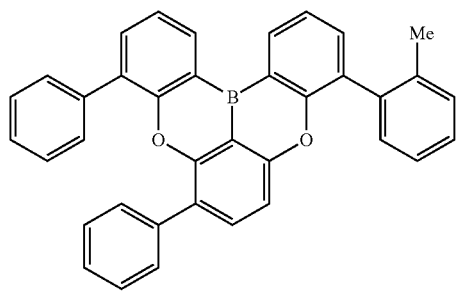
(1-1033-3)
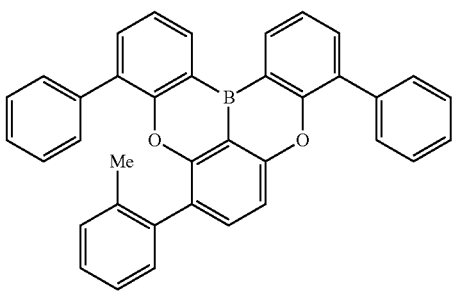
(1-1033-4)
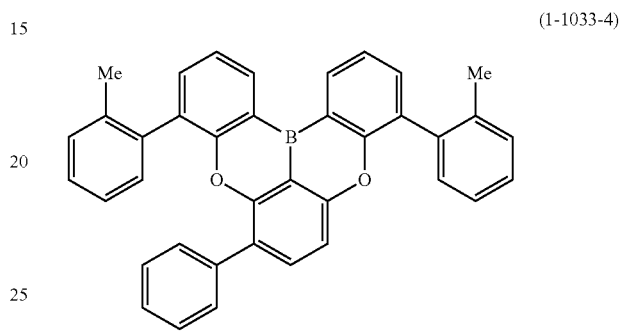
(1-1033-5)
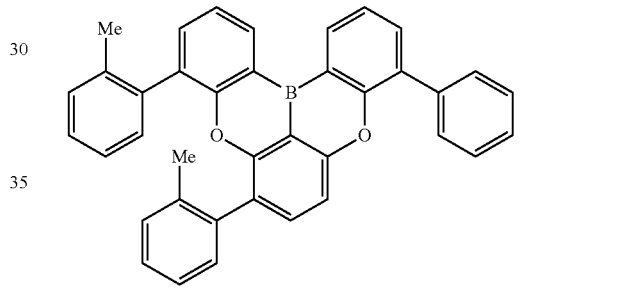
(1-1033-6)
(1-1033-7)
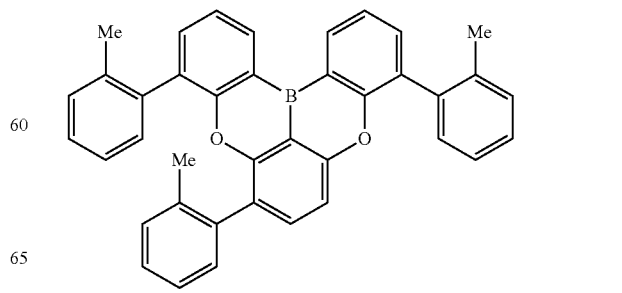

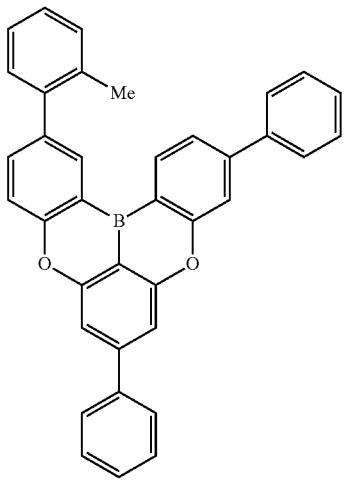
(1-1034-1)
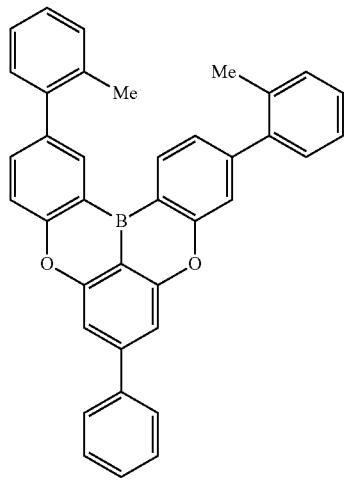
(1-1034-4)
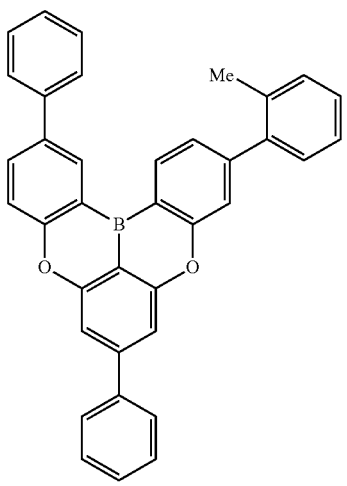
(1-1034-2)
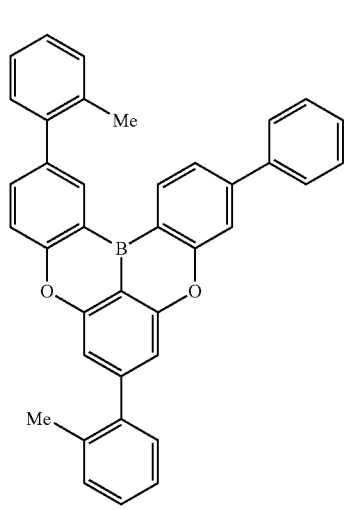
(1-1034-5)
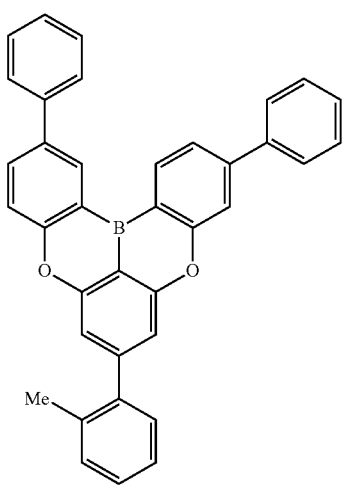
(1-1034-3)
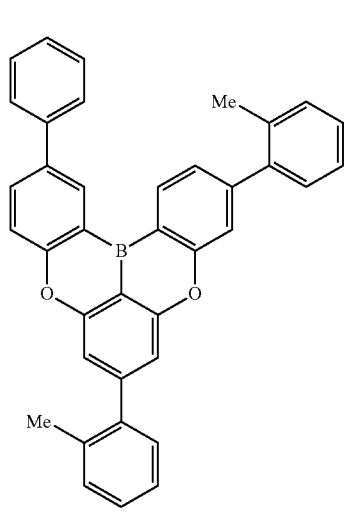
(1-1034-6)

(1-1034-7)
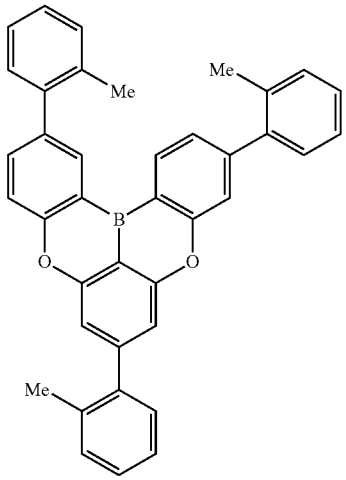
(1-1035-3)
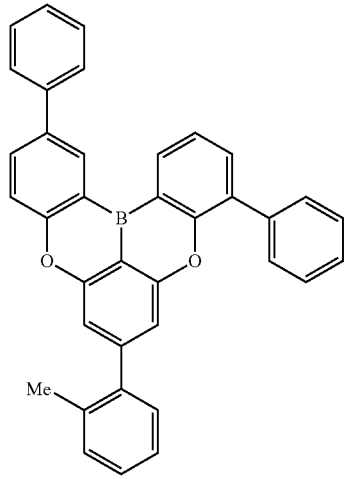
(1-1035-1)
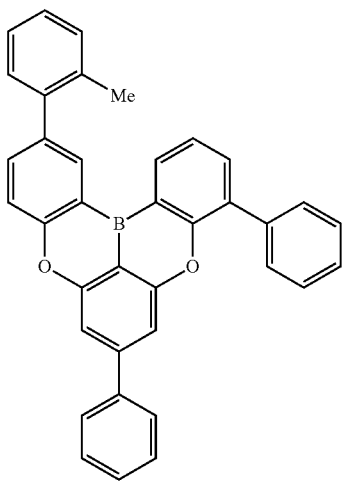
(1-1035-4)
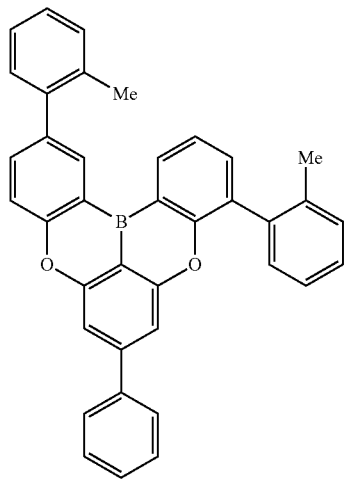
(1-1035-2)
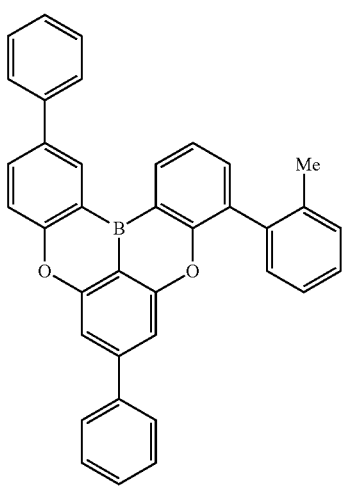
(1-1035-5)
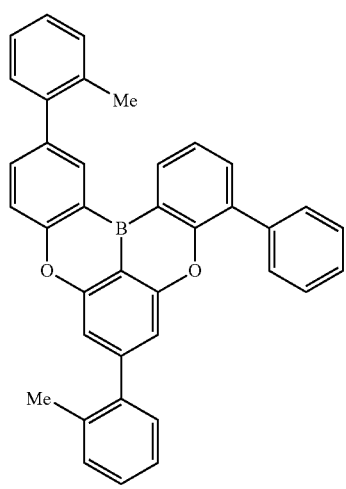

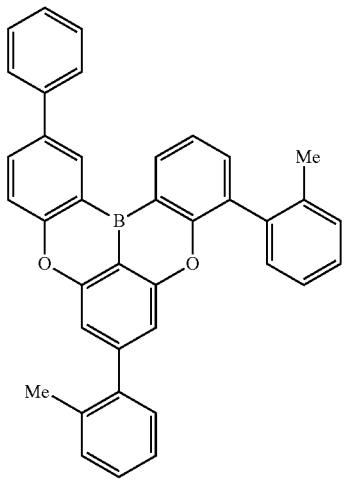
(1-1035-6)
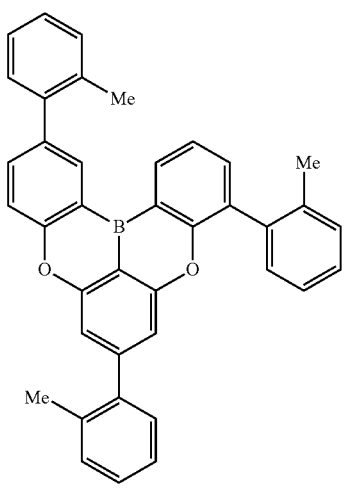
(1-1035-7)
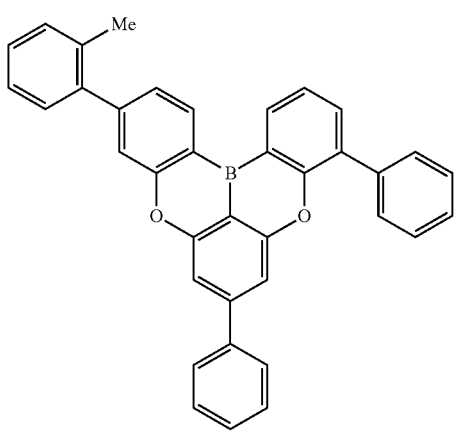
(1-1036-1)
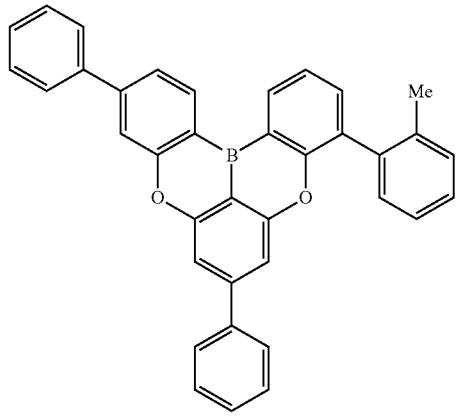
(1-1036-2)
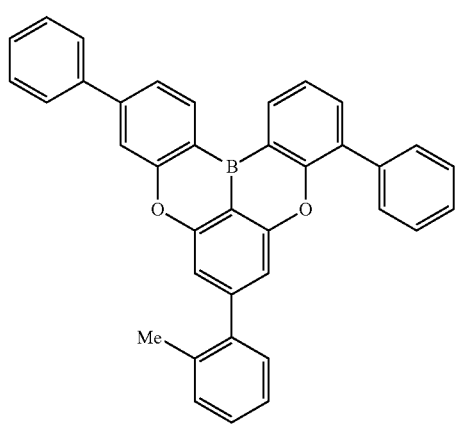
(1-1036-3)
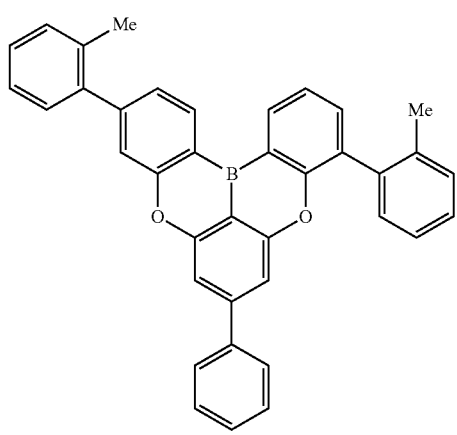
(1-1036-4)

-continued
(1-1036-5)
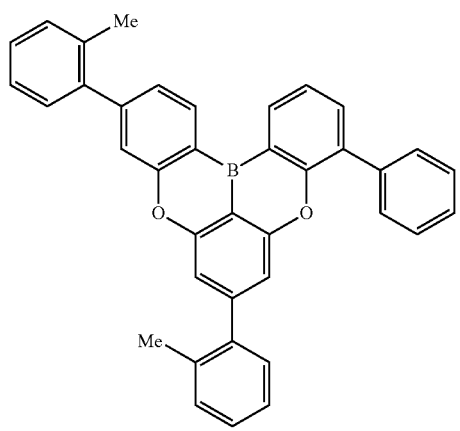
(1-1036-6)
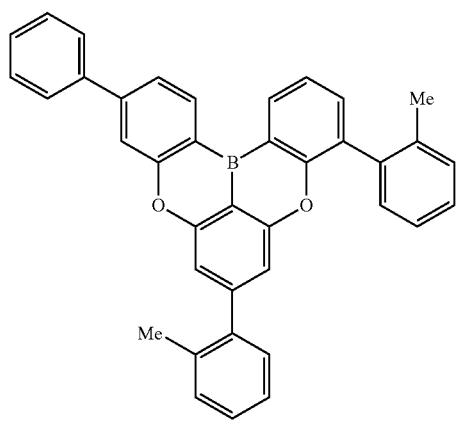
(1-1036-7)
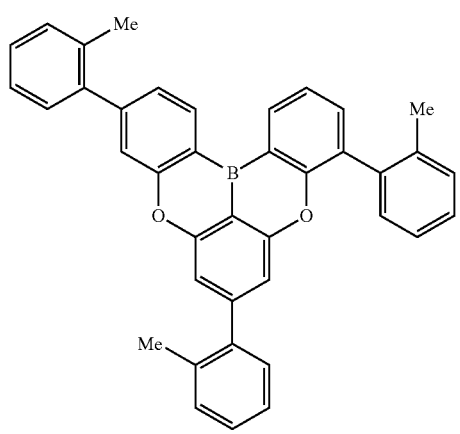
(1-1037-1)
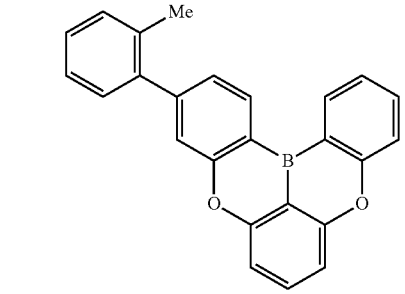
-continued
(1-1038-1)
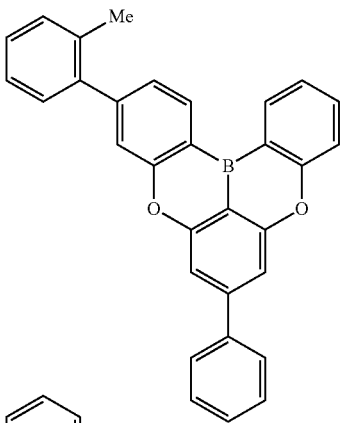
(1-1038-2)
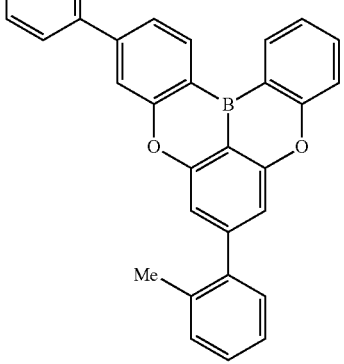
(1-1038-3)
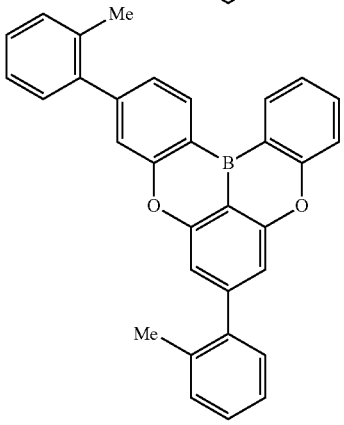
(1-1039-1)
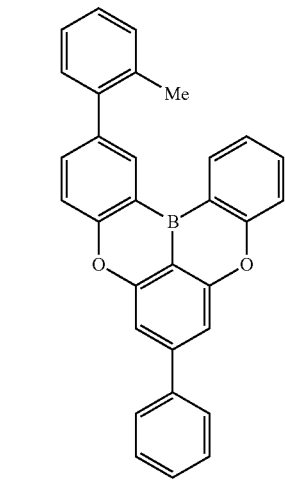

(1-1039-2) 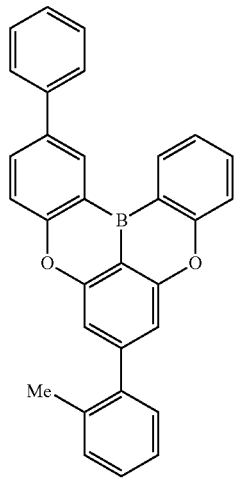
(1-1048-2) 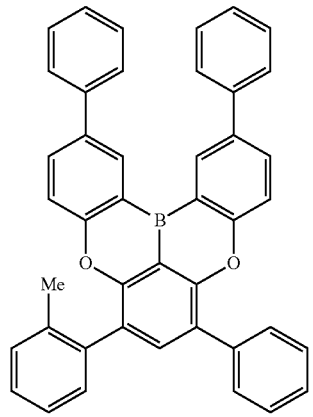
(1-1039-3) 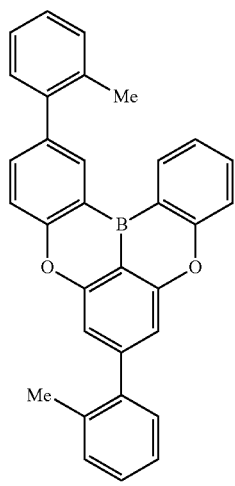
(1-1048-3) 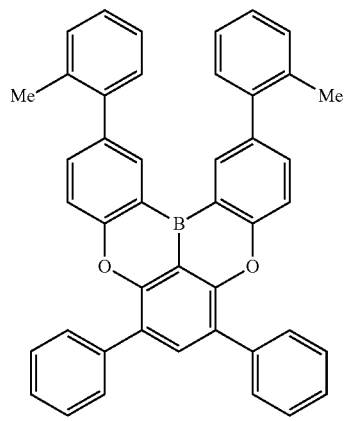
(1-1048-1) 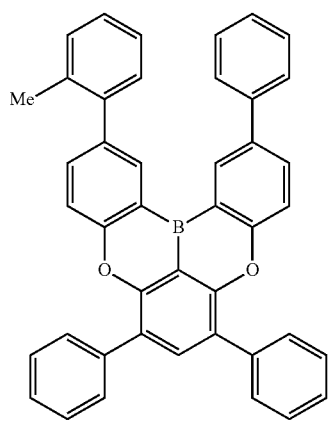
(1-1048-4) 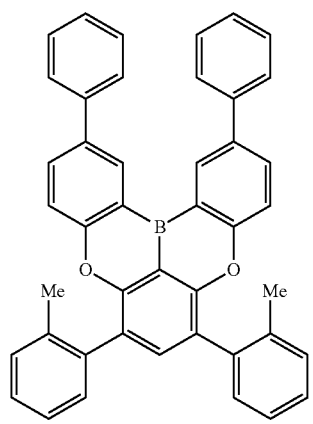

(1-1048-5)
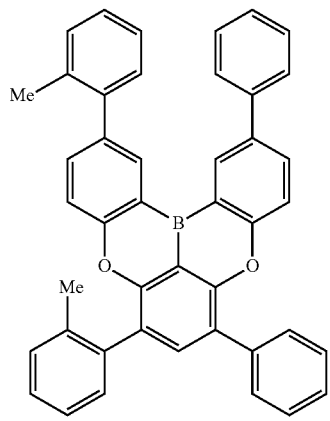
(1-1048-6)
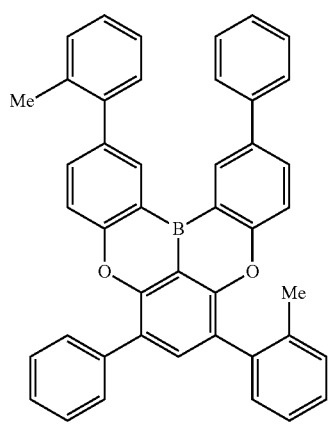
(1-1048-7)
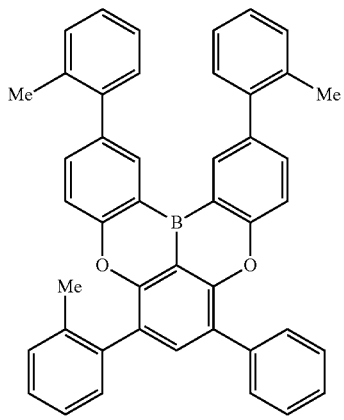
(1-1048-8)
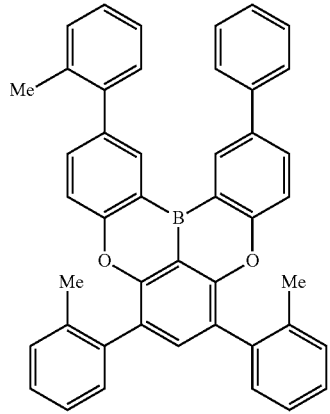
(1-1048-9)
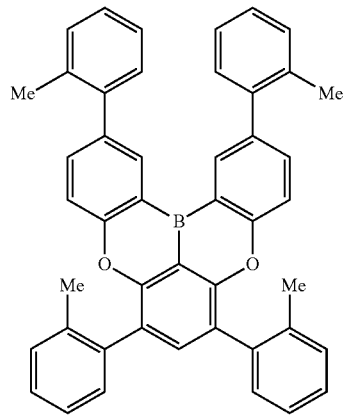
(1-1049-1)
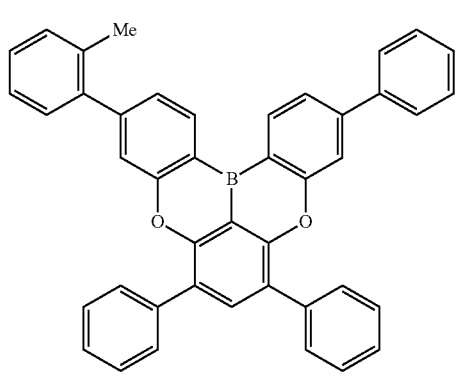
(1-1049-2)
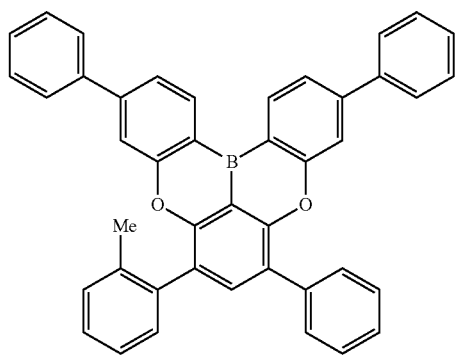
(1-1049-3)
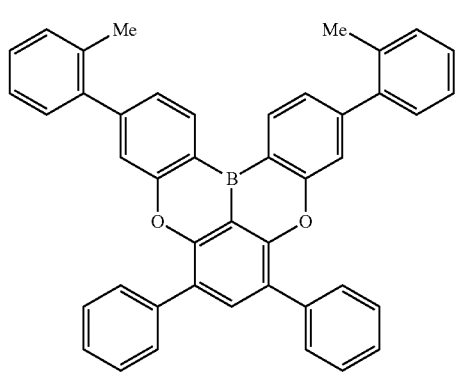

(1-1049-4)
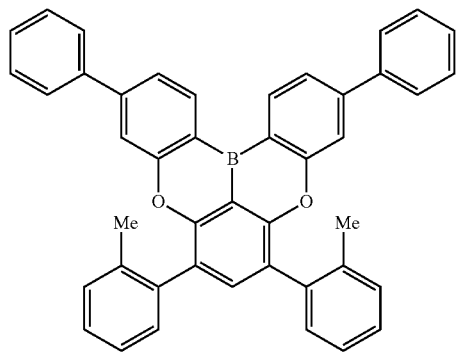
(1-1049-5)
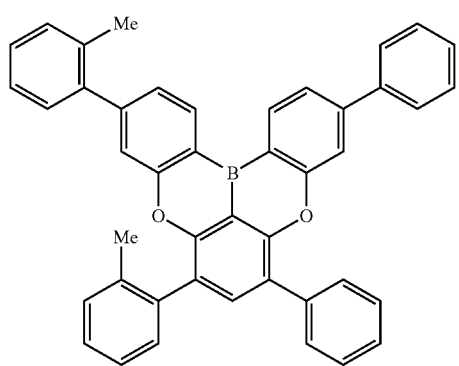
(1-1049-6)
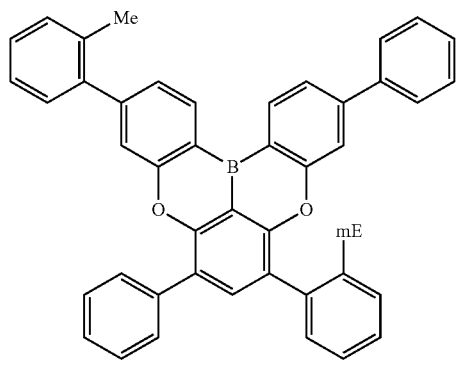
(1-1049-7)
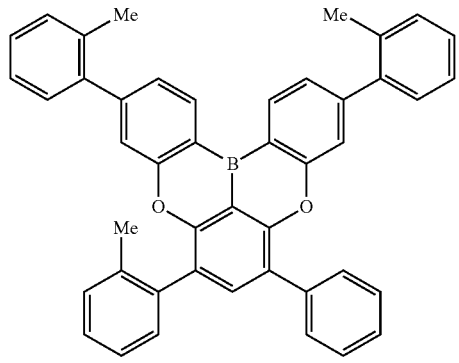
(1-1049-8)
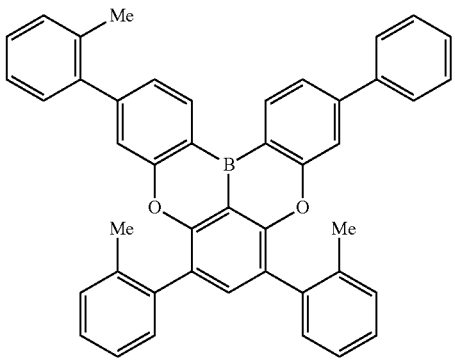
(1-1049-9)
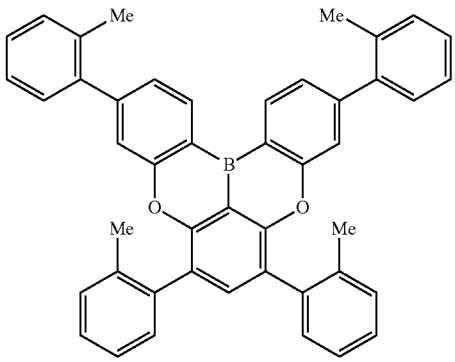
(1-1050-1)
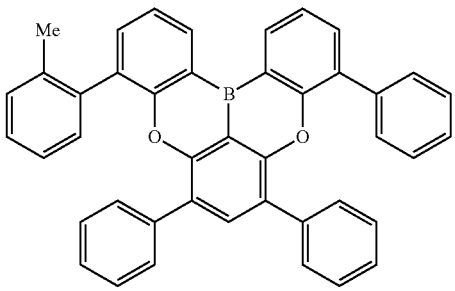
(1-1050-2)
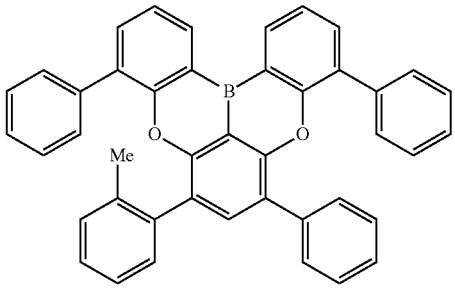

(1-1050-3)
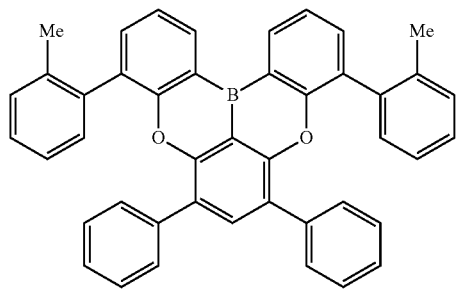
(1-1050-4)
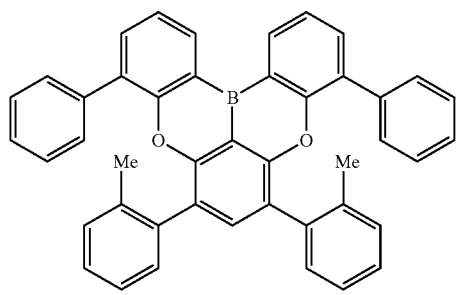
(1-1050-5)
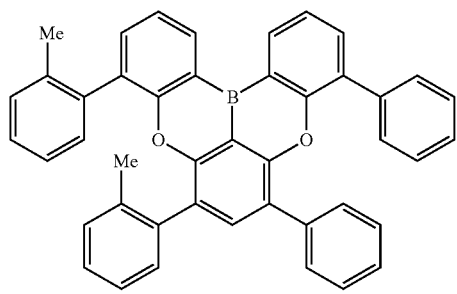
(1-1050-6)
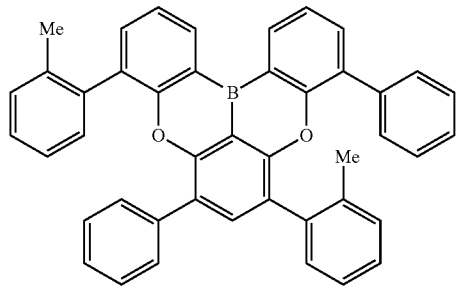
(1-1050-7)
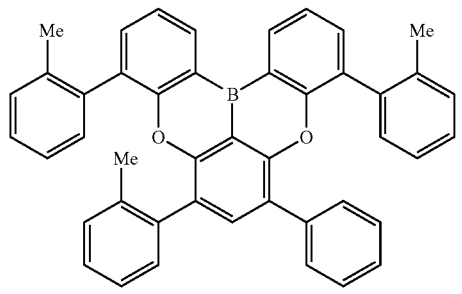
(1-1050-8)
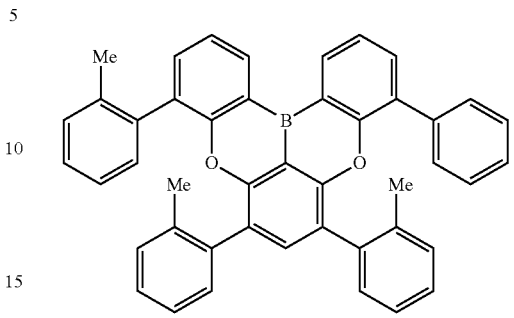
(1-1050-9)
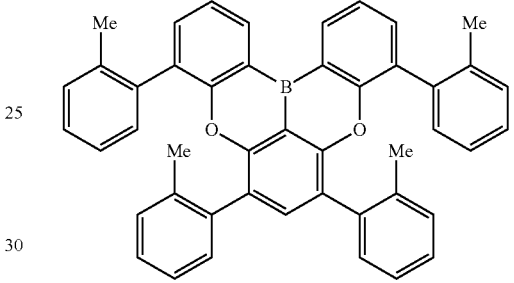
(1-1177-1)
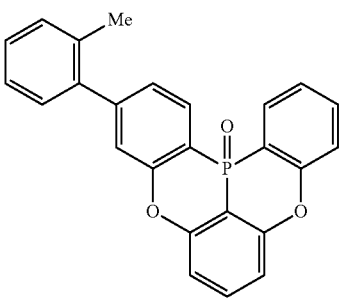
(1-1178-1)
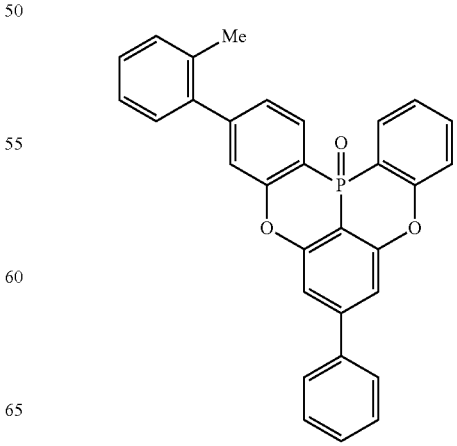

(1-1178-2)
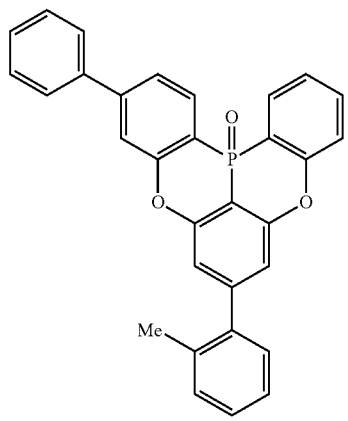
(1-1179-2)
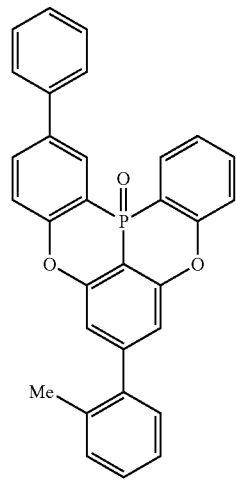
(1-1178-3)
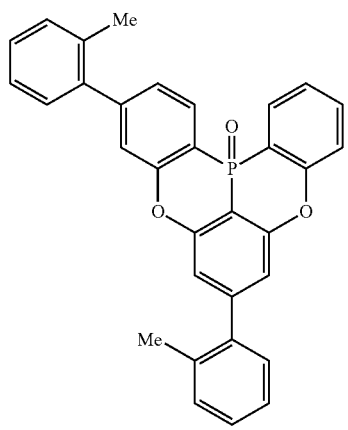
(1-1179-3)
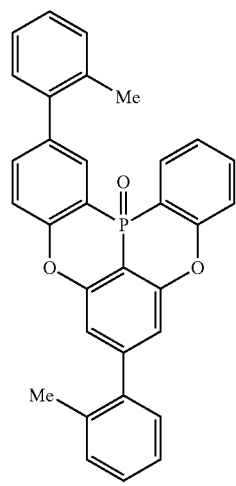
(1-1179-1)
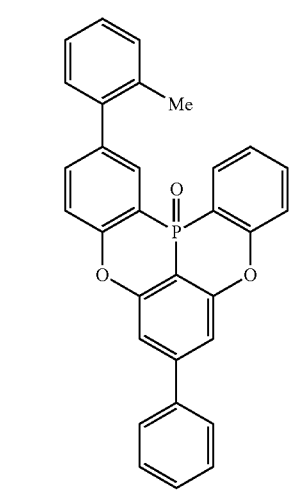
(1-1187-1)
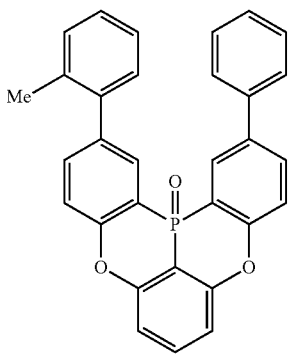

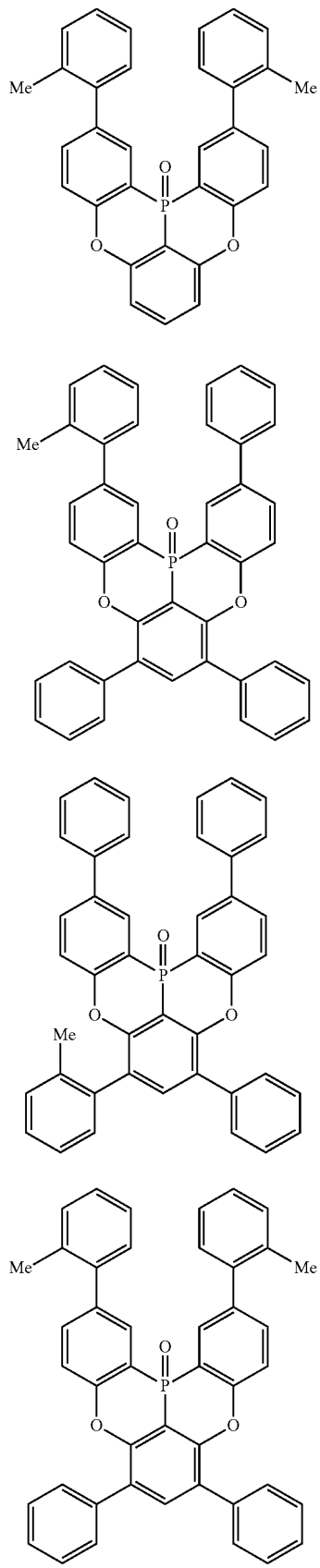
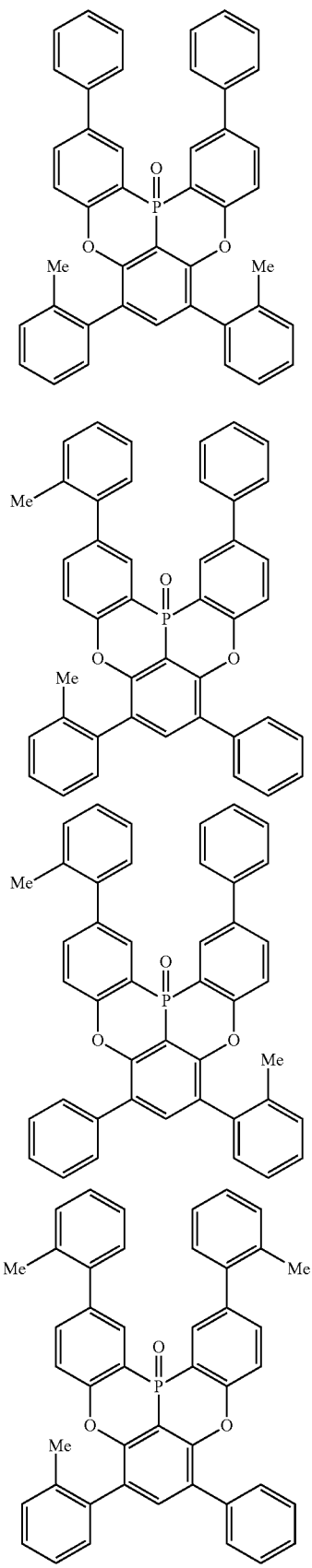

-continued
(1-1190-8)
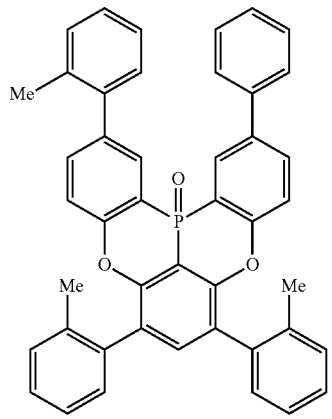
(1-1190-9)
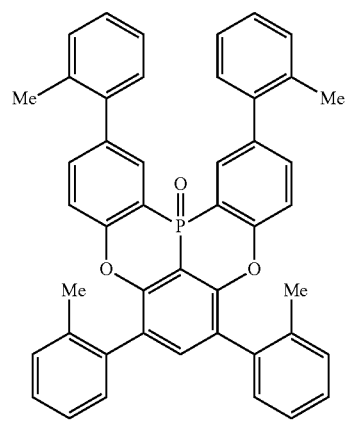
(1-1191-1)
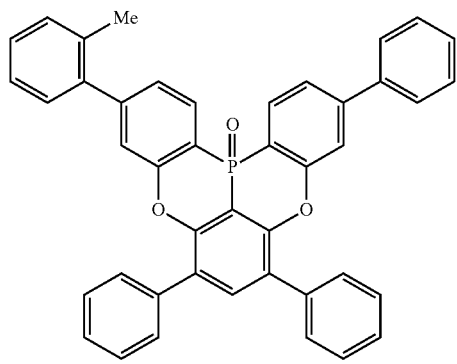
(1-1191-2)
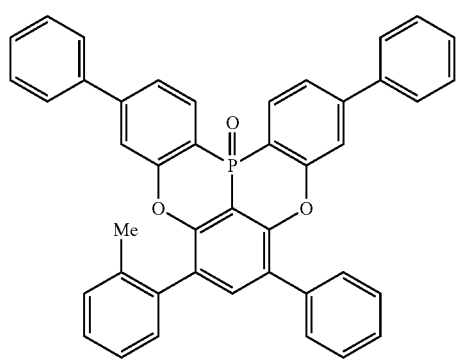
-continued
(1-1191-3)
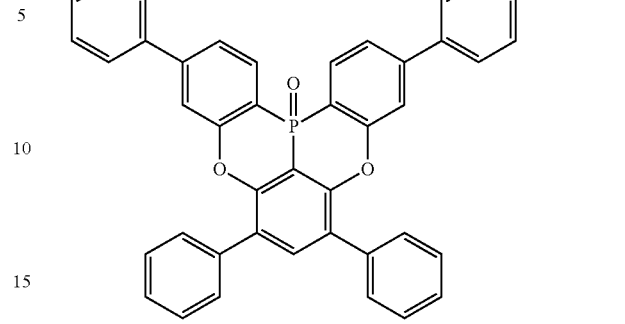
(1-1191-4)
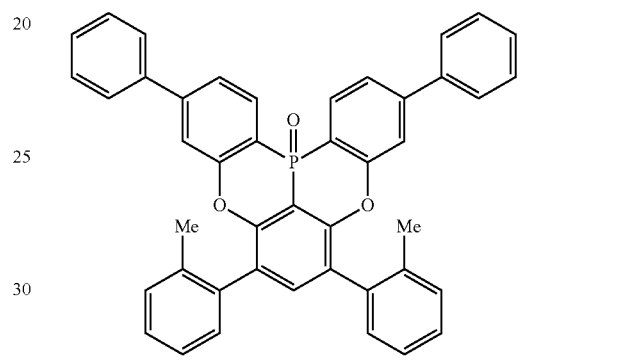
(1-1191-5)
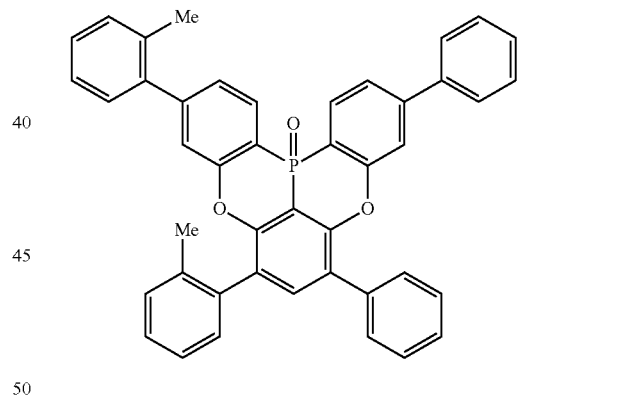
(1-1191-6)
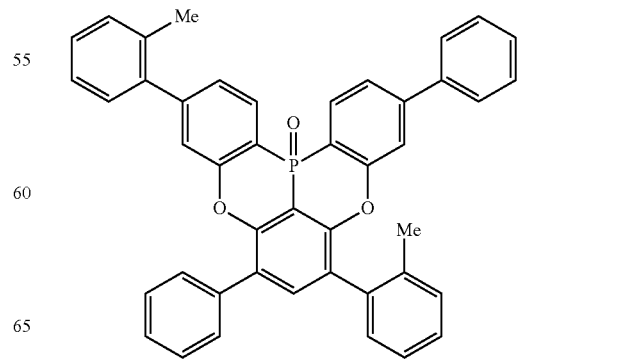

199
-continued
(1-1191-7)
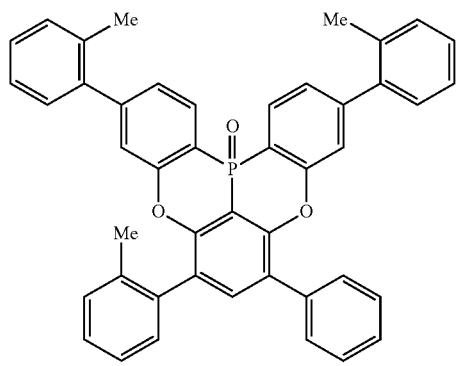
(1-1191-8)
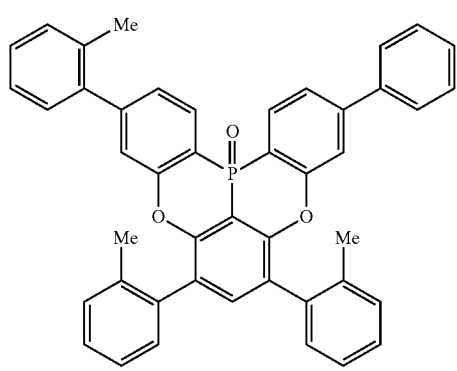
(1-1191-9)
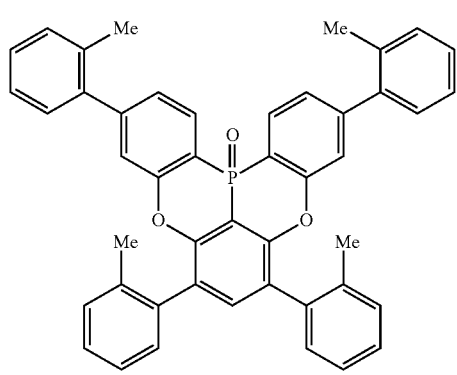
(1-1192-1)
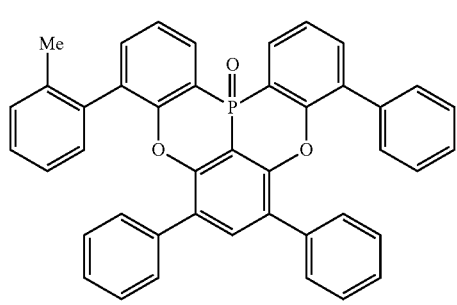
200
-continued
(1-1192-2)
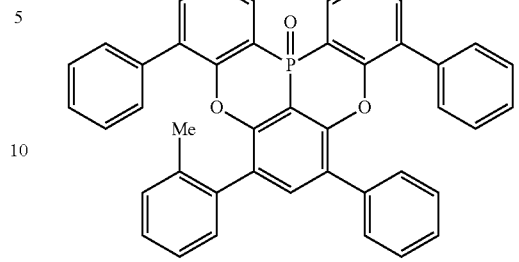
(1-1192-3)
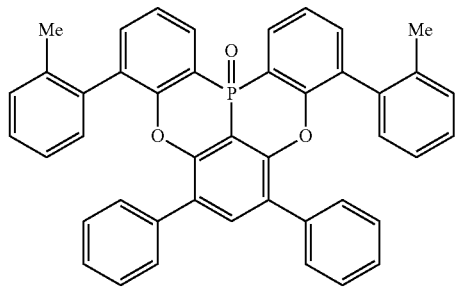
(1-1192-4)
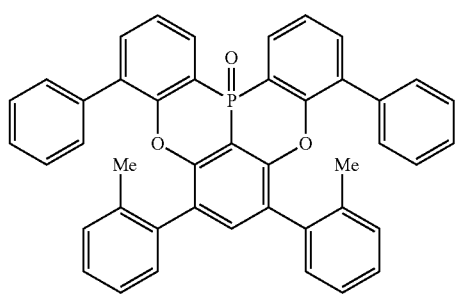
(1-1192-5)
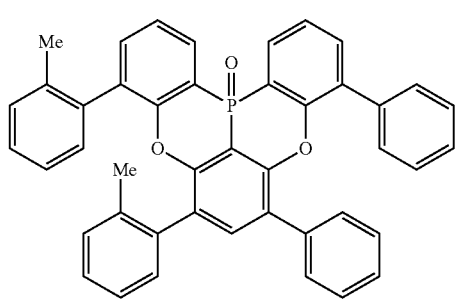
(1-1192-6)
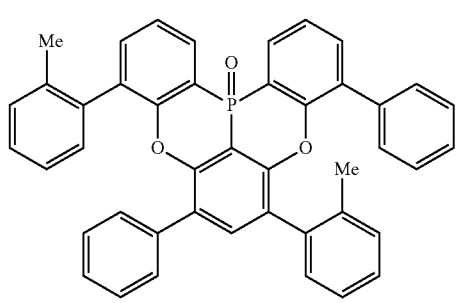

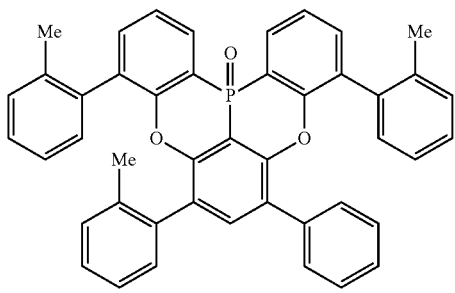

(1-1192-7)


(1-1192-8)

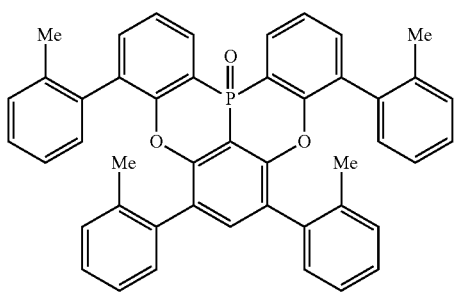

(1-1192-9)

2. Method for Producing Polycyclic Aromatic Compound and Oligomer Thereof

In regard to the polycyclic aromatic compound represented by general formula (1) or (2) and an oligomer thereof, basically, an intermediate is produced by first linking the ring A (ring a), ring B (ring b) and ring C (ring c) via linking groups (groups containing $X^1$ or $X^2$) (first reaction), and then a final product can be produced by linking the ring A (ring a), ring B (ring b) and ring C (ring c) via linking groups (groups containing $Y^1$) (second reaction). In the first reaction, for example, in the case of an etherification reaction, a general reaction such as a nucleophilic substitution reaction, or the Ullmann reaction can be utilized, and in the case of an amination reaction, a general reaction such as the Buchwald-Hartwig reaction can be utilized. Also, in the second reaction, the Tandem Hetero-Friedel-Crafts reaction can be utilized.

The second reaction is a reaction for introducing $Y^1$ that links the ring A (ring a), ring B (ring b) and ring C (ring c) as illustrated in the following scheme (1) or (2), and as an example, the case in which $Y^1$ represents a boron atom; and $X^1$ and $X^2$ represent oxygen atoms is shown below. First, the hydrogen atom between $X^1$ and $X^2$ is ortho-metalated with n-butyllithium, sec-butyllithium or t-butyllithium. Subsequently, boron trichloride, boron tribromide or the like is added thereto to conduct lithium-boron metal exchange, and then a Brønsted base such as N,N-diisopropylethylamine is added thereto to induce a Tandem Bora-Friedel-Crafts reaction. Thus, an intended product may be obtained. In the second reaction, a Lewis acid such as aluminum trichloride may also be added in order to accelerate the reaction.

Scheme (1)

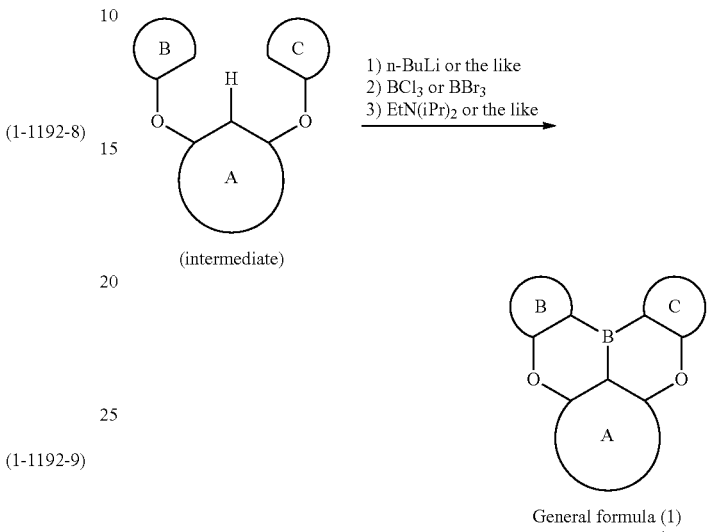

Scheme (2)

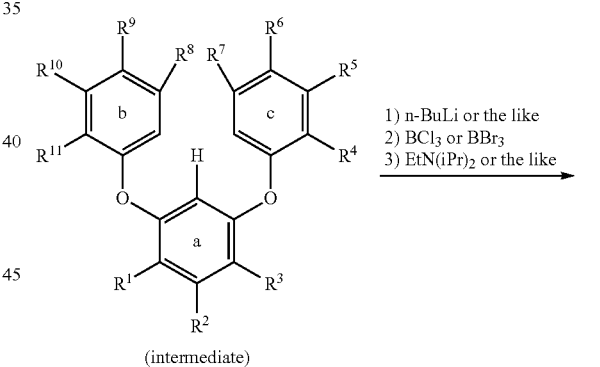

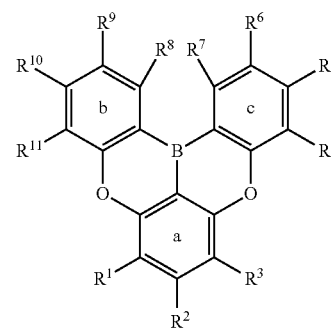

General formula (2) type compound

Meanwhile, the scheme (1) or (2) mainly illustrates the method for producing a polycyclic aromatic compound represented by general formula (1) or (2); however, an oligomer thereof can be produced by using an intermediate having plural ring A's (ring a's), ring B's (ring b's) and ring C's (ring c's). More specifically, the production method may be explained by the following schemes (3) to (5). In this case, the intended product may be obtained by increasing the amount of the reagent used therein such as butyllithium to a double amount or a triple amount.

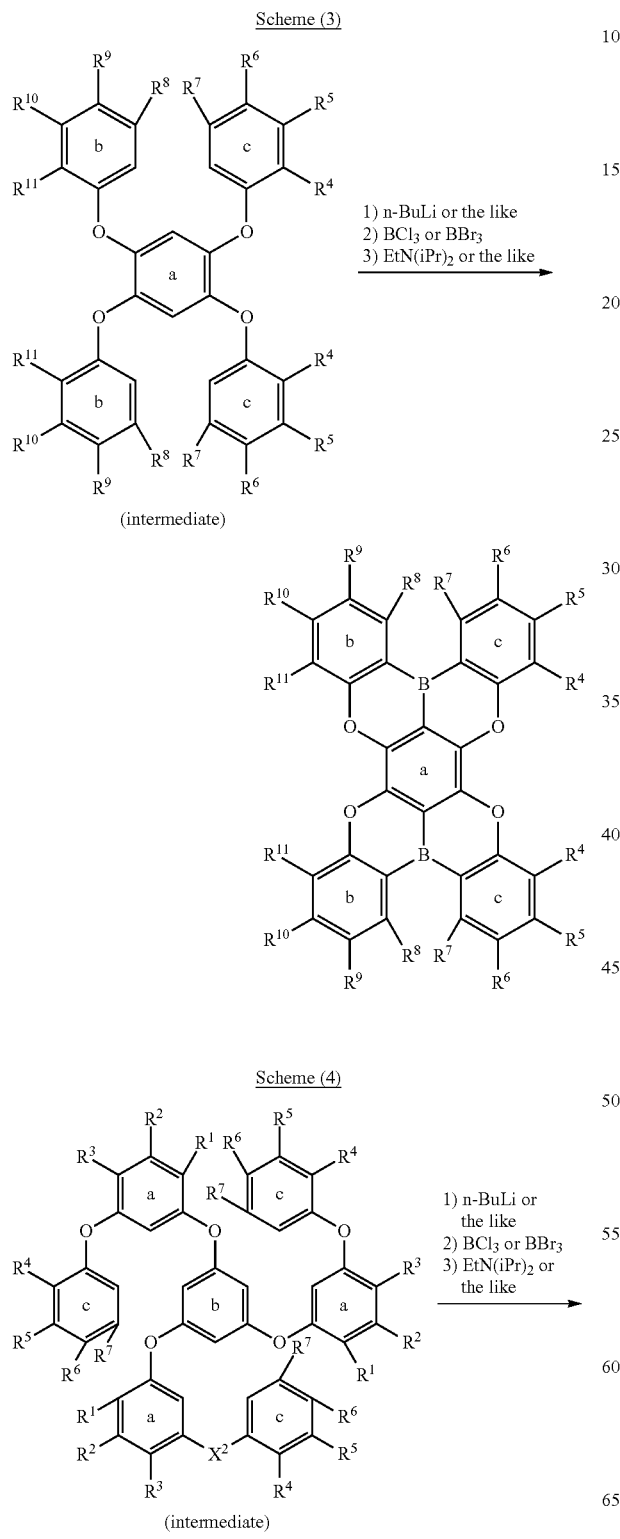

In the above schemes, lithium is introduced into a desired position by ortho-metalation; however, lithium can also be introduced into a desired position by halogen-metal exchange by introducing a bromine atom or the like to a position to which it is wished to introduce lithium, as in the following schemes (6) and (7).

Scheme (6)

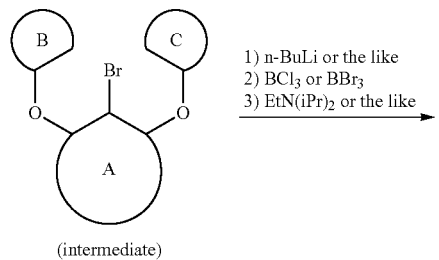

(intermediate)

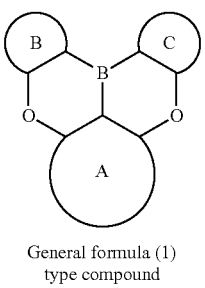

General formula (1) type compound

Scheme (7)

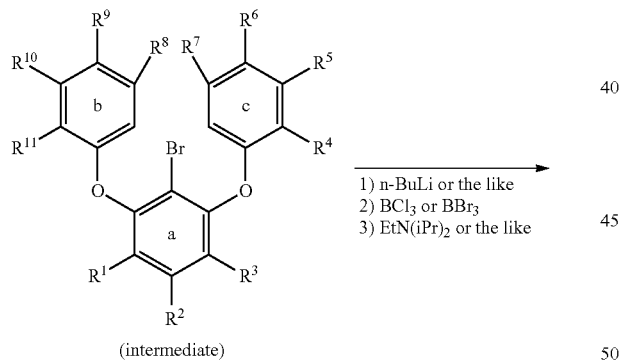

(intermediate)

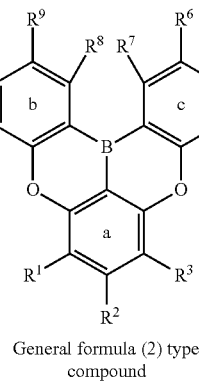

General formula (2) type compound

Furthermore, also in regard to the method for producing an oligomer described in the scheme (3), lithium can be introduced to a desired position also by halogen-metal exchange by introducing halogen such as a bromine atom or a chlorine atom to a position to which it is wished to introduce lithium, as in the above schemes (6) and (7) (following schemes (8), (9) and (10)).

Scheme (8)

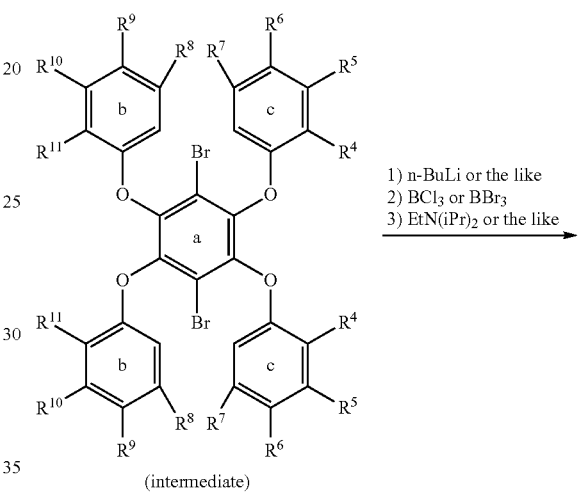

(intermediate)

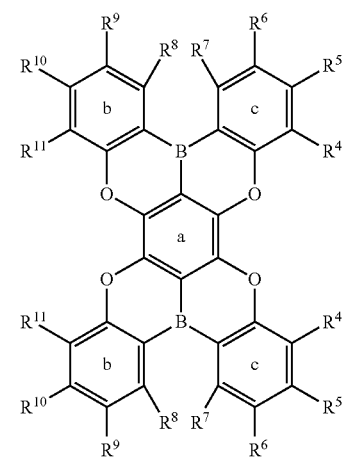

Scheme (9)

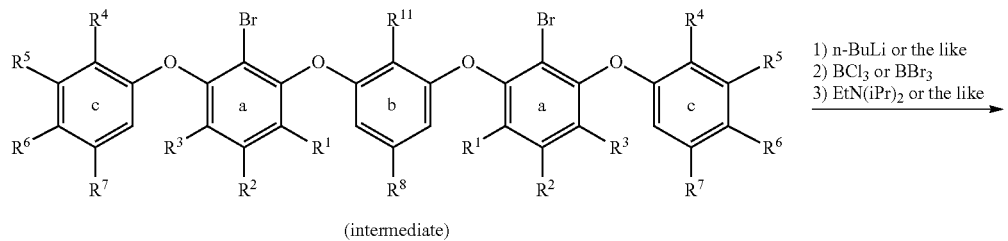

Scheme (10)

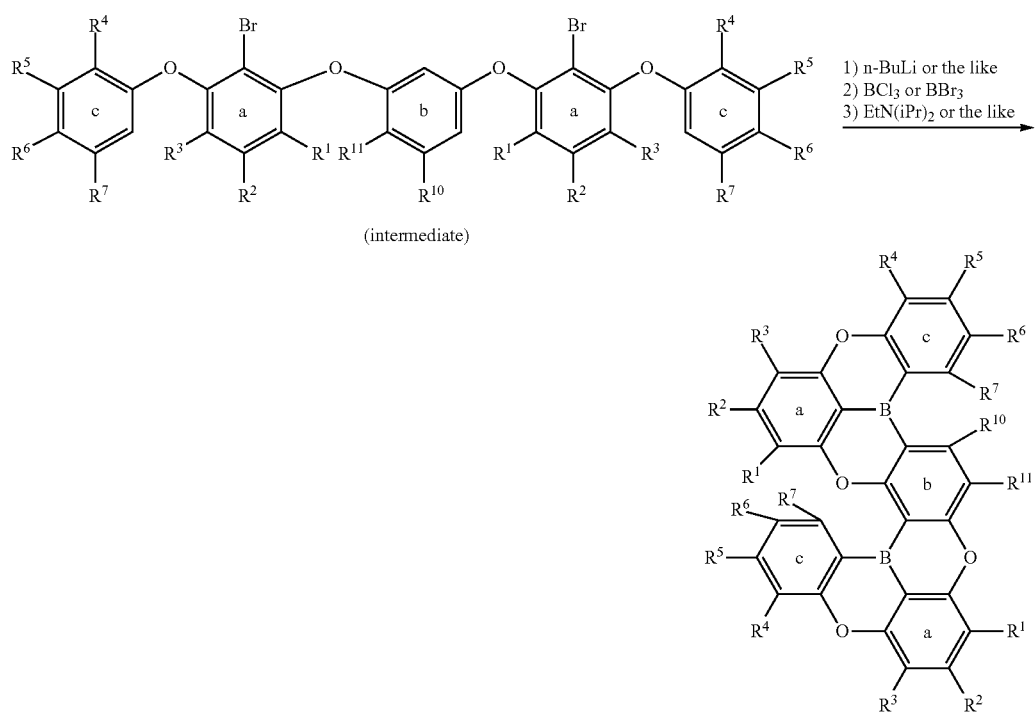

According to this method, an intended product can also be synthesized even in a case in which ortho-metalation cannot be achieved due to the influence of substituents, and therefore, the method is useful.

By appropriately selecting the synthesis method described above and appropriately selecting the raw materials to be used, a polycyclic aromatic compound having substituents at desired positions, with $Y^1$ being a boron atom and $X^1$ and $X^2$ being oxygen atoms, and an oligomer thereof can be synthesized.

Next, the case in which $Y^1$ represents a boron atom and $X^1$ and $X^2$ represent nitrogen atoms, is illustrated as an example in the following schemes (11) and (12). Similarly to the case in which $X^1$ and $X^2$ are oxygen atoms, first, the hydrogen atom between $X^1$ and $X^2$ is ortho-metalated with n-butyllithium or the like. Subsequently, boron tribromide or the like is added thereto to induce lithium-boron metal exchange, and then a Brønsted base such as N,N-diisopropylethylamine is added thereto to induce a Tandem Bora-Friedel-Crafts reaction. Thus, an intended product may be obtained. In this reaction, a Lewis acid such as aluminum trichloride may also be added in order to accelerate the reaction.

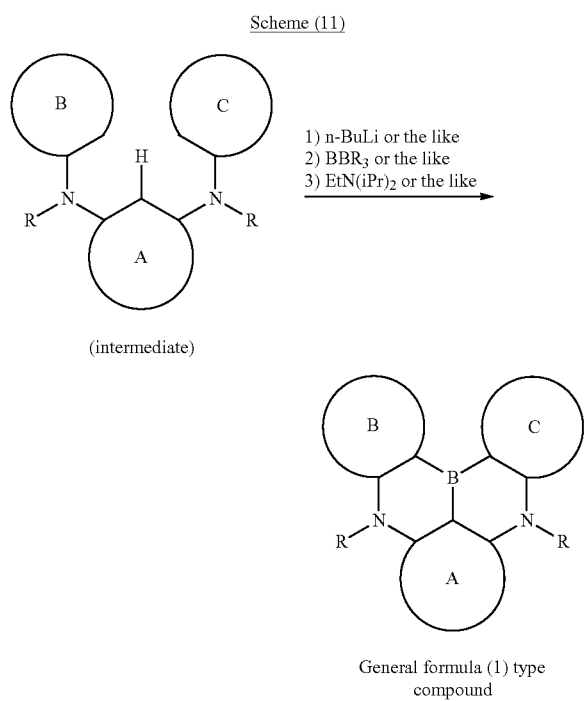

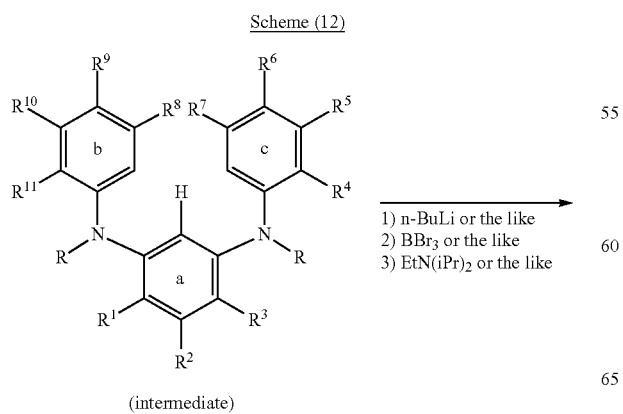

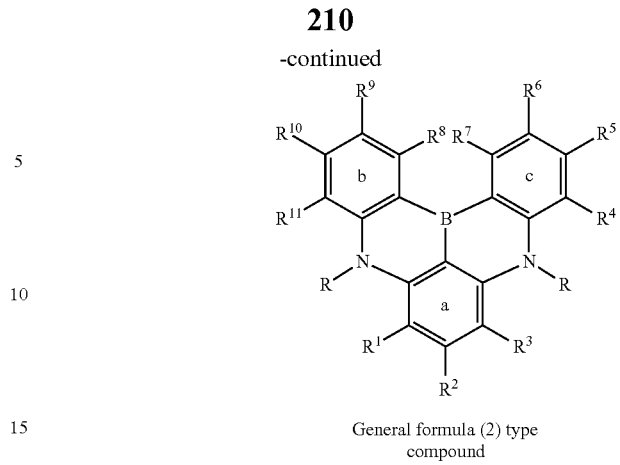

General formula (2) type compound

Furthermore, even for an oligomer in the case in which $Y^1$ represents a boron atom; and $X^1$ and $X^2$ represent nitrogen atoms, lithium can be introduced to a desired position also by halogen-metal exchange by introducing halogen such as a bromine atom or a chlorine atom to a position to which it is wished to introduce lithium, as in the case of the schemes (6) and (7) (following schemes (13), (14) and (15)).

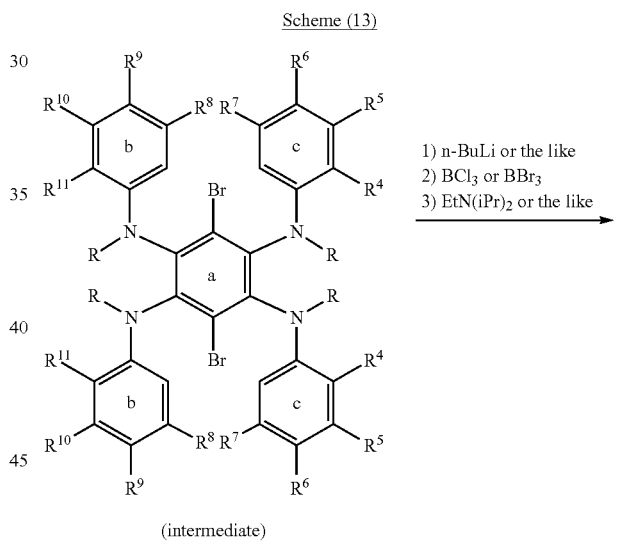

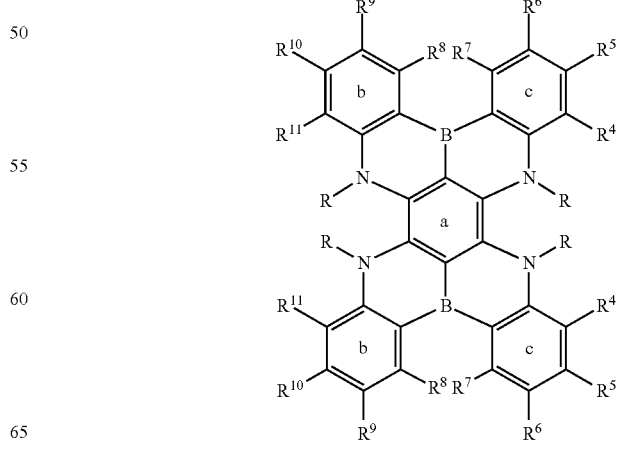

Scheme (14)

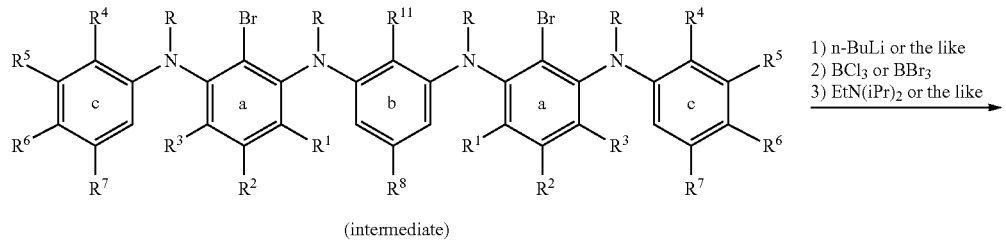

1) n-BuLi or the like
2) BCl₃ or BBr₃
3) EtN(iPr)₂ or the like (intermediate)

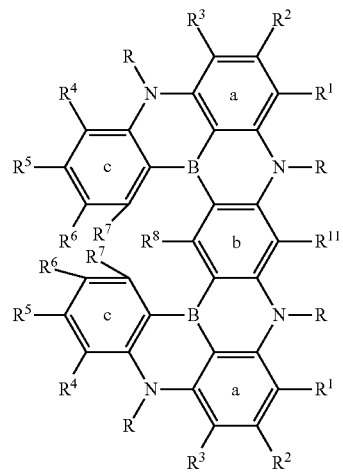

Scheme (15)

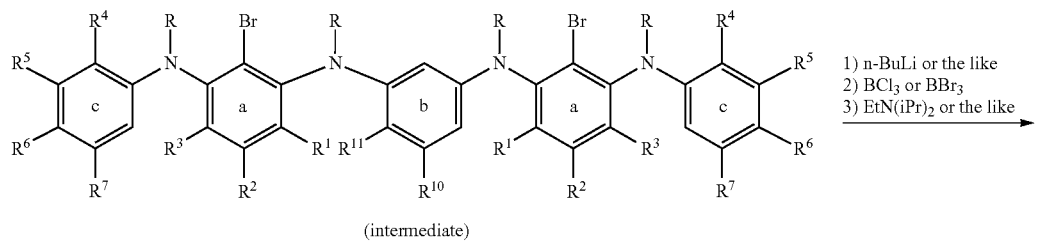

1) n-BuLi or the like
2) BCl₃ or BBr₃
3) EtN(iPr)₂ or the like (intermediate)

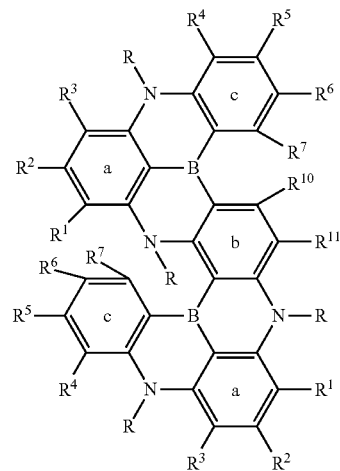

Next, the case in which $Y^1$ represents phosphorus sulfide, phosphorous oxide or a phosphorus atom; and $X^1$ and $X^2$ represent oxygen atoms, is illustrated as an example in the following schemes (16) to (19). Similarly to the cases explained thus far, first, the hydrogen atom between $X^1$ and $X^2$ is ortho-metalated with n-butyllithium or the like. Subsequently, phosphorus trichloride and sulfur are added thereto in this order, and finally a Lewis acid such as aluminum trichloride and a Brønsted base such as N,N-diisopropylethylamine are added thereto to induce the Tandem Phospha-Friedel-Crafts reaction. Thus, a compound in which $Y^1$ is phosphorus sulfide can be obtained. Furthermore, when the phosphorus sulfide compound thus obtained is treated with m-chloroperbenzoic acid (m-CPBA), a compound in which $Y^1$ is phosphorus oxide can be obtained, while the phosphorus sulfide compound is treated with triethylphosphine, a compound in which $Y^1$ is a phosphorus atom can be obtained.

Scheme (16)

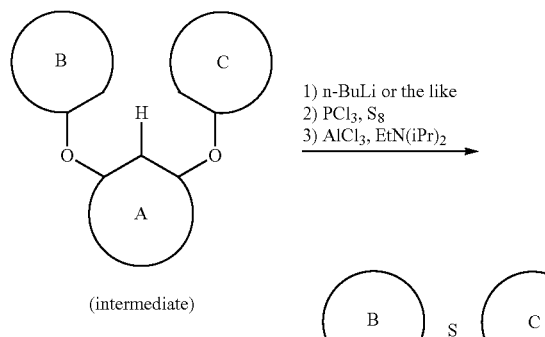

Scheme (17)

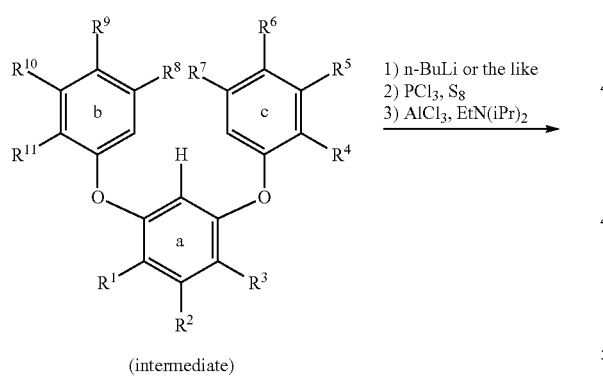

Scheme (18)

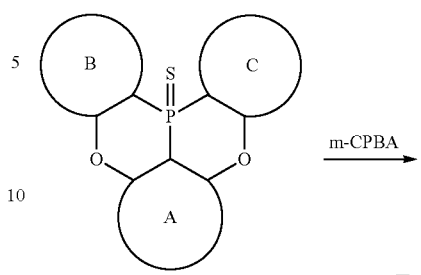

Scheme (19)

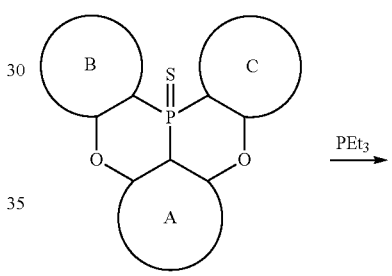

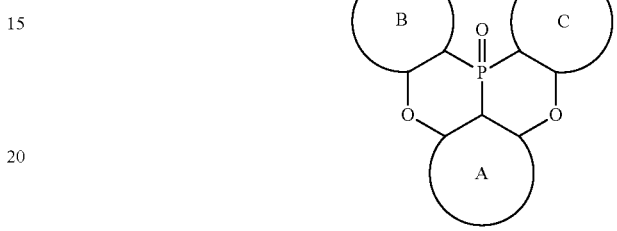

Furthermore, also for an oligomer in the case where $Y^1$ is phosphorus sulfide; and $X^1$ and $X^2$ are oxygen atoms, lithium can be introduced to a desired position also by halogen-metal exchange by introducing halogen such as a bromine atom or a chlorine atom to a position to which it is wished to introduce lithium, similarly to the schemes (6) and (7) (following schemes (20), (21) and (22)). Furthermore, when the oligomer obtained in this manner in which $Y^1$ represents phosphorus sulfide; and $X^1$ and $X^2$ represents oxygen atoms, is treated with m-chloroperbenzoic acid (m-CPBA) in the same manner as in the schemes (18) and (19), a compound in which $Y^1$ is phosphorus oxide can be obtained, and when the oligomer is treated with triethylphosphine, a compound in which $Y^1$ is a phosphorus atom can be obtained.

Scheme (20)
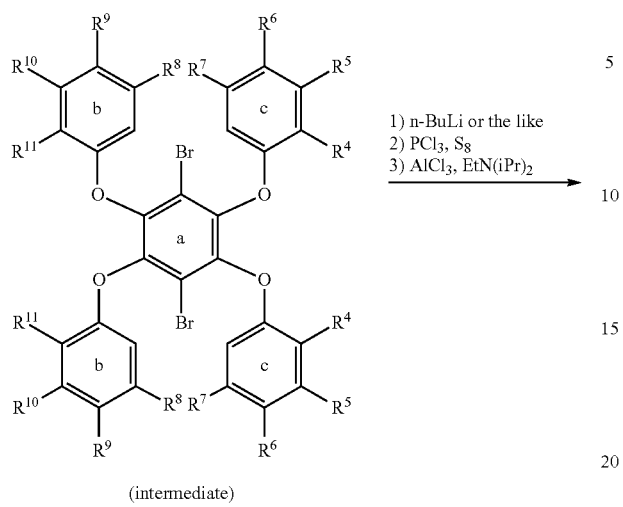
(intermediate)
1) n-BuLi or the like
2) $PCl_3$, $S_8$
3) $AlCl_3$, $EtN(iPr)_2$
-continued
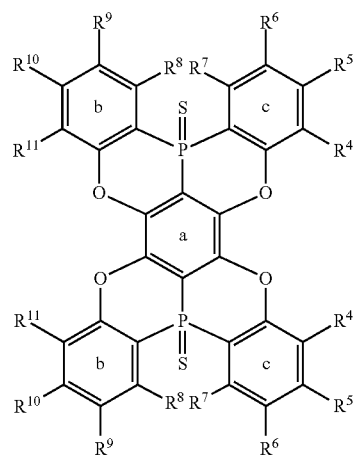
Scheme (21)
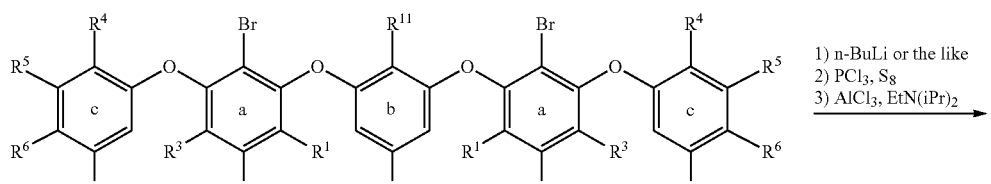
(intermediate)
1) n-BuLi or the like
2) $PCl_3$, $S_8$
3) $AlCl_3$, $EtN(iPr)_2$
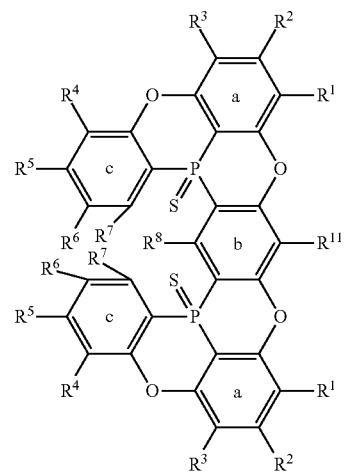
Scheme (22)
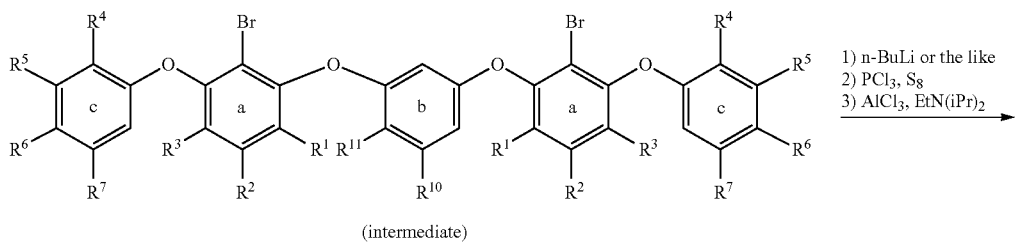
(intermediate)
1) n-BuLi or the like
2) $PCl_3$, $S_8$
3) $AlCl_3$, $EtN(iPr)_2$

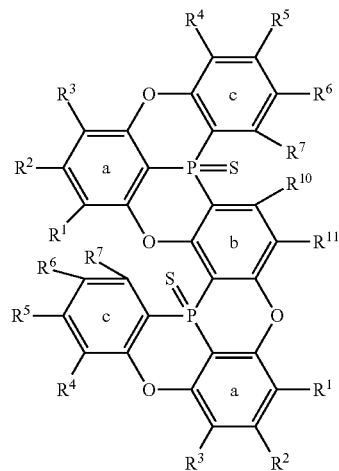

Here, an example in which $Y^1$ represents B, P, P=O or P=S; and $X^1$ and $X^2$ represent O or NR is described; however, a compound in which $Y^1$ represents Al, Ga, As, Si—R or Ge—R; or $X^1$ and $X^2$ represent S can also be synthesized by appropriately modifying the raw materials.

Specific examples of the solvent used in the above reactions include t-butylbenzene and xylene.

Furthermore, in general formula (2), adjacent groups among the substituents $R^1$ to $R^{11}$ of the ring a, ring b and ring c may be bonded to each other and form an aryl ring or a heteroaryl ring together with the ring a, ring b or ring c, and at least one hydrogen atom in the ring thus formed may be substituted by an aryl or a heteroaryl. Therefore, the polycyclic aromatic compound represented by general formula (2) is such that the ring structure that constitutes the compound changes as represented by formula (2-1) and formula (2-2) of the following schemes (23) and (24), due to the mutual bonding form of substituents in the ring a, ring b and ring c. These compounds can be synthesized by applying the synthesis methods shown in the above schemes (1) to (19) to the intermediates shown in the following schemes (23) and (24).

Scheme (23)

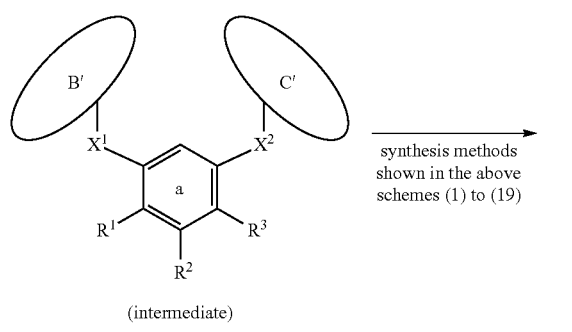

(intermediate)

synthesis methods shown in the above schemes (1) to (19) →

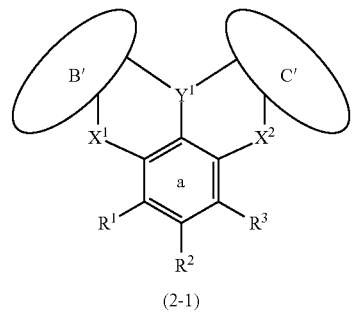

(2-1)

Scheme (24)

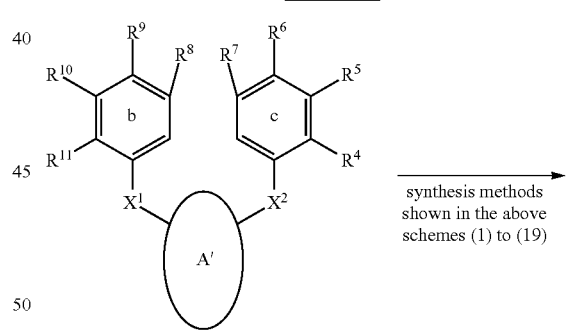

(intermediate)

synthesis methods shown in the above schemes (1) to (19) →

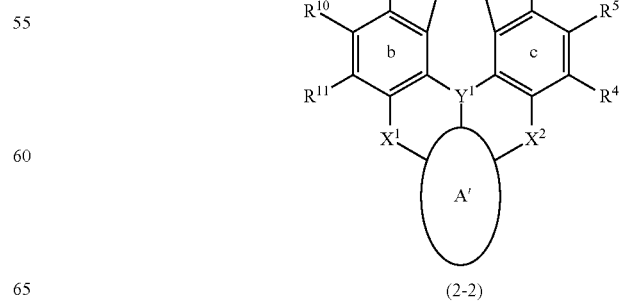

(2-2)

Ring A', ring B' and ring C' in the above formula (2-1) and formula (2-2) represent aryl rings or heteroaryl rings formed by bonding between adjacent groups among the substituents $R^1$ to $R^{11}$ together with the ring a, ring b, and ring c, respectively (may also be fused rings obtained as other ring structures are fused to the ring a, ring b or ring c). Meanwhile, although it is not suggested in the formulas, there is also a compound in which all of the ring a, ring b and ring c have been converted to ring A', ring B', and ring C').

Furthermore, the provision that "R of the moiety N—R is linked to the ring b and/or ring c via —O—, —S—, —C(—R)$_2$— or a single bond" in general formula (2) can be expressed as a compound having a ring structure represented by formula (2-3) of the following scheme (25), in which $X^1$ or $X^2$ is incorporated into the fused ring B' and fused ring C'. Such a compound can be synthesized by applying the synthesis methods illustrated in the schemes (1) to (19) to the intermediate represented by the following scheme (25).

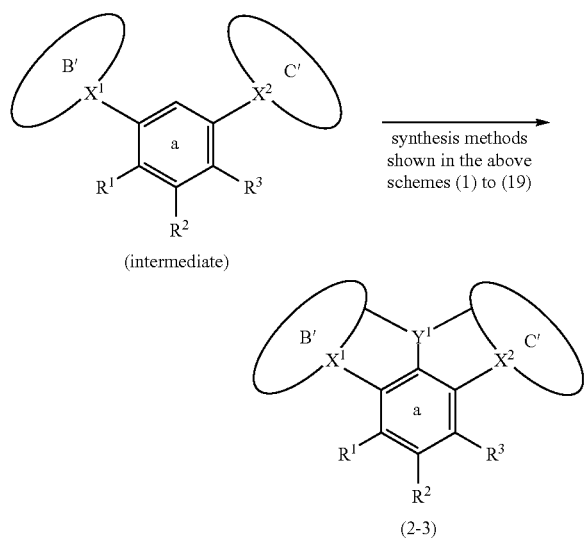

Furthermore, regarding the synthesis methods of the above schemes (1) to (17) and (20) to (25), there is shown an example of carrying out the Tandem Hetero-Friedel-Crafts reaction by ortho-metalating the hydrogen atom (or a halogen atom) between $X^1$ and $X^2$ with butyllithium or the like, before boron trichloride, boron tribromide or the like is added. However, the reaction may also be carried out by adding boron trichloride, boron tribromide or the like without conducting ortho-metalation using butyllithium or the like.

The polycyclic aromatic compound of the present invention or an oligomer thereof also includes compounds in which at least a portion of hydrogen atoms have been substituted by deuterium atoms or substituted by fluorine atoms; however, these compounds can be synthesized as described above by using raw materials that are deuterated or fluorinated at desired sites.

The polycyclic aromatic compound according to the present invention and an oligomer thereof can be used as a material for organic devices. Examples of the organic devices include an organic electroluminescent element, an organic field effect transistor, and an organic thin film solar cell.

3. Organic Electroluminescent Element

The polycyclic aromatic compound according to the present invention and an oligomer thereof can be used as, for example, a material for an organic electroluminescent element. Hereinafter, an organic EL element related to the present exemplary embodiment will be described in detail based on the drawings. The FIGURE is an outline cross-sectional diagram illustrating an organic EL element related to the present exemplary embodiment.

<Structure of Organic Electroluminescent Element>

The organic electroluminescent element 100 illustrated in the FIGURE includes a substrate 101; a positive electrode 102 provided on the substrate 101; a hole injection layer 103 provided on the positive electrode 102; a hole transport layer 104 provided on the hole injection layer 103; a light emitting layer 105 provided on the hole transport layer 104; an electron transport layer 106 provided on the light emitting layer 105; an electron injection layer 107 provided on the electron transport layer 106; and a negative electrode 108 provided on the electron injection layer 107.

The organic electroluminescent element 100 may also be configured, by reversing the production procedure, to include, for example, a substrate 101; a negative electrode 108 provided on the substrate 101; an electron injection layer 107 provided on the negative electrode 108; an electron transport layer 106 provided on the electron injection layer 107; a light emitting layer 105 provided on the electron transport layer 106; a hole transport layer 104 provided on the light emitting layer 105; a hole injection layer 103 provided on the hole transport layer 104; and a positive electrode 102 provided on the hole injection layer 103.

Not all of the various layers are essential, and the configuration may include a positive electrode 102, a light emitting layer 105, and a negative electrode 108 as the minimum constituent units, while the hole injection layer 103, the hole transport layer 104, the electron transport layer 106, and the electron injection layer 107 are optionally provided layers. Also, each of the various layers described above may be composed of a single layer, or may be composed of plural layers.

Embodiments of the layers that constitute an organic electroluminescent element may include, in addition to the configuration embodiment of "substrate/positive electrode/hole injection layer/hole transport layer/light emitting layer/electron transport layer/electron injection layer/negative electrode" described above, configuration embodiments of "substrate/positive electrode/hole transport layer/light emitting layer/electron transport layer/electron injection layer/negative electrode", "substrate/positive electrode/hole injection layer/light emitting layer/electron transport layer/electron injection layer/negative electrode", "substrate/positive electrode/hole injection layer/hole transport layer/light emitting layer/electron injection layer/negative electrode", "substrate/positive electrode/hole injection layer/hole transport layer/light emitting layer/electron transport layer/negative electrode", "substrate/positive electrode/light emitting layer/electron transport layer/electron injection layer/negative electrode", "substrate/positive electrode/hole transport layer/light emitting layer/electron injection layer/negative electrode", "substrate/positive electrode/hole transport layer/light emitting layer/electron transport layer/negative electrode", "substrate/positive electrode/hole injection layer/light emitting layer/electron injection layer/negative electrode", "substrate/positive electrode/hole injection layer/light emitting layer/electron transport layer/negative electrode", "substrate/positive electrode/light emitting layer/electron transport layer/negative electrode", and "substrate/positive electrode/light emitting layer/electron injection layer/negative electrode".

<Substrate in Organic Electroluminescent Element>

The substrate 101 serves as a support of the organic electroluminescent element 100, and usually, quartz, glass, metals, plastics and the like are used. The substrate 101 is formed into a plate shape, a film shape or a sheet shape according to the purpose, and for example, a glass plate, a metal plate, a metal foil, a plastic film, and a plastic sheet are used. Among them, a glass plate, and a plate made of a transparent synthetic resin such as polyester, polymethacrylate, polycarbonate or polysulfone are preferred. For the glass substrate, soda lime glass, alkali-free glass and the like are used, and furthermore, the thickness is desirably a thickness sufficient for maintaining the mechanical strength. Therefore, the thickness is desirably 0.2 mm or more. The upper limit value of the thickness is, for example, 2 mm or less, and preferably 1 mm or less. Regarding the material of glass, since a glass having fewer ions eluted from the glass is desirable, alkali-free glass is preferred. However, since soda lime glass provided with a barrier coat of $SiO_2$ or the like is also commercially available, this can be used. Furthermore, the substrate 101 may be provided with a gas barrier film such as a dense silicon oxide film on at least one surface in order to increase the gas barrier properties, and particularly in the case of using a plate, a film or a sheet made of a synthetic resin having low gas barrier properties as the substrate 101, it is preferable to provide a gas barrier film.

<Positive Electrode in Organic Electroluminescent Element>

The positive electrode 102 is a member that accomplishes the role of injecting holes to the light emitting layer 105. In addition, when a hole injection layer 103 and/or hole transport layer 104 is provided between the positive electrode 102 and the light emitting layer 105, holes are injected into the light emitting layer 105 through these layers.

Examples of the material that forms the positive electrode 102 include inorganic compounds and organic compounds. Examples of the inorganic compounds include metals (aluminum, gold, silver, nickel, palladium, chromium and the like), metal oxides (oxides of indium, oxides of tin, indium tin oxide (ITO), indium zinc oxide (IZO), and the like), metal halides (copper iodide and the like), copper sulfide, carbon black, ITO glass, and Nesa glass. Examples of the organic compounds include electrically conductive polymers such as polythiophene such as poly(3-methylthiophene), polypyrrole, and polyaniline. In addition to them, the material can be appropriately selected for use from the materials used as the positive electrode of organic electroluminescent elements.

The resistance of a transparent electrode is not limited because it is desirable if sufficient electric current can be supplied to the light emission of a light emitting element; however, from the viewpoint of the consumption power of the light emitting element, lower resistance is preferred. For example, an ITO substrate having a resistance of 300Ω/□ or less functions as an element electrode; however, since substrates having a resistance of about 10Ω/□ can also be supplied, it is particularly preferable to use a low resistance product having a resistance of, for example, 100 to 5Ω/□, and preferably 50 to 5Ω/□. The thickness of ITO can be arbitrarily selected according to the resistance value, but many products having a thickness between 50 nm and 300 nm are usually used.

<Hole Injection Layer and Hole Transport Layer in Organic Electroluminescent Element>

The hole injection layer 103 is a layer that accomplishes the role of efficiently injecting holes that migrate from the positive electrode 102 into the light emitting layer 105 or into the hole transport layer 104. The hole transport layer 104 is a layer that accomplishes the role of efficiently transporting the holes injected from the positive electrode 102 or the holes injected from the positive electrode 102 through the hole injection layer 103, to the light emitting layer 105. The hole injection layer 103 and the hole transport layer 104 are respectively formed by laminating and mixing one kind or two or more kinds of hole injecting/transporting materials, or by a mixture of hole injecting/transporting materials and a polymer binder. Furthermore, the layers may also be formed by adding an inorganic salt such as iron(III) chloride to hole injecting/transporting materials.

A hole injecting/transporting substance needs to be capable of efficiently injecting/transporting holes from the positive electrode between electrodes to which an electric field is applied, and a substance having high hole injection efficiency and being capable of efficiently transporting injected holes is desired. For this purpose, a substance which has low ionization potential, large hole mobility, and excellent stability, and in which impurities that serve as traps are not easily generated at the time of production and at the time of use, is preferred.

Regarding the material that forms the hole injection layer 103 and the hole transport layer 104, a polycyclic aromatic compound represented by the above general formula (1) or an oligomer thereof can be used. Furthermore, in regard to photoconductive material, any compound can be selected for use among the compounds that have been conventionally used as charge transporting materials for holes, p-type semiconductors, and known compounds that are used in hole injection layers and hole transport layers of organic electroluminescent elements. Specific examples thereof include heterocyclic compounds, including carbazole derivatives (N-phenylcarbazole, polyvinylcarbazole, and the like); bis-carbazole derivatives such as bis(N-arylcarbazole) and bis(N-alkylcarbazole); triarylamine derivatives (a polymer having an aromatic tertiary amino in the main chain or a side chain, 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-di amine, N,N'-dinaphthyl-N,N'-diphenyl-4,4'-dphenyl-1,1'-diamine, $N^4,N^{4'}$-diphenyl-$N^4,N^{4'}$-bis(9-phenyl-9H-carbazol-3-yl)-[1,1'-biphenyl]-4,4'-diamine, $N^4,N^4,N^{4'}N^{4'}$-tetra [1,1'-biphenyl]-4-yl)-[1,1'-biphenyl]-4,4'-diamine, triphenylamine derivatives such as 4,4',4"-tris(3-methylphenyl(phenyl)amino)triphenylamine, starburst amine derivatives, and the like); stilbene derivatives; phthalocyanine derivatives (metal-free, copper phthalocyanine, and the like); pyrazoline derivatives; hydrazone-based compounds; benzofuran derivatives; thiophene derivatives; oxadiazole derivatives; quinoxaline derivatives (for example, 1,4,5,8,9,12-hexaazatriphenylene-2,3,6,7,10,11-hexacarbonitrile, and the like); and porphyrin derivatives; and polysilanes. In a polymeric system, a polycarbonate, a styrene derivative, a polyvinylcarbazole, a polysilane and the like, which have the above-mentioned monomers in side chains, are preferred; however, there are no particular limitations as long as the compound is capable of forming a thin film that is needed for the production of a light emitting element, injecting holes from a positive electrode, and transporting holes.

Furthermore, it is also known that electroconductivity of an organic semiconductor is strongly affected by doping of the material. Such an organic semiconductor matrix substance is composed of a compound having satisfactory electron donating properties, or a compound having satisfactory electron accepting properties. For the doping of electron-donating substances, there are known strong electron acceptors such as tetracyanoquinonedimethane (TCNQ) and 2,3,5,6-tetrafluorotetracyano-1,4-benzoquinonedimethane (F4TCNQ) (see, for example, "M. Pfeiffer, A. Beyer, T. Fritz, K. Leo, Appl. Phys. Lett., 73(22), 3202-3204 (1998)" and "J. Blochwitz, M. Pfeiffer, T. Fritz, K. Leo, Appl. Phys. Lett., 73(6), 729-731 (1998)"). These compounds produce so-called holes by an electron transfer process in an electron-donating type base substance (hole transporting substance). Electroconductivity of the base substance changes fairly significantly depending on the number and mobility of the holes. Known examples of a matrix substance having hole transporting characteristics include benzidine derivatives (TPD and the like), starburst amine derivatives (TDATA and the like), and particular metal phthalocyanines (particularly, zinc phthalocyanine (ZnPc) and the like) (JP 2005-167175 A).

<Light Emitting Layer in Organic Electroluminescent Element>

The light emitting layer 105 is a layer that is disposed between electrodes to which an electric field is applied, and emits light by recombining the holes injected from the positive electrode 102 and the electron injected from the negative electrode 108. The material that forms the light emitting layer 105 may be any compound that is excited by recombination of holes and electrons and emits light (luminescent compound), and is preferably a compound that can form a stable thin film shape, and exhibits strong light emission (fluorescence) efficiency in a solid state. In the present invention, the polycyclic aromatic compound represented by the above general formula (1) or an oligomer thereof can be used as the material for light emitting layer.

The light emitting layer may be any of a single layer or plural layers, and each layer is formed by a material for light emitting layer (a host material and a dopant material). The host material and the dopant material may be respectively composed of a single kind, or may be respectively a combination of plural kinds. The dopant material may be included wholly in the host material, or may be partially included. Regarding the doping method, the light emitting layer can be formed by a co-deposition method with a host material; or alternatively, a dopant material may be mixed in advance with a host material, and then deposition may be carried out simultaneously.

The amount of use of the host material may vary with the kind of the host material, and the amount of use may be determined according to the characteristics of the host material. The reference of the amount of use of the host material is preferably 50 to 99.999% by weight, more preferably 80 to 99.95% by weight, and even more preferably 90 to 99.9% by weight, relative to the total amount of the material for light emitting layer. The polycyclic aromatic compound represented by the above general formula (1) or an oligomer thereof can also be used as the host material.

The amount of use of the dopant material may vary with the kind of the dopant material, and the amount of use may be determined according to the characteristics of the dopant material. The reference of the amount of use of the dopant material is preferably 0.001 to 50% by weight, more preferably 0.05 to 20% by weight, and even more preferably 0.1 to 10% by weight, relative to the total amount of the material for light emitting layer. When the amount of use is in the range described above, for example, it is preferable from the viewpoint that a concentration quenching phenomenon can be prevented. The polycyclic aromatic compound represented by the above general formula (1) or an oligomer thereof can also be used as the dopant material.

Examples of the host material that can be used in combination with the polycyclic aromatic compound represented by the above general formula (1) or an oligomer thereof include fused ring derivatives of anthracene, pyrene and the like that have been traditionally known as luminous bodies, bisstyryl derivatives such as bisstyrylanthracene derivatives and distyrylbenzene derivatives, tetraphenylbutadiene derivatives, cyclopentadiene derivatives, fluorene derivatives, and benzofluorene derivatives.

Furthermore, the dopant material that can be used in combination with the polycyclic aromatic compound represented by the above general formula (1) or an oligomer thereof is not particularly limited, and existing compounds can be used. The dopant material can be selected from various materials depending on the desired color of emitted light. Specific examples thereof include fused ring derivatives of phenanthrene, anthracene, pyrene, tetracene, pentacene, perylene, naphthopyrene, dibenzopyrene, rubrene, chrysene and the like; benzoxazole derivatives, benzothiazole derivatives, benzimidazole derivatives, benzotriazole derivatives, oxazole derivatives, oxadiazole derivatives, triazole derivatives, imidazole derivatives, thiadiazole derivatives, triazole derivatives, pyrazoline derivatives, stilbene derivatives, thiophene derivatives, tetraphenylbutadiene derivatives, cyclopentadiene derivatives, bisstyryl derivatives such as bisstyrylanthracene derivatives and distyrylbenzene derivatives (JP 1-245087 A), bisstyrylarylene derivatives (JP 2-247278 A), diazaindacene derivatives, furan derivatives, benzofuran derivatives; isobenzofuran derivatives such as phenylisobenzofuran, dimesitylisobenzofuran, di(2-methylphenyl)isobenzofuran, di(2-trifluoromethylphenyl)isobenzofuran, and phenylisobenzofuran; dibenzofuran derivatives; coumarin derivatives such as 7-dialkylaminocoumarin derivatives, 7-piperidinocoumarin derivatives, 7-hydroxycoumarin derivatives, 7-methoxycoumarin derivatives, 7-acetoxycoumarin derivatives, 3-benzothiazolylcoumarin derivatives, 3-benzimidazolylcoumarin derivatives, and 3-benzoxazolylcoumarin derivatives; dicyanomethylenepyran derivatives, dicyanomethylenethiopyran derivatives, polymethine derivatives, cyanine derivatives, oxobenzoanthracene derivatives, xanthene derivatives, rhodamine derivatives, fluorescein derivatives, pyrylium derivatives, carbostyryl derivatives, acridine derivatives, oxazine derivatives, phenylene oxide derivatives, quinacridone derivatives, quinazoline derivatives, pyrrolopyridine derivatives, furopyridine derivatives, 1,2,5-thiadiazolopyrene derivatives, pyromethene derivatives, perinone derivatives, pyrrolopyrrole derivatives, squarylium derivatives, violanthrone derivatives, phenazine derivatives, acridone derivatives, deazaflavine derivatives, fluorene derivatives, and benzofluorene derivatives.

To list the examples of each of the light colors, examples of blue to bluish green dopant materials include aromatic hydrocarbon compounds and derivatives thereof, such as naphthalene, anthracene, phenanthrene, pyrene, triphenylene, perylene, fluorene, indene, and chrysene; aromatic heterocyclic compounds and derivatives thereof, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, and thioxanthene; distyrylbenzene derivatives, tetraphenylbutadiene derivatives, stilbene derivatives, aldazine derivatives, coumarin derivatives; azole derivatives such as imidazole, triazole, thiadiazole, carbazole, oxazole, oxadiazole, and triazole, and metal complexes thereof; and aromatic amine derivatives represented by N,N'-diphenyl-N,N'-di(3-methylphenyl)-4,4'-diphenyl-1,1'-di amine.

Furthermore, examples of green-yellow dopant materials include coumarin derivatives, phthalimide derivatives, naphthalimide derivatives, perinone derivatives, pyrrolopyrrole derivatives, cyclopentadiene derivatives, acridone derivatives, quinacridone derivatives, and naphthacene derivatives such as rubrene. Furthermore, suitable examples thereof include compounds in which substituents capable of shifting to a longer wavelength, such as an aryl, a heteroaryl, an arylvinyl, an amino, and a cyano are introduced to the above compounds listed as an example of blue to bluish green dopant materials.

Furthermore, examples of orange to red dopant materials include naphthalimide derivatives such as bis(diisopropylphenyl)perylene tetracarboxylic acid imide; perinone derivatives; rare earth complexes such as Eu complexes containing acetylacetone, benzoylacetone and phenanthroline as ligands; 4-(dicyanomethylene)-2-methyl-6-(p-dimethylaminostyryl)-4H-pyran and analogues thereof; metal phthalocyanine derivatives such as magnesium phthalocyanine and aluminum chlorophthalocyanine; rhodamine compounds; deazaflavine derivatives; coumarin derivatives; quinacridone derivatives; phenoxazine derivatives; oxazine derivatives; quinazoline derivatives; pyrrolopyridine derivatives; squarylium derivatives; violanthrone derivatives; phenazine derivatives; phenoxazone derivatives, and thiadiazolopyrene derivatives. Furthermore, suitable examples thereof include compounds in which substituents capable of shifting to a longer wavelength, such as an aryl, a heteroaryl, an arylvinyl, an amino, and a cyano are introduced to the above compounds listed as an example of blue to bluish green and green-yellow dopant materials.

In addition to them, dopants can be appropriately selected for used from the compounds described in "Kagaku Kogyo (Chemical Industry)", June 2004, p. 13, and reference documents described therein.

Among the dopant materials described above, particularly an amine having a stilbene structure, a perylene derivative, a borane derivative, an aromatic amine derivative, a coumarin derivative, a pyran derivative, and a pyrene derivative are preferred.

An amine having a stilbene structure is represented by the following formula:

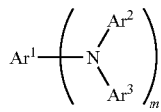

wherein $Ar^1$ represents an m-valent group derived from an aryl having 6 to 30 carbon atoms; $Ar^2$ and $Ar^3$ each independently represent an aryl having 6 to 30 carbon atoms, while at least one of $Ar^1$ to $Ar^3$ has a stilbene structure; $Ar^1$ to $Ar^3$ may be substituted; and m represents an integer from 1 to 4.

The amine having a stilbene structure is more preferably a diaminostilbene represented by the following formula:

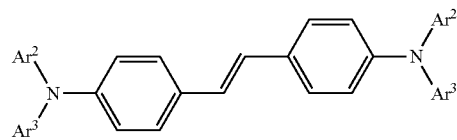

wherein $Ar^2$ and $Ar^3$ each independently represent an aryl having 6 to 30 carbon atoms, and $Ar^2$ and $Ar^3$ may be substituted.

Specific examples of the aryl having 6 to 30 carbon atoms include benzene, naphthalene, acenaphthylene, fluorene, phenalene, phenanthrene, anthracene, fluoranthene, triphenylene, pyrene, chrysene, naphthacene, perylene, stilbene, distyrylbenzene, distyrylbiphenyl, and distyrylfluorene.

Specific examples of the amine having a stilbene structure include
N,N,N',N'-tetra(4-biphenylyl)-4,4'-diaminostilbene,
N,N,N',N'-tetra(1-naphthyl)-4,4'-diaminostilbene,
N,N,N',N'-tetra(2-naphthyl)-4,4'-diaminostilbene,
N,N'-di(2-naphthyl)-N,N'-diphenyl-4,4'-diaminostilbene,
N,N'-di(9-phenanthryl)-N,N'-diphenyl-4,4'-diaminostilbene,
4,4'-bis[4''-bis(diphenylamino)styryl]-biphenyl,
1,4-bis[4'-bis(diphenylamino)styryl]-benzene,
2,7-bis[4'-bis(diphenylamino)styryl]-9,9-dimethylfluorene,
4,4'-bis(9-ethyl-3-carbazovinylene)-biphenyl, and
4,4'-bis(9-phenyl-3-carbazovinylene)-biphenyl.

Furthermore, the amines having a stilbene structure described in JP 2003-347056 A, JP 2001-307884 A and the like may also be used.

Examples of the perylene derivative include
3,10-bis(2,6-dimethylphenyl)perylene,
3,10-bis(2,4,6-trimethylphenyl)perylene,
3,10-diphenylperylene, 3,4-diphenylperylene,
2,5,8,11-tetra-t-butylperylene,
3,4,9,10-tetraphenylperylene,
3-(1'-pyrenyl)-8,11-di(t-butyl)perylene,
3-(9'-anthryl)-8,11-di(t-butyl)perylene, and
3,3'-bis(8,11-di(t-butyl)perylenyl).

Furthermore, the perylene derivatives described in JP 11-97178 A, JP 2000-133457 A, JP 2000-26324 A, JP 2001-267079 A, JP 2001-267078 A, JP 2001-267076 A, JP 2000-34234 A, JP 2001-267075 A, JP 2001-217077 A and the like may also be used.

Examples of the borane derivative include
1,8-diphenyl-10-(dimesitylboryl)anthracene,
9-phenyl-10-(dimesitylboryl)anthracene,
4-(9'-anthryl)dimesitylborylnaphthalene,
4-(10'-phenyl-9'-anthryl)dimesitylborylnaphthalene,
9-(dimesitylboryl)anthracene,
9-(4'-biphenylyl)-10-(dimesitylboryl)anthracene, and
9-(4'-(N-carbazolyl)phenyl)-10-(dimesitylboryl)anthracene.

Furthermore, the borane derivatives described in WO 2000/40586 may also be used.

An aromatic amine derivative is represented by, for example, the following formula:

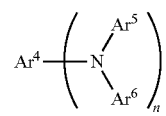

wherein Ar⁴ represents an n-valent group derived from an aryl having 6 to 30 carbon atoms; Ar⁵ and Ar⁶ each independently represent an aryl having 6 to 30 carbon atoms, while Ar⁴ to Ar⁶ may be substituted; and n represents an integer from 1 to 4.

Particularly, an aromatic amine derivative in which Ar⁴ represents a divalent group derived from anthracene, chrysene, fluorene, benzofluorene or pyrene; Ar⁵ and Ar⁶ each independently represent an aryl having 6 to 30 carbon atoms; Ar⁴ to Ar⁶ may be substituted; and n represents 2, is more preferred.

Specific examples of the aryl having 6 to 30 carbon atoms include benzene, naphthalene, acenaphthylene, fluorene phenalene, phenanthrene, anthracene, fluoranthene, triphenylene, pyrene, chrysene, naphthacene, perylene, and pentacene.

Examples of chrysene-based aromatic amine derivatives include N,N,N',N'-tetraphenylchrysene-6,12-diamine, N,N,N',N'-tetra(p-tolyl)chrysene-6,12-diamine, N,N,N',N'-tetra(m-tolyl)chrysene-6,12-diamine, N,N,N',N'-tetrakis(4-isopropylphenyl)chrysene-6,12-diamine, N,N,N',N'-tetra(naphthalen-2-yl)chrysene-6,12-diamine, N,N'-diphenyl-N,N'-di(p-tolyl)chrysene-6,12-diamine, N,N'-diphenyl-N,N'-bis(4-ethylphenyl)chrysene-6,12-diamine, N,N'-diphenyl-N,N'-bis(4-isopropylphenyl)chrysene-6,12-diamine, N,N'-diphenyl-N,N'-bis(4-t-butylphenyl)chrysene-6,12-diamine, and N,N'-bis(4-isopropylphenyl)-N,N'-di(p-tolyl)chrysene-6,12-diamine.

Furthermore, examples of pyrene-based aromatic diamine derivatives include N,N,N',N'-tetraphenylpyrene-1,6-diamine, N,N,N',N'-tetra(p-tolyl)pyrene-1,6-diamine, N,N,N',N'-tetra(m-tolyl)pyrene-1,6-diamine, N,N,N',N'-tetrakis(4-isopropyophenyl)pyrene-1,6-diamine, N,N,N',N'-tetrakis(3,4-dimethylphenyl)pyrene-1,6-diamine, N,N'-diphenyl-N,N'-di(p-tolyl)pyrene-1,6-diamine, N,N'-diphenyl-N,N'-bis(4-ethylphenyl)pyrene-1,6-diamine, N,N'-diphenyl-N,N'-bis(4-isopropylphenyl)pyrene-1,6-diamine, N,N'-diphenyl-N,N'-bis(4-t-butylphenyl)pyrene-1,6-diamine, N,N'-bis(4-isopropylphenyl)-N,N'-di(p-tolyl)pyrene-1,6-diamine, and N,N,N',N'-tetrakis(3,4-dimethylphenyl)-3,8-diphenylpyrene-1,6-diamine.

Furthermore, examples of anthracene-based aromatic amine derivatives include
N,N,N,N-tetraphenylanthracene-9,10-diamine,
N,N,N',N'-tetra(p-tolyl)anthracene-9,10-diamine,
N,N,N',N'-tetra(m-tolyl)anthracene-9,10-diamine,
N,N,N',N'-tetrakis(4-isopropylphenyl)anthracene-9,10-diamine,
N,N'-diphenyl-N,N'-di(p-tolyl)anthracene-9,10-diamine,
N,N'-diphenyl-N,N'-di(m-tolyl)anthracene-9,10-diamine,
N,N'-diphenyl-N,N'-bis(4-ethylphenyl)anthracene-9,10-diamine,
N,N'-diphenyl-N,N'-bis(4-isopropylphenyl)anthracene-9,10-di amine,
N,N'-diphenyl-N,N'-bis(4-t-butylphenyl)anthracene-9,10-diamine,
N,N'-bis(4-isopropylphenyl)-N,N'-di(p-tolyl)anthracene-9,10-diamine,
2,6-di-t-butyl-N,N,N',N'-tetra(p-tolyl)anthracene-9,10-diamine,
2,6-di-t-butyl-N,N'-diphenyl-N,N'-bis(4-isopropylphenyl) anthracene-9,10-diamine,
2,6-di-t-butyl-N,N'-bis(4-isopropylphenyl)-N,N'-di(p-tolyl) anthracene-9,10-diamine,
2,6-dicyclohexyl-N,N'-bis(4-isopropylphenyl)-N,N'-di(p-tolyl)-anthracene-9,10-diamine,
2,6-dicyclohexyl-N,N'-bis(4-isopropylphenyl)-N,N'-bis(4-t-butylphenyl)anthracene-9,10-diamine,
9,10-bis(4-diphenylaminophenyl)anthracene-9,10-bis(4-di(1-naphthylamino)phenyl)anthracene,
9,10-bis(4-di(2-naphthylamino)phenyl)anthracene,
10-di-p-tolylamino-9-(4-di-p-tolylamino-1-naphthyl)anthracene,
10-diphenylamino-9-(4-diphenylamino-1-naphthyl)anthracene, and
10-diphenylamino-9-(6-diphenylamino-2-naphthyl)anthracene.

Furthermore, examples of pyrene-based aromatic amine derivatives include
N,N,N,N-tetraphenyl-1,8-pyrene-1,6-diamine,
N-biphenyl-4-yl-N-biphenyl-1,8-pyrene-1,6-diamine, and
N¹,N⁶-diphenyl-N¹,N⁶-bis(4-trimethylsilanyl-phenyl)-1H,8H-pyrene-1,6-diamine.

Furthermore, other examples include
[4-(4-diphenylaminophenyl)naphthalene-1-yl]-diphenylamine,
[6-(4-diphenylaminophenyl)naphthalen-2-yl]-diphenylamine,
4,4'-bis[4-diphenylaminonaphthalen-1-yl]biphenyl,
4,4'-bis[6-diphenylaminonaphthalen-2-yl]biphenyl,
4,4"-bis[4-diphenylaminonaphthalen-1-yl]-p-terphenyl, and
4,4"-bis[6-diphenylaminonaphthalen-2-yl]-p-terphenyl.

Furthermore, the aromatic amine derivatives described in JP 2006-156888 A and the like may also be used.

Examples of the coumarin derivatives include coumain-6 and coumarin-334.

Furthermore, the coumarin derivatives described in JP 2004-43646 A, JP 2001-76876 A, JP 6-298758 A and the like may also be used.

Examples of the pyran derivatives include DCM and DCJTB described below.

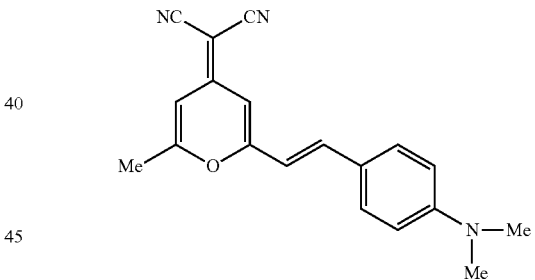

DCM

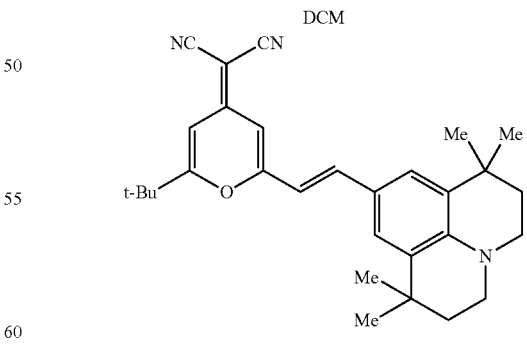

DCJTB

Furthermore, the pyran derivatives described in JP 2005-126399 A, JP 2005-097283 A, JP 2002-234892 A, JP 2001-220577 A, JP 2001-081090 A, JP 2001-052869 A, and the like may also be used.

<Electron Injection Layer and Electron Transport Layer in Organic Electroluminescent Element>

The electron injection layer 107 is a layer that accomplishes the role of efficiently injecting the electrons migrating from the negative electrode 108 into the light emitting layer 105 or the electron transport layer 106. The electron transport layer 106 is a layer that accomplishes the role of efficiently transporting the electrons injected from the negative electrode 108, or the electrons injected from the negative electrode 108 through the electron injection layer 107, to the light emitting layer 105. The electron transport layer 106 and the electron injection layer 107 are respectively formed by laminating and mixing one kind or two or more kinds of electron transporting/injecting materials, or by a mixture of an electron transporting/injecting material and a polymeric binder.

An electron injection/transport layer is a layer that manages injection of electrons from the negative electrode and transport of electrons, and is preferably a layer that has high electron injection efficiency and is capable of efficiently transporting injected electrons. In order to do so, a substance which has high electron affinity, large electron mobility, and excellent stability, and in which impurities that serve as traps are not easily generated at the time of production and at the time of use, is preferred. However, when the transport balance between holes and electrons is considered, in a case in which the electron injection/transport layer mainly accomplishes the role of efficiently preventing holes coming from the positive electrode from flowing toward the negative electrode side without being recombined, even if the electron transporting ability is not so high, the effect of enhancing the light emission efficiency is equal to that of a material having high electron transporting ability. Therefore, the electron injection/transport layer according to the present exemplary embodiment may also include the function of a layer that can efficiently prevent migration of holes.

As the material that forms the electron transport layer 106 or the electron injection layer 107 (electron transporting material), the polycyclic aromatic compound represented by the above general formula (1) or an oligomer thereof can be used. Furthermore, the material can be arbitrarily selected for use from compounds that have been conventionally used as electron transferring compounds in photoconducting materials, and known compounds that are used in electron injection layers and electron transport layers of organic electroluminescent elements.

Regarding the material that is used in the electron transport layer or electron injection layer, it is preferable that the material includes at least one selected from compounds formed from aromatic rings or heteroaromatic rings composed of one or more kinds of atoms selected from carbon, hydrogen, oxygen, sulfur, silicon and phosphorus; pyrrole derivatives and fused ring derivatives thereof; and metal complexes having electron-accepting nitrogen. Specific examples thereof include fused ring-based aromatic ring derivatives such as naphthalene and anthracene; styryl-based aromatic ring derivatives represented by 4,4'-bis(diphenylethenyl)biphenyl; perinone derivatives; coumarin derivatives; naphthalimide derivatives; quinone derivatives such as anthraquinone and diphenoquinone; phosphorus oxide derivatives; carbazole derivatives; and indole derivatives. Examples of a metal complex having electron-accepting nitrogen include hydroxyazole complexes such as hydroxyphenyloxazole complexes, azomethine complexes, tropolone-metal complexes, flavonol-metal complexes, and benzoquinoline-metal complexes. These materials are used singly, but may also be used as mixtures with other materials.

Furthermore, specific examples of other electron transferring compounds include pyridine derivatives, naphthalene derivatives, anthracene derivatives, phenanthroline derivatives, perinone derivatives, coumarin derivatives, naphthalimide derivatives, anthraquinone derivatives, diphenoquinone derivatives, diphenylquinone derivatives, perylene derivatives, oxadiazole derivatives (1,3-bis[(4-t-butylphenyl)-1,3,4-oxadiazolyl]phenylene, and the like), thiophene derivatives, triazole derivatives (N-naphthyl-2,5-diphenyl-1,3,4-triazole, and the like), thiadiazole derivatives, metal complexes of oxine derivatives, quinolinol-based metal complexes, quinoxaline derivatives, polymers of quinoxaline derivatives, benzazole compounds, gallium complexes, pyrazole derivatives, perfluorinated phenylene derivatives, triazine derivatives, pyrazine derivatives, benzoquinoline derivatives (2,2'-bis(benzo[h]quinolin-2-yl)-9,9'-spirobifluorene, and the like), imidazopyridine derivatives, borane derivatives, benzimidazole derivatives (tris(N-phenylbenzimidazol-2-yl)benzene, and the like), benzoxazole derivatives, benzothiazole derivatives, quinoline derivatives, oligopyridine derivatives such as terpyridine, bipyridine derivatives, terpyridine derivatives (1,3-bis(4'-(2,2':6'2"-terpyridinyl))benzene, and the like), naphthyridine derivatives (bis(1-naphthyl)-4-(1,8-naphthyridin-2-yl)phenylphosphine oxide, and the like), aldazine derivatives, carbazole derivatives, indole derivatives, phosphorus oxide derivatives, and bisstyryl derivatives.

Furthermore, metal complexes having electron-accepting nitrogen can also be used, and examples thereof include quinolinol-based metal complexes, hydroxyazole complexes such as hydroxyphenyloxazole complexes, azomethine complexes, tropolone-metal complexes, flavonol-metal complexes, and benzoquinoline-metal complexes.

The materials described above are used singly, but may also be used as mixtures with other materials.

Among the materials described above, quinolinol-based metal complexes, bipyridine derivatives, phenanthroline derivatives, and borane derivatives are preferred.

A quinolinol-based metal complex is a compound represented by the following general formula (E-1):

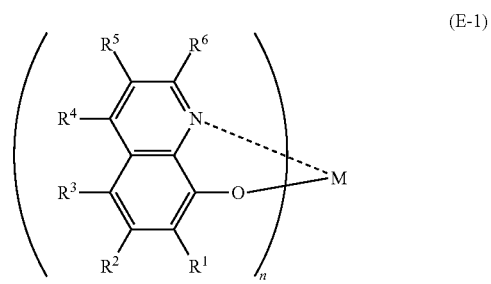

wherein $R^1$ to $R^6$ each represent a hydrogen atom or a substituent; M represents Li, Al, Ga, Be, or Zn; and n represents an integer from 1 to 3.

Specific examples of the quinolinol-based metal complex include 8-quinolinollithium, tris(8-quinolinolato)aluminum, tris(4-methyl-8-quinolinolato)aluminum, tris(5-methyl-8-quinolinolato)aluminum, tris(3,4-dimethyl-8-quiolinolato)aluminum, tris(4,5-dimethyl-8-quinolinolato)aluminum, tris(4,6-dimethyl-8-quinolinolato)aluminum, bis(2-methyl-8-quinolinolato)(phenolato)aluminum, bis(2-methyl-8- quinolinolato)(2-methylphenolato)aluminum, bis(2-methyl-8-quinolinolato)(3-methylphenolato)aluminum, bis(2-methyl-8-quinolinolato)(4-methylphenolato)aluminum, bis(2-methyl-8-quinolinolato)(2-phenylphenolato)aluminum, bis(2-methyl-8-quinolinolato)(3-phenylphenolato)aluminum, bis(2-methyl-8-quinolinolato)(4-phenylphenolato)aluminum, bis(2-methyl-8-quinolinolato)(2,3-dimethylphenolato)aluminum, bis(2-methyl-8-quinolinolato)(2,6-dimethylphenolato)aluminum, bis(2-methyl-8-quinolinolato)(3,4-dimethylphenolato)aluminum, bis(2-methyl-8-quinolinolato)(3,5-dimethylphenolato)aluminum, bis(2-methyl-8-quinolinolato)(3,5-di-t-butylphenolato)aluminum, bis(2-methyl-8-quinolinolato)(2,6-diphenylphenolato)aluminum, bis(2-methyl-8-quinolinolato)(2,4,6-triphenylphenolato)aluminum, bis(2-methyl-8-quinolinolato)(2,4,6-trimethylphenolato)aluminum, bis(2-methyl-8-quinolinolato)(2,4,5,6-tetramethylphenolato)aluminum, bis(2-methyl-8-quinolinolato)(1-naphtholato)aluminum, bis(2-methyl-8-quinolinolato)(2-naphtholato)aluminum, bis(2,4-dimethyl-8-quinolinolato)(2-phenylphenolato)aluminum, bis(2,4-dimethyl-8-quinolinolato)(3-phenylphenolato)aluminum, bis(2,4-dimethyl-8-quinolinolato)(4-phenylphenolato)aluminum, bis(2,4-dimethyl-8-quinolinolato)(3,5-dimethylphenolato)aluminum, bis(2,4-dimethyl-8-quinolinolato)(3,5-di-t-butylphenolato)aluminum, bis(2-methyl-8-quinolinolato)aluminum-μ-oxo-bis(2-methyl-8-quinolinolato)aluminum, bis(2,4-dimethyl-8-quinolinolato)aluminum-μ-oxo-bis(2,4-dimethyl-8-quinolinolato)aluminum, bis(2-methyl-4-ethyl-8-quinolinolato)aluminum-μ-oxo-bis(2-ethyl-4-ethyl-8-quinolinolato)aluminum, bis(2-methyl-4-methoxy-8-quinolinolato)aluminum-μ-oxo-bis(2-methyl-4-methoxy-8-quinolinolato)aluminum, bis(2-methyl-5-cyano-8-quinolinolato)aluminum-μ-oxo-bis(2-methyl-5-cyano-8-quinolinolato)aluminum, bis(2-methyl-5-trifluoromethyl-8-quinolinolato)aluminum-μ-oxo-bis(2-methy-5-trifluoromethyl-8-quiolinolato)aluminum, and bis(10-hydroxybenzo[h]quinoline)beryllium.

A bipyridine derivative is a compound represented by the following general formula (E-2):

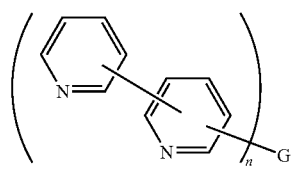
(E-2)

wherein G represents a simple linking bond or an n-valent linking group; n represents an integer from 2 to 8; and the carbon atoms that are not used in the pyridine-pyridine linkage or pyridine-G linkage may be substituted.

Examples of G of the general formula (E-2) include groups represented by the following structural formulas. Meanwhile, R's in the following structural formulas each independently represent a hydrogen atom, methyl, ethyl, isopropyl, cyclohexyl, phenyl, 1-naphthyl, 2-naphthyl, biphenylyl, or terphenylyl.

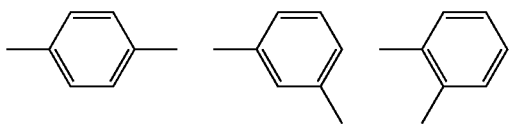

-continued

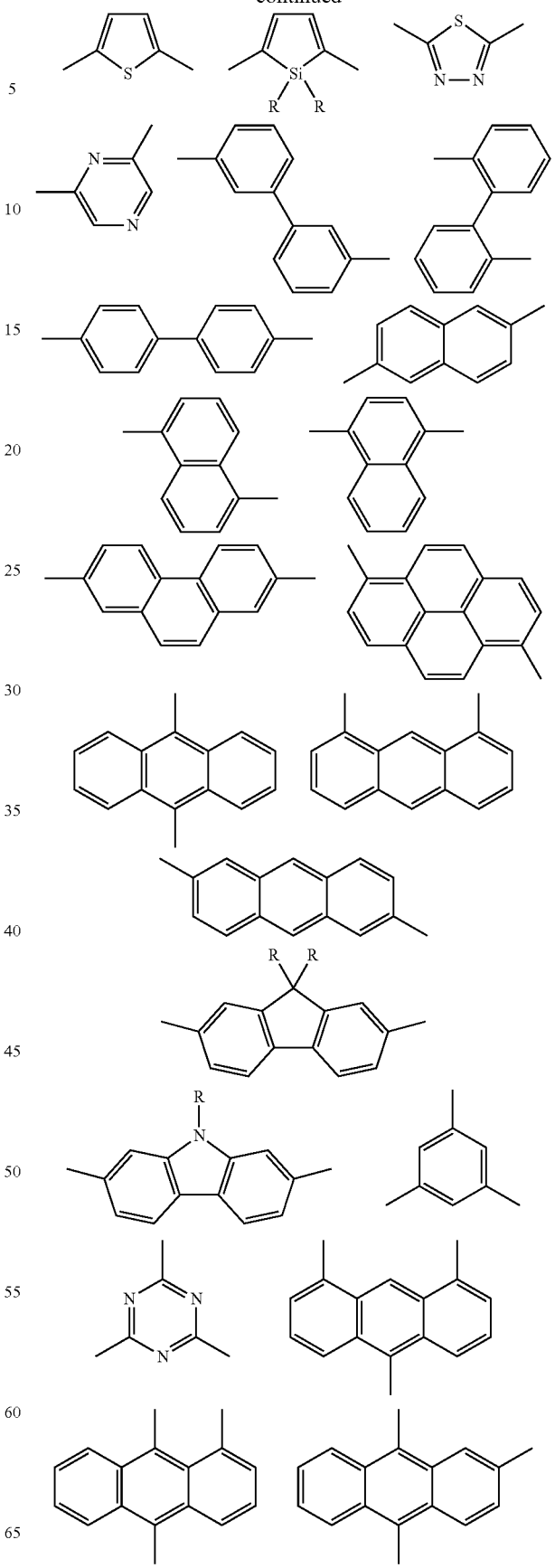

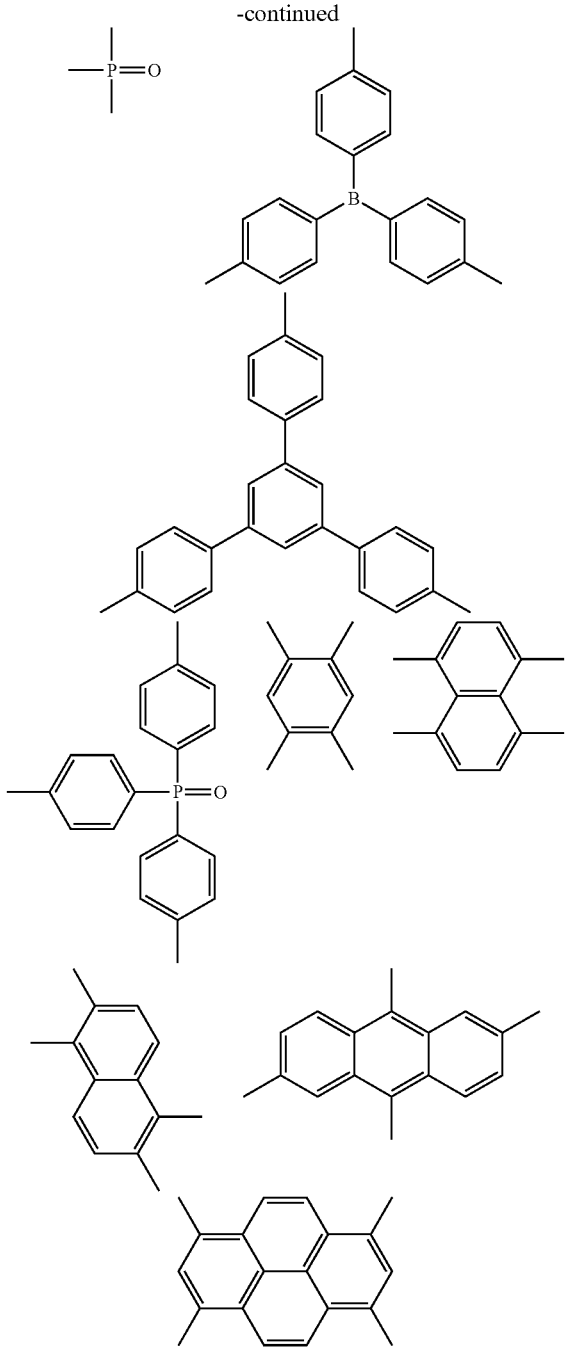

Specific examples of the pyridine derivative include
2,5-bis(2,2'-pyridin-6-yl)-1,1-dimethyl-3,4-diphenylsilole,
2,5-bis(2,2'-pyridin-6-yl)-1,1-dimethyl-3,4-dimesitylsilole,
2,5-bis(2,2'-pyridin-5-yl)-1,1-dimethyl-3,4-diphenylsilole,
2,5-bis(2,2'-pyridin-5-yl)-1,1-dimethyl-3,4-dimesitylsilole,
9,10-di(2,2'-pyridin-6-yl)anthracene,
9,10-di(2,2'-pyridin-5-yl)anthracene,
9,10-di(2,3'-pyridin-6-yl)anthracene,
9,10-di(2,3'-pyridin-5-yl)anthracene,
9,10-di(2,3'-pyridin-6-yl)-2-phenylanthracene,
9,10-di(2,3'-pyridin-5-yl)-2-phenylanthracene,
9,10-di(2,2'-pyridin-6-yl)-2-phenylanthracene,
9,10-di(2,2'-pyridin-5-yl)-2-phenylanthracene,
9,10-di(2,4'-pyridin-6-yl)-2-phenylanthracene,
9,10-di(2,4'-pyridin-5-yl)-2-phenylanthracene,
9,10-di(3,4'-pyridin-6-yl)-2-phenylanthracene,
9,10-di(3,4'-pyridin-5-yl)-2-phenylanthracene,
3,4-diphenyl-2,5-di(2,2'-pyridin-6-yl)thiophene,
3,4-diphenyl-2,5-di(2,3'-pyridin-5-yl)thiophene, and,
6',6"-di(2-pyridyl)-2,2':4',4":2",2"'-quaterpyridine.

A phenanthroline derivative is a compound represented by the following general formula (E-3-1) or (E-3-2):

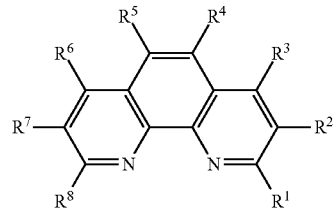
(E-3-1)

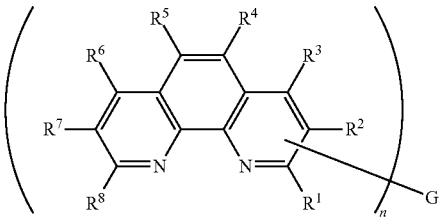
(E-3-2)

wherein $R^1$ to $R^8$ each represent a hydrogen atom or a substituent; adjacent groups may be bonded to each other and form a fused ring; G represents a simple linking bond or an n-valent linking group; and n represents an integer from 2 to 8. Examples of G of the general formula (E-3-2) include the same groups as those described in the section of the bipyridine derivative.

Specific examples of the phenanthroline derivative include 4,7-diphenyl-1,10-phenanthroline, 2,9-dimethyl-4,7-diphenyl-1,10-phenanthroline, 9,10-di(1,10-phenanthrolin-2-yl)anthracene, 2,6-di(1,10-phenanthrolin-5-yl)pyridine, 1,3,5-tri(1,10-phenanthrolin-5-yl)benzene, 9,9'-difluoro-bis(1,10-phenanthrolin-5-yl), bathocuproine, and 1,3-bis(2-phenyl-1,10-phenanthrolin-9-yl)benzene.

Particularly, the case of using a phenanthroline derivative in an electron transport layer or an electron injection layer will be explained. In order to obtain stable light emission over a long time, a material having excellent thermal stability or thin film formability is preferred, and among phenanthroline derivatives, a phenanthroline derivative in which a substituent itself has a three-dimensional steric structure, or the derivative has a three-dimensional steric structure as a result of steric repulsion between a substituent and the phenanthroline skeleton or between a substituent and an adjacent substituent, or a phenanthroline derivative having plural phenanthroline skeletons linked together, is preferred. Furthermore, in the case of linking plural phenanthroline skeletons, a compound containing conjugated bonds, a substituted or unsubstituted aromatic hydrocarbon, or a substituted or unsubstituted heterocyclic aromatic ring in the linked units, is more preferred.

A borane derivative is a compound represented by the following general formula (E-4), and specific examples are disclosed in JP 2007-27587 A.

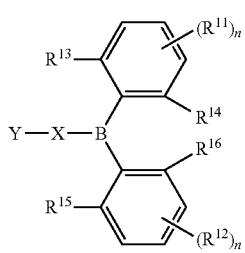
(E-4)

wherein $R^{11}$ and $R^{12}$ each independently represent at least one of a hydrogen atom, an alkyl, an aryl which may be substituted, a silyl which may be substituted, a nitrogen-containing heterocyclic ring which may be substituted, and cyano; $R^{13}$ to $R^{16}$ each independently represent an alkyl which may be substituted, or an aryl which may be substituted; X represents an arylene which may be substituted; Y represents an aryl having 16 or fewer carbon atoms which may be substituted, a boryl which may be substituted, or a carbazolyl which may be substituted; and n's each independently represent an integer from 0 to 3.

Among compounds represented by the above general formula (E-4), compounds represented by the following general formula (E-4-1), and compounds represented by the following general formulas (E-4-1-1) to (E-4-1-4), are preferred. Specific examples thereof include
9-[4-(4-dimesitylborylnaphthalen-1-yl)phenyl]carbazole and
9-[4-(4-dimesitylborylnaphthalen-1-yl)naphthalen-1-yl]carbazole.

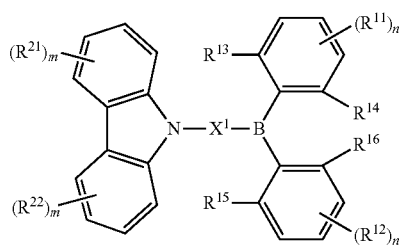
(E-4-1)

wherein $R^{11}$ and $R^{12}$ each independently represent at least one of a hydrogen atom, an alkyl, an aryl which may be substituted, a silyl which may be substituted, a nitrogen-containing heterocyclic ring which may be substituted, and cyano; $R^{13}$ to $R^{16}$ each independently represent an alkyl which may be substituted, or an aryl which may be substituted; $R^{21}$ and $R^{22}$ each independently represent at least one of a hydrogen atom, an alkyl, an aryl which may be substituted, a silyl which may be substituted, a nitrogen-containing heterocyclic ring which may be substituted, and cyano; $X^1$ represents an arylene having 20 or fewer carbon atoms which may be substituted; n's each independently represent an integer from 0 to 3; and m's each independently represent an integer from 0 to 4.

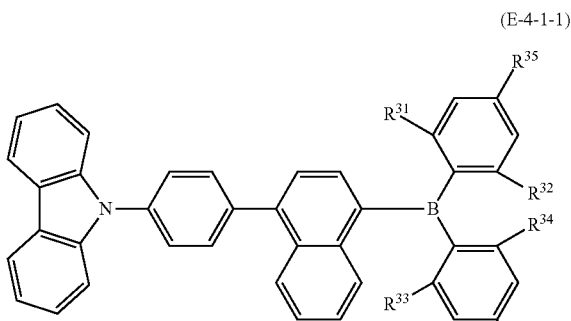
(E-4-1-1)

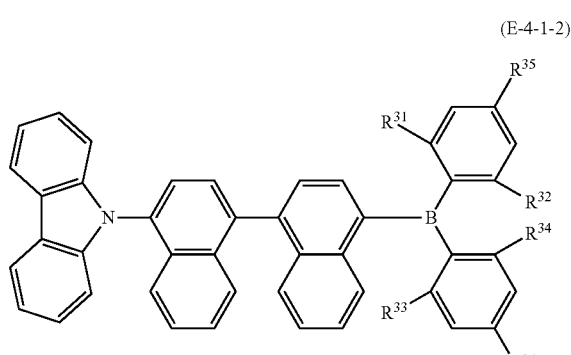
(E-4-1-2)

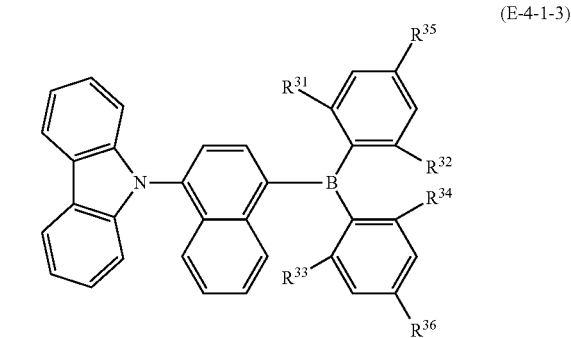
(E-4-1-3)

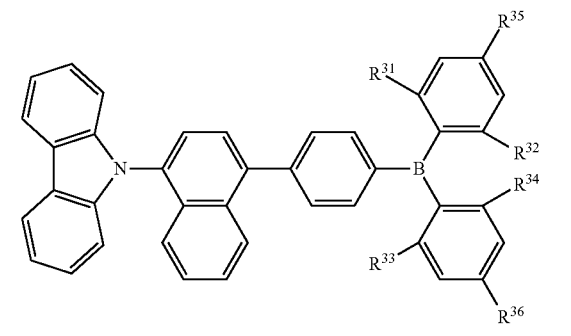
(E-4-1-4)

wherein in the respective formulas, $R^{31}$ to $R^{34}$ each independently represent any one of methyl, isopropyl or phenyl; and $R^{35}$ and $R^{36}$ each independently represent any one of a hydrogen atom, methyl, isopropyl or phenyl.

Among compounds represented by the above general formula (E-4), compounds represented by the following general formula (E-4-2), and a compound represented by the following general formula (E-4-2-1) are preferred.

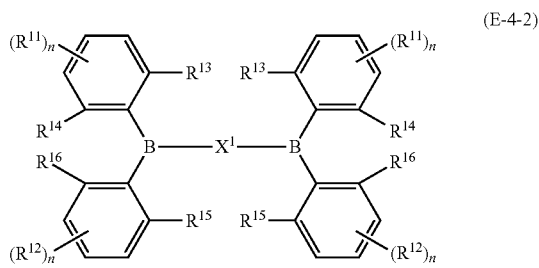

(E-4-2)

wherein $R^{11}$ and $R^{12}$ each independently represent at least one of a hydrogen atom, an alkyl, an aryl which may be substituted, a silyl which may be substituted, a nitrogen-containing heterocyclic ring which may be substituted, and cyano; $R^{13}$ to $R^{16}$ each independently represent an alkyl which may be substituted, or an aryl which may be substituted; $X^1$ represents an arylene having 20 or fewer carbon atoms which may be substituted; and n's each independently represent an integer from 0 to 3.

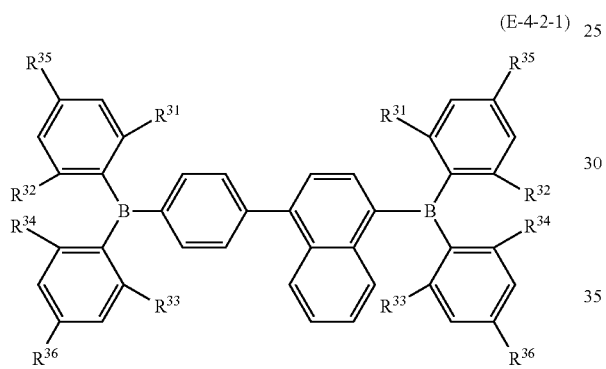

(E-4-2-1)

wherein $R^{31}$ to $R^{34}$ each independently represent anyone of methyl, isopropyl, or phenyl; and $R^{35}$ and $R^{36}$ each independently represent any one of a hydrogen atom, methyl, isopropyl, or phenyl.

Among compounds represented by the above general formula (E-4), compounds represented by the following general formula (E-4-3), and compounds represented by the following general formulas (E-4-3-1) and (E-4-3-2) are preferred.

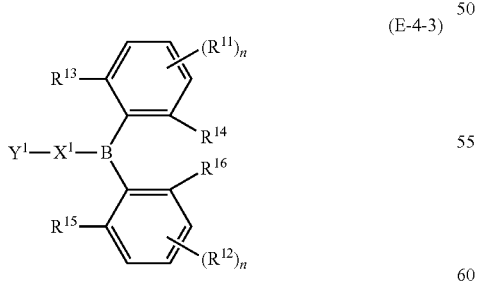

(E-4-3)

wherein $R^{11}$ and $R^{12}$ each independently represent at least one of a hydrogen atom, an alkyl, an aryl which may be substituted, a silyl which may be substituted, a nitrogen-containing heterocyclic ring which may be substituted, or cyano; $R^{13}$ to $R^{16}$ each independently represent an alkyl which may be substituted, or an aryl which may be substituted; $X^1$ represents an arylene having 10 or fewer carbon atoms which may be substituted; $Y^1$ represents an aryl having 14 or fewer carbon atoms which may be substituted; and n's each independently represent an integer from 0 to 3.

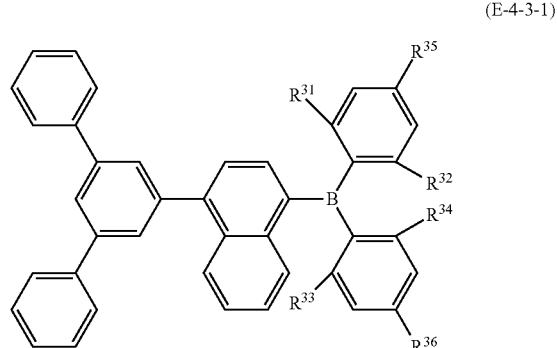

(E-4-3-1)

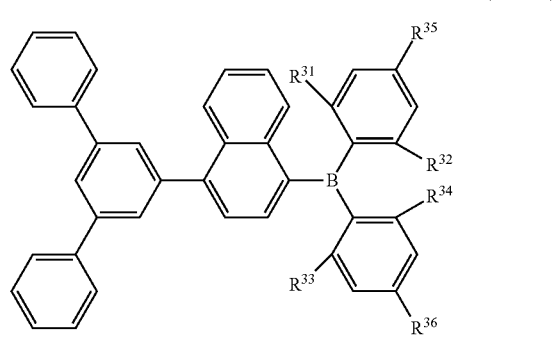

(E-4-3-2)

wherein $R^{31}$ to $R^{34}$ each independently represent anyone of methyl, isopropyl, or phenyl; and $R^{35}$ and $R^{36}$ each independently represent any one of a hydrogen atom, methyl, isopropyl, or phenyl.

A benzimidazole derivative is a compound represented by the following general formula (E-5):

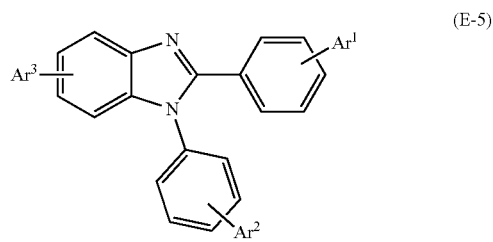

(E-5)

wherein $Ar^1$ to $Ar^3$ each independently represent a hydrogen atom or an aryl having 6 to 30 carbon atoms which may be substituted. Particularly, a benzimidazole derivative in which $Ar^1$ represents an anthryl which may be substituted is preferred.

Specific examples of the aryl having 6 to 30 carbon atoms include phenyl, 1-naphthyl, 2-naphthyl, acenaphthylen-1-yl, acenaphthylen-3-yl, acenaphthylen-4-yl, acenaphthylen-5-yl, fluoren-1-yl, fluoren-2-yl, fluoren-3-yl, fluoren-4-yl, fluoren-9-yl, phenalen-1-yl, phenalen-2-yl, 1-phenanthryl, 2-phenanthryl, 3-phenanthryl, 4-phenanthryl, 9-phenanthryl, 1-anthryl, 2-anthryl, 9-anthryl, fluoranthen-1-yl, fluoranthen-2-yl, fluoranthen-3-yl, fluoranthen-7-yl, fluoranthen-8-yl, triphenylen-1-yl, triphenylen-2-yl, pyren-1-yl, pyren-2-yl, pyren-4-yl, chrysen-1-yl, chrysen-2-yl, chrysen-3-yl, chrysen-4-yl, chrysen-5-yl, chrysen-6-yl, naphthacen-1-yl, naphthacen-2-yl, naphthacen-5-yl, perylen-1-yl, perylen-2-yl, perylen-3-yl, pentacen-1-yl, pentacen-2-yl, pentacen-5-yl, and pentacen-6-yl.

Specific examples of the benzimidazole derivative include
1-phenyl-2-(4-(10-phenylanthracen-9-yl)phenyl)-1H-benzo[d]imidazole,
2-(4-(10-(naphthalen-2-yl)anthracen-9-yl)phenyl)-1-phenyl-1H-benzo[d]imidazole,
2-(3-(10-(naphthalen-2-yl)anthracen-9-yl)phenyl)-1-phenyl-1H-benzo[d]imidazole,
5-(10-(naphthalen-2-yl)anthracen-9-yl)-1,2-diphenyl-1H-benzo[d]imidazole,
1-(4-(10-(naphthalen-2-yl)anthracen-9-yl)phenyl)-2-phenyl-1H-benzo[d]imidazole,
2-(4-(9,10-di(naphthalen-2-yl)anthracen-2-yl)phenyl)-1-phen yl-1H-benzo[d]imidazole,
1-(4-(9,10-di(naphthalen-2-yl)anthracen-2-yl)phenyl)-2-phen yl-1H-benzo[d]imidazole, and
5-(9,10-di(naphthalen-2-yl)anthracen-2-yl)-1,2-diphenyl-1H-benzo[d]imidazole.

The electron transport layer or the electron injection layer may further contain a substance that can reduce the material that forms the electron transport layer or electron injection layer. Regarding this reducing substance, various substances may be used as long as they have reducibility to a certain extent. For example, at least one selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals, and organic complexes of rare earth metals, can be suitably used.

Preferred examples of the reducing substance include alkali metals such as Na (work function 2.36 eV), K (work function 2.28 eV), Rb (work function 2.16 eV), and Cs (work function 1.95 eV); and alkaline earth metals such as Ca (work function 2.9 eV), Sr (work function 2.0 to 2.5 eV), and Ba (work function 2.52 eV). A reducing substance having a work function of 2.9 eV or less is particularly preferred. Among these, more preferred examples of the reducing substance include alkali metals such as K, Rb and Cs; even more preferred examples include Rb and Cs; and the most preferred example is Cs. These alkali metals have particularly high reducing ability, and can promote an enhancement of the emission luminance or lengthening of the service life in organic EL elements when the alkali metals are added in a relatively small amount to the material that forms the electron transport layer or electron injection layer. Furthermore, as the reducing substance having a work function of 2.9 eV or less, a combination of two or more kinds of these alkali metals is also preferred, and particularly, a combination including Cs, for example, a combination of Cs with Na, a combination of Cs with K, a combination of Cs with Rb, or a combination of Cs with Na and K, is preferred. When Cs is incorporated, the reducing ability can be efficiently manifested, and an enhancement of the emission luminance or lengthening of the service life in organic EL elements can be promoted by adding Cs to the material that forms the electron transport layer or electron injection layer.

<Negative Electrode in Organic Electroluminescent Element>

The negative electrode 108 is a member that accomplishes the role of injecting electrons to the light emitting layer 105 through the electron injection layer 107 and the electron transport layer 106.

The material that forms the negative electrode 108 is not particularly limited as long as it is a substance capable of efficiently injecting electrons to an organic layer; however, the same materials as the materials that form the positive electrode 102 can be used. Among them, preferred examples include metals such as tin, indium, calcium, aluminum, silver, copper, nickel, chromium, gold, platinum, iron, zinc, lithium, sodium, potassium, cesium and magnesium, and alloys thereof (a magnesium-silver alloy, a magnesium-indium alloy, an aluminum-lithium alloy such as lithium fluoride/aluminum, and the like). In order to enhance the element characteristics by increasing the electron injection efficiency, lithium, sodium, potassium, cesium, calcium, magnesium, or alloys thereof containing low work function-metals are effective. However, many of these low work function-metals are generally unstable in air. In order to ameliorate this, for example, a method of using an electrode having high stability obtained by doping a trace amount of lithium, cesium or magnesium to an organic layer, is known. Other examples of the dopant that can be used include inorganic salts such as lithium fluoride, cesium fluoride, lithium oxide, and cesium oxide. However, the present invention is not intended to be limited to these.

Furthermore, in order to protect the electrode, a metal such as platinum, gold, silver, copper, iron, tin, aluminum or indium; an alloy using these metals; an inorganic substance such as silica, titania or silicon nitride; polyvinyl alcohol, vinyl chloride, a hydrocarbon-based polymer compound; or the like may be laminated thereon according to a preferred embodiment. The method for producing these electrodes is not particularly limited as long as the method is capable of conduction, such as resistance heating, electron beam, sputtering, ion plating and coating.

<Binder that May be Used in Various Layers>

The materials used in the above-described hole injection layer, hole transport layer, light emitting layer, electron transport layer, and electron injection layer can form the various layers by being used singly; however, it is also possible to use the materials after dispersing them in a solvent-soluble resin such as polyvinyl chloride, polycarbonate, polystyrene, poly(N-vinylcarbazole), polymethyl methacrylate, polybutyl methacrylate, polyester, polysulfone, polyphenylene oxide, polybutadiene, a hydrocarbon resin, a ketone resin, a phenoxy resin, polyamide, ethyl cellulose, a vinyl acetate resin, an ABS resin, or a polyurethane resin; or a curable resin such as a phenolic resin, a xylene resin, a petroleum resin, a urea resin, a melamine resin, an unsaturated polyester resin, an alkyd resin, an epoxy resin, or a silicone resin.

<Method for Producing Organic Electroluminescent Element>

The various layers that constitute an organic electroluminescent element can be formed by forming thin films of the materials that will constitute the various layers, by methods such as a vapor deposition method, resistance heating deposition, electron beam deposition, sputtering, a molecular lamination method, a printing method, a spin coating method, a casting method, and a coating method. There are no particular limitations on the film thickness of the various layers thus formed, and the film thickness can be appropriately set depending on the properties of the material, but the film thickness is usually in the range of 2 nm to 5000 nm. The film thickness can be usually measured using a crystal oscillation type film thickness analyzer or the like. In the case of forming a thin film using a vapor deposition method, the deposition conditions vary with the kind of the material, the intended crystal structure and association structure of the film, and the like. It is preferable to appropriately set the vapor deposition conditions generally in the ranges of a boat heating temperature of +50° C. to +400° C., a degree of vacuum of $10^{-6}$ to $10^{-3}$ Pa, a rate of deposition of 0.01 to 50 nm/second, a substrate temperature of −150° C. to +300° C., and a film thickness of 2 nm to 5 μm.

Next, a method for producing an organic electroluminescent element configured to include positive electrode/hole injection layer/hole transport layer/light emitting layer formed from a host material and a dopant material/electron transport layer/electron injection layer/negative electrode, is explained as an example of the method for producing an organic electroluminescent element. On an appropriate substrate, a positive electrode is produced by forming a thin film of a positive electrode material by a vapor deposition method or the like, and then thin films of a hole injection layer and a hole transport layer are formed on this positive electrode. A thin film is formed thereon by co-depositing a host material and a dopant material, and thereby a light emitting layer is obtained. An electron transport layer and an electron injection layer are formed on this light emitting layer, and a thin film formed from a substance for negative electrode is formed by a vapor deposition method or the like as a negative electrode. Thereby, an intended organic electroluminescent element is obtained. Furthermore, in regard to the production of the organic electroluminescent element described above, it is also possible to produce the element by reversing the order of production, that is, in the order of a negative electrode, an electron injection layer, an electron transport layer, a light emitting layer, a hole transport layer, a hole injection layer, and a positive electrode.

In a case in which a direct current voltage is applied to an organic electroluminescent element obtained in this manner, it is desirable to apply the positive polarity to the positive electrode and the negative polarity to the negative electrode, and when a voltage of 2 to 40 V is applied, light emission can be observed from a transparent or semitransparent electrode side (the positive electrode or the negative electrode, or both). Also, this organic electroluminescent element also emits light even when a pulse current or an alternating current is applied. The waveform of the alternating current applied may be any waveform.

<Application Examples of Organic Electroluminescent Element>

Furthermore, the present invention can also be applied to a display apparatus including an organic electroluminescent element, or a lighting apparatus including an organic electroluminescent element.

A display apparatus or lighting apparatus including an organic electroluminescent element can be produced according to a known method such as connecting the organic electroluminescent element according to the present exemplary embodiment and a known driving apparatus. The organic electroluminescent element can be driven by appropriately using a known driving method such as direct current driving, pulse driving or alternating current driving.

Examples of the display apparatus include panel displays such as color flat panel displays; and flexible displays such as flexible organic electroluminescent (EL) displays (see, for example, JP 10-335066 A, JP 2003-321546 A, JP 2004-281086 A, and the like). Furthermore, the display mode of the display may be, for example, a matrix and/or segment mode. Meanwhile, the matrix display and the segment display may co-exist in the same panel.

A matrix refers to a system in which pixels for display are arranged two-dimensionally as in a lattice form or a mosaic form, and characters or images are displayed by collections of pixels. The shape or size of the pixel is determined according to the use. For example, in the display of images and characters of personal computers, monitors and televisions, square pixels each having a size of 300 μm or less on each side are usually used, and in the case of large-sized displays such as display panels, pixels having a size in the order of millimeters on each side are used. In the case of monochromic display, it is desirable to arrange pixels of the same color; however, in the case of color display, display is achieved by arranging pixels of red, green and blue colors. In this case, typically, there are available delta type displays and stripe type displays. Regarding this matrix driving method, any of a line sequential driving method or an active matrix method may be employed. Line sequential driving has an advantage of having a simpler structure; however, there are occasions in which the active matrix method is superior when the operation characteristics are taken into consideration. Therefore, it is necessary to use the driving method appropriately according to the use.

In the segment mode (type), a pattern is formed so as to display predetermined information, and the determined regions are induced to emit light. Examples thereof include the display of time or temperature in a digital clock or a digital thermometer, the display of the state of operation in an audio instrument or an electronic cooker, and the panel display in an automobile.

Examples of the lighting apparatus include the light apparatuses for indoor lighting or the like, and the backlight of a liquid crystal display apparatus (see, for example, JP 2003-257621 A, JP 2003-277741 A, and JP 2004-119211 A). A backlight is mainly used for the purpose of enhancing visibility of a display apparatus that is not self-luminous, and is used in liquid crystal display apparatuses, timepieces, audio apparatuses, automotive panels, display panels, signs, and the like. Particularly, regarding the backlight for the use in liquid crystal display apparatuses, among others, for the use in personal computers where thickness reduction has been a problem to be solved, when it is considered that thickness reduction is difficult because the backlights of conventional types are constructed from fluorescent lamps or light waveguides, a backlight employing the luminescent element according to the present exemplary embodiment is characterized by its thinness and lightweightness.

4. Other Organic Devices

The polycyclic aromatic compound according to the present invention and an oligomer thereof can be used in the production of an organic field effect transistor, an organic thin film solar cell or the like, in addition to the organic electroluminescent element described above.

An organic field effect transistor is a transistor that controls the electric current by means of an electric field generated by voltage input, and is provided with a source electrode, a drain electrode, and a gate electrode. When a voltage is applied to the gate electrode, an electric field is generated, and the field effect transistor can control the electric current by arbitrarily damming the flow of electrons (or holes) that flow between the source electrode and the drain electrode. The field effect transistor can be easily miniaturized compared with simple transistors (bipolar transistors), and can be effectively used as elements that constitute an integrated circuit or the like.

The structure of an organic field effect transistor is usually such that a source electrode and a drain electrode are provided in contact with an organic semiconductor active layer that is formed using the polycyclic aromatic compound according to the present invention and an oligomer thereof, and it is desirable if a gate electrode is provided so as to interpose an insulating layer (dielectric layer) that is in contact with the organic semiconductor active layer. Examples of the element structure include the following structures.

(1) Substrate/gate electrode/insulator layer/source elctrode•drain electrode/organic semiconductor active layer (2) Substrate/gate electrode/insulator layer/organic semiconductor active layer/source electrode•drain electrode (3) Substrate/organic semiconductor active layer/source electrode•drain electrode/insulator layer/gate electrode (4) Substrate/source electrode•drain electrode/organic semiconductor active layer/insulator layer/gate electrode.

An organic field effect transistor configured as such can be applied as a pixel driving switching element of a liquid crystal display or organic electroluminescent display of active matrix-driven type, or the like.

An organic thin film solar cell has a structure in which a positive electrode such as ITO, a hole transport layer, a photoelectric conversion layer, an electron transport layer, and a negative electrode are laminated on a transparent substrate of glass or the like. The photoelectric conversion layer has a p-type semiconductor layer on the positive electrode side, and has an n-type semiconductor layer on the negative electrode side. The polycyclic aromatic compound according to the present invention and an oligomer thereof can be used as the materials of a hole transport layer, a p-type semiconductor layer, an n-type semiconductor layer, or an electron transport layer, depending on the properties. The polycyclic aromatic compound according to the present invention and an oligomer thereof can function as a hole transporting material or an electron transporting material in an organic thin film solar cell. The organic thin film solar cell may appropriately include a hole blocking layer, an electron blocking layer, an electron injection layer, a hole injection layer, a smoothing layer and the like, in addition to the members described above. In the organic thin film solar cell, existing materials that are conventionally used in organic thin film solar cells can be appropriately selected and used in combination.

EXAMPLES

Hereinafter, the present invention will be explained more specifically by way of Examples, but the present invention is not intended to be limited to these. First, Synthesis Examples of polycyclic aromatic compounds are described below.

Synthesis Example (1)

Synthesis of 5,9-dioxa-13b-boranaphtho[3,2,1-de]anthracene

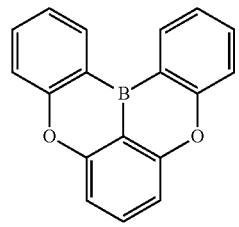

(1-1)

First, a 1.6 M n-butyllithium hexane solution (0.75 ml) was introduced at 0° C. into a flask containing diphenoxybenzene (0.26 g) and ortho-xylene (3.0 ml) in a nitrogen atmosphere. After the contents were stirred for 30 minutes, the temperature was increased to 70° C., and the mixture was further stirred for 4 hours. Hexane was distilled off by heating and stirring the mixture at 100° C. under a nitrogen gas stream, and then the mixture was cooled to −20° C. Boron tribromide (0.114 ml) was added thereto, and the mixture was stirred for one hour. The temperature of the mixture was raised to room temperature, the mixture was stirred for one hour, subsequently N,N-diisopropylethylamine (0.342 ml) was added thereto, and the resulting mixture was heated and stirred at 120° C. for 5 hours. Thereafter, N,N-diisopropylethylamine (0.171 ml) was added thereto, and the mixture was filtered using a Florisil short pass column. The solvent was distilled off under reduced pressure, and thus a crude purification product was obtained. The crude product was washed using methanol, and thus a compound (0.121 g) represented by formula (1-1) was obtained as a white solid.

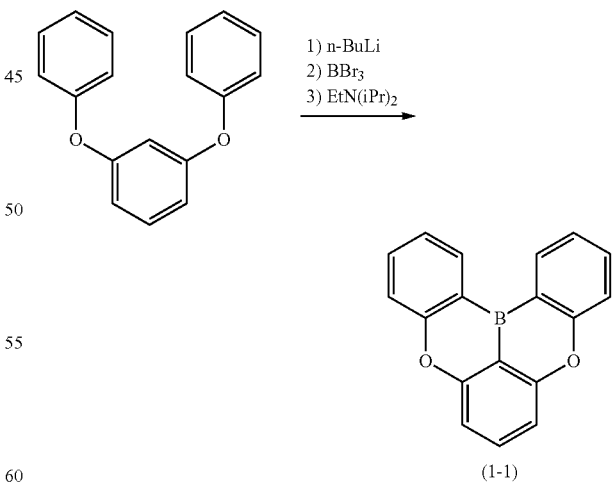

The structure of the compound thus obtained was identified by an NMR analysis.

$^1$H-NMR (400 MHz, CDCl$_3$): δ=8.69 (dd, 2H), 7.79 (t, 1H), 7.70 (ddd, 2H), 7.54 (dt, 2H), 7.38 (ddd, 2H), 7.22 (d, 2H).

Synthesis Example (2)

Synthesis of 15b-bora-5,9-dioxaphenanthro[1,2,3-ij]tetraphene

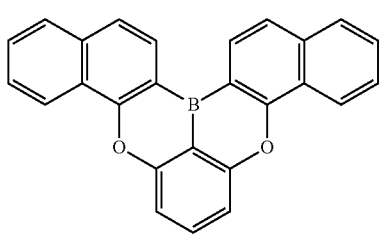

(1-2)

First, 1-bromonaphthalene (0.154 ml) was introduced into a flask containing copper(I) iodide (19.7 mg), α-picolinic acid (26.2 mg), potassium phosphate (0.429 g), resorcinol (57.5 mg) and dimethyl sulfoxide (2.0 ml), at room temperature in a nitrogen atmosphere. The contents were heated and stirred for 33.5 hours at 90° C., 1 Normal aqueous ammonia (3.0 ml) was subsequently added thereto at room temperature, and the aqueous layer was extracted three times with toluene. Subsequently, the solvent was distilled off under reduced pressure. A solid thus obtained was purified by silica gel column chromatography (developing liquid: toluene), and thus 1,3-bis(1-naphthyloxy)benzene (0.155 g) was obtained as a white solid.

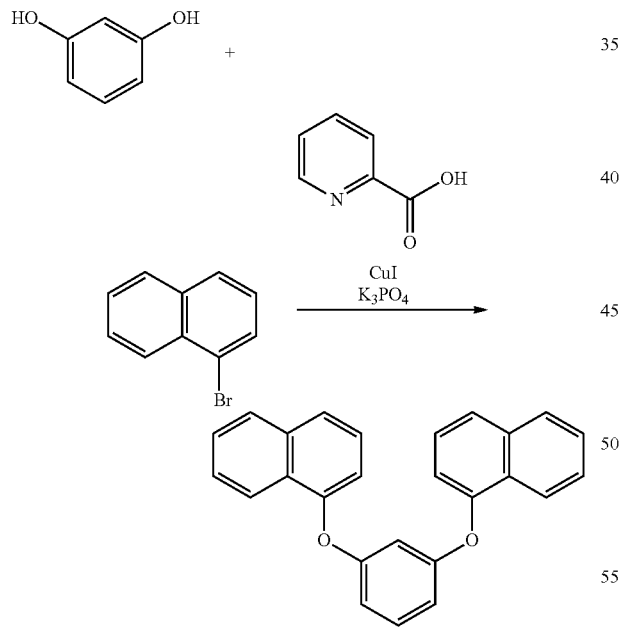

A 1.6 M n-butyllithium hexane solution (9.0 ml) was added dropwise to a flask containing 1,3-bis(1-naphthyloxy)benzene (4.45 g) and ortho-xylene (36 ml), at 0° C. in a nitrogen atmosphere. The temperature was increased to 70° C., and the contents were stirred for 4 hours. Subsequently, the temperature was increased to 100° C., and hexane was distilled off. The residue was cooled to 0° C., boron tribromide (1.37 ml) was added thereto, and the mixture was stirred for 2 hours. Subsequently, the temperature of the mixture was increased to room temperature, and the mixture was stirred for 12 hours. The mixture as cooled again to 0° C., N,N-diisopropylethylamine (6.16 ml) was added thereto, subsequently the temperature of the mixture was increased to 120° C., and the mixture was stirred for 8 hours. N,N-diisopropylethylamine (3.08 ml) was added to the mixture at 0° C., and then the mixture was filtered using a Florisil short pass column. The solvent was distilled off under reduced pressure, and thus a crude product was obtained. The crude product was washed using methanol and acetonitrile, and thereby a compound (0.405 g) represented by formula (1-2) was obtained as a white solid.

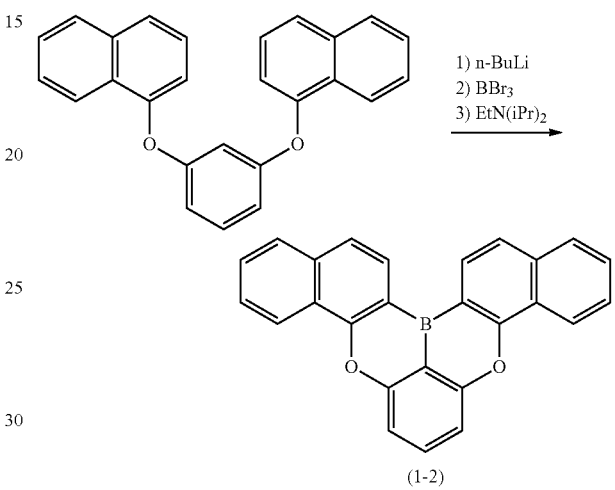

(1-2)

The structure of the compound thus obtained was identified by an NMR analysis.

$^1$H-NMR (400 MHz, CDCl$_3$): δ=8.82-8.85 (m, 2H), 8.71 (d, 2H), 7.94-7.97 (m, 2H), 7.89 (t, 1H), 7.78 (d, 2H), 7.66-7.71 (m, 4H), 7.48 (d, 2H).

Synthesis Example (3)

Synthesis of 2,12-diphenyl-5,9-dioxa-13b-boranaphtho[3,2,1-de]anthracene

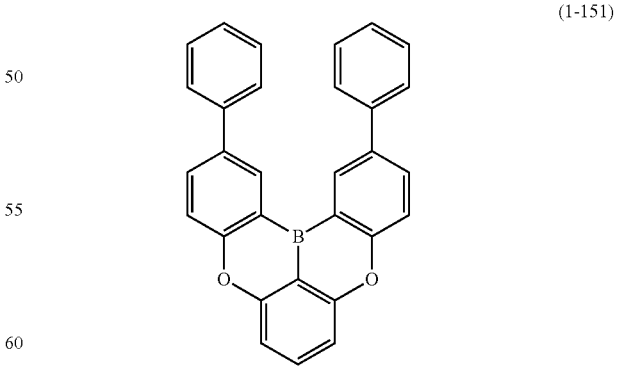

(1-151)

Copper(I) iodide (1.0 g) and iron(III) acetylacetonate (3.7 g) were added to an NMP (120 ml) solution of 1,3-dibromobenzene (25 g), [1,1'-biphenyl]-4-ol (39.7 g) and potassium carbonate (58.6 g) in a nitrogen atmosphere, the temperature of the mixture was increased to 150° C., and the mixture was stirred for 4 hours. The reaction liquid was cooled to room temperature, and a salt precipitated by adding ethyl acetate and aqueous ammonia thereto was removed by suction filtration using a Hirsch funnel covered with Celite. The filtrate was partitioned, and the solvent of the organic layer was distilled off under reduced pressure. Subsequently, the residue was dissolved in ethyl acetate, and the residue was reprecipitated by adding heptane thereto. The precipitate was further passed through a silica gel short pass column (developing liquid: heated chlorobenzene), and a solid obtained by distilling off the solvent under reduced pressure was reprecipitated from ethyl acetate/heptane. Thus, 1,3-bis([1,1'-biphenyl]-4-yloxy)benzene (33.0 g) was obtained.

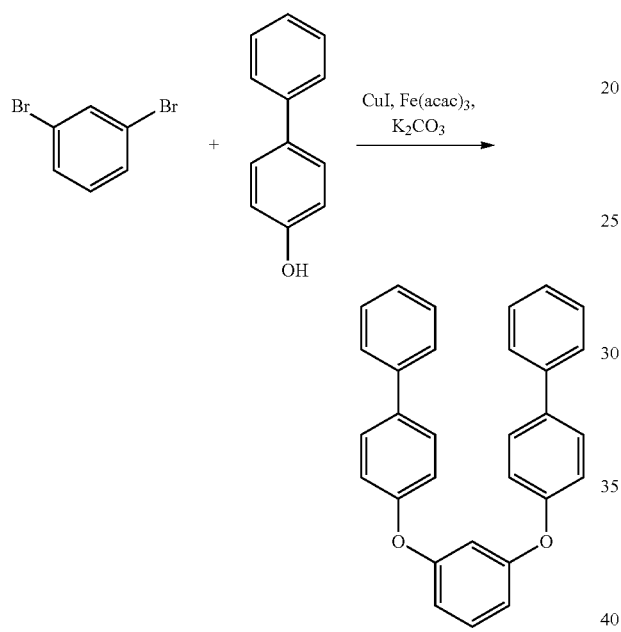

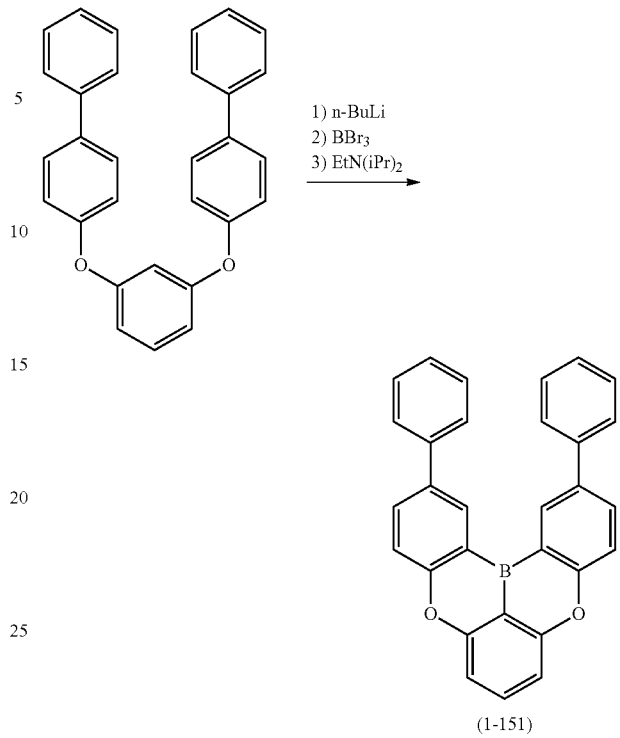

A 2.6 M n-butyllithium hexane solution (29.2 ml) was introduced into a flask containing 1,3-bis([1,1'-biphenyl]-4-yloxy)benzene (30.0 g) and ortho-xylene (500 ml), at 0° C. in a nitrogen atmosphere. After completion of dropwise addition, the temperature of the mixture was increased to 70° C., and the mixture was stirred for one hour. The temperature of the mixture was further increased to 100° C., and hexane was distilled off. The mixture was stirred overnight at room temperature, and then the mixture was cooled to −30° C. Boron tribromide (8.4 ml) was added thereto, the temperature of the mixture was increased to room temperature, and the mixture was stirred for one hour. Thereafter, the mixture was cooled to 0° C. again, N,N-diisopropylethylamine (25.0 ml) was added thereto, and the mixture was stirred at room temperature until heat generation was settled, and then was heated and stirred for 4 hours at 120° C. The reaction liquid was cooled to room temperature, and crystals thus precipitated were collected by suction filtration and washed with an aqueous solution of sodium acetate. Furthermore, the crystals were washed with heptane, ethyl acetate and methanol in this order, and thereby a compound (16.6 g) represented by formula (1-151) was obtained.

The structure of a compound thus obtained was identified by an NMR analysis.

$^1$H-NMR (400 MHz, CDCl$_3$): δ=8.96 (m, 2H), 7.97 (dd, 2H), 7.83 (t, 1H), 7.74 (m, 4H), 7.64 (d, 2H), 7.51 (t, 4H), 7.40 (t, 2H), 7.28 (d, 2H).

Synthesis Example (4)

Synthesis of 6,8-diphenyl-5,9-dioxa-13b-boranaphtho[3,2,1-de]anthracene

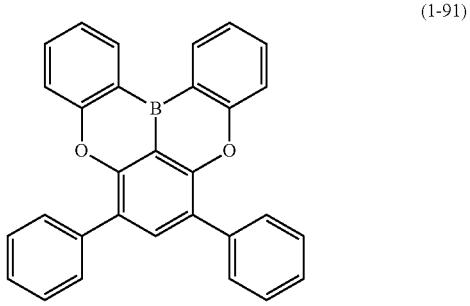 [SMILES: c1ccc(-c2cc(-c3ccccc3)c3c4c2Oc2ccccc2B4c2ccccc2O3)cc1]

A flask containing 1,5-dibromo-2,4-difluorobenzene (30.0 g), phenol (31.2 g), potassium carbonate (45.7 g) and NMP (150 ml) was heated with stirring at 160° C. The reaction liquid was cooled to room temperature, and NMP was distilled off under reduced pressure. Subsequently, water and toluene were added thereto, and the reaction liquid was partitioned. The solvent was distilled off under reduced pressure, and then the residue was purified using a silica gel short pass column (developing liquid: heptane/toluene=1 (volume ratio)). Thus, ((4,6-dibromo-1,3-phenylene)bis(oxy))dibenzene (44.0 g) was obtained.

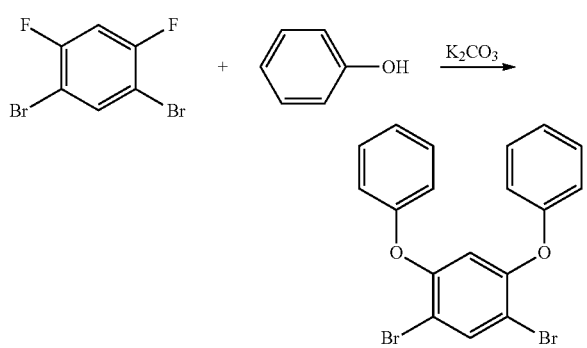

In a nitrogen atmosphere, Pd(PPh$_3$)$_4$ (5.5 g) was added to a suspension solution of ((4,6-dibromo-1,3-phenylene)bis(oxy))dibenzene (40.0 g), phenylboronic acid (34.8 g), sodium carbonate (60.6 g), toluene (500 ml), isopropanol (100 ml) and water (100 ml), and the mixture was stirred for 8 hours at the reflux temperature. The reaction liquid was cooled to room temperature, water and toluene were added thereto, and then the mixture was partitioned. The solvent of the organic layer was distilled off under reduced pressure. A solid thus obtained was dissolved in heated chlorobenzene, and the solution was passed through a silica gel short pass column (developing liquid: toluene). An appropriate amount of the solvent was distilled off, and then reprecipitation was carried out by adding heptane to the residue. Thus, 4',6'-diphenoxy-1,1':3',1''-terphenyl (41.0 g) was obtained.

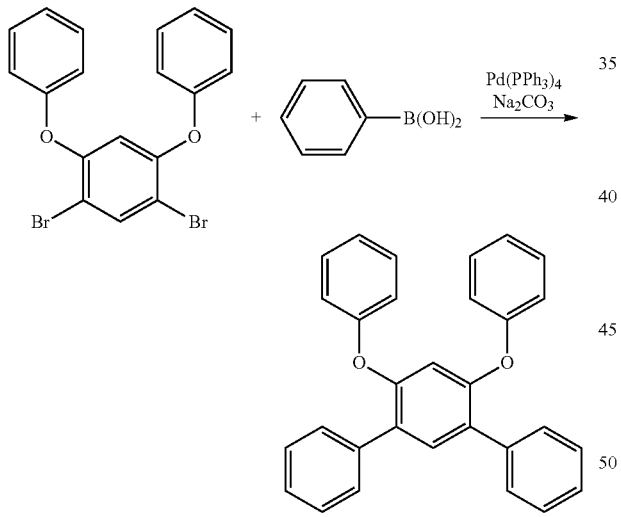

A 2.6 M n-butyllithium hexane solution (29.0 ml) was introduced into a flask containing 4',6'-diphenoxy-1,1':3',1''-terphenyl (30.0 g) and ortho-xylene (300 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off. The mixture was cooled to −50° C., and boron tribromide (8.4 ml) was added thereto. The temperature of the mixture was increased to room temperature, and the mixture was stirred for one hour. Thereafter, the mixture was cooled again to 0° C., N,N-diisopropylethylamine (25.0 ml) was added thereto, and the mixture was stirred at room temperature until heat generation was settled, and then was heated and stirred for 4 hours at 120° C. The reaction liquid was cooled to room temperature, and an organic material was extracted with toluene. Water was added to the toluene solution thus obtained, the mixture was partitioned, and the solvent was distilled off under reduced pressure. A solid thus obtained was dissolved in chlorobenzene, subsequently an appropriate amount was distilled off under reduced pressure, and reprecipitation was carried out by adding heptane thereto. Reprecipitation was further carried out in the same manner except that heptane was replaced with ethyl acetate. Thus, a compound (4.2 g) represented by formula (1-91) was obtained.

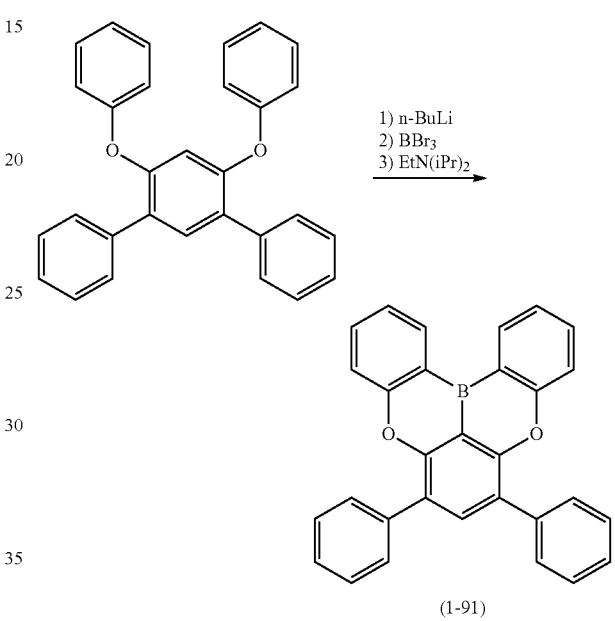

(1-91)

The structure of the compound thus obtained was identified by an NMR analysis.

$^1$H-NMR (400 MHz, CDCl$_3$): δ=8.74 (d, 2H), 8.00 (s, 1H), 7.81 (d, 4H), 7.69 (t, 2H), 7.54 (t, 4H), 7.49 (m, 2H), 7.37-7.46 (m, 4H).

Synthesis Example (5)

Synthesis of 6,8-di(9H-carbazol-9-yl)-5,9-dioxa-13b-boranaphtho[3,2,1-de]anthracene

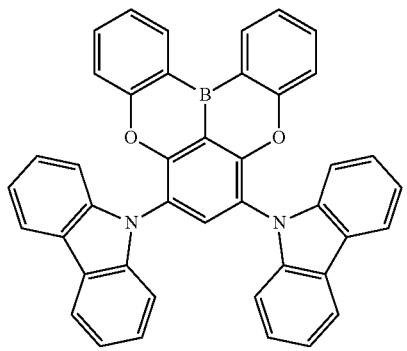

(1-100)

In a nitrogen atmosphere, a solution of 1,5-dibromo-2,4-difluorobenzene (600.0 g), carbazole (81.1 g), potassium carbonate (91.0 g) and NMP (300 ml) was heated to 155° C., and the mixture was stirred for 4 hours. The reaction liquid was cooled to room temperature, water was added thereto to dissolve inorganic salts, and an organic material was collected by suction filtration. The organic material was washed with ethyl acetate, and then was dissolved in heated ortho-dichlorobenzene. The solution was passed through a silica gel short pass column (developing liquid: ortho-dichlorobenzene). The solvent was distilled off under reduced pressure, and then the residue was further washed with ethyl acetate. Thus, 9,9'-(4,6-dibromo-1,3-phenylene)bis(9H-carbazole) (108.0 g) was obtained.

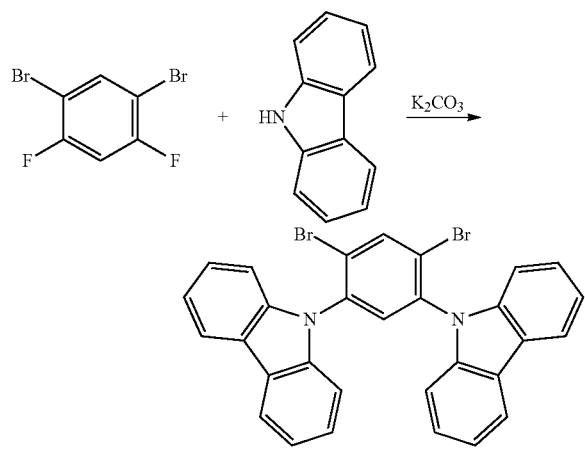

Copper(I) iodide (0.84 g) and iron(III) acetylacetonate (3.1 g) were added to an NMP (200 ml) solution of 9,9'-(4,6-dibromo-1,3-phenylene)bis(9H-carbazole) (50.0 g), phenol (10.0 g) and potassium carbonate (49.0 g) in a nitrogen atmosphere, and the temperature of the mixture was increased to 150° C. The mixture was stirred for 4 hours. The reaction liquid was cooled to room temperature, ethyl acetate and aqueous ammonia were added thereto, and then the mixture was partitioned. The solvent of the organic layer was distilled off under reduced pressure. Subsequently, the residue was purified by silica gel column chromatography (developing liquid: toluene/heptane=1 (volume ratio)), and then a solid obtained by distilling off the solvent under reduced pressure was washed with heptane. Thus, 9,9'-(4,6-diphenoxy-1,3-phenylene)bis(9H-carbazole) (16.8 g) was obtained.

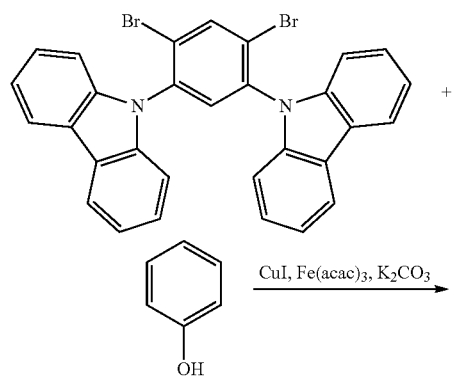

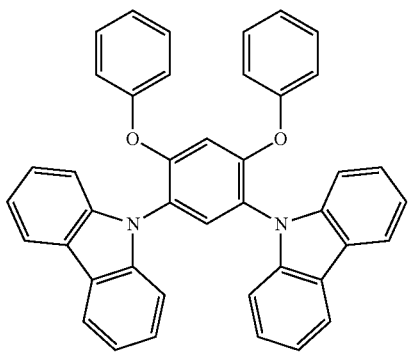

A 2.6 M n-butyllithium hexane solution (11.2 ml) was introduced into a flask containing 9,9'-(4,6-diphenoxy-1,3-phenylene)bis(9H-carbazole) (16.5 g) and ortho-xylene (150 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off under reduced pressure. The mixture was cooled to −50° C., boron tribromide (3.2 ml) was added thereto, the temperature of the mixture was increased to room temperature, and the mixture was stirred for one hour. Thereafter, the mixture was cooled again to 0° C., and N,N-diisopropylethylamine (25.0 ml) was added thereto. The mixture was stirred at room temperature until heat generation was settled, and then the mixture was heated and stirred for 4 hours at 120° C. The reaction liquid was cooled to room temperature, an aqueous solution of sodium acetate and ethyl acetate were added thereto, and then the mixture was partitioned. A solid precipitated by distilling off the solvent under reduced pressure was collected by suction filtration, and the solid was washed with heptane. From a chlorobenzene solution of the solid thus obtained, an appropriate amount of the solvent was distilled off under reduced pressure, and the solid was reprecipitated by further adding ethyl acetate. Thus, a compound (9.5 g) represented by formula (1-100) was obtained.

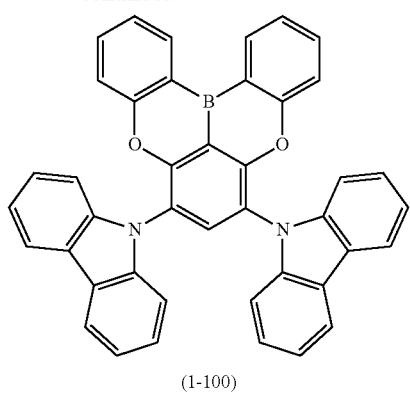
(1-100)

The structure of the compound thus obtained was identified by an NMR analysis.

$^1$H-NMR (400 MHz, CDCl$_3$): δ=8.77 (d, 2H), 8.25 (s, 1H), 8.21 (d, 4H), 7.61 (t, 2H), 7.42 (m, 6H), 7.33 (m, 8H), 7.10 (d, 2H).

Synthesis Example (6)

Synthesis of N$^6$,N$^6$,N$^8$,N$^8$-tetraphenyl-5,9-dioxa-13b-boranaphtho[3,2,1-de]anthracene-6,8-diamine

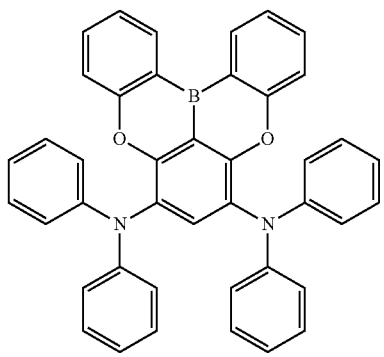
(1-141)

A flask containing ((4,6-dibromo-1,3-phenylene)bis(oxy))dibenzene (45.0 g), diphenylamine (45.0 g), Pd(dba)$_2$ (1.2 g), (4-(N,N-dimethylamino)phenyl)-di-t-butylphosphine (A-$^{ta}$Phos) (1.1 g), NaOtBu (25.7 g) and toluene (250 ml) was heated to 100° C. and stirred for 4 hours. The reaction liquid was cooled to room temperature, water and ethyl acetate were added thereto, the mixture was partitioned, and then the solvent was distilled off under reduced pressure. Subsequently, the residue was purified by silica gel column chromatography (developing liquid: toluene/heptane=1 (volume ratio)), and was dissolved in ethyl acetate. The residue was reprecipitated by adding heptane thereto. Thus, 4,6-diphenoxy-N$^1$,N$^1$,N$^3$,N$^3$-tetrapheylbenzene-1,3-diamine (17.6 g) was obtained.

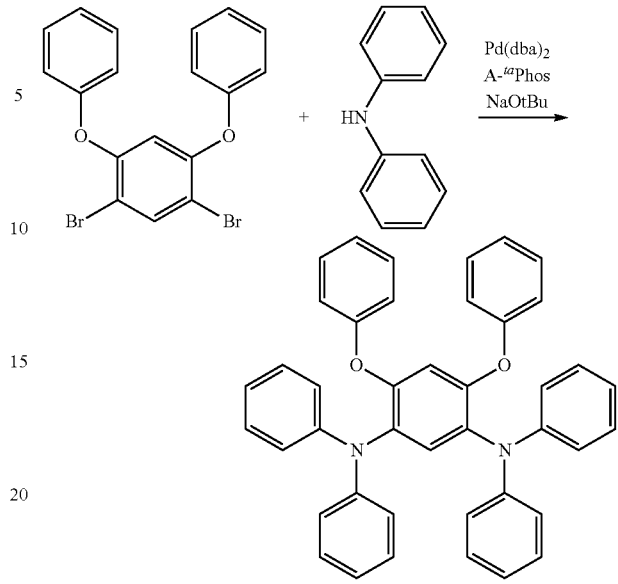

A 2.6 M n-butyllithium hexane solution (11.8 ml) was introduced into a flask containing 4,6-diphenoxy-N$^1$,N$^1$,N$^3$,N$^3$-tetraphenylbenzene-1,3-diamine (17.5 g) and ortho-xylene (130 ml), at 0° C. in a nitrogen atmosphere. After completion of dropwise addition, the temperature of the mixture was increased to 70° C., and the mixture was stirred for 4 hours. Furthermore, the temperature of the mixture was increased to 100° C., and hexane was distilled off. The mixture was cooled to −50° C., boron tribromide (3.4 ml) was added thereto, the temperature of the mixture was increased to room temperature, and the mixture was stirred for one hour. Thereafter, the mixture was cooled again to 0° C., N,N-diisopropylethylamine (10.0 ml) was added thereto, and the mixture was stirred at room temperature until heat generation was settled. Subsequently, the mixture was heated and stirred for 4 hours at 120° C. The reaction liquid was cooled to room temperature, an aqueous solution of sodium acetate and ethyl acetate were added thereto, and then the mixture was partitioned. Precipitation was induced by distilling off the solvent under reduced pressure, and then the precipitate was purified by silica gel column chromatography (developing liquid: heptane/toluene=3/2 (volume ratio)). Furthermore, the product was dissolved in chlorobenzene, and then was reprecipitated by distilling off an appropriate amount of the solvent under reduced pressure. Thus, a compound (5.5 g) represented by formula (1-141) was obtained.

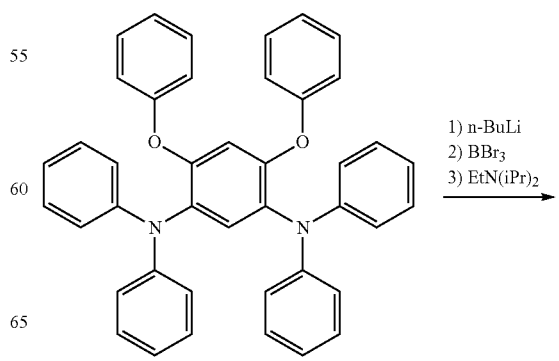

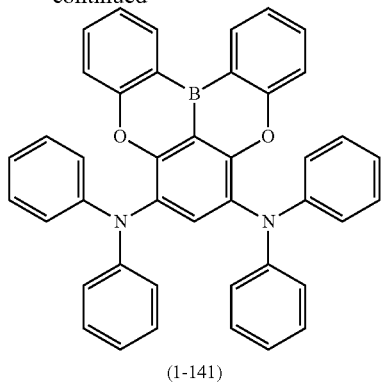

(1-141)

The structure of the compound thus obtained was identified by an NMR analysis.

$^1$H-NMR (400 MHz, CDCl$_3$): δ=8.60 (d, 2H), 7.80 (s, 1H), 7.55 (t, 2H), 7.30 (t, 2H), 7.22 (m, 8H), 7.12 (m, 8H), 7.02 (d, 2H), 6.94 (t, 4H).

Synthesis Example (7)

Synthesis of 5,13-diphenyl-7,11-dioxa-18b-bora-phenaleno[2,1-b:8,9-b']dicarbazole

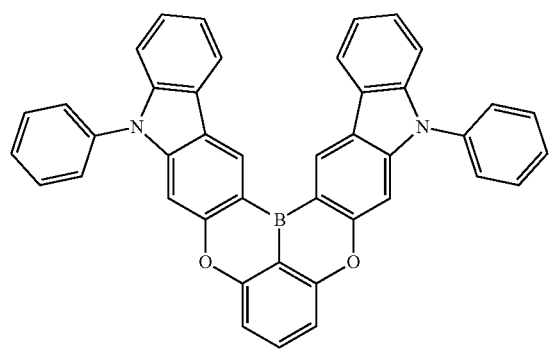

(1-10)

In a nitrogen atmosphere, a flask containing 9H-carbazol-2-ol (25.0 g), iodobenzene (30.6 g), Pd(dba)$_2$ (2.4 g), a 1 M tri-t-butylphosphine toluene solution (8.2 ml), NaOtBu (33.0 g), and 1,2,4-trimethylbenzene (250 ml) was heated to 120° C. and stirred for 6 hours. The reaction liquid was cooled to room temperature, water and ethyl acetate were added thereto, and the mixture was neutralized by adding dilute hydrochloric acid. The solvent was distilled off under reduced pressure, and then the residue was purified by silica gel column chromatography (developing liquid: toluene/heptane=1 (volume ratio)) and was further washed with heptane. Thus, 9-phenyl-9H-carbazol-2-ol (30.8 q) was obtained.

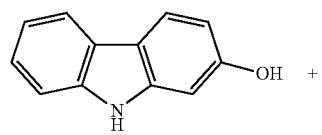

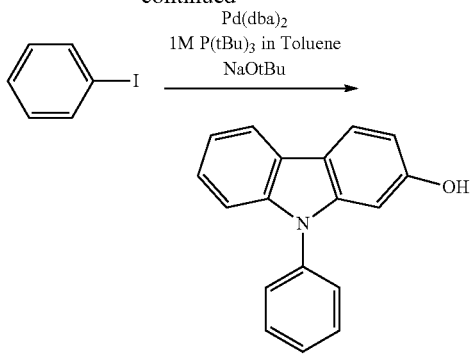

Copper(I) iodide (0.51 g) and iron(III) acetylacetonate (1.9 g) were added to an NMP (150 ml) solution of 9-phenyl-9H-carbazol-2-ol (30.7 g), 1,3-dibromobenzene (12.7 g) and potassium carbonate (30.0 g) in a nitrogen atmosphere, and the temperature of the mixture was increased to 150° C. and stirred for 8 hours. The reaction liquid was cooled to room temperature, ethyl acetate and aqueous ammonia were added thereto, and then the mixture was partitioned. The solvent of the organic layer was distilled off under reduced pressure. Subsequently, the residue was purified by silica gel column chromatography (developing liquid: toluene/heptane=4/6 (volume ratio)), and thus 1,3-bis((9-phenyl-9H-carbazol-2-yl)oxy)benzene (22.0 g) was obtained.

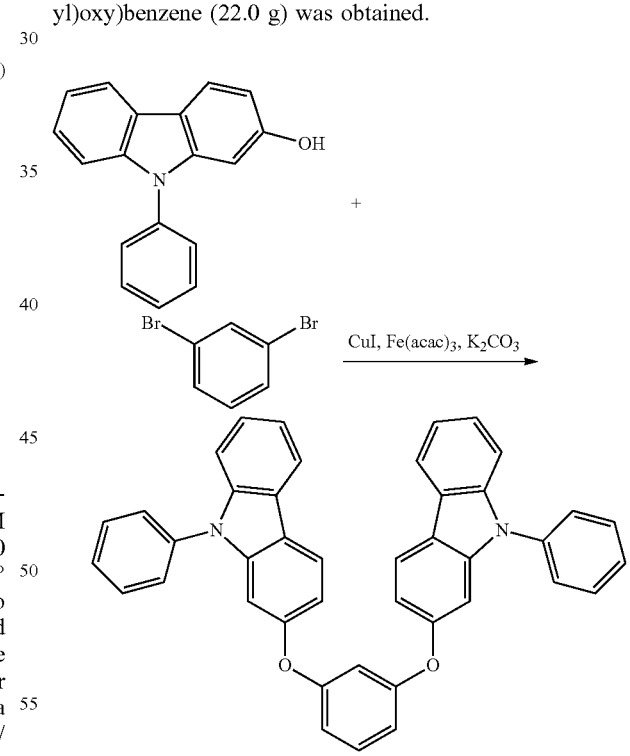

A 2.6 M n-butyllithium hexane solution (15.0 ml) was introduced into a flask containing 1,3-bis((9-phenyl-9H-carbazol-2-yl)oxy)benzene (22.0 g) and t-butylbenzene (120 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off. The residue was cooled to −50° C., boron tribromide (11 g) was added thereto, and the temperature of the mixture was increased to room temperature. The mixture was stirred for one hour. Thereafter, the mixture was cooled again to 0° C., N,N-diisopropylethylamine (9.6 g) was added thereto, and the mixture was stirred at room temperature until heat generation was settled. Subsequently, the mixture was heated and stirred for 2 hours at 120° C. The reaction liquid was cooled to room temperature, and a precipitate generated by adding an aqueous solution of sodium acetate thereto was collected by suction filtration. The precipitate was washed with heptane, ethyl acetate and methanol in this order, and was further washed with refluxed chlorobenzene. Thus, a compound (6.8 g) represented by formula (1-10) was obtained.

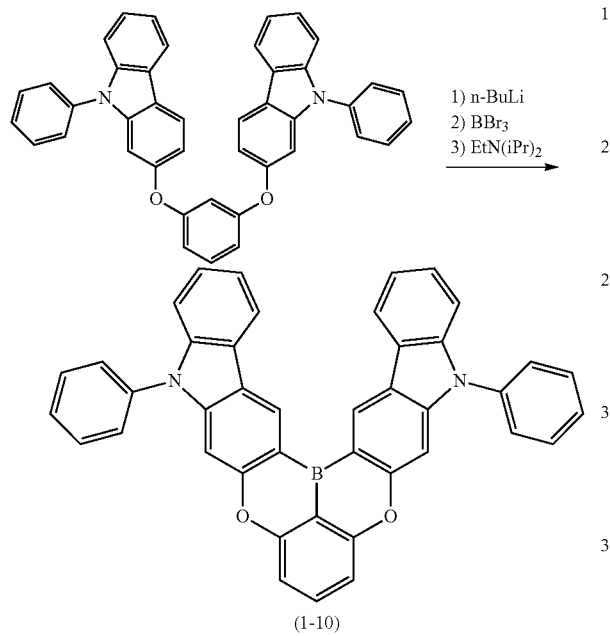

(1-10)

The structure of the compound thus obtained was identified by an NMR analysis.

$^1$H-NMR (400 MHz, CDCl$_3$): δ=9.61 (s, 2H), 8.42 (m, 2H), 7.64-7.77 (m, 9H), 7.52-7.58 (m, 2H), 7.42-7.51 (m, 8H), 7.13 (d, 2H).

Synthesis Example (8)

Synthesis of N$^3$,N$^3$,N$^{11}$,N$^{11}$-tetraphenyl-5,9-dioxa-13b-boranaphtho[3,2,1-de]anthracene-3,11-diamine (1-176)

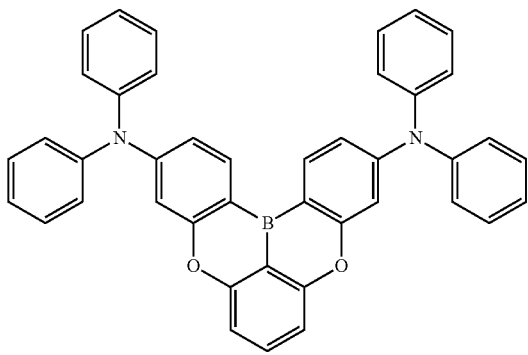

A flask containing diphenylamine (41.0 g), 3-bromophenol (40.0 g), Pd(dba)$_2$ (0.7 g), A-$^{ta}$Phos (0.6 g), NaOtBu (56.0 g), and toluene (400 ml) was heated to 80° C. and stirred for one hour. The reaction liquid was cooled to room temperature, subsequently water and ethyl acetate were added thereto, and then the mixture was partitioned. The solvent was distilled off under reduced pressure. The residue was purified by silica gel column chromatography (developing liquid: toluene/heptane=1 (volume ratio)), and a solid thus obtained was washed with heptane. Thus, 3-(diphenylamino)phenol (69.5 g) was obtained.

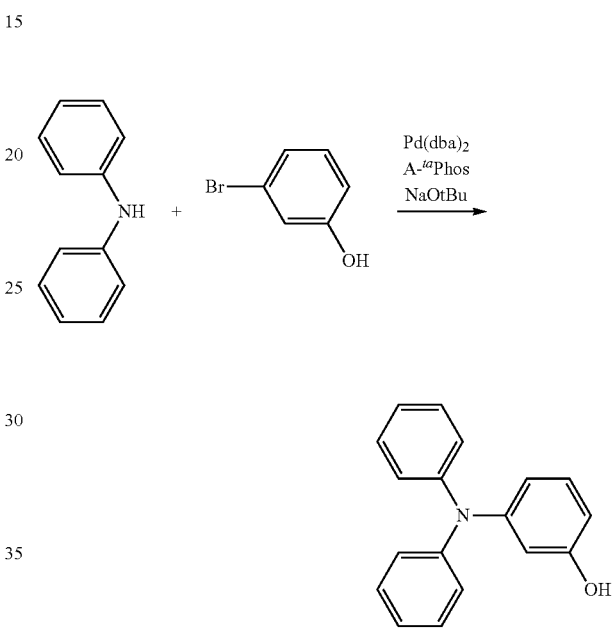

Copper(I) iodide (0.56 g) and iron(III) acetylacetonate (2.1 g) were added to an NMP (150 ml) solution of 3-(diphenylamino)phenol (34.1 g), 1,3-dibromobenzene (14.0 g) and potassium carbonate (33.0 g) in a nitrogen atmosphere. The temperature of the mixture was increased to 150° C., and the mixture was stirred for 10 hours. The reaction liquid was cooled to room temperature, ethyl acetate and aqueous ammonia were added thereto, and then the mixture was partitioned. The solvent of the organic layer was distilled off under reduced pressure. Subsequently, the residue was purified by silica gel column chromatography (developing liquid: toluene/heptane=4/6 (volume ratio)), and 3,3'-(1,3-phenylenebis(oxy))bis(N,N-diphenylaniline) (27.0 g was obtained.

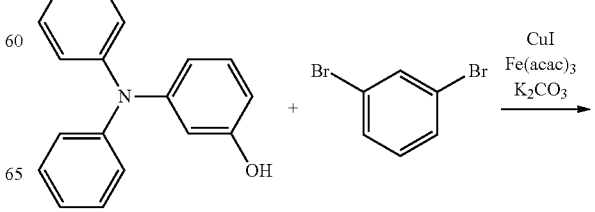

-continued

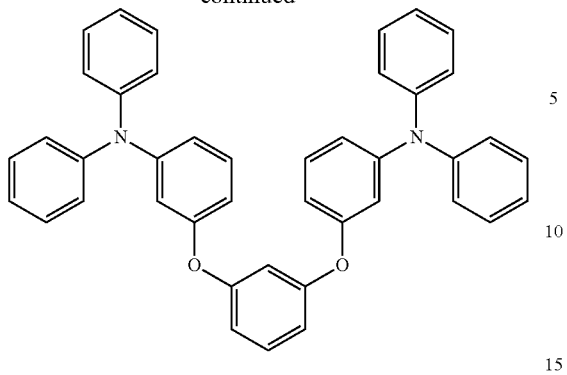

A 2.6 M n-butyllithium hexane solution (18.3 ml) was introduced into a flask containing 3,3'-(1,3-phenylenebis(oxy))bis(N,N-diphenylaniline) (27.0 g) and xylene (150 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off. The mixture was cooled to −50° C., boron tribromide (13.6 g) was added thereto, the temperature of the mixture was increased to room temperature, and the mixture was stirred for one hour. Thereafter, the mixture was cooled again to 0° C., N,N-diisopropylethylamine (11.7 g) was added thereto, and the mixture was stirred at room temperature until heat generation was settled. Subsequently, the mixture was heated and stirred for 2 hours at 120° C. The reaction liquid was cooled to room temperature, and a precipitate generated by adding an aqueous solution of sodium acetate was collected by suction filtration. The solid thus obtained was dissolved in ortho-dichlorobenzene, and reprecipitation was carried out by concentrating the solution. Thus, a compound (6.2 g) represented by formula (1-176) was obtained.

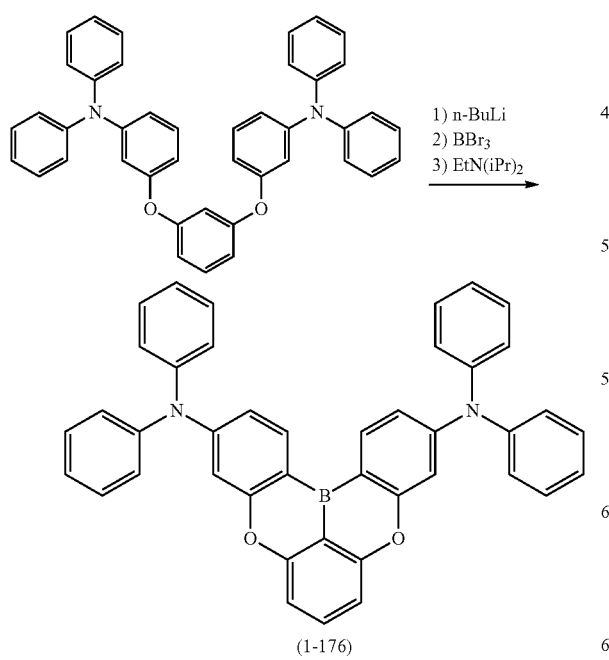

The structure of the compound thus obtained was identified by an NMR analysis.

$^1$H-NMR (400 MHz, CDCl$_3$): δ=8.35 (d, 2H), 7.61 (t, 1H), 7.34 (t, 8H), 7.23 (d, 8H), 7.15 (t, 4H), 7.02 (m, 4H), 6.98 (m, 2H).

Synthesis Example (9)

Synthesis of 9-(5,9-dioxa-13b-boranaphtho[3,2,1-de]anthracen-7-yl)-9H-carbazole (1-49)

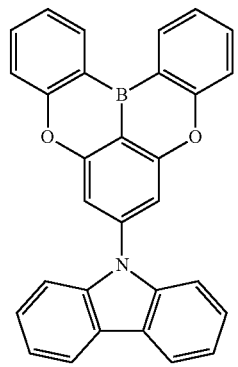

In a nitrogen atmosphere, a flask containing 1,3-dibromo-5-fluorobenzene (50.0 g), carbazole (39.5 g), cesium carbonate (96.2 g) and DMSO (500 ml) was heated to 150° C. and stirred for 10 hours. The reaction liquid was cooled to room temperature, and a precipitate precipitated by adding water thereto was collected by suction filtration. A solid thus obtained was purified by silica gel column chromatography (developing liquid: toluene/heptane=1/10 (volume ratio)), and then the solid was recrystallized from a mixed solvent of toluene/heptane. Thus, 9-(3,5-dibromophenyl)-9H-carbazole (49.0 g) was obtained.

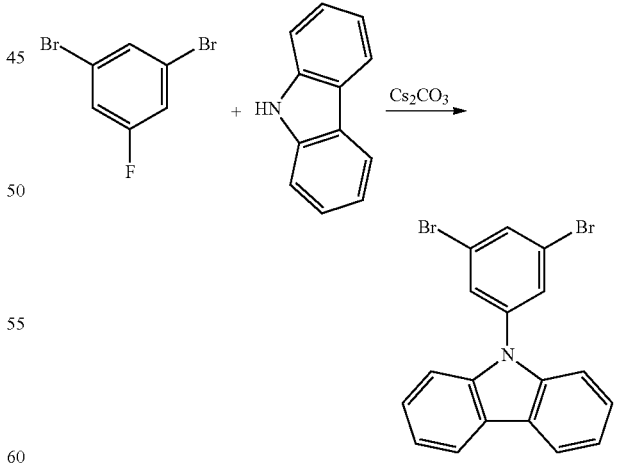

Copper(I) iodide (0.71 g) and iron(III) acetylacetonate (2.6 g) were added to an NMP (240 ml) solution of phenol (21.1 g), 9-(3,5-dibromophenyl)-9H-carbazole (30.0 g) and potassium carbonate (41.3 g) in a nitrogen atmosphere. The temperature of the mixture was increased to 150° C., and the mixture was stirred for 6 hours. The reaction liquid was cooled to room temperature, subsequently toluene was added thereto, and the mixture was suction filtered using a Hirsch funnel covered with Celite. A saturated sodium chloride solution was added to the filtrate, and the mixture was partitioned. The organic layer was distilled off under reduced pressure, and the residue was purified by silica gel column chromatography (developing liquid: toluene/heptane=2/1 (volume ratio)). Thus, 9-(3,5-diphenoxyphenyl)-9H-carbazole (27.3 g) was obtained.

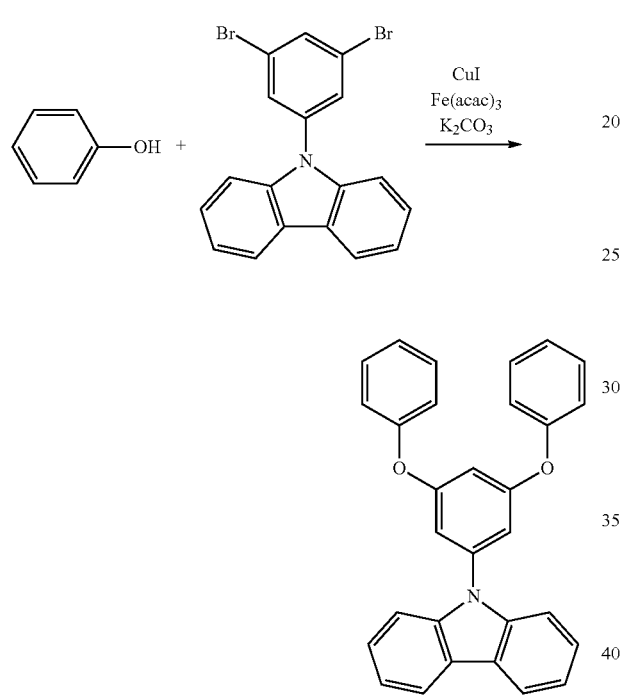

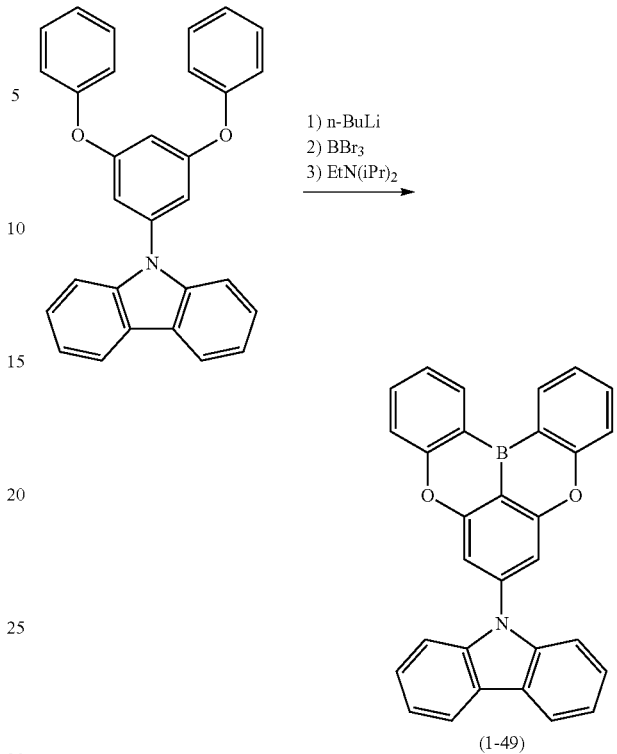

A 1.6 M n-butyllithium hexane solution (16.1 ml) was introduced into a flask containing 9-(3,5-diphenoxyphenyl)-9H-carbazole (10.0 g) and xylene (100 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off. The mixture was cooled to −50° C., boron tribromide (2.7 ml) was added thereto, the temperature of the mixture was increased to room temperature, and the mixture was stirred for one hour. Thereafter, the mixture was cooled again to 0° C., N,N-diisopropylethylamine (8.1 ml) was added thereto, and the mixture was stirred at room temperature until heat generation was settled. Subsequently, the mixture was heated and stirred for 8 hours at 120° C. The reaction liquid was cooled to room temperature, an aqueous solution of sodium acetate and toluene were added thereto, and then the mixture was partitioned. Subsequently, the solvent was distilled off under reduced pressure. A solid thus obtained was recrystallized from toluene, and thus a compound (1.7 g) represented by formula (1-49) was obtained.

The structure of the compound thus obtained was identified by an NMR analysis.

$^1$H-NMR (400 MHz, CDCl$_3$): δ=8.75 (d, 2H), 8.18 (d, 2H), 7.75 (t, 2H), 7.71 (d, 2H), 7.58 (d, 2H), 7.50 (s, 2H), 7.42-7.49 (m, 4H), 7.35 (t, 2H).

Synthesis Example (10)

Synthesis of 10-(5,9-dioxa-13b-boranaphtho[3,2,1-de]anthracen-7-yl)-10H-phenoxazine

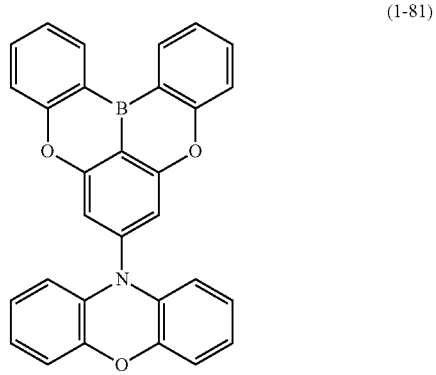 [SMILES: c1ccc2c(c1)Oc1cc(N3c4ccccc4Oc4ccccc43)cc3c1B2c1ccccc1O3]

In a nitrogen atmosphere, a solution of 1-bromo-3,5-difluorobenzene (23.0 g), phenol (33.6 g), potassium carbonate (49.4 g) and NMP (150 ml) was heated to 170° C. and was stirred for 10 hours. The reaction liquid was cooled to room temperature, toluene and a saturated aqueous solution of sodium chloride were added thereto, and then the mixture was partitioned. The solvent was distilled off under reduced pressure. Subsequently, the residue was purified by silica gel column chromatography (developing liquid: heptane), and ((5-bromo-1,3-phenylene)bis(oxy))dibenzene (35.9 g) was obtained.

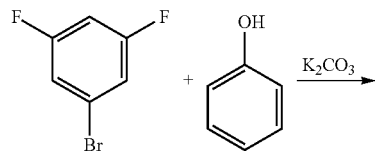

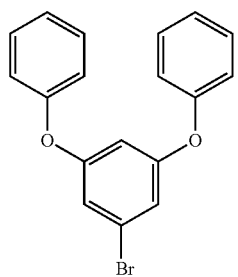

In a nitrogen atmosphere, a flask containing ((5-bromo-1,3-phenylene)bis(oxy))dibenzene (14.0 g), phenoxazine (8.3 g), Pd(dba)$_2$ (0.71 g), A-$^{ta}$Phos (0.98 g), NaOtBu (5.9 g), and ortho-xylene (100 ml) was heated to 120° C. and stirred for one hour. The reaction liquid was cooled to room temperature, subsequently water and toluene were added thereto, and then the mixture was partitioned. The solvent was distilled off under reduced pressure. A solid thus obtained was purified by silica gel column chromatography (developing liquid: toluene/heptane=1/5 (volume ratio)) was purified, and thus 10-(3,5-diphenoxyphenyl)-10H-phenoxazine (18.0 g) was obtained.

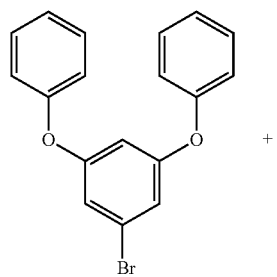

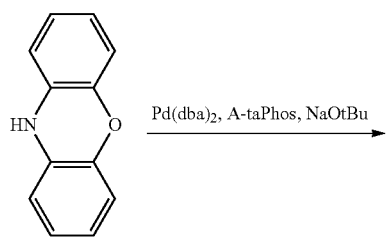

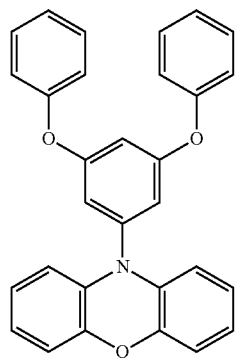

A 1.6 M n-butyllithium hexane solution (15.5 ml) was introduced into a flask containing 10-(3,5-diphenoxyphenyl)-10H-phenoxazine (10.0 g) and xylene (100 ml), at 0° C. in a nitrogen atmosphere. After completion of dropwise addition, the temperature was increased to 70° C., and the mixture was stirred for 4 hours. The temperature of the mixture was further increased to 100° C., and hexane was distilled off. The mixture was cooled to −50° C., boron tribromide (2.6 ml) was added thereto, the temperature of the mixture was increased to room temperature, and the mixture was stirred for one hour. Thereafter, the mixture was cooled again to 0° C., N,N-diisopropylethylamine (7.8 ml) was added thereto, and the mixture was stirred at room temperature until heat generation was settled. Subsequently, the mixture was heated and stirred for 8 hours at 120° C. The reaction liquid was cooled to room temperature, an aqueous solution of sodium acetate and toluene were added thereto, and then the mixture was partitioned. Subsequently, the solvent was distilled off under reduced pressure. A solid thus obtained was purified by silica gel column chromatography (developing liquid: toluene/heptane=1/10 (volume ratio)) and was recrystallized from toluene. Thus, a compound (1.8 g) represented by formula (1-81) was obtained.

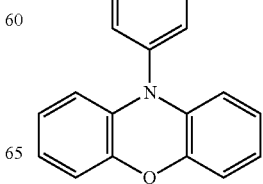

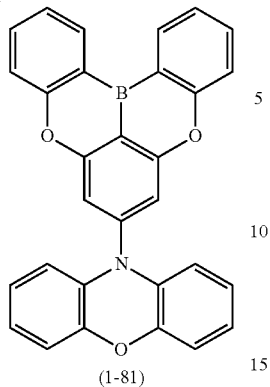

(1-81)

The structure of the compound thus obtained was identified by an NMR analysis.

$^1$H-NMR (400 MHz, CDCl$_3$): δ=8.73 (d, 2H), 7.75 (t, 2H), 7.56 (d, 2H), 7.44 (t, 2H), 7.25 (s, 2H), 6.57-6.80 (m, 6H), 6.13 (br, 2H).

Synthesis Example (11)

Synthesis of 5,9-dimethyl-5,9-diaza-13b-boranaphtho[3,2,1-de]anthracene

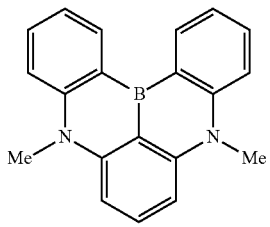

(1-411)

A 1.6 M n-butyllithium hexane solution (25.0 ml) was added to a t-butylbenzene (20 ml) solution of N$^1$,N$^3$-dimethyl-N$^1$,N$^3$-diphenylbenzene-1,3-diamine (2.9 g) at 0° C. in a nitrogen atmosphere. The temperature of the mixture was increased to 100° C., hexane was distilled off, and the residue was further heated and stirred for 21 hours. The mixture was cooled to −40° C., THF (10 ml) was added thereto, and then boron tribromide (1.9 ml) was added thereto. The temperature of the mixture was increased to room temperature over one hour, and then the mixture was cooled to 0° C. N,N-diisopropylamine (5.2 ml) was added thereto, and the mixture was filtered using a Florisil short pass column. The solvent was distilled off under reduced pressure, and then the residue was washed with acetonitrile. Thus, a compound (0.96 g) represented by formula (1-411) was obtained as a yellowish green solid.

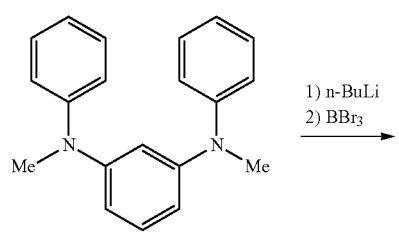

1) n-BuLi
2) BBr$_3$

→

(1-411)

The structure of the compound thus obtained was identified by an NMR analysis.

$^1$H-NMR (400 MHz, CDCl$_3$): δ=8.73 (dd, 2H), 7.75 (t, 1H), 7.67 (m, 2H), 7.57 (dd, 2H), 7.29 (m, 2H), 7.00 (d, 2H), 3.91 (s, 6H).

Synthesis Example (12)

Synthesis of 5,9-dioxa-13b-thiophosphanaphtho[3,2,1-de]anthracene

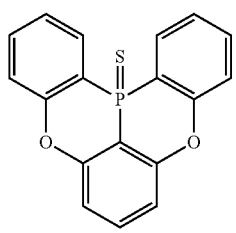

(1-701)

A 1.6 M n-butyllithium hexane solution (15.0 mL) was added to a benzene (60 mL) solution of m-diphenoxybenzene (5.25 g) at 0° C. in a nitrogen atmosphere. The temperature of the mixture was increased to 70° C., the mixture was stirred for 4 hours, and then phosphorus trichloride (4.12 g) that had been cooled to 0° C. was added thereto. The mixture was heated to 80° C. and stirred for one hour, and then sulfur (1.15 g) was added thereto. The mixture was further stirred for one hour at 80° C. The mixture was cooled again to 0° C., aluminum trichloride (18.7 g) and N,N-diisopropylethylamine (6.20 g) were added thereto. Then, the temperature of the mixture was increased to 80° C., and the mixture was stirred for 20 hours. The mixture was cooled to room temperature, and then the reaction liquid was added to a dichloromethane (300 ml) solution of 1,4-diazabicyclo[2.2.2]octane (31.4 g). Subsequently, the mixture was suction filtered using a Hirsch funnel covered with Celite, and the solvent was distilled off under reduced pressure. A yellowish brown oily substance thus obtained was purified using a silica gel short pass column (developing liquid: dichloromethane). The solvent was distilled off under reduced pressure, and a crude product was washed using acetonitrile. Thus, a compound (3.56 g) represented by formula (1-701) was obtained as a white solid.

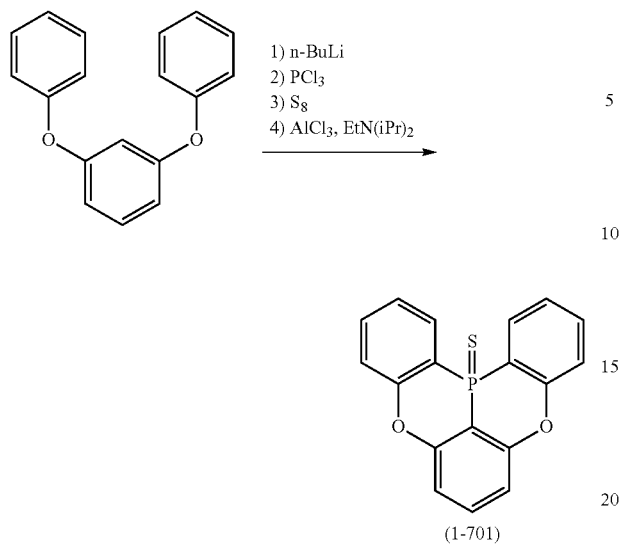

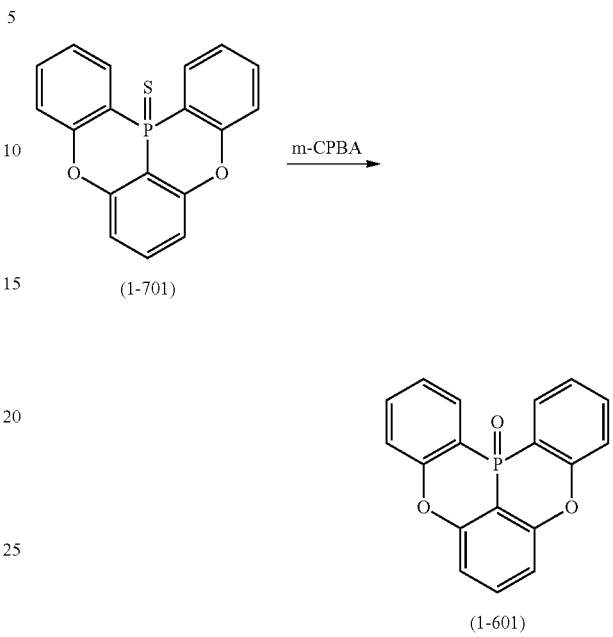

The structure of the compound thus obtained was identified by an NMR analysis.

¹H-NMR (400 MHz, CDCl₃): δ=8.14 (m, 2H), 7.55 (m, 2H), 7.53 (t, 1H), 7.35-7.37 (m, 4H), 7.12 (dd, 2H).

¹H NMR (δ ppm in CDCl₃); 7.13 (dd, 2H, J=4.4 Hz, 8.0 Hz), 7.34-7.40 (m, 4H), 7.53 (t, 1H, J=8.0 Hz), 7.55 (ddd, 2H, J=0.8 Hz, 1.6, 7.6 Hz), 8.15 (ddd, 2H, J=1.6 Hz, 7.6 Hz, 13.2 Hz).

¹³C NMR (δ ppm in CDCl₃); 102.5 (d, 1C, J=82.8 Hz), 112.8 (d, 2C, J=4.8 Hz), 119.7 (d, 2C, J=92.4 Hz), 119.8 (d, 2C, J=5.8 Hz), 125.1 (d, 2C, J=10.6 Hz), 129.0 (d, 2C, J=6.7 Hz), 132.9 (2C), 133.2, 155.7 (2C), 156.1 (2C).

Synthesis Example (13)

Synthesis of 5,9-dioxa-13b-oxophosphanaphtho[3,2,1-de]anthracene

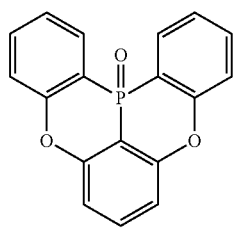

m-Chloroperbenzoic acid (m-CPBA) (1.61 g) was added to a dichloromethane (100 ml) solution of 5,9-dioxa-13b-thiophosphanaphtho[3,2,1-de]anthracene (1.79 g) at 0° C., and then the mixture was stirred for 22 hours at room temperature. A saturated aqueous solution of sodium sulfite (10.0 ml) was added thereto, and the mixture was stirred at room temperature. Insoluble materials were separated by filtration, and the mixture was partitioned. The solvent was distilled off under reduced pressure, and the residue was purified using a silica gel short pass column (developing liquid: dichloromethane/ethyl acetate=1 (volume ratio)). Subsequently, a crude product thus obtained was washed using hexane, and a compound (1.07 g) represented by formula (1-601) was obtained.

The structure of the compound thus obtained was identified by an NMR analysis.

¹H-NMR (400 MHz, CDCl₃): δ=8.22 (m, 2H), 7.64 (dd, 2H), 7.62 (t, 1H), 7.39-7.43 (m, 4H), 7.17 (dd, 2H).

Furthermore, m-chloroperbenzoic acid (1.24 g, 77 wt %, 5.55 mmol) was added to 13b-thiophospha-5,9-dioxanaphtho[3,2,1-de]anthracene (1.79 g, 5.55 mmol) and dichloromethane (100 mL) at 0° C., and the mixture was stirred at room temperature. After 22 hours, m-chloroperbenzoic acid (0.373 g, 77 wt %, 1.66 mmol) was added thereto at 0° C., and the mixture was stirred at room temperature. After one hour, a saturated solution of sodium sulfite (10.0 ml) was added thereto, and the mixture was stirred at room temperature. Insoluble materials were removed by filtration, the filtrate was partitioned into a dichloromethane layer, and then the aqueous layer was extracted with dichloromethane. The organic layers thus obtained were combined and concentrated, and then the combined organic layer was passed through a silica gel short pass column using dichloromethane and ethyl acetate as developing solvents. The solvent of the filtrate was distilled off under reduced pressure. A crude product thus obtained was washed using hexane, and thus a compound represented by formula (1-601) was obtained as a white solid (1.07 g, yield 63%).

The structure of the compound thus obtained was identified by an NMR analysis.

¹H NMR (δ ppm in CDCl₃); 7.16 (dd, 2H, J=4.0 Hz, 8.4 Hz), 7.37-7.44 (m, 4H), 7.61 (t, 1H, J=8.4 Hz), 7.62 (dd, 2H, J=1.6 Hz, 7.6 Hz), 8.21 (ddd, 2H, J=1.6 Hz, 7.6 Hz, 12.0 Hz).

¹³C NMR (δ ppm in CDCl₃); 103.7 (d, 1C, J=98.2 Hz), 112.2 (d, 2C, J=4.8 Hz), 117.6 (d, 2C, J=116.3 Hz), 119.9 (d, 2C, J=5.8 Hz), 124.5 (d, 2C, J=11.5 Hz), 129.4 (d, 2C, J=4.8 Hz), 133.6 (2C), 134.1, 156.6 (2C), 157.4 (2C).

Synthesis Example (14)

Synthesis of 5,9-dioxa-13b-phosphanaphtho[3,2,1-de]anthracene

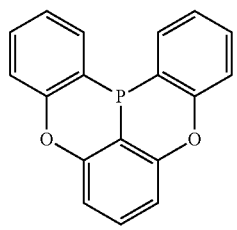
(1-501)

Triethylphosphine (0.168 g) was introduced into a flask containing 5,9-dioxa-13b-thiophosphanaphtho[3,2,1-de]anthracene (0.32 g) and degassed o-xylene (3.0 mL) in a nitrogen atmosphere, and then the mixture was stirred for 21 hours at 120° C. The solvent and triethylphosphine sulfide that was produced as a side product were distilled off under reduced pressure, and thus a compound (0.08 g) represented by formula (1-501) was obtained.

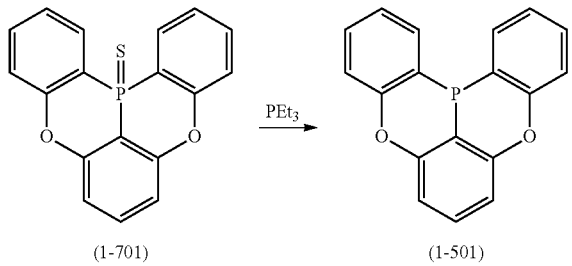 [SMILES: S=P12c3ccccc3Oc3cccc(c31)Oc1ccccc12 ; c1ccc2c(c1)Oc1cccc3c1P2c1ccccc1O3 ; "PEt3"]

The structure of the compound thus obtained was identified by an NMR analysis.

$^1$H-NMR (400 MHz, CDCl$_3$): δ=7.77 (m, 2H), 7.33 (m, 2H), 7.25 (m, 1H), 7.18-7.22 (m, 4H), 6.93 (dd, 2H).

Furthermore, triethylphosphine (0.130 g, 1.10 mmol) was added to 5,9-dioxa-13b-thiophosphanaphtho[3,2,1-de]anthracene (0.322 g, 1.00 mmol) and degassed o-xylene (6.0 mL) in a nitrogen atmosphere, and the mixture was stirred at 120° C. After 14 hours, the solvent and triethylphosphine sulfide that was produced as a side product were distilled off under reduced pressure, and thus a compound represented by formula (1-501) was obtained as a white solid (0.283 g, yield 97%).

The structure of the compound thus obtained was identified by an NMR analysis.

$^1$H NMR (δ ppm in CDCl$_3$); 6.94 (dd, 2H, J=2.0 Hz, 8.4 Hz), 7.18-7.22 (m, 4H), 7.25 (dt, 1H, J=1.2 Hz, 8.4 Hz), 7.33 (ddd, 2H, J=0.8 Hz, 1.6 Hz, 7.6 Hz), 7.77 (ddd, 2H, J=1.6 Hz, 6.4 Hz, 7.6 Hz).

$^{13}$C NMR (δ ppm in CDCl$_3$); 107.2 (d, 1C, J=4.8 Hz), 112.5 (2C), 118.7 (2C), 121.5 (d, 2C, J=28.0 Hz), 124.6 (d, 2C, J=3.8 Hz), 129.7 (d, 2C, J=4.8 Hz), 129.8, 129.9 (2C), 153.7 (d, 2C, J=8.7 Hz), 154.5 (d, 2C, J=6.8 Hz).

Synthesis Example (15)

Synthesis of 7,11-dioxa-17c-boraphenanthro[2,3,4-no]tetraphene

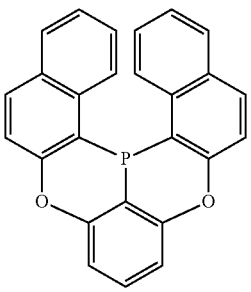
(1-4)

First, 2-bromonaphthalene (50.6 g) was added to a flask containing copper iodide (4.9 g), α-picolinic acid (6.3 g), potassium phosphate (101.9 g), resorcinol (12.8 g) and dimethyl sulfoxide (DMSO) (400 ml) in a nitrogen atmosphere, and the mixture was heated and stirred for 17 hours at 130°. After the reaction was terminated, the reaction liquid was cooled to 0° C., 1 Normal aqueous ammonia (160 ml) was added thereto, toluene was added thereto, and then the mixture was partitioned. The solvent was distilled off under reduced pressure, and a solid thus obtained was washed with methanol. Thus, 1,3-bis(2-naphthyloxy)benzene (34.5 g) was obtained as a white solid.

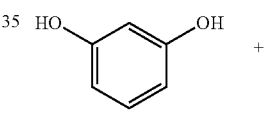

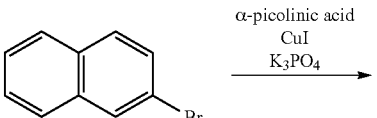

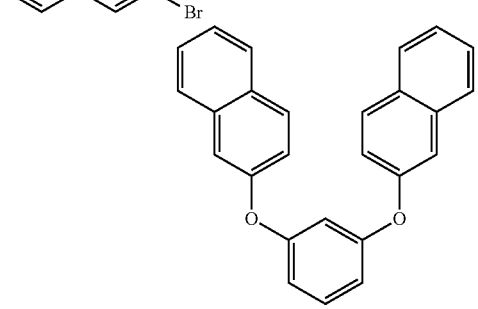

In a nitrogen atmosphere, a flask containing 1,3-bis(2-naphthyloxy)benzene (1.8 g) and t-butylbenzene (15 ml) was cooled at 0° C., and a 1.6 M n-butyllithium hexane solution (4.7 ml) was added dropwise thereto. After completion of dropwise addition, hexane was distilled off by heating and stirring the mixture for 0.5 hours at 90° C., and the residue was further heated and stirred for 3.5 hours at this temperature. Thereafter, the reaction liquid was cooled to −40° C., boron tribromide (0.95 ml) was added thereto, and the mixture was stirred for 2 hours. Furthermore, the mixture was stirred for 13 hours at room temperature, and then was cooled to 0° C. N,N-diisopropylethylamine (1.74 ml) was added thereto. Furthermore, the mixture was heated and stirred for 24 hours at 100° C., and then the mixture was filtered using a Florisil short pass column. The solvent was distilled off under reduced pressure. A solid thus obtained was washed using acetonitrile, and thus a compound (0.6 g) represented by formula (1-4) was obtained.

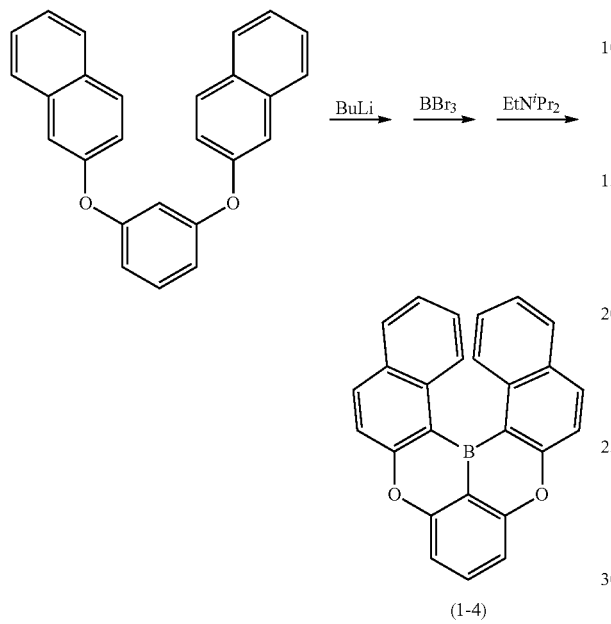

(1-4)

The structure of the compound thus obtained was identified by an NMR analysis.

$^1$H-NMR (400 MHz, CDCl$_3$): δ=8.16 (d, 2H), 7.91 (d, 2H), 7.80 (t, 1H), 7.76 (d, 2H), 7.74 (d, 2H), 7.42 (dd, 2H), 7.39 (d, 2H), 7.09 (dd, 2H).

Synthesis Example (16)

Synthesis of 5,9-diphenyl-7-(N,N-diphenylamino)-5,9-diaza-13b-boranaphtho[3,2,1-de]anthracene

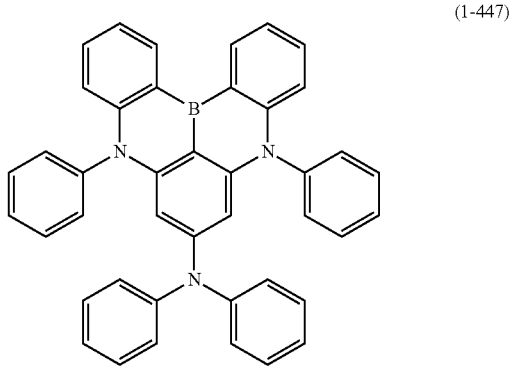 [SMILES: c1ccc(N(c2ccccc2)c2cc3c4c(c2)N(c2ccccc2)c2ccccc2B4c2ccccc2N3c2ccccc2)cc1]

(1-447)

In a nitrogen atmosphere, boron tribromide (0.06 ml) was introduced into a flask containing N$^1$,N$^1$,N$^3$,N$^3$,N$^5$,N$^5$-hexaphenylbenzene-1,3,5-triamine (0.29 g) and t-butylbenzene (3 ml) at room temperature, and then the mixture was heated for 37 hours at 90° C. The mixture was further heated for 37 hours at 170° C., subsequently the reaction liquid was cooled to 0° C., and N,N-diisopropylethylamine (0.26 ml) was added thereto. The solution was filtered using a Florisil short pass column, and a solid obtained by distilling off the solvent under reduced pressure was washed with diethyl ether. Thus, a compound (0.16 g) represented by formula (1-447) was obtained as a greenish yellow solid.

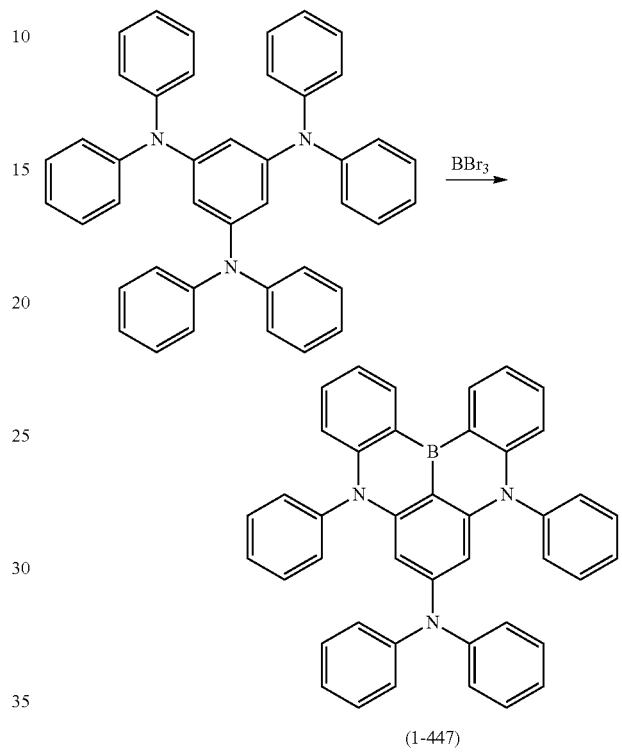

(1-447)

The structure of the compound thus obtained was identified by an NMR analysis.

$^1$H-NMR (400 MHz, CDCl$_3$): δ=8.89 (dd, 2H), 7.47 (t, 4H), 7.39 (m, 4H), 7.24 (m, 6H), 7.10 (m, 4H), 6.94 (m, 6H), 6.72 (d, 2H), 5.22 (m, 2H).

Furthermore, boron tribromide (3.78 mL, 40 mmol) was added to N$^1$,N$^1$,N$^3$,N$^3$,N$^5$,N$^5$-hexaphenylbenzene-1,3,5-triamine (11.6 g, 20 mmol) and ortho-dichlorobenzene (ODCB, 120 mL) at room temperature in a nitrogen atmosphere, and then the mixture was heated and stirred for 48 hours at 170° C. Thereafter, the reaction solution was distilled off under reduced pressure at 60° C. The reaction solution was filtered using a Florisil short pass column, the solvent was distilled off under reduced pressure, and a crude product was obtained. The crude product was washed using hexane, and thus a compound represented by formula (1-447) was obtained as a yellow solid (11.0 g, yield 94%).

The structure of the compound thus obtained was identified by an NMR analysis.

$^1$H NMR (400 MHz, CDCl$_3$) δ 5.62 (brs, 2H), 6.71 (d, 2H), 6.90-6.93 (m, 6H), 7.05-7.09 (m, 4H), 7.20-7.27 (m, 6H), 7.33-7.38 (m, 4H), 7.44-7.48 (m, 4H), 8.90 (dd, 2H).

$^{13}$C NMR (101 MHz, CDCl$_3$) δ 98.4 (2C), 116.8 (2C), 119.7 (2C), 123.5 (2C), 125.6 (4C), 128.1 (2C), 128.8 (4C), 130.2 (4C), 130.4 (2C), 130.7 (4C), 134.8 (2C), 142.1 (2C), 146.6 (2C), 147.7 (2C), 147.8 (2C), 151.1.

Synthesis Example (17)

Synthesis of 3,11-diphenyl-5,9-dioxa-13b-boranaphtho[3,2,1-de]anthracene

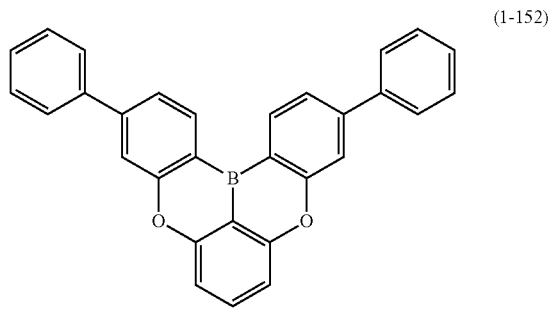 [SMILES: c1ccc(-c2ccc3c(c2)Oc2cccc4c2B3c2ccc(-c3ccccc3)cc2O4)cc1]

(1-152)

A flask containing 2-bromo-1,3-difluorobenzene (12.0 g), [1,1'-biphenyl]-3-ol (23.0 g), potassium carbonate (34.0 g) and NMP (130 ml) was heated and stirred for 10 hours at 170° C. in a nitrogen atmosphere. After the reaction was terminated, the reaction liquid was cooled to room temperature, water and toluene were added thereto, and then the mixture was partitioned. The solvent was distilled off under reduced pressure, and then the residue was purified by silica gel column chromatography (developing liquid: heptane/toluene=7/3 (volume ratio)). Thus, 3,3''-((2-bromo-1,3-phenylene)bis(oxy))di-1,1'-biphenyl (26.8 g) was obtained.

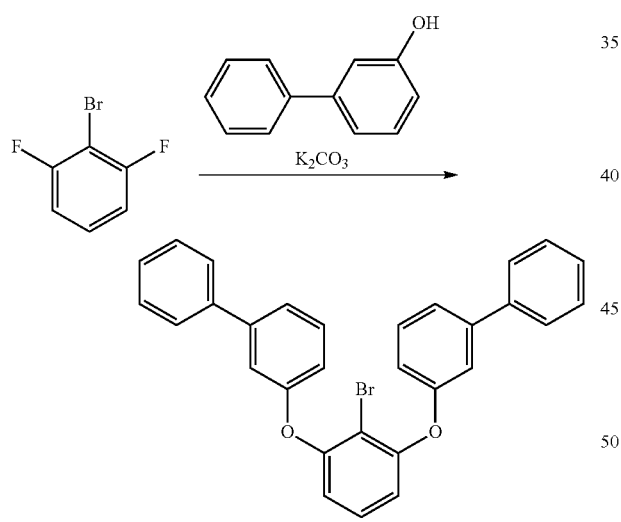

In a nitrogen atmosphere, a flask containing 3,3''-((2-bromo-1,3-phenylene)bis(oxy))di-1,1'-biphenyl (14.0 g) and xylene (100 ml) was cooled to −40° C., and a 2.6 M n-butyllithium hexane solution (11.5 ml) was added dropwise thereto. After completion of the dropwise addition, the temperature of the mixture was increased to room temperature, and then was decreased again to −40° C. Boron tribromide (3.3 ml) was added thereto. The temperature of the mixture was increased to room temperature, the mixture was stirred for 13 hours, and then the mixture was cooled to 0° C. N,N-diisopropylethylamine (9.7 ml) was added thereto, and the mixture was heated and stirred for 5 hours at 130° C. The reaction liquid was cooled to room temperature, an aqueous solution of sodium acetate that had been cooled in an ice bath was added thereto, and the mixture was stirred. A solid thus precipitated was collected by suction filtration. The solid thus obtained was washed with water, methanol, and heptane in this order, and was further recrystallized from chlorobenzene. Thus, a compound (8.9 g) represented by formula (1-152) was obtained.

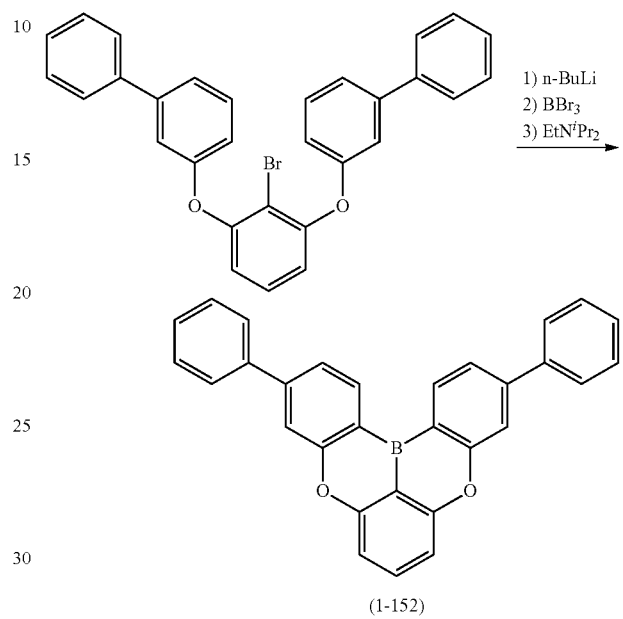

The structure of the compound thus obtained was identified by an NMR analysis.

$^1$H-NMR (400 MHz, CDCl$_3$): δ=8.75 (d, 2H), 7.75-7.84 (m, 7H), 7.65 (d, 2H), 7.53 (t, 4H), 7.44 (t, 2H), 7.25 (d, 2H).

Synthesis Example (18)

Synthesis of 2,6,8,12-tetraphenyl-5,9-dioxa-13b-boranaphtho[3,2,1-de]anthracene

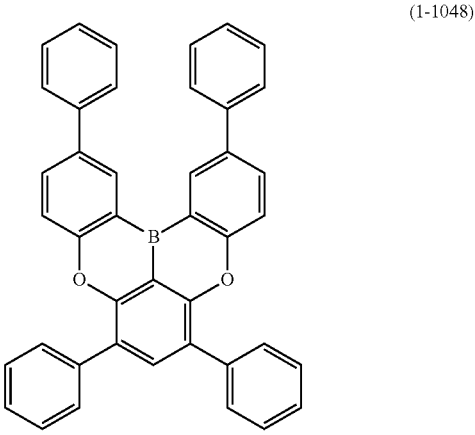 [SMILES: c1ccc(-c2ccc3c(c2)B2c4cc(-c5ccccc5)ccc4Oc4c(-c5ccccc5)cc(-c5ccccc5)c(c42)O3)cc1]

(1-1048)

A flask containing 1,5-bromo-2,4-difluorobenzene (90.0 g), phenylboronic acid (88.6 g), tripotassium phosphate (154.0 g), Pd-132 (Johnson Matthey) (1.6 g), toluene (900 ml), isopropanol (300 ml) and water (150 ml) was heated and stirred for one hour at the reflux temperature in a nitrogen atmosphere. After the reaction was terminated, the reaction liquid was cooled to room temperature, water was added thereto, and then the mixture was partitioned. The solvent was distilled off under reduced pressure, and then the residue was purified using a silica gel short pass column (developing liquid: heptane/toluene=1 (volume ratio)), and thus 4',6'-difluoro-1,1':3',1''-terphenyl (86.0 g) was obtained.

pressure, subsequently water and toluene were added thereto, and then the mixture was partitioned. The solvent was distilled off under reduced pressure, and then the residue was purified by silica gel column chromatography (developing liquid: heptane/toluene=7/3 (volume ratio)). The residue was dissolved in ethyl acetate, and then was reprecipitated by adding heptane thereto. Thus, 4',6'-bis([1,1'-biphenyl]-4-yloxy)-5'-bromo-1,1':3',1''-terphenyl (38.2 g) was obtained.

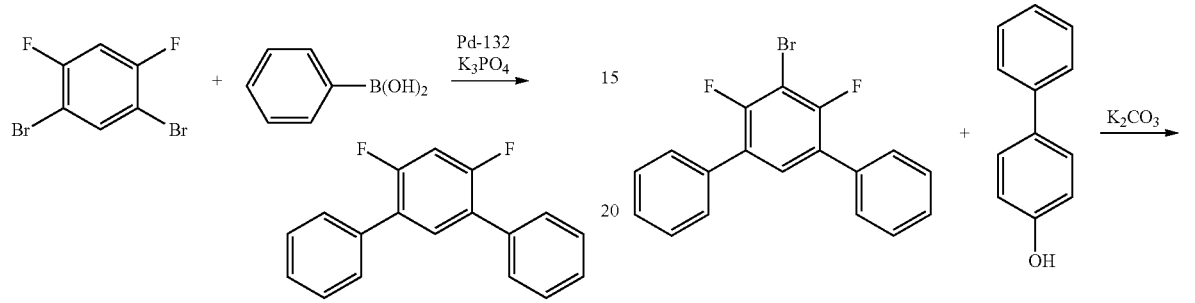

In a nitrogen atmosphere, a flask containing 4',6'-difluoro-1,1':3',1''-terphenyl (35.0 g) and THF (200 ml) was cooled to −78° C., and a 1 M sec-butyllithium cyclohexane solution (138 ml) was added dropwise thereto. The mixture was stirred for 30 minutes, and then bromine (23.0 g) was added dropwise. After completion of the dropwise addition, an aqueous solution of sodium sulfite was added thereto, and the mixture was stirred at room temperature. Water and toluene were added thereto, and then the mixture was partitioned. The solvent was distilled off under reduced pressure, and an oily crude purification product thus obtained was reprecipitated by adding heptane thereto. Thus, 5'-bromo-4',6'-difluoro-1,1':3',1''-terphenyl (41.7 g) was obtained.

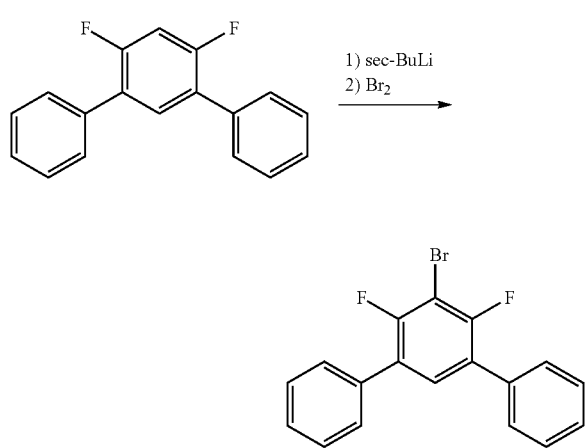

A flask containing 5'-bromo-4',6'-difluoro-1,1':3',1''-terphenyl (23.0 g), [1,1'-biphenyl]-4-ol (25.0 g), potassium carbonate (37.0 g) and NMP (120 ml) was heated and stirred for 2 hours at 200° C. in a nitrogen atmosphere. After the reaction was terminated, the reaction liquid was cooled to room temperature, NMP was distilled off under reduced

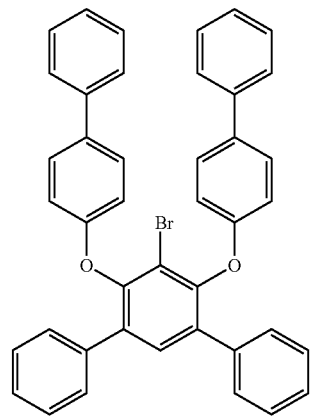

In a nitrogen atmosphere, a flask containing 4',6'-bis([1,1'-biphenyl]-4-yloxy)-5'-bromo-1,1':3',1''-terphenyl (19.0 g) and xylene (200 ml) was cooled to −40° C., and a 1.0 M sec-butyllithium cyclohexane solution (31.0 ml) was added dropwise thereto. After completion of the dropwise addition, the temperature of the mixture was increased to about 60° C., and distillation was carried out under reduced pressure. The reaction liquid was cooled again to −40° C., and boron tribromide (3.3 ml) was added thereto. The temperature of the mixture was increased to room temperature, and the mixture was stirred for 0.5 hours. Subsequently, the mixture was cooled to 0° C., N,N-diisopropylethylamine (9.7 ml) was added thereto, the temperature of the mixture was increased to 130° C., and the mixture was heated and stirred for 3 hours. The reaction liquid was cooled to room temperature, an aqueous solution of sodium acetate that had been cooled in an ice bath was added thereto, and the mixture was stirred. A solid thus precipitated was collected by suction filtration. The solid thus obtained was washed with water, methanol and heptane in this order, and was further washed with toluene that had been heated to the reflux temperature, and with chlorobenzene that had been heated to the reflux temperature. Thus, a compound (9.2 g) represented by formula (1-1048) was obtained.

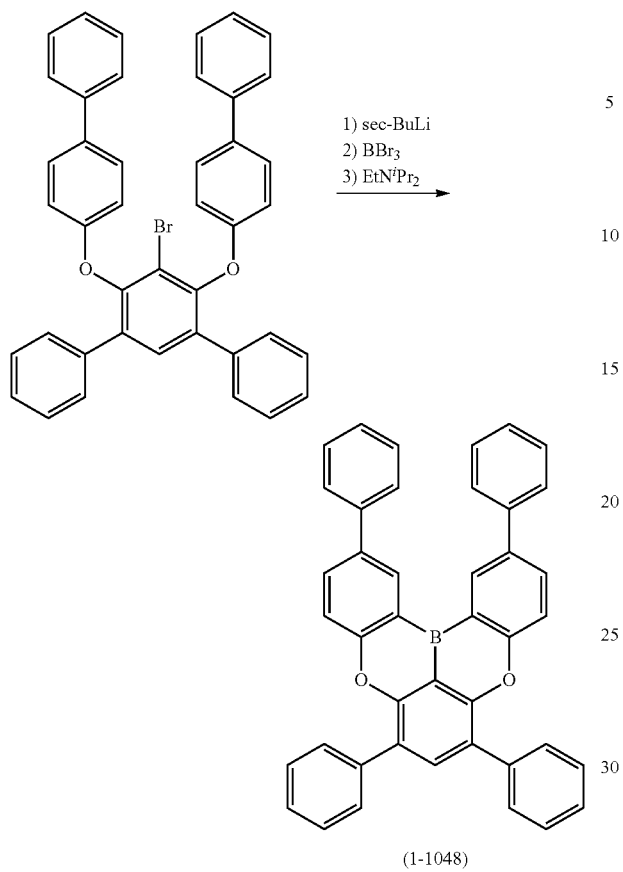

(1-1048)

The structure of the compound thus obtained was identified by an NMR analysis.

$^1$H-NMR (400 MHz, CDCl$_3$): δ=9.00 (m, 2H), 8.03 (s, 1H), 7.96 (dd, 2H), 7.84 (d, 4H), 7.75 (d, 4H), 7.50-7.60 (m, 10H), 7.46 (t, 2H), 7.40 (t, 2H).

Synthesis Example (19)

Synthesis of 3,6,8,11-tetraphenyl-5,9-dioxa-13b-boranaphtho[3,2,1-de]anthracene

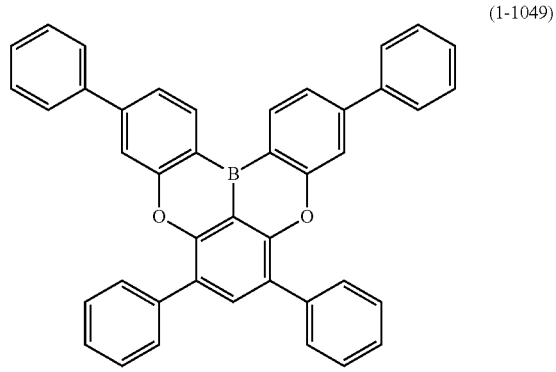 [SMILES: c1ccc(-c2ccc3c(c2)Oc2c(-c4ccccc4)cc(-c4ccccc4)c4c2B3c2ccc(-c3ccccc3)cc2O4)cc1]

(1-1049)

A flask containing 5'-bromo-4',6'-difluoro-1,1':3',1"-terphenyl (23.0 g), [1,1'-biphenyl]-3-ol (25.0 g), potassium carbonate (37.0 g) and NMP (120 ml) was heated and stirred for 2 hours at 200° C. in a nitrogen atmosphere. After the reaction was terminated, the reaction liquid was cooled to room temperature, NMP was distilled off under reduced pressure, water and toluene were added thereto, and then the mixture was partitioned. The solvent was distilled off under reduced pressure, and then the residue was purified by silica gel column chromatography (developing liquid: heptane/toluene=7/3 (volume ratio)). The purification product was further washed with heptane, and thus 4',6'-bis([1,1'-biphenyl]-3-yloxy)-5'-bromo-1,1':3',1"-terphenyl (40.0 g) was obtained.

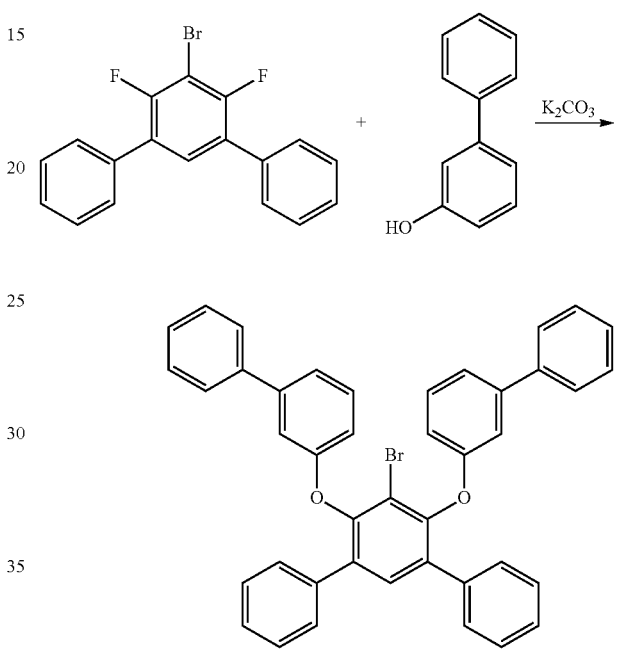

In a nitrogen atmosphere, a flask containing 4',6'-bis([1,1'-biphenyl]-3-yloxy)-5'-bromo-1,1':3',1"-terphenyl (20.0 g) and xylene (150 ml) was cooled to −40° C., and a 1.0 M sec-butyllithium cyclohexane solution (33.0 ml) was added dropwise thereto. After completion of the dropwise addition, the temperature of the mixture was increased to about 60° C., and distillation was carried out under reduced pressure. The resultant was cooled again to −40° C., and boron tribromide (3.5 ml) was added thereto. The temperature of the mixture was increased to room temperature, and the mixture was stirred for 0.5 hours. Subsequently, the mixture was cooled to 0° C., N,N-diisopropylethylamine (10.8 ml) was added thereto, the temperature of the mixture was increased to 120° C., and the mixture was heated and stirred for 3 hours. The reaction liquid was cooled to room temperature, an aqueous solution of sodium acetate that had been cooled in an ice bath was added thereto, and then the mixture was stirred. A solid thus precipitated was collected by suction filtration. The solid thus obtained was washed with water, methanol and heptane in this order, and was further washed with ethyl acetate that had been heated to the reflux temperature, and with chlorobenzene that had been heated to the reflux temperature. Thus, a compound (10.0 g) represented by formula (1-1049) was obtained.

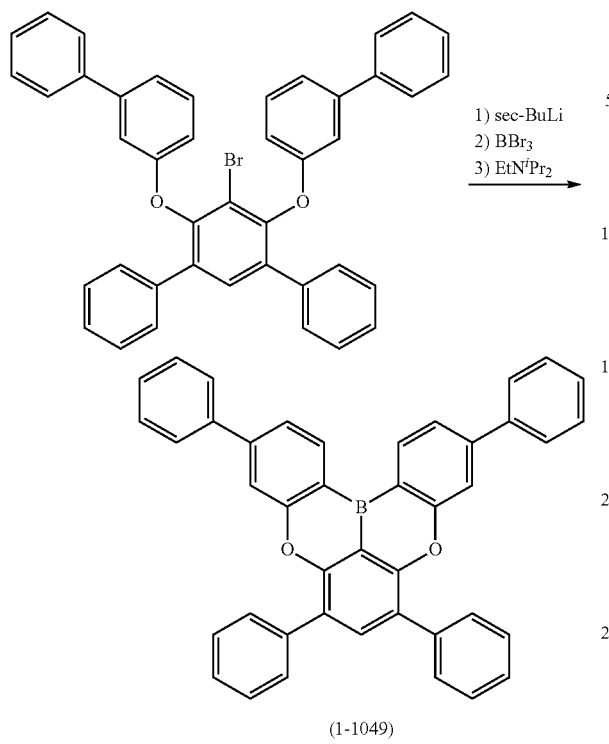

(1-1049)

The structure of the compound thus obtained was identified by an NMR analysis.

$^1$H-NMR (400 MHz, CDCl$_3$): δ=8.76 (d, 2H), 7.98 (s, 1H), 7.82 (d, 4H), 7.71 (d, 4H), 7.64 (m, 4H), 7.55 (t, 4H), 7.50 (t, 4H), 7.40-7.47 (m, 4H).

Synthesis Example (20)

Synthesis of 3,6,8,11-tetraphenyl-5,9-dioxa-13b-boranaphtho[3,2,1-de]anthracene

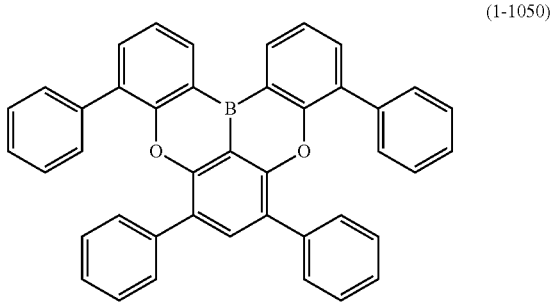 [SMILES: c1ccc(-c2cccc3c2Oc2c(-c4ccccc4)cc(-c4ccccc4)c4c2B3c2cccc(-c3ccccc3)c2O4)cc1]

(1-1050)

A flask containing 5'-bromo-4',6'-difluoro-1,1':3',1''-terphenyl (23.0 g), [1,1'-biphenyl]-2-ol (25.0 g), potassium carbonate (37.0 g) and NMP (120 ml) was heated and stirred for 4 hours at 200° C. in a nitrogen atmosphere. After the reaction was terminated, the reaction liquid was cooled to room temperature, NMP was distilled off under reduced pressure, subsequently water and toluene were added thereto, and then the mixture was partitioned. The solvent was distilled off under reduced pressure, and then the residue was purified by silica gel column chromatography (developing liquid: heptane/toluene=7/3 (volume ratio)). Thus, 4',6'-bis([1,1'-biphenyl]-2-yloxy)-5'-bromo-1,1':3',1''-terphenyl (38.2 g) was obtained.

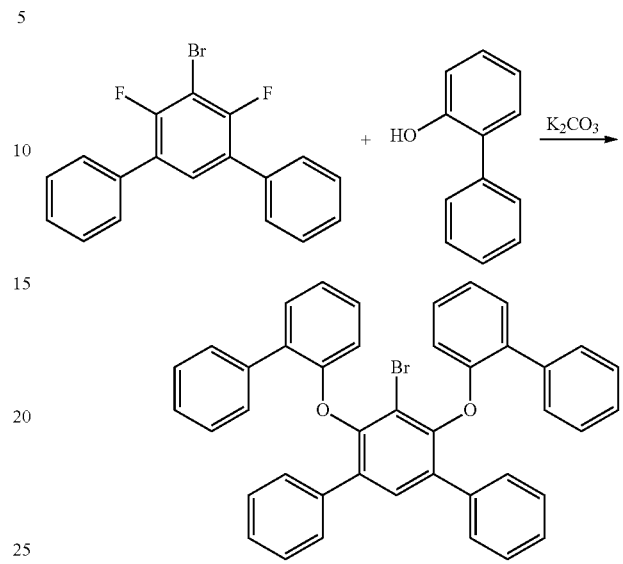

In a nitrogen atmosphere, a flask containing 4',6'-bis([1,1'-biphenyl]-2-yloxy)-5'-bromo-1,1':3',1''-terphenyl (20.0 g) and xylene (150 ml) was cooled to −40° C., and a 1.0 M sec-butyllithium cyclohexane solution (33.0 ml) was added dropwise thereto. After completion of the dropwise addition, the temperature of the mixture was increased to about 60° C., and components having boiling points lower than that of xylene were distilled off under reduced pressure. The residue was cooled again to −40° C., and boron tribromide (3.5 ml) was added thereto. The temperature of the mixture was increased to room temperature, the mixture was stirred for 0.5 hours, and then the mixture was cooled to 0° C. N,N-diisopropylethylamine (10.8 ml) was added thereto, the temperature of the mixture was increased to 130° C., and the mixture was heated and stirred for 4 hours. The reaction liquid was cooled to room temperature, an aqueous solution of sodium acetate that had been cooled in an ice bath was added thereto, and the mixture was stirred. A solid thus precipitated was collected by suction filtration. The solid thus obtained was washed with water, methanol and heptane in this order, and was further recrystallized from toluene. Thus, a compound (14.1 g) represented by formula (1-1050) was obtained.

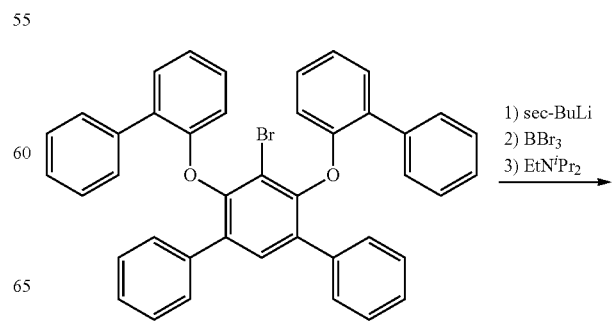

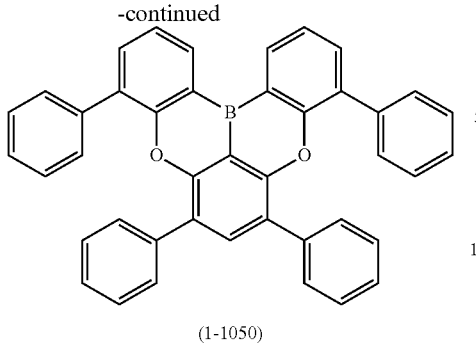

(1-1050)

The structure of the compound thus obtained was identified by an NMR analysis.

$^1$H-NMR (400 MHz, CDCl$_3$): δ=8.78 (d, 2H), 7.81 (s, 1H), 7.68 (d, 2H), 7.48 (t, 2H), 7.38 (d, 4H), 7.35 (d, 4H), 7.27 (m, 2H), 7.19 (m, 6H), 7.10 (t, 4H).

Synthesis Example (21)

Synthesis of 6,8-diphenyl-N$^3$,N$^3$,N$^{11}$,N$^{11}$-tetra-p-tolyl-5,9-dioxa-13b-boranaphtho[3,2,1-de]anthracene-3,11-diamine

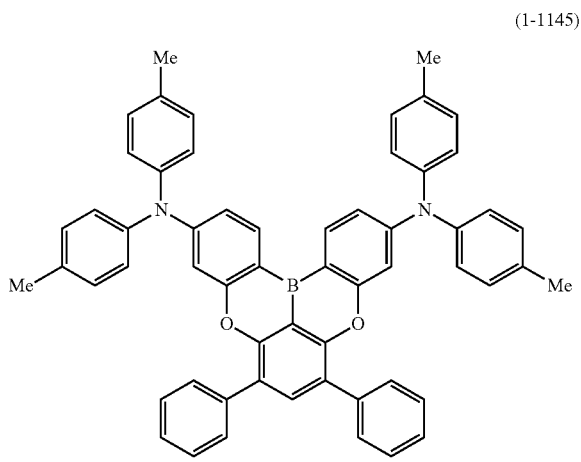 [SMILES: Cc1ccc(N(c2ccc(C)cc2)c2ccc3c(c2)Oc2c(-c4ccccc4)cc(-c4ccccc4)c4c2B3c2ccc(N(c3ccc(C)cc3)c3ccc(C)cc3)cc2O4)cc1]

(1-1145)

A flask containing di-p-tolylamine (36.0 g), 3-bromophenol (30.0 g), Pd-132 (Johnson Matthey) (0.6 g), NaOtBu (42.0 g), and toluene (300 ml) was heated to 90° C. and stirred for one hour. The reaction liquid was cooled to room temperature, subsequently water and ethyl acetate were added thereto, and the mixture was partitioned. Furthermore, the resultant was purified by silica gel column chromatography (developing liquid: toluene/heptane=1/1 (volume ratio)), and a solid thus obtained was washed with heptane. Thus, 3-(di-p-tolylamino)phenol (60.0 g) was obtained.

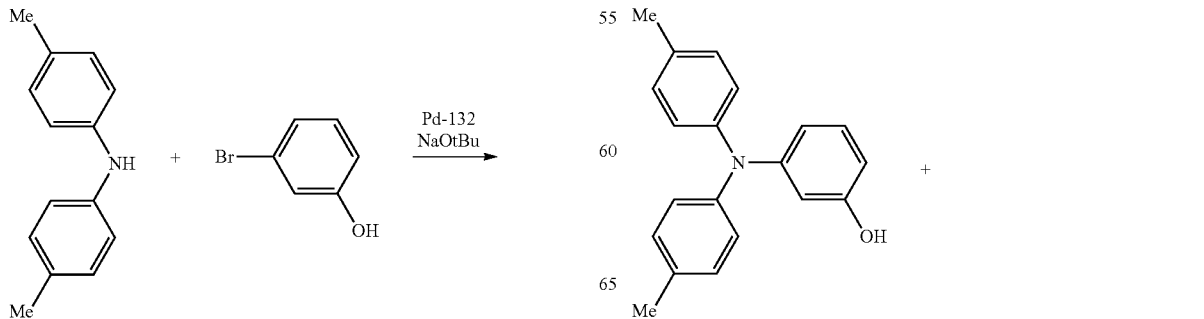

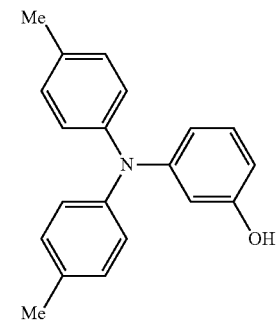

In a nitrogen atmosphere, a flask containing 1,5-dibromo-2,4-difluorobenzene (30.0 g), phenylboronic acid (29.6 g), Pd(PPh3)4 (2.6 g), tripotassium phosphate (51.0 g), toluene (400 ml), isopropanol (100 ml) and water (50 ml) was heated and stirred for 5 hours at the reflux temperature. The reaction liquid was cooled to room temperature, water and toluene were added to the mixture, and the mixture was partitioned. Subsequently, the resultant was purified by silica gel column chromatography (developing liquid: heptane), and thus 4',6'-difluoro-1,1':3',1''-terphenyl (25.0 g) was obtained.

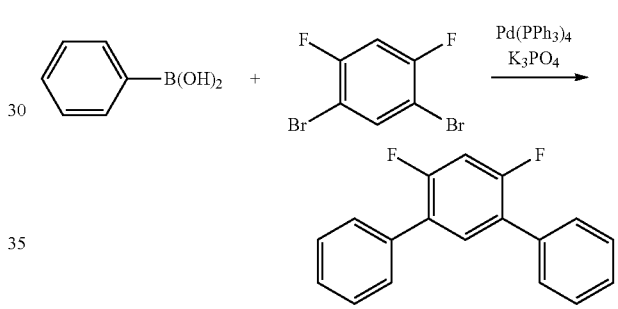

In a nitrogen atmosphere, a flask containing 3-(di-p-tolylamino)phenol (28.7 g), 4',6'-difluoro-1,1':3',1''-terphenyl (12.0 g), potassium carbonate (19.0 g), and NMP (120 ml) was heated and stirred for 5 hours at 200° C. The reaction liquid was cooled to room temperature, water and ethyl acetate were added to the reaction liquid, and the mixture was partitioned. Subsequently, the resultant was purified by silica gel column chromatography (developing liquid: toluene/heptane=4/6 (volume ratio)), and thus 3,3'-([1,1':3',1''-terphenyl]-4',6'-diylbis(oxy))bis(N,N-di-p-tolylaniline) (33.0 g) was obtained.

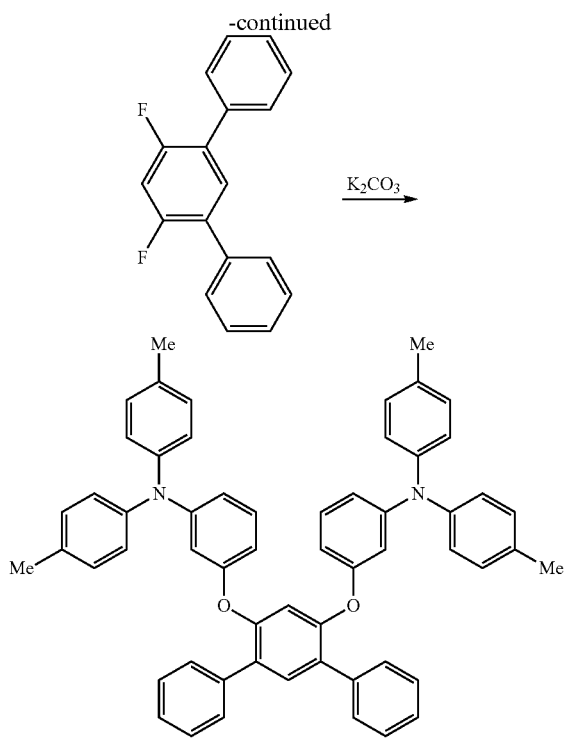

A 2.6 M n-butyllithium hexane solution (18.3 ml) was introduced into a flask containing 3,3'-([1,1':3',1"-terphenyl]-4',6'-diylbis(oxy))bis(N,N-di-p-tolylaniline) (27.0 g) and xylene (150 ml), at 0° C. in a nitrogen atmosphere. After completion of dropwise addition, the temperature of the mixture was increased to 70° C., and the mixture was stirred for 4 hours. The temperature of the mixture was further increased to 100° C., and hexane was distilled off. The mixture was cooled to −50° C., boron tribromide (13.6 g) was added thereto, the temperature of the mixture was increased to room temperature, and the mixture was stirred for one hour. Thereafter, the mixture was cooled again to 0° C., N,N-diisopropylethylamine (11.7 g) was added thereto, and the mixture was stirred at room temperature until heat generation was settled. Subsequently, the temperature of the mixture was increased to 120° C., and the mixture was heated and stirred for one hour. The reaction liquid was cooled to room temperature, an aqueous solution of sodium acetate and ethyl acetate were added thereto, and the mixture was partitioned. Subsequently, the resultant was purified by silica gel column chromatography (developing liquid: toluene/heptane=3/7 (volume ratio)), and was further purified by activated carbon column chromatography (developing liquid: toluene). A solid obtained by distilling off the solvent under reduced pressure was dissolved in chlorobenzene, and was reprecipitated by adding heptane thereto. Thus, a compound (2.5 g) represented by formula (1-1145) was obtained.

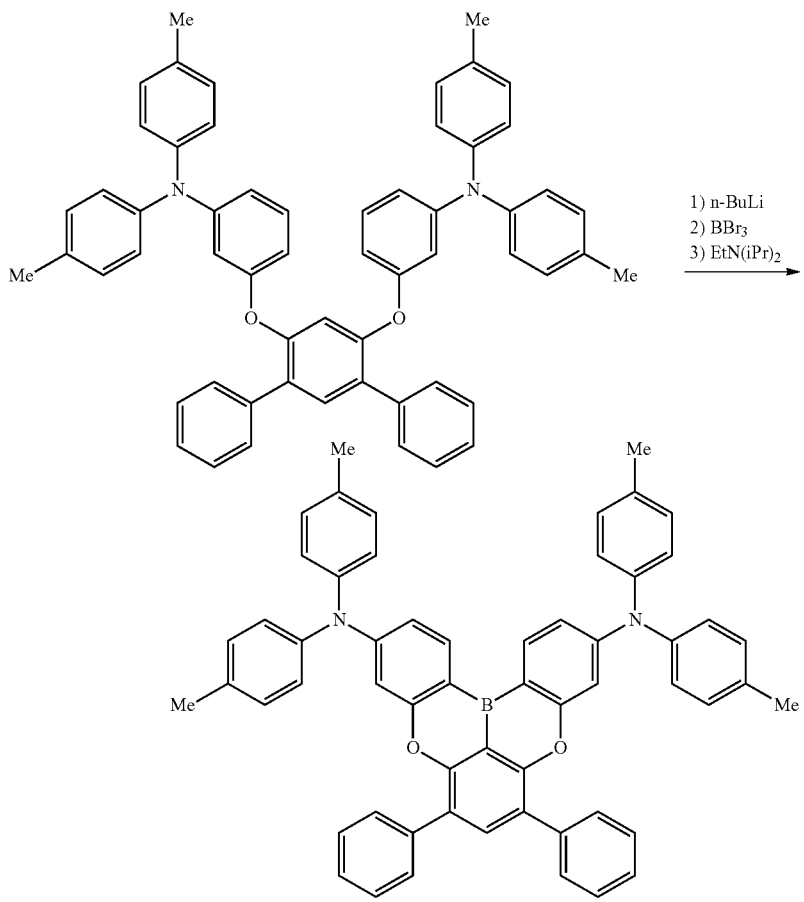

The structure of the compound thus obtained was identified by an NMR analysis.

¹H-NMR (400 MHz, CDCl₃): δ=8.34 (d, 2H), 7.79 (s, 1H), 7.71 (d, 4H), 7.43 (t, 4H), 7.34 (t, 2H), 7.05-7.15 (m, 16H), 6.90 (m, 4H), 2.34 (s, 12H).

Synthesis Example (22)

Synthesis of 9-(4-(5,9-dioxa-13b-boranaphtho[3,2,1-de]anthracen-7-yl)phenyl)-9H-carbazole

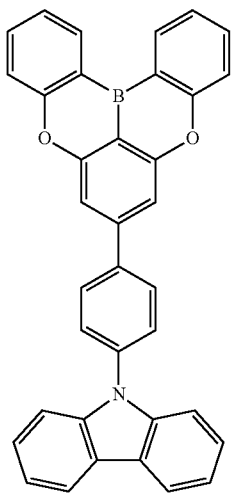
(1-50)

In a nitrogen atmosphere, a flask containing ((5-bromo-1,3-phenylene)bis(oxy))dibenzene (27.0 g), (4-(9H-carbazol-9-yl)phenyl)boronic acid (25.0 g), tripotassium phosphate (34.0 g), Pd-132 (Johnson Matthey) (0.3 g), toluene (400 ml), isopropanol (100 ml) and water (50 ml) was heated and stirred for one hour at the reflux temperature. After the reaction was terminated, the reaction liquid was cooled to room temperature, water was added thereto, and the mixture was partitioned. The solvent was distilled off under reduced pressure, and then the residue was purified using a silica gel short pass column (developing liquid: toluene). Thus, 9-(3',5'-diphenoxy[1,1'-biphenyl]-4-yl)-9H-carbazole (38.0 g) was obtained.

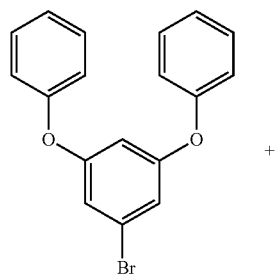

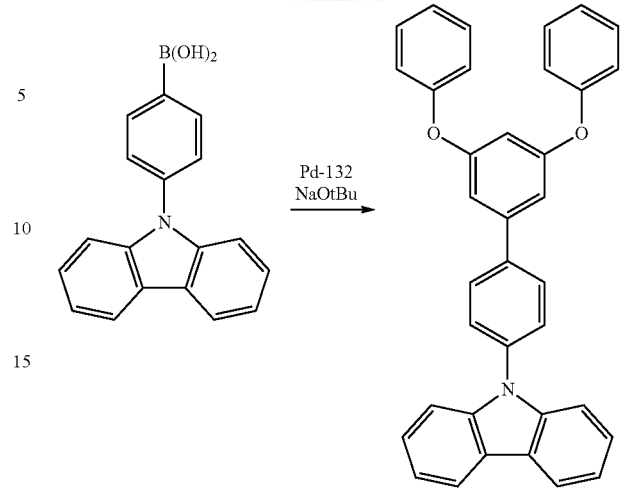

A 1.0 M sec-butyllithium cyclohexane solution (39.6 ml) was introduced to a flask containing 9-(3,5'-diphenoxy[1,1'-biphenyl]-4-yl)-9H-carbazole (19.0 g) and xylene (130 ml), at 0° C. in a nitrogen atmosphere. After completion of dropwise addition, the temperature of the mixture was increased to 70° C., the mixture was stirred for 3 hours, and then components having boiling points lower than that of xylene were distilled off under reduced pressure. The mixture was cooled to −50° C., boron tribromide (4.3 ml) was added thereto, the temperature of the mixture was increased to room temperature, and the mixture was stirred for 0.5 hours. Thereafter, the mixture was cooled again to 0° C., N,N-diisopropylethylamine (13.1 ml) was added thereto, and the mixture was stirred at room temperature until heat generation was settled. Subsequently, the temperature of the mixture was increased to 120° C., and the mixture was heated and stirred for 2 hours. The reaction liquid was cooled to room temperature, and a solid produced by adding an aqueous solution of sodium acetate that had been cooled in an ice bath and then adding heptane thereto was collected by suction filtration. The solid thus obtained was washed with water and then with toluene, and then was washed with refluxed ethyl acetate. The solid was further recrystallized from chlorobenzene, and thus a compound (15.6 g) represented by formula (1-50) was obtained.

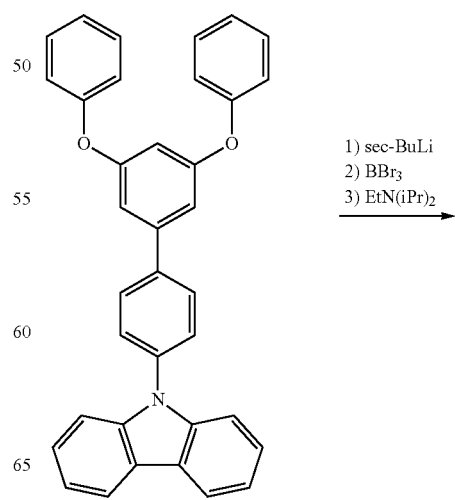

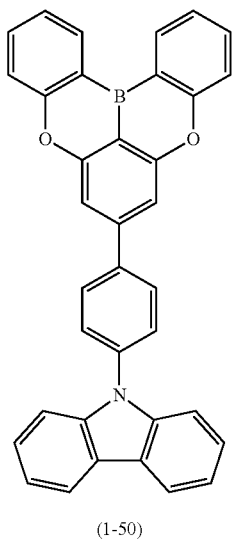

(1-50)

The structure of the compound thus obtained was identified by an NMR analysis.

$^1$H-NMR (400 MHz, CDCl$_3$): δ=8.73 (d, 2H), 8.17 (d, 2H), 8.01 (d, 2H), 7.74 (m, 4H), 7.60 (d, 2H), 7.58 (s, 2H), 7.53 (d, 2H), 7.40-7.48 (m, 4H), 7.32 (t, 2H).

Synthesis Example (23)

Synthesis of 9-(4-(5,9-dioxa-13b-boranaphtho[3,2,1-de]anthracen-2-yl)phenyl)-9H-carbazole

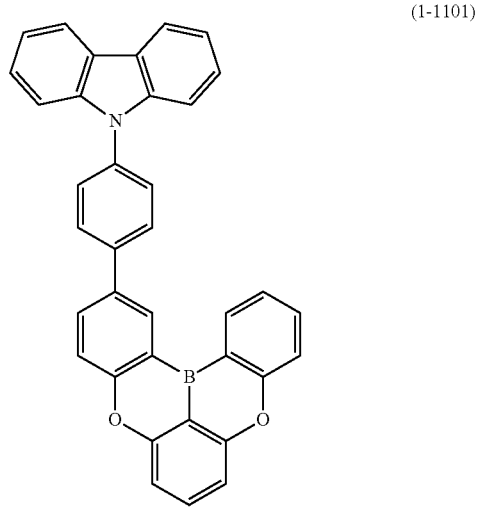 [SMILES: c1ccc2c(c1)Oc1cccc3c1B2c1cc(-c2ccc(-n4c5ccccc5c5ccccc54)cc2)ccc1O3]

(1-1101)

In a nitrogen atmosphere, copper(I) iodide (1.6 g) and iron (III) acetylacetonate (6.1 g) were added to an NMP (300 ml) solution of 1-bromo-3-fluorobenzene (50.0 g), phenol (30.0 g) and potassium carbonate (79.0 g) in a nitrogen atmosphere. The temperature of the mixture was increased to 150° C., and the mixture was stirred for 4 hours. The reaction liquid was cooled to room temperature, and a salt precipitated by adding ethyl acetate and aqueous ammonia thereto was removed by suction filtration using a Hirsch funnel covered with Celite. The filtrate was partitioned, and the solvent of the organic layer was distilled off under reduced pressure. Subsequently, the residue was purified using a silica gel short pass column (developing liquid: toluene/heptane=2/8 (volume ratio)), and thus 1-fluoro-3-phenoxybenzene (41.0 g) was obtained.

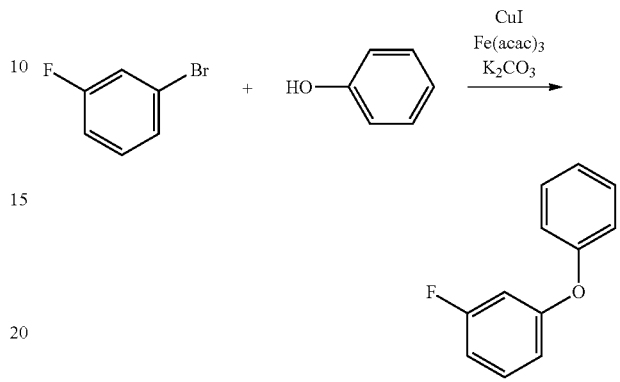

A flask containing 4'-bromo-[1,1'-biphenyl]-4-ol (25.0 g), carbazole (18.5 g), Pd(dba)$_2$, a 1 M tri-t-butylphosphine toluene solution (4.0 ml), NaOtBu (24.0 g) and 1,2,4-trimethylbenzene (300 ml) was heated and stirred for 2 hours at 150° C. The reaction liquid was cooled to room temperature, and then a solid precipitated by adding dilute hydrochloric acid was collected by suction filtration. The solid thus obtained was washed with water, and was purified using a silica gel short pass column (chlorobenzene/ethyl acetate/ethanol=5/4/1 (volume ratio)). The solvent was distilled off under reduced pressure, and a solid thus obtained was washed with chlorobenzene. Furthermore, the solid was dissolved in chlorobenzene, and was reprecipitated by adding ethyl acetate and ethanol thereto. Thus, 4'-(9H-carbazol-9-yl)-[1,1'-biphenyl]-4-ol (29.3 g) was obtained.

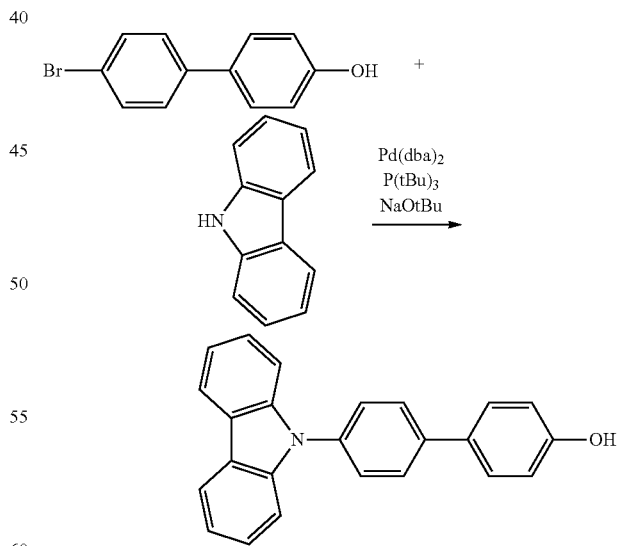

A flask containing 1-fluoro-3-phenoxybenzene (16.3 g), 4'-(9H-carbazol-9-yl)-[1,1'-biphenyl]-4-ol (29.0 g), potassium carbonate (29.0 g), and NMP (150 ml) was heated and stirred for 4 hours at 200° C. in a nitrogen atmosphere. Since the progress of the reaction was slow at this time point, cesium carbonate (31.0 g) was added thereto, and the mixture was further heated and stirred for 8 hours. After the reaction was terminated, the reaction liquid was cooled to room temperature, NMP was distilled off under reduced pressure, subsequently water and ethyl acetate were added to the residue, and the mixture was partitioned. The solvent was distilled off under reduced pressure, and then the residue was purified by silica gel column chromatography (developing liquid: heptane/toluene=8/2 (volume ratio)). Thus, 9-(4'-(3-phenoxyphenoxy)-[1,1'-biphenyl]-4-yl)-9H-carbazole (37.1 g) was obtained.

and the mixture was stirred at room temperature until heat generation was settled. Subsequently, the temperature of the mixture was increased to 120° C., and the mixture was heated and stirred for 2 hours. The reaction liquid was cooled to room temperature, and a solid produced by adding an aqueous solution of sodium acetate that had been cooled in an ice bath and then ethyl acetate was collected by suction filtration. The solid thus obtained was washed with refluxed ethyl acetate, and then was purified using a silica gel short pass column (developing liquid: heated chlorobenzene). The solid was further recrystallized from chlorobenzene, and thus a compound (6.9 g) represented by formula (1-1101) was obtained.

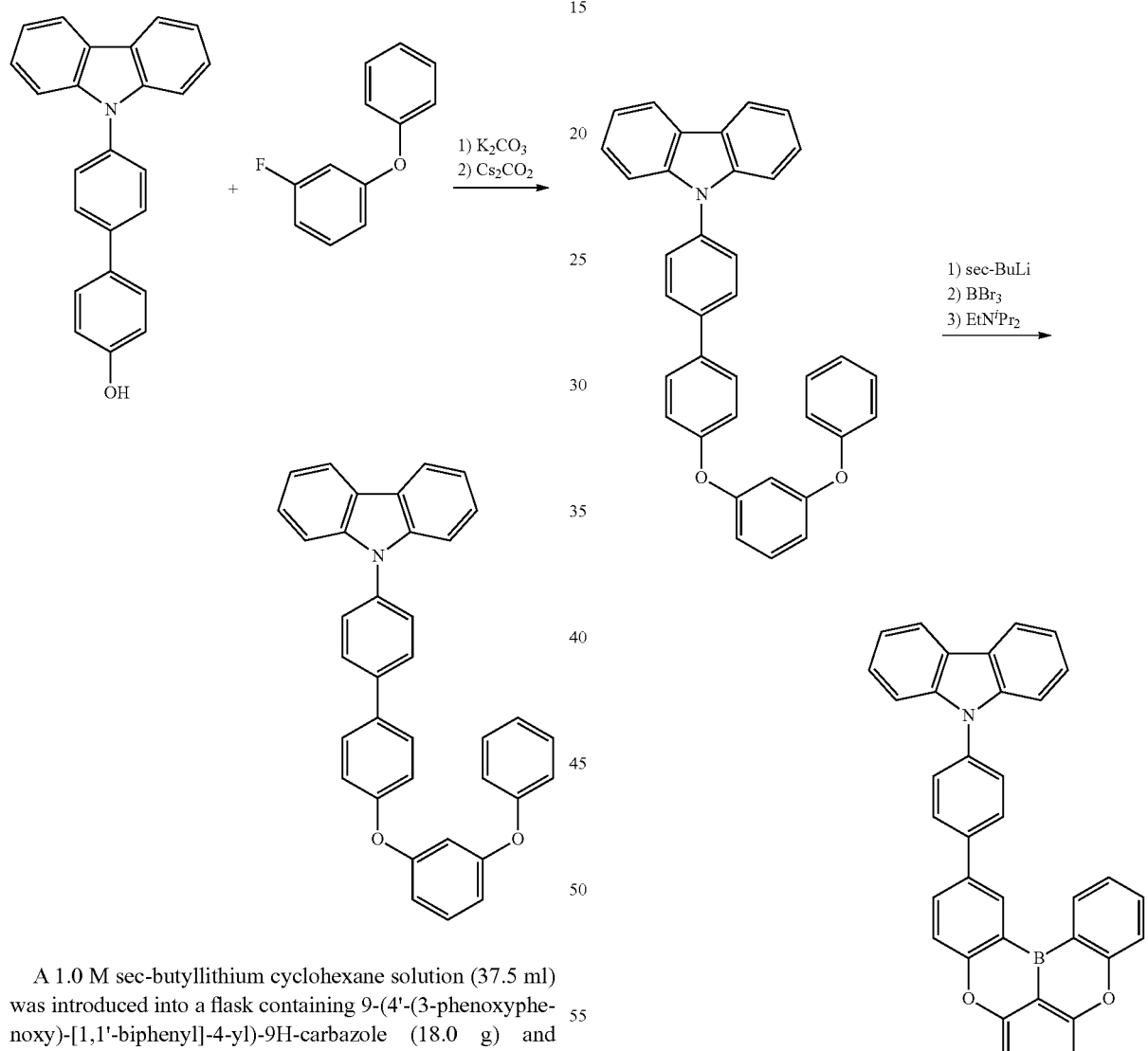

A 1.0 M sec-butyllithium cyclohexane solution (37.5 ml) was introduced into a flask containing 9-(4'-(3-phenoxyphenoxy)-[1,1'-biphenyl]-4-yl)-9H-carbazole (18.0 g) and xylene (130 ml), at 0° C. in a nitrogen atmosphere. After completion of dropwise addition, the temperature of the mixture was increased to 70° C., the mixture was stirred for 4 hours, and then components having boiling points lower than that of xylene were distilled off under reduced pressure. The mixture was cooled to −50° C., boron tribromide (4.0 ml) was added thereto, the temperature of the mixture was increased to room temperature, and the mixture was stirred for 0.5 hours. Thereafter, the mixture was cooled again to 0° C., N,N-diisopropylethylamine (13.4 ml) was added thereto, The structure of the compound thus obtained was identified by an NMR analysis.

$^1$H-NMR (400 MHz, CDCl$_3$): δ=8.98 (m, 1H), 8.80 (d, 1H), 8.18 (d, 2H), 8.04 (dd, 1H), 7.96 (d, 2H), 7.84 (t, 1H), 7.72-7.78 (m, 3H), 7.70 (d, 1H), 7.60 (d, 1H), 7.54 (d, 2H), 7.43-7.48 (m, 3H), 7.26-7.34 (m, 4H).

Synthesis Example (24)

Synthesis of 9-(4-(5,9-dioxa-13b-boranaphtho[3,2,1-de]anthracen-3-yl)phenyl)-9H-carbazole (1-1102)

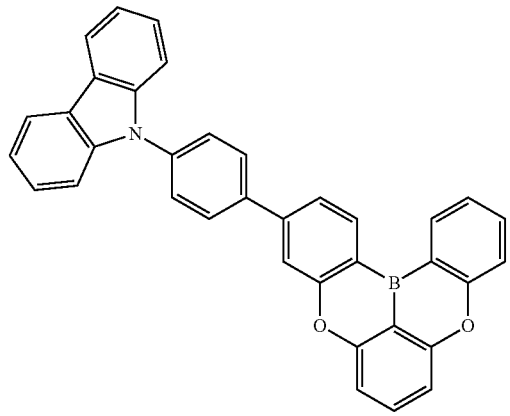

In a nitrogen atmosphere, a flask containing 1-bromo-3-fluorobenzene (50.0 g), phenol (30.0 g), potassium carbonate (80.0 g) and NMP (300 ml) was heated and stirred for 12 hours at 200° C. The reaction liquid was cooled to room temperature, NMP was distilled off under reduced pressure, subsequently water and ethyl acetate were added thereto, and the mixture was partitioned. The solvent of the organic layer was distilled off under reduced pressure, and then the residue was purified using a silica gel short pass column (developing liquid: toluene/heptane=2/8 (volume ratio)). Thus, 1-bromo-3-phenoxybenzene (58.2 g) was obtained.

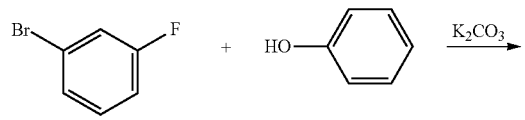

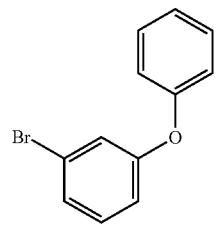

A flask containing 3-bromophenol (10.0 g), (4-(9H-carbazol-9-yl)phenyl)boronic acid (18.5 g), Pd-132 (Johnson Matthey) (0.2 g), tripotassium phosphate (25.0 g), toluene (200 ml), isopropanol (50 ml), and water (25 ml) was heated and stirred for one hour at the reflux temperature. The reaction liquid was cooled to room temperature, subsequently water and toluene were added thereto, and the mixture was partitioned. Subsequently, the reaction liquid was purified using a silica gel short pass column (developing liquid: heated chlorobenzene), and a solid obtained by distilling off the solvent under reduced pressure was washed with refluxed heptane. Thus, 4'-(9H-carbazol-9-yl)-[1,1'-biphenyl]-3-ol (18.5 g) was obtained.

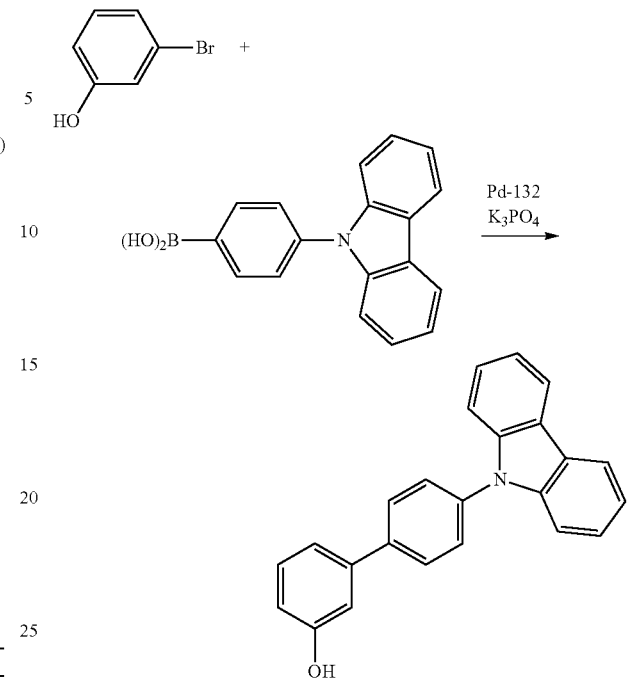

Copper(I) iodide (0.3 g) and iron(III) acetylacetonate (1.1 g) were added to an NMP (100 ml) solution of 1-bromo-3-phenoxybenzene (12.5 g), 4'-(9H-carbazol-9-yl)-[1,1'-biphenyl]-3-ol (18.5 g) and potassium carbonate (14.0 g) in a nitrogen atmosphere. The temperature of the mixture was increased to 160° C., and the mixture was stirred for 6 hours. The reaction liquid was cooled to room temperature, NMP was distilled off under reduced pressure, and then a solid precipitated by adding ethyl acetate and aqueous ammonia thereto was removed by suction filtration using a Hirsch filter covered with Celite. The filtrate was partitioned, the solvent of the organic layer was distilled off under reduced pressure, and then the residue was purified by silica gel column chromatography (developing liquid: toluene/heptane=3/7 (volume ratio)). Thus, 9-(3'-(3-phenoxyphenoxy)-[1,1'-biphenyl]-4-yl)-9H-carbazole (21.0 g) was obtained.

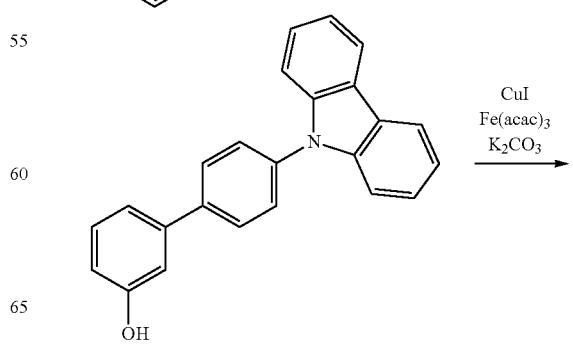

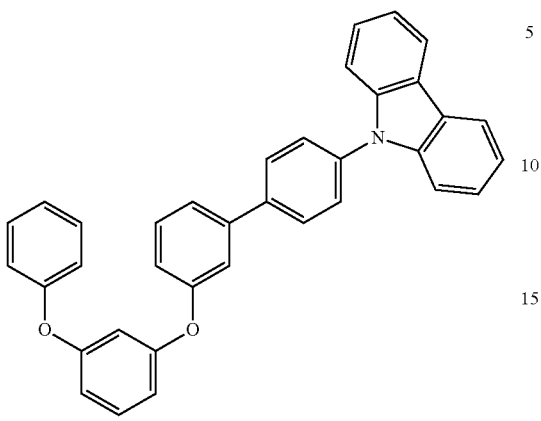

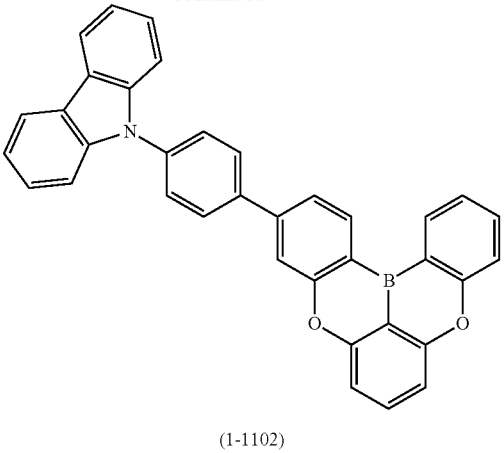

(1-1102)

A 1.0 M sec-butyllithium cyclohexane solution (43.8 ml) was introduced into a flask containing 9-(3'-(3-phenoxyphenoxy)-[1,1'-biphenyl]-4-yl)-9H-carbazole (21.0 g) and xylene (130 ml), at 0° C. in a nitrogen atmosphere. After completion of dropwise addition, the temperature of the mixture was increased to 70° C., the mixture was stirred for 3 hours, and then components having boiling points lower than that of xylene were distilled off under reduced pressure. The reaction liquid was cooled to −50°, boron tribromide (4.7 ml) was added thereto, the temperature of the mixture was increased to room temperature, and the mixture was stirred for 0.5 hours. Thereafter, the mixture was cooled again to 0° C., N,N-diisopropylethylamine (14.6 ml) was added thereto, and the mixture was stirred at room temperature until heat generation was settled. Subsequently, the temperature of the mixture was increased to 130° C., and the mixture was heated and stirred for 2 hours. The reaction liquid was cooled to room temperature, and a solid produced by adding an aqueous solution of sodium acetate that had been cooled in an ice bath and then adding heptane thereto was collected by suction filtration. The solid thus obtained was washed with refluxed ethyl acetate, and then was recrystallized from chlorobenzene. Thus, a compound (13.6 g) represented by formula (1-1102) was obtained.

The structure of the compound thus obtained was identified by an NMR analysis.

$^1$H-NMR (400 MHz, CDCl$_3$): δ=8.81 (d, 1H), 8.75 (d, 1H), 8.18 (d, 2H), 8.00 (d, 2H), 7.89 (m, 1H), 7.83 (t, 1H), 7.71-7.77 (m, 4H), 7.58 (d, 1H), 7.53 (d, 2H), 7.41-7.48 (m, 3H), 7.26-7.34 (m, 4H).

Synthesis Example (25)

Synthesis of 9-(4-(5,9-dioxa-13b-boranaphtho[3,2,1-de]anthracen-4-yl)phenyl)-9H-carbazole

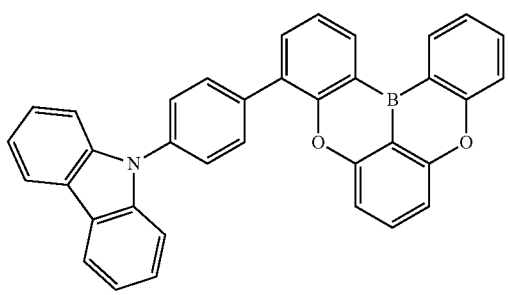

(1-1103)

A flask containing 2-bromophenol (10.0 g), (4-(9H-carbazol-9-yl)phenyl)boronic acid (18.2 g), Pd-132 (Johnson Matthey) (0.2 g), tripotassium phosphate (25.0 g), toluene (200 ml), isopropanol (50 ml), and water (25 ml) was heated and stirred for one hour at the reflux temperature. The reaction liquid was cooled to room temperature, subsequently water and toluene were added thereto, and the mixture was partitioned. Subsequently, the reaction liquid was purified using a silica gel short pass column (developing liquid: heated toluene), and then a solid obtained by distilling off the solvent under reduced pressure was washed with refluxed heptane. Thus, 4'-(9H-carbazol-9-yl)-[1,1'-biphenyl]-2-ol (18.7 g) was obtained.

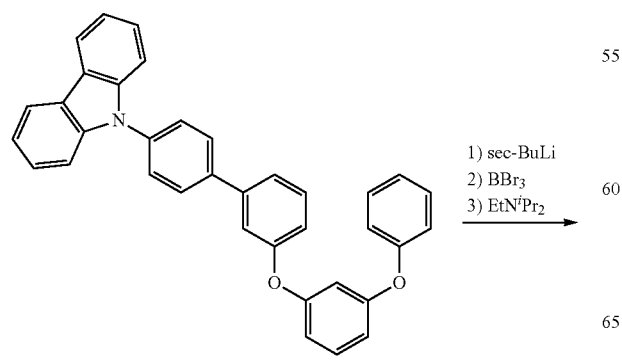

1) sec-BuLi
2) BBr$_3$
3) EtN$^i$Pr$_2$

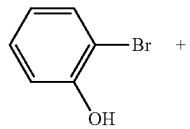

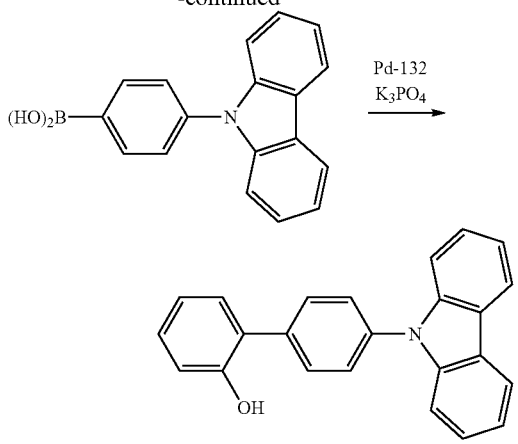

Copper(I) iodide (0.5 g) and iron(III) acetylacetonate (1.8 g) were added to an NMP (100 ml) solution of 1-bromo-3-phenoxybenzene (12.6 g), 4'-(9H-carbazol-9-yl)-[1,1'-biphenyl]-2-ol (18.7 g) and potassium carbonate (14.0 g) in a nitrogen atmosphere. The temperature of the mixture was increased to 150° C., and the mixture was stirred for 6 hours. The reaction liquid was cooled to room temperature, NMP was distilled off under reduced pressure, and then a solid precipitated by adding ethyl acetate and aqueous ammonia thereto was removed by suction filtration using a Hirsch funnel covered with Celite. The filtrate was partitioned, and the solvent of the organic layer was distilled off under reduced pressure. Subsequently, the residue was purified by silica gel column chromatography (developing liquid: toluene/heptane=3/7 (volume ratio)), and thus 9-(2'-(3-phenoxyphenoxy)-[1,1'-biphenyl]-4-yl)-9H-carbazole (20.0 g) was obtained.

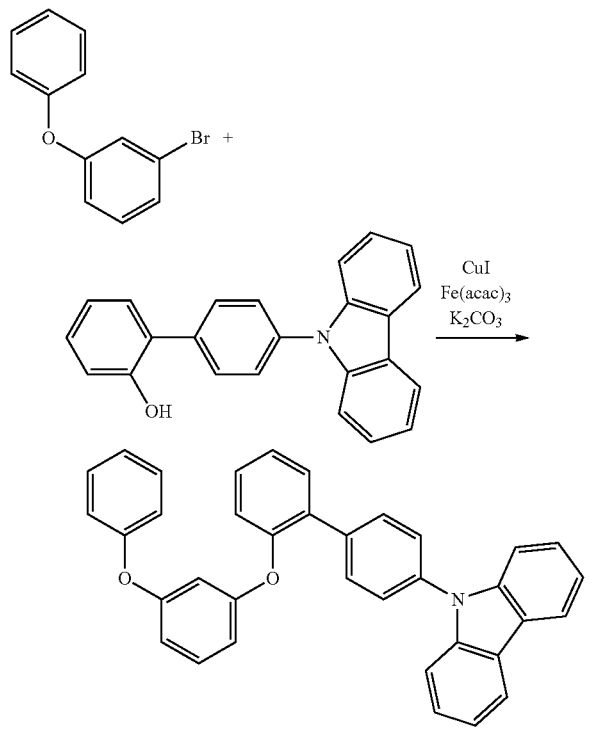

A 1.0 M sec-butyllithium cyclohexane solution (41.7 ml) was introduced into a flask containing 9-(2'-(3-phenoxyphenoxy)-[1,1'-biphenyl]-4-yl)-9H-carbazole (20.0 g) and xylene (130 ml), at 0° C. in a nitrogen atmosphere. After completion of dropwise addition, the temperature of the mixture was increased to 70° C., the mixture was stirred for 3 hours, and then components having boiling points lower than that of xylene were distilled off under reduced pressure. The mixture was cooled to −50° C., boron tribromide (4.5 ml) was added thereto, the temperature of the mixture was increased to room temperature, and the mixture was stirred for 0.5 hours. Thereafter, the mixture was cooled again to 0° C., N,N-diisopropylethylamine (13.9 ml) was added thereto, and the mixture was stirred at room temperature until heat generation was settled. Subsequently, the temperature of the mixture was increased to 130° C., and the mixture was heated and stirred for 3 hours. The reaction liquid was cooled to room temperature, and a solid produced by adding an aqueous solution of sodium acetate that had been cooled in an ice bath and then adding heptane was collected by suction filtration. The solid obtained was washed with refluxed ethyl acetate, and then was dissolved in chlorobenzene. Reprecipitation was carried out by adding heptane to the solution, and thus a compound (8.5 g) represented by formula (1-1103) was obtained.

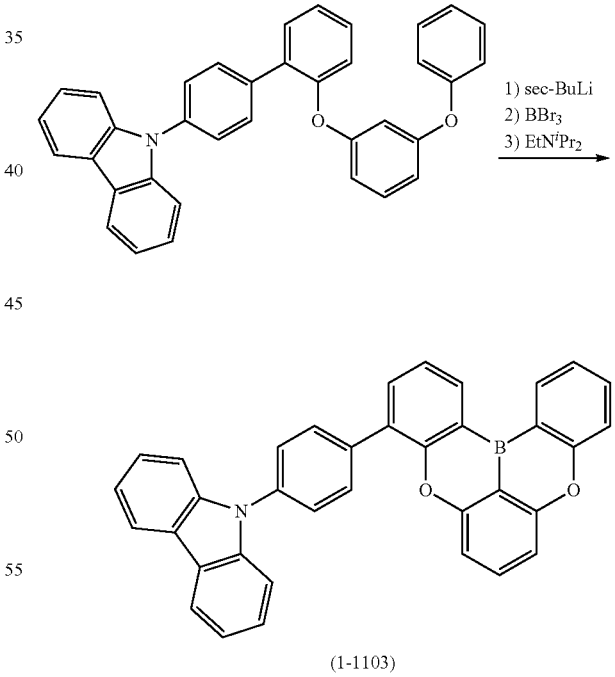

(1-1103)

The structure of the compound thus obtained was identified by an NMR analysis.

$^1$H-NMR (400 MHz, CDCl$_3$): δ=8.77 (t, 2H), 8.19 (d, 2H), 7.96 (d, 2H), 7.86 (d, 1H), 7.80 (t, 1H), 7.72-7.77 (m, 3H), 7.59 (d, 3H), 7.54 (t, 1H), 7.47 (t, 2H), 7.44 (t, 1H), 7.33 (t, 2H), 7.26 (m, 1H), 7.19 (d, 1H).

Synthesis Example (26)

Synthesis of 9-(4-(5,9-dioxa-13b-boranaphtho[3,2,1-de]anthracen-8-yl)phenyl)-9H-carbazole (1-1092)

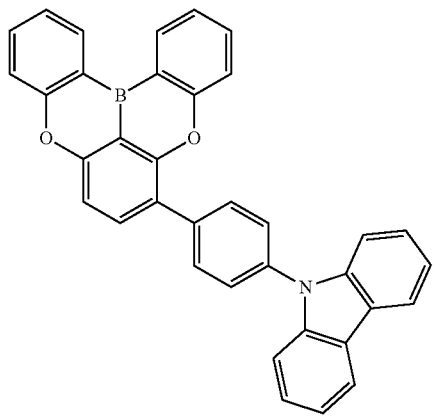

In a nitrogen atmosphere, a flask containing 1-bromo-2,4-difluorobenzene (46.6 g), phenol (50.0 g), potassium carbonate (133.0 g) and NMP (300 ml) was heated and stirred for 8 hours at 200° C. The reaction liquid was cooled to room temperature, NMP was distilled off under reduced pressure, subsequently water and ethyl acetate were added thereto, and the mixture was partitioned. The solvent of the organic layer was distilled off under reduced pressure, and then the residue was purified by silica gel column chromatography (developing liquid: toluene/heptane=2/8 (volume ratio)). Thus, ((4-bromo-1,3-phenylene)bis(oxy))dibenzene (58.2 g) was obtained.

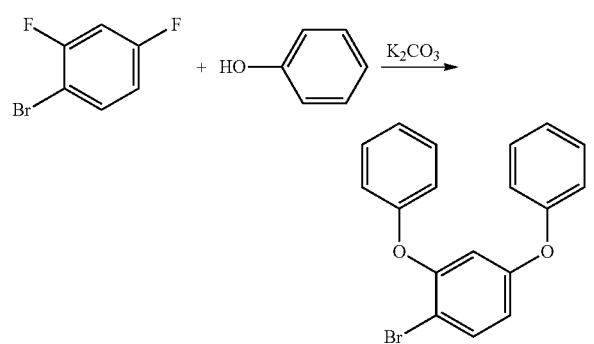

A flask containing ((4-bromo-1,3-phenylene)bis(oxy))dibenzene (15.0 g), (4-(9H-carbazol-9-yl)phenyl)boronic acid (13.9 g), Pd-132 (Johnson Matthey) (0.2 g), tripotassium phosphate (19.0 g), toluene (200 ml), isopropanol (50 ml) and water (25 ml) was heated and stirred for 2 hours at the reflux temperature. The reaction liquid was cooled to room temperature, subsequently water and toluene were added thereto, and the mixture was partitioned. Subsequently, the resultant was purified by silica gel column chromatography (developing liquid: toluene/heptane mixed solvent), and thus 9-(2',4'-diphenoxy[1,1'-biphenyl]-4-yl)-9H-carbazole (20.0 g) was obtained. At this time, the proportion of toluene in the developing liquid was gradually increased by making reference to the method described in "Introduction to Organic Chemical Experiments (1)—Handling of Materials and Separation/Purification", published by Kagaku-Dojin Publishing Co., Inc., p. 94, and thereby the target substance was eluted.

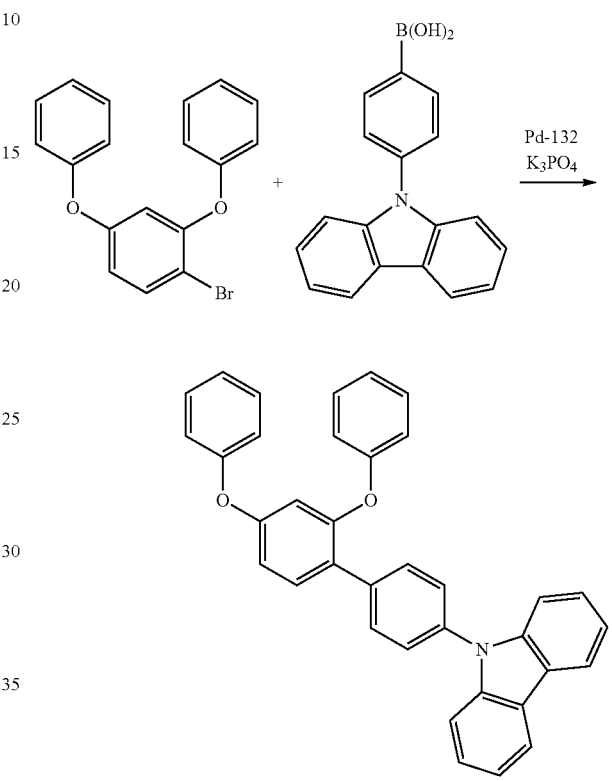

A 1.0 M sec-butyllithium cyclohexane solution (41.7 ml) was introduced into a flask containing 9-(2',4'-diphenoxy[1,1'-biphenyl]-4-yl)-9H-carbazole (20.0 g) and xylene (130 ml), at 0° C. in a nitrogen atmosphere. After completion of dropwise addition, the temperature of the mixture was increased to 70° C., the mixture was stirred for 3 hours, and then components having boiling points lower than that of xylene were distilled off under reduced pressure. The mixture was cooled to −50° C., boron tribromide (4.5 ml) was added thereto, the temperature of the mixture was increased to room temperature, and the mixture was stirred for 0.5 hours. Thereafter, the mixture was cooled again to 0° C., N,N-diisopropylethylamine (13.9 ml) was added thereto, and the mixture was stirred at room temperature until heat generation was settled. Subsequently, the temperature of the mixture was increased to 130° C., and the mixture was heated and stirred for 3 hours. The reaction liquid was cooled to room temperature, and a solid produced by adding an aqueous solution of sodium acetate that had been cooled in an ice bath and then adding heptane thereto was collected by suction filtration. The solid thus obtained was washed with refluxed ethyl acetate, and then was recrystallized from chlorobenzene. Thus, a compound (12.9 g) represented by formula (1-1092) was obtained.

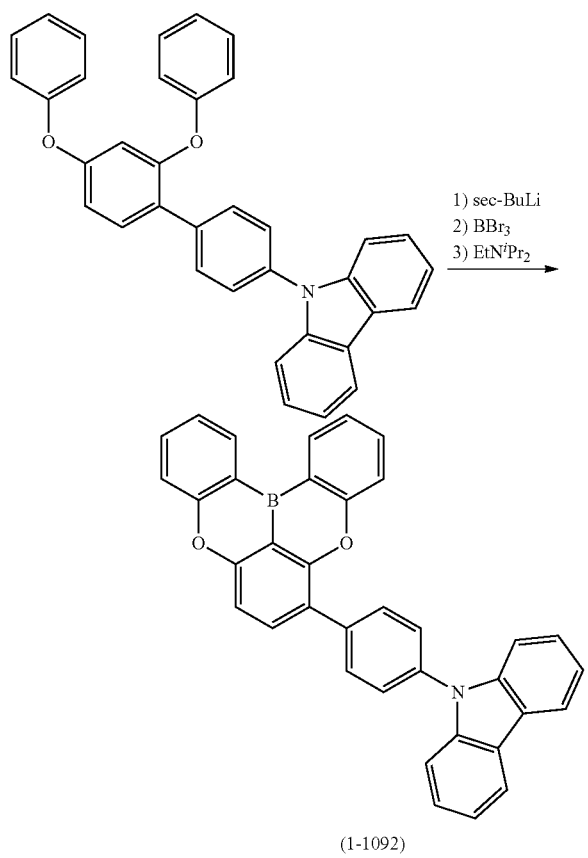

(1-1092)

The structure of the compound thus obtained was identified by an NMR analysis.

$^1$H-NMR (400 MHz, CDCl$_3$): δ=8.75 (d, 2H), 8.19 (d, 2H), 8.02 (m, 3H), 7.70-7.78 (m, 4H), 7.54-7.62 (m, 4H), 7.38-7.50 (m, 5H), 7.32 (t, 2H).

Synthesis Example (27)

Synthesis of 9-(5,9-dioxa-13b-boranaphtho[3,2,1-de]anthracen-7-yl)-9'-phenyl-9H,9'H-3,3'-bicarbazole (1-1069)

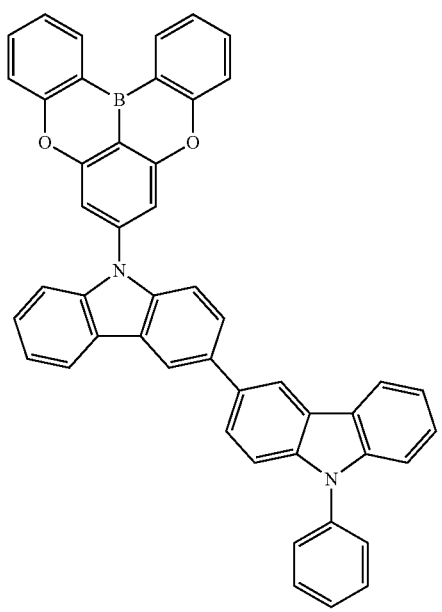

A flask containing (9-phenyl-9H-carbazol-3-yl)boronic acid (50.0 g), 3-bromo-9H-carbazole (39.0 g), Pd-132 (Johnson Matthey) (1.2 g), sodium carbonate (46.1 g), toluene (400 ml), ethanol (100 ml) and water (100 ml) was heated and stirred for 2 hours at the reflux temperature. The reaction liquid was cooled to room temperature, subsequently water and toluene were added thereto, and the mixture was partitioned. Subsequently, the resultant was purified by amino group-modified silica gel (NH DM1020: manufactured by Fuji Silysia Chemical, Ltd.) column chromatography (developing liquid: toluene). Thus, 9-phenyl-9H,9'H-3,3'-bicarbazole (52.0 g) was obtained.

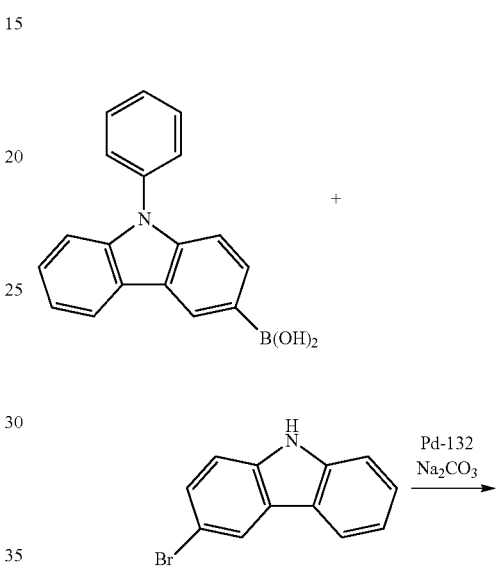

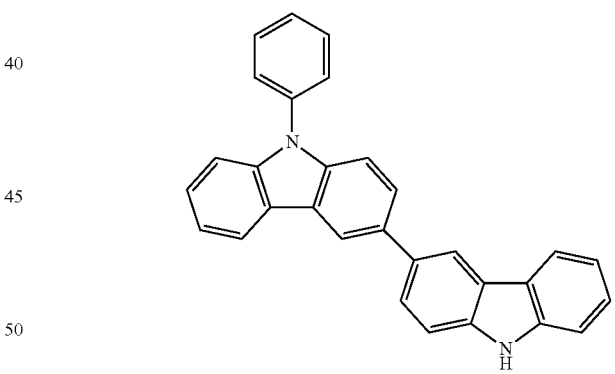

A flask containing ((5-bromo-1,3-phenylene)bis(oxy))dibenzene (29.2 g), 9-phenyl-9H,9'H-3,3'-bicarbazole (35.0 g), Pd(dba)$_2$ (0.5 g), dicyclohexyl(1-methyl-2,2-diphenylcyclopropyl)phosphine (Cy-cBRIDP) (0.9 g), NaOtBu (24.7 g), and xylene (300 ml) was heated to 150° C., and the mixture was stirred for 17 hours. The reaction liquid was cooled to room temperature, water was added thereto, and the mixture was partitioned. Subsequently, the solvent was distilled off under reduced pressure. Subsequently, the residue was purified by silica gel column chromatography (developing liquid: toluene/heptane=1/4 (volume ratio)), and thus 9-(3,5-diphenoxyphenyl)-9'-phenyl-9H, 9'H-3,3'-bicarbazole (46.5 g) was obtained.

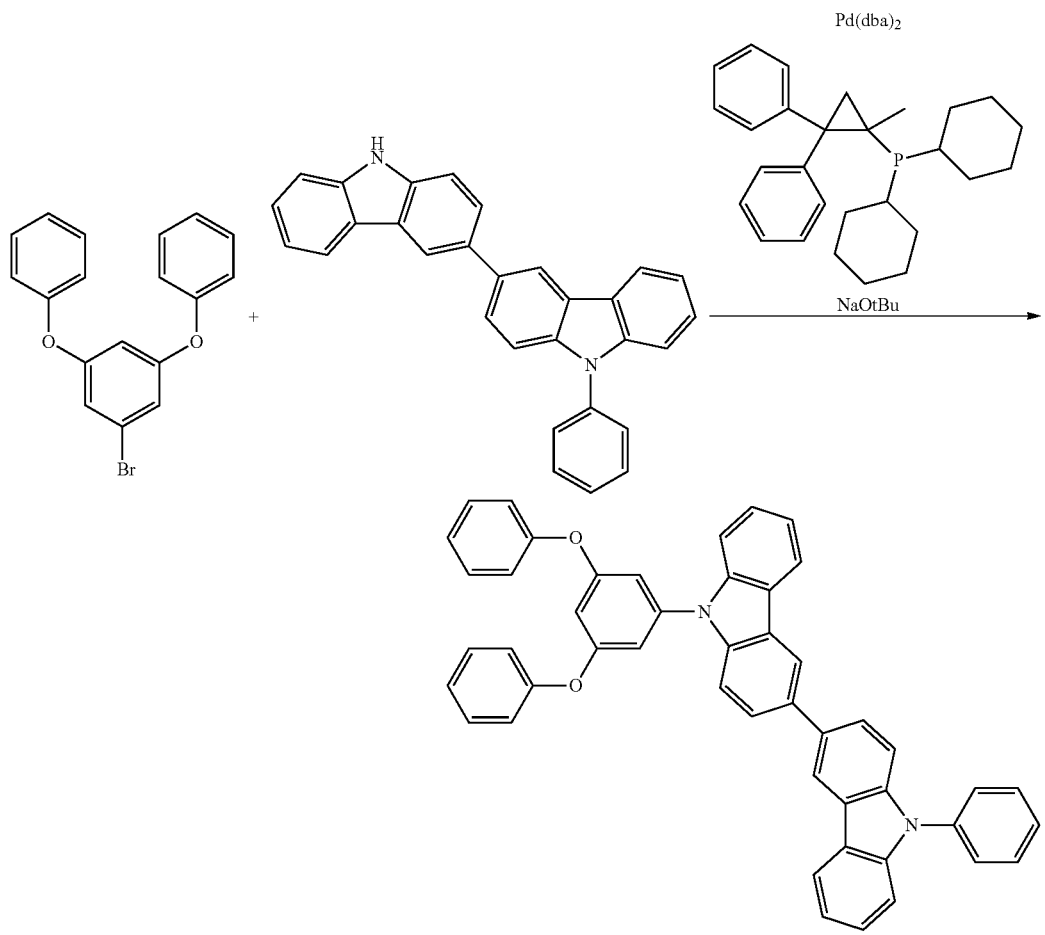

A 1.0 M sec-butyllithium cyclohexane solution (28.5 ml) was introduced into a flask containing 9-(3,5-diphenoxyphenyl)-9'-phenyl-9H,9'H-3,3'-bicarbazole (20.0 g) and xylene (100 ml), at 0° C. in a nitrogen atmosphere. After completion of dropwise addition, the temperature of the mixture was increased to 70° C., the mixture was stirred for 3 hours, and then components having boiling points lower than that of xylene were distilled off under reduced pressure. The mixture was cooled to −50° C., boron tribromide (3.4 ml) was added thereto, the temperature of the mixture was increased to room temperature, and the mixture was stirred for 0.5 hours. Thereafter, the mixture was cooled again to 0° C., N,N-diisopropylethylamine (10.4 ml) was added thereto, and the mixture was stirred at room temperature until heat generation was settled. Subsequently, the temperature of the mixture was increased to 130° C., and the mixture was heated and stirred for 4 hours. The reaction liquid was cooled to room temperature, an aqueous solution of sodium acetate that had been cooled in an ice bath and then toluene were added thereto, and the mixture was partitioned. The resultant was purified by silica gel column chromatography (developing liquid: toluene/heptane=1/1 (volume ratio)), and then a solid obtained by distilling off the solvent under reduced pressure was dissolved in toluene. The solid was reprecipitated by adding heptane to the solution, and thus a compound (1.0 g) represented by formula (1-1069) was obtained.

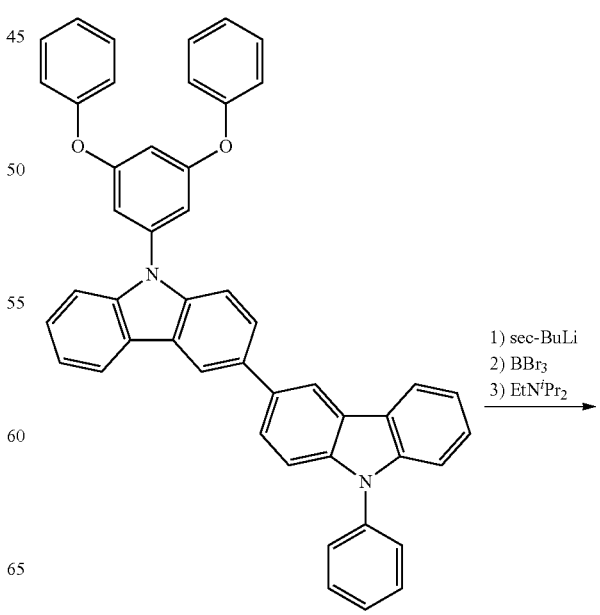

-continued

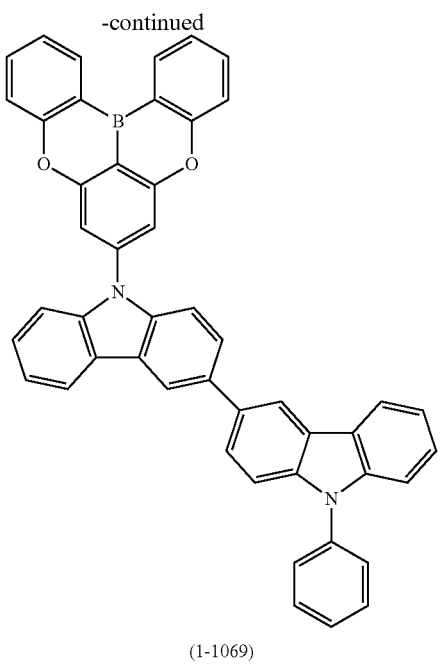

(1-1069)

The structure of the compound thus obtained was identified by an NMR analysis.

$^1$H-NMR (400 MHz, CDCl$_3$): δ=8.76 (dd, 2H), 8.48 (s, 2H), 8.26 (t, 2H), 7.73-7.86 (m, 6H), 7.58-7.67 (m, 6H), 7.41-7.57 (m, 9H), 7.38 (t, 1H), 7.33 (m, 1H).

Synthesis Example (28)

Synthesis of 8-(naphthalen-1-yl)-5,9-dioxa-13b-boranaphtho[3,2,1-de]anthracene (1-1084)

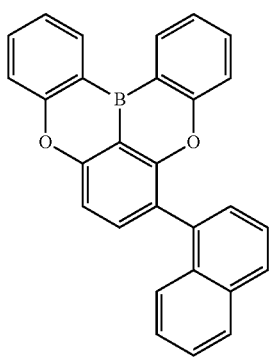

A flask containing ((4-bromo-1,3-phenylene)bis(oxy)) dibenzene (25.0 g), 1-naphthaleneboronic acid (13.9 g), Pd-132 (Johnson Matthey) (0.1 g), potassium carbonate (20.2 g), tetrabutylammonium bromide (TBAB) (0.7 g), SOLMIX A-11 (200 ml) and water (50 ml) was heated and stirred for 2 hours at the reflux temperature. The reaction liquid was cooled to room temperature, subsequently water and toluene were added thereto, and the mixture was partitioned. Subsequently, the resultant was purified by silica gel column chromatography (developing liquid: toluene/heptane mixed solvent). At this time, the proportion of toluene in the developing liquid was gradually increased, and thereby the target substance was eluted. The target substance was further recrystallized from a SOLMIX A-11/toluene mixed solvent, and thus 1-(2,4-diphenoxyphenyl)naphthalene (22.9 g) was obtained.

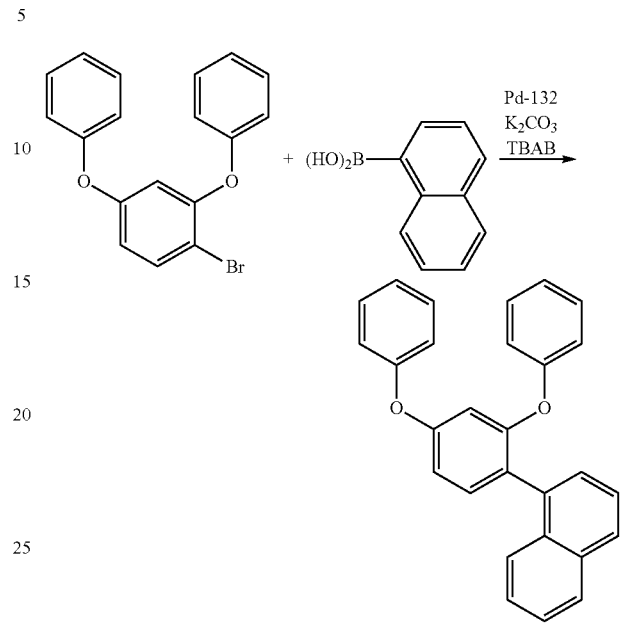

A 1.6 M n-butyllithium hexane solution (22.6 ml) was introduced into a flask containing 1-(2,4-diphenoxyphenyl) naphthalene (13.0 g) and xylene (100 ml), at 0° C. in a nitrogen atmosphere. After completion of dropwise addition, the temperature of the mixture was increased to 80° C., the mixture was stirred for 4 hours, and then components having boiling points lower than that of xylene were distilled off under reduced pressure. The mixture was cooled to −50° C., boron tribromide (3.8 ml) was added thereto, the temperature of the mixture was increased to room temperature, and the mixture was stirred for 0.5 hours. Thereafter, the mixture was cooled again to 0° C., N,N-diisopropylethylamine (11.7 ml) was added thereto, and the mixture was stirred at room temperature until heat generation was settled. Subsequently, the temperature of the mixture was increased to 120° C., and the mixture was heated and stirred for 4 hours. The reaction liquid was cooled to room temperature, an aqueous solution of sodium acetate that had been cooled in an ice bath and then toluene were added thereto, and the mixture was partitioned. Subsequently, recrystallization from toluene/heptane was carried out, and then a compound (4.0 g) represented by formula (1-1084) was obtained.

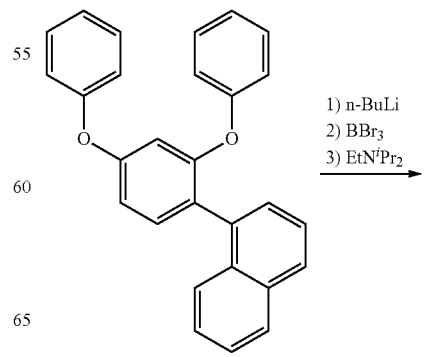

-continued

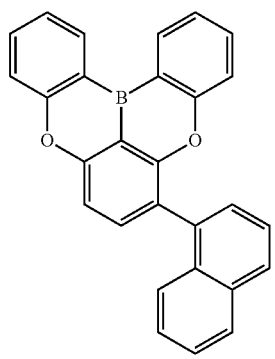

(1-1084)

The structure of the compound thus obtained was identified by an NMR analysis.

$^{1}$H-NMR (400 MHz, CDCl$_3$): δ=8.87 (m, 2H), 7.98 (d, 2H), 7.85 (d, 1H), 7.75 (t, 1H), 7.67 (d, 1H), 7.62 (m, 3H), 7.51 (m, 2H), 7.30-7.43 (m, 4H), 7.02 (d, 1H).

Synthesis Example (29)

Synthesis of 8-(pyren-1-yl)-5,9-dioxa-13b-boranaphtho[3,2,1-de]anthracene

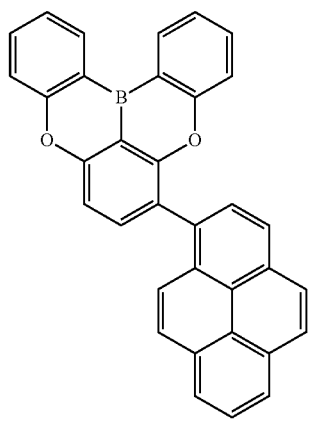

(1-1090)

A flask containing ((4-bromo-1,3-phenylene)bis(oxy)) dibenzene (12.0 g), 1-pyreneboronic acid (9.5 g), Pd-132 (Johnson Matthey) (0.03 g), potassium carbonate (9.7 g), TBAB (3.4 g), SOLMIX A-11 (60 ml) and water (24 ml) was heated and stirred for one hour at the reflux temperature. The reaction liquid was cooled to room temperature, subsequently water and toluene were added thereto, and the mixture was partitioned. Subsequently, the reaction liquid was purified using a silica gel short pass column (developing liquid: toluene), and was recrystallized from a SOLMIX A-11/ethyl acetate mixed solvent. Thus, 1-(2,4-diphenoxyphenyl)pyrene (13.3 g) was obtained.

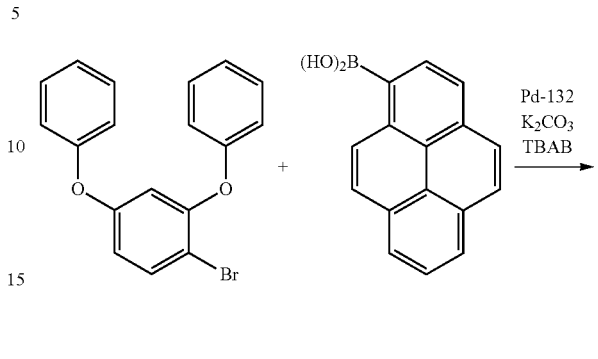

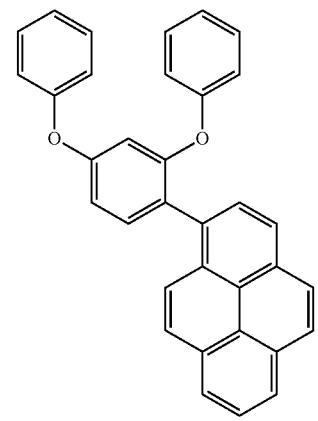

A 1.6 M n-butyllithium hexane solution (18.2 ml) was introduced into a flask containing 1-(2,4-diphenoxyphenyl)pyrene (12.5 g) and xylene (100 ml), at 0° C. in a nitrogen atmosphere. After completion of dropwise addition, the temperature of the mixture was increased to 80° C., the mixture was stirred for 4 hours, and then components having boiling points lower than that of xylene were distilled off under reduced pressure. The mixture was cooled to −50° C., boron tribromide (3.1 ml) was added thereto, the temperature of the mixture was increased to room temperature, and the mixture was stirred for 0.5 hours. Thereafter, the mixture was cooled again to 0° C., N,N-diisopropylethylamine (9.4 ml) was added thereto, and the mixture was stirred at room temperature until heat generation was settled. Subsequently, the temperature of the mixture was increased to 120°, and the mixture was heated and stirred for 4 hours. The reaction liquid was cooled to room temperature, and a solid precipitated by adding an aqueous solution of sodium acetate that had been cooled in an ice bath and then adding heptane was collected by suction filtration. The solid was washed with water and SOLMIX A-11 in this order, and then was recrystallized from xylene. The resultant was further recrystallized from chlorobenzene, and thus a compound (3.3 g) represented by formula (1-1090) was obtained.

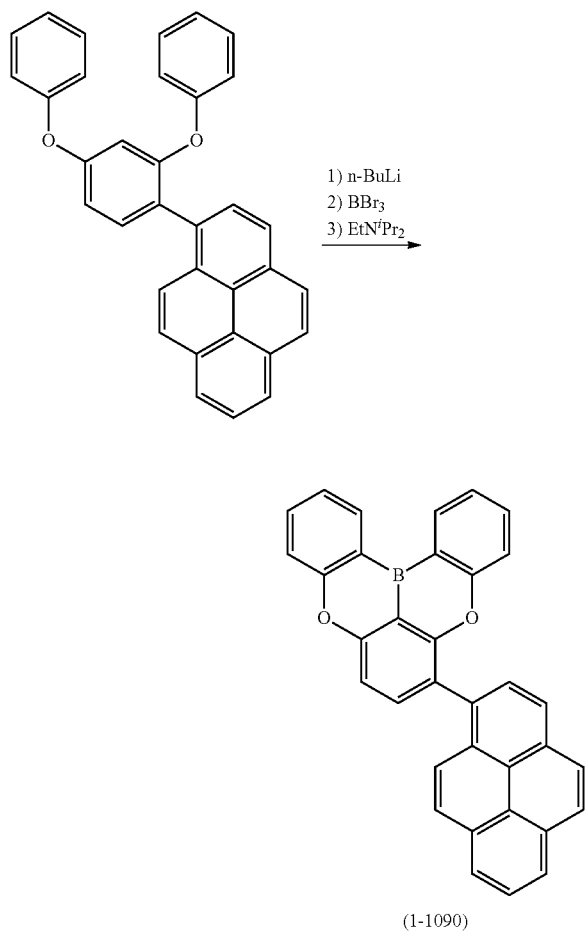

(1-1090)

The structure of the compound thus obtained was identified by an NMR analysis.

$^1$H-NMR (400 MHz, CDCl$_3$): δ=8.76 (d, 1H), 8.71 (d, 1H), 8.32 (d, 1H), 8.23 (d, 1H), 8.18 (m, 4H), 7.95-8.05 (m, 4H), 7.79 (t, 1H), 7.64 (d, 1H), 7.45 (m, 3H), 7.35 (t, 1H), 6.97 (d, 1H).

Synthesis Example (30)

Synthesis of 3,6,8,11-tetraphenyl-5,9-dioxa-13b-thiophosphanaphtho[3,2,1-de]anthracene In a nitrogen atmosphere, a flask containing 4',6'-bis([1,1'-biphenyl]-2-yloxy)-5'-bromo-1,1':3',1"-terphenyl (17.0 g) and xylene (150 ml) was cooled to −40° C., and a 1.0 M sec-butyllithium cyclohexane solution (27.1 ml) was added dropwise thereto. After completion of the dropwise addition, the temperature of the mixture was increased to about 80° C., and components having boiling points lower than that of xylene were distilled under reduced pressure. Subsequently, the mixture was cooled to −10° C., and phosphorus trichloride (3.5 ml) was added thereto. The temperature of the mixture was increased to 80° C., the mixture was stirred for one hour, subsequently sulfur (12.2 g) was added thereto, and the mixture was heated and stirred for another one hour. Subsequently, the mixture was first cooled to −10° C., and aluminum chloride (24.6 g) and N,N-diisopropylethylamine (11.0 ml) were added thereto. The temperature of the mixture was increased to 120° C., and then the mixture was heated and stirred for 12 hours. The reaction liquid was cooled to room temperature, the reaction liquid was added to a toluene solution of 1,4-diazabicyclo[2.2.2]octane, and the mixture was stirred. Water, toluene and ethyl acetate were added thereto, the mixture was partitioned, and the solvent was distilled off under reduced pressure. Subsequently, the product thus obtained was dissolved in toluene, and a solid precipitated by adding heptane thereto was separated by filtration. The filtrate was purified by silica gel column chromatography (developing liquid: toluene/heptane mixed solvent). At this time, the proportion of toluene in the developing liquid was gradually increased, and the intended substance was eluted. The resultant was further washed with ethyl acetate, and thus a compound (4.7 g) represented by formula (1-1252) was obtained.

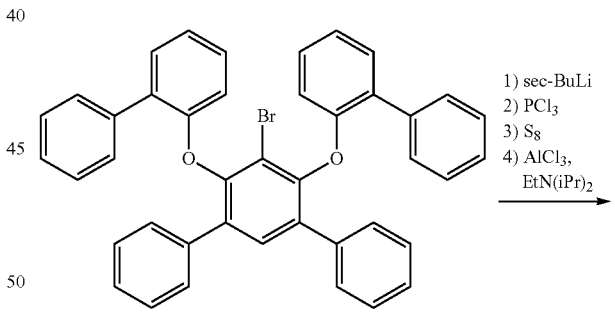

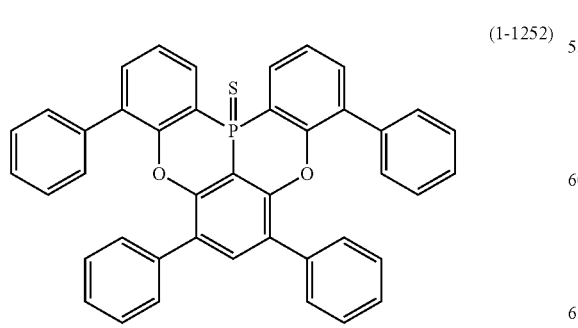

(1-1252)

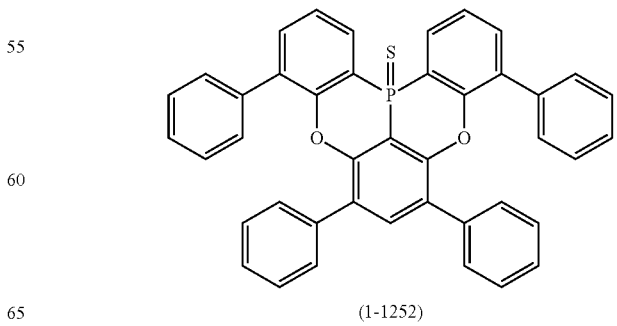

(1-1252)

Synthesis Example (31)

Synthesis of 3,6,8,11-tetraphenyl-5,9-dioxa-13b-oxophosphanaphtho[3,2,1-de]anthracene

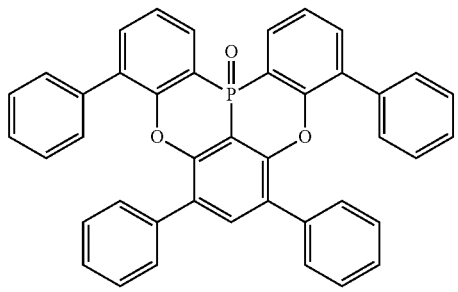
(1-1192)

m-CPBA (1.9 g) was added to a dichloromethane (150 mL) solution of the compound (4.7 g) represented by the above formula (1-1252) at 0° C., subsequently the temperature of the mixture was increased to room temperature, and the mixture was stirred for 5 hours. A saturated aqueous solution of sodium sulfite was added thereto, the mixture was stirred at room temperature, subsequently insoluble materials were separated by filtration, and the filtrate was further partitioned. The solvent was distilled off under reduced pressure, and the residue was purified by silica gel column chromatography (developing liquid: toluene/ethyl acetate mixed solvent). At this time, the proportion of ethyl acetate in the developing liquid was gradually increased, and the intended substance was eluted. The solvent was distilled off under reduced pressure, a solid thus obtained was dissolved in toluene, and the solid was reprecipitated by adding heptane thereto. Thus, a compound (1.1 g) represented by formula (1-1192) was obtained.

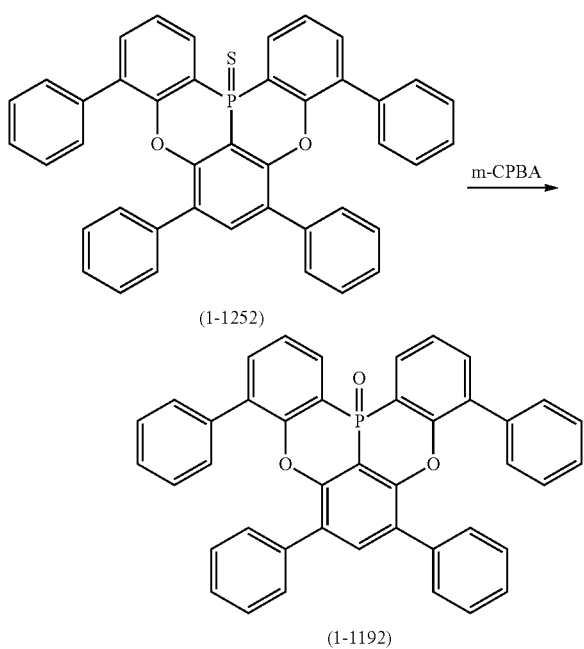 [SMILES: Brc1c(Oc2ccccc2-c2ccccc2)c(-c2ccccc2)cc(-c2ccccc2)c1Oc1ccccc1-c1ccccc1 ; S=P12c3cccc(-c4ccccc4)c3Oc3c(-c4ccccc4)cc(-c4ccccc4)c(c31)Oc1c(-c3ccccc3)cccc12]

The structure of the compound thus obtained was identified by an NMR analysis.

$^{1}$H-NMR (400 MHz, CDCl$_3$): δ=8.29 (m, 2H), 7.56 (d, 2H), 7.53 (s, 1H), 7.47 (t, 2H), 7.16-7.23 (m, 12H), 7.07-7.10 (m, 8H).

Synthesis Example (32)

Synthesis of 5,9-diphenyl-5,9-diaza-13b-boranaphtho[3,2,1-de]anthracene (1-401)

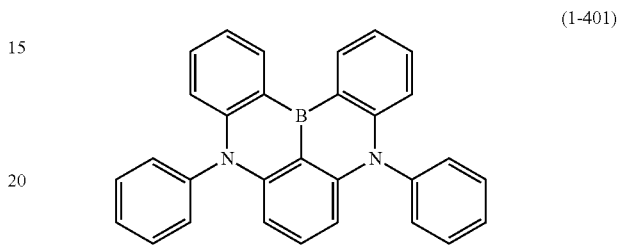

In a nitrogen atmosphere, a flask containing diphenylamine (66.0 g), 1-bromo-2,3-dichlorobenzene (40.0 g), Pd-132 (Johnson Matthey) (1.3 g), NaOtBu (43.0 g) and xylene (400 ml) was heated and stirred for 2 hours at 80° C. Subsequently, the temperature of the mixture was increased to 120° C., and the mixture was heated and stirred for 3 hours. The reaction liquid was cooled to room temperature, and then a solid precipitated by adding water and ethyl acetate was collected by suction filtration. Subsequently, the solid was purified using a silica gel short pass column (developing liquid: heated toluene). The solvent was distilled off under reduced pressure, and a solid thus obtained was washed with heptane. Thus, 2-chloro-N$^1$,N$^1$,N$^3$,N$^3$-tetraphenylbenzene-1,3-diamine (65.0 g) was obtained.

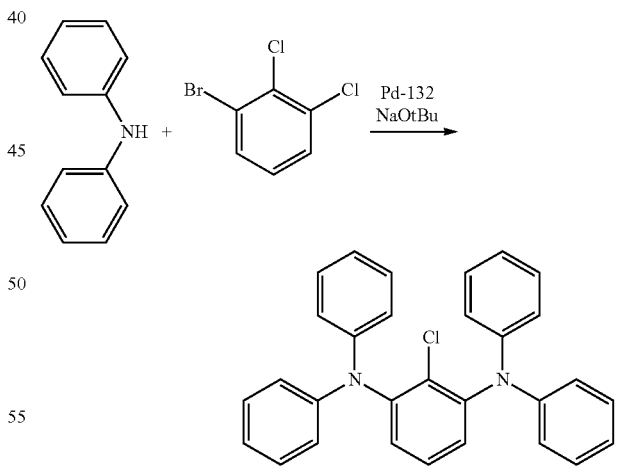

A 1.7 M tert-butyllithium pentane solution (27.6 ml) was introduced into a flask containing 2-chloro-N$^1$,N$^1$,N$^3$,N$^3$-tetraphenylbenzene-1,3-diamine (20.0 g) and tert-butylbenzene (150 ml), at −30° C. in a nitrogen atmosphere. After completion of dropwise addition, the temperature of the mixture was increased to 60° C., the mixture was stirred for 2 hours, and then components having boiling points lower than that of tert-butylbenzene were distilled off under reduced pressure. The mixture was cooled to −30° C., boron tribromide (5.1 ml) was added thereto, the temperature of the mixture was increased to room temperature, and the mixture was stirred for 0.5 hours. Thereafter, the mixture was cooled again to 0° C., N,N-diisopropylethylamine (15.6 ml) was added thereto, and the mixture was stirred at room temperature until heat generation was settled. Subsequently, the temperature of the mixture was increased to 120° C., and the mixture was heated and stirred for 3 hours. The reaction liquid was cooled to room temperature, an aqueous solution of sodium acetate that had been cooled in an ice bath and then heptane were added thereto, and the mixture was partitioned. Subsequently, the reaction liquid was purified using a silica gel short pass column (additive liquid: toluene), and then a solid obtained by distilling off the solvent under reduced pressure was dissolved in toluene and reprecipitated by adding heptane thereto. Thus, a compound (6.0 g) represented by formula (1-401) was obtained.

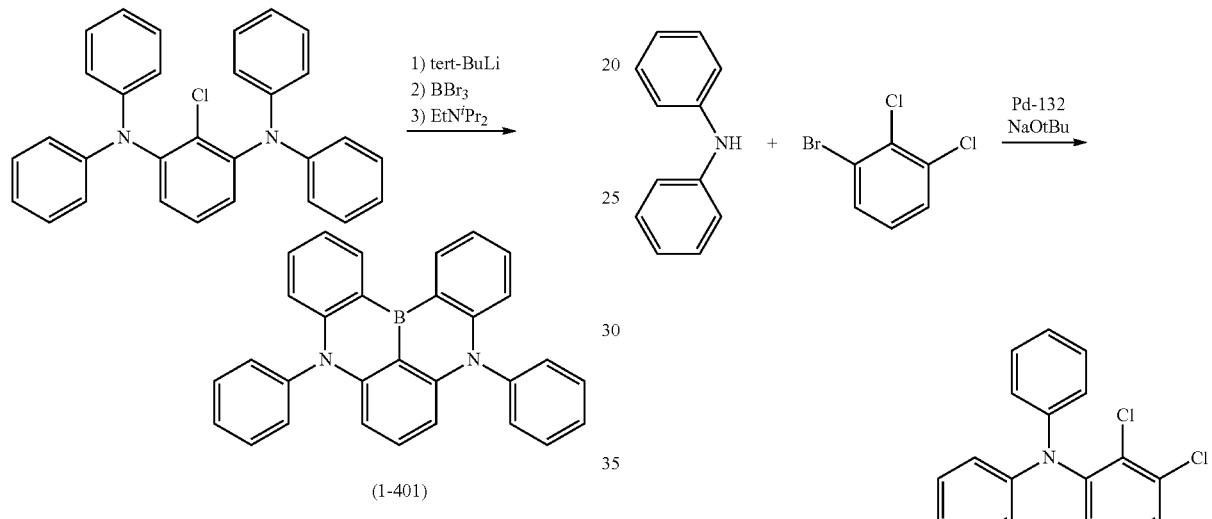

(1-401)

The structure of the compound thus obtained was identified by an NMR analysis.

$^1$H-NMR (400 MHz, CDCl$_3$): δ=8.94 (d, 2H), 7.70 (t, 4H), 7.60 (t, 2H), 7.42 (t, 2H), 7.38 (d, 4H), 7.26 (m, 3H), 6.76 (d, 2H), 6.14 (d, 2H).

Synthesis Example (33)

Synthesis of 9-([1,1'-biphenyl]-4-yl)-5,12-diphenyl-5,9-diaza-13b-boranaphtho[3,2,1-de]anthracene (1-1152)

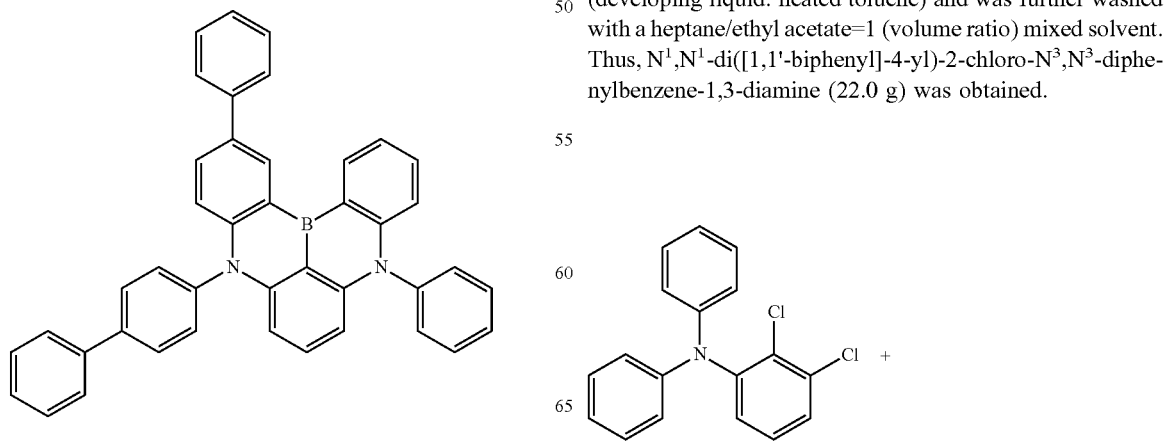

In a nitrogen atmosphere, a flask containing diphenylamine (37.5 g), 1-bromo-2,3-dichlorobenzene (50.0 g), Pd-132 (Johnson Matthey) (0.8 g), NaOtBu (32.0 g) and xylene (500 ml) was heated and stirred for 4 hours at 80° C., subsequently the temperature of the mixture was increased to 120° C., and the mixture was heated and stirred for 3 hours. The reaction liquid was cooled to room temperature, water and ethyl acetate were added thereto, and the mixture was partitioned. Subsequently, the resultant was purified by silica gel column chromatography (developing liquid: toluene/heptane=1/20 (volume ratio)), and thus 2,3-dichloro-N,N-diphenylaniline (63.0 g) was obtained.

In a nitrogen atmosphere, a flask containing 2,3-dichloro-N,N-diphenylaniline (16.2 g), di([1,1'-biphenyl]-4-yl)amine (15.0 g), Pd-132 (Johnson Matthey) (0.3 g), NaOtBu (6.7 g) and xylene (150 ml) was heated and stirred for one hour at 120° C. The reaction liquid was cooled to room temperature, subsequently water and ethyl acetate were added thereto, and the mixture was partitioned. Subsequently, the reaction liquid was purified using a silica gel short pass column (developing liquid: heated toluene) and was further washed with a heptane/ethyl acetate=1 (volume ratio) mixed solvent. Thus, $N^1,N^1$-di([1,1'-biphenyl]-4-yl)-2-chloro-$N^3,N^3$-diphenylbenzene-1,3-diamine (22.0 g) was obtained.

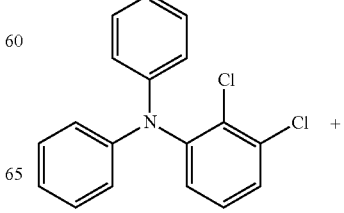

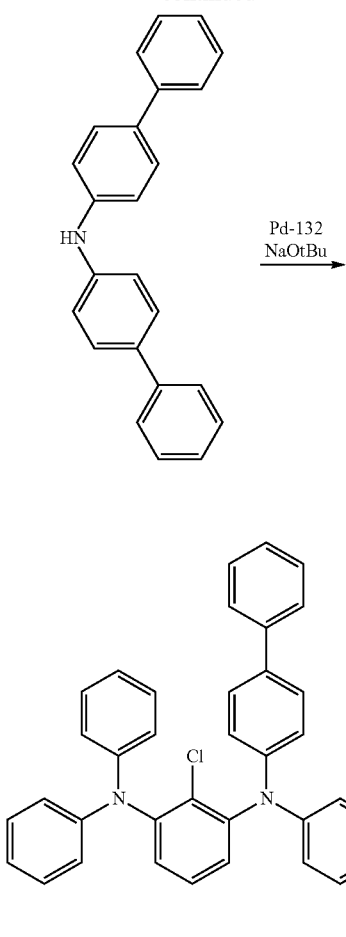

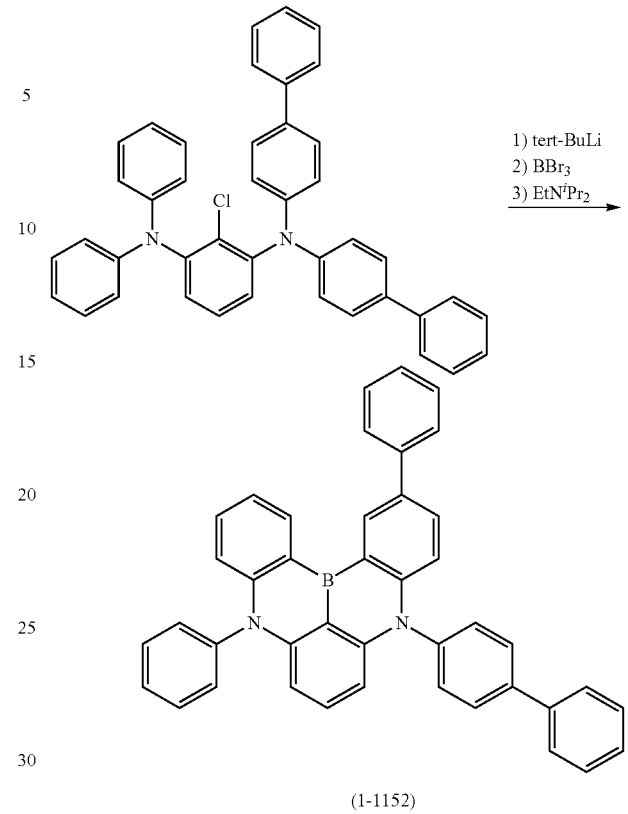

(1-1152)

A 1.6 M tert-butyllithium pentane solution (37.5 ml) was introduced into a flask containing $N^1,N^1$-di([1,1'-biphenyl]-4-yl)-2-chloro-$N^3,N^3$-diphenylbenzene-1,3-diamine (22.0 g) and tert-butylbenzene (130 ml), at −30° C. in a nitrogen atmosphere. After completion of dropwise addition, the temperature of the mixture was increased to 60° C., the mixture was stirred for one hour, and then components having boiling points lower than that of tert-butylbenzene were distilled off under reduced pressure. The mixture was cooled to −30° C., boron tribromide (6.2 ml) was added thereto, the temperature of the mixture was increased to room temperature, and the mixture was stirred for 0.5 hours. Thereafter, the mixture was cooled again to 0° C., N,N-diisopropylethylamine (12.8 ml) was added thereto, and the mixture was stirred at room temperature until heat generation was settled. Subsequently, the temperature of the mixture was increased to 120° C., and the mixture was heated and stirred for 2 hours. The reaction liquid was cooled to room temperature, an aqueous solution of sodium acetate that had been cooled in an ice bath and then ethyl acetate were added thereto, and the mixture was partitioned. Subsequently, the reaction liquid was purified using a silica gel short pass column (developing liquid: heated chlorobenzene). The resultant was washed with refluxed heptane and refluxed ethyl acetate, and then was reprecipitated from chlorobenzene. Thus, a compound (5.1 g) represented by formula (1-1152) was obtained.

The structure of the compound thus obtained was identified by an NMR analysis.

$^1$H-NMR (400 MHz, CDCl$_3$): δ=9.17 (s, 1H), 8.99 (d, 1H), 7.95 (d, 2H), 7.68-7.78 (m, 7H), 7.60 (t, 1H), 7.40-7.56 (m, 10H), 7.36 (t, 1H), 7.30 (m, 2H), 6.95 (d, 1H), 6.79 (d, 1H), 6.27 (d, 1H), 6.18 (d, 1H).

Synthesis Example (34)

Synthesis of 5,9,11,15-tetraphenyl-5,9,11,15-tetraaza-19b,20b-diboranaphtho[3,2,1-de:1',2',3'-jk]pentacene (1-422)

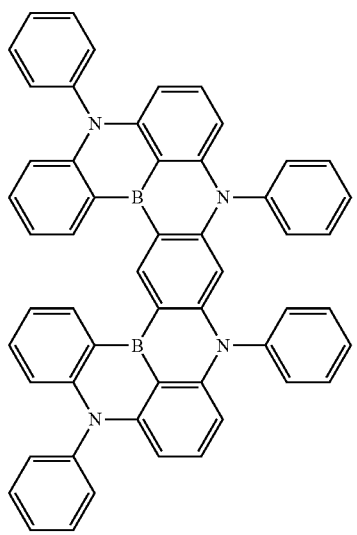

In a nitrogen atmosphere, a flask containing 2,3-dichloro-N,N-diphenylaniline (36.0 g), $N^1,N^3$-diphenylbenzene-1,3-diamine (12.0 g), Pd-132 (Johnson Matthey) (0.3 g), NaOtBu (11.0 g) and xylene (150 ml) was heated and stirred for 3 hours at 120° C. The reaction liquid was cooled to room temperature, subsequently water and ethyl acetate were added thereto, and the mixture was partitioned. Subsequently, the resultant was purified by silica gel column chromatography (developing liquid: toluene/heptane mixed solvent). At this time, the proportion of toluene in the developing liquid was gradually increased, and thereby the intended substance was eluted. The intended substance was further purified by activated carbon column chromatography (developing liquid: toluene), and thus $N^1,N^{1'}$-(1,3-phenylene)bis(2-chloro-$N^1,N^3,N^3$-triphenylbenzene-1,3-diamine) (22.0 g) was obtained.

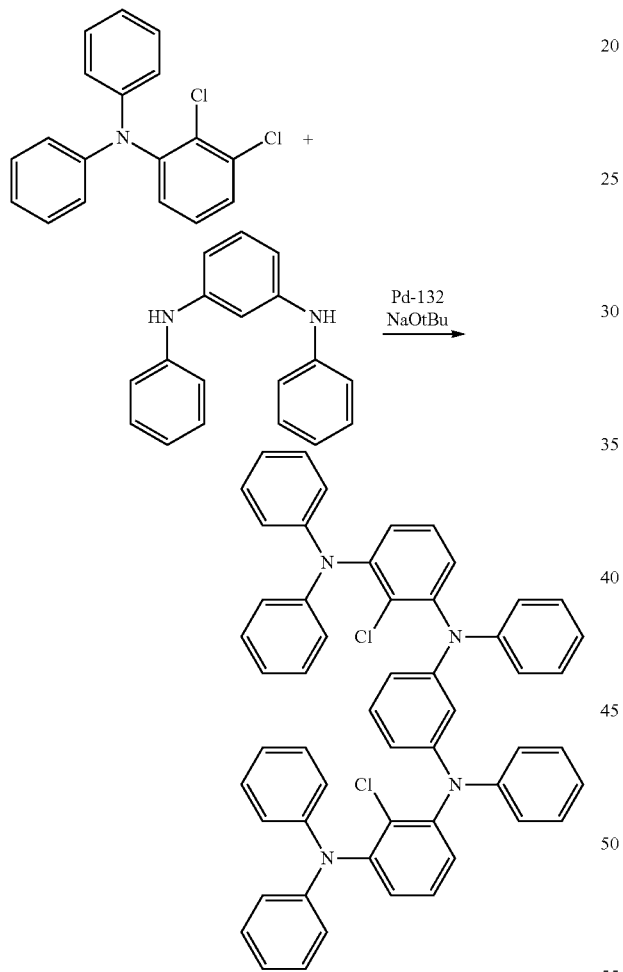

A 1.6 M tert-butyllithium pentane solution (42.0 ml) was introduced into a flask containing $N^1,N^{1'}$-(1,3-phenylene)bis(2-chloro-$N^1,N^3,N^3$-triphenylbenzene-1,3-diamine) (22.0 g) and tert-butylbenzene (150 ml), at −30° C. in a nitrogen atmosphere. After completion of dropwise addition, the temperature of the mixture was increased to 60° C., the mixture was stirred for 5 hours, and components having boiling points lower than that of tert-butylbenzene were distilled off under reduced pressure. The mixture was cooled to −30° C., boron tribromide (7.6 ml) was added thereto, the temperature of the mixture was increased to room temperature, and the mixture was stirred for 0.5 hours. Thereafter, the mixture was cooled again to 0° C., N,N-diisopropylethylamine (18.9 ml) was added thereto, and the mixture was stirred at room temperature until heat generation was settled. Subsequently, the temperature of the mixture was increased to 120° C., and the mixture was heated and stirred for 2 hours. The reaction liquid was cooled to room temperature, an aqueous solution of sodium acetate that had been cooled in an ice bath was added thereto, and a solid thus precipitated was separated by filtration. A filtrate was partitioned, and the organic layer was purified by silica gel column chromatography (developing liquid: toluene/heptane=1 (volume ratio)). The solvent was distilled off under reduced pressure, a solid thus obtained was dissolved in chlorobenzene, and the solid was reprecipitated by adding ethyl acetate. Thus, a compound (0.6 g) represented by formula (1-422) was obtained.

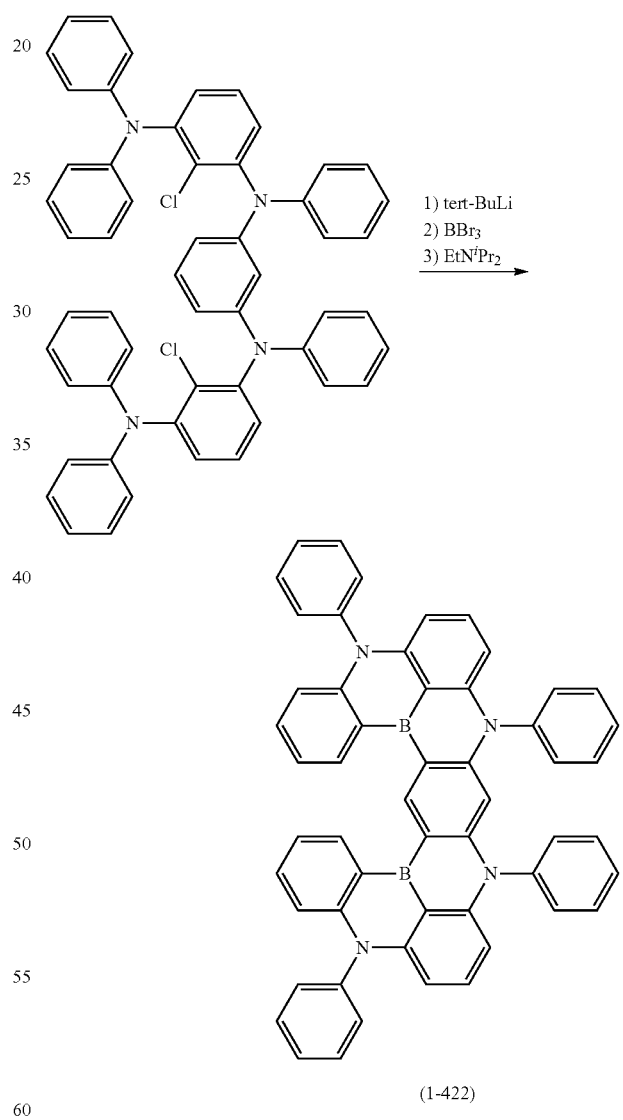

(1-422)

The structure of the compound thus obtained was identified by an NMR analysis.

$^1$H-NMR (400 MHz, DMSO-d6): δ=10.38 (s, 1H), 9.08 (d, 2H), 7.81 (t, 4H), 7.70 (t, 2H), 7.38-7.60 (m, 14H), 7.30 (t, 2H), 7.18 (d, 4H), 6.74 (d, 2H), 6.07 (d, 2H), 6.02 (d, 2H), 5.78 (s, 1H).

Synthesis Example (35)

Synthesis of N¹-(5,9-diphenyl-5,9-diaza-13b-boranaphtho[3,2,1-de]anthracen-3-yl)-N¹,N³,N³-triphenylbenzene-1,3-diamine

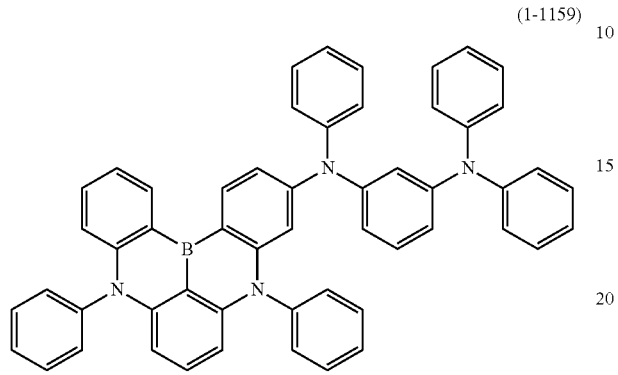

(1-1159)

During the silica gel column chromatographic purification of the compound (0.6 g) represented by formula (1-422), a fraction containing the relevant derivative was fractionated. The fraction was further washed with refluxed heptane, and then was reprecipitated from chlorobenzene/ethyl acetate. Thus, a compound (1.1 g) represented by formula (1-1159) was obtained.

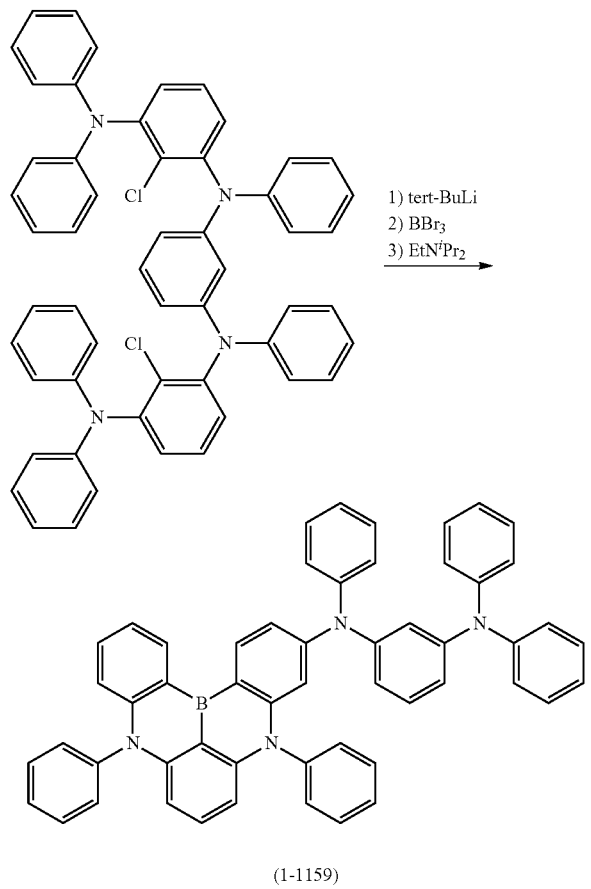

(1-1159)

The structure of the compound thus obtained was identified by an NMR analysis.

¹H-NMR (400 MHz, DMSO-d6): δ=8.78 (d, 1H), 8.66 (d, 1H), 7.69 (t, 2H), 7.59 (t, 1H), 7.59 (t, 2H), 7.49 (m, 2H), 7.40 (d, 2H), 7.22-7.32 (m, 10H), 7.18 (t, 1H), 6.97-7.07 (m, 9H), 6.89 (d, 1H), 6.60-6.70 (m, 4H), 6.11 (s, 1H), 5.96 (m, 2H).

Synthesis Example (36)

Synthesis of 9-phenyl-9H-5-oxa-9-aza-13b-boranaphtho[3,2,1-de]anthracene

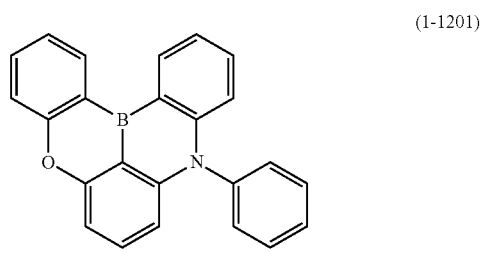 [SMILES: c1ccc(N2c3ccccc3B3c4ccccc4Oc4cccc2c43)cc1]

(1-1201)

In a nitrogen atmosphere, a flask containing 1-bromo-2-chloro-3-fluorobenzene (25.0 g), phenol (12.3 g), potassium carbonate (33.0 g) and NMP (150 ml) was heated and stirred for 4 hours at 180° C. The reaction liquid was cooled to room temperature, NMP was distilled off under reduced pressure, subsequently water and ethyl acetate were added thereto, and the mixture was partitioned. Subsequently, the reaction liquid was purified using a silica gel short pass column (developing liquid: toluene/heptane=1/1 (volume ratio)), and thus 1-bromo-2-chloro-3-phenoxybenzene (32.0 g) was obtained.

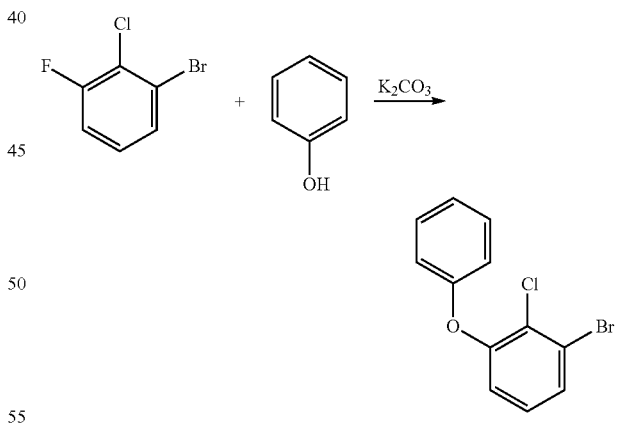

In a nitrogen atmosphere, a flask containing diphenylamine (21.0 g), 1-bromo-2-chloro-3-phenoxybenzene (32.0 g), Pd-132 (Johnson Matthey) (0.4 g), NaOtBu (16.0 g) and xylene (200 ml) was heated and stirred for 4 hours at 80° C. The reaction liquid was cooled to room temperature, subsequently water and ethyl acetate were added thereto, and the mixture was partitioned. Subsequently, the resultant was purified by silica gel column chromatography (developing liquid: toluene/heptane=2/8 (volume ratio), and was further reprecipitated from heptane. Thus, 2-chloro-3-phenoxy-N,N-diphenylaniline (35.0 g) was obtained.

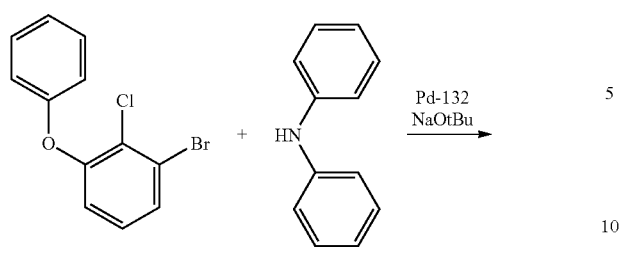 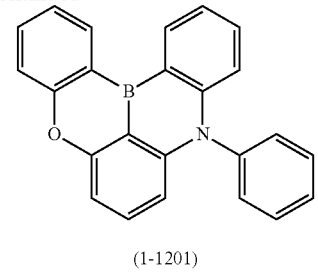

(1-1201)

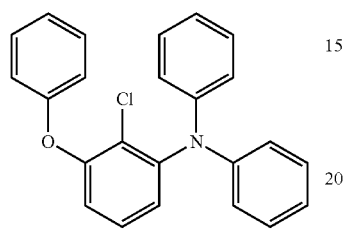

A 1.7 M tert-butyllithium pentane solution (26.5 ml) was introduced into a flask containing 2-chloro-3-phenoxy-N,N-diphenylaniline (16.0 g) and tert-butylbenzene (150 ml), at −30° C. in a nitrogen atmosphere. After completion of dropwise addition, the temperature of the mixture was increased to 15° C., and the mixture was stirred for 2 hours. The mixture was cooled again to −30° C., and boron tribromide (4.9 ml) was added thereto. Subsequently, the temperature of the mixture was increased to 60° C. while pressure was reduced, and components having boiling points lower than that of tert-butylbenzene were distilled off under reduced pressure. Thereafter, the mixture was cooled to 0° C., N,N-diisopropylethylamine (15.0 ml) was added thereto, and the mixture was stirred at room temperature until heat generation was settled. Subsequently, the temperature of the mixture was increased to 120° C., and the mixture was heated and stirred for one hour. The reaction liquid was cooled to room temperature, an aqueous solution of sodium acetate that had been cooled in an ice bath and then ethyl acetate were added thereto, and the mixture was partitioned. The resultant was purified by silica gel column chromatography (developing liquid: toluene/heptane mixed solvent). At this time, the proportion of toluene in the developing liquid was gradually increased, and thereby the intended substance was eluted. The intended substance was further purified by activated carbon column chromatography (developing liquid: toluene), and thus a compound (0.8 g) represented by formula (1-1201) was obtained.

The structure of the compound thus obtained was identified by an NMR analysis.

$^1$H-NMR (400 MHz, CDCl$_3$): δ=8.92 (d, 1H), 8.78 (d, 1H), 7.70 (t, 2H), 7.66 (t, 1H), 7.61 (t, 1H), 7.53 (m, 2H), 7.47 (t, 1H), 7.37 (m, 3H), 7.27 (t, 1H), 7.11 (d, 1H), 6.80 (d, 1H), 6.31 (d, 1H).

Synthesis Example (37)

Synthesis of N,N,9-triphenyl-9H-5-oxa-9-aza-13b-boranaphtho[3,2,1-de]anthracene-3-amine (1-1210)

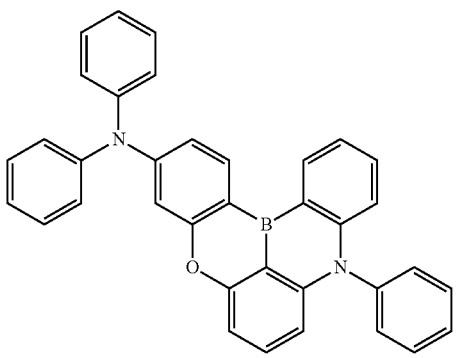

In a nitrogen atmosphere, a flask containing 1-bromo-2-chloro-3-fluorobenzene (20.0 g), 3-(diphenylamino)phenol (27.4 g), potassium carbonate (26.4 g) and NMP (150 ml) was heated and stirred for 6 hours at 180° C. The reaction liquid was cooled to room temperature, NMP was distilled off under reduced pressure, subsequently water and toluene were added thereto, and the mixture was partitioned. Subsequently, the resultant was purified by silica gel column chromatography (developing liquid: toluene/heptane=2/1 (volume ratio)), and thus 3-(3-bromo-2-chlorophenoxy)-N,N'-diphenylaniline (31.6 g) was obtained.

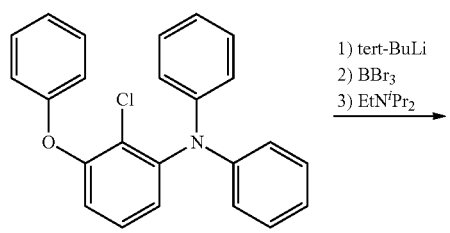 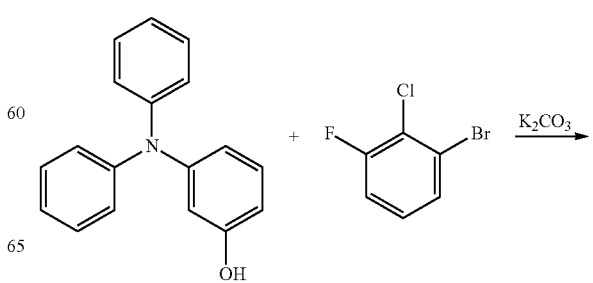

321
-continued

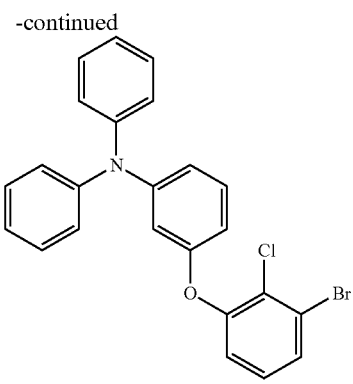

In a nitrogen atmosphere, a flask containing diphenylamine (13.0 g), 3-(3-bromo-2-chlorophenoxy)-N,N'-diphenylaniline (31.6 g), Pd-132 (Johnson Matthey) (0.5 g), NaOtBu (10.1 g), and 1,2,4-trimethylbenzene (150 ml) was heated and stirred for one hour at the reflux temperature. The reaction liquid was cooled to room temperature, and then insoluble salts were removed by suction filtration. Subsequently, the filtrate was purified using an activated carbon short pass column (developing liquid: toluene), and was further purified by silica gel column chromatography (developing liquid: toluene/heptane=1/6 (volume ratio)). Thus, 2-chloro-3-(3-diphenylamino)phenoxy-N,N-diphenylaniline (26.3 g) was obtained.

322

A 1.6 M tert-butyllithium pentane solution (31.4 ml) was introduced into a flask containing 2-chloro-3-(3-diphenylamino)phenoxy-N,N-diphenylaniline (26.3 g) and tert-butylbenzene (150 ml), at −30° C. in a nitrogen atmosphere. After completion of dropwise addition, the temperature of the mixture was increased to room temperature, and the mixture was stirred overnight. The mixture was cooled again to −30° C., and boron tribromide (5.4 ml) was added thereto. Subsequently, the temperature of the mixture was increased to 60° C. while pressure was reduced, and components having boiling points lower than that of tert-butylbenzene were distilled off under reduced pressure. Thereafter, the mixture was cooled to 0° C., N,N-diisopropylethylamine (17.0 ml) was added thereto, and the mixture was stirred at room temperature until heat generation was settled. Subsequently, the temperature of the mixture was increased to 120° C., and the mixture was heated and stirred for 5.5 hours. The reaction liquid was cooled to room temperature, an aqueous solution of sodium acetate that had been cooled in an ice bath and then ethyl acetate were added thereto, and the mixture was partitioned. The mixture was purified by silica gel column chromatography (developing liquid: toluene), and recrystallization from toluene was carried out. Thus, a compound (0.6 g) represented by formula (1-1210) was obtained.

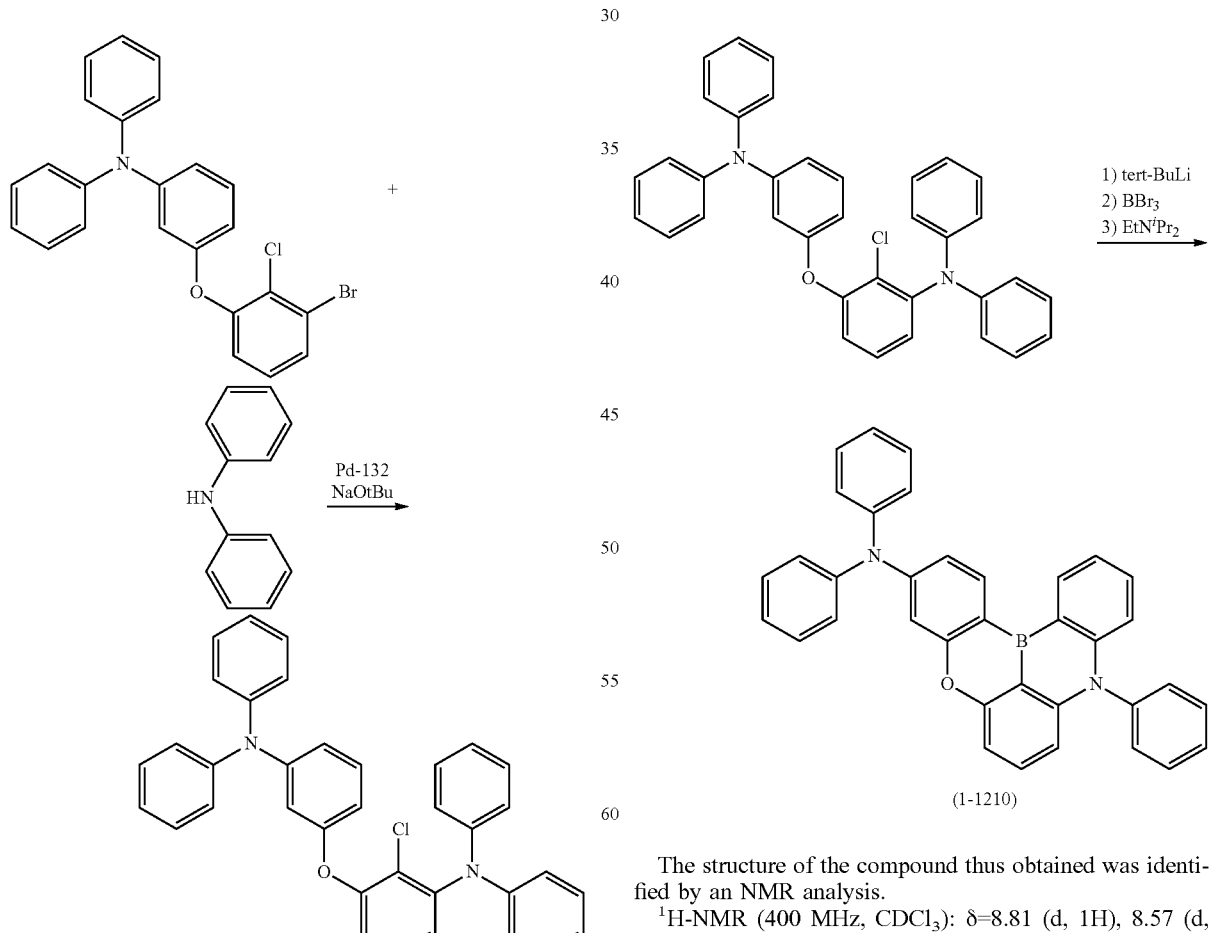

(1-1210)

The structure of the compound thus obtained was identified by an NMR analysis.

$^1$H-NMR (400 MHz, CDCl$_3$): δ=8.81 (d, 1H), 8.57 (d, 1H), 7.70 (t, 2H), 7.61 (t, 1H), 7.44 (m, 2H), 7.37 (t, 6H), 7.12-7.30 (m, 7H), 7.03 (m, 2H), 6.92 (d, 1H), 6.76 (d, 1H), 6.26 (d, 1H).

Synthesis Example (38)

Synthesis of 5,11-diphenyl-6,10-dioxa-16b-boraanthra[3,2,1-de]tetracene

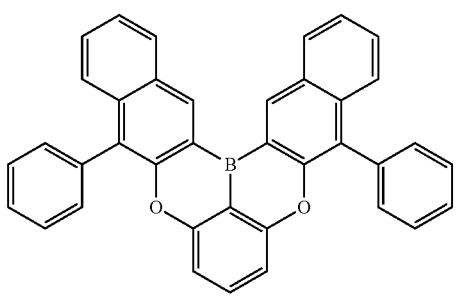

(1-1271)

Copper(I) iodide (0.8 g) and iron(III) acetylacetonate (3.0 g) were added to an NMP (100 ml) solution of 1-phenylnaphthalen-2-ol (20.0 g) synthesized by the method described in Angew. Chem. Int. Ed. 2013, 52, 10598-10601, 1,3-dibromobenzene (9.7 g) and potassium carbonate (23.0 g) in a nitrogen atmosphere. The temperature of the mixture was increased to 150° C., and the mixture was stirred for 6 hours. The reaction liquid was cooled to room temperature, and a salt precipitated by adding aqueous ammonia thereto was removed by suction filtration using a Hirsch funnel covered with Celite. Ethyl acetate was added to the filtrate, and the mixture was partitioned. Subsequently, the resultant was purified by silica gel column chromatography (developing liquid: toluene/heptane=3/7), and thus 1,3-bis((1-phenylnaphthalen-2-yl)oxy)benzene (12.0 g) was obtained.

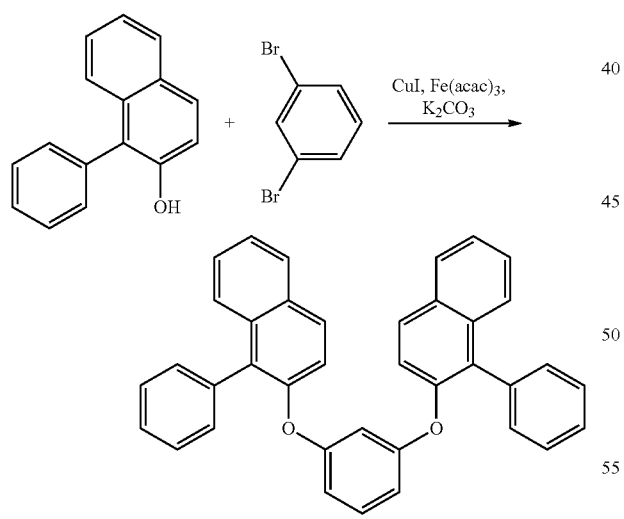

A 2.6 M n-butyllithium hexane solution (24.5 ml) was introduced into a flask containing 1,3-bis((1-phenylnaphthalen-2-yl)oxy)benzene (12.0 g) and ortho-xylene (100 ml), at 0° C. in a nitrogen atmosphere. After completion of dropwise addition, the temperature of the mixture was increased to 70° C., the mixture was stirred for 2 hours, and then components having boiling points lower than that of xylene were distilled off under reduced pressure. The mixture was cooled to −50° C., boron tribromide (4.9 ml) was added thereto, the temperature of the mixture was increased to room temperature, and the mixture was stirred for 0.5 hours. Thereafter, the mixture was cooled again to 0° C., N,N-diisopropylethylamine (8.1 ml) was added thereto, and the mixture was stirred at room temperature until heat generation was settled. Subsequently, the temperature of the mixture was increased to 120° C., and the mixture was heated and stirred for 3 hours. In order to further accelerate the reaction, aluminum chloride (6.2 g) was added thereto, and the mixture was heated and stirred for 2 hours at 130° C. The reaction liquid was cooled to room temperature, and a suspension produced by adding an aqueous solution of sodium acetate that had been cooled in an ice bath was directly partitioned. Subsequently, a solid produced by adding heptane to the organic layer was collected by suction filtration. The solid thus obtained was washed with refluxed ethyl acetate, toluene and chlorobenzene in this order, and thus a compound (5.3 g) represented by formula (1-1271) was obtained.

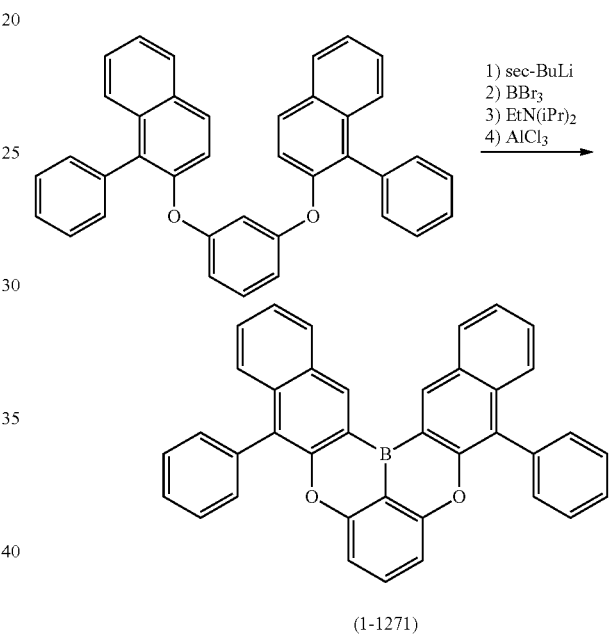

(1-1271)

The structure of the compound thus obtained was identified by an NMR analysis.

$^1$H-NMR (400 MHz, CDCl$_3$): δ=9.56 (s, 2H), 8.28 (d, 2H), 7.74 (m, 2H), 7.50-7.66 (m, 15H), 6.90 (d, 2H).

Synthesis Example (39)

Synthesis of 5,9-dithia-13b-boranaphtho[3,2,1-de]anthracene

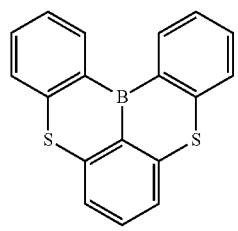

(1-201)

In a nitrogen atmosphere, a solution of 2-bromo-1,3-difluorobenzene (23.6 g), benzenethiol (27.2 g), potassium carbonate (67.0 g) and NMP (150 ml) was heated to 180° C. and stirred for 12 hours. The reaction liquid was cooled to room temperature, NMP was distilled off under reduced pressure, subsequently water and ethyl acetate were added thereto, and the mixture was partitioned. Subsequently, the resultant was purified by silica gel column chromatography (developing liquid: toluene/heptane=1/9 (volume ratio)). A crude purification product thus obtained was dissolved in toluene and was reprecipitated by adding heptane. Thus, (2-bromo-1,3-phenylene)bis(phenylsulfane) (9.5 g) was obtained.

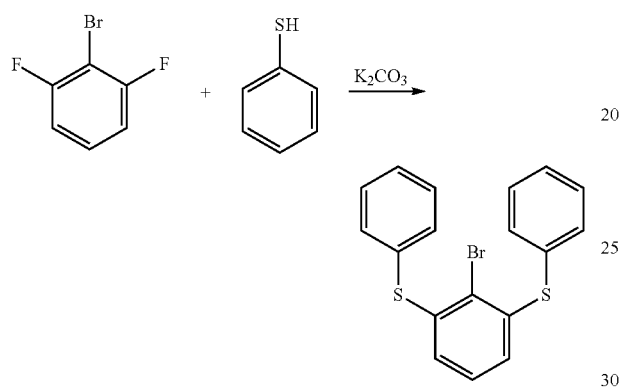

In a nitrogen atmosphere, a flask containing (2-bromo-1,3-phenylene)bis(phenylsulfane) (9.5 g) and xylene (100 ml) was cooled to −40° C., and a 1.0 M sec-butyllithium cyclohexane solution (26.7 ml) was added dropwise thereto. After completion of dropwise addition, the temperature of the mixture was increased to about 60° C., and components having boiling points lower than that of xylene were distilled off under reduced pressure. The mixture was cooled again to −40° C., and boron tribromide (2.9 ml) was added thereto. The temperature of the mixture was increased to room temperature, and the mixture was stirred for 0.5 hours. Subsequently, the mixture was cooled to 0° C., and N,N-diisopropylethylamine (8.9 ml) was added thereto. The temperature of the mixture was increased to 120° C., and the mixture was heated and stirred for 2 hours. The reaction liquid was cooled to room temperature, an aqueous solution of sodium acetate that had been cooled in an ice bath and ethyl acetate were added thereto, and the mixture was partitioned. The solvent was distilled off under reduced pressure, and reprecipitation was carried out by adding heptane to an oily substance thus obtained. A solid thus obtained was washed with ethyl acetate, and thus a compound (4.6 g) represented by formula (1-201) was obtained.

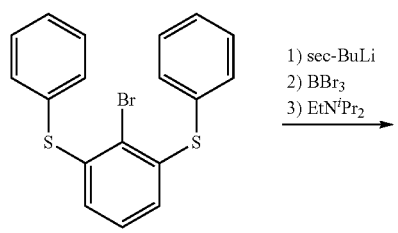

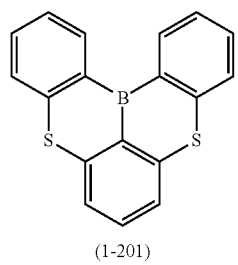

(1-201)

The structure of the compound thus obtained was identified by an NMR analysis.

$^1$H-NMR (400 MHz, CDCl$_3$): δ=8.30 (d, 2H), 7.72 (d, 2H), 7.54-7.62 (m, 4H), 7.50 (t, 1H), 7.43 (t, 2H).

Synthesis Example (40)

Synthesis of 9,10,19,20-tetraoxa-4b,14b-diboradinaphtho[1,2,3-fg:1',2',3'-qr]pentacene

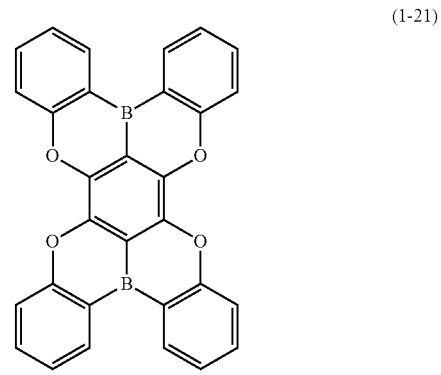 [SMILES: c1ccc2c(c1)Oc1c3c4c(c5c1B2c1ccccc1O5)Oc1ccccc1B4c1ccccc1O3]

(1-21)

In a nitrogen atmosphere, a flask containing 1,4-dibromo-2,3,5,6-tetrafluorobenzene (6.24 g), phenol (9.53 g), potassium carbonate (14.0 g) and NMP (20 ml) was heated and stirred for 18 hours at 140° C. The reaction liquid was cooled to room temperature, saturated brine and toluene were added thereto, and the mixture was partitioned. The solvent was distilled off under reduced pressure, and then the residue was purified using a silica gel short pass column (developing liquid: toluene). The solvent was distilled off under reduced pressure, and a crude purification product was washed using methanol. Thus, 1,4-dibromo-2,3,5,6-tetraphenoxybenzene (9.64 g) was obtained.

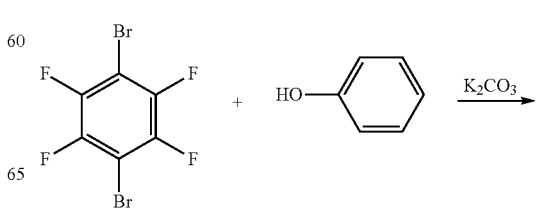

-continued

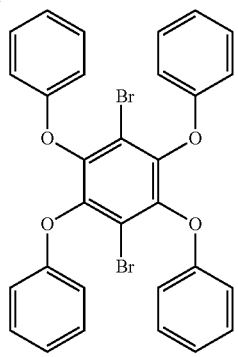

A 1.6 M n-butyllithium hexane solution (0.610 ml) was added to a t-butylbenzene (3.0 ml) solution of 1,4-dibromo-2,3,5,6-tetraphenoxybenzene (0.604 g), at 0° C. in a nitrogen atmosphere. The mixture was stirred for one hour, subsequently the temperature of the mixture was increased to room temperature, and t-butylbenzene (4.0 ml) was added thereto. The mixture was cooled to −50° C., boron tribromide (0.105 ml) was added thereto, and the mixture was stirred for 30 minutes. The temperature of the mixture was increased to 0° C., the mixture was stirred for 30 minutes, subsequently the temperature of the mixture was increased to 60° C., and the mixture was stirred for 10 hours. Thereafter, the mixture was cooled to 0° C., N,N-diisopropylethylamine (0.350 ml) was added thereto, and the mixture was heated and stirred for 17 hours at the reflux temperature. The reaction liquid was cooled to room temperature, and was filtered using a Florisil short pass column. The solvent was distilled off under reduced pressure, and then the residue was washed with hexane. Thus, 7-bromo-6,8-diphenoxy-5,9-dioxa-13b-boranaphtho[3,2,1-de]anthracene (0.106 g) was obtained as a pale orange-colored product.

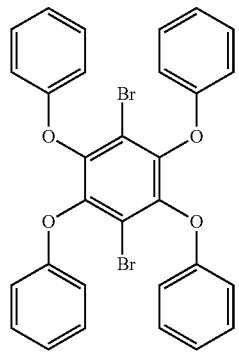

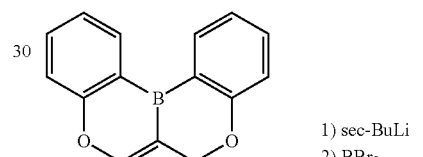

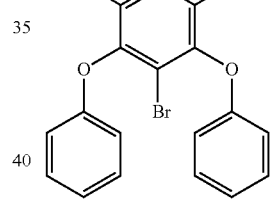

A 1.1 M sec-butyllithium hexane solution (1.98 ml) was added to a t-butylbenzene (2.5 ml) solution of 7-bromo-6,8-diphenoxy-5,9-dioxa-13b-boranaphtho[3,2,1-de]anthracene (0.103 g), at −50° C. in a nitrogen atmosphere. After the mixture was stirred for 30 minutes, the temperature of the mixture was increased to 0° C., and the mixture was stirred for 2 hours. The mixture was cooled again to −50° C., boron tribromide (0.220 ml) was added thereto, the temperature of the mixture was increased to room temperature, and the mixture was stirred for 30 minutes. Thereafter, N,N-diisopropylethylamine (65.9 μl) was added thereto, and the mixture was heated and stirred for 11 hours at the reflux temperature. The reaction liquid was cooled to room temperature, and was suction filtered using a glass filter covered with Celite. The solvent was distilled off under reduced pressure, and a crude product was obtained. The crude product was washed using hexane and chloroform, and thereby a compound (4.10 mg) represented by formula (1-21) was obtained as an orange-colored solid.

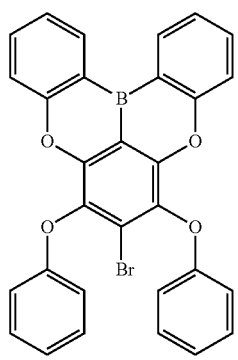

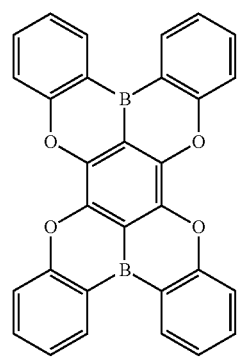

(1-21)

The structure of the compound thus obtained was identified by an NMR analysis.

$^1$H NMR (δ ppm in CDCl$_3$); 8.80 (dd, J=1.6, 7.8 Hz, 4H), 7.83 (ddd, J=1.6, 6.0, 8.4 Hz, 4H), 7.81 (dd, J=2.0, 8.4 Hz, 4H), 7.46 (ddd, J=2.0, 6.0, 7.8 Hz, 4H).

LRMS (EI+) m/z 462 (M$^+$)

Synthesis Examples (41) and (42)

Synthesis of 19b,20b-dibora-5,9,11,15-tetraoxadinaphtho[3,2,1-de:1',2',3'-jk]pentacene (1-24)

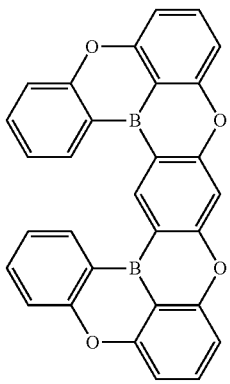

Synthesis of 4b,13b-dibora-5,9,16,20-tetraoxadinaphtho[3,2,1-de:3',2',1'-pq]pentaphene (1-23)

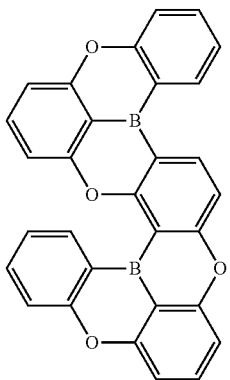

1-Bromo-2,6-difluorobenzene (25.2 g, 0.130 mol) was added to phenol (12.3 g, 0.130 mol), potassium carbonate (18.0 g, 0.130 mol) and N-methylpyrrolidone (NMP, 250 mL) at room temperature in a nitrogen atmosphere, and the mixture was heated and stirred for 160 hours at 120° C. Thereafter, NMP was distilled off under reduced pressure, and then toluene was added thereto. The mixture was filtered using a silica gel short pass column, and the solvent was distilled off under reduced pressure. Thus, 2-bromo-1-fluoro-3-phenoxybenzene was obtained as a pale red liquid (26.4 g, yield 76%).

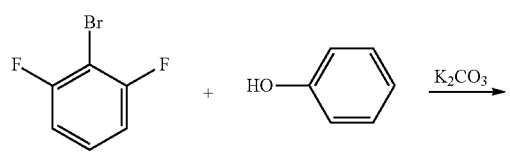

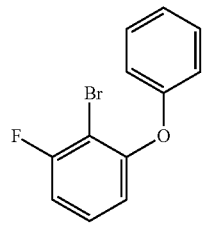

2-Bromo-1-fluoro-3-phenoxybenzene (7.67 g, 28.7 mmol) was added to resorcinol (14.4 g, 14.4 mmol), potassium carbonate (3.97 g, 28.7 mmol), and NMP (57.4 mL) at room temperature in a nitrogen atmosphere, and the mixture was heated and stirred for 160 hours at 150° C. and then heated and stirred for 22 hours at 160° C. Thereafter, NMP was distilled off under reduced pressure, and then toluene was added thereto. The mixture was filtered using a Florisil short pass column, the solvent was distilled off under reduced pressure, and a crude product was obtained. The crude product was recrystallized using toluene, and thus 1,3-bis(2-bromo-3-phenoxyphenoxy)benzene was obtained as a white solid (5.35 g, yield 62%).

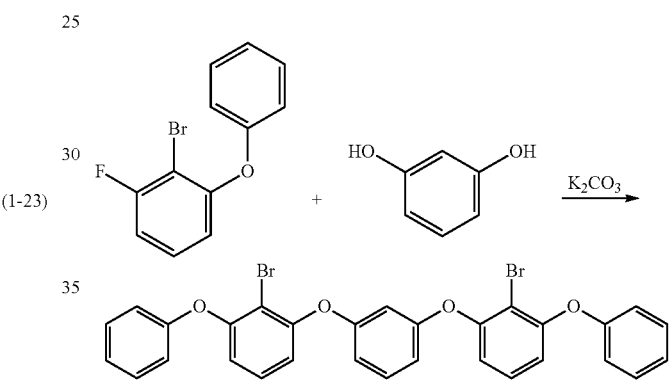

A hexane solution of butyllithium (0.688 mL, 1.64 M, 1.1 mmol) was added to 1,3-bis(2-bromo-3-phenoxyphenoxy)benzene (0.302 g, 0.50 mmol) and tert-butylbenzene (5.0 mL), at −42° C. in a nitrogen atmosphere, and then the mixture was stirred for 22 hours at room temperature. Boron tribromide (0.142 mL, 1.5 mmol) was added thereto at −42° C., and the mixture was stirred for 3 hours at 50° C. The mixture was stirred for another 17 hours at 70° C., and then 10% of the reaction solution was distilled off at 0° C. under reduced pressure. N,N-diisopropylethylamine (0.348 mL, 2.0 mmol) was added thereto at 0° C., and the mixture was heated and stirred for 20 hours at 150° C. Subsequently, the mixture was filtered using a Florisil short pass column, the solvent was distilled off under reduced pressure, and a crude product was obtained. The crude product was washed using dichloromethane and acetonitrile, and thereby a white solid was obtained. Next, the white solid was recrystallized using ethyl acetate, and thereby a compound represented by formula (1-24) was obtained as a white solid (19.2 mg, yield 8.3%). Furthermore, the solvent of the filtrate was distilled off under reduced pressure, and thereby a compound represented by formula (1-24) as a pale yellow-colored solid and a compound represented by formula (1-23) was obtained as a mixture at a ratio of 1:5 (30.8 mg, yield 13%). From these results, the yield of the compound represented by formula (1-24) was calculated to be 11% (24.3 mg), and the yield of the compound represented by formula (1-23) was calculated to be 11% (25.7 mg).

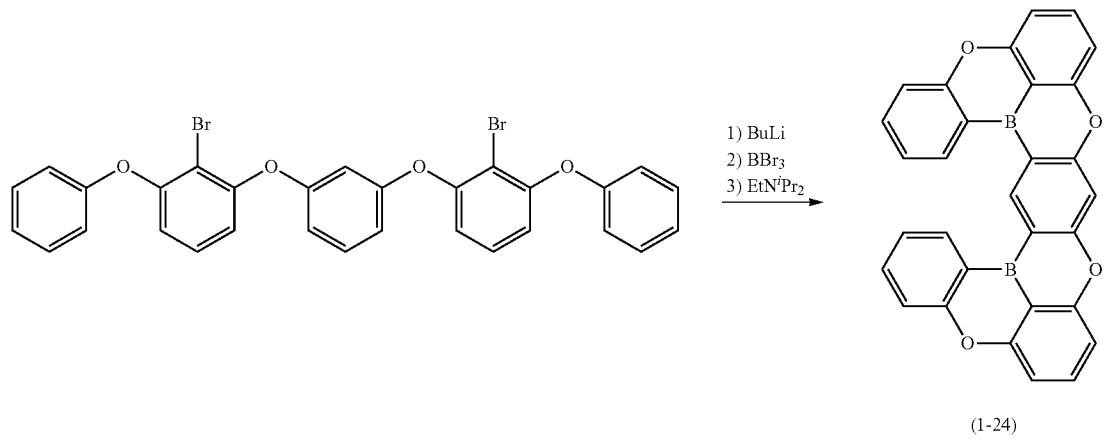

(1-24)

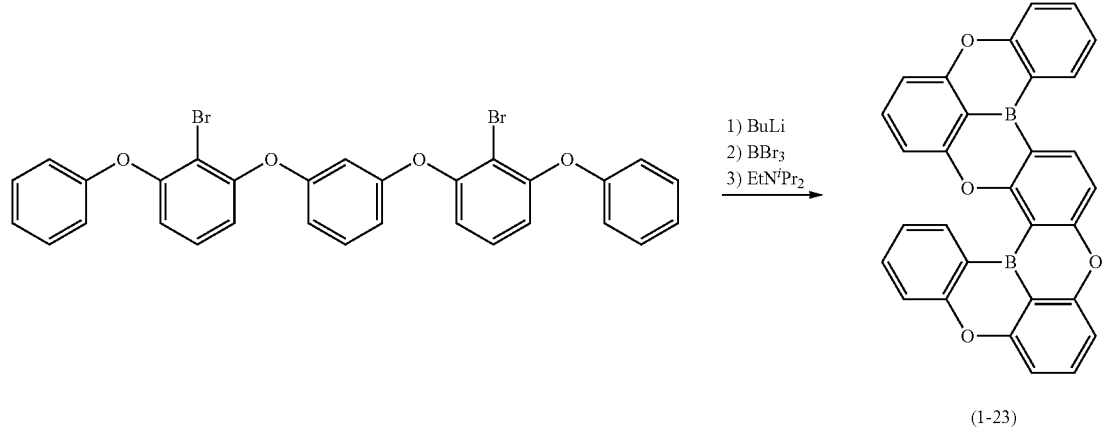

(1-23)

The structure of the compound represented by formula (1-24) was identified by an NMR analysis.

¹H NMR (δ ppm in CDCl$_3$); 10.13 (s, 1H), 8.92 (dd, J=1.6, 8.0 Hz, 2H), 7.82 (t, J=8.0 Hz, 2H), 7.78 (ddd, J=1.6, 6.8, 8.0 Hz, 2H), 7.62 (d, J=7.6 Hz, 4H), 7.51-7.54 (m, 4H), 6.98 (s, 1H).

LRMS (EI+) m/z 462 (M$^+$)

The structure of the compound represented by formula (1-23) was identified by an NMR analysis.

¹H NMR (δ ppm in DMSO-D6); 8.92 (d, J=8.8 Hz, 1H), 8.77 (dd, J=1.6, 7.6 Hz, 1H), 8.57 (d, J=8.4 Hz, 1H), 7.93 (t, J=8.0 Hz, 1H), 7.81 (ddd, J=1.6, 7.2, 8.4 Hz, 1H), 7.67 (t, J=8.0 Hz, 1H), 7.58-7.63 (m, 2H), 7.47-7.50 (m, 3H), 7.35 (dd, J=1.6, 8.4 Hz, 1H), 7.31 (t, J=8.0 Hz, 1H), 7.28 (d, J=8.4 Hz, 1H), 7.19 (t, J=8.0 Hz, 2H).

LRMS (EI+) m/z 462 (M$^+$)

Synthesis Example (43)

Synthesis of 2,6,8,12-tetraphenyl-5,9-dioxa-13b-thiophosphanaphtho[3,2,1-de]anthracene

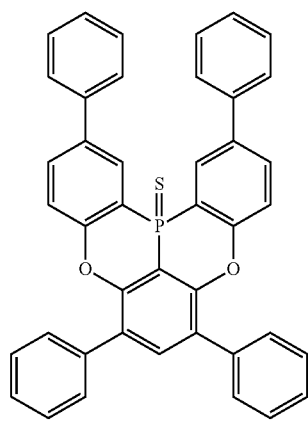

(1-1250)

First, a hexane solution of butyllithium (12.2 mL, 1.64 M, 20.0 mmol) was added to 4',6'-bis([1,1'-biphenyl]-4-yloxy)-5'-bromo-1,1':3',1''-terphenyl (12.9 g, 20.0 mmol) and benzene (36 mL), at 0° C. in a nitrogen atmosphere, and the mixture was stirred for one hour at room temperature. Phosphorus trichloride (1.90 mL, 22.0 mmol) was added thereto at 0° C., and the mixture was stirred for one hour at 80° C. The solvent was distilled off under reduced pressure, sulfur (0.770 g, 24.0 mmol) and o-dichlorobenzene (60 mL) were added thereto, and the mixture was stirred for one hour at 80° C. Aluminum trichloride (18.6 g, 0.140 mol) at −70° C. and N,N-diisopropylethylamine (8.20 mL, 48.0 mmol) at 0° C. were added thereto, and the mixture was stirred for 16 hours at 100° C. The mixture was cooled to room temperature, and then the reaction liquid was added to a dichloromethane (300 ml) solution of 1,4-diazabicyclo[2.2.2]octane (31.4 g, 0.280 mol). Subsequently, the mixture was suction filtered using a glass filter covered with Celite, and the solvent of the filtrate was distilled off under reduced pressure. The residue was dissolved in toluene, the solution was suction filtered using a glass filter covered with silica gel, and then the solvent of the filtrate was distilled off under reduced pressure. The residue was dissolved in dichloromethane, water was added thereto, and then the dichloromethane layer was separated, while the aqueous layer was extracted with dichloromethane. The solvent was distilled off under reduced pressure, and a crude product was washed using hexane, methanol, acetonitrile, and ethyl acetate. Thus, a compound (0.723 g) represented by formula (1-1250) was obtained as a white solid.

The structure of the compound thus obtained was identified by an NMR analysis.

$^1$H NMR (δ ppm in CDCl$_3$); 7.33 (dd, J$_{HP}$=6.2 Hz, J=8.7 Hz, 2H), 7.38-7.55 (m, 12H), 7.68 (d, J=7.2 Hz, 4H), 7.63 (d, J=7.3 Hz, 4H), 7.71 (s, 1H), 7.74 (dd, J$_{HP}$=2.2 Hz, J=8.7 Hz, 2H), 8.41 (dd, J$_{HP}$=13.4 Hz, J=2.2 Hz, 2H).

$^{13}$C NMR (δ ppm in CDCl$_3$); 103.2 (d, J$_{CP}$=81.9 Hz), 119.9 (d, J$_{CP}$=81.4 Hz, 2C), 120.3 (2C), 126.9 (2C), 127.0 (4C), 127.3 (d, J$_{CP}$=7.3 Hz, 2C), 127.8 (2C), 128.0 (2C), 128.4 (4C), 129.1 (4C), 129.6 (4C), 131.7 (2C), 135.9, 136.0 (2C), 138.6 (d, J$_{CP}$=10.1 Hz, 2C), 139.3 (2C), 151.8 (2C), 155.2 (2C).

Synthesis Example (44)

Synthesis of 2,6,8,12-tetraphenyl-5,9-dioxa-13b-oxophosphanaphtho[3,2,1-de]anthracene

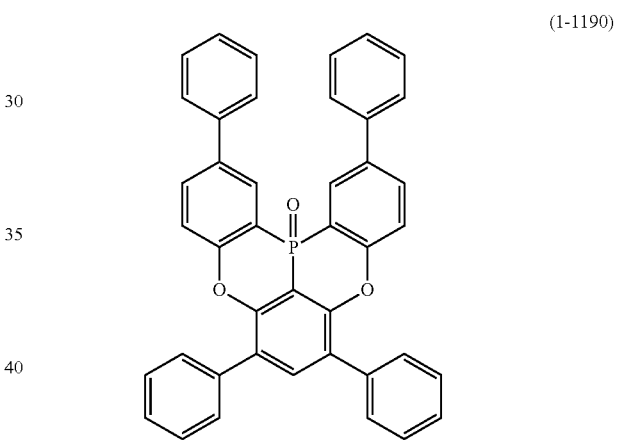

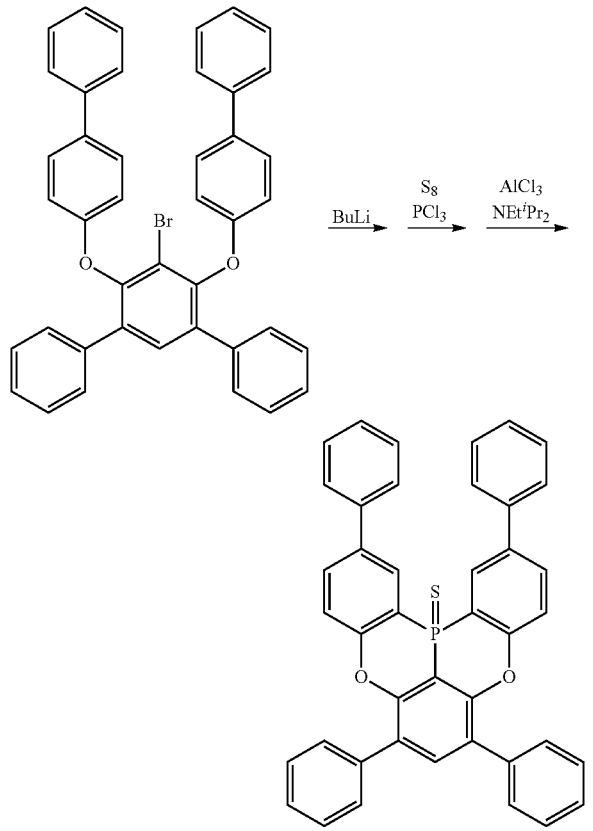

m-Chloroperbenzoic acid (0.247 g, 77 wt %, 1.10 mmol) at 0° C. was added to the compound represented by the above formula (1-1250) (0.633 g, 1.01 mmol) and dichloromethane (100 mL), and the mixture was stirred at room temperature. After 6 hours, m-chloroperbenzoic acid (44.9 mg, 77 wt %, 0.200 mmol) was added thereto at 0° C., and the mixture was stirred at room temperature. After 14 hours, a saturated solution of sodium sulfite (10.0 ml) was added thereto, and the mixture was stirred at room temperature. Insoluble materials were removed by filtration, a dichloromethane layer was separated, and then the aqueous layer was extracted with dichloromethane. The organic layers thus obtained were combined and concentrated, and the combined organic layer was subjected to a silica gel short pass column using dichloromethane and ethyl acetate as developing solvents. The solvent of the filtrate was distilled off under reduced pressure. A crude product thus obtained was washed using methanol, and thus a compound (0.580 g) represented by formula (1-1190) was obtained as a white solid.

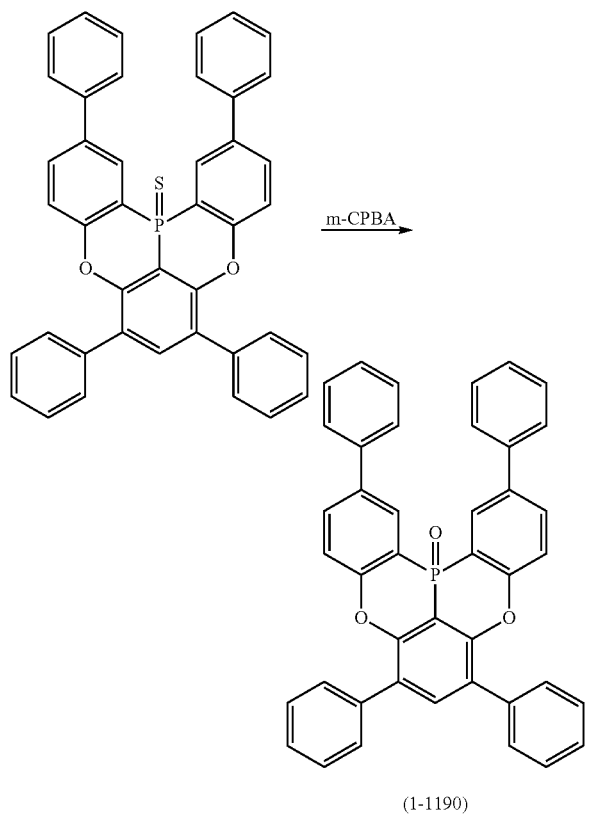

(1-1190)

The structure of the compound thus obtained was identified by an NMR analysis.

$^1$H NMR (δ ppm in CDCl$_3$); 7.37-7.56 (m, 14H), 7.62 (d, J=7.3 Hz, 4H), 7.69 (d, J=7.9 Hz, 4H), 7.79 (s, 1H), 7.80 (dd, J=2.3, 8.7 Hz, 2H), 8.44 (dd, J=2.3 Hz, 2H).

$^{13}$C NMR (δ ppm in CDCl$_3$); 104.0 (d, J$_{CP}$=97.3 Hz), 117.6 (d, J$_{CP}$=116.6 Hz, 2C), 120.4 (2C), 126.3 (2C), 127.0 (4C), 127.4 (d, J$_{CP}$=4.8 Hz, 2C), 127.7 (2C), 127.9 (2C), 128.4 (4C), 129.0 (4C), 129.6 (4C), 132.4 (2C), 136.0, 136.7 (2C), 138.0 (d, J$_{CP}$=10.6 Hz, 2C), 139.3 (2C), 152.1 (2C), 156.7 (2C).

Synthesis Example (45)

Synthesis of 2,12-diphenyl-5,9-dioxa-13b-thiophosphanaphtho[3,2,1-de]anthracene (1-1247)

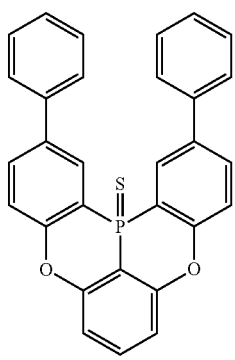

First, a hexane solution of butyllithium (11.0 mL, 1.64 M, 18.0 mmol) was added to 1,3-bis([1,1'-biphenyl]-4-yloxy) benzene (6.22 g, 15.0 mmol) and benzene (120 mL), at 0° C. in a nitrogen atmosphere, and the mixture was stirred for 18 hours at 70° C. Phosphorus trichloride (1.76 mL, 22.5 mmol) was added thereto at 0° C., and the mixture was stirred for 2 hours at 80° C. The solvent was distilled off under reduced pressure, and then sulfur (0.866 g, 27.0 mmol) and o-dichlorobenzene (60 mL) were added thereto, and the mixture was stirred for one hour at 80° C. Aluminum trichloride (14.0 g, 105 mmol) at −95° C. and N,N-diisopropylethylamine (6.18 mL, 36.0 mmol) at 0° C. were added thereto, and the mixture was stirred for 16 hours at 80° C. The mixture was cooled to room temperature, and then the reaction mixed liquid was added to a dichloromethane (300 ml) solution of 1,4-diazabicyclo[2.2.2]octane (23.6 g, 210 mmol). Subsequently, the mixture was suction filtered using a glass filter covered with Celite, and was purified using a silica gel short pass column (developing liquid: dichloromethane). The solvent was distilled off under reduced pressure, and a crude product was washed using methanol and toluene. Thus, a compound (1.31 g) represented by formula (1-1247) was obtained as a white solid.

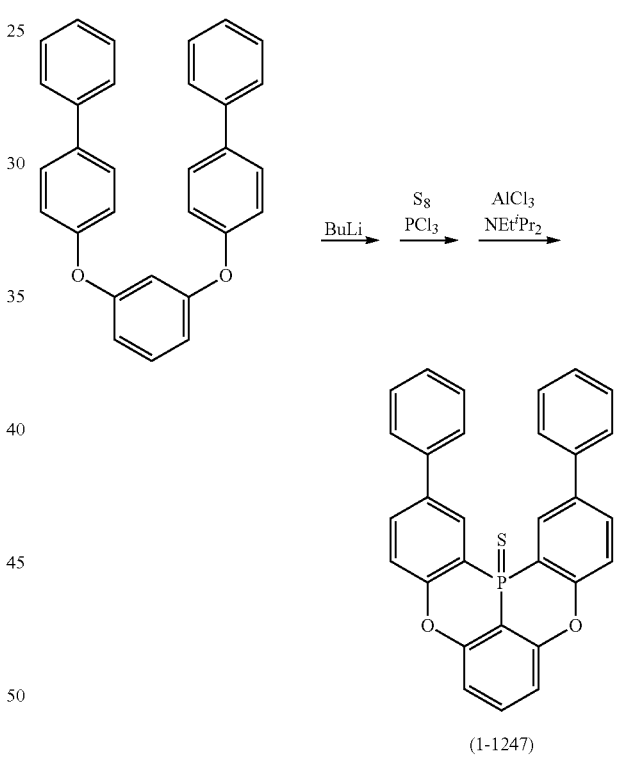

(1-1247)

The structure of the compound thus obtained was identified by an NMR analysis.

$^1$H NMR (δ ppm in CDCl$_3$); 7.17 (dd, J$_{HP}$=4 0.1 Hz, J=8.2 Hz, 2H), 7.41 (tt, J=1.4, 7.3 Hz, 2H), 7.46 (dd, J$_{HP}$=2.3 Hz, J=8.7 Hz, 2H), 7.49 (dd, J=7.3, 8.0 Hz, 4H), 7.57 (t, J=8.2 Hz 1H), 7.63 (d, J=8.0 Hz, 4H), 7.78 (dd, J=2.3, 8.7 Hz, 2H), 8.39 (dd J=2.3 Hz, J$_{HP}$=13.5 Hz, 2H).

$^{13}$C NMR (δ ppm in CDCl$_3$); 102.4 (d, J$_{CP}$=82.4 Hz), 112.9 (d, J$_{CP}$=4.8 Hz, 2C), 120.1 (d, J$_{CP}$=92 Hz, 2C), 120.3 (d, J$_{CP}$=6.7 Hz 2C), 127.0 (4C), 127.5 (d, J$_{CP}$=5.8 Hz, 2C), 127.9 (2C), 129.1 (4C), 131.7 (J$_{CP}$=1.9 Hz, 2C), 133.3, 138.5 (J$_{CP}$=11.5 Hz, 2C), 139.3 (2C), 155.1 (J$_{CP}$=2.9 Hz, 2C), 156.2 (2C).

Synthesis Example (46)

Synthesis of 2,12-diphenyl-5,9-dioxa-13b-oxophos-phanaphtho[3,2,1-de]anthracene

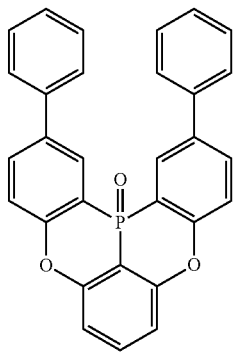

(1-1187)

m-Chloroperbenzoic acid (1.16 g, 77 wt %, 5.16 mmol) at 0° C. was added to the compound represented by formula (1-1247) (2.45 g, 5.17 mmol) and dichloromethane (500 mL), and the mixture was stirred at room temperature. After 5 hours, m-chloroperbenzoic acid (0.350 g, 77 wt %, 1.56 mmol) was added thereto at 0° C., and the mixture was stirred at room temperature. After 16 hours, a saturated solution of sodium sulfite (20.0 ml) was added thereto, and the mixture was stirred at room temperature. A dichloromethane layer was separated, and then the aqueous layer was extracted with dichloromethane. The organic layers thus obtained were combined and concentrated, and then the combined organic layer was purified using a silica gel short pass column using dichloromethane and dichloromethane/ethyl acetate=1 (volume ratio) as developing solvents. A filtrate thus obtained was distilled off under reduced pressure, and thus a compound (2.32 g) represented by formula (1-1187) was obtained.

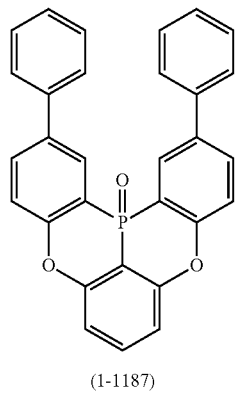

(1-1187)

The structure of the compound thus obtained was identified by an NMR analysis.

$^1$H NMR (δ ppm in CDCl$_3$); 7.20 (dd, J$_{HP}$=4.1 Hz, J=8.5 Hz, 2H), 7.41 (tt, J=1.4, 7.4 Hz, 2H), 7.48 (d, J=7.4 Hz, 2H), 7.52 (d, J=8.7, Hz, 4H), 7.62 (dd, J=1.4, 7.5 Hz, 4H), 7.64 (t, J=8.5 Hz, 1H), 7.83 (dd, J=2.2, 8.7 Hz, 2H), 8.41 (dd, J$_{HP}$=12.4 Hz, J=2.2 Hz, 2H).

$^{13}$C NMR (δ ppm in CDCl$_3$); 103.6 (d, J$_{CP}$=97.8 Hz), 112.4 (d, J$_{CP}$=4.8 Hz, 2C), 118.0 (d, J$_{CP}$=116.0 Hz, 2C), 120.5 (d, J$_{CP}$=6.7 Hz, 2C), 127.1 (4C), 127.5 (d, J$_{CP}$=5.8 Hz, 2C), 128.0 (2C), 129.2 (4C), 132.6 (2C), 134.3, 138.0 (d, J$_{CP}$=10.5 Hz, 2C), 139.5 (2C), 156.8 (2C), 156.8 (d, J$_{CP}$=6.9 Hz, 2C).

Synthesis Example (47)

Synthesis of 3,6,8,11-tetraphenyl-5,9-dioxa-13b-thiophosphanaphtho[3,2,1-de]anthracene

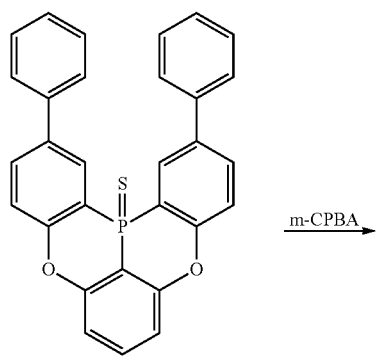

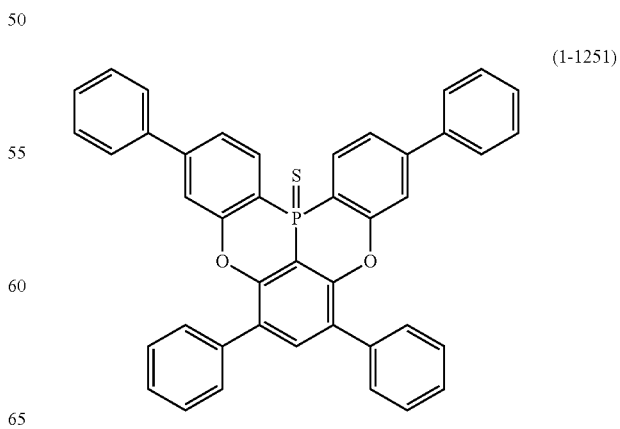

(1-1251)

First, a hexane solution of butyllithium (12.2 mL, 1.64 M, 20.0 mmol) was added to 4',6'-bis([1,1'-biphenyl-3-yloxy])-5'-bromo-1,1':3',1''-terphenyl (12.9 g, 20.0 mmol) and benzene (70 mL), at 0° C. in a nitrogen atmosphere, and the mixture was stirred for 2 hours. Phosphorus trichloride (1.92 mL, 22.0 mmol) was added thereto at 0° C., and the mixture was stirred for one hour at 80° C. The solvent was distilled off under reduced pressure, sulfur (0.768 g, 24.0 mmol) and o-dichlorobenzene (60 mL) were added thereto, and the mixture was stirred for one hour at 80° C. Aluminum trichloride (18.7 g, 140 mmol) at −95° C. and N,N-diisopropylethylamine (8.20 mL, 48.0 mmol) at 0° C. were added thereto, and the mixture was stirred for 16 hours at 100° C. The mixture was cooled to room temperature, and then the reaction liquid was added to a dichloromethane (300 ml) solution of 1,4-diazabicyclo[2.2.2]octane (31.4 g, 280 mmol). Subsequently, the mixture was suction filtered using a glass filter covered with Celite, and the filtrate was concentrated under reduced pressure and was diluted using toluene. Insoluble materials were removed by filtration. The solvent of the filtrate was distilled off under reduced pressure, and then the residue was purified using a silica gel short pass column (developing liquid: dichloromethane). The solvent was distilled off under reduced pressure, and then the residue was purified using a silica gel short pass column (developing liquid: toluene). The solvent was distilled off under reduced pressure, and a crude product was washed using acetonitrile and hexane. Thus, a compound (1.22 g) represented by formula (1-1251) was obtained as a white solid.

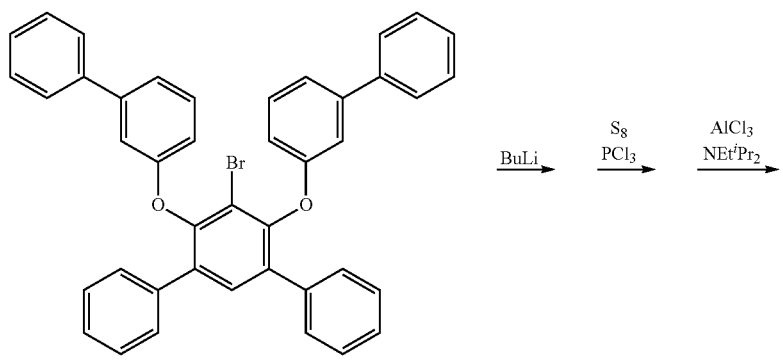

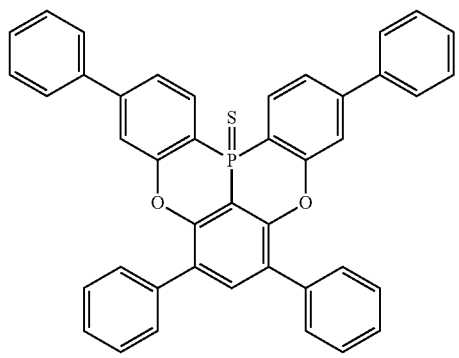

(1-1251)

The structure of the compound thus obtained was identified by an NMR analysis.

$^1$H NMR (δ ppm in CDCl$_3$); 7.40-7.50 (m, 10H), 7.52 (dd, J=7.2 Hz, 7.6 Hz, 4H), 7.59 (d, J=7.2 Hz, 4H), 7.63 (ddd, J$_{HP}$=1.8 Hz, J=1.8 Hz, 8.0 Hz, 2H), 7.67-7.70 (m, 5H), 8.26 (dd, J$_{HP}$=12.8 Hz, J=8.0 Hz, 2H).

$^{13}$C NMR (δ ppm in CDCl$_3$); 103.5 (d, J$_{CP}$=80.5 Hz), 117.9 (d, J$_{CP}$=93.9 Hz, 2C), 118.2 (d, J$_{CP}$=5.8 Hz, 2C), 124.2 (d, J$_{CP}$=11.5 Hz, 2C), 126.9 (d, J$_{CP}$=5.8 Hz, 2C), 127.3 (4C), 127.7 (2C), 128.4 (4C), 128.6 (2C), 129.0 (4C), 129.3 (d, J$_{CP}$=5.8 Hz, 2C), 129.6 (4C), 135.9, 136.1 (2C), 139.0 (2C), 146.3 (2C), 151.7 (2C), 156.1 (2C).

Synthesis Example (48)

Synthesis of 3,6,8,11-tetraphenyl-5,9-dioxa-13b-oxophosphanaphtho[3,2,1-de]anthracene

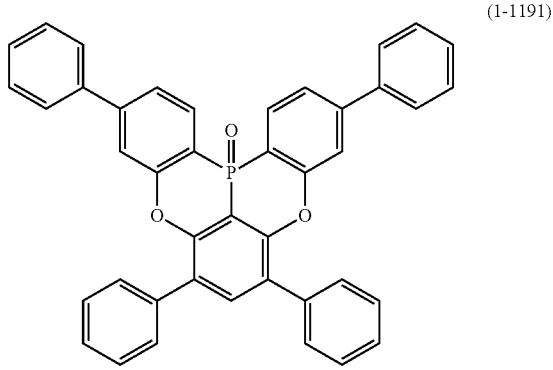 [SMILES: O=P12c3ccc(-c4ccccc4)cc3Oc3c(-c4ccccc4)cc(-c4ccccc4)c(c31)Oc1cc(-c3ccccc3)ccc12]

(1-1191)

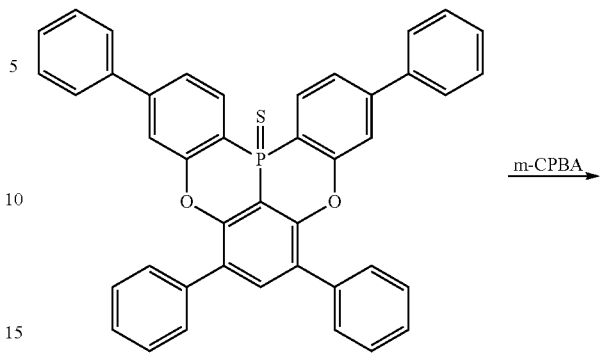

m-CPBA

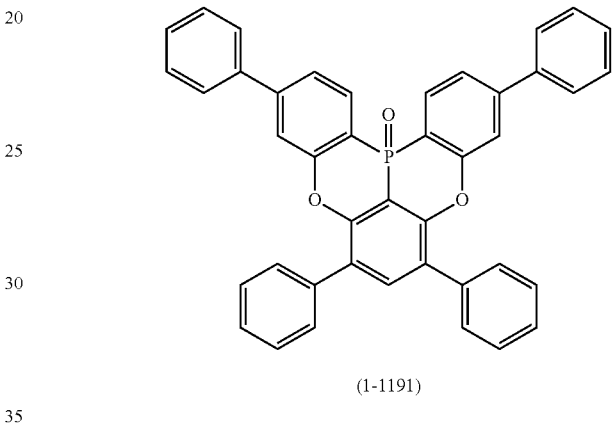

(1-1191)

m-Chloroperbenzoic acid (0.404 g, 77 wt %, 1.79 mmol) at 0° C. was added to the compound represented by the above formula (1-1251) (1.12 g, 1.79 mmol) and dichloromethane (150 mL), and the mixture was stirred at room temperature. After 5 hours, m-chloroperbenzoic acid (0.674 g, 77 wt %, 0.391 mmol) was added thereto at 0° C., and the mixture was stirred at room temperature. After 16 hours, a saturated solution of sodium sulfite (10 ml) and water (40 ml) were added thereto, and the mixture was stirred at room temperature. Insoluble materials were removed by filtration, a dichloromethane layer was separated, and then the aqueous layer was extracted with dichloromethane. The organic layers thus obtained were combined and concentrated, and then the combined organic layer was subjected to a silica gel short pass column using dichloromethane and dichloromethane/ethyl acetate=1 (volume ratio) as developing solvents. The solvent of the filtrate was distilled off under reduced pressure. A crude product thus obtained was washed using methanol, and thus a compound (1.04 g) represented by formula (1-1191) was obtained as a white solid.

The structure of the compound thus obtained was identified by an NMR analysis.

$^1$H NMR (δ ppm in CDCl); 7.40-7.50 (m, 10H), 7.53 (t, J=7.1 Hz, 4H), 7.61 (d, J=6.9 Hz, 4H), 7.64 (dt, J$_{HP}$=1.9 Hz, J=1.9 Hz, 8.0 Hz, 2H), 7.69 (d, J=7.1 Hz, 4H), 7.77 (s, 1H), 8.32 (dd, J$_{HP}$=11.7 Hz, J=8.0 Hz, 2H).

$^{13}$C NMR (δ ppm in CDCl); 104.3 (d, J$_{CP}$=96.8 Hz), 115.9 (d, J$_{CP}$=117.9 Hz, 2C), 118.2 (d, J$_{CP}$=5.8 Hz, 2C), 123.5 (d, J$_{CP}$=10.5 Hz, 2C), 126.3 (d, J$_{CP}$=4.8 Hz, 2C), 127.3 (4C), 127.7 (2C), 128.5 (4C), 128.6 (2C), 129.0 (4C), 129.6 (4C), 129.7 (d, J$_{CP}$=8.6 Hz, 2C), 136.1, 136.7 (2C), 139.0 (2C), 146.9 (2C), 152.2 (2C), 157.7 (2C).

Other polycyclic aromatic compounds of the present invention can be synthesized by methods according to the Synthesis Examples described above, by appropriately changing the compounds of raw materials.

Hereinafter, various Examples will be described in order to explain the present invention in more detail, but the present invention is not intended to be limited to these.

Organic EL elements related to Examples 1 and 2 were produced, and the external quantum efficiency obtainable when each of the organic EL elements was driven at a current density capable of giving a luminance of 100 cd/m$^2$ was measured. The material configurations of the various layers in the organic EL elements thus produced are shown in the following Table 1.

TABLE 1

| | Hole Injection Layer 1 (65 nm) | Hole Injection Layer 2 (5 nm) | Hole Transport Layer (60 nm) | Light Emitting Layer (25 nm) Host | Light Emitting Layer (25 nm) Dopant | Electron Transport Layer 2 (20 nm) | Electron Transport Layer 1 (10 nm) | Negative Electrode (1 nm/100 nm) |
|---|---|---|---|---|---|---|---|---|
| Ex. 1 | HI | HAT-CN | HT | BH1 | Compound (1-176) | ET2 | ET1 | LiF/Al |
| Ex. 2 | HI | HAT-CN | HT | BH1 | Compound (1-100) | ET2 | ET1 | LiF/Al |

In Table 1, "HI" means $N^4,N^{4'}$-diphenyl-$N^4,N^{4'}$-bis(9-phenyl-9H-carbazol-3-yl)-[1,1'-biphenyl]-4,4'-diamine; "HAT-CN" means 1,4,5,8,9,12-hexaazatriphenylenehexacarbonitrile; "HT" means N-([1,1'-biphenyl]-4-yl)-N-(4-(9-phenyl-9H-carbazol-3-yl)phenyl)-[1,1'-biphenyl]-4-amine; "BH1" means 9-phenyl-10-(4-phenylnaphthalen-1-yl)anthracene; "ET2" means 9-(4'-(dimesitylboryl)-[1,1'-binaphthalen]-4-yl)-9H-carbazole; and "ET1" means 5,5"-(2-phenylanthracene-9,10-diyl)di-2,2'-bipyridine (the same in the following tables). Chemical structures thereof are shown below.

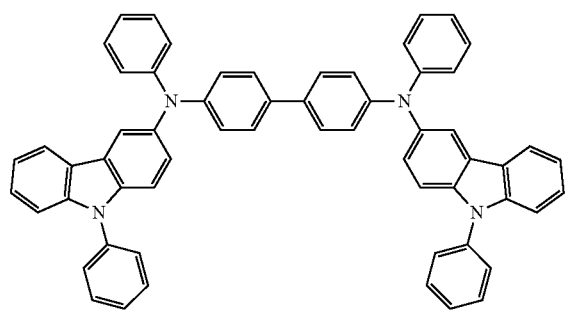

HI

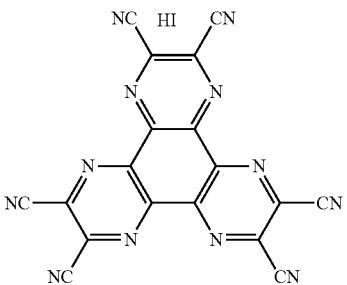

HAT-CN

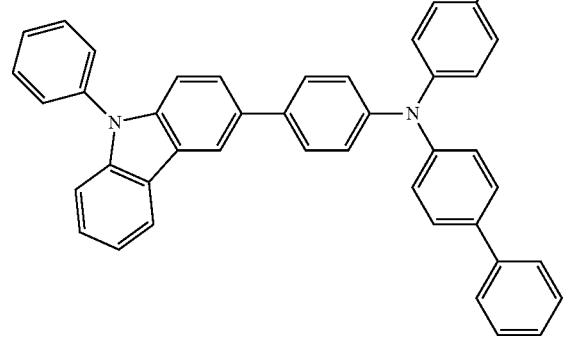

HT

-continued

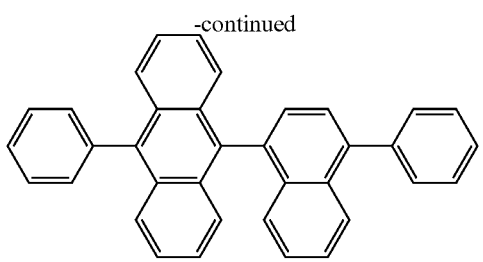

BH1

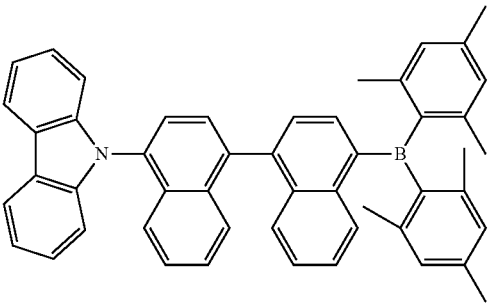

ET-2

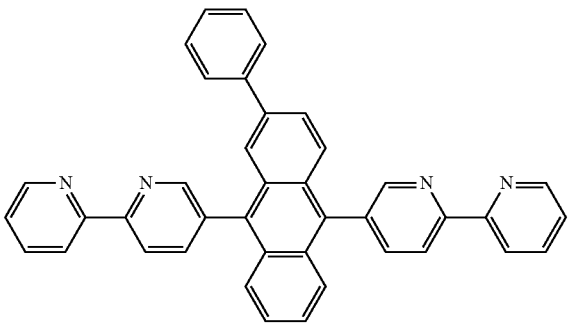

ET-1

Example 1

Element Using Compound (1-176) as Dopant Material of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Showa Shinku Co., Ltd.), and a vapor deposition boat made of molybdenum and containing HI, a vapor deposition boat made of molybdenum and containing HAT- CN, a vapor deposition boat made of molybdenum and containing HT, a vapor deposition boat made of molybdenum and containing BH1, a vapor deposition boat made of molybdenum and containing compound (1-176) of the present invention, a vapor deposition boat made of molybdenum and containing ET2, a vapor deposition boat made of molybdenum and containing ET1, a vapor deposition boat made of molybdenum and containing LiF, and a vapor deposition boat made of tungsten and containing aluminum, were mounted in the apparatus.

Various layers as described below were formed sequentially on the ITO film of the transparent supporting substrate. The pressure in a vacuum chamber was reduced to 5×10⁻⁴ Pa, and first, a hole injection layer 1 was formed by heating the vapor deposition boat containing HI and thereby performing vapor deposition to obtain a film thickness of 65 nm. Subsequently, a hole injection layer 2 was formed by heating the vapor deposition boat containing HAT-CN and thereby performing deposition to obtain a film thickness of 5 nm. Furthermore, a hole transport layer was formed by heating the vapor deposition boat containing HT and thereby performing deposition to obtain a film thickness of 60 nm. Next, a light emitting layer was formed by simultaneously heating the vapor deposition boat containing BH1 and the vapor deposition boat containing compound (1-176) and thereby performing deposition to obtain a film thickness of 25 nm. The rate of deposition was regulated such that the weight ratio of BH1 and the compound (1-176) would be approximately 80:20. Next, an electron transport layer 2 was formed by heating the vapor deposition boat containing ET2 and thereby conducting deposition to obtain a film thickness of 20 nm, and an electron transport layer 1 was formed by heating the vapor deposition boat containing ET1 and thereby performing deposition to obtain a film thickness of 10 nm. The rate of deposition for each layer was 0.01 to 1 nm/second.

Thereafter, the vapor deposition boat containing LiF was heated, and thereby vapor deposition was conducted at a rate of deposition of 0.01 to 0.1 nm/second so as to obtain a film thickness of 1 nm. Subsequently, a negative electrode was formed by heating the vapor deposition boat containing aluminum and thereby performing deposition at a rate of deposition of 0.01 to 2 nm/second so as to obtain a film thickness of 100 nm. Thus, an organic EL element was obtained.

When a direct current voltage was applied to the ITO electrode as the positive electrode and the LiF/aluminum electrode as the negative electrode, blue light emission having a peak top at about 437 nm was obtained. The external quantum efficiency at a luminance of 100 cd/m² was 3.39%.

Example 2

Element Using Compound (1-100) as Dopant Material of Light Emitting Layer

An organic EL element was obtained by a method equivalent to that of Example 1, except that the compound (1-176) as the dopant material of the light emitting layer was changed to compound (1-100). When a direct current voltage was applied to the two electrodes, blue light emission having a peak top at about 457 nm was obtained. The external quantum efficiency at a luminance of 100 cd/m² was 2.78%.

Furthermore, organic EL elements related to Examples 3 and 4 were produced, and the external quantum efficiency obtainable when each element was driven at a current density that could give a luminance of 100 cd/m², was measured. The material configurations of the various layers in the organic EL elements thus produced are shown in the following Table 2.

TABLE 2

|  | Hole Injection Layer (10 nm) | Hole Transport Layer (30 nm) | Light Emitting Layer (30 nm) Host | Light Emitting Layer (30 nm) Dopant | Electron Transport Layer (50 nm) | Negative Electrode (1 nm/100 nm) |
|---|---|---|---|---|---|---|
| Ex. 3 | HAT-CN | TBB | CBP | Compound (1-141) | TPBi | LiF/Al |
| Ex. 4 | HAT-CN | TBB | CBP | Compound (1-81) | TPBi | LiF/Al |

In Table 2, "TBB" means N⁴,N⁴,N⁴',N⁴'-tetra([1,1'-biphenyl]-4-yl)-[1,1'-biphenyl]-4,4'-diamine; "CBP" means 4,4'-di(9H-carbazolyl-9-yl)-1,1'-biphenyl; and "TPBi" means 1,3,5-tris(1-phenyl-1H-benzo[d]imidazol-2-yl)benzene. The chemical structures thereof are shown below.

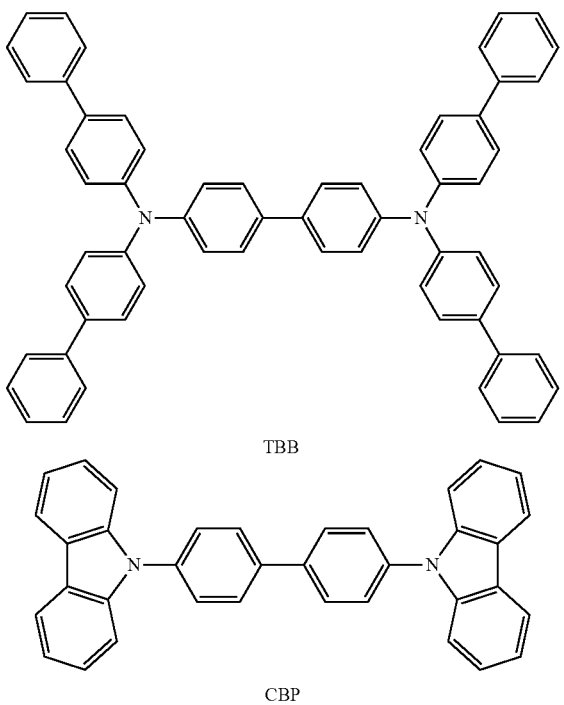

TBB

CBP

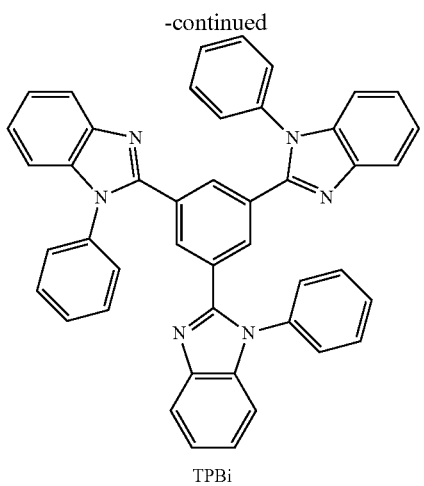

TPBi

Example 3

Element Using Compound (1-141) as Dopant Material of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Showa Shinku Co., Ltd.), and a vapor deposition boat made of molybdenum and containing HAT-CN, a vapor deposition boat made of molybdenum and containing TBB, a vapor deposition boat made of molybdenum and containing CBP, a vapor deposition boat made of molybdenum and containing compound (1-141) of the present invention, a vapor deposition boat made of molybdenum and containing TPBi, a vapor deposition boat made of molybdenum and containing LiF, and a vapor deposition boat made of tungsten and containing aluminum, were mounted in the apparatus.

Various layers as described below were formed sequentially on the ITO film of the transparent supporting substrate. The pressure in a vacuum chamber was reduced to 5×10$^{-4}$ Pa, and first, a hole injection layer was formed by heating the vapor deposition boat containing HAT-CN and thereby performing vapor deposition to obtain a film thickness of 10 nm. Subsequently, a hole transport layer was formed by heating the vapor deposition boat containing TBB and thereby performing deposition to obtain a film thickness of 30 nm. Next, a light emitting layer was formed by simultaneously heating the vapor deposition boat containing CBP and the vapor deposition boat containing compound (1-141) and thereby performing deposition to obtain a film thickness of 30 nm. The rate of deposition was regulated such that the weight ratio of CBP and the compound (1-141) would be approximately 80:20. Next, an electron transport layer was formed by heating the vapor deposition boat containing TPBi and thereby performing deposition to obtain a film thickness of 50 nm. The rate of deposition for each layer was 0.01 to 1 nm/second.

Thereafter, the vapor deposition boat containing LiF was heated, and thereby vapor deposition was conducted at a rate of deposition of 0.01 to 0.1 nm/second so as to obtain a film thickness of 1 nm. Subsequently, a negative electrode was formed by heating the vapor deposition boat containing aluminum and thereby performing deposition at a rate of deposition of 0.01 to 2 nm/second so as to obtain a film thickness of 100 nm. Thus, an organic EL element was obtained.

When a direct current voltage was applied to the ITO electrode as the positive electrode and the LiF/aluminum electrode as the negative electrode, green light emission having a peak top at about 534 nm was obtained. The external quantum efficiency at a luminance of 100 cd/m$^2$ was 6.29%.

Example 4

Element Using Compound (1-81) as Dopant Material of Light Emitting Layer

An organic EL element was obtained by a method equivalent to that of Example 3, except that the compound (1-141) as the dopant material of the light emitting layer was changed to compound (1-81). When a direct current voltage was applied to the two electrodes, green light emission having a peak top at about 512 nm was obtained. The external quantum efficiency at a luminance of 100 cd/m$^2$ was 8.37%.

Furthermore, an organic EL element related to Example 5 was produced, and the external quantum efficiency obtainable when the organic EL element was driven at a current density that could give a luminance of 1000 cd/m$^2$ or 100 cd/m$^2$, was measured. The material configurations of the various layers in the organic EL element thus produced are shown in the following Table 3.

TABLE 3

| | Hole Injection Layer (10 nm) | Hole Transport Layer (30 nm) | Light Emitting Layer (30 nm) | | Electron Transport Layer (50 nm) | Negative Electrode (1 nm/100 nm) |
|---|---|---|---|---|---|---|
| | | | Host | Dopant | | |
| Ex. 5 | HAT-CN | TBB | Compound (1-91) | Ir(PPy)$_3$ | TPBi | LiF/Al |

In Table 3, "Ir(PPy)$_3$" means tris(2-phenylpyridine) iridium(III). The chemical structure thereof is shown below.

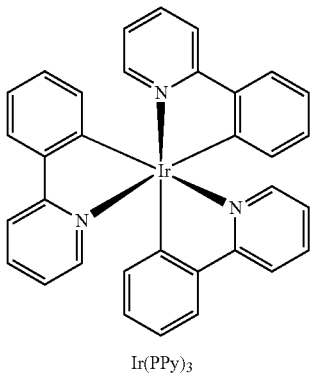

Ir(PPy)$_3$

Example 5

Element Using Compound (1-91) as Host Material of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Showa Shinku Co., Ltd.), and a vapor deposition boat made of molybdenum and containing HAT-CN, a vapor deposition boat made of molybdenum and containing TBB, a vapor deposition boat made of molybdenum and containing compound (1-91) of the present invention, a vapor deposition boat made of molybdenum and containing Ir(PPy)$_3$, a vapor deposition boat made of molybdenum and containing TPBi, a vapor deposition boat made of molybdenum and containing LiF, and a vapor deposition boat made of tungsten and containing aluminum, were mounted in the apparatus.

Various layers as described below were formed sequentially on the ITO film of the transparent supporting substrate. The pressure in a vacuum chamber was reduced to 5×10$^{-4}$ Pa, and first, a hole injection layer was formed by heating the vapor deposition boat containing HAT-CN and thereby performing vapor deposition to obtain a film thickness of 10 nm. Subsequently, a hole transport layer was formed by heating the vapor deposition boat containing TBB and thereby performing deposition to obtain a film thickness of 30 nm. Next, a light emitting layer was formed by simultaneously heating the vapor deposition boat containing compound (1-91) and the vapor deposition boat containing Ir(PPy)$_3$ and thereby performing deposition to obtain a film thickness of 30 nm. The rate of deposition was regulated such that the weight ratio of the compound (1-91) and Ir(PPy)$_3$ would be approximately 95:5. Next, an electron transport layer was formed by heating the vapor deposition boat containing TPBi and thereby performing deposition to obtain a film thickness of 50 nm. The rate of deposition for each layer was 0.01 to 1 nm/second.

Thereafter, the vapor deposition boat containing LiF was heated, and thereby vapor deposition was conducted at a rate of deposition of 0.01 to 0.1 nm/second so as to obtain a film thickness of 1 nm. Subsequently, a negative electrode was formed by heating the vapor deposition boat containing aluminum and thereby performing deposition at a rate of deposition of 0.01 to 2 nm/second so as to obtain a film thickness of 100 nm. Thus, an organic EL element was obtained.

When a direct current voltage was applied to the ITO electrode as the positive electrode and the LiF/aluminum electrode as the negative electrode, green light emission having a peak top at about 512 nm was obtained. The external quantum efficiency at a luminance of 1000 cd/m$^2$ was 10.88%. Also, the external quantum efficiency at a luminance of 100 cd/m$^2$ was 14.76%.

Furthermore, organic EL elements related to Examples 6 to 14 were produced, and the external quantum efficiency obtainable when each of the organic EL elements was driven at a current density that could give a luminance of 1000 cd/m$^2$ or 100 cd/m$^2$, was measured. The material configurations of the various layers in the organic EL elements thus produced are shown in the following Table 4.

TABLE 4

| | Hole Injection Layer | Hole Transport Layer | Light Emitting Layer (30 nm) | | Electron Transport Layer | Negative Electrode |
|---|---|---|---|---|---|---|
| | (10 nm) | (30 nm) | Host | Dopant | (50 nm) | (1 nm/100 nm) |
| Ex. 6 | HAT-CN | TBB | Compound (1-152) | Ir(PPy)$_3$ | TPBi | LiF/Al |
| Ex. 7 | HAT-CN | TBB | Compound (1-1048) | Ir(PPy)$_3$ | TPBi | LiF/Al |
| Ex. 8 | HAT-CN | TBB | Compound (1-1049) | Ir(PPy)$_3$ | TPBi | LiF/Al |
| Ex. 9 | HAT-CN | TBB | Compound (1-1050) | Ir(PPy)$_3$ | TPBi | LiF/Al |
| Ex. 10 | HAT-CN | TBB | Compound (1-100) | Ir(PPy)$_3$ | TPBi | LiF/Al |
| Ex. 11 | HAT-CN | TBB | Compound (1-49) | Ir(PPy)$_3$ | TPBi | LiF/Al |
| Ex. 12 | HAT-CN | TBB | Compound (1-176) | Ir(PPy)$_3$ | TPBi | LiF/Al |
| Ex. 13 | HAT-CN | TBB | Compound (1-1069) | Ir(PPy)$_3$ | TPBi | LiF/Al |
| Ex. 14 | HAT-CN | TBB | Compound (1-1201) | Ir(PPy)$_3$ | TPBi | LiF/Al |

Example 6

Element Using Compound (1-152) as Host Material of Light Emitting Layer

An organic EL element was obtained by a method equivalent to that of Example 5, except that the compound (1-91) as the host material of the light emitting layer was changed to compound (1-152). When a direct current voltage was applied to the two electrodes, green light emission having a peak top at about 512 nm was obtained. The external quantum efficiency at a luminance of 1000 cd/m$^2$ was 9.36%. The external quantum efficiency at a luminance of 100 cd/m$^2$ was 13.26%.

Example 7

Element Using Compound (1-1048) as Host Material of Light Emitting Layer

An organic EL element was obtained by a method equivalent to that of Example 5, except that the compound (1-91) as the host material of the light emitting layer was changed to compound (1-1048). When a direct current voltage was applied to the two electrodes, green light emission having a peak top at about 512 nm was obtained. The external quantum efficiency at a luminance of 1000 cd/m$^2$ was 9.50%. The external quantum efficiency at a luminance of 100 cd/m$^2$ was 12.43%.

Example 8

Element Using Compound (1-1049) as Host Material of Light Emitting Layer

An organic EL element was obtained by a method equivalent to that of Example 5, except that the compound (1-91) as the host material of the light emitting layer was changed to compound (1-1049). When a direct current voltage was applied to the two electrodes, green light emission having a peak top at about 512 nm was obtained. The external quantum efficiency at a luminance of 1000 cd/m$^2$ was 6.54%. The external quantum efficiency at a luminance of 100 cd/m$^2$ was 7.44%.

Example 9

Element Using Compound (1-1050) as Host Material of Light Emitting Layer

An organic EL element was obtained by a method equivalent to that of Example 5, except that the compound (1-91) as the host material of the light emitting layer was changed to compound (1-1050). When a direct current voltage was applied to the two electrodes, green light emission having a peak top at about 512 nm was obtained. The external quantum efficiency at a luminance of 1000 cd/m$^2$ was 10.98%. The external quantum efficiency at a luminance of 100 cd/m$^2$ was 12.32%.

Example 10

Element Using Compound (1-100) as Host Material of Light Emitting Layer

An organic EL element was obtained by a method equivalent to that of Example 5, except that the compound (1-91) as the host material of the light emitting layer was changed to compound (1-100). When a direct current voltage was applied to the two electrodes, green light emission having a peak top at about 512 nm was obtained. The external quantum efficiency at a luminance of 1000 cd/m$^2$ was 5.73%. The external quantum efficiency at a luminance of 100 cd/m$^2$ was 8.75%.

Example 11

Element Using Compound (1-49) as Host Material of Light Emitting Layer

An organic EL element was obtained by a method equivalent to that of Example 5, except that the compound (1-91) as the host material of the light emitting layer was changed to compound (1-49). When a direct current voltage was applied to the two electrodes, green light emission having a peak top at about 512 nm was obtained. The external quantum efficiency at a luminance of 1000 cd/m$^2$ was 7.33%. The external quantum efficiency at a luminance of 100 cd/m$^2$ was 10.36%.

Example 12

Element Using Compound (1-176) as Host Material of Light Emitting Layer

An organic EL element was obtained by a method equivalent to that of Example 5, except that the compound (1-91) as the host material of the light emitting layer was changed to compound (1-176). When a direct current voltage was applied to the two electrodes, green light emission having a peak top at about 512 nm was obtained. The external quantum efficiency at a luminance of 1000 cd/m$^2$ was 10.74%. The external quantum efficiency at a luminance of 100 cd/m$^2$ was 11.77%.

Example 13

Element Using Compound (1-1069) as Host Material of Light Emitting Layer

An organic EL element was obtained by a method equivalent to that of Example 5, except that the compound (1-91) as the host material of the light emitting layer was changed to compound (1-1069). When a direct current voltage was applied to the two electrodes, green light emission having a peak top at about 512 nm was obtained. The external quantum efficiency at a luminance of 1000 cd/m$^2$ was 8.96%. The external quantum efficiency at a luminance of 100 cd/m$^2$ was 11.80%.

Example 14

Element Using Compound (1-1201) as Host Material of Light Emitting Layer

An organic EL element was obtained by a method equivalent to that of Example 5, except that the compound (1-91) as the host material of the light emitting layer was changed to compound (1-1201). When a direct current voltage was applied to the two electrodes, green light emission having a peak top at about 512 nm was obtained. The external quantum efficiency at a luminance of 1000 cd/m$^2$ was 10.14%. The external quantum efficiency at a luminance of 100 cd/m$^2$ was 12.17%.

Furthermore, organic EL elements related to Examples 15 and 16 were produced, and the external quantum efficiency obtainable when each of the organic EL elements was driven at a current density that could give a luminance of 1000 cd/m², was measured. The material configurations of the various layers in the organic EL elements thus produced are shown in the following Table 5.

TABLE 5

|  | Hole Injection Layer 1 | Hole Injection Layer 2 | Hole Transport Layer | Light Emitting Layer (20 nm) | | Electron Transport Layer 2 | Electron Transport Layer 1 | Negative Electrode |
|---|---|---|---|---|---|---|---|---|
|  | (40 nm) | (5 nm) | (25 nm) | Host | Dopant | (20 nm) | (10 nm) | (1 nm/100 nm) |
| Ex. 15 | HI | HAT-CN | HT | BH1 | Compound (1-1145) | ET2 | ET1 | LiF/Al |
| Ex. 16 | HI | HAT-CN | HT | BH1 | Compound (1-401) | ET2 | ET1 | LiF/Al |

Example 15

Element Using Compound (1-1145) as Dopant Material of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Showa Shinku Co., Ltd.), and a vapor deposition boat made of molybdenum and containing HI, a vapor deposition boat made of molybdenum and containing HAT-CN, a vapor deposition boat made of molybdenum and containing HT, a vapor deposition boat made of molybdenum and containing BH1, a vapor deposition boat made of molybdenum and containing compound (1-1145) of the present invention, a vapor deposition boat made of molybdenum and containing ET2, a vapor deposition boat made of molybdenum and containing ET1, a vapor deposition boat made of molybdenum and containing LiF, and a vapor deposition boat made of tungsten and containing aluminum, were mounted in the apparatus.

Various layers as described below were formed sequentially on the ITO film of the transparent supporting substrate. The pressure in a vacuum chamber was reduced to 5×10⁻⁴ Pa, and first, a hole injection layer 1 was formed by heating the vapor deposition boat containing HI and thereby performing vapor deposition to obtain a film thickness of 40 nm. Subsequently, a hole injection layer 2 was formed by heating the vapor deposition boat containing HAT-CN and thereby performing deposition to obtain a film thickness of 5 nm. Furthermore, a hole transport layer was formed by heating the vapor deposition boat containing HT and thereby performing deposition to obtain a film thickness of 25 nm. Next, a light emitting layer was formed by simultaneously heating the vapor deposition boat containing BH1 and the vapor deposition boat containing compound (1-1145) and thereby performing deposition to obtain a film thickness of 20 nm. The rate of deposition was regulated such that the weight ratio of BH1 and the compound (1-1145) would be approximately 95:5. Next, an electron transport layer 2 was formed by heating the vapor deposition boat containing ET2 and thereby performing deposition to obtain a film thickness of 20 nm, and an electron transport layer 1 was formed by heating the vapor deposition boat containing ET1 and thereby performing deposition to obtain a film thickness of 10 nm. The rate of deposition for each layer was 0.01 to 1 nm/second.

Thereafter, the vapor deposition boat containing LiF was heated, and thereby vapor deposition was conducted at a rate of deposition of 0.01 to 0.1 nm/second so as to obtain a film thickness of 1 nm. Subsequently, a negative electrode was formed by heating the vapor deposition boat containing aluminum and thereby performing deposition at a rate of deposition of 0.01 to 2 nm/second so as to obtain a film thickness of 100 nm. Thus, an organic EL element was obtained.

When a direct current voltage was applied to the ITO electrode as the positive electrode and the LiF/aluminum electrode as the negative electrode, blue light emission having a peak top at about 449 nm was obtained. The external quantum efficiency at a luminance of 1000 cd/m² was 4.75%.

Example 16

Element Using Compound (1-401) as Dopant Material of Light Emitting Layer

An organic EL element was obtained by a method equivalent to that of Example 15, except that the compound (1-1145) as the dopant material of the light emitting layer was changed to compound (1-401). When a direct current voltage was applied to the two electrodes, blue light emission having a peak top at about 458 nm was obtained. The external quantum efficiency at a luminance of 1000 cd/m² was 4.33%.

Furthermore, organic EL elements related to Examples 17 to 19 were produced, and the external quantum efficiency obtainable when each of the organic EL elements was driven at a current density that could give a luminance of 1000 cd/m², was measured. The material configurations of the various layers in the organic EL elements thus produced are shown in the following Table 6.

TABLE 6

| | Hole Injection Layer | Hole Transport Layer 1 | Hole Transport Layer 2 | Light Emitting Layer (30 nm) | | Electron Transport Layer | Negative Electrode |
|---|---|---|---|---|---|---|---|
| | (10 nm) | (20 nm) | (10 nm) | Host | Dopant | (50 nm) | (1 nm/100 nm) |
| Ex. 17 | HAT-CN | TBB | TcTa | Compound (1-1101) | Ir(PPy)$_3$ | TPBi | LiF/Al |
| Ex. 18 | HAT-CN | TBB | TcTa | Compound (1-1102) | Ir(PPy)$_3$ | TPBi | LiF/Al |
| Ex. 19 | HAT-CN | TBB | TcTa | Compound (1-1103) | Ir(PPy)$_3$ | TPBi | LiF/Al |

In Table 6, "TcTa" means tris(4-carbazolyl-9-ylphenyl) amine. The chemical structure thereof is shown below.

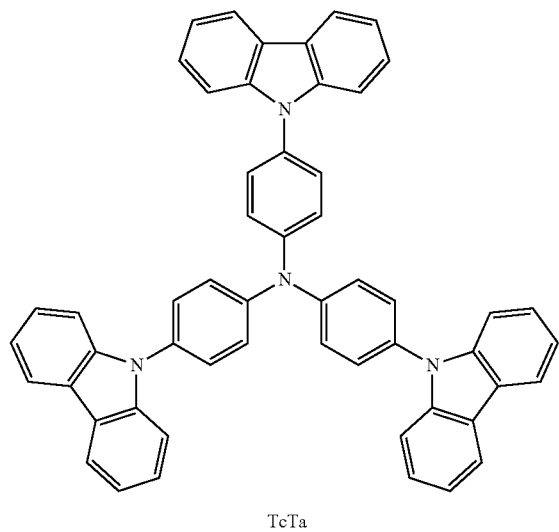 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1 ; "TcTa"]

TcTa

Example 17

Element Using Compound (1-1101) as Host Material of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition crucible made of tantalum and containing HAT-CN, a vapor deposition crucible made of tantalum and containing TBB, a vapor deposition crucible made of tantalum and containing TcTa, a vapor deposition crucible made of tantalum and containing compound (1-1101) of the present invention, a vapor deposition crucible made of tantalum and containing Ir(PPy)$_3$, a vapor deposition crucible made of tantalum and containing TPBi, a vapor deposition crucible made of tantalum and containing LiF, and a vapor deposition crucible made of aluminum nitride and containing aluminum, were mounted in the apparatus.

Various layers as described below were formed sequentially on the ITO film of the transparent supporting substrate. The pressure in a vacuum chamber was reduced to 2.0×10$^{-4}$ Pa. First, the vapor deposition crucible containing HAT-CN was heated, and thereby vapor deposition was performed so as to obtain a film thickness of 10 nm. Subsequently, the vapor deposition crucible containing TBB was heated, and thereby vapor deposition was performed so as to obtain a film thickness of 20 nm. Further, the vapor deposition crucible containing TcTa was heated, and thereby vapor deposition was performed so as to obtain a film thickness of 20 nm. Thus, hole injection layers and hole transport layers composed of three layers were formed. Next, the vapor deposition crucible containing compound (1-1101) of the present invention and the vapor deposition crucible containing Ir(PPy)$_3$ were simultaneously heated, and thereby vapor deposition was performed so as to obtain a film thickness of 30 nm. Thus, a light emitting layer was formed. The rate of deposition was regulated such that the weight ratio of the compound (1-1101) of the present invention and Ir(PPy)$_3$ would be approximately 95:5. Next, the vapor deposition crucible containing TPBi was heated, and thereby vapor deposition was performed so as to obtain a film thickness of 50 nm. Thus, an electron transport layer was formed. The rate of deposition for each layer was 0.01 to 1 nm/second.

Thereafter, the vapor deposition crucible containing LiF was heated, and thereby vapor deposition was performed at a rate of deposition of 0.01 to 0.1 nm/second so as to obtain a film thickness of 1 nm. Subsequently, the vapor deposition crucible containing aluminum was heated, and thereby vapor deposition was performed so as to obtain a film thickness of 100 nm. Thus, a negative electrode was formed. At this time, the negative electrode was formed by performing vapor deposition at a rate of deposition of 0.1 nm/sec to 2 nm/sec, and thus an organic electroluminescent element was obtained.

When a direct current voltage was applied to the ITO electrode as the positive electrode and the LiF/aluminum electrode as the negative electrode, green light emission having a peak top at about 512 nm was obtained. The external quantum efficiency at a luminance of 1000 cd/m$^2$ was 10.09%.

Example 18

Element Using Compound (1-1102) as Host Material of Light Emitting Layer

An organic EL element was obtained by a method equivalent to that of Example 17, except that the compound (1-1101) as the host material of the light emitting layer was changed to compound (1-1102). When a direct current voltage was applied to the two electrodes, green light emission having a peak top at about 512 nm was obtained. The external quantum efficiency at a luminance of 1000 cd/m$^2$ was 7.99%.

Example 19

Element Using Compound (1-1103) as Host Material of Light Emitting Layer

An organic EL element was obtained by a method equivalent to that of Example 17, except that the compound (1-1101) as the host material of the light emitting layer was changed to compound (1-1103). When a direct current voltage was applied to the two electrodes, green light emission having a peak top at about 512 nm was obtained. The external quantum efficiency at a luminance of 1000 cd/m$^2$ was 9.05%.

Furthermore, organic EL elements related to Examples 20 and 21 were produced, and the external quantum efficiency obtainable when each of the organic EL elements was driven at a current density that could give a luminance of 1000 cd/m$^2$, was measured. The material configurations of the various layers in the organic EL elements thus produced are shown in the following Table 7.

TABLE 7

|  | Hole Injection Layer | Hole Transport Layer 1 | Hole Transport Layer 2 | Light Emitting Layer (30 nm) | | Electron Transport Layer 1 | Electron Transport Layer 2 | Negative Electrode |
|---|---|---|---|---|---|---|---|---|
|  | (10 nm) | (20 nm) | (10 nm) | Host | Dopant | | | (1 nm/100 nm) |
| Ex. 20 | HAT-CN | TBB | TcTa | CBP | Ir(PPy)$_3$ | Compound (1-1192) 50 nm | — | LiF/Al |
| Ex. 21 | HAT-CN | TBB | TcTa | CBP | Ir(PPy)$_3$ | Compound (1-1192) 10 nm | ET-3 40 nm | LiF/Al |

In Table 7, "ET-3" means 3-(3-10-(naphthalen-2-yl)anthracen-9-yl)phenyl)pyridine. The chemical structure thereof is shown below.

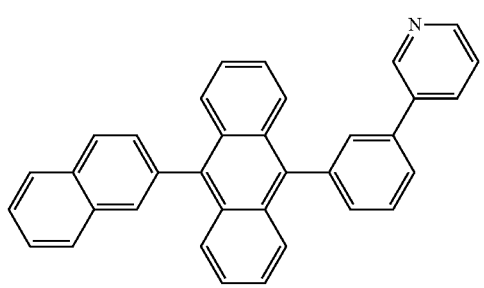

ET-3

Example 20

Element Using Compound (1-1192) in Electron Transport Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition crucible made of tantalum and containing HAT-CN, a vapor deposition crucible made of tantalum and containing TBB, a vapor deposition crucible made of tantalum and containing TcTa, a vapor deposition crucible made of tantalum and containing CBP, a vapor deposition crucible made of tantalum and containing Ir(PPy)$_3$, a vapor deposition crucible made of tantalum and containing compound (1-1192) of the present invention, a vapor deposition crucible made of tantalum and containing ET-3, a vapor deposition crucible made of tantalum and containing LiF, and a vapor deposition crucible made of aluminum nitride and containing aluminum, were mounted in the apparatus.

Various layers as described below were formed sequentially on the ITO film of the transparent supporting substrate. The pressure in a vacuum chamber was reduced to 2.0×10$^{-4}$ Pa. First, the vapor deposition crucible containing HAT-CN was heated, and thereby vapor deposition was performed so as to obtain a film thickness of 10 nm. Subsequently, the vapor deposition crucible containing TBB was heated, and thereby vapor deposition was performed so as to obtain a film thickness of 20 nm. Further, the vapor deposition crucible containing TcTa was heated, and thereby vapor deposition was performed so as to obtain a film thickness of 10 nm. Thus, hole injection layers and hole transport layers composed of three layers were formed. Next, the vapor deposition crucible containing CBP and the vapor deposition crucible containing Ir(PPy)$_3$ were simultaneously heated, and thereby vapor deposition was performed so as to obtain a film thickness of 30 nm. Thus, a light emitting layer was formed. The rate of deposition was regulated such that the weight ratio of CBP and Ir(PPy)$_3$ would be approximately 95:5. Next, the vapor deposition crucible containing the compound (1-1192) of the present invention was heated, and thereby vapor deposition was performed so as to obtain a film thickness of 50 nm. Thus, an electron transport layer was formed. The rate of deposition for each layer was 0.01 to 1 nm/second.

Thereafter, the vapor deposition crucible containing LiF was heated, and thereby vapor deposition was performed at a rate of deposition of 0.01 to 0.1 nm/second so as to obtain a film thickness of 1 nm. Subsequently, the vapor deposition crucible containing aluminum was heated, and thereby vapor deposition was performed so as to obtain a film thickness of 100 nm. Thus, a negative electrode was formed. At this time, the negative electrode was formed by performing vapor deposition at a rate of deposition of 0.1 nm/sec to 2 nm/sec, and thus an organic electroluminescent element was obtained.

When a direct current voltage was applied to the ITO electrode as the positive electrode and the LiF/aluminum electrode as the negative electrode, green light emission having a peak top at about 512 nm was obtained. The external quantum efficiency at a luminance of 1000 cd/m² was 13.49%.

Example 21

Element Using Compound (1-1192) in Electron Transport Layer 1 and ET-3 in Electron Transport Layer 2

An organic EL element was obtained by a method equivalent to that of Example 20, except that the compound (1-1192) was deposited to a thickness of 10 nm as an electron transport layer 1, and then ET-3 was deposited to a thickness of 40 nm as an electron transport layer 2 so that the electron transport layer was changed to two layers. When a direct current voltage was applied to the two electrodes, green light emission having a peak top at about 512 nm was obtained. The external quantum efficiency at a luminance of 1000 cd/m² was 11.54%.

Furthermore, an organic EL element related to Example 22 was produced, and the external quantum efficiency obtainable when the organic EL element was driven at a current density that could give a luminance of 1000 cd/m², was measured. The material configurations of the various layers in the organic EL element thus produced is shown in the following Table 8.

Example 22

Element Using Compound (1-447) as Dopant of Light Emitting Layer

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition crucible made of tantalum and containing HI, a vapor deposition crucible made of tantalum and containing HAT-CN, a vapor deposition crucible made of tantalum and containing HT, a vapor deposition crucible made of tantalum and containing BH2, a vapor deposition crucible made of tantalum and containing compound (1-447) of the present invention, a vapor deposition crucible made of tantalum and containing ET-4, a vapor deposition crucible made of tantalum and containing ET-3, a vapor deposition crucible made of tantalum and containing LiF, and a vapor deposition crucible made of aluminum nitride and containing aluminum, were mounted in the apparatus.

TABLE 8

| | Hole Injection Layer 1 | Hole Injection Layer 2 | Hole Transport Layer | Light Emitting Layer (20 nm) | | Electron Transport | Electron Transport Layer 2 | Negative Electrode |
|---|---|---|---|---|---|---|---|---|
| | (40 nm) | (5 nm) | (25 nm) | Host | Dopant | Layer 1 (20 nm) | (10 nm) | (1 nm/100 nm) |
| Ex. 22 | HI | HAT-CN | HT | BH2 | Compound(1-447) | ET-4 | ET-3 | LiF/Al |

In Table 8, "BH2" means 1,3-di(pyren-1-yl)benzene, and "ET-4" means 3,9-di(naphthalen-2-yl)spiro[benzo[a]fluorene-11,9'-fluoren e]. The chemical structures thereof are shown below.

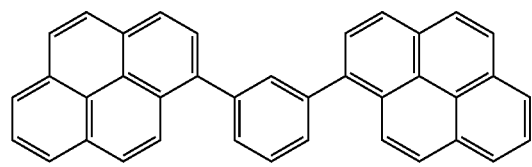

BH2

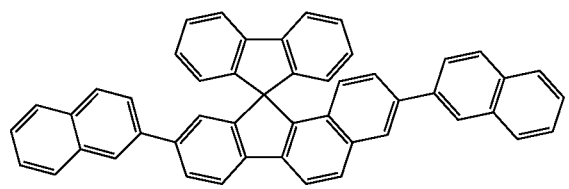

ET-4

Various layers as described below were formed sequentially on the ITO film of the transparent supporting substrate. The pressure in a vacuum chamber was reduced to 2.0×10⁻⁴ Pa. First, the vapor deposition crucible containing HI was heated, and thereby vapor deposition was performed so as to obtain a film thickness of 40 nm. Subsequently, the vapor deposition crucible containing HAT-CN was heated, and thereby vapor deposition was performed so as to obtain a film thickness of 5 nm. Further, the vapor deposition crucible containing HT was heated, and thereby vapor deposition was performed so as to obtain a film thickness of 25 nm. Thus, hole injection layers and hole transport layers composed of three layers were formed. Next, the vapor deposition crucible containing BH2 and the vapor deposition crucible containing the compound (1-447) of the present invention were simultaneously heated, and thereby vapor deposition was performed so as to obtain a film thickness of 20 nm. Thus, a light emitting layer was formed. The rate of deposition was regulated such that the weight ratio of BH2 and compound (1-447) of the present invention would be approximately 95:5. Next, the vapor deposition crucible containing ET-4 was heated, and thereby vapor deposition was performed so as to obtain a film thickness of 20 nm. Subsequently, the vapor deposition crucible containing ET-3 was heated, and thereby vapor deposition was performed so as to obtain a film thickness of 10 nm. Thus, an electron transport layer composed of two layers was formed. The rate of deposition for each layer was 0.01 to 1 nm/second.

Thereafter, the vapor deposition crucible containing LiF was heated, and thereby vapor deposition was performed at a rate of deposition of 0.01 to 0.1 nm/second so as to obtain a film thickness of 1 nm. Subsequently, the vapor deposition crucible containing aluminum was heated, and thereby vapor deposition was performed so as to obtain a film thickness of 100 nm. Thus, a negative electrode was formed. At this time, the negative electrode was formed by performing vapor deposition at a rate of deposition of 0.1 nm/sec to 2 nm/sec, and thus an organic electroluminescent element was obtained.

When a direct current voltage was applied to the ITO electrode as the positive electrode and the LiF/aluminum electrode as the negative electrode, blue light emission having a peak top at about 457 nm was obtained. The external quantum efficiency at a luminance of 1000 cd/m$^2$ was 6.15%.

Furthermore, organic EL elements related to Examples 23 to 27 were produced, and the external quantum efficiency obtainable when each of the organic EL elements was driven at a current density that could give a luminance of 1000 cd/m$^2$, was measured. The material configurations of the various layers in the organic EL elements thus produced are shown in the following Table 9.

Example 23

Element Using Compound (1-50) in Electron Transport Layer 1 and ET-1 in Electron Transport Layer 2

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Choshu Industry Co., Ltd.), and a vapor deposition crucible made of tantalum and containing HI, a vapor deposition crucible made of tantalum and containing HAT-CN, a vapor deposition crucible made of tantalum and containing HT, a vapor deposition crucible made of tantalum and containing BH1, a vapor deposition crucible made of tantalum and containing BD1, a vapor deposition crucible made of tantalum and containing the compound (1-50) of the present invention, a vapor deposition crucible made of

TABLE 9

| | Hole Injection Layer 1 (40 nm) | Hole Injection Layer 2 (5 nm) | Hole Transport Layer (25 nm) | Light Emitting Layer (20 nm) Host | Light Emitting Layer (20 nm) Dopant | Electron Transport Layer 1 (20 nm) | Electron Transport Layer 2 (10 nm) | Negative Electrode (1 nm/100 nm) |
|---|---|---|---|---|---|---|---|---|
| Ex. 23 | HI | HAT-CN | HT | BH1 | BD1 | Compound (1-50) | ET-1 | LiF/Al |
| Ex. 24 | HI | HAT-CN | HT | BH1 | BD1 | Compound (1-49) | ET-1 | LiF/Al |
| Ex. 25 | HI | HAT-CN | HT | BH1 | BD1 | Compound (1-50) | ET-3 | LiF/Al |
| Ex. 26 | HI | HAT-CN | HT | BH1 | BD1 | Compound (1-49) | ET-3 | LiF/Al |
| Ex. 27 | HI | HAT-CN | HT | BH1 | BD1 | Compound (1-50) (30 nm) | — | LiF/Al |
| Ex. 28 | HI | HAT-CN | HT | BH1 | BD1 | Compound (1-1050) (30 nm) | — | LiF/Al |
| Ex. 29 | HI | HAT-CN | HT | BH1 | BD1 | Compound (1-1102) (30 nm) | — | LiF/Al |
| Ex. 30 | HI | HAT-CN | HT | BH1 | BD1 | Compound (1-1050) | ET-1 | LiF/Al |
| Ex. 31 | HI | HAT-CN | HT | BH1 | BD1 | Compound (1-1102) | ET-1 | LiF/Al |

In Table 9, "BD1" means 7,7-dimethyl-N$^5$,N$^9$-diphenyl-N$^5$,N$^9$-bis(4-(trimethylsilyl)phen yl)-7H-benzo[c]fluorene-5,9-diamine. The chemical structure thereof is shown below.

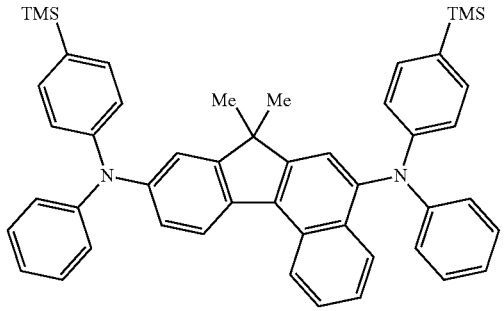

BD1 tantalum and containing ET-1, a vapor deposition crucible made of tantalum and containing ET-3, a vapor deposition crucible made of tantalum and containing LiF, and a vapor deposition crucible made of aluminum nitride and containing aluminum, were mounted in the apparatus.

Various layers as described below were formed sequentially on the ITO film of the transparent supporting substrate. The pressure in a vacuum chamber was reduced to 2.0×10$^{-4}$ Pa. First, the vapor deposition crucible containing HI was heated, and thereby vapor deposition was performed so as to obtain a film thickness of 40 nm. Subsequently, the vapor deposition crucible containing HAT-CN was heated, and thereby vapor deposition was performed so as to obtain a film thickness of 5 nm. Further, the vapor deposition crucible containing HT was heated, and thereby vapor deposition was performed so as to obtain a film thickness of 25 nm. Thus, hole injection layers and hole transport layers composed of three layers were formed. Next, the vapor deposition crucible containing BH1 and the vapor deposition crucible containing BD1 were simultaneously heated, and thereby vapor deposition was performed so as to obtain a film thickness of 20 nm. Thus, a light emitting layer was formed. The rate of deposition was regulated such that the weight ratio of BH1 and BD1 would be approximately 95:5. Next, the vapor deposition crucible containing the compound (1-50) of the present invention was heated, and thereby vapor deposition was performed so as to obtain a film thickness of 20 nm. Subsequently, the vapor deposition crucible containing ET-1 was heated, and thereby vapor deposition was performed so as to obtain a film thickness of 10 nm. Thus, an electron transport layer composed of two layers was formed. The rate of deposition for each layer was 0.01 to 1 nm/second.

Thereafter, the vapor deposition crucible containing LiF was heated, and thereby vapor deposition was performed at a rate of deposition of 0.01 to 0.1 nm/second so as to obtain a film thickness of 1 nm. Subsequently, the vapor deposition crucible containing aluminum was heated, and thereby vapor deposition was performed so as to obtain a film thickness of 100 nm. Thus, a negative electrode was formed. At this time, the negative electrode was formed by performing vapor deposition at a rate of deposition of 0.1 nm/sec to 2 nm/sec, and thus an organic electroluminescent element was obtained.

When a direct current voltage was applied to the ITO electrode as the positive electrode and the LiF/aluminum electrode as the negative electrode, blue light emission having a peak top at about 456 nm was obtained. The external quantum efficiency at a luminance of 1000 cd/m$^2$ was 8.08%.

Example 24

Element Using Compound (1-49) in Electron Transport Layer 1 and ET-1 in Electron Transport Layer 2

An organic EL element was obtained by a method equivalent to that of Example 23, except that the material of the electron transport layer 1 was changed to compound (1-49). When a direct current voltage was applied to the two electrodes, blue light emission having a peak top at about 456 nm was obtained. The external quantum efficiency at a luminance of 1000 cd/m$^2$ was 8.86%.

Example 25

Element Using Compound (1-50) in Electron Transport Layer 1 and ET-3 in Electron Transport Layer 2

An organic EL element was obtained by a method equivalent to that of Example 23, except that the material of the electron transport layer 2 was changed to ET-3. When a direct current voltage was applied to the two electrodes, blue light emission having a peak top at about 456 nm was obtained. The external quantum efficiency at a luminance of 1000 cd/m$^2$ was 8.16%.

Example 26

Element Using Compound (1-49) in Electron Transport Layer 1 and ET-3 in Electron Transport Layer 2

An organic EL element was obtained by a method equivalent to that of Example 23, except that the material of the electron transport layer 1 was changed to the compound (1-49), and the material of the electron transport layer 2 to ET-3. When a direct current voltage was applied to the two electrodes, blue light emission having a peak top at about 456 nm was obtained. The external quantum efficiency at a luminance of 1000 cd/m$^2$ was 8.94%.

Example 27

Element Using Compound (1-50) in Electron Transport Layer 1

An organic EL element was obtained by a method equivalent to that of Example 23, except that the electron transport layer 2 was removed, and the film thickness of the electron transport layer 1 was changed to 30 nm. When a direct current voltage was applied to the two electrodes, blue light emission having a peak top at about 456 nm was obtained. The external quantum efficiency at a luminance of 1000 cd/m$^2$ was 4.63%.

Example 28

Element Using Compound (1-1050) in Electron Transport Layer 1

An organic EL element was obtained by a method equivalent to that of Example 23, except that the electron transport layer 2 was removed, and the film thickness of the electron transport layer 1 was changed to 30 nm. When a direct current voltage was applied to the two electrodes, blue light emission having a peak top at about 456 nm was obtained. The external quantum efficiency at a luminance of 1000 cd/m$^2$ was 3.39%.

Example 29

Element Using Compound (1-1102) in Electron Transport Layer 1

An organic EL element was obtained by a method equivalent to that of Example 23, except that the electron transport layer 2 was removed, and the film thickness of the electron transport layer 1 was changed to 30 nm. When a direct current voltage was applied to the two electrodes, blue light emission having a peak top at about 456 nm was obtained. The external quantum efficiency at a luminance of 1000 cd/m$^2$ was 4.54%.

Example 30

Element Using Compound (1-1050) in Electron Transport Layer 1 and ET-1 in Electron Transport Layer 2

An organic EL element was obtained by a method equivalent to that of Example 23, except that the material of the electron transport layer 1 was changed to compound (1-1050). When a direct current voltage was applied to the two electrodes, blue light emission having a peak top at about 456 nm was obtained. The external quantum efficiency at a luminance of 1000 cd/m$^2$ was 7.88%.

Example 31

Element Using Compound (1-1102) in Electron Transport Layer 1 and ET-1 in Electron Transport Layer 2

An organic EL element was obtained by a method equivalent to that of Example 23, except that the material of the electron transport layer 1 was changed to compound (1-1102). When a direct current voltage was applied to the two electrodes, blue light emission having a peak top at about 456 nm was obtained. The external quantum efficiency at a luminance of 1000 cd/m$^2$ was 8.54%.

INDUSTRIAL APPLICABILITY

According to the present invention, since a novel polycyclic aromatic compound is provided, the range of selection of the material for organic EL elements can be widened. Also, when a novel polycyclic aromatic compound is used as a material for an organic electroluminescent element, an excellent organic EL element, a display apparatus including the EL element, and a lighting apparatus including the EL element can be provided.

REFERENCE SIGNS LIST

100 Organic electroluminescent element
101 Substrate
102 Positive electrode
103 Hole injection layer
104 Hole transport layer
105 Light emitting layer
106 Electron transport layer
107 Electron injection layer
108 Negative electrode

The invention claimed is:

1. A polycyclic aromatic compound represented by the following general formula (2), or an oligomer of a polycyclic aromatic compound having plural structures each represented by the following general formula (2):

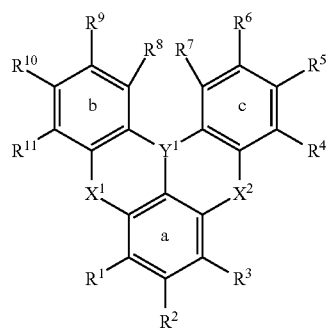

(2)

wherein in formula (2),
each of $R^4$, $R^5$, $R^6$, $R^7$, $R^8$, $R^9$, $R^{10}$ and $R^{11}$ is independently selected from a hydrogen atom, an aryl, a heteroaryl, a diarylamino, a diheteroarylamino, an arylheteroarylamino, an alkyl, an alkoxy or an aryloxy, wherein at least one hydrogen atom in these may be substituted by an aryl, a heteroaryl or an alkyl;
each of $R^1$, $R^2$ and $R^3$ is independently selected from a hydrogen atom, an aryl, a heteroaryl having 2-15 carbon atoms, a diarylamino, a diheteroarylamino, an arylheteroarylamino, an alkyl, an alkoxy or an aryloxy, wherein at least one hydrogen atom in these may be substituted by an aryl, a heteroaryl having 2-15 carbon atoms or an alkyl, or wherein adjacent groups among $R^1$ to $R^{11}$ are bonded to each other and form an aryl ring or a heteroaryl ring together with the ring a, ring b or ring c, wherein at least one hydrogen atom in the ring thus formed may be substituted by an aryl, a heteroaryl, a diarylamino, a diheteroarylamino, an arylheteroarylamino, an alkyl, an alkoxy or an aryloxy, and at least one hydrogen atom in these substituents may be substituted by an aryl, a heteroaryl or an alkyl;
for the polycyclic aromatic compound, $Y^1$ represents B or P=S, while for the oligomer, $Y^1$ represents B, P=O, or P=S;
when $Y^1$ represents B, $X^1$ and $X^2$ each independently represent O, N—R, S or Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$;
when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$; and
at least one hydrogen atom in the compound or structure represented by formula (2) may be substituted by a deuterium atom,
wherein the oligomer is in a form in which a plural number of the unit structures each represented by the general formula (2) are linked such that any ring contained in the unit structure is shared by the plural unit structures, or in a form in which a plural number of the unit structures each represented by the general formula (2) are linked such that any rings contained in the unit structures are fused.

2. The polycyclic aromatic compound of claim 1, which is represented by the following formula (1-21), the following formula (1-23), the following formula (1-24), the following formula (1-50), the following formula (1-152), the following formula (1-201), the following formula (1-401), the following formula (1-422), the following formula (1-1048), the following formula (1-1049), the following formula (1-1050), the following formula (1-1069), the following formula (1-1084), the following formula (1-1090), the following formula (1-1092), the following formula (1-1101), the following formula (1-1102), the following formula (1-1103), the following formula (1-1145), the following formula (1-1152), the following formula (1-1159), the following formula (1-1201), the following formula (1-1210), the following formula (1-1247), the following formula (1-1250), the following formula (1-1251), the following formula (1-1252), or the following formula (1-1271):
(1-21)
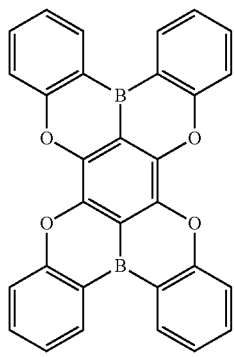
(1-23)
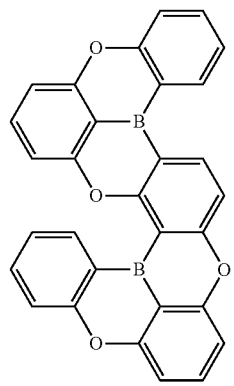
(1-24)
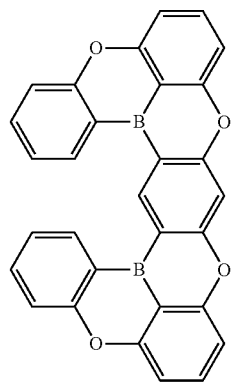
-continued
(1-50)
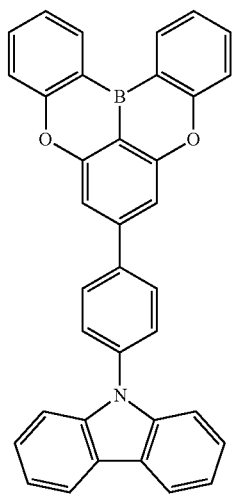
(1-152)
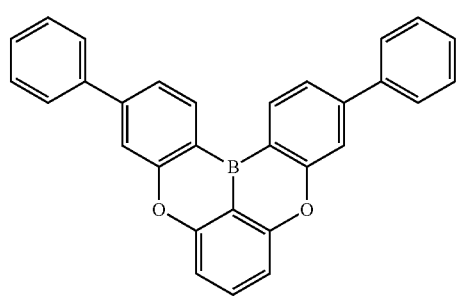
(1-201)
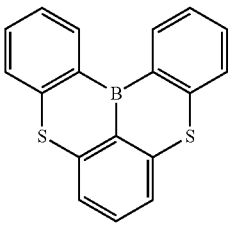
(1-401)
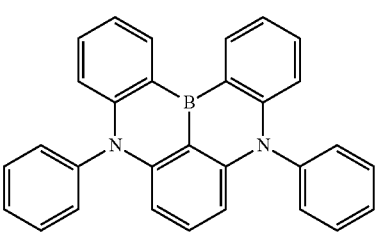

(1-422)
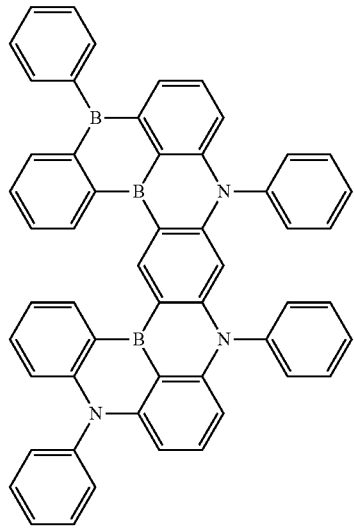
(1-1069)
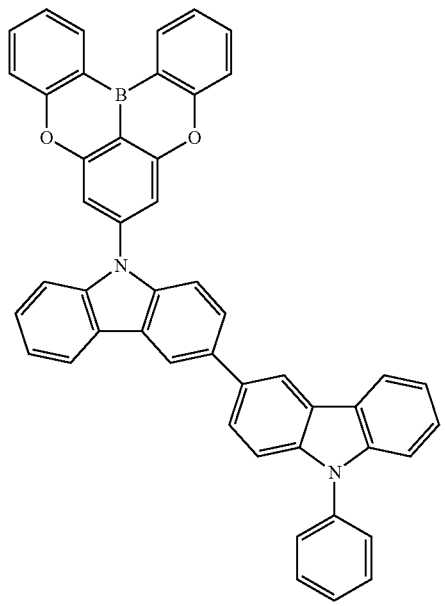
(1-1048)
(1-1049)
(1-1050)
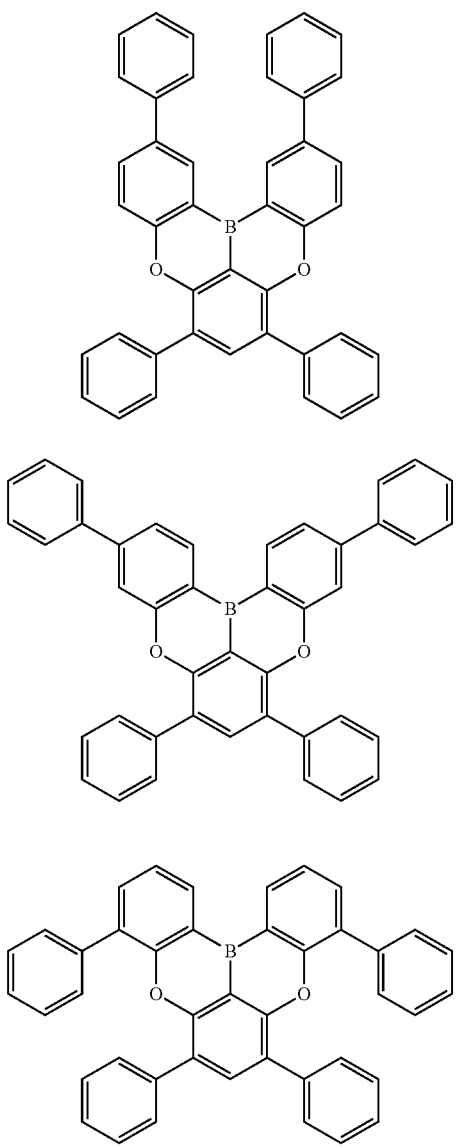
(1-1084)
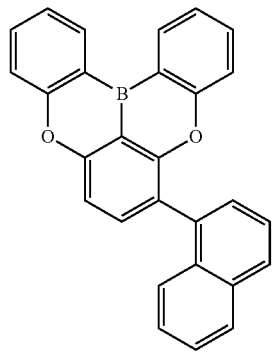
(1-1090)
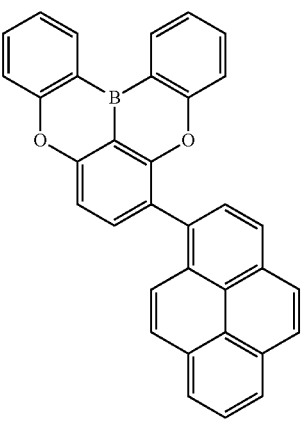

(1-1092)
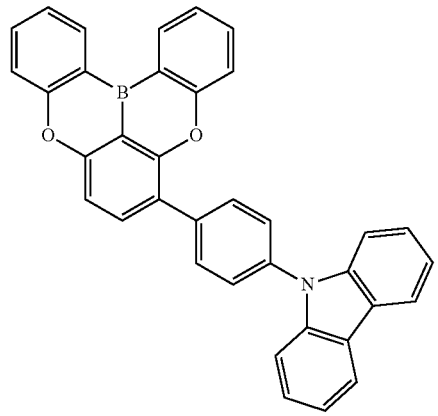
(1-1101)
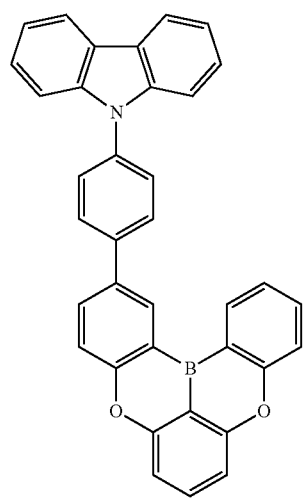
(1-1102)
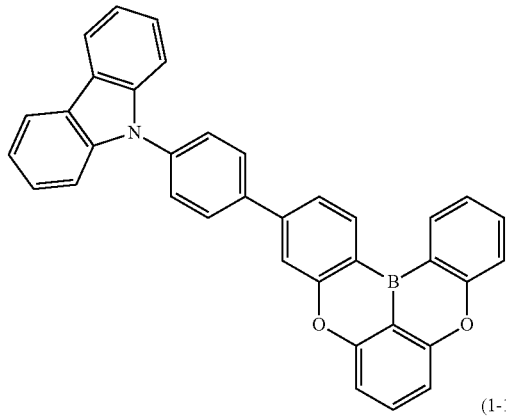
(1-1103)
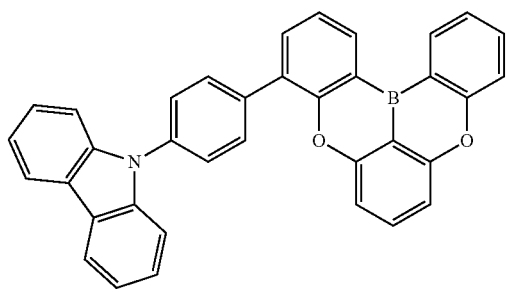
(1-1145)
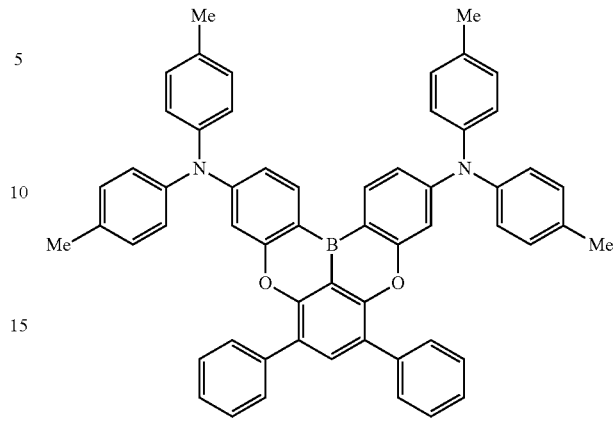
(1-1152)
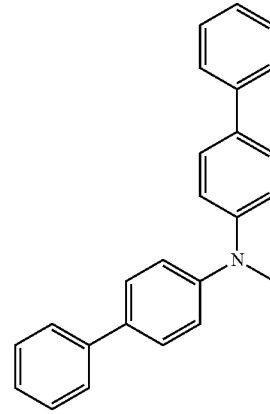
(1-1159)
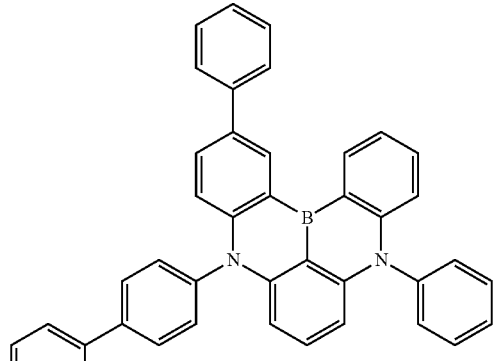
(1-1201)
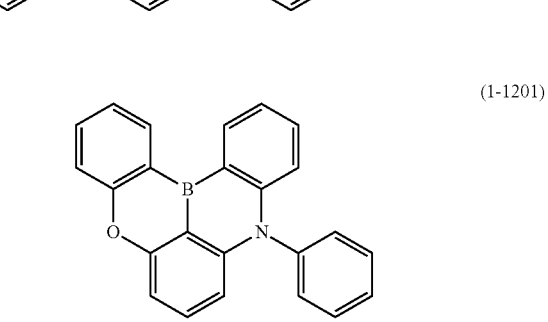

(1-1210)

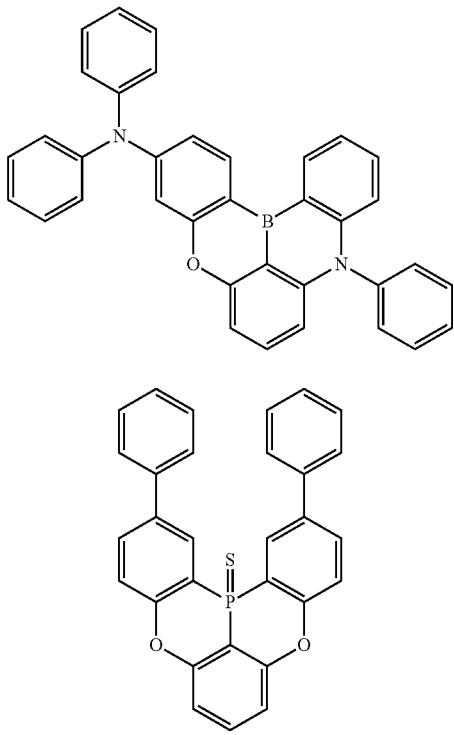

(1-1247)

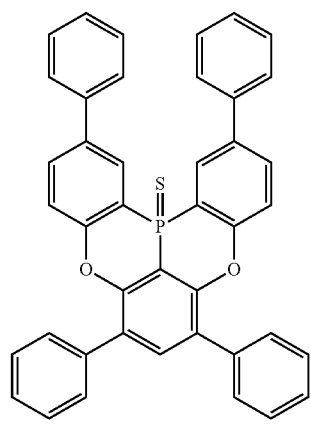

(1-1250)

(1-1251)

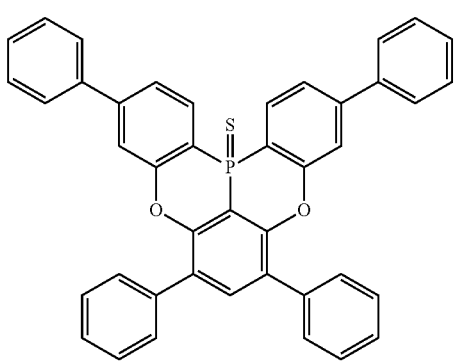

(1-1252)

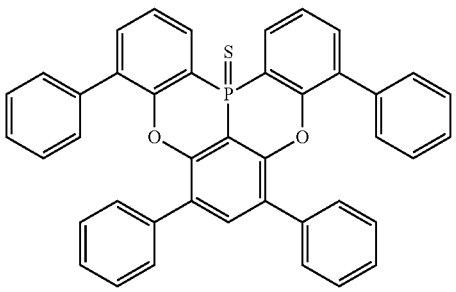

(1-1271)

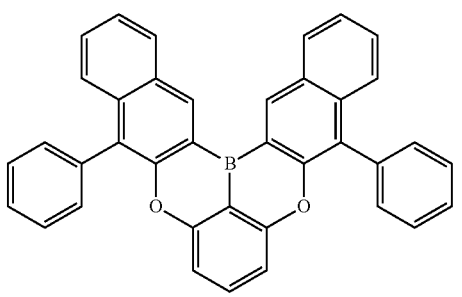

3. The polycyclic aromatic compound of claim 1, which is represented by the following formula (1-1-1), the following formula (1-79), the following formula (1-142), the following formula (1-152-2), the following formula (1-158), the following formula (1-159), the following formula (1-721), the following formula (1-1006), the following formula (1-1104), the following formula (1-1149), the following formula (1-1150), the following formula (1-1301), the following formula (1-1351), the following formula (1-2305), the following formula (1-2626), the following formula (1-2657), the following formula (1-2662), the following formula (1-2665), the following formula (1-2676), the following formula (1-2678), the following formula (1-2679), the following formula (1-2680), the following formula (1-2681), the following formula (1-2682), the following formula (1-2683), the following formula (1-2691), the following formula (1-2699), the following formula (1-4114), the following formula (1-4150), the following formula (1-4341), the following formula (1-4346), the following formula (1-4401), or the following formula (1-4421-1):

(1-1-1)

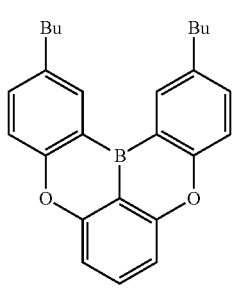

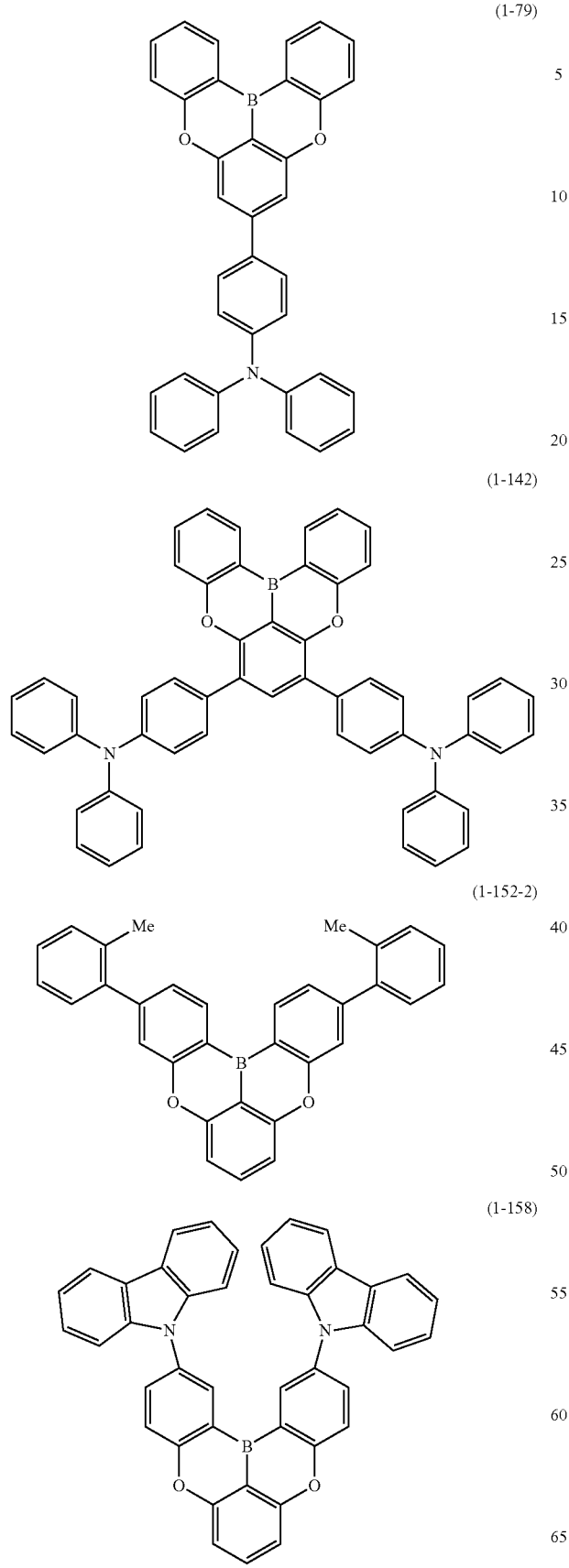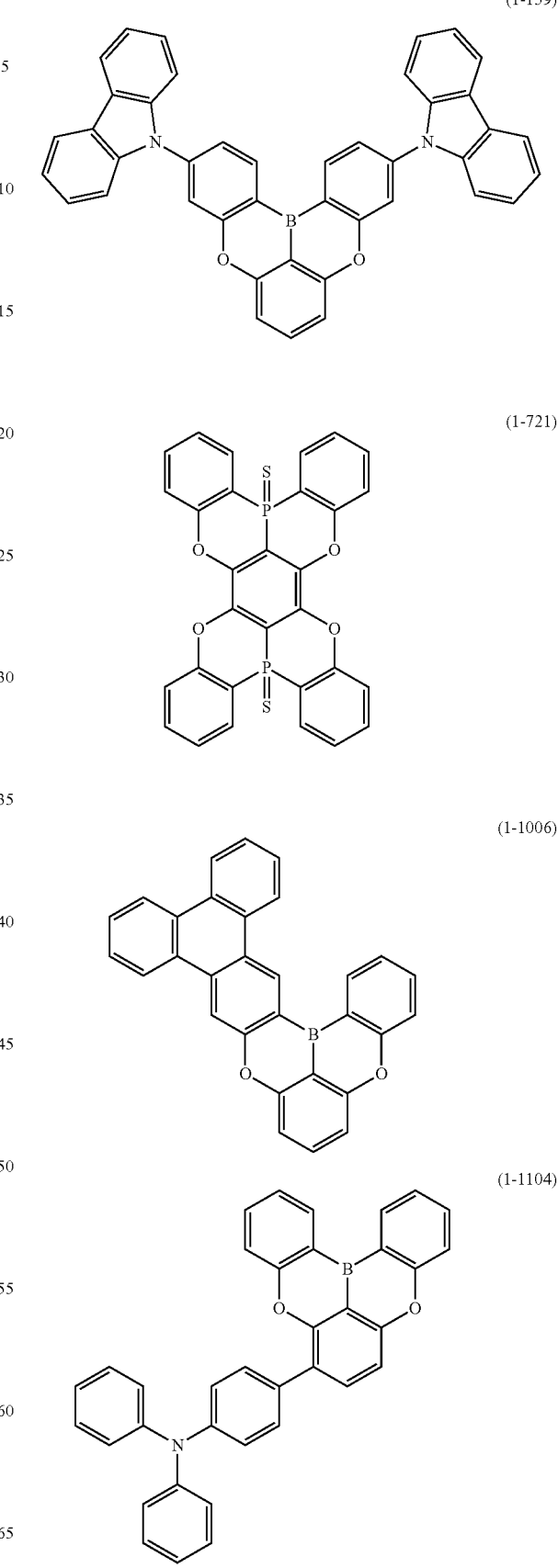

(1-1149)
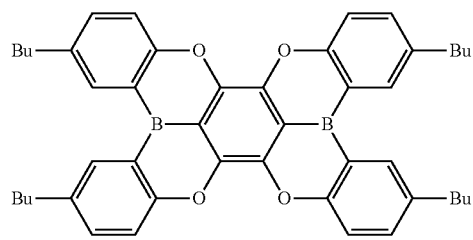
(1-2626)
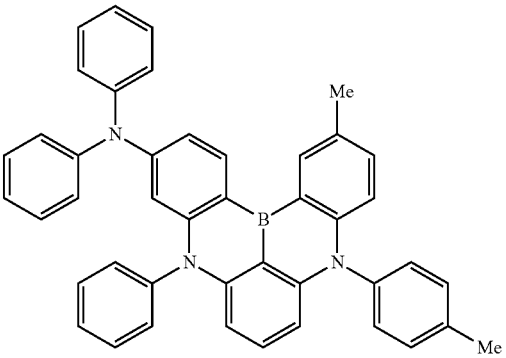
(1-1150)
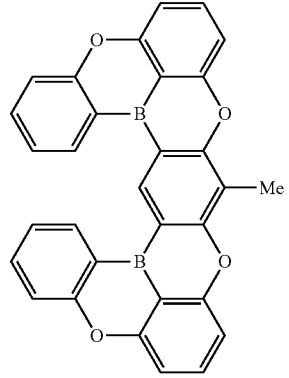
(1-2657)
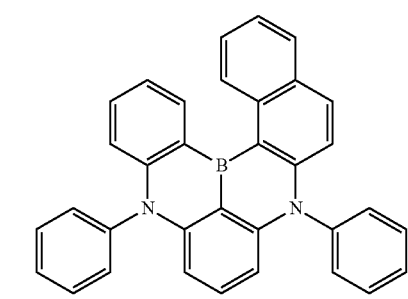
(1-1301)
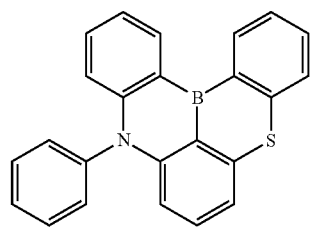
(1-1351)
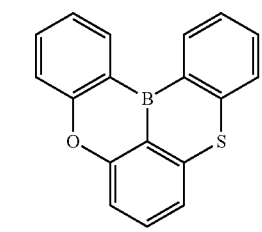
(1-2662)
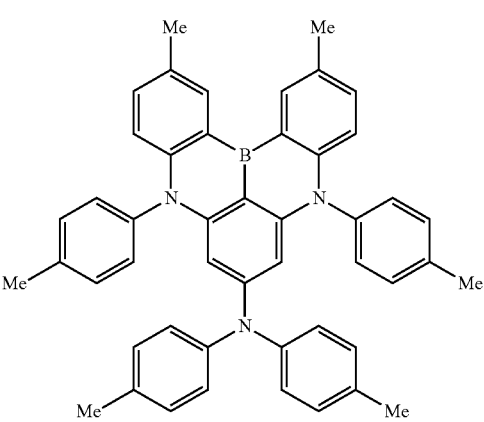
(1-2305)
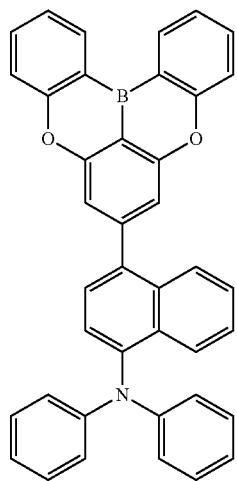
(1-2665)
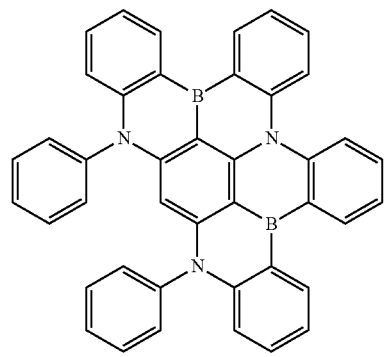

(1-2676)
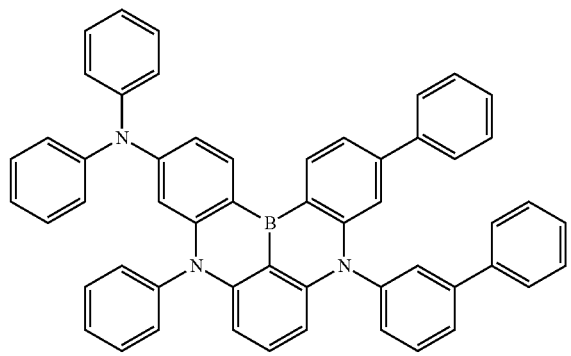
(1-2678)
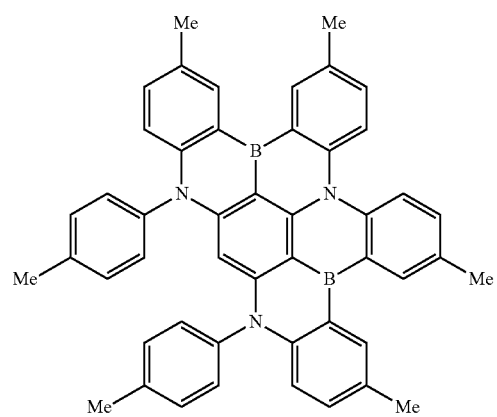
(1-2679)
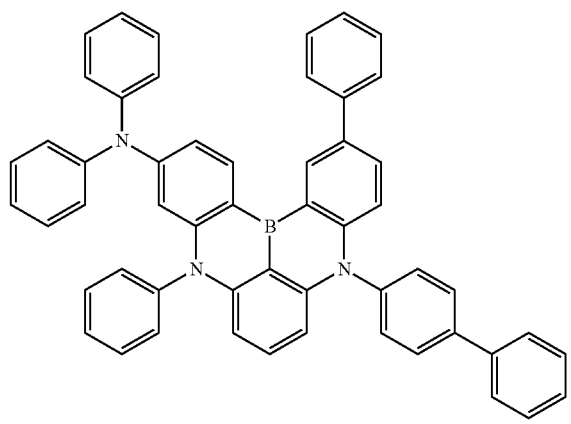
(1-2680)
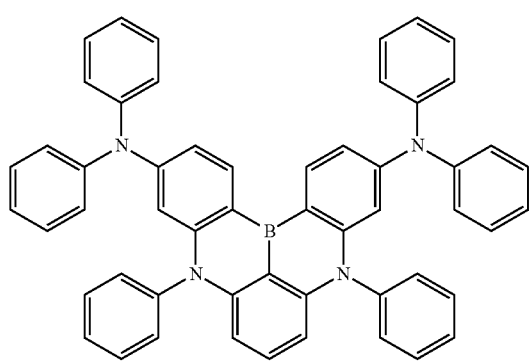
(1-2681)
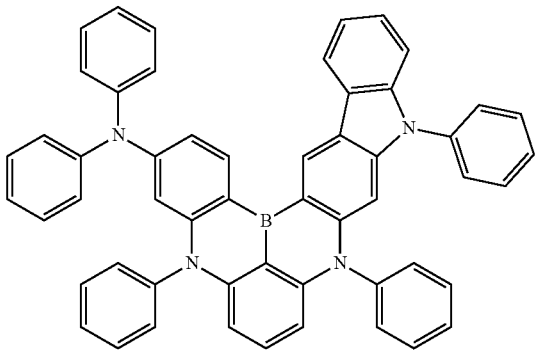
(1-2682)
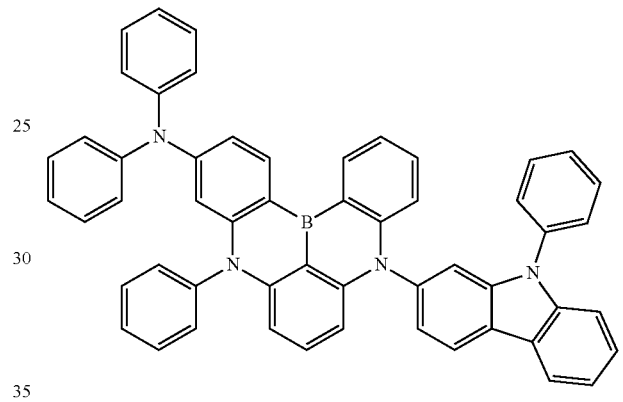
(1-2683)
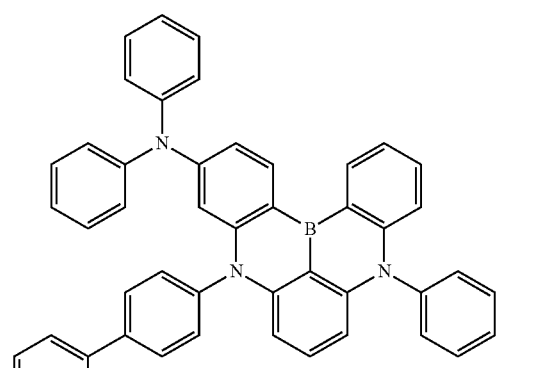
(1-2691)
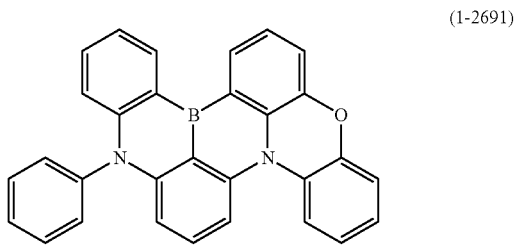

-continued (1-2699)
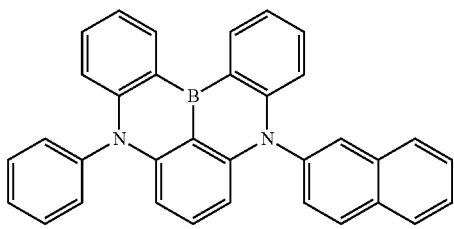

(1-4114)
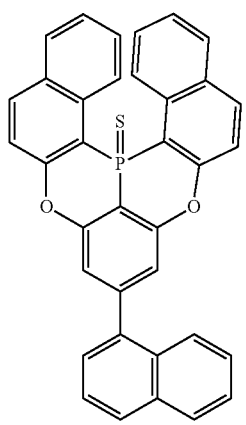

(1-4150)
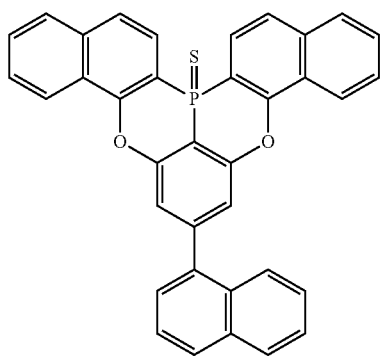

(1-4341)
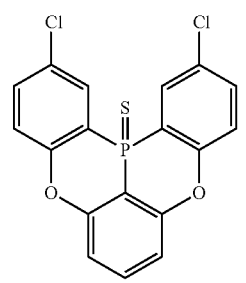

(1-4346)
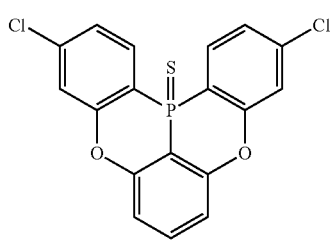

-continued (1-4401)
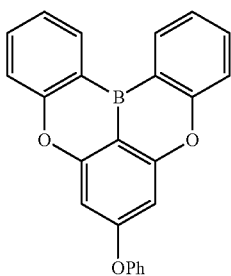

(1-4421-1)
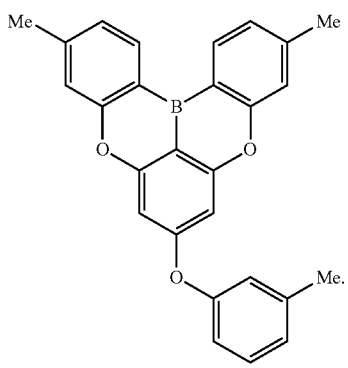

4. A material for an organic device, comprising the polycyclic aromatic compound or the oligomer thereof of claim 1.

5. The material for an organic device of claim 4, wherein the material for an organic device is a material for an organic electroluminescent element, a material for an organic field effect transistor, or a material for an organic thin film solar cell.

6. The material for an organic electroluminescent element of claim 5, which is a material for a light emitting layer.

7. An organic electroluminescent element, comprising a pair of electrodes composed of a positive electrode and a negative electrode; and a light emitting layer that is disposed between the pair of electrodes and contains the material for a light emitting layer of claim 6.

8. The organic electroluminescent element of claim 7, further comprising an electron transport layer and/or an electron injection layer that is disposed between the negative electrode and the light emitting layer, wherein at least one of the electron transport layer and the electron injection layer contains at least one selected from the group consisting of a quinolinol-based metal complex, a pyridine derivative, a phenanthroline derivative, a borane derivative, and a benzimidazole derivative.

9. The organic electroluminescent element of claim 8, wherein the electron transport layer and/or electron injection layer further contains at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

10. A display apparatus comprising the organic electroluminescent element of claim 7.

11. A lighting apparatus comprising the organic electroluminescent element of claim 7.

12. The material for an organic electroluminescent element of claim 5, which is a material for an electron injection layer or a material for an electron transport layer.

13. An organic electroluminescent element, comprising a pair of electrodes composed of a positive electrode and a negative electrode; a light emitting layer that is disposed between the pair of electrodes; and an electron injection layer and/or an electron transport layer that is disposed between the negative electrode and the light emitting layer and contains the material for an electron injection layer and/or material for an electron transport layer of claim 12.

14. The material for an organic electroluminescent element of claim 2, which is a material for a hole injection layer or a material for a hole transport layer.

15. An organic electroluminescent element, comprising a pair of electrodes composed of a positive electrode and a negative electrode; a light emitting layer that is disposed between the pair of electrodes; and a hole injection layer and/or a hole transport layer that is disposed between the positive electrode and the light emitting layer and contains the material for a hole injection layer and/or the material for a hole transport layer of claim 14.

16. The polycyclic aromatic compound or the oligomer thereof of claim 1, wherein each of $R^4$, $R^5$, $R^6$, $R^7$, $R^8$, $R^9$, $R^{10}$ and $R^{11}$ is independently selected from a hydrogen atom, an aryl having 6 to 30 carbon atoms, a heteroaryl having 2 to 30 carbon atoms, a diarylamino (provided that the each aryl is an aryl having 6 to 30 carbon atoms), a diheteroarylamino (provided that the each heteroaryl is an heteroaryl having 2 to 30 carbon atoms), an arylheteroarylamino (provided that the aryl is an aryl having 6 to 30 carbon atoms and the heteroaryl is an heteroaryl having 2 to 30 carbon atoms), an alkyl which is a linear alkyl having 1 to 24 carbon atoms or a branched alkyl having 3 to 24 carbon atoms, an alkoxy which is a linear alkoxy having 1 to 24 carbon atoms or a branched alkoxy having 3 to 24 carbon atoms or an aryloxy having 6 to 30 carbon atoms, wherein at least one hydrogen atom in these may be substituted by an aryl having 6 to 30 carbon atoms, a heteroaryl having 2 to 30 carbon atoms or an alkyl which is a linear alkyl having 1 to 24 carbon atoms or a branched alkyl having 3 to 24 carbon atoms;

each of $R^1$, $R^2$ and $R^3$ is independently selected from a hydrogen atom, an aryl having 6 to 30 carbon atoms, a heteroaryl having 2 to 15 carbon atoms, a diarylamino (provided that the each aryl is an aryl having 6 to 30 carbon atoms), a diheteroarylamino (provided that the each heteroaryl is an heteroaryl having 2 to 30 carbon atoms), an arylheteroarylamino (provided that the aryl is an aryl having 6 to 30 carbon atoms and the heteroaryl is an heteroaryl having 2 to 30 carbon atoms), an alkyl which is a linear alkyl having 1 to 24 carbon atoms or a branched alkyl having 3 to 24 carbon atoms, an alkoxy which is a linear alkoxy having 1 to 24 carbon atoms or a branched alkoxy having 3 to 24 carbon atoms or an aryloxy having 6 to 30 carbon atoms, wherein at least one hydrogen atom in these may be substituted by an aryl having 6 to 30 carbon atoms, a heteroaryl having 2 to 15 carbon atoms or an alkyl which is a linear alkyl having 1 to 24 carbon atoms or a branched alkyl having 3 to 24 carbon atoms, or wherein adjacent groups among $R^1$ to $R^{11}$ are bonded to each other and form an aryl ring having 9 to 30 carbon atoms or a heteroaryl ring having 6 to 30 carbon atoms together with the ring a, ring b or ring c, wherein at least one hydrogen atom in the ring thus formed may be substituted by an aryl having 6 to 30 carbon atoms, a heteroaryl having 2 to 30 carbon atoms, a diarylamino (provided that the each aryl is an aryl having 6 to 30 carbon atoms), a diheteroarylamino (provided that the each heteroaryl is an heteroaryl having 2 to 30 carbon atoms), an arylheteroarylamino (provided that the aryl is an aryl having 6 to 30 carbon atoms and the heteroaryl is an heteroaryl having 2 to 30 carbon atoms), an alkyl which is a linear alkyl having 1 to 24 carbon atoms or a branched alkyl having 3 to 24 carbon atoms, an alkoxy which is a linear alkoxy having 1 to 24 carbon atoms or a branched alkoxy having 3 to 24 carbon atoms or an aryloxy having 6 to 30 carbon atoms, and at least one hydrogen atom in these substituents may be substituted by an aryl having 6 to 30 carbon atoms, a heteroaryl having 2 to 30 carbon atoms or an alkyl which is a linear alkyl having 1 to 24 carbon atoms or a branched alkyl having 3 to 24 carbon atoms;

for the polycyclic aromatic compound, $Y^1$ represents B or P=S, while for the oligomer, $Y^1$ represents B, P=O, or P=S;

when $Y^1$ represents B, $X^1$ and $X^2$ each independently represent O, N—R, S or Se, wherein R of the moiety N—R represents an aryl having 6 to 30 carbon atoms which may be substituted by an alkyl which is a linear alkyl having 1 to 24 carbon atoms or a branched alkyl having 3 to 24 carbon atoms, a heteroaryl having 2 to 30 carbon atoms which may be substituted by an alkyl which is a linear alkyl having 1 to 24 carbon atoms or a branched alkyl having 3 to 24 carbon atoms, or an alkyl which is a linear alkyl having 1 to 24 carbon atoms or a branched alkyl having 3 to 24 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 24 carbon atoms or a branched alkyl having 3 to 24 carbon atoms, while the adjacent carbon atom is not a carbon atom that constitutes the central fused bicyclic structure of the said formula (2) composed of $Y^1$, $X^1$ and $X^2$;

when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl having 6 to 30 carbon atoms which may be substituted by an alkyl which is a linear alkyl having 1 to 24 carbon atoms or a branched alkyl having 3 to 24 carbon atoms, a heteroaryl having 2 to 30 carbon atoms which may be substituted by an alkyl which is a linear alkyl having 1 to 24 carbon atoms or a branched alkyl having 3 to 24 carbon atoms, or an alkyl which is a linear alkyl having 1 to 24 carbon atoms or a branched alkyl having 3 to 24 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 24 carbon atoms or a branched alkyl having 3 to 24 carbon atoms, while the adjacent carbon atom is not a carbon atom that constitutes the central fused bicyclic structure of the said formula (2) composed of $Y^1$, $X^1$ and $X^2$.

17. The polycyclic aromatic compound of claim 16.

18. The polycyclic compound of claim 17, wherein $Y^1$ is B.

19. The oligomer of claim 16.

20. The polycyclic aromatic compound or the oligomer thereof of claim 1, wherein

- each of $R^4$, $R^5$, $R^6$, $R^7$, $R^8$, $R^9$, $R^{10}$ and $R^{11}$ is independently selected from a hydrogen atom, an aryl having 6 to 30 carbon atoms, a heteroaryl having 2 to 30 carbon atoms, a diarylamino (provided that the each aryl is an aryl having 6 to 30 carbon atoms), an alkyl which is a linear alkyl having 1 to 24 carbon atoms or a branched alkyl having 3 to 24 carbon atoms, or an aryloxy having 6 to 30 carbon atoms, wherein at least one hydrogen atom in these may be substituted by an aryl having 6 to 30 carbon atoms, or an alkyl which is a linear alkyl having 1 to 24 carbon atoms or a branched alkyl having 3 to 24 carbon atoms;
- each of $R^1$, $R^2$ and $R^3$ is independently selected from a hydrogen atom, an aryl having 6 to 30 carbon atoms, a heteroaryl having 2 to 15 carbon atoms, a diarylamino (provided that the each aryl is an aryl having 6 to 30 carbon atoms), an alkyl which is a linear alkyl having 1 to 24 carbon atoms or a branched alkyl having 3 to 24 carbon atoms, or an aryloxy having 6 to 30 carbon atoms, wherein at least one hydrogen atom in these may be substituted by an aryl having 6 to 30 carbon atoms, or an alkyl which is a linear alkyl having 1 to 24 carbon atoms or a branched alkyl having 3 to 24 carbon atoms, or wherein adjacent groups among $R^1$ to $R^{11}$ are bonded to each other and form an aryl ring having 9 to 30 carbon atoms or a heteroaryl ring having 6 to 30 carbon atoms together with the ring a, ring b or ring c, wherein at least one hydrogen atom in the ring thus formed may be substituted by an aryl having 6 to 30 carbon atoms, a heteroaryl having 2 to 30 carbon atoms, a diarylamino (provided that the each aryl is an aryl having 6 to 30 carbon atoms), an alkyl which is a linear alkyl having 1 to 24 carbon atoms or a branched alkyl having 3 to 24 carbon atoms, or an aryloxy having 6 to 30 carbon atoms, and at least one hydrogen atom in these substituents may be substituted by an aryl having 6 to 30 carbon atoms, or an alkyl which is a linear alkyl having 1 to 24 carbon atoms or a branched alkyl having 3 to 24 carbon atoms;
- for the polycyclic aromatic compound, $Y^1$ represents B or P=S, while for the oligomer, $Y^1$ represents B, P=O, or P=S;
- when $Y^1$ represents B, $X^1$ and $X^2$ each independently represent O, N—R, S or Se, wherein R of the moiety N—R represents an aryl having 6 to 30 carbon atoms which may be substituted by an alkyl which is a linear alkyl having 1 to 24 carbon atoms or a branched alkyl having 3 to 24 carbon atoms, a heteroaryl having 2 to 30 carbon atoms which may be substituted by an alkyl which is a linear alkyl having 1 to 24 carbon atoms or a branched alkyl having 3 to 24 carbon atoms, or an alkyl which is a linear alkyl having 1 to 24 carbon atoms or a branched alkyl having 3 to 24 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 24 carbon atoms or a branched alkyl having 3 to 24 carbon atoms, while the adjacent carbon atom is not a carbon atom that constitutes the central fused bicyclic structure of the said formula (2) composed of $Y^1$, $X^1$ and $X^2$;
- when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl having 6 to 30 carbon atoms which may be substituted by an alkyl which is a linear alkyl having 1 to 24 carbon atoms or a branched alkyl having 3 to 24 carbon atoms, a heteroaryl having 2 to 30 carbon atoms which may be substituted by an alkyl which is a linear alkyl having 1 to 24 carbon atoms or a branched alkyl having 3 to 24 carbon atoms, or an alkyl which is a linear alkyl having 1 to 24 carbon atoms or a branched alkyl having 3 to 24 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 24 carbon atoms or a branched alkyl having 3 to 24 carbon atoms, while the adjacent carbon atom is not a carbon atom that constitutes the central fused bicyclic structure of the said formula (2) composed of $Y^1$, $X^1$ and $X^2$.

21. The polycyclic aromatic compound of claim 20.

22. The polycyclic compound of claim 21, wherein $Y^1$ is B.

23. The oligomer of claim 20.

24. The polycyclic aromatic compound or the oligomer thereof of claim 1, wherein

- each of $R^4$, $R^5$, $R^6$, $R^7$, $R^8$, $R^9$, $R^{10}$ and $R^{11}$ is independently selected from a hydrogen atom, an aryl having 6 to 16 carbon atoms, a heteroaryl having 2 to 15 carbon atoms, a diarylamino (provided that the each aryl is an aryl having 6 to 16 carbon atoms), an alkyl which is a linear alkyl having 1 to 12 carbon atoms or a branched alkyl having 3 to 12 carbon atoms, or an aryloxy having 6 to 16 carbon atoms, wherein at least one hydrogen atom in these may be substituted by an aryl having 6 to 16 carbon atoms, or an alkyl which is a linear alkyl having 1 to 12 carbon atoms or a branched alkyl having 3 to 12 carbon atoms;
- each of $R^1$, $R^2$ and $R^3$ is independently selected from a hydrogen atom, an aryl having 6 to 16 carbon atoms, a heteroaryl having 2 to 15 carbon atoms, a diarylamino (provided that the each aryl is an aryl having 6 to 16 carbon atoms), an alkyl which is a linear alkyl having 1 to 12 carbon atoms or a branched alkyl having 3 to 12 carbon atoms, or an aryloxy having 6 to 16 carbon atoms, wherein at least one hydrogen atom in these may be substituted by an aryl having 6 to 16 carbon atoms, or an alkyl which is a linear alkyl having 1 to 12 carbon atoms or a branched alkyl having 3 to 12 carbon atoms, or wherein adjacent groups among $R^1$ to $R^{11}$ are bonded to each other and form an aryl ring having 9 to 16 carbon atoms or a heteroaryl ring having 6 to 15 carbon atoms together with the ring a, ring b or ring c, wherein at least one hydrogen atom in the ring thus formed may be substituted by an aryl having 6 to 16 carbon atoms, a heteroaryl having 2 to 16 carbon atoms, a diarylamino (provided that the each aryl is an aryl having 6 to 16 carbon atoms), an alkyl which is a linear alkyl having 1 to 12 carbon atoms or a branched alkyl having 3 to 12 carbon atoms, or an aryloxy having 6 to 16 carbon atoms, and at least one hydrogen atom in these substituents may be substituted by an aryl having 6 to 16 carbon atoms, or an alkyl which is a linear alkyl having 1 to 12 carbon atoms or a branched alkyl having 3 to 12 carbon atoms;

for the polycyclic aromatic compound, $Y^1$ represents B or P=S, while for the oligomer, $Y^1$ represents B, P=O, or P=S;

when $Y^1$ represents B, $X^1$ and $X^2$ each independently represent O, N—R, S or Se, wherein R of the moiety N—R represents an aryl having 6 to 16 carbon atoms which may be substituted by an alkyl which is a linear alkyl having 1 to 12 carbon atoms or a branched alkyl having 3 to 12 carbon atoms, a heteroaryl having 2 to 15 carbon atoms which may be substituted by an alkyl which is a linear alkyl having 1 to 12 carbon atoms or a branched alkyl having 3 to 12 carbon atoms, or an alkyl which is a linear alkyl having 1 to 12 carbon atoms or a branched alkyl having 3 to 12 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 12 carbon atoms or a branched alkyl having 3 to 24 carbon atoms, while the adjacent carbon atom is not a carbon atom that constitutes the central fused bicyclic structure of the said formula (2) composed of $Y^1$, $X^1$ and $X^2$;

when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl having 6 to 16 carbon atoms which may be substituted by an alkyl which is a linear alkyl having 1 to 12 carbon atoms or a branched alkyl having 3 to 12 carbon atoms, a heteroaryl having 2 to 15 carbon atoms which may be substituted by an alkyl which is a linear alkyl having 1 to 12 carbon atoms or a branched alkyl having 3 to 12 carbon atoms, or an alkyl which is a linear alkyl having 1 to 12 carbon atoms or a branched alkyl having 3 to 12 carbon atoms, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl which is a linear alkyl having 1 to 12 carbon atoms or a branched alkyl having 3 to 12 carbon atoms, while the adjacent carbon atom is not a carbon atom that constitutes the central fused bicyclic structure of the said formula (2) composed of $Y^1$, $X^1$ and $X^2$.

25. The polycyclic aromatic compound of claim 24.

26. The polycyclic compound of claim 25, wherein $Y^1$ is B.

27. The oligomer of claim 24.

28. The polycyclic compound of claim 1.

29. The polycyclic compound of claim 28, wherein $Y^1$ is B.

30. The oligomer of claim 1.

31. A method for producing a polycyclic aromatic compound represented by the following general formula (2) or an oligomer of a polycyclic aromatic compound having plural structures each represented by the following general formula (2), the method comprising:

linking ring a, ring b and ring c in the following intermediate via $Y^1$ through a continuous aromatic electrophilic substitution reaction, using a reagent selected from the group consisting of a halide of $Y^1$, an amination halide of $Y^1$, an alkoxylation product of $Y^1$ and an aryloxylation product of $Y^1$, and optionally a Brønsted base:

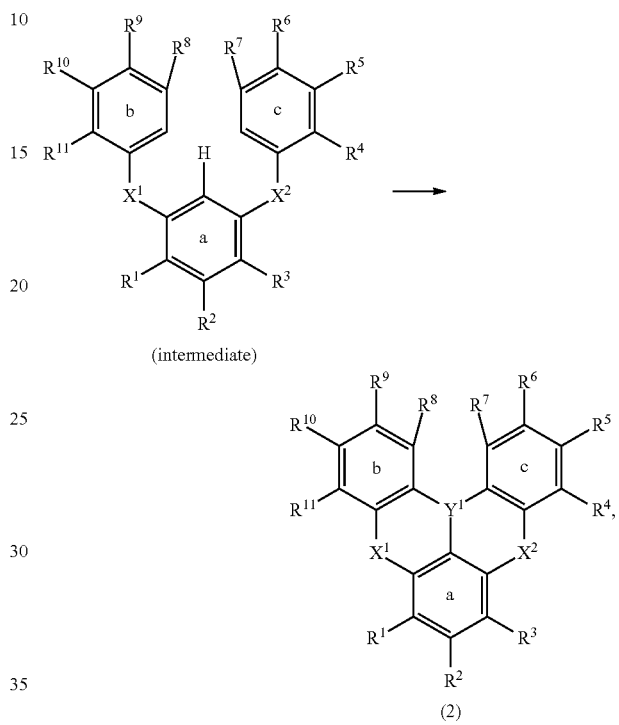

wherein in the intermediate and the formula (2):
each of $R^4$, $R^5$, $R^6$, $R^7$, $R^8$, $R^9$, $R^{10}$ and $R^{11}$ is independently selected from a hydrogen atom, an aryl, a heteroaryl, a diarylamino, a diheteroarylamino, an arylheteroarylamino, an alkyl, an alkoxy or an aryloxy, wherein at least one hydrogen atom in these may be substituted by an aryl, a heteroaryl or an alkyl, each of $R^1$, $R^2$ and $R^3$ is independently selected from a hydrogen atom, an aryl, a heteroaryl having 2-15 carbon atoms, a diarylamino, a diheteroarylamino, an arylheteroarylamino, an alkyl, an alkoxy or an aryloxy, wherein at least one hydrogen atom in these may be substituted by an aryl, a heteroaryl having 2-15 carbon atoms or an alkyl, or wherein adjacent groups among $R^1$ to $R^{11}$ are bonded to each other and form an aryl ring or a heteroaryl ring together with the ring a, ring b or ring c, wherein at least one hydrogen atom in the ring thus formed may be substituted by an aryl, a heteroaryl, a diarylamino, a diheteroarylamino, an arylheteroarylamino, an alkyl, an alkoxy or an aryloxy, and at least one hydrogen atom in these substituents may be substituted by an aryl, a heteroaryl or an alkyl;

for the polycyclic aromatic compound, $Y^1$ represents B or P=S, while for the oligomer, $Y^1$ represents B, P=O, or P=S;

when $Y^1$ represents B, $X^1$ and $X^2$ each independently represent O, N—R, S or Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$;

when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$; and at least one hydrogen atom in the compound or structure represented by formula (2) may be substituted by a deuterium atom, wherein the oligomer is in a form in which a plural number of the unit structures each represented by the general formula (2) are linked such that any ring contained in the unit structure is shared by the plural unit structures, or in a form in which a plural number of the unit structures each represented by the general formula (2) are linked such that any rings contained in the unit structures are fused.

32. A method for producing the polycyclic aromatic compound represented by the following general formula (2) or the oligomer of a polycyclic aromatic compound having plural structures each represented by the following general formula (2) of claim 31, the method comprising:

ortho-metalating a hydrogen atom present between $X^1$ and $X^2$ in the following intermediate using an organic alkali compound;

exchanging the metal for $Y^1$ using a reagent selected from the group consisting of a halide of $Y^1$, an aminated halide of $Y^1$, an alkoxylation product of $Y^1$, and an aryloxylation product of $Y^1$; and linking ring a, ring b, and ring c in the following intermediate via $Y^1$ through a continuous aromatic electrophilic substitution reaction using a Brønsted base:

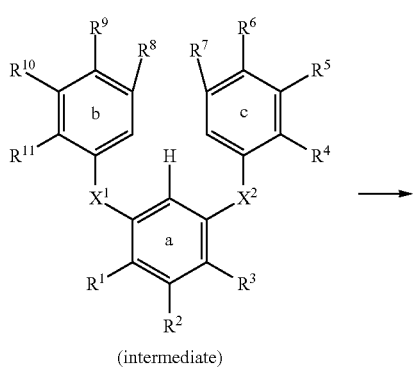

(intermediate)

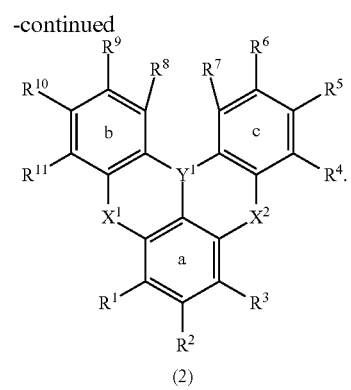

(2)

33. The method of claim 4, wherein in the linking ring a, ring b, and ring s in the intermediate via $Y^1$ through the continuous aromatic electrophilic substitution reaction, the reactions are accelerated by further adding a Lewis acid to the reaction system.

34. The method of claim 31, wherein in the linking ring a, ring b, and ring c in the intermediate via $Y^1$ through the continuous aromatic electrophilic substitution reaction, the reactions are accelerated by further adding a Lewis acid to the reaction system.

35. A method for producing a polycyclic aromatic compound represented by the following general formula (2) or an oligomer of a polycyclic aromatic compound having plural structures each represented by the following general formula (2), the method comprising:

linking ring a, ring b and ring c in the following intermediate via $Y^1$ through a continuous aromatic electrophilic substitution reaction, using a reagent selected from the group consisting of a halide of $Y^1$, an amination halide of $Y^1$, an alkoxylation product of $Y^1$ and an aryloxylation product of $Y^1$, and optionally a Brønsted base:

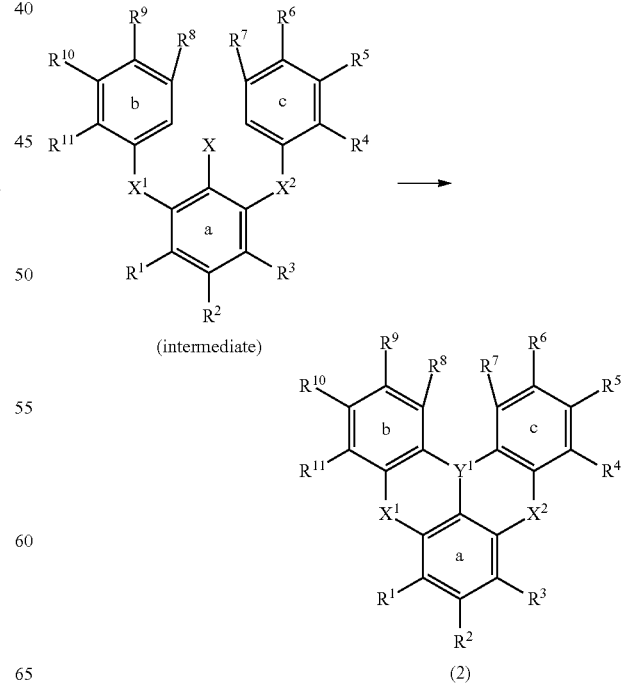

wherein in the intermediate and the formula (2),
X represents a halogen atom;
each of $R^4$, $R^5$, $R^6$, $R^7$, $R^8$, $R^9$, $R^{10}$ and $R^{11}$ is independently selected from a hydrogen atom, an aryl, a heteroaryl, a diarylamino, a diheteroarylamino, an arylheteroarylamino, an alkyl, an alkoxy or an aryloxy, wherein at least one hydrogen atom in these may be substituted by an aryl, a heteroaryl or an alkyl,
each of $R^1$, $R^2$ and $R^3$ is independently selected from a hydrogen atom, an aryl, a heteroaryl having 2-15 carbon atoms, a diarylamino, a diheteroarylamino, an arylheteroarylamino, an alkyl, an alkoxy or an aryloxy, wherein at least one hydrogen atom in these may be substituted by an aryl, a heteroaryl having 2-15 carbon atoms or an alkyl, or wherein adjacent groups among $R^1$ to $R^{11}$ are bonded to each other and form an aryl ring or a heteroaryl ring together with the ring a, ring b or ring c, wherein at least one hydrogen atom in the ring thus formed may be substituted by an aryl, a heteroaryl, a diarylamino, a diheteroarylamino, an arylheteroarylamino, an alkyl, an alkoxy or an aryloxy, and at least one hydrogen atom in these substituents may be substituted by an aryl, a heteroaryl or an alkyl;
for the polycyclic aromatic compound, $Y^1$ represents B or P=S, while for the oligomer $Y^1$ represents B, P=O, or P=S;
when $Y^1$ represents B, $X^1$ and $X^2$ each independently represent O, N—R, S or Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$;
when $Y^1$ represents P=O or P=S, $X^1$ and $X^2$ both represent O, S or Se, one of $X^1$ and $X^2$ represents O while the other represents S or Se, one of $X^1$ and $X^2$ represents N—R while the other represents Se, or one of $X^1$ and $X^2$ represents S while the other represents Se, wherein R of the moiety N—R represents an aryl which may be substituted by an alkyl, a heteroaryl which may be substituted by an alkyl, or an alkyl which may be substituted by an alkyl, R of the moiety N—R may be bonded to a carbon atom adjacent to the position (atom) of bonding to $X^1$ or $X^2$ in the ring a, ring b and/or ring c via —O—, —S—, —C(—$R^a$)$_2$— or a single bond, wherein $R^a$ represents a hydrogen atom or an alkyl, while the adjacent carbon atom is not a carbon atom that constitutes the central fused bicyclic structure of the said formula (2) composed of $Y^1$, $X^1$ and $X^2$; and
at least one hydrogen atom in the compound or structure represented by formula (2) may be substituted by a deuterium atom,
wherein the oligomer is in a form in which a plural number of the unit structures each represented by the general formula (2) are linked such that any ring contained in the unit structure is shared by the plural unit structures, or in a form in which a plural number of the unit structures each represented by the general formula (2) are linked such that any rings contained in the unit structures are fused.

36. A method for producing the polycyclic aromatic compound represented by the following general formula (2) or the oligomer of a polycyclic aromatic compound having plural structures each represented by the following general formula (2) of claim 35, the method comprising:
ortho-metalating a halogen atom present between $X^1$ and $X^2$ in the following intermediate using an organic alkali compound;
exchanging the metal for $Y^1$ using a reagent selected from the group consisting of a halide of $Y^1$, an aminated halide of $Y^1$, an alkoxylation product of $Y^1$, and an aryloxylation product of $Y^1$; and
linking ring a, ring b, and ring c in the following intermediate via $Y^1$ through a continuous aromatic electrophilic substitution reaction using a Brøonsted base:

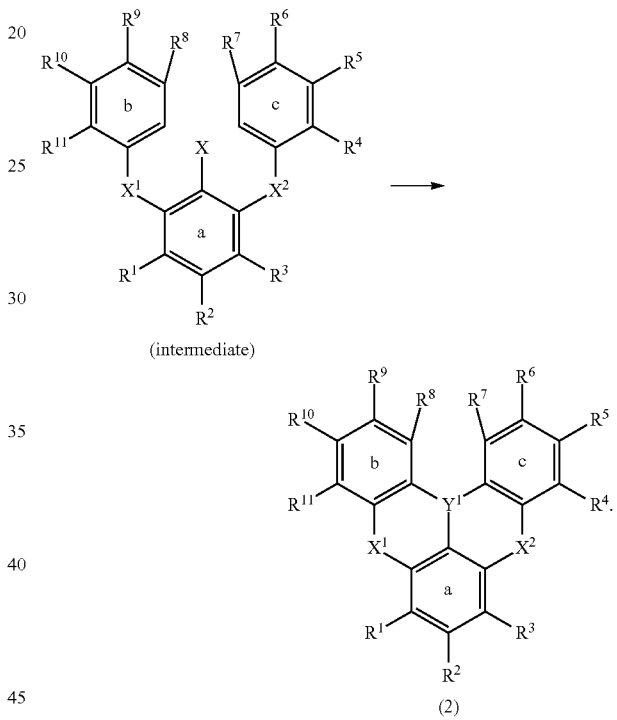

37. The method of claim 36, wherein in the linking ring a, ring b, and ring c in the intermediate via $Y^1$ through the continuous aromatic electrophilic substitution reaction, the reactions are accelerated by further adding a Lewis acid to the reaction system.

38. The method of claim 35, wherein in the linking ring a, ring b, and ring c in the intermediate via $Y^1$ through the continuous aromatic electrophilic substitution reaction, the reactions are accelerated by further adding a Lewis acid to the reaction system.

39. The polycyclic aromatic compound of claim 1, which is represented by the following formula (1-1), the following formula (1-2), the following formula (1-4), the following formula (1-10), the following formula (1-49), the following formula (1-81), the following formula (1-91), the following formula (1-100), the following formula (1-141), the following formula (1-151), the following formula (1-176), the following formula (1-411), the following formula (1-447), or the following formula (1-701):

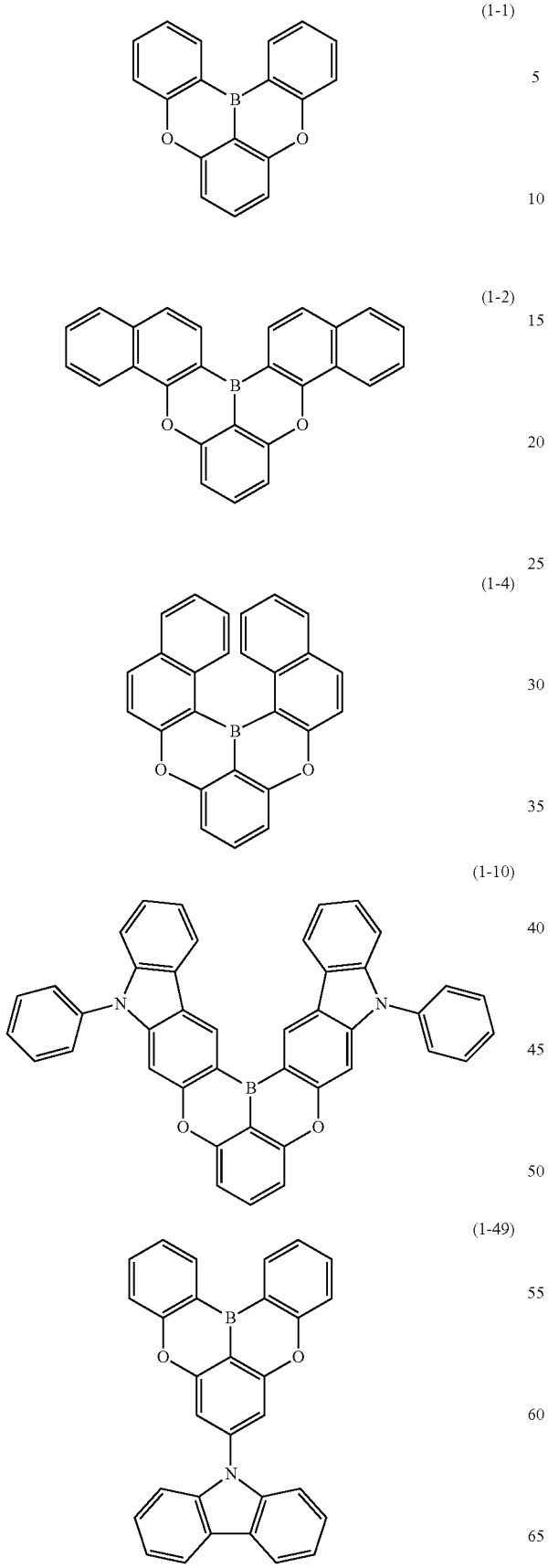
(1-1)
(1-2)
(1-4)
(1-10)
(1-49)
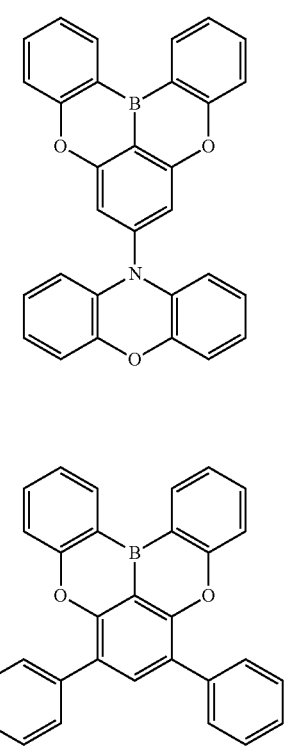
(1-81)
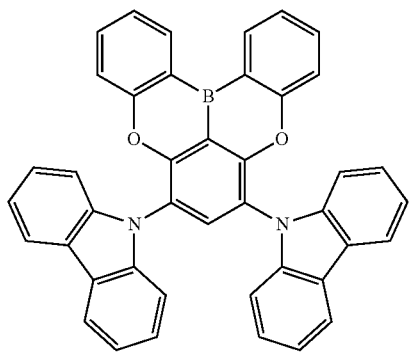
(1-91)
(1-100)
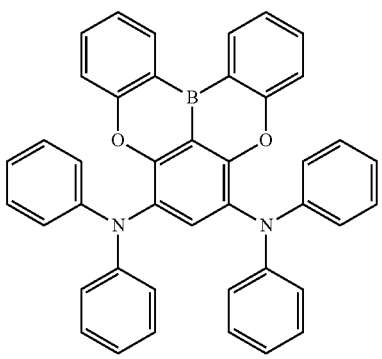
(1-141)

(1-151)
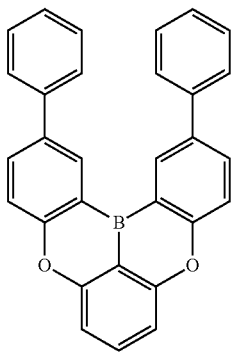

(1-176)
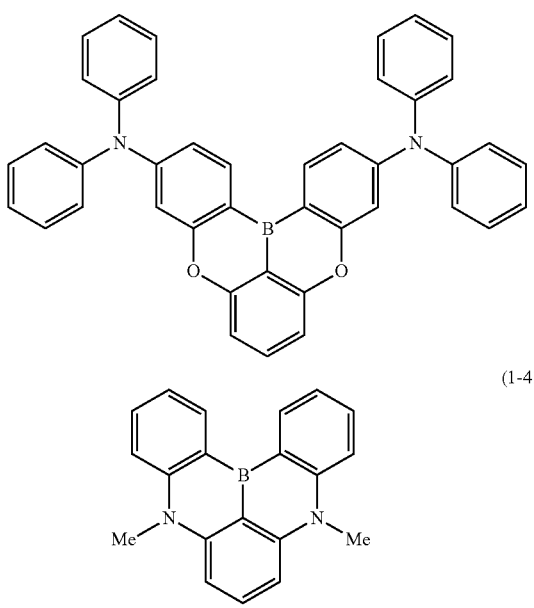

(1-411)
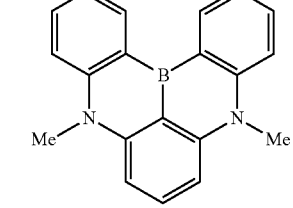

(1-447)
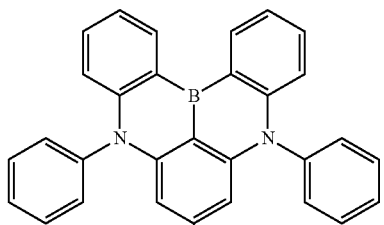

(1-701)
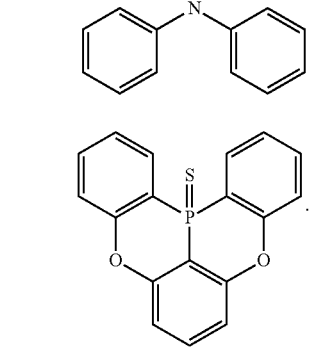

40. The polycyclic aromatic compound of claim 1, which is represented by the following formula (1-1), the following formula (1-2), the following formula (1-4), the following formula (1-10), the following formula (1-49), the following formula (1-81), the following formula (1-91), the following formula (1-100), the following formula (1-141), the following formula (1-151), the following formula (1-176), the following formula (1-411), or the following formula (1-447):

(1-1)
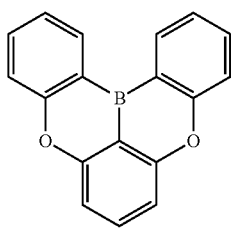

(1-2)
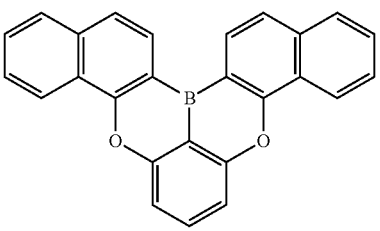

(1-4)
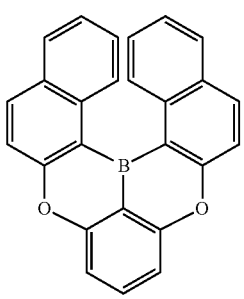

(1-10)
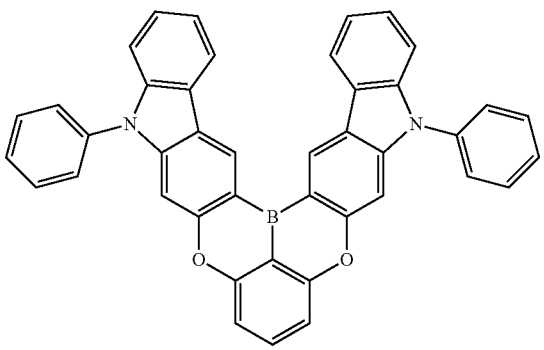

-continued
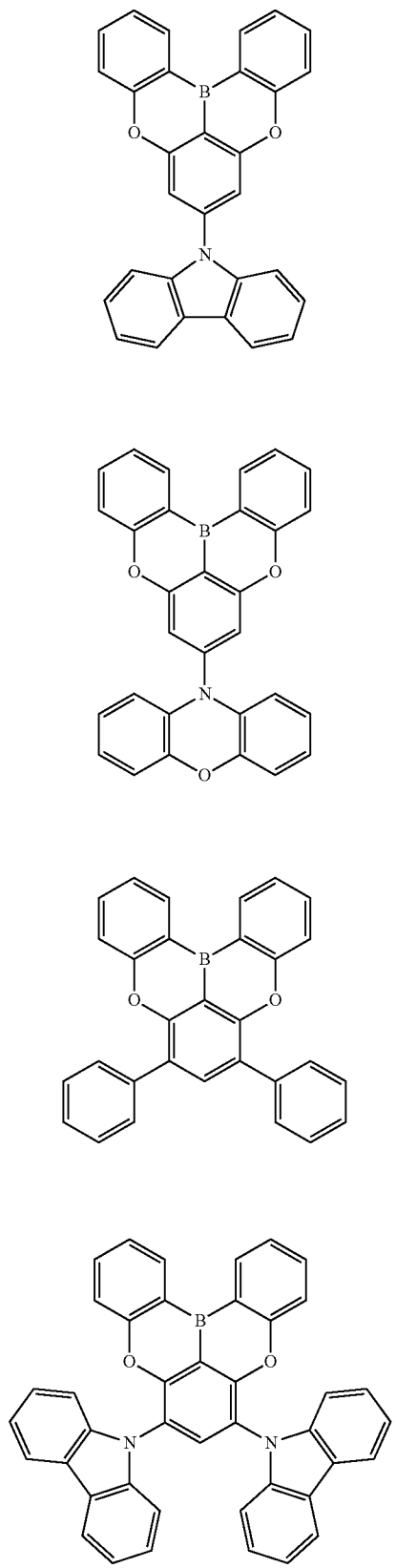
(1-49)
(1-81)
(1-91)
(1-100)
-continued
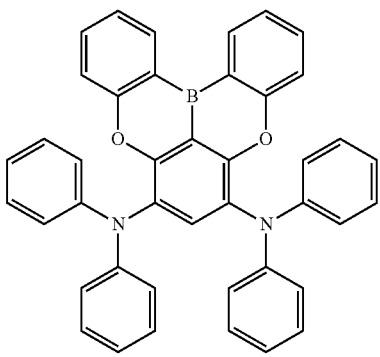
(1-141)
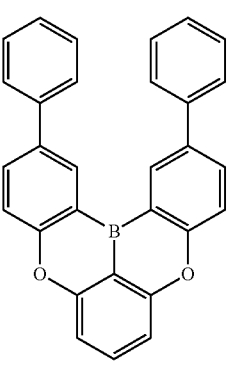
(1-151)
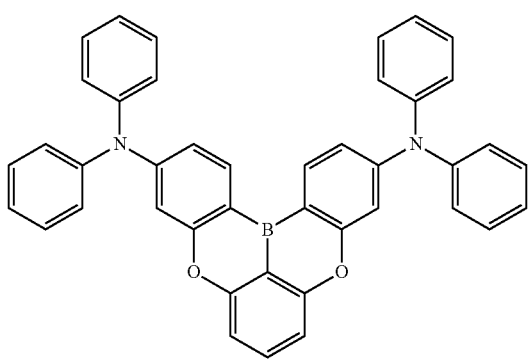
(1-176)
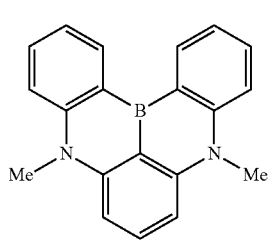
(1-411)

(1-447)

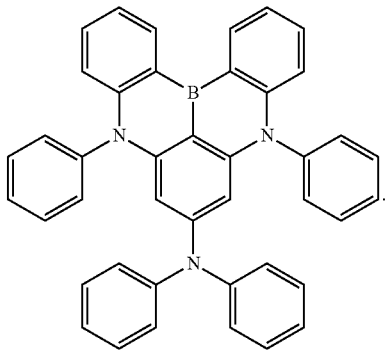

41. The polycyclic aromatic compound of claim 1, which is represented by the following formula (1-21), the following formula (1-23), the following formula (1-24), the following formula (1-50), the following formula (1-152), the following formula (1-201), the following formula (1-401), the following formula (1-422), the following formula (1-1048), the following formula (1-1049), the following formula (1-1050), the following formula (1-1069), the following formula (1-1084), the following formula (1-1090), the following formula (1-1092), the following formula (1-1101), the following formula (1-1102), the following formula (1-1103), the following formula (1-1145), the following formula (1-1152), the following formula (1-1159), the following formula (1-1201), the following formula (1-1210), or the following formula (1-1271):

(1-21)

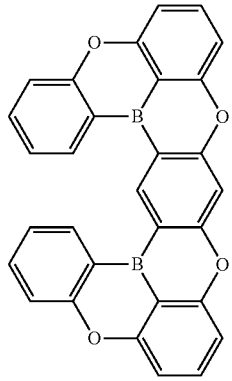

(1-23)

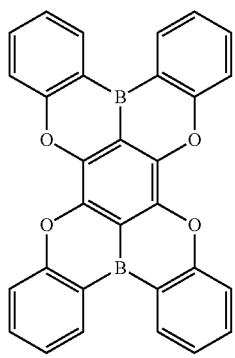

(1-24)

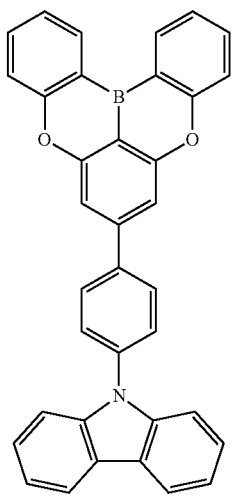

(1-50)

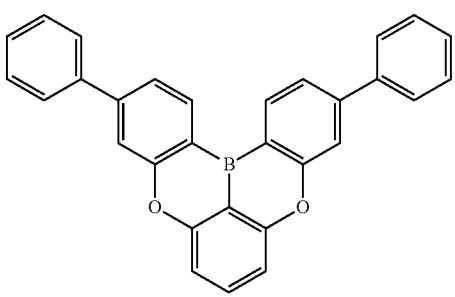

(1-152)

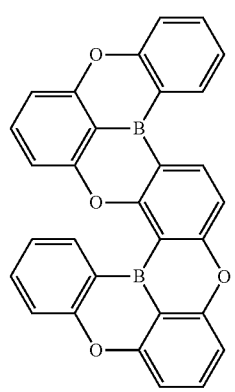

(1-201)

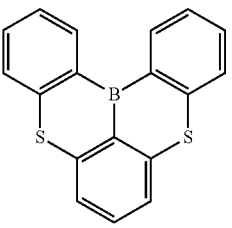

(1-401)

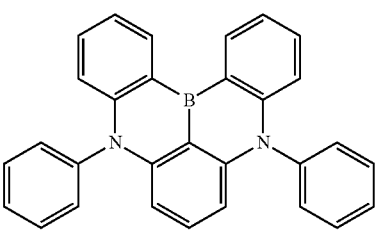

-continued
(1-422)
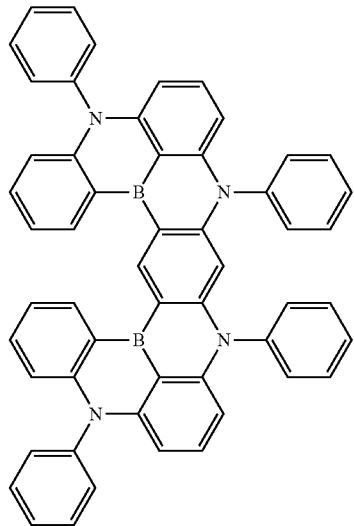
(1-1048)
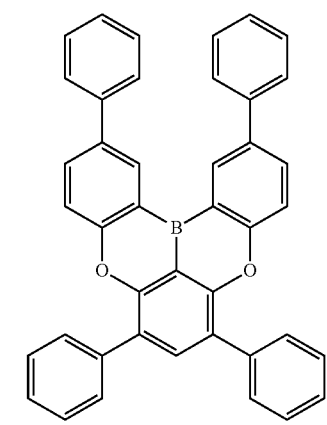
(1-1049)
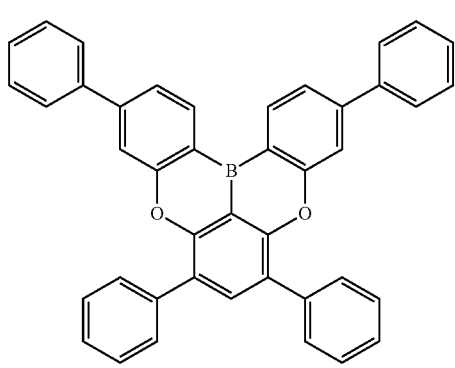
(1-1050)
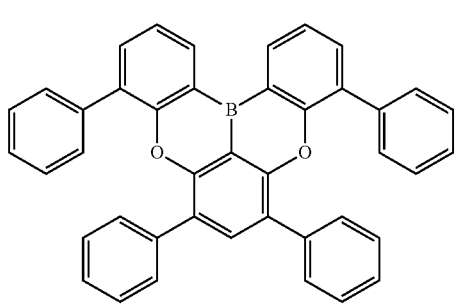
-continued
(1-1069)
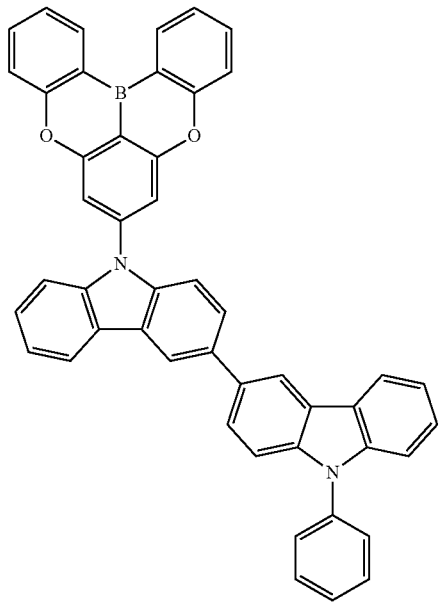
(1-1084)
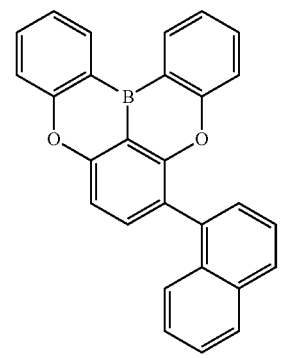
(1-1090)
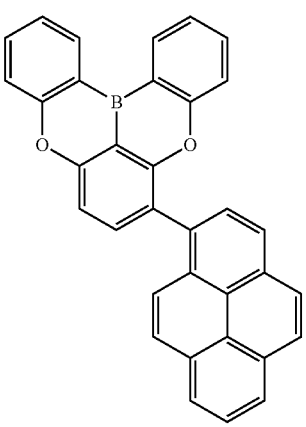

(1-1092)
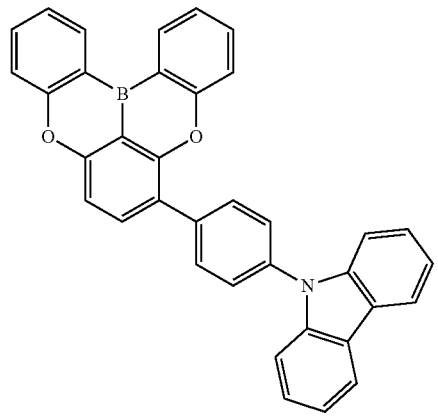
(1-1101)
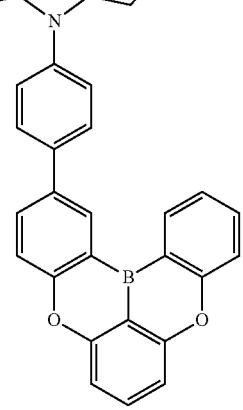
(1-1102)
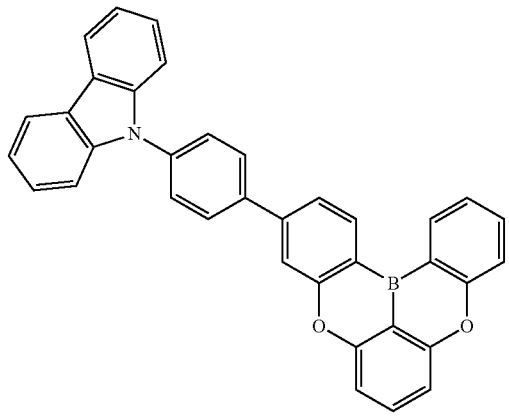
(1-1103)
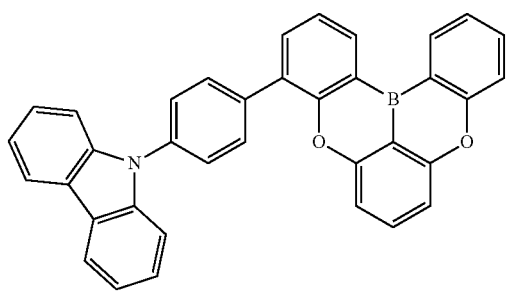
(1-1145)
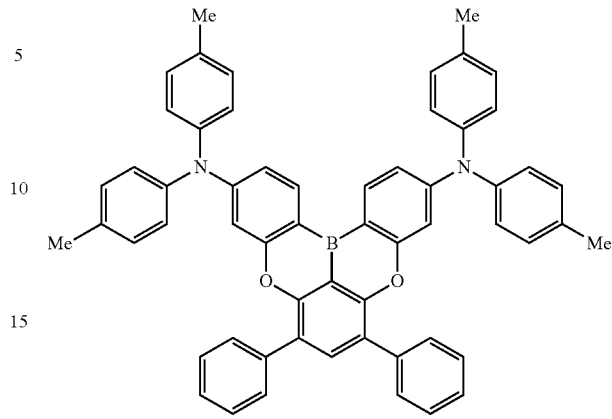
(1-1152)
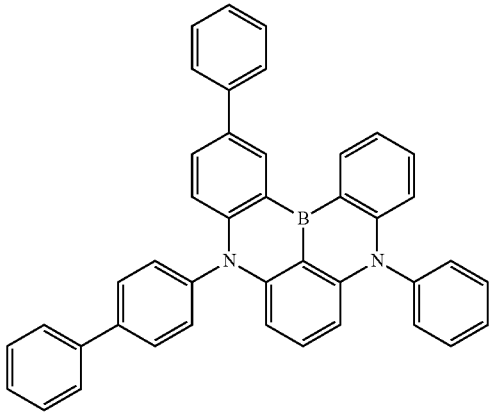
(1-1159)
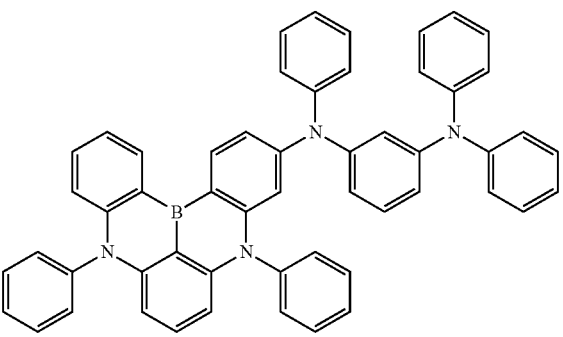
(1-1201)
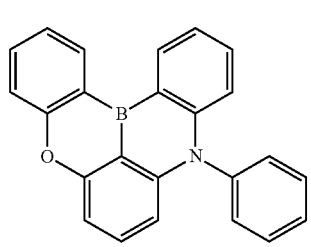

(1-1210)

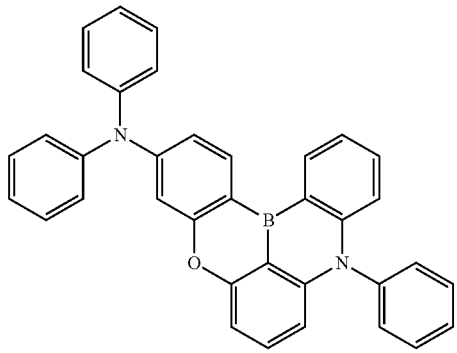

(1-1271)

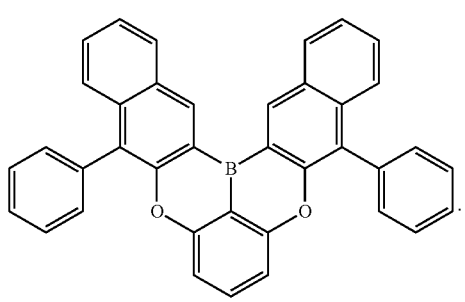

42. The polycyclic aromatic compound of claim 1, which is represented by the following formula (1-1-1), the following formula (1-79), the following formula (1-142), the following formula (1-152-2), the following formula (1-158), the following formula (1-159), the following formula (1-1006), the following formula (1-1104), the following formula (1-1149), the following formula (1-1150), the following formula (1-1301), the following formula (1-1351), the following formula (1-2305), the following formula (1-2626), the following formula (1-2657), the following formula (1-2662), the following formula (1-2665), the following formula (1-2676), the following formula (1-2678), the following formula (1-2679), the following formula (1-2680), the following formula (1-2681), the following formula (1-2682), the following formula (1-2683), the following formula (1-2691), the following formula (1-2699), the following formula (1-4401), or the following formula (1-4421-1):

(1-1-1)

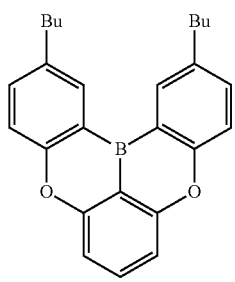

(1-79)

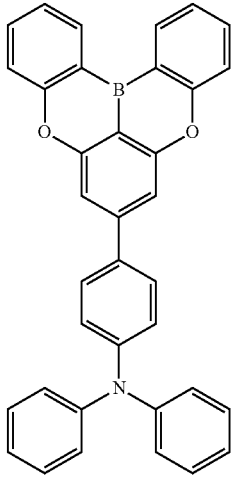

(1-142)

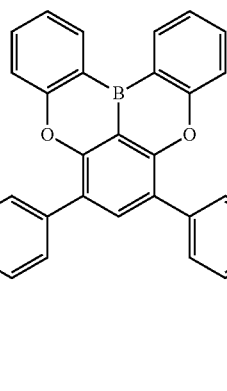

(1-152-2)

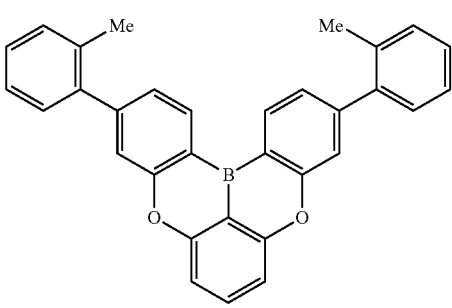

(1-158)

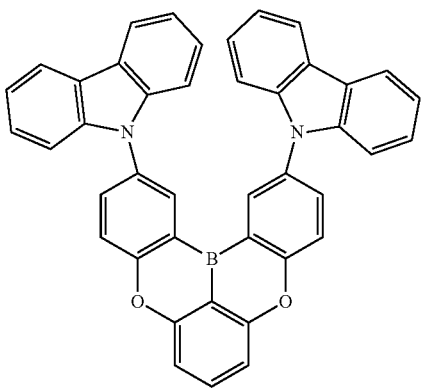

-continued
(1-159)
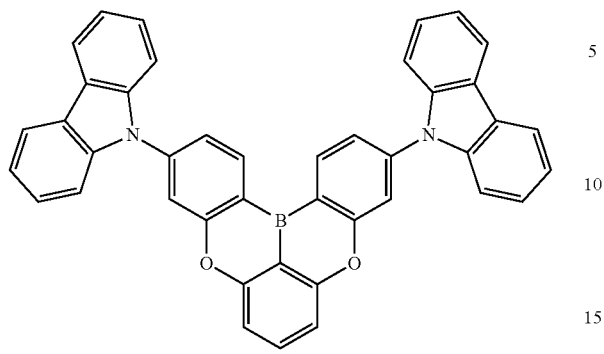
(1-1006)
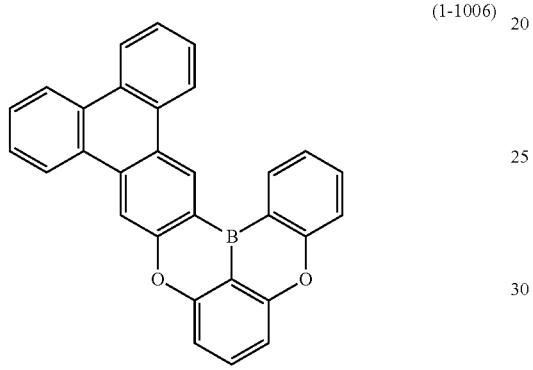
(1-1104)
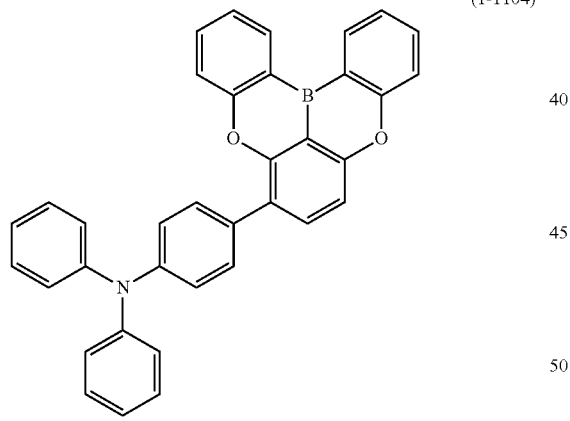
(1-1149)
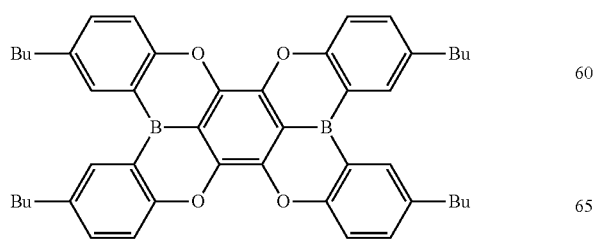
-continued
(1-1150)
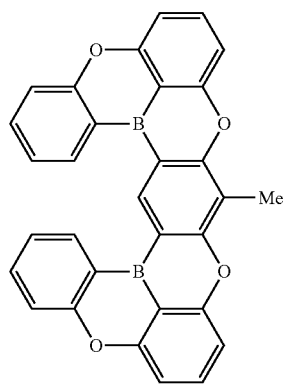
(1-1301)
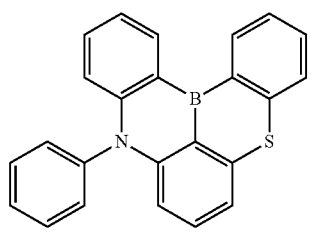
(1-1351)
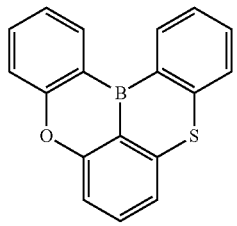
(1-2305)
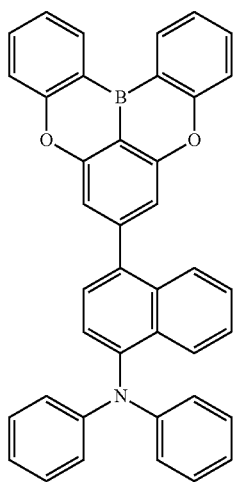

-continued
(1-2626)
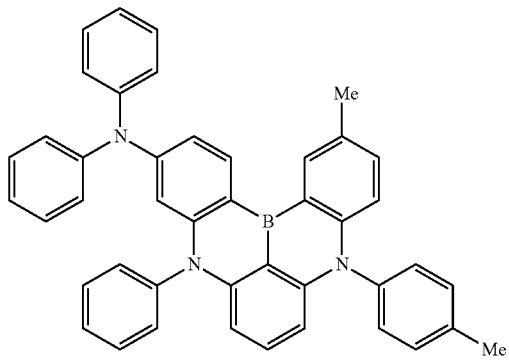
(1-2676)
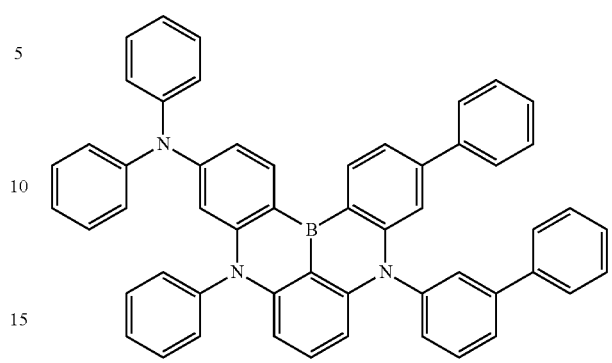
(1-2657)
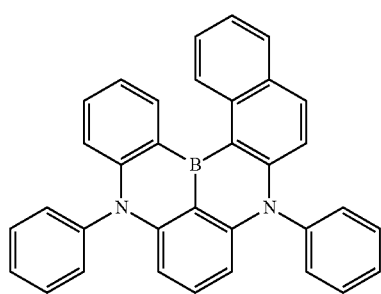
(1-2678)
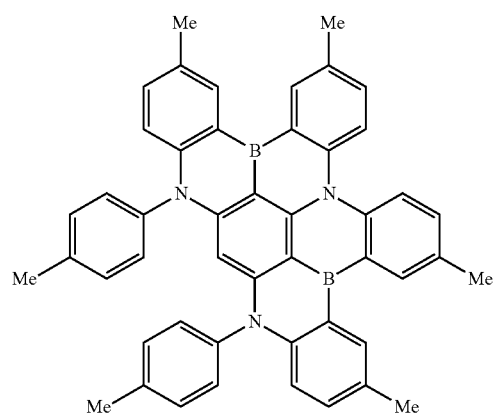
(1-2662)
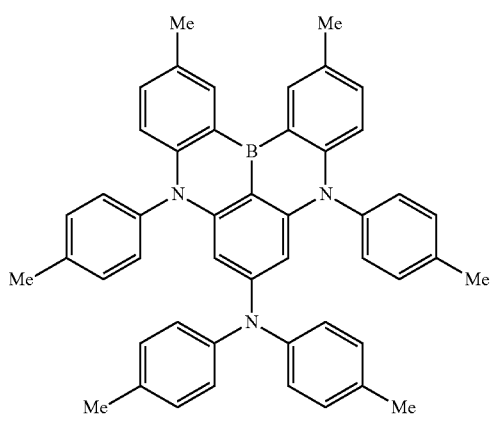
(1-2679)
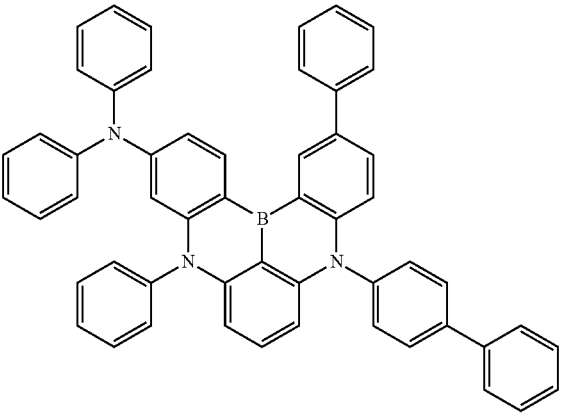
(1-2665)
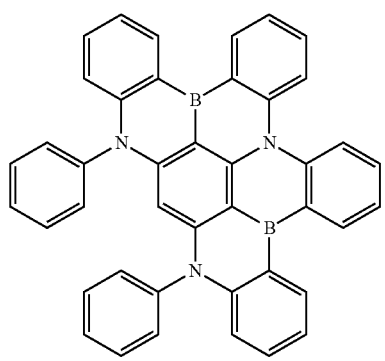
(1-2680)
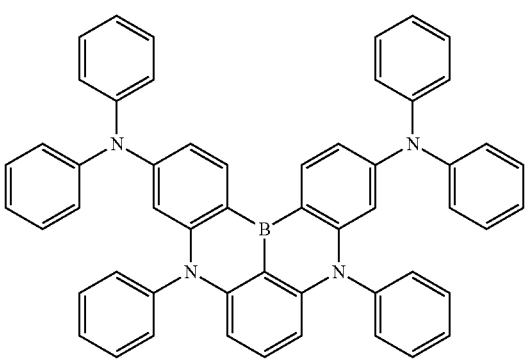

(1-2681)
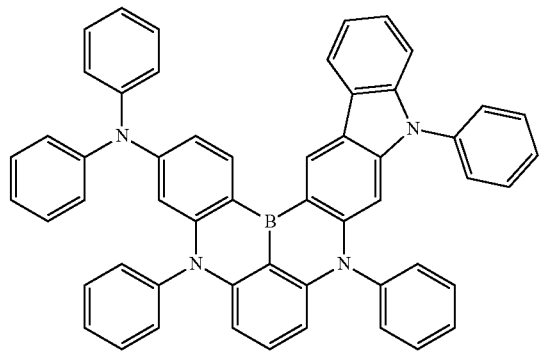
(1-2682)
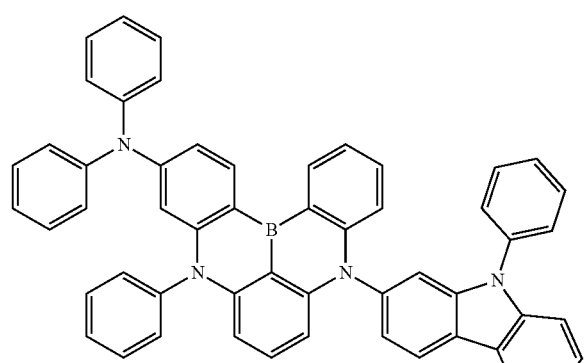
(1-2683)
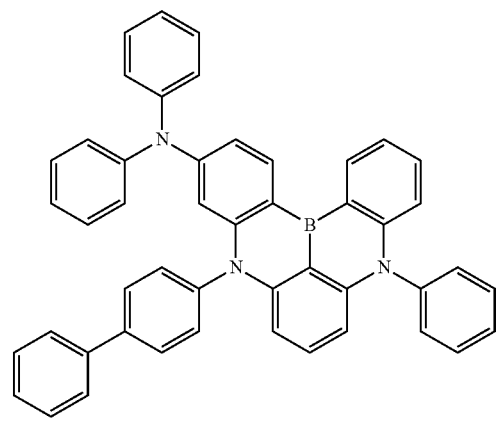
(1-2691)
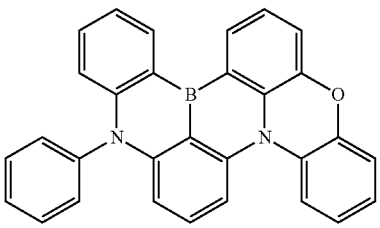
(1-2699)
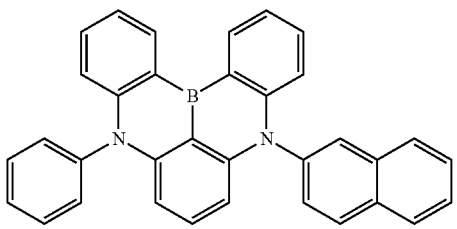
(1-4401)
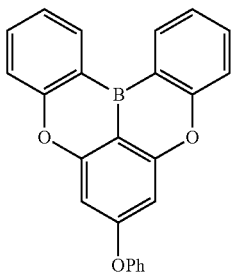
(1-4421-1)
* * * * *